US008957040B2

(12) United States Patent
Bennett et al.

(10) Patent No.: US 8,957,040 B2
(45) Date of Patent: Feb. 17, 2015

(54) SELECTIVE REDUCTION OF ALLELIC VARIANTS

(75) Inventors: C. Frank Bennett, Carlsbad, CA (US); Susan M. Freier, San Diego, CA (US); Sarah Greenlee, San Diego, CA (US); Eric E. Swayze, Encinitas, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 13/577,616

(22) PCT Filed: Feb. 8, 2011

(86) PCT No.: PCT/US2011/024103
§ 371 (c)(1),
(2), (4) Date: Oct. 4, 2012

(87) PCT Pub. No.: WO2011/097643
PCT Pub. Date: Aug. 11, 2011

(65) Prior Publication Data
US 2013/0046007 A1    Feb. 21, 2013

Related U.S. Application Data

(60) Provisional application No. 61/302,469, filed on Feb. 8, 2010, provisional application No. 61/371,635, filed on Aug. 6, 2010.

(51) Int. Cl.
*C12N 15/11* (2006.01)
*C12Q 1/68* (2006.01)
*C12N 15/113* (2010.01)

(52) U.S. Cl.
CPC .......... *C12N 15/113* (2013.01); *C12N 2310/11* (2013.01); *C12N 2310/315* (2013.01); *C12N 2310/3231* (2013.01); *C12N 2310/3341* (2013.01); *C12N 2310/341* (2013.01); *C12N 2310/346* (2013.01); *C12N 2320/34* (2013.01)
USPC ...................................... 514/44 A; 435/6.11

(58) Field of Classification Search
CPC .......... C12Q 1/6883; C12Q 2600/156; C12N 2310/14; C12N 15/113; A61K 31/713; G01N 2500/00
See application file for complete search history.

(56) References Cited

U.S. PATENT DOCUMENTS

| | | |
|---|---|---|
| 5,801,154 A | 9/1998 | Baracchini et al. |
| 6,268,490 B1 | 7/2001 | Imanishi et al. |
| 6,525,191 B1 | 2/2003 | Ramasamy |
| 6,582,908 B2 | 6/2003 | Fodor et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,399,845 B2 | 7/2008 | Seth et al. |
| 7,951,934 B2 | 5/2011 | Freier et al. |
| 2001/0053519 A1 | 12/2001 | Fodor et al. |
| 2002/0081611 A1 | 6/2002 | O'Brien et al. |
| 2002/0187931 A1 | 12/2002 | Hayden et al. |
| 2003/0073123 A1 | 4/2003 | Shen et al. |
| 2003/0109476 A1 | 6/2003 | Kmiec et al. |
| 2003/0228597 A1 | 12/2003 | Cowsert et al. |
| 2004/0171570 A1 | 9/2004 | Allerson et al. |
| 2006/0063730 A1 | 3/2006 | Monia et al. |
| 2007/0031844 A1 | 2/2007 | Khvorova et al. |
| 2007/0161590 A1 | 7/2007 | Van Bilsen et al. |
| 2007/0287831 A1 | 12/2007 | Seth et al. |
| 2008/0015162 A1 | 1/2008 | Bhanot et al. |
| 2008/0039418 A1 | 2/2008 | Freier |
| 2008/0039618 A1 | 2/2008 | Allerson et al. |
| 2009/0012281 A1 | 1/2009 | Swayze et al. |
| 2009/0318536 A1 | 12/2009 | Freier et al. |
| 2010/0069472 A1 | 3/2010 | Hung et al. |
| 2010/0299768 A1 | 11/2010 | Perrin et al. |

FOREIGN PATENT DOCUMENTS

| | | |
|---|---|---|
| WO | WO 99/14226 | 3/1999 |
| WO | WO 03/004602 | 1/2003 |
| WO | WO 2004/106356 | 12/2004 |
| WO | WO 2007/002904 | 1/2007 |
| WO | WO 2007/134181 | 11/2007 |
| WO | WO 2008/005562 | 1/2008 |
| WO | WO 2008/049085 | 4/2008 |
| WO | WO 2008066776 A2 * | 6/2008 |
| WO | WO 2008/147930 | 12/2008 |
| WO | WO 2008/150729 | 12/2008 |

(Continued)

OTHER PUBLICATIONS

Fluiter et al, Tumor Genotype-specific Growth Inhibition in Vivo by Antisense Oligonucleotides against a Polymorphic Site of the Large Subunit of Human RNA Polymerase II, Apr. 2002, Cancer Research, 62: 2024-2028.*

Albaek et al., "Analogues of a Locked Nucleic Acid with Three-Carbon 2',4'-Linkages: Synthesis by Ring-Closing Metathetsis and Influence on Nucleic Acid Duplex Stability and Structure" J. Org. Chem. (2006) 71:7731-7740.

Altmann et al., "Second Generation of Antisense Oligonucleotides: From Nuclease Resistance to Biological Efficacy in Animals" Chimia (1996) 50:168-176.

(Continued)

*Primary Examiner* — Tracy Vivlemore
*Assistant Examiner* — Kate Poliakova-Georgantas
(74) *Attorney, Agent, or Firm* — Isis Pharmaceuticals, Inc. Patent Dept; Casimir Jones, S.C.

(57) ABSTRACT

Disclosed herein are antisense compounds and methods for selectively of reducing expression of an allelic variant of a gene containing a single nucleotide polymorphism (SNP). Such methods, compounds, and composition are useful to treat, prevent, or ameliorate diseases, including neurodegenerative, such as Huntington's Disease (HD).

16 Claims, 161 Drawing Sheets

(56) References Cited

FOREIGN PATENT DOCUMENTS

| WO | WO 2008/154401 | 12/2008 |
|---|---|---|
| WO | WO 2009/006478 | 1/2009 |
| WO | WO 2009/135322 | 11/2009 |
| WO | WO 2010/048585 | 4/2010 |

OTHER PUBLICATIONS

Altmann et al., "Second-generation antisense oligonucleotides: structure-activity relationships and the design of improved signal-transduction inhibitors" Biochem. Soc. Trans. (1996) 24:630-637.
Altmann et al., "Second Generation Antisense Oligonucleotides—Inhibition of Pkc-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides Nucleotides (1997) 16:917-926.
Bonini et al., "Silencing Polyglutam ne Degeneration with RNAi" Neuron (2005) 48:715-718.
Braasch Et al., "Locked nucleic acid (LNA): fine-tuning the recognition of DNA and RNA" Chem. Biol. (2001) 8:1-7.
Branch et al., "A good antisense molecule is hard to find," TIBS (1998) 23:45-50.
Brookes, "The essence of SNPs" Gene (1999) 234(2):177-186.
Gossen et al., "Tight control of gene expression in mammalian cells by tetracycline-responsive promoters." PNAS (1992) 89:5547-5551.
Chan et al., "Antisense Oligonucleotides: From Design to Therapeutic Application" Clin. Exp. Pharmacol. Physiol. (2006) 33:533-540.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.
Denovan-Wright et al., "RNAi: a potential therapy for dominantly inherited nucleotide repeat diseases" Gene Therapy (2006) 13(6):525-531.
Dragatsis et al., "Inactivation of Hdh in the brain and testis results in progressive neurodegeneration and sterility in mice" Nat. Genet. (2000) 26:300-306.
Elayadi Et al., "Application of PNA and LNA oligomers to chemotherapy" Curr. Opinions Invens. Drugs (2001) 2:558-561.
Ellis, "Spot-On SNP Genotyping" Genome Res. (2000) 10:895-897.
Freier et al., "The ups and downs of nucleic acid duplex stability: structure-stability studies on chemically-modified DNA:RNA duplexes" Nucleic Acids Res. (1997) 25:4429-4443.
Frieden et al., "Expanding the design horizon of antisense oligonucleotides with alpha-L-LNA" Nucleic Acids Research (2003) 21:6365-6372.
Gautschi et al., "Activity of a Novel bcl-2/bcl-xL-Bispecific Antisense Oligonucleotide Against Tumors of Diverse Histologic Origins" J. Natl. Cancer Inst. (2001) 93:463-471.
Gray et al., "Full-Length Human Mutant Huntingtin with a Stable Polyglutamine Repeat Can Elicit Progressive and Selective Neuropathogenesis in BACHD Mice" J. Neurosc. (2008) 28(24):6182-6195.
Griffin et al., "Single-nucleotide polymorphism analysis by MALDI-TOF mass spectrometry" Trends Biotechnol. (2000) 18(2):77-84.
Gutekunst et al., "Identification and localization of huntingtin in brain and human lymphoblastoid cell lines with anti-fusion protein antibodies" PNAS (1995) 92(19):8710-8714.
Handley et al., "Pharmaceutical, cellular and genetic therapies for Huntington's disease" Clin. Sci. (2006) 110:73-88.
Kordasiewicz et al., "Sustained Therapeutic Reversal of Huntington's Disease by Transient Repression of Huntingtin Synthesis" Neuron (2012) 74:1031-1044.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.

Kumar et al., "The First Analogues of LNA (Locked Nucleic Acids): Phosphorothioate-LNA and 2'-Thio-LNA" Bioorg. Med. Chem. Lett. (1998) 8:2219-2222.
Leumann, "DNA Analogues: From Supramolecular Principles to Biological Properties" Bioorganic & Medicinal Chemistry (2002) 10:841-854.
MacDonald et al., "A novel gene containing a trinucleotide repeat that is expanded and unstable on Huntington's disease chromosomes" Huntington's Disease Collaborative Research Group, Cell (1993) 72(6):971-983.
Maher et al., "Comparative hybrid arrest by tandem antisense oligodeoxyribonucleotides or oligodeoxyribonucleoside methylphosphonates in a cell-free system" Nuc. Acid. Res. (1988) 16:3341-3358.
Nasir et al., "Targeted disruption of the Huntington's disease gene results in embryonic lethality and behavioral and morphological changes in heterozygotes" Cell (1995) 81(5):811-823.
New England Biolabs 1998/99 Catalog (cover page and pp. 121 and 284).
Orum et al., "Locked nucleic acids: A promising molecular family for gene-function analysis and antisense drug development" Curr. Opinion Mol. Ther. (2001) 3:239-243.
Reynolds et al., "Rational siRNA design for RNA interference" Nature Biotechnology (2004) 22(31:326- 330.
Sanghvi et al., "Heterocyclic Base Modifications in Nucleic Acids and Their Applications in Antisense Oligonucleotides" Antisense Research and Applications (1993) pp. 273-288.
Singh et al., "LNA (locked nucleic acids): synthesis and high-affinity nucleic acid reconition" Chem. Commun. (1998) 4:455-456.
Singh et al., "Synthesis of 2'-Amino-LNA: A Novel Conformationally Restricted High-Affinity Oligonucleotide Analogue with a Handle" J. Org. Chem. (1998) 63:10035-10039.
Srivastava et al., "Five- and Six-Membered Conformationally Locked 2',4'-Carbocyclic riboThymidines: Synthesis, Structure, and Biochemical Studies" J. Am. Chem. Soc. (2007) 129(26):8362-8379.
Wahlestedt et al., "Potent and nontoxic antisense oligonucleotides containing locked nucleic acids" PNAS (2000) 97:5633-5638.
Warby et al., "CAG expansion in the Huntington disease gene is associated with a specific and targetable predisposing haplogroup" The American Journal of Human Genetics (2009) 84(3):351-366.
Woolf et al., "Specificity of antisense oligonucleotide in vivo" PNAS (1992) 89:7305-7309.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
European Search report for application EP 09741640.8 dated Dec. 11, 2012.
International Search Report for application PCT/CA2009/000645 dated Aug. 25, 2009.
International Search Report for application PCT/US11/24103 dated Jul. 15, 2011.
International Search Report for application PCT/US11/24104 dated Jul. 20, 2011.
Carroll et al., "Potent and Selective Antisense Oligonucleotides Targeting Single-Nucleotide Polymorphisms in the Huntington Disease Gene / Allele-Specific Silencing of Mutant Huntingtin" Molecular Therapy (2011) 19(12):2178-2185.
Alves et al., "Allele-Specific RNA Silencing of Mutan Ataxin-3 Mediates Neuroprotection in a Rat Model of Machado-Joseph Disease" PLOS ONE (2008) 3(10): e3341.
Hu et al., "Allele-specific silencing of mutant huntingtin and ataxin-3 genes by targeing expanded CAG repeats in mRNAs" Nature Biotechnology (2009) 27(5):478-484.
Van Bilsen et al., "Identification and allele-specific silencing of the mutant huntingtin allele in Hunington's disease patient-derived fibroblasts" Human Gene Therapy (2008) 19:710-718.
European Search report for application EP 11740543 dated Sep. 18, 2013.
International Search Report for application PCT/US12/50015 dated Nov. 2, 2012.

(56) References Cited

OTHER PUBLICATIONS

International Search Report for application PCT/US12/50023 dated Oct. 16, 2012.
Lombardi et al., "A majority of Huntington's disease patients may be treatable by individualized allele-specific RNA interference" Experimental Neurology (2009) 217(2): 312-319.
Schwarz et al., "Designing siRNA that distinguish between genes that differ by a single nucleotide" PLOS Genetics (2006) 2(9): p. e140.
European Search report for application EP 11740542.3 dated Aug. 14, 2014.

* cited by examiner

FIG. 1A

```
CLUSTAL 2.0.12 multiple sequence alignment genome      GCCCAGCAGGTGTCAGCCTCATTTTACCCCGCCCCTATTCAAGATGAAGTTGTTCTGGTT 60
mRNA        ------------------------------------------------------------ genome      CCAACGCCTCTGACATATTAGCTGCATCATTTTACATTTCTTTTTTTTTTCCTTTTAA 120
mRNA        ------------------------------------------------------------ genome      ATGGGGTCTTGCTCTGTCACCCAGGCTGGAGTGCTGTGGTATGATCTCGGCTCACTGCAA 180
mRNA        ------------------------------------------------------------ genome      TCTCCACCTCCGAGGTTCCAGCGATTCTCTTGCCTCAGCCTCCCGAGTAGCTGGGACTAC 240
mRNA        ------------------------------------------------------------ genome      AGGCACCCACCATCATACTGGGCTAATTTTTGTGTTTTAGTAGAGATGGGGTTTCCCCA 300
mRNA        ------------------------------------------------------------ genome      TGTTGCCCAGGCTGATCTCAAACTCCTGGGCTTAAGCAATACAGCCGCGTTGGCCTCCCA 360
mRNA        ------------------------------------------------------------ genome      AAGTGTTGGGATTACAAGCATGAGCTACCCCACCCAGCTCATTTTACATTTCCACTTGTT 420
mRNA        ------------------------------------------------------------ genome      AAACTGAAAACTGGCCCGAGAAAGCTTCTGTACTGCCATCCTTGCGTCCTTGCAGATGAA 480
mRNA        ------------------------------------------------------------ genome      TCGTAACCTAGCATAGTAGGTAGGCAGACTGAAAACCTAACTTAGCAGTAGGCTTCTGTA 540
mRNA        ------------------------------------------------------------ genome      ACAACAGCTGTGTCTCAGCCAGTTCCTGCAGCCAGACTTCAACCACTCACAGGCCGCAAA 600
mRNA        ------------------------------------------------------------ genome      CTGTTCAAACTGTGTTCGGAGAAGGCGAATTCATCTGGCTGTTAACGTGCCTCACTTCTG 660
mRNA        ------------------------------------------------------------ genome      CTTTCTGTGGCCACTTTCCCTTTTCTGTCCATAAATTTGCTTTGACCACACAGCATCCCT 720
mRNA        ------------------------------------------------------------ genome      AGAGTCTCCCTGAATCTGCTGTGATTCTGGGACCTGCACCATTTGTGAATTGTTTTTTTT 780
mRNA        ------------------------------------------------------------ genome      TTCCTTGATCAGCTAAACTCTGTTCAATTCAATTTGTTGGAAGTTTTTAACATACCAATG 840
mRNA        ------------------------------------------------------------ genome      GTGCACCAAGGTTCCAATTTCTCCACTTCCTCATAAATAAGTCATTTTAAATGGCTTTTC 900
mRNA        ------------------------------------------------------------ genome      AGTATTCCAATATTTGGAAGTATTAATGTTTCTACCAATTTTCTATTTTTGGACATTGAG 960
mRNA        ------------------------------------------------------------ genome      GTTGTTTCATTTTTTTTCTTTTTTTGAGACAGAGTCTCGCTCCGTCACCCAGGCTGGA 1020
mRNA        ------------------------------------------------------------ genome      GTGCAGTGGCCTGATCCCGGCCCACTGCAACCTCCACCTCCCTCCTCAGCCTCCTGAGTA 1080
mRNA        ------------------------------------------------------------ genome      GCTGGGATTACAGGTGCATGCACCACCACACCCAGCTAATTTTTGTATTTTTAGTAGAGA 1140
mRNA        ------------------------------------------------------------ genome      TGGGGTTTCACCATGTTGGTCAGGCTGGTCTCAAACTCCTGACCTCAGGTGGTCCACCTG 1200
mRNA        ------------------------------------------------------------ genome      CCTTGGCCTCCCAAAATGCTGGGATTACAGGCCTGAGCCACTGCGCCTGGCCTCATCTTC 1260
```

FIG. 1 B

| | | |
|---|---|---|
| mRNA | ------------------------------------------------------------ | |
| genome | TTGATATTAATGTTGCTTTAACATCTTTGTCCCTGTGTTTTTGTTTTTTTTTTGAGAC | 1320 |
| mRNA | ------------------------------------------------------------ | |
| genome | GGAGTCTCATTCATTCTGTCACCCAGGCTGGAGTTCAGTGGCGTGATCTCAGCTCACTGC | 1380 |
| mRNA | ------------------------------------------------------------ | |
| genome | AACCTCTGTCTCCTGGGTTCCAGTGATTCTCCTGCGTCGGTCTCCTGAGTAGCTGTGTTC | 1440 |
| mRNA | ------------------------------------------------------------ | |
| genome | CTGGGTCTTTCGATGGTTATTTAATACTTCCCTACAGTAATGCCCTGTGCGTACATGCTA | 1500 |
| mRNA | ------------------------------------------------------------ | |
| genome | AGTGTGATGAAATGGTTGGCACAGTTAAATCTTTTGAAAGACATTGCCAAGTCACTCTTC | 1560 |
| mRNA | ------------------------------------------------------------ | |
| genome | AGAAAAGTGATAGGAGGTCATAGCAATTTTAAGAAGTCCTCATTTCTACATTTCCTTACT | 1620 |
| mRNA | ------------------------------------------------------------ | |
| genome | AATCTCGGTTGGTGTCTCTTCAATCTTTCCTCACACTTTTCTTGGGTTTTTCCTGAATCA | 1680 |
| mRNA | ------------------------------------------------------------ | |
| genome | TGAGTCTACTACATTTACACATTTTAAAGCATCTTTAGAAACAGGATCTCATTTTGTTGC | 1740 |
| mRNA | ------------------------------------------------------------ | |
| genome | CCAGGCTAGAGTTTGGTGGCATGATTATAGCTCCTCATACTCCTGGGCTCAAGTGATCCT | 1800 |
| mRNA | ------------------------------------------------------------ | |
| genome | TCCACCTCTGAAACCCCAAAATTTGAGAAAGGTCTCATTTAATTTAGAAAGTTTATTTTG | 1860 |
| mRNA | ------------------------------------------------------------ | |
| genome | CCAAGGTTGAGGGTGCACACCTGTGATGATATACGAGTTAAAAGAAATTATTTAGGCAG | 1920 |
| mRNA | ------------------------------------------------------------ | |
| genome | ATACTGAGGGTAAGAAAGTCCTCGGTAAGGTTTTCTTTTCAA<span style="border:1px solid">T</span>GAAAAGCAGCCCCCAAG<br>                                          rs2857936 | 1980 |
| mRNA | ------------------------------------------------------------ | |
| genome | CATTTCTTTTCTAACAAAGAGCAGCCTGTAAAATCGAGCTGCAGACATACACAAGCAAG | 2040 |
| mRNA | ------------------------------------------------------------ | |
| genome | CTGGAAGCTTGCACAGGTGAATGCTGGCAGCTGTGCCAATAAGAAAAGGCTACCTGGGGC | 2100 |
| mRNA | ------------------------------------------------------------ | |
| genome | CAGGCAGATCCAACATGGCGGCTCCATCTTCCCTTTCCTTGTCAACCATGTGCACAGTAA | 2160 |
| mRNA | ------------------------------------------------------------ | |
| genome | GGAGCAGGCAACATAGTGTCCCCCGAGTAGAGACCAATTTGCATAATAAAAGGTGAGGGT | 2220 |
| mRNA | ------------------------------------------------------------ | |
| genome | AGGGTGGGCAGCTTCTTTGCATGCTATGTAAACATTATGCCTGGTCCAACCAATCTTTGG | 2280 |
| mRNA | ------------------------------------------------------------ | |
| genome | GCCCTGTGTAAATTAGACACCACCTCCTCAAGCCTGTCTATAAAACCCTGTCCATTCTGC | 2340 |
| mRNA | ------------------------------------------------------------ | |
| genome | CGCAGGCTGGAAGACCCACTGGGGCACCCCTCTCTCTCTATAGGAGACAGCTATTCATTT | 2400 |
| mRNA | ------------------------------------------------------------ | |
| genome | TTCTCTTTCTTTCACCTATTAAAGCTCCACTCTTAACCCCACTCCGTGTGTATCTATGTT | 2460 |
| mRNA | ------------------------------------------------------------ | |
| genome | CTTGATTTCCTTGGCATGAGGCAATGAACCTTGGGTATTACCCCAGAACCTTGGGTATTA | 2520 |

FIG. 1 C

| | | |
|---|---|---|
| mRNA | ------------------------------------------------------------ | |
| genome | TGCCACTTCAGTGACACAGCCTCAGGAAATCCTGATGACATGTTCCCAAGATGGTCGGGG | 2580 |
| mRNA | ------------------------------------------------------------ | |
| genome | CACAGCTTGGTTTTATACATTTTAGGGAGACATGAGACGTCAATTCATATATGTAAGAAG | 2640 |
| mRNA | ------------------------------------------------------------ | |
| genome | TACATTGGTTCCGTCCAGAAAGGCGGGGACAACTTGAGGCAGGGAGAGAGCTTCTAGGTC | 2700 |
| mRNA | ------------------------------------------------------------ | |
| genome | ACAGGTAGACAAATGGTTGCATTCTTTTGAATCTCCGATAAGCCTTTCCAAAGGAGGCAA | 2760 |
| mRNA | ------------------------------------------------------------ | |
| genome | TCAGAATATGCGTCTATTGACTGGGCGCAGTGGCTCATGCCTGTAATGCCAGCACTTTGG | 2820 |
| mRNA | ------------------------------------------------------------ | |
| genome | GAGGCGGAGGTGGGTGGATCACCTGAGGTCAGGAGTTTGAGAGCAGCCCGGCCAACATGG | 2880 |
| mRNA | ------------------------------------------------------------ | |
| genome | TGAAACCCTGTCTCTACTAAAAATACAAAAAATTAGCTGGGCGTGGTGGCGGGCGCCTGT | 2940 |
| mRNA | ------------------------------------------------------------ | |
| genome | AATCCCAGCTACTCGGGAGGCTGAGGCAGGAGAATAGCTTGAACCCAGAAGGAAGAGGTT | 3000 |
| mRNA | ------------------------------------------------------------ | |
| genome | GCAGTGAGCTGAGATGGTGCCATTGCACTCCAGCCTGGGCAACAAGAGTGAAACTCCATC | 3060 |
| mRNA | ------------------------------------------------------------ | |
| genome | TCAGAAAAAAAAAAAAAAGGCCTGGGCAAAGTGGCTCACGCCTGTAATCCCAGCACTTTG | 3120 |
| mRNA | ------------------------------------------------------------ | |
| genome | GGAAGCCGAGGCGGGCAGGTCACAAAGTCAGGAGATTGAGACCATCCTGGCTAACATGAT | 3180 |
| mRNA | ------------------------------------------------------------ | |
| genome | GAAACCCCATCTCTACTAAAAAATACAAAAAACTAGCTGGGTGTGGTGGCGAGCACCTGT | 3240 |
| mRNA | ------------------------------------------------------------ | |
| genome | AGTCCCAGCTACTCGGCAGGCTGAGGCAGGAGAATGGCGTGAACCGGGGAGGCGGAGCTT | 3300 |
| mRNA | ------------------------------------------------------------ | |
| genome | GCAGTGAGCCGAGATCACACCACTGCACTCCAGCCCGGACGACAGGGCAAGACTCTATCT | 3360 |
| mRNA | ------------------------------------------------------------ | |
| genome | CAAATTAAAAAAAAAAAAAAAAAAAAAAAAAAGAGAGAGAATATGCATCTATCTCAG | 3420 |
| mRNA | ------------------------------------------------------------ | |
| genome | TGAGCAGAAGGATGACTTTGAATGGAATGGGAGCAGTTCCTAGCTTGAACTTCCCCTTTA | 3480 |
| mRNA | ------------------------------------------------------------ | |
| genome | GCTTCAGTGATTTGGGGGCTCAAGGTATGTTCCTTTCACATACCTCAGCCTCCCAAGTAG | 3540 |
| mRNA | ------------------------------------------------------------ | |
| genome | CTGGGACCACAAGTGCATGCCACCACACGTGGCTAATGTTTTATTTTTTTTGTAGGAATA | 3600 |
| mRNA | ------------------------------------------------------------ | |
| genome | GGGTCTCACTATGTGTCCAGGCTGGTCTAAAACCCCTGAGCTCAAATGGTCCTCCCGCCT | 3660 |
| mRNA | ------------------------------------------------------------ | |
| | rs12506200 | |
| genome | CAGCCTCCCGAAATGCTGGGATTACAGGCATGAGCCAGCATGCCCGGCCTAGTCTACATT | 3720 |
| mRNA | ------------------------------------------------------------ | |

FIG. 1 D

| | | |
|---|---|---|
| genome | TTTATAAATTGCTAATTCAAAGTTCCCTCTCCAAAACCTCATGGTTTTCCCTGTTCTCAT | 3780 |
| mRNA | ------------------------------------------------------------ | |
| genome | CCCCTGCACCCTCCCTTCCCCTGGAGTACTCACCTGGCCTTGGAGGTCTGGTGTGAGCCC | 3840 |
| mRNA | ------------------------------------------------------------ | |
| genome | GGACTTCGATTCTAGGCACAGCATGTGATGAGCGCCCCAGGTCAAACACCTCCCCTCTG | 3900 |
| mRNA | ------------------------------------------------------------ | |
| genome | CGGCCTGTGCTTCACCGCCTTGACAGTGAGAAAGGTCTCCCTTCGGCTCATTCTCGAAGT | 3960 |
| mRNA | ------------------------------------------------------------ | |
| genome | CTCAAACTTCACTTCTCCTGTGCGCTGATTCTGAATTCAGCCCCCGTCCAAGGTCCTGGC | 4020 |
| mRNA | ------------------------------------------------------------ | |
| genome | CCCTTTCTCTTCTGCTTGGCGTGTTGTTCATCACCACTGTGCACTGCTGAGGGTAAGTGC | 4080 |
| mRNA | ------------------------------------------------------------ | |
| genome | GGTTCTCTGGACCTCTGCTTTATCATTAGAACAGACTCTTGCGGTTTCCCACGACATTCC | 4140 |
| mRNA | ------------------------------------------------------------ | |
| genome | TTTCACTTCTCACTTGGAAGATGAGCCGTGAGGAAATCCTGTGTTGTGTGGTATGTGGGC | 4200 |
| mRNA | ------------------------------------------------------------ | |
| genome | TGTGCTTCTGCTTGACTTGAGGGCCAAGCAGCATTGCAAGCCATGGTTTTAAATAAGAAA | 4260 |
| mRNA | ------------------------------------------------------------ | |
| genome | GAACATTTCTAACCTTCATCTTCTAGTAAGGAAACAAGTGGGCTTTAGAGTTCTTGCTCA | 4320 |
| mRNA | ------------------------------------------------------------ | |
| genome | GGAAAGACCTATGTCCCAGTCCAACCGGACCTTTTACTAAAGAGATCTTCCTGATCCTCC | 4380 |
| mRNA | ------------------------------------------------------------ | |
| genome | TCCCCAGGCCAGGGGAGGGGTCCTCCCTGGGGTTGGAGCCTTTAGTAGGGGGTCGGAGAC | 4440 |
| mRNA | ------------------------------------------------------------ | |
| genome | ACGACGTAGCCTTCATGACATTCATAGTCTAGTTACACGATCCCTGTAAGGGTCAGTTGA | 4500 |
| mRNA | ------------------------------------------------------------ | |
| genome | AGTAAGTGCTACAAAGGAAGGGAGGTGCTCAGTGGAGAGGGCTCTCTTTTATGTATTATA | 4560 |
| mRNA | ------------------------------------------------------------ | |
| genome | TTTCTTTCATGGGGAGGGATATGGATCAGGGATCAGCAGAGGTGTTTCAGTCCCGAGGGA | 4620 |
| mRNA | ------------------------------------------------------------ | |
| genome | AAGAAAGTCAGCGTGGCTTGGGAGTTGGGAGCAGCAAGACAGTGGCTCAAGATATCTTAA | 4680 |
| mRNA | ------------------------------------------------------------ | |
| genome | GACTAGTGGAGTACACCTTGCATGTTAAAAGCCTTGCTCAGGGCTGCCTGGTTCTTGTAG | 4740 |
| mRNA | ------------------------------------------------------------ | |
| genome | GACGACAGAGATGGCCTAGCTCTGCATACTGCACCCCCAGGGGCTCAGAACAGTGCAAAT | 4800 |
| mRNA | ------------------------------------------------------------ | |
| genome | GTCAGTCTATCTGTCAGTGGCAGAGCCAGCCTTGGAGCAGGGGTGCAAGGAGGTCTCTGC | 4860 |
| mRNA | ------------------------------------------------------------ | |
| genome | ACTGGCCAGGCATGCAGAACATTCTGTTCAGTAGCACTGGACAGAAGGCCCCATCTAGAT | 4920 |
| mRNA | ------------------------------------------------------------ | |
| genome | GAGACAGAGCTGGTGGGCAGGACAAAGACTCCTGGCAGCTCAAACGGCCTGGCAGATGC | 4980 |
| mRNA | ------------------------------------------------------------ | |

FIG. 1 E

```
genome    TTGGAGAGAGGGGGCTTCTTGAGACAGCACCATTTCTGGGAAGAGAGTCACCTGGGAGGG 5040
mRNA      ------------------------------------------------------------ genome    ATGAGGCCACGCTCCGGCTTGGAGGTGAAGAGAGGGGCTGCTGCAAGAAAGAATTAGAGA 5100
mRNA      ------------------------------------------------------------ genome    CATGCCAGCCTTTGCTGTGTTGCCCAGGCTGGTCATGAACTCTTGGCCTCAAGCAATCTT 5160
mRNA      ------------------------------------------------------------ genome    CCCACCTCAGCCTCCCCAAGCGCTGGGATTATAGACATGAGCCCCCATGCTGGCCAATAA 5220
mRNA      ------------------------------------------------------------ genome    AAGATGATTTTATGGAGGGGATGGTGGTGAAGGTTGTGGGTGGTATGAAATAGTAAGAAA 5280
mRNA      ------------------------------------------------------------ genome    TATATATTGGTCTGCACCCAGTTCCTGCCACAGAGCTCCTAAAATCCTGAGAACTTCCTG 5340
mRNA      ------------------------------------------------------------ genome    GGTGAGCATCTTTTGTTCTAATGAGGTGACTCTTGGTGGCTCCTGGATAGGAGTGAATCA 5400
mRNA      ------------------------------------------------------------ genome    CCAGAAAGATCAAGCCAGAGTTAGAAGCAGAAAGTGCTGGCTATAACACAGGAAAGCTGT 5460
mRNA      ------------------------------------------------------------ genome    AACACAAATAATAAAGTTTTTTTTTTTTTTTTGAGATGGAGCCTCACTCTGTTGCCCAG 5520
mRNA      ------------------------------------------------------------ genome    GCTGGAGTGCAATGGTGCAATCTCAGCTCACTACAAGCTCTGCCTCCCAGGTTCAAGTGA 5580
mRNA      ------------------------------------------------------------ genome    TTCTCCTGCCTCAGCCTCCTGAGCAGTTGGGACTACAGGTGTGTGCCACCACATCTGGCT 5640
mRNA      ------------------------------------------------------------ genome    AATTTTTGTATTTTTAGCAGAGACGGGGTTTCACCATATTAACCAGGCTGGCCTCAAACT 5700
mRNA      ------------------------------------------------------------ genome    CCTTACCTTGTGATCCGCCTGCCTCAGCCTCCCAAAGTGCTGGGATTACAGGCATGAGCC 5760
mRNA      ------------------------------------------------------------ genome    ACCGTGCCTGGCCAAAAGACATTGTTCTTAAAAGAATCAACTAACTAACCAAATAAATAA 5820
mRNA      ------------------------------------------------------------ genome    AAATCTAACCTAATTAAGAAACTAAAAATACACAAAAATTAATTTCAAGGGGAGAAAAAT 5880
mRNA      ------------------------------------------------------------ genome    CATGTAAAGAGAGAAAGATAATGAATACTTTGCAGAAATTTATGAACATAAACATAAAAC 5940
mRNA      ------------------------------------------------------------ genome    TTGGATGAAATGCATTTCTAGGAAAACATAATTTATCAAAACTAACCACAAGTAAAATAG 6000
mRNA      ------------------------------------------------------------ genome    AAGCCTAAATAGGATATTTTCAAGAGAAGAAGTAAAGTTGTCAAAGTGCTACCCTTCAAA 6060
mRNA      ------------------------------------------------------------ genome    AAAACACCAGGCTCAAACAATCTGACATGGGAATGTTAGCACACCTTAGAGAGCAAATAA 6120
mRNA      ------------------------------------------------------------ genome    AACTTTGAATGGGCTTGAAATATTCCAGACTCTAGAAAAACAAAACTTCCCAATTCTTTT 6180
mRNA      ------------------------------------------------------------ genome    TATAAAGCAAGTATAAATTGATACCAAAATCTTATAAAGACCTTATACAAAACTTCATAC 6240
mRNA      ------------------------------------------------------------
```

FIG. 1 F

| | | |
|---|---|---|
| genome | CAATCTCTTTTATGAATACAAAACCCTTAATAAAGTATTACCAGACAGAACCCAACAATA | 6300 |
| mRNA | ------------------------------------------------------------ | |
| genome | CATAAAAATGTCACATCATAACATAGTGGGGTTTATTTCAATAATGCATGGATGGTTCAA | 6360 |
| mRNA | ------------------------------------------------------------ | |
| genome | TACAAGGAAATTCAGTAACACAATATAATAGATCATGTGAATATACCCAAAGAAAAAATA | 6420 |
| mRNA | ------------------------------------------------------------ | |
| genome | GATTATTTTCATAGATGCTGTAAAGGCATTTGACCAAATTCAACACCTACTTTTTAGGTG | 6480 |
| mRNA | ------------------------------------------------------------ | |
| genome | GTCAATAAAATAAATTAGTTACTCCTTCTTTAGCATGATAAAATATATTTATCAGCCCAG | 6540 |
| mRNA | ------------------------------------------------------------ | |
| genome | AAGGCATCATTTTACCCGATAAGGGCACACGCTGGAGGGAATAATGTTAAAATTAGGAAT | 6600 |
| mRNA | ------------------------------------------------------------ | |
| genome | AAGAGGATAGCTAGTTTCTTTCTTCTTTTTTTTTTTGAGACGGAGTCTTGCTCTGTTGC | 6660 |
| mRNA | ------------------------------------------------------------ | |
| genome | CAGGCTGGAGTGCAGTGGTGCAATGTTGGCTCACTGCACGCCCCCCGCCTCCCAGGTTCA | 6720 |
| mRNA | ------------------------------------------------------------ | |
| genome | AGCGATTCTCCTGCCTCAGCCTCCCGAGTAGCTGGGACTACAGGCGCGCACCACCATGCC | 6780 |
| mRNA | ------------------------------------------------------------ | |
| genome | CGGCTAATTTTTTTTTGTATTTTAGTAGAGATGGGGTTTCACCATGTTGGTCAGGCTGGT | 6840 |
| mRNA | ------------------------------------------------------------ | |
| genome | CTTGAACTCCCAACCTCACGTACTGGGATTACCGGTGTGAGCCACCACGCCAGCCCAACT | 6900 |
| mRNA | ------------------------------------------------------------ | |
| genome | ACTTTCAACATTATCCTTAATACTGATGCTTATTGACTTACTATGGGGTTACCTCTAGAT | 6960 |
| mRNA | ------------------------------------------------------------ | |
| genome | AAATCCATAATAAGTTGAAAATATAAGTAAAAAATGCCCTTAATACACCTAACCTACCAA | 7020 |
| mRNA | ------------------------------------------------------------ | |
| genome | ACATCATAGCTGAGCCCAGCCTGCCTTAGCTATGCTCAGACACTGACGTCAGCCTACAAT | 7080 |
| mRNA | ------------------------------------------------------------ | |
| genome | TGGCAAAATCACACAGCAGCACAGTCTACTGCAGAGCATCTGCTGTTTGCCCTTGTGACT | 7140 |
| mRNA | ------------------------------------------------------------ | |
| genome | GCGTGGCTGCCTGGGAGCTTCCCAGCTTCACAAGACAGTATTACGTAGCACATCACTAGC | 7200 |
| mRNA | ------------------------------------------------------------ | |
| genome | CTGGGGAAAGATCAAAGTTGAAAATTTGAAGTGTGGTTTCCATTGAATGTGTACTGCTTT | 7260 |
| mRNA | ------------------------------------------------------------ | |
| genome | TGCACCATCATCAAGTCAAAAAATTTTAGTTGAACCAGCCTAAGTTTGGGACCATCTTTA | 7320 |
| mRNA | ------------------------------------------------------------ | |
| genome | TTTTCAGGAGGAACTTCCATGTACATTGATGACGGACGATAGAATCCGTTTCTATCATCC | 7380 |
| mRNA | ------------------------------------------------------------ | |
| genome | TAATGAACATAATGAATAAATCCAGACAAACATAAACATTAACAGAGTAAGCAGCTTTCG | 7440 |
| mRNA | ------------------------------------------------------------ | |
| genome | GGGCTGGAAGCCAGAAGAGGGTGGGAGCGCAGAGAGAGAGGCCAAACACCAGGGCTGCTT | 7500 |
| mRNA | ------------------------------------------------------------ | |

FIG. 1 G

| | | |
|---|---|---|
| genome | CTGCTTTGCGGGTATTTGCTGATCTGGACAAGGTATCTGGAAGGCTGAGCTAAGCCTCCT | 7560 |
| mRNA | ------------------------------------------------------------ | |
| genome | TTTTTTTTGAGGTGGCGTCTCACTCTGTTGCCAGGCTGGAGTGCAATGGTGCGATCTCAG | 7620 |
| mRNA | ------------------------------------------------------------ | |
| genome | CTCACTGCAACCTCCACCTCCCTGGTTCAAGCGATTCTCCTGCCTCAGCCTCCCGAGTAG | 7680 |
| mRNA | ------------------------------------------------------------ | |
| genome | CTGGGATTACAGGCTCCCGCCACTACACCCAGCTGATTTTTGTAATTTTAGTAGAGACGG | 7740 |
| mRNA | ------------------------------------------------------------ | |
| genome | GGTTTCACCATGTTGGCCAGGATGGTCTCGATCTCTTGACGTCATGATCTGTCCACCTCG | 7800 |
| mRNA | ------------------------------------------------------------ | |
| genome | GCCTCCCAAAGTGCTGGGATTATAGGCGTGACCCACCGTGCCCCGTCTGAGCTAAGCCTC | 7860 |
| mRNA | ------------------------------------------------------------ | |
| genome | TTGAGCATAGGGGACTAAAAATGAAATCTAGCGCATGCCAAGTTTAGGGTCCCAGGCAAT | 7920 |
| mRNA | ------------------------------------------------------------ | |
| genome | TCCTTTCCACTTTGGGGTCCACTTTGGGGTCCACCCCACCCAAGAAGAAGGATGACTTGG | 7980 |
| mRNA | ------------------------------------------------------------ | |
| genome | AAGTAAACCAGCTCTGAAATATGGATGGTCCTCTGGGACCATACCAATCCCTTCATATCA | 8040 |
| mRNA | ------------------------------------------------------------ | |
| genome | ACCACATCCAGTTCCTCAAAACTGGAACTTGGATTAAGATGGCCTAGGACTTCTAGTGTC | 8100 |
| mRNA | ------------------------------------------------------------ | |
| genome | CCAGGAGCCTGGCATTGCAAACAAAAATCCTCTCCGGAAGAAGATAATACCTTAAGCTTC | 8160 |
| mRNA | ------------------------------------------------------------ | |
| genome | AAATGACTCTCTAATAAATTTCAAATACAATGTCCAGCACACAAACACAAATTACCAGGA | 8220 |
| mRNA | ------------------------------------------------------------ | |
| genome | ACGTGATATGAGGCCTGATGGATGGGAATTAGCAGAAACTTCAGGCATGAGAAACATACC | 8280 |
| mRNA | ------------------------------------------------------------ | |
| genome | CTCAGAGGCCTAGAATCTATCTAGTGTCTAGATAATGGAGATATGAAATACAGACACTTA | 8340 |
| mRNA | ------------------------------------------------------------ | |
| genome | AACAACTATGTTTCCCATGTTCAAAGAGGAAATTTGCAAAACTTGAAAGTGTTGGCAGGA | 8400 |
| mRNA | ------------------------------------------------------------ | |
| genome | AATCAGAAACTATAAAATGTGACAACAGCATACTTTAGAGTCAGTATAAATTACGGTCCC | 8460 |
| mRNA | ------------------------------------------------------------ | |
| genome | GAAAACTGCAGAATTCCAGAACTTAATGGTAAAGCAAGGGTTTAACAGCAGAATAGAAAT | 8520 |
| mRNA | ------------------------------------------------------------ | |
| genome | AGCCAGAGAGAACTAGGAAGTAAGTCAGATGACACTACCCAGAATAAGGCACTGAGAGGC | 8580 |
| mRNA | ------------------------------------------------------------ | |
| genome | CAAGGAATGGAAAATGCAGAAGAAAGGATATGGTGAGAGGATCTAATATACATTTATTTG | 8640 |
| mRNA | ------------------------------------------------------------ | |
| genome | GAGTACCAGGGAGAGAGAGAAGGAGAAGAACAGAAGCCGTGTTTCAAGGACGGTGACTGA | 8700 |
| mRNA | ------------------------------------------------------------ | |
| genome | GAGGCTTCGAAACTGATGAAAGCCATCAGTTCACAAATTCAAAGCCCAGTGAATTCCAAG | 8760 |
| mRNA | ------------------------------------------------------------ | |

FIG. 1 H

| | | |
|---|---|---|
| genome | GAGAAAAAAAGAAATCCATACTGTGAAAGCAAGTCCAGACAATGACAAACACCATCAACA | 8820 |
| mRNA | ------------------------------------------------------------ | |
| genome | ATACACAGGACAGGCATAAGATGCATTTAATGGGGACACTCAGAGGCAGAGGGTTATCAG | 8880 |
| mRNA | ------------------------------------------------------------ | |
| genome | AAGGAGGCACTTCTCTCCCAAGTTCTCATCATCCCAGGGCCAGGGACAGCTGGTCACACC | 8940 |
| mRNA | ------------------------------------------------------------ | |
| genome | TTAGGGAGTTCACTAGGAGAGGGATCTGGCTTCTTGTCATTCTGGGTATTTGTAGGGAAA | 9000 |
| mRNA | ------------------------------------------------------------ | |
| genome | TTGGAAGGGAACCGAGAGCACCTAGCCAATCGCATAGCAATGGGAGATTTCAGGCTGTGG | 9060 |
| mRNA | ------------------------------------------------------------ | |
| genome | GGAATGTCTTTGCTGGTGAAAAGAACATCCTGACCTTAGAAATCTTTCACCGAGGGGAT | 9120 |
| mRNA | ------------------------------------------------------------ | |
| genome | CTGCGTTCCAGAACTTCTGGAGCTGGTATAGGTAAGGCTTTGAGCTTTCCTACTGAGCCA | 9180 |
| mRNA | ------------------------------------------------------------ | |
| genome | GCCTGTTGCTAGGTTACCAAAGGGGACCTCGAGGGCCATCTGGCCAACAAGCAGACTTGT | 9240 |
| mRNA | ------------------------------------------------------------ | |
| genome | CTCTCCTTACACCCCCAGACGTATCACTGCAAAACTACAGAAAACCAAAGACAGAGAAAA | 9300 |
| mRNA | ------------------------------------------------------------ | |
| genome | TCTTAAAAGCAGCCAGATTTAAAAAATGGCATATTAGTTTCAAAGCAGCAGCCATGAAAT | 9360 |
| mRNA | ------------------------------------------------------------ | |
| genome | TGACAGCTGATGTCTCAACAGCAAGAATGAAAAGTGGAAGACAGGCCAGGTGTGGTGGCT | 9420 |
| mRNA | ------------------------------------------------------------ | |
| genome | CAGGCCTGTAATCCCAGCACTTTGGGAGGCCGAGGCGGGTGGATCACGAGGTCAGGAGAC | 9480 |
| mRNA | ------------------------------------------------------------ | |
| genome | CAAGACCATCCTGGCTAACATGGTGAAACCCCGTCTCTACTAAAAATACAAAAAAATTAG | 9540 |
| mRNA | ------------------------------------------------------------ | |
| genome | TCGGGCATGGTGGTGGGTGCCTGTAGTCCCAGCTACTCGGGAGGCTGAGGCAGGAGAATG | 9600 |
| mRNA | ------------------------------------------------------------ | |
| genome | GCGTGAACCCGGGAGGCGGAGCTTGCAGTGAGCCGAGATTGTGCCACTGCACTCCAGCCT | 9660 |
| mRNA | ------------------------------------------------------------ | |
| genome | GGGTGACAGAGCAAGACTCTGTCTCAAAAAAAAAAAAAAAAAAAAAAAAAAGGGTGAC | 9720 |
| mRNA | ------------------------------------------------------------ | |
| genome | GAAGCTTCAATCTCCTGAAAGGAAGCAACTGCCGCCTTTGATTCGATACCCACCAAAATC | 9780 |
| mRNA | ------------------------------------------------------------ | |
| genome | CGTGAAGAAGGAAGGCAAAATAAAAACACTTCCTGATTGAACTGGAAAGATTTCCGCAAT | 9840 |
| mRNA | ------------------------------------------------------------ | |
| genome | AGAAGACCCACTGTCCAAGGAATTCTAAAGGATGCTTTCCAGGCAGAAGAAAATGACCCC | 9900 |
| mRNA | ------------------------------------------------------------ | |
| genome | AGAGGAAGATCAGAGATTCAGGAAAGAAATGGAGAGTGATAAAAATGGAAAATTCGGGGG | 9960 |
| mRNA | ------------------------------------------------------------ | |
| genome | CCAATTTAAACAAAAGCTGACTGCTCTACAACTGTTGTGTCTCTATCTTTTGTAACATAT | 10020 |
| mRNA | ------------------------------------------------------------ | |
| genome | ATGTGTGTGTAGCTTTTTTTTTTTTTTTGTCAAGATGGATTCTCACTCTGTCGCCCAGG | 10080 |

FIG. 1 I

| | | |
|---|---|---|
| mRNA | ------------------------------------------------------------ | |
| genome | CTACAGTGAAATGGCACGGTCTCGGCTCACTGCAACCTCTGCCCCTTGGGCTCAAATGAT | 10140 |
| mRNA | ------------------------------------------------------------ | |
| genome | TCTCTTGCCTCAGCCTCCTGAGTAGCTGAGATTACAGGTGCCTGGCACAATGCCTGGCTA | 10200 |
| mRNA | ------------------------------------------------------------ | |
| genome | ATTTTTGTATTTTTACTAGAGATGGGATTTCTCCATGTTGGCCAGGCTGGTCTTGAACAC | 10260 |
| mRNA | ------------------------------------------------------------ | |
| genome | CTGACCTCAGGTGATCCACCTGCCTGGGCCTCCCAAAGTGCTAGGATTACAGGCGCGAGC | 10320 |
| mRNA | ------------------------------------------------------------ | |
| genome | CACTGCATCTGGCCTATGTGTGTGTTTATATGGAATTAAAACACATGGCAATAATACCCT | 10380 |
| mRNA | ------------------------------------------------------------ | |
| genome | CCAAATTGGGAGAAACCAAAAATAGCATTTAAATGTTGTAAGCTCCCTGCATAATCAAGA | 10440 |
| mRNA | ------------------------------------------------------------ | |
| genome | AGAGAATAGATTTACGTTAGATTTTGATACCTGGAGGATGAATGTTGTAATTTCTAGGGT | 10500 |
| mRNA | ------------------------------------------------------------ | |
| genome | GACCATGAAAAGAGGAGACAACGGTGTATGTTTTTTTTTTTTGAGATGGAGTCTCACTT | 10560 |
| mRNA | ------------------------------------------------------------ | |
| genome | TGTCACCCAGGCTGGAGTGTTGTGGTGTGATCTTGGCTCACTGCAACCTCCTCCTCTTGG | 10620 |
| mRNA | ------------------------------------------------------------ | |
| genome | GTTCAGGCCATCCTCCCACCTAGGCCTCCAGAGTAGGTGGGATCACAGGCACCTGCCACC | 10680 |
| mRNA | ------------------------------------------------------------ | |
| genome | ACACCTGGCTAATTTTTTTTTTTTTAAATATTTAGTAGAGATGGGGTTTCACCATGTT | 10740 |
| mRNA | ------------------------------------------------------------ | |
| genome | GGCCAGGCTGGTCTTGAACTCCTGACCTCAGGCGATCTGCCTACCTCTGCCTCTCAAAGT | 10800 |
| mRNA | ------------------------------------------------------------ | |
| genome | GCTGGGATTACAGGTGTGAGCCATCGCGCCCGGCCAACAGTGATCACTTTCAAACTAACA | 10860 |
| mRNA | ------------------------------------------------------------ | |
| genome | GAGGTTCAAAAATAAAATCAGACTTAACCAAAAACCAGGTAACAGAGCTGGTAGGATATA | 10920 |
| mRNA | ------------------------------------------------------------ | |
| genome | CAGAAAGACTGACCTCACGTATATCAACGATTACAGTTAATATTAATGAAGGAAATGCTC | 10980 |
| mRNA | ------------------------------------------------------------ | |
| genome | TAGTTTAAAAACGAGGGTTGTCAAAGACCCCACATAAGAAGCTCCTTACCAGCGGTGCAC | 11040 |
| mRNA | ------------------------------------------------------------ | |
| genome | CTAGAACCTAAGGAAACAGGACAGATGAAGGAGGACGCGCCCCCGCCGCTGTCCTGCGCC | 11100 |
| mRNA | ------------------------------------------------------------ | |
| genome | TCAGCCATCCTATGAGACGGGAAAGGTTTCTGTCTGCAGCTGGGCCCGTGCTCTTTACCA | 11160 |
| mRNA | ------------------------------------------------------------ | |
| genome | GCTCCTGGCTTTCTTCTCTGGAAGGTTCCTGCCTGTTTTGCCCTCACACCTGCTCCTCTC | 11220 |
| mRNA | ------------------------------------------------------------ | |
| genome | TCAGCCCTCTCAGGGGTGGGGCTGGAGGCCACCAAAGAGCCTCCTCTGCTCTCCAGTTGC | 11280 |
| mRNA | ------------------------------------------------------------ | |
| genome | TCGACTGCTCCTCATTTCCCCCTGGGGTCTGCGTCAGGGTTTCCTTCTTTTCCAGCCCCA | 11340 |

FIG. 1J

```
mRNA       ------------------------------------------------------------
genome     CCCCGCGTGCATCCCACCTGGTCTCGGGTCGGGGCTGCTCCCGCTTACTGCCCCCTGCCC 11400
mRNA       ------------------------------------------------------------
genome     AGGCTGGTGTGCACCCCCTCTGGCTGCTTTCAAGGCCTCTTCTCTCTTCTCGGCAGGACA 11460
mRNA       ------------------------------------------------------------
genome     GGCACAGGCAGGTGGCCAGGTGTCATGCTTAGCTCCCCGCCCAGTGAGATTCTTTCATTT 11520
mRNA       ------------------------------------------------------------
genome     AACAATCTTCCCCTGAATAGTTCATGTTCATTGCTGAAAATTTGAAAAATATGGAAAAGC 11580
mRNA       ------------------------------------------------------------
genome     ACAAAGATTAAGATATAAACCGCCCTCAATTCCCCTGCCCAGAGAGAGTCACTGCTATGA 11640
mRNA       ------------------------------------------------------------
genome     CTTGGTGACTAGGAACCTTATTTCTCTCTCGCTCTTTTTTTTTTTTGAGACAGAGTCT 11700
mRNA       ------------------------------------------------------------
genome     TGCTCTGTCACCCAGGCTGGAGTGCAGTGGCTCGATCTCAGCTCACTGCAACCTCCGCCT 11760
mRNA       ------------------------------------------------------------
genome     CCTGGGTTCAAGCGATTCTCCTGCCTCAGCCTCTTGAGTAGCTGGGATTACAGGCACCTG 11820
mRNA       ------------------------------------------------------------
genome     CCACCATGCCCGGCTAATTTTTGTATTTTTAGTTGAGAGAGGGTTTCATCTTGTTGGTCA 11880
mRNA       ------------------------------------------------------------
genome     GGCGGACTTGAACTCCTGACCTCAGGTGATCAGCCCACCTCGGCCTCCCAAAGTGCTGGG 11940
mRNA       ------------------------------------------------------------
genome     ATTACAGGTGTGAGCCACTGCGCCTTCATCTCTCTTCTGTGTATGTGTACGCTGTTTTTT 12000
mRNA       ------------------------------------------------------------
genome     CTTTAGAATGGGGGACGTTATCAGGCTCTACATGGTGTGTAGTCGGCTAGCATGTTGTAA 12060
mRNA       ------------------------------------------------------------
genome     GCCTTTCCCTGTGTCACAAGTGCTCATCTGGAACAGGATTCTAATGACTGCCTGTGGCTA 12120
mRNA       ------------------------------------------------------------
genome     TGTTGGGATTCCTTTAACTCAGCTCCTTCTGCCCAGCATCTATCTTTTTTCCATCTTTTG 12180
mRNA       ------------------------------------------------------------
genome     TCCTAAGTGTTGCTATAATAAATCATTGATCACACATGCCTGACTGTTTGCATAGGATAA 12240
mRNA       ------------------------------------------------------------
genome     ATTACGGGAAATGTTTTGCTGTTCAGGGACTGTGCCCATTTTTAGGCCTCAGAGACACC 12300
mRNA       ------------------------------------------------------------
genome     ATGCCAGACTGCCCAGTATTGATCTTTACTCTTTTTAGATGATGCCAAACTTTTCTGTGA 12360
mRNA       ------------------------------------------------------------
genome     ACTTTAAAAACCTGTGTCTTGACAGTCCATTTCTGTAAGTCTTTCACATTAGATTTCCTG 12420
mRNA       ------------------------------------------------------------
genome     TCAGGATGATAGTCAATTCTAGGCAGATGATGTTTTCTCAGCCATGGCTGAAGCAGTTGT 12480
mRNA       ------------------------------------------------------------
genome     GATTTGTTGTGGCCATGTAAAGTCCCGATGATCCATTGCCTCCCTGGATGGGTTGGAATA 12540
mRNA       ------------------------------------------------------------
genome     ATTTGGTTTGGGAGCATATAACAGAATGACCTGGAGTCACAGCAGCTCAGACGGAAGTGT 12600
```

FIG. 1 K

| | | |
|---|---|---|
| mRNA | ------------------------------------------------------------ | |
| genome | ATTTCTCCCTTACAGATGAAAGAATTCCAGGCCAGGCTGGAATGACAACTGCACACAGTC | 12660 |
| mRNA | ------------------------------------------------------------ | |
| genome | ATCTGGGCCCCCTCCTTCCAGCTCCCATCACCCCAGGATGTGGCTTTTATGCAGATGATC | 12720 |
| mRNA | ------------------------------------------------------------ | |
| genome | CAAAATGGCTGCTCAAGTCCCAGCCAACACATCCCATTCCAGGGAGCAGGAAAAAGGTGT | 12780 |
| mRNA | ------------------------------------------------------------ | |
| genome | GTCTTTCCCTTCATTTTATGTGATTCCTTTCTAGAAGTACTACTCATTACTTCTGCTTGC | 12840 |
| mRNA | ------------------------------------------------------------ | |
| genome | ATCTCCCTGGCTAGCACTTACTTAGTTATATGGCCATAGCTAGCTGAAGGAAGGACAGGG | 12900 |
| mRNA | ------------------------------------------------------------ | |
| genome | ACTGTCATACACTAGCTAAGAGGCAAACTGCTTAGATAAAAAGGTCTCTAAAGAAGGTCA | 12960 |
| mRNA | ------------------------------------------------------------ | |
| genome | GAGCGGCTGCTAGGGTGCAACTCTATTACTTATTGTTATGGGACGAACTGTGTCCCTCAT | 13020 |
| mRNA | ------------------------------------------------------------ | |
| genome | TCAGGTTGATGTCCTAAGCCCCAGAACCTCAGAATGGGATTGTATTTGGAGACAGGTTCT | 13080 |
| mRNA | ------------------------------------------------------------ | |
| genome | TTAAGGAGGTAAGGAGGCTAAAATGAGATCATTAGGGTGGGCCATAATCCGACTGATGTC | 13140 |
| mRNA | ------------------------------------------------------------ | |
| genome | TTACAAGAAGAGATTAGGACACGGACATGCTCAGAGGGACGGCCACGTGAGGACACCAAG | 13200 |
| mRNA | ------------------------------------------------------------ | |
| genome | AAAGGCAGCTGTCTGCAAGTCAAGGACAGGGCTCAGGGGAAACCAACCTTGCCAACACCT | 13260 |
| mRNA | ------------------------------------------------------------ | |
| genome | TCATCTCGGACTTCTAGCCTCTAGGACCATGAGAAGATACATTTCTGTTGTTTAAGCTGC | 13320 |
| mRNA | ------------------------------------------------------------ | |
| genome | CCGGTCTGTGGTACTTTGTTATGGCAGCCCAAGTAAACAAATACAGTCATCTGCTGCTGG | 13380 |
| mRNA | ------------------------------------------------------------ | |
| genome | AACAAATCACCCCAGCACTGTGGCTTGGCAGCACACATGTCTAGTCATAGAGTTATATGT | 13440 |
| mRNA | ------------------------------------------------------------ | |
| genome | AGTTACGTGTAGAGCCATATGTATCGTCACACGTTCTGTGGGTCAGGAATTTGGACCCAG | 13500 |
| mRNA | ------------------------------------------------------------ | |
| genome | CTTAACCAGCTCCACTTCTCGCCAGGGTTCAGTCAAATACCAGCTGCCTCCCACCTGAGA | 13560 |
| mRNA | ------------------------------------------------------------ | |
| genome | GCTCAGCCGGGGAAGGGTCCCTTTCCAATCTCACGTGGTGTTGGCAGGATCCAGTTCCTC | 13620 |
| mRNA | ------------------------------------------------------------ | |
| genome | ATGGCCTGCTGGACTGAGAACCTCAGTTCTCACTGCCTGTTGGCCAGAGGCCGCCTTTAT | 13680 |
| mRNA | ------------------------------------------------------------ | |
| genome | GTCCTCGCCATGTGGGCCTCTCCAACATGGCAGCTGACTTCATCAGAGCATCCATGCCAA | 13740 |
| mRNA | ------------------------------------------------------------ | |
| genome | GAAGGCAACAGAGAGGGCCAGGGAGACTGAAGTCATACCCTTTTGCGACCTAGTCATGGG | 13800 |
| mRNA | ------------------------------------------------------------ | |
| genome | GTGACATTCCATCACCTTTGCCCATTGGTTAGAAGCAGGCCACCAGGTACAGCCCAAGCT | 13860 |

FIG. 1 L

| | | |
|---|---|---|
| mRNA | ------------------------------------------------------------ | |
| genome | CACGGGGAGGGGTCATACAAGGGTGTCAATACCAGGAGGTGAGGGGTGCTGGGGCCATCT | 13920 |
| mRNA | ------------------------------------------------------------ | |
| genome | TATGAGTCTGCCCACTGAGGTAACTAACAACCTTGAGGCCTGACACAGTGGACAAAGGCC | 13980 |
| mRNA | ------------------------------------------------------------ | |
| genome | CTTATTAACAGCAGAGAACTGGGAACTTTATTTATTTATTTATTTTTGAGACAGAGTCTC | 14040 |
| mRNA | ------------------------------------------------------------ | |
| genome | ACTCTTGTCACCCAGGCTGGAGTGCAATGGCATGATCTTGGCTCACTGCAACCTCCACCT | 14100 |
| mRNA | ------------------------------------------------------------ | |
| genome | CCCAGGTTCAAGCAATTCTGCCTCAGCCTCCGGAATAGCTGGGACTACAGGCATGCACCA | 14160 |
| mRNA | ------------------------------------------------------------ | |
| genome | CTACACCCGGCTAATTTTTGTATTTTTAGTAGAGACAGGGTTTCGCCATGTTGGCCAGGC | 14220 |
| mRNA | ------------------------------------------------------------ | |
| genome | TGGTCTCGAACTCCTGACCTCTGGTGATCTGCCTGCCTTGGCCTCCCAAAGTGCTGGGAT | 14280 |
| mRNA | ------------------------------------------------------------ | |
| genome | TACAGGCGTGAGCCACCGCACCTCGCTGGAACTTAATTTTTTTAGAGACAGTGTCGCTCT | 14340 |
| mRNA | ------------------------------------------------------------ | |
| genome | ATCACCCAAGCTGGAGTGCAGTGGTGCAATCCTAGCTCACTTGCAGCCTCAAATTCCTGG | 14400 |
| mRNA | ------------------------------------------------------------ rs762855 | |
| genome | GTTCAGGTGATCCTCCCACATCAGCCTCCCAAGAACTGGGAACTAACAGCTGTTTCTCTG | 14460 |
| mRNA | ------------------------------------------------------------ | |
| genome | CTGTCCTTCTCAAGAAAAGGGAGGCTACTGCTACCCCACTGGGGACAATGCTGGGTTTCC | 14520 |
| mRNA | ------------------------------------------------------------ | |
| genome | CTTTAGGACAGGCTCTGAGACAAGGCGGAGGTGCTGTTTGTGGCCACAGAGCAGGGGACT | 14580 |
| mRNA | ------------------------------------------------------------ | |
| genome | CTGGGTTGCAGGTGTGGCCTGGCTAAAGTAGGCTTTACTGGGCTCCTCTCTGCCTGCATC | 14640 |
| mRNA | ------------------------------------------------------------ | |
| genome | ACCCCCCGGCTGGGCGGTTGTCTCTGAGGCCAACCTTACTCCCTGCTGGGCAGGCTGGAC | 14700 |
| mRNA | ------------------------------------------------------------ | |
| genome | AGCTGCCCTCTCCGTTTGCCCCTCTACCACCCAAAAGGCAGGAGGCTCTGGAGACCAGGA | 14760 |
| mRNA | ------------------------------------------------------------ | |
| genome | CCCTGCCCGCCACGGCCTGTGTCCCAGGCGTGAGGGGGTGCCCCACAGACCTCTGCTGAG | 14820 |
| mRNA | ------------------------------------------------------------ | |
| genome | CTGCTGCTGAATGACGCCCCTTGGGGGTCCTGCCGGAAGGTCAGAGCAGGGGTGCACTCC | 14880 |
| mRNA | ------------------------------------------------------------ | |
| genome | CATAAAGAAACGCCCCCAGGTCGGGACTCATTCCTGTGGGCGGCATCTTGTGGCCATAGC | 14940 |
| mRNA | ------------------------------------------------------------ | |
| genome | TGCTTCTCGCTGCACTAATCACAGTGCCTCTGTGGGCAGCAGGCGCTGACCACCCAGGCC | 15000 |
| mRNA | ------------------------------------------------------------ | |
| genome | TGCCCCAGACCCTCTCCTCCCTTCCGGGGCGCTGCGCTGGGACCGATGGGGGGCGCCAGG | 15060 |
| mRNA | ------------------------------------------------------------ | |
| genome | CCTGTGGACACCGCCCTGCAGGGGCCTCTCCAGCTCACTGGGGGTGGGGTGGGGGTCACA | 15120 |

FIG. 1 M

| | | |
|---|---|---|
| mRNA | ------------------------------------------------------------ | |
| genome | CTTGGGGTCCTCAGGTCGTGCCGACCACGCGCATTCTCTGCGCTCTGCGCAGGAGCTCGC | 15180 |
| mRNA | ------------------------------------------------------------ | |
| genome | CCACCCTCTCCCCGTGCAGAGAGCCCCGCAGCTGGCTCCCCGCAGGGCTGTCCGGGTGAG | 15240 |
| mRNA | ------------------------------------------------------------ | |
| genome | TATGGCTCTGGCCACGGGCCAGTGTGGCGGGAGGGCAAACCCCAAGGCCACCTCGGCTCA | 15300 |
| mRNA | ------------------------------------------------------------ | |
| genome | GAGTCCACGGCCGGCTGTCGCCCCGCTCCAGGCGTCGGCGGGGGATCCTTTCCGCATGGG | 15360 |
| mRNA | ------------------------------------------------------------ | |
| genome | CCTGCGCCCGCGCTCGGCGCCCCCTCCACGGCCCCGCCCCGTCCATGGCCCCGTCCTTCA | 15420 |
| mRNA | ------------------------------------------------------------ | |
| genome | TGGGCGAGCCCCTCCATGGCCCTGCCCCTCCGCGCCCCACCCCTCCCTCGCCCCACCTCT | 15480 |
| mRNA | ------------------------------------------------------------ | |
| genome | CACCTTCCTGCCCCGCCCCCAGCCTCCCCACCCCTCACCGGCCAGTCCCCTCCCCTATCC | 15540 |
| mRNA | ------------------------------------------------------------ | |
| genome | CGCTCCGCCCCTCAGCCGCCCCGCCCCTCAGCCGGCCTGCCTAATGTCCCCGTCCCCAGC | 15600 |
| mRNA | ------------------------------------------------------------ | |
| genome | ATCGCCCCGCCCCGCCCCCGTCTCGCCCCGCCCCTCAGGCGGCCTCCCTGCTGTGCCCCG | 15660 |
| mRNA | ------------------------------------------------------------ | |
| genome | CCCCGGCCTCGCCACGCCCCTACCTCACCACGCCCCCCGCATCGCCACGCCCCCCGCATC | 15720 |
| mRNA | ------------------------------------------------------------ | |
| genome | GCCACGCCTCCCTTACCATGCAGTCCCGCCCCGTCCCTTCCTCGTCCCGCCTCGCCGCGA | 15780 |
| mRNA | ------------------------------------------------------------ | |
| genome | CACTTCACACACAGCTTCGCCTCACCCCATTACAGTCTCACCACGCCCCGTCCCCTCTCC | 15840 |
| mRNA | ------------------------------------------------------------ | |
| genome | GTTGAGCCCCGCGCCTTCGCCCGGGTGGGGCGCTGCGCTGTCAGCGGCCTTGCTGTGTGA | 15900 |
| mRNA | ------------------------------------------------------------ | |
| genome | GGCAGAACCTGCGGGGGCAGGGGCGGGCTGGTTCCCTGGCCAGCCATTGGCAGAGTCCGC | 15960 |
| mRNA | ------------------------------------------------------------ | |
| genome | AGGCTAGGGCTGTCAATCATGCTGGCCGGCGTGGCCCCGCCTCCGCCGGCGCGGCCCCGC | 16020 |
| mRNA | ------------------------------------------------------------ | |
| genome | CTCCGCCGGCGCAGCGTCTGGGACGCAAGGCGCCGTGGGGGCTGCCGGGACGGGTCCAAG | 16080 |
| mRNA | ------------------------------------------------------------ | |
| genome | ATGGACGGCCGCTCAGGTTCTGCTTTTACCTGCGGCCCAGAGCCCCATTCATTGCCCCGG | 16140 |
| mRNA | ------------------------------------------------------------ | |
| genome | TGCTGAGCGGCGCCGCGAGTCGGCCCGAGGCCTCCGGGGACTGCCGTGCCGGGCGGGAGA | 16200 |
| mRNA | ------------------------------------------------------------ | |
| genome | CCGCCATGGCGACCCTGGAAAAGCTGATGAAGGCCTTCGAGTCCCTCAAGTCCTTCCAGC | 16260 |
| mRNA | ------------------------------------------------------------ | |
| genome | AGCAGCAGCAGCAGCAGCAGCAGCAGCAGCAGCAGCAGCAGCAGCAGCAGCAACAGCAGC | 16320 |
| mRNA | ------------------------------------------------------------ | |
| genome | CGCCACCGCCGCCGCCGCCGCCGCCTCCTCAGCTTCCTCAGCCGCCGCCGCAGGCAC | 16380 |

FIG. 1 N

| | | |
|---|---|---|
| mRNA | ------------------------------------------------------------ | |
| genome | AGCCGCTGCTGCCTCAGCCGCAGCCGCCCCCGCCGCCGCCCCCGCCGCCACCCGGCCCGG | 16440 |
| mRNA | ------------------------------------------------------------ | |
| genome | CTGTGGCTGAGGAGCCGCTGCACCGACCGTGAGTTTGGGCCCGCTGCAGCTCCCTGTCCC | 16500 |
| mRNA | ------------------------------------------------------------ | |
| genome | GGCGGGTCCCAGGCTACGGCGGGGATGGCGGTAACCCTGCAGCCTGCGGGCCGGCGACAC | 16560 |
| mRNA | ------------------------------------------------------------ | |
| genome | GAACCCCCGGCCCCGCAGAGACAGAGTGACCCAGCAACCCAGAGCCCATGAGGGACACCC | 16620 |
| mRNA | ------------------------------------------------------------ | |
| genome | GCCCCCTCCTGGGGCGAGGCCTTCCCCCACTTCAGCCCCGCTCCCTCACTTGGGTCTTCC | 16680 |
| mRNA | ------------------------------------------------------------ | |
| genome | CTTGTCCTCTCGCGAGGGGAGGCAGAGCCTTGTTGGGGCCTGTCCTGAATTCACCGAGGG | 16740 |
| mRNA | ------------------------------------------------------------ | |
| genome | GAGTCACGGCCTCAGCCCTCTCGCCCTTCGCAGGATGCGAAGAGTTGGGGCGAGAACTTG | 16800 |
| mRNA | ------------------------------------------------------------ | |
| genome | TTTCTTTTTATTTGCGAGAAACCAGGGCGGGGGTTCTTTTAACTGCGTTGTGAAGAGAAC | 16860 |
| mRNA | ------------------------------------------------------------ | |
| genome | TTGGAGGAGCCGAGATTTGCTCAGTGCCACTTCCCTCTTCTAGTCTGAGAGGGAAGAGGG | 16920 |
| mRNA | ------------------------------------------------------------ | |
| genome | CTGGGGGCGCGGGACACTTCGAGAGGAGGCGGGGTTTGGAGCTGGAGAGATGTGGGGGCA | 16980 |
| mRNA | ------------------------------------------------------------ | |
| genome | GTGGATGACATAATGCTTTTAGGACGCCTCGGCGGGAGTGGCGGGGCAGGGGGGGGCGG | 17040 |
| mRNA | ------------------------------------------------------------ | |
| genome | GGAGTGAGGGCGCGTCCAATGGGAGATTTCTTTTCCTAGTGGCACTTAAAACAGCCTGAG | 17100 |
| mRNA | ------------------------------------------------------------ | |
| genome | ATTTGAGGCTCTTCCTACATTGTCAGGACATTTCATTTAGTTCATGATCACGGTGGTAGT | 17160 |
| mRNA | ------------------------------------------------------------ | |
| genome | AACACGATTTTAAGCACCACCTAAGAGATCTGCTCATCTAAGCCTAAGTTGGTCTGCAGG | 17220 |
| mRNA | ------------------------------------------------------------ | |
| genome | CGTTTGAATGAGTTGTGGTTGCCAAGTAAAGTGGTGAACTTACGTGGTGATTAATGAAAT | 17280 |
| mRNA | ------------------------------------------------------------ | |
| genome | TATCTTAAATATTAGGAAGAGTTGATTGAAGTTTTTGCCTATGTGTGTTGGGAATAAAA | 17340 |
| mRNA | ------------------------------------------------------------ | |
| genome | CCAACACGTTGCTGATGGGGAGGTTAATTGCCGAGGGATGAATGAGGTGTACATTTTACC | 17400 |
| mRNA | ------------------------------------------------------------ | |
| genome | AGTATTCCAGTCAGGCTTGCCAGAATACGGGGGGTCCGCAGACTCCGTGGGCATCTCAGA | 17460 |
| mRNA | ------------------------------------------------------------ | |
| genome | TGTGCCAGTGAAAGGGTTTCTGTTTGCTTCATTGCTGACAGCTTGTTACTTTTTGGAAGC | 17520 |
| mRNA | ------------------------------------------------------------ | |
| genome | TAGGGGTTTCTGTTGCTTGTTCTTGGGGAGAATTTTTGAAACAGGAAAAGAGAGACCATT | 17580 |
| mRNA | ------------------------------------------------------------ | |
| genome | AAAACATCTAGCGGAACCCCAGGACTTTCCCTGGAAGTCTGTGTGTCGAGTGTACAGTAG | 17640 |

FIG. 1 O

| | | |
|---|---|---|
| mRNA | ------------------------------------------------------------ | |
| genome | GAGTTAGGAAGTACTCTGGTGCAGTTCAGGCCTTTCTCTTACCTCTCAGTATTCTATTTC | 17700 |
| mRNA | ------------------------------------------------------------ | |
| genome | CGATCTGGATGTGTCCCAGATGGCATTTGGTAAGAATATCTCTGTTAAGACTGATTAATT | 17760 |
| mRNA | ------------------------------------------------------------ | |
| genome | TTTAGTAATATTTCTTGTTCTTTGTTTCTGTTATGATCCTTGTCTCGTCTTCAAAGTTTA | 17820 |
| mRNA | ------------------------------------------------------------ | |
| genome | ATTAGAAAATGATTCGGAGAGCAGTGTTAGCTTATTTGTTGGAATAAAATTTAGGAATAA | 17880 |
| mRNA | ------------------------------------------------------------ | |
| genome | ATTATTCTAAAGGATGGAAAAACTTTTTGGATATTTGGAGAAATTTTAAAACAATTTGGC | 17940 |
| mRNA | ------------------------------------------------------------ | |
| genome | TTATCTCTTCAGTAAGTAATTTCTCATCCAGAAATTTACTGTAGTGCTTTTCTAGGAGGT | 18000 |
| mRNA | ------------------------------------------------------------ | |
| genome | AGGTGTCATAAAAGTTCACACATTGCATGTATCTTGTGTAAACACTAAACAGGGCTCCTG | 18060 |
| mRNA | ------------------------------------------------------------ | |
| genome | ATGGGAAGGAAGACCTTTCTGCTGGGCTGCTTCAGACACTTGATCATTCTAAAAATATGC | 18120 |
| mRNA | ------------------------------------------------------------ | |
| genome | CTTCTCTTTCTTATGCTGATTTGACAGAACCTGCATTTGCTTATCTTCAAAATATGGGTA | 18180 |
| mRNA | ------------------------------------------------------------ | |
| genome | TCAAGAAATTTCCTTTGCTGCCTTGACAAAGGAGATAGATTTTGTTTCATTACTTTAAGG | 18240 |
| mRNA | ------------------------------------------------------------ | |
| genome | TAATATATGATTACCTTATTTAAAAAATTTAATCAGGACTGGCAAGGTGGCTTACACCTT | 18300 |
| mRNA | ------------------------------------------------------------ | |
| genome | TAATCCGAGCACTTTGGGAGGCCTAGGTGGACGAATCACCTGAGGTCAGGAGTTTGAGAC | 18360 |
| mRNA | ------------------------------------------------------------ | |
| genome | CAGCCTGGCTAACATGGTGAAACCCTGTCTCTACTAAAAATACAAAAATTAGCTGGTCAT | 18420 |
| mRNA | ------------------------------------------------------------ | |
| genome | GGTGGCACGTGCCTGTAATCCAAGCTACCTGGGAGGCTGAGGCAGGAAAATCGCTTGAAC | 18480 |
| mRNA | ------------------------------------------------------------ | |
| genome | CCGGGAGGCAGAGTCTGCAGTGAGTTGAGATCACGCCACTGCACTCCAGCCTGGGTGACA | 18540 |
| mRNA | ------------------------------------------------------------ | |
| genome | GAGCGAGACTCTATCTCAAAAAAAATTTTTTTTAATGTATTATTTTTGCATAAGTAATAC | 18600 |
| mRNA | ------------------------------------------------------------ | |
| genome | ATTGACATGATACAAATTCTGTAATTACAAAAGGGCAATAATTAAAATATCTTCCTTCCA | 18660 |
| mRNA | ------------------------------------------------------------ | |
| genome | CCCCTTTCCTCTGAGTACCTAACTTTGTCCCCAAGAACAAGCACTATTTCAGTTCCTCAT | 18720 |
| mRNA | ------------------------------------------------------------ | |
| genome | GTATCCTGCCAGATATAACCTGTTCATATTGTAAGATAGATTTAAAATGCTCTAAAAACA | 18780 |
| mRNA | ------------------------------------------------------------ | |
| genome | AAAGTAGTTTAGAATAATATATATCTATATATTTTTTGAGATGTAGTCTCACATTGTCAC | 18840 |
| mRNA | ------------------------------------------------------------ | |
| genome | CCAGGCTGGAGTGCAGTGATACAATCTCGGCTCACTGCAGTCTCTGCCTCCCAGGTTCAA | 18900 |

FIG. 1 P

```
mRNA        ------------------------------------------------------------
genome      ATGCTTCTCCTGCCTCAGCCTTCTGAGTAGCTGGGATTACAGGCGCCCACCACCATGTCC  18960
mRNA        ------------------------------------------------------------ genome      AGCTAATTTTTGTATTTTTAGTAGAGATGGGGTTTCACCATGTTGGCCAGGCTGGTCTTG  19020
mRNA        ------------------------------------------------------------ genome      AACTCCTGACCTTGTGATCTGTCCACCTCGGCCTCCCAAAGTGCTGGGATTACAGGTGTG  19080
mRNA        ------------------------------------------------------------ genome      AGCCACCATGCCTGGCTAGAATAATAACTTTTAAAGGTTCTTAGCATGCTCTGAAATCAA  19140
mRNA        ------------------------------------------------------------ genome      CTGCATTAGGTTTATTTATAGTTTTATAGTTATTTTAAATAAAATGCATATTTGTCATAT  19200
mRNA        ------------------------------------------------------------ genome      TTCTCTGTATTTTGCTGTTGAGAAAGGAGGTATTCACTAATTTTGAGTAACAAACACTGC  19260
mRNA        ------------------------------------------------------------ genome      TCACAAAGTTTGGATTTTGGCAGTTCTGTTCACGTGCTTCAGCCAAAAAATCCTCTTCTC  19320
mRNA        ------------------------------------------------------------ genome      AAAGTAAGATTGATGAAAGCAATTTAGAAAGTATCTGTTCTGTTTTTATGGCTCTTGCTC  19380
mRNA        ------------------------------------------------------------ genome      TTTGGTGTGGAACTGTGGTGTCACGCCATGCATGGGCCTCAGTTTATGAGTGTTTGTGCT  19440
mRNA        ------------------------------------------------------------ genome      CTGCTCAGCATACAGGATGCAGGAGTTCCTTATGGGGCTGGCTGCAGGCTCAGCAAATCT  19500
mRNA        ------------------------------------------------------------ genome      AGCATGCTTGGGAGGGTCCTCACAGTAATTAGGAGGCAATTAATACTTGCTTCTGGCAGT  19560
mRNA        ------------------------------------------------------------ genome      TTCTTATTCTCCTTCAGATTCCTATCTGGTGTTTCCCTGACTTTATTCATTCATCAGTAA  19620
mRNA        ------------------------------------------------------------ genome      ATATTTACTAAACATGTACTATGTGCCTGGCACTGTTATAGGTGCAGGGCTCAGCAGTGA  19680
mRNA        ------------------------------------------------------------ genome      GCAGACAAAGCTCTGCCCTCGTGAAGCTTTCATTCTAATGAAGGACATAGACAGTAAGCA  19740
mRNA        ------------------------------------------------------------ genome      AGATAGATAAGTAAAATATACAGTACGTTAATACGTGGAGGAACTTCAAAGCAGGGAAGG  19800
mRNA        ------------------------------------------------------------
                                             rs3856973
genome      GGATAGGGAAATGTCAGGGTTAATCGAGTGTTAACTTATTTTTATTTTTAAAAAAATTGT  19860
mRNA        ------------------------------------------------------------ genome      TAAGGGCTTTCCAGCAAAACCCAGAAAGCCTGCTAGACAAATTCCAAAAGAGCTGTAGCA  19920
mRNA        ------------------------------------------------------------ genome      CTAAGTGTTGACATTTTTATTTTATTTTGTTTTGTTTTGTTTTTTTGAGACAGTTCTTG  19980
mRNA        ------------------------------------------------------------ genome      CTCTATCAGCCAGGCTGGAGTGCACTAGTGTGATCTTGGCTCACTGCAACCTCTGCCTCT  20040
mRNA        ------------------------------------------------------------ genome      TGGGTTCAAGTGATTCTCATGCCTCAGCCTCCTGTTTAGCTGGGATTATAGACATGCACT  20100
mRNA        ------------------------------------------------------------ genome      GCCATGCCTGGGTAATTTTTTTTTTTCCCCCGAGACGGAGTCTTGCTCTGTCGCCCAGG  20160
```

FIG. 1 Q

```
mRNA       ------------------------------------------------------------
genome     CTGGAGTGCAGTGGCGCGATCTCAGCTCACTGCAAGCTCCGCTTCCCGAGTTCACGCCAT 20220
mRNA       ------------------------------------------------------------
genome     TCTCCTGCCTCAGTCTCCCAAGTAGCTGGGACTACAGGCGCCTGCCACCACGTCCAGCTA 20280
mRNA       ------------------------------------------------------------
genome     ATTTTTTTGTATTTTTAATAGAGACGGGGTTTCACCGTGTTAGCCAGGATGATCTTGATC 20340
mRNA       ------------------------------------------------------------
genome     TCCTGACCTCGTCATCCGCCGACCTTGTGATCCGCCCACCTCGGCCTCCCAAAGTGCTGG 20400
mRNA       ------------------------------------------------------------
genome     GATTACAGGCATGAGCCACTGTGCCCGGCCACGCCTGGGTAATTTTTGTATTTTTAGTAG 20460
mRNA       ------------------------------------------------------------
genome     AGATGGGGTTTTGCCATGATGAGCAGGCTGGTCTCGAACTCCCGGCCTCATGTGATCTGC 20520
mRNA       ------------------------------------------------------------
genome     CTGCCTTGGCCTCCCAAAGTGCTAGGATTACAGGCATGAGCCACCATACCTGGCCAGTGT 20580
mRNA       ------------------------------------------------------------
genome     TGATATTTTAAATACGGTGTTCAGGGAAGGTCCACTGAGAAGACAGCTTTTTTTTTTTTT 20640
mRNA       ------------------------------------------------------------
genome     TTTTTGGGGTTGGGGGGCAAGGTCTTGCTCTTTAACCCAGGCTGGAATGCAGTATCACT 20700
mRNA       ------------------------------------------------------------
genome     ATCGTAGCTCACTTCAGCCTTGAACTCCTGGGCTCAAGTGATCCTCCCACCTCAACCTCA 20760
mRNA       ------------------------------------------------------------
genome     CAATGTGTTGGGACTATAGGTGTGAGCCATCACACCTGGCCAGATGATGGCTTTTGAGTA 20820
mRNA       ------------------------------------------------------------
genome     AAGACCTCAAGCGAGTTAAGAGTCTAGTGTAAGGGTGTATGAAGTAGTGGTATTCCAGAT 20880
mRNA       ------------------------------------------------------------
genome     GGGGGGAACAGGTCCAAAATCTTCCTGTTTCAGGAATAGCAAGGATGTCATTTTAGTTGG 20940
mRNA       ------------------------------------------------------------
genome     GTGAATTGAGTGAGGGGGACATTTGTAGTAAGAAGTAAGGTCCAAGAGGTCAAGGGAGTG 21000
mRNA       ------------------------------------------------------------
genome     CCATATCAGACCAATACTACTTGCCTTGTAGATGGAATAAAGATATTGGCATTTATGTGA 21060
mRNA       ------------------------------------------------------------
genome     GTGAGATGGGATGTCACTGGAGGATTAGAGCAGAGGAGTAGCATGATCTGAATTTCAATC 21120
mRNA       ------------------------------------------------------------
genome     TTAAGTGAACTCTGGCTGACAACAGAGTGAAGGGGAACACCGGCAAAAGCAGAAACCAGT 21180
mRNA       ------------------------------------------------------------
genome     TAGGAAGCCACTGCAGTGCTCAGATAAGCATGGTGGGTTCTGTCAGGGTACCGGCTGTCG 21240
mRNA       ------------------------------------------------------------
genome     GCTGTGGGCAGTGTGAGGAATGACTGACTGGATTTTGAATGCGGAACCAACTGCACTTGT 21300
mRNA       ------------------------------------------------------------
genome     TGAACTCTGCTAAGTATAACAATTTAGCAGTAGCTTGCGTTATCAGGTTTGTATTCAGCT 21360
mRNA       ------------------------------------------------------------
genome     GCAAGTAACAGAAAATCCTGCTGCAATAGCTTAAACTGGTAACAAGCAAGAGCTTATCAG 21420
```

FIG. 1 R

```
mRNA      ------------------------------------------------------------
genome    AAGACAAAAATAAGTCTGGGGAAATTCAACAATAAGTTAAGGAACCCAGGCTCTTTCTTT  21480
mRNA      ------------------------------------------------------------
genome    TTTTTTTTTTTGAAACGGAGTTTCGCTCTTGTCACCCGGGCTGGAGTGCAATGATGTGAT  21540
mRNA      ------------------------------------------------------------
genome    CTCAGCTCACTAAAACCTCTACCTCCTGGGTTCAAGTGATTCTTCTGCCTCAGCCTCCCA  21600
mRNA      ------------------------------------------------------------
genome    AGTAACTGGGATTACAGGCGTATACCACCATGCCCAGCTAATTTTTGTGTTTTTAGTAGA  21660
mRNA      ------------------------------------------------------------
genome    GATGGGGTTTCACCATGTTGGCCAGGCTGGTCTCGAACTTCTGACCTCAGGTGATCCACT  21720
mRNA      ------------------------------------------------------------
genome    CGCCTCAGCCTGCCAAAGTGCTGGGATTACAGGTTTGGGCCACTGCACCCGGTCAGAACC  21780
mRNA      ------------------------------------------------------------
genome    CAGGCTCTTTCTTATACTTACCTTGCAAACCCTTGTTCTCATTTTTTCCCTTTGTATTTT  21840
mRNA      ------------------------------------------------------------
genome    TATTGTTGAATTGTAATAGTTCTTTATATATTCTGGATACTGGATTCTTATCAGATAGAT  21900
mRNA      ------------------------------------------------------------
genome    GATTTGTAAAAACTCTCCCTTCCTTTGGATTGTCTTTTTACTTTCTTGATAGTGTCTTTT  21960
mRNA      ------------------------------------------------------------
genome    GAAGTGTAAAAGTTTTTAATTTTGATGAAGTCGAGTTTATCTATTTTGTCTTTGGTTGCT  22020
mRNA      ------------------------------------------------------------
genome    GTGCTTCAAGTGTCATATCTAAGAAATCATTGTCTAATCCAAAGTCAAAAAGGTTTACTC  22080
mRNA      ------------------------------------------------------------
genome    CTATGTTTTCTTCTAAGAATTTTAGAGTTTTACATTTAAGTCTGATCCATTTTGAGTTAA  22140
mRNA      ------------------------------------------------------------
genome    TTTTTATATATGGTTCAGGTAGAAGTCCAACTTTATTCTTTTCCATGTGGTTATTCAGTT  22200
mRNA      ------------------------------------------------------------
genome    GTCCCAGCACTGTTTGTTGAAGAGACTATTCTTTCCCCATGGAATTATCTTAGTACCCTT  22260
mRNA      ------------------------------------------------------------
genome    GTTGAAAATTAATCGTCCTTAATTGTATAAATTTATTTCTAGACTGTCAGTTCTACCTGT  22320
mRNA      ------------------------------------------------------------
genome    TGGTCTTTATGTCGATCCTGTGCCAGTACCATACAGTCTTGATTACTGAAGTTTGTGTCA  22380
mRNA      ------------------------------------------------------------
genome    CAGTTTAAATTCATGAAATGTGAGTTCTCCAACTTTGTTCCTTTTCAAGATTGATTTGGC  22440
mRNA      ------------------------------------------------------------
genome    CATGCTGGGTCCCTTGCATTTCCGTACGAATTGTAGGATCAGCTTGTCAGTTTCAACAAA  22500
mRNA      ------------------------------------------------------------
genome    GAAGCCAAGTAGGATTCTGAGAGGGATTGTGTTGAATCTGTAGATCAACTTGGGGAGTAT  22560
mRNA      ------------------------------------------------------------
genome    TCGCATCTTAACAATATTGTCTTCCACCTATGAACATGGGCAAACTTTGTGTAAATGGTC  22620
mRNA      ------------------------------------------------------------
genome    AGATTGTAAGTATTTCGGGCTGTGTGGGCACAGTGTCTCTGTCACAGCTACGCGGCTCTG  22680
```

FIG. 1 S

| | | |
|---|---|---|
| mRNA | ------------------------------------------------------------ | |
| genome | CCATTGTAGCATGAAAGTAGCCATAAGCAATATGTATGAGTGTCTGTGTTCCAATAGAAT | 22740 |
| mRNA | ------------------------------------------------------------ | |
| genome | TTTATTAATGACAAGGAAGTTTGAATTTCATATAATTTTCACCTGTCATGAGATAGTATT | 22800 |
| mRNA | ------------------------------------------------------------ | |
| genome | TGATTATTTTGGTCAACCATTTAAAAATGTAAAAACATTTCTTAGCTTGTGAACTAGCCA | 22860 |
| mRNA | ------------------------------------------------------------ | |
| genome | AAAATATGCAGGTTATAGTTTTCCCACTCCTAGGTTAAAATATGATAGGACCACATTTGG | 22920 |
| mRNA | ------------------------------------------------------------ | |
| genome | AAAGCATTTCTTTTTTTTTTTTTTTTTTTTTTTGAGACGGAGTTTCACTCTTGTTGCC | 22980 |
| mRNA | ------------------------------------------------------------ | |
| genome | CAGGCTGGAGTGCAGTGGCGCGATCTCGGCTCACTGCAACCTCTGCCTCCCAGGTTCAAG | 23040 |
| mRNA | ------------------------------------------------------------ | |
| genome | ACATTCTCCTGCACGGCCTCCCTAGTAGCTGGGATTACAGGCATGCGCCACCACACCCAG | 23100 |
| mRNA | ------------------------------------------------------------ | |
| genome | CTAATTTTGTATTTTTAGTAGAGACGGGGTTTCTCCATGTTGGTCAGGCTGGTCTTGAAC | 23160 |
| mRNA | ------------------------------------------------------------ | |
| genome | TCCTGACCTCAGGTGATCCACCCGCCTCAGCCTCCCAAAGTGCTGGGATTACAGGGTGTG | 23220 |
| mRNA | ------------------------------------------------------------ | |
| genome | AGCCACCACACCCTGCTGGAAAGCATTTCTTTTTTGGCTGTTTTTGTTTTTTTTTAAAC | 23280 |
| mRNA | ------------------------------------------------------------ | |
| genome | TAGTTTTGAAAATTATAAAAGTTACACATATACATTATAAAAATATCTTCAAGCAGCACA | 23340 |
| mRNA | ------------------------------------------------------------ | |
| genome | GATGAAAAACAAAGCCCTTCTTGCAAGTCTGTCATCTTTGTCTAACTTCCTAAGAACAAA | 23400 |
| mRNA | ------------------------------------------------------------ | |
| genome | AGTGTTTCTTGTGTCTTCTTCCCAGATTTTAATATGCATATACAAGCATTTAAATGTGTC | 23460 |
| mRNA | ------------------------------------------------------------ | |
| genome | ATTTTTTGTTTGCTTGACTGAGATCACATTACATATGTATTTTTTACTTAACAATGTGT | 23520 |
| mRNA | ------------------------------------------------------------ | |
| genome | CATAGATATTGTTCCATAGCAGTACCTGTAATTCTTATTAATTGCTATGTAATATTTTAG | 23580 |
| mRNA | ------------------------------------------------------------ | |
| genome | AATTTCTTTTTAAAAGAGGACTTTTGGAGATGTAAAGGCAAAGGTCTCACATTTTTGTGG | 23640 |
| mRNA | ------------------------------------------------------------ | |
| genome | CTGTAGAATGTGCTGGTGACATATTCTCTCTACCTTGAGAAGTCCCCATCCCCATCACCT | 23700 |
| mRNA | ------------------------------------------------------------ | |
| genome | CCATTTCCTGTAAATAAGTCAACCACTTGATAAACTACCTTTGAATGGATCCACACTCAA | 23760 |
| mRNA | ------------------------------------------------------------ | |
| genome | AACATTTAGTCTTATTCAGACAACAAGGAGGAAAAATAAAATACCTTATAAAGCACTGTT | 23820 |
| mRNA | ------------------------------------------------------------ | |
| genome | TAATATTGTATTAAATTGGATCAATTTGGGGGCTAGAATGTATGTTAGAGACATGATATG | 23880 |
| mRNA | ------------------------------------------------------------ | |
| genome | TCCATAGGTCCTTGCTATCACAGTGAGGTCTCAGGGACAGTCGTTTGGTATCATTTGGGA | 23940 |

FIG. 1 T

| | | |
|---|---|---|
| mRNA | ------------------------------------------------------------ | |
| genome | TCTCATAAGCAGACTCTCTCTGCTTGACCTGACAAATCAGAGTCTGTGTTTTAACAGGTT | 24000 |
| mRNA | ------------------------------------------------------------ | |
| genome | CAGTGAGTGACTTACATGCACATTGGAGTTTGGGAAGCTCCACTGTAGGTGCTTAGACCT | 24060 |
| mRNA | ------------------------------------------------------------ | |
| genome | TACCTTTGTTGTTGCTAATAACAATGCAAGCATTTGGGAGGAAGACCTGTGTTGCTCATA | 24120 |
| mRNA | ------------------------------------------------------------ | |
| genome | TGTGTCCAGGTGTAGCTGAGGTGGCCTTGCTTATCTGCTGTAGGGCCGTTGAGCATTTCT | 24180 |
| mRNA | ------------------------------------------------------------ | |
| genome | GTAGCTGTGATGAGTGAGCTGAGGTGAGCCTGCGGAGAGCTCCCAGCCATTGGTAGTGGG | 24240 |
| mRNA | ------------------------------------------------------------ | |
| genome | ACTCGCTTAGATGAACTGGAAGGACCCTTTCATCTGAGCAGCCACTATGGAGAAAAACAA | 24300 |
| mRNA | ------------------------------------------------------------ | |
| genome | CCGAATGAGGGAGAGACAATGTGCAATTTTATTTAGGGCACAAAGGAGAGCTGTGGTTA | 24360 |
| mRNA | ------------------------------------------------------------ | |
| genome | GAAGGTGACATTTGAGTGGAAAGGGGGCAAGCCATGTGTATAGCGGGAGAAGAGAGGTCC | 24420 |
| mRNA | ------------------------------------------------------------ | |
| genome | AGGCAGAGTTAACAGAAGGCAGAAATGCTTTCCATGTTTGAGAACCAGTAAGGAGGCCAG | 24480 |
| mRNA | ------------------------------------------------------------ | |
| genome | TGGCTGAAGTAAGGTGAAGGGCAGAAATAAGGATGAGGCTGCGAGAGATGAGAGGTTAGA | 24540 |
| mRNA | ------------------------------------------------------------ | |
| genome | GACGAGCGTCTTGTGCACCAAGATAAGCTTGTGTGGTCAAAACAAGTAGTTTAATTTATG | 24600 |
| mRNA | ------------------------------------------------------------ | |
| genome | TTTTTAAAAGATCATTTTGGCTGGGCACAATGGTTCATGCCTGTAATACCAGTAGTTTGA | 24660 |
| mRNA | ------------------------------------------------------------ | |
| genome | GACGGTGTGGTGGGAGGATTGCCTGAGGCCAGACGACCAGCATAGCCAACATAGCAGCAC | 24720 |
| mRNA | ------------------------------------------------------------ | |
| genome | CTATAAGGTCTCTACAAAAAACTTTAAAAAATTAGCTGGGCATAGTGGTGTGTGCCTGTA | 24780 |
| mRNA | ------------------------------------------------------------ | |
| genome | GTCCCAGCTACTCAGGAGGCTGAGGAGGCTGGAGGATTGCTTGAGTCCAGGAGTTTGAGG | 24840 |
| mRNA | ------------------------------------------------------------ | |
| genome | CTGCAGTGAGCTATGATTATGCCACTACACTACAACCTGGGCAAGAGAGTGAGACCCTGT | 24900 |
| mRNA | ------------------------------------------------------------ | |
| genome | CTCTAAATATACACACACACACACACACACACACACACACACACACACACACACACACAC | 24960 |
| mRNA | ------------------------------------------------------------ | |
| genome | ACACACATATATATGTATATATATGCATTTAGATGAAAAGATCACTTTGACAATACCACA | 25020 |
| mRNA | ------------------------------------------------------------ | |
| genome | TGCTGGTGAGGATTTAGAAAAACTAGGTCACTTATTGCTGGTGGGAATATAATATAGTAC | 25080 |
| mRNA | ------------------------------------------------------------ | |
| genome | GGCCACTCTGGAAAACAGTTTGGCAGTTTGTCATAAAACTGAACATACCGTTAGTATACA | 25140 |
| mRNA | ------------------------------------------------------------ | |
| genome | GCCCAGCAGCAACTACAATCCTGGGCATTAATCCTAGAGAAATGAAACCTTAATGTTCAC | 25200 |

FIG. 1 U

| | | |
|---|---|---|
| mRNA | ------------------------------------------------------------ | |
| genome | ATAAAAACCTATACTCAAGTATGCATAGCAGCTTTACCCATAATATCTAAGAACTGGAAT | 25260 |
| mRNA | ------------------------------------------------------------ | |
| genome | CAGCTCAGATGTCCTTCAACAGGTGAATGGTTAAACTACTCAGTAATAAAAAGGAATGAG | 25320 |
| mRNA | ------------------------------------------------------------ | |
| genome | CTACTGATAGCATGCAACAGTTTAGGTGAAGTTATGCTAATGAAAAAAGCCAATCCCAAA | 25380 |
| mRNA | ------------------------------------------------------------ | |
| genome | AGGTTATACATACTGTATGATTCTATGTTTTTTTGCAATGGCACAGTTTTAGGGATGGAG | 25440 |
| mRNA | ------------------------------------------------------------ | |
| genome | AATAGATTAGTGGTTGCCTGGGGTTAGAGATGGGGTAGTAGAGTAGGTTAGTGGTGGCAG | 25500 |
| mRNA | ------------------------------------------------------------ | |
| genome | AGGAGAGAAAAGAGAGGGAGGTGAATGTGGTTATAAAAGGACAACACAGGGGAATACTTG | 25560 |
| mRNA | ------------------------------------------------------------ | |
| genome | TAATGGAAATGCTTTGTCTTTTTTTTTTTTTTTTTTTTGGCGACAGAGTCTTGCTCT | 25620 |
| mRNA | ------------------------------------------------------------ | |
| genome | GTTGCCCAGGCTGGAGTGCAGTGGCATGATCTTTTCTCACTGCAACCTCTGCCTCCTGGG | 25680 |
| mRNA | ------------------------------------------------------------ | |
| genome | TTCAAGTGATACTTGTGTCTCAGTCTCCCATGTTCAGAGTGAAACAAACCAGAGGTAATG | 25740 |
| mRNA | ------------------------------------------------------------ | |
| genome | TTCATCCAAATAATCCAACACACATGACATTAAAACATCAAGATCAGGTCGGACGTGGTG | 25800 |
| mRNA | ------------------------------------------------------------ | |
| genome | GCTCATGCCTGTAATCCCAGCACTTTTGGGAGGCCAAGGTGGGCAGATCACTTGAGGTCA | 25860 |
| mRNA | ------------------------------------------------------------ | |
| genome | GGAGTTCGAGACCAGCCGGGCCAACATGATGAAACCCCATCTTGACTAAAAATACAAAAA | 25920 |
| mRNA | ------------------------------------------------------------ | |
| genome | TTAGCCGGGCATGGTGGTGTGCACCTGTAGTCCCAGCTACTTGGGAGGCTGAGGCAAGAG | 25980 |
| mRNA | ------------------------------------------------------------ | |
| genome | AACTGCTTGAACCCGAGGGGCAGAGGTTGCAGTGAGCTGAGAGTGCGCCATTGCACTTCA | 26040 |
| mRNA | ------------------------------------------------------------ | |
| genome | GCCTGTGTGACAGAGTAAGACTCCATCTCCAAAAAAAAAAAAACCAAGATCAATTAAAATA | 26100 |
| mRNA | ------------------------------------------------------------ | |
| genome | CAGCATTACTGGGCCGGGTGTGGTGGCTCACACCTGTAATCCCAGCACTTTGGGAGGCCG | 26160 |
| mRNA | ------------------------------------------------------------ | |
| genome | AGATGGGCAGATCACGAGGTCAGGAGATCCAGACCATCCCGGCTAACACGGTGAAACCCC | 26220 |
| mRNA | ------------------------------------------------------------ | |
| genome | GTCTCTACTAAAAAATACAAAAAATTAGCCGGGTATAGTGGTGGGTGCCTGTAGTCCCAG | 26280 |
| mRNA | ------------------------------------------------------------ | |
| genome | CTACTTGGGAGGCTGAAGCAGGAGAATGGTGTGAACCCGGGAGGCAGAGCTGGCAGTGAG | 26340 |
| mRNA | ------------------------------------------------------------ | |
| genome | CTGAGATCGCGCCACTGCACTCCAGCCTGGGCGACAGAGCAAGACTCCGTCTCGGGGGAA | 26400 |
| mRNA | ------------------------------------------------------------ | |
| genome | AAAAAAAAATAAATAAATAGAATGCTGTAGTGTCCTTGAGTTTACATGCCCCTCCTTACG | 26460 |

FIG. 1 V

| | | |
|---|---|---|
| mRNA | ------------------------------------------------------------ | |
| genome | CTTGTGTGCCCGTGCAGATTGCTTGATTACACAATTAGAGGAGGCTGGCGGAGGATTGTT | 26520 |
| mRNA | ------------------------------------------------------------ | |
| genome | TTAATTTTTTTTTTTTGAGACAGTCTGGCTCTGTTCCCCAGGCTAGAGTGCAATGGCGC | 26580 |
| mRNA | ------------------------------------------------------------ | |
| genome | AATCTTGGTGCACTGCAACCTCTGCCTCCTGGGTTCAAGCAGTTCTTCTGCCGCAGCCTC | 26640 |
| mRNA | ------------------------------------------------------------ | |
| genome | CCGAGTAGCTGGGATTATAGGCGCCCGCCACCACGCCCAACTATTTTTGTATTTTTAGT | 26700 |
| mRNA | ------------------------------------------------------------ | |
| genome | AGAGCAGCGTTTCACCATGCTGGCCAGGCTGGTCTCGAACTCCTGACCTCAGATGATCTG | 26760 |
| mRNA | ------------------------------------------------------------ | |
| genome | CTGCCCCAGCCTCCCAAAGTGCTGGGATTACAGGCGTGAGCCACACCTGGCCGTTTGTTT | 26820 |
| mRNA | ------------------------------------------------------------ | |
| genome | TAATTTTGAAGGTGAAGTGAAAGTGACTACATTTACCAAAAGTGATTGAAAAGCCAGGAC | 26880 |
| mRNA | ------------------------------------------------------------ | |
| genome | TGTTCTTACCCTGTTTTTCCAGTTCTTGCTCAGAGCAAGGTGGTTTCTTTTTCACTTAAT | 26940 |
| mRNA | ------------------------------------------------------------ | |
| genome | CACCATACTTACTTTTCATGTAGAACAAGTCAGTTTGAGTTATCAGTTCATCATCTTAAC | 27000 |
| mRNA | ------------------------------------------------------------ | |
| genome | TAAATTCCATGGGGGAAGGAATTAGTTTTAGTTTCTTAAACTTCCAGGTTTGCTTATTGG | 27060 |
| mRNA | ------------------------------------------------------------ | |
| genome | ACAAAATGAGATAGCAAGGCAGTGTTTTAAGTTAGATTTTTATTTCTTTGGTAATACA | 27120 |
| mRNA | ------------------------------------------------------------ | |
| genome | ATTTTCTCAGAAACTTAGTAGTCTTTTAGTTTAGTTGTTTTAGTTGGTCCTATGTTTTG | 27180 |
| mRNA | ------------------------------------------------------------ | |
| genome | GATCACCCCTCTCTACTTTATTTTGATAGTGCCAACTGTGAAGACATCTGAAGCCATAGG | 27240 |
| mRNA | ------------------------------------------------------------ | |
| genome | TTTGGATGGGAAGGAGGCATCTTTAGCCTGATCATCTTCGCCAGGCTGTTTATCTCCTTT | 27300 |
| mRNA | ------------------------------------------------------------ | |
| genome | TGCTTGGCTGAGAAGTCTTAATAGGAGGCTTATTCCCAGCTATTTGGGGACATAGAAGCA | 27360 |
| mRNA | ------------------------------------------------------------ | |
| genome | GTTAGCCATTGCTTATATTTTACTGAGGTCTGTGTGGTATGTTGATTGTAGTCAGTTAAC | 27420 |
| mRNA | ------------------------------------------------------------ | |
| genome | GATTTTGAGAACTGAAGGCAGCCTGGTATATATAGAGTAGGTATTAGACTGTGTTTCTTC | 27480 |
| mRNA | ------------------------------------------------------------ | |
| genome | TAATTGAATTTCCCATCTCTTGTAATCTATGCCATCATCTTCTGTACTGCTGAGAAAGAA | 27540 |
| mRNA | ------------------------------------------------------------ | |
| genome | AGAAAGTTTCTAATCAAACTATACCACTGGTTGTAAGATGCAGTTTGGCTTTAGTGATGT | 27600 |
| mRNA | ------------------------------------------------------------ | |
| genome | TAACACATGATTCAAACGTGAAATTGATTGAGTATTGGTGAAATACAGAGGAGATTTAAA | 27660 |
| mRNA | ------------------------------------------------------------ | |
| genome | GCCAGAAGACCTGGGTTTAAATGCTGGCTGTATGACTTCATATCTGTGTGATCTTGGGCA | 27720 |

FIG. 1 W

| | |
|---|---|
| mRNA | ------------------------------------------------------------ |
| genome | TGTCATGGTTGGCACTTCAATTTCTTCTCTCTATAATGGGGGAAGTGAGGCCAGTCATGG 27780 |
| mRNA | ------------------------------------------------------------ |
| genome | TGGCTCATACCTATAATCCCAGTGCTTTGGGAGGCCAAGATGGGAAGATCGCTTGAGGCC 27840 |
| mRNA | ------------------------------------------------------------ |
| genome | AGGAGTTTGAGCAATTGGGCAACATCGTGAGGCCCCGTCTCTACAAAATATTTTGAAAAA 27900 |
| mRNA | ------------------------------------------------------------ |
| genome | ATTAGCCAGGCCCAGTGGTGCGTGCCTGTGGTCCGCGCCACTCAGGAGGCTGAGACGGGA 27960 |
| mRNA | ------------------------------------------------------------ |
| genome | GGATCCTTTCAGCCTAGGAGTTTAAGGCTAAAGTGAGCCATGATTGTGCTATCGTACTCC 28020 |
| mRNA | ------------------------------------------------------------ |
| genome | AGCCTGGGCAGCAGAGCAAGATCCTGACTCTAAAAAAAAGTAAAATAAAGTAAAATGGGG 28080 |
| mRNA | ------------------------------------------------------------ |
| genome | GAAATGAACTGCTTTAGTAACATCATCTGTTTTTTCTGTGAGCAGCGTAGCTTGACAGCC 28140 |
| mRNA | ------------------------------------------------------------ |
| genome | ATTGGTGAACTCGTGCCCTGTGCTTCCCTGTCCAGATCCCCATTCTGCCCGCAACATGGA 28200 |
| mRNA | ------------------------------------------------------------ |
| genome | GTATAACGGTTTATTCATAGTAGTCGAGAAACACTCACTGAATGAATGAATGAGGTGTAG 28260 |
| mRNA | ------------------------------------------------------------ |
| genome | AACTAAGTGGAGTGGGTAATTCAACACATATTAATTTCCTTCTTTTTTTTATTTTTAGAA 28320 |
| mRNA | ------------------------------------------------------------ |
| genome | AGAAAGAACTTTCAGCTACCAAGAAAGACCGTGTGAATCATTGTCTGACAATATGTGAAA 28380 |
| mRNA | ------------------------------------------------------------ |
| genome | ACATAGTGGCACAGTCTGTCAGGTAATTGCACTTTGAACTGTCTAGAGAAAATAAGAACT 28440 |
| mRNA | ------------------------------------------------------------ |
| genome | TTGTATATTTTCAGTCTTAATGGGCTAGAATATTCTTTGTGTCCCAGCTATTTTAAATGG 28500 |
| mRNA | ------------------------------------------------------------ |
| genome | ATTCAGAAATCCATTTAAGATGAAGAAGGACCCTTTTCCCATATTTCTGGCTATATACAA 28560 |
| mRNA | ------------------------------------------------------------ |
| genome | GGATATCCAGACACTGAAATGAATAATGTTCCCTTTTTGTAATCTTTTATGCAAAAATTA 28620 |
| mRNA | ------------------------------------------------------------ |
| genome | AAACCATTATGGTAATTGAACAACATGTTTATGTTTAGTTAACACCCTTAGCAACTATAG 28680 |
| mRNA | ------------------------------------------------------------ |
| genome | TTATTTTAAAACCATCTATGGTTTGATATTTTTGCATTTGTTGCAATAGTAGGAACAGCA 28740 |
| mRNA | ------------------------------------------------------------ |
| genome | CAAGACAGTTCAGTTTGTCTCTCTTATTTGCTTTTTCTTGGCAGTTTGCTGTCCTATTGT 28800 |
| mRNA | ------------------------------------------------------------ |
| genome | ACCTCTGCTCCTAGCAGTGGCTGGAGCCCACTCCTCTGTGCTTCGGGATTAGTGGGGATC 28860 |
| mRNA | ------------------------------------------------------------ |
| | rs2285086 |
| genome | GTGGGGCATTGACTGTAGGTCAGCTTTCCTTGCTTGATCTTTCTCACTGGGATGAACTAG 28920 |
| mRNA | ------------------------------------------------------------ |
| genome | CAGCACCTTCTTTTGTAGCTGCTTTGCTTTTGACTATCTTTCTGACCGTTGTTCCTAGTA 28980 |

FIG. 1 X

| | | |
|---|---|---|
| mRNA | ------------------------------------------------------------ | |
| genome | GCTGTAGATGGTAAATATATTTAGGCCTGTTTCCAATGGCTCAGTAGGAGACATATTCAC | 29040 |
| mRNA | ------------------------------------------------------------ | |
| genome | CTATGATATCTGAATTCTGTTACCCACATGGGCATGCGTGAAATAGTTGCCTTGCCTTAC | 29100 |
| mRNA | ------------------------------------------------------------ | |
| genome | TTTCCCTTGGAATAAATAATTCATGTTATTCTCCTGGTAGAAGCTAGAAAAAGCCTTTAT | 29160 |
| mRNA | ------------------------------------------------------------ | |
| genome | AGTCAGTCAGAAAAAAATTTTTAGACAAATAATCTTGATTTTAGTACTGACAAAAACGTG | 29220 |
| mRNA | ------------------------------------------------------------ | |
| genome | TGGTGATTCTTTTTTTAATTTTTTTTTGAGACGGAGTTTCACTCTTGTTGCCCAGGCTGG | 29280 |
| mRNA | ------------------------------------------------------------ | |
| genome | AGTGCAATGGCGTGATCTCGGCTCACTGCAACCTCTGCCTCCTGGGTTCAAGTGATTCTC | 29340 |
| mRNA | ------------------------------------------------------------ | |
| genome | CTGCCTCAGCCTCCCAAGTAGCTGGAGTTACAGGCATGTGCTACTGTGCCCAGCTAATTT | 29400 |
| mRNA | ------------------------------------------------------------ | |
| genome | TGTATTTTTAGTAGAGATGTTGGTCAGGCTGATCTCGAACTCCCAACCTTAGGTGATCTG | 29460 |
| mRNA | ------------------------------------------------------------ | |
| genome | CCCGCCTCAGCCTCCCAAAGTGCTGGGATTACAGGCGTGAGCCAGGGCGCCCGGTGATTC | 29520 |
| mRNA | ------------------------------------------------------------ | |
| genome | ATTTGTTTTTTCAAAAAATTTCCTCTTGGCCATTGCTTTTCACTTTTGTTTTTTTTTTTT | 29580 |
| mRNA | ------------------------------------------------------------ | |
| genome | TTTTGAGACGGAGTCACGATCTGTCACCCAGGCTGGAGTGCAGTGGCATGATCTTGGCTT | 29640 |
| mRNA | ------------------------------------------------------------ | |
| genome | ACTGCAAGCTCTGCCTCCCAGGTTCACGCCATTCTCCTGCTTCAGCCTGGCGAGTAGCTG | 29700 |
| mRNA | ------------------------------------------------------------ | |
| genome | GGACTACAGGTGCTCGCCACCACACCCGGCTAATTTTTGTATTTTTAGTAGAGATGGGG | 29760 |
| mRNA | ------------------------------------------------------------ | |
| genome | TTTCACCGTGGTCTTGATCTCCTGACCTCATGACCCGCTCAACTCAGCCTCCCAAAGTGC | 29820 |
| mRNA | ------------------------------------------------------------ | |
| genome | TGGGATTACAGGCGTGAGCCACCGCGCCCGGCCCTCTCTTGTCTTTTTATTGTGGTAAAA | 29880 |
| mRNA | ------------------------------------------------------------ | |
| genome | TGCACATAAAATTGACTGTCTTAACCATTTTTAGGGGTACAGTTCAGTATATATATTCGT | 29940 |
| mRNA | ------------------------------------------------------------ | |
| genome | AATGTTGTACAGCCATCACTGCCATCTACTTCATAAGTTTTTCTTCTGTCAAAACTGAAC | 30000 |
| mRNA | ------------------------------------------------------------ | |
| genome | ATCTGTCTTCATTAAACTCCCTATCATCCATTCTTTCCTGTAGTCCCTTTCTACTTTCTG | 30060 |
| mRNA | ------------------------------------------------------------ | |
| genome | TCTGTATGAGTGTAACTGCTCTGGAGACCTCATGTAAGTGGATTCCTACAGGATTTGTGT | 30120 |
| mRNA | ------------------------------------------------------------ | |
| genome | TTTTTTTTTGGTGATCTGCTTATTTTTAATGCCTCTGTGCATTTGTATTATATACTTTCA | 30180 |
| mRNA | ------------------------------------------------------------ | |
| genome | AAGTGATTTCACAAAACCGTTTCATTTTAGGTTAACTCATTTCTGTTGTTTGTGAAATAC | 30240 |

FIG. 1 Y

| | | |
|---|---|---|
| mRNA | ------------------------------------------------------------ | |
| genome | TGTGTATGATTCTGTTCTGTTTCTGTCTAATTTGTGGAAATGTTGTGGGAAGAAAATGAA | 30300 |
| mRNA | ------------------------------------------------------------ | |
| genome | ATAACAAATGAGCATATGTCCTGAAAATAAAAATATAAAAATTCTAAGTTAGCATGCTAT | 30360 |
| mRNA | ------------------------------------------------------------ | |
| genome | TGTAGAATACAACGCTATGATAAAAGTAGGAAAAAAAAAGGTTTGAATTCTATCTCTGCT | 30420 |
| mRNA | ------------------------------------------------------------ | |
| genome | ACCTGTGTAAGCTGGGTGACTTTAGATAAGCTGTAACGTGTTTGAGCCTTACTGGCTCAT | 30480 |
| mRNA | ------------------------------------------------------------ | |
| genome | TTTTGAAATGTAATCCCTAGTTACACAGTTCTTGTGGGATCAGATGGTACATGTGAAACA | 30540 |
| mRNA | ------------------------------------------------------------ | |
| genome | CTGTGAAAAGCAACTGCATAGATATGTTCATTAGCCACCTGAGCGGGAAGCGTATCCCA | 30600 |
| mRNA | ------------------------------------------------------------ | |
| genome | TTGCGATGCCCATCATCCAAAGCTATATGTTATCTTTACTTTTTTTTTTTGAGACAGAG | 30660 |
| mRNA | ------------------------------------------------------------ | |
| genome | TCTTGCTCTGTTGCCCAGGCTAGAGTGCAGTGGTGCAATCTCAGCTCACTGCAAGCTCCA | 30720 |
| mRNA | ------------------------------------------------------------ | |
| genome | CCTCCCGGGTTCACGCTATTCTCCTGCCCCAGCCTCCCAAGTAGCTGGGACTACAGGCAC | 30780 |
| mRNA | ------------------------------------------------------------ | |
| genome | CCGCCACCATGCCTGGCTAAATTTTGTATTTTTAGTAGAGATGGGGTTTCACCGTGTTA | 30840 |
| mRNA | ------------------------------------------------------------ | |
| genome | GCCAGGATGGTCTTGATCTCCTGACCTCGTGATCCGCCCGCCTCGGCCTCCCAAAGTGCT | 30900 |
| mRNA | ------------------------------------------------------------ | |
| genome | GGGATTACAGGCGTGAGCCACTGCCCCTGGCCATCTTTACTTTTTTGTGAAATGACTTT | 30960 |
| mRNA | ------------------------------------------------------------ | |
| genome | AAATACTTGGCAAACATTTGGTCATTGTTCATCTGATCTCCACCATCCAGGTCTCAGAGA | 31020 |
| mRNA | ------------------------------------------------------------ | |
| genome | ACATAATTTCTCTCTGAAAGCTTATTGACCCAGGAAATAAGATCTCTTTCAATCTGAGTG | 31080 |
| mRNA | ------------------------------------------------------------ | |
| genome | CGTCAGGCTTTATTCTTGTCATTTTGTCTTTTGATAATTTTCAAATGGAATTCATGGAAT | 31140 |
| mRNA | ------------------------------------------------------------ | |
| genome | GTTGGCTTATATTCATATATTAGTAAAGTATGTTGAGACATCTTAAGATTGATTTGTGGT | 31200 |
| mRNA | ------------------------------------------------------------ | |
| genome | TCTATATGCCATATTAAATCAAAATAATAGCTGTTAATGGTTTTCACATTAGTCTGTCTC | 31260 |
| mRNA | ------------------------------------------------------------ | |
| genome | TTGTTTTTATGGAGTAATGCTGAGAGTTCATTATGCTTGTTCTACAGAAGAGCATGTTAA | 31320 |
| mRNA | ------------------------------------------------------------ | |
| genome | AAGGAGTTTTTGGAGTCAGAGAGGTTATTCTTGGTTTCATAGGATACACTCTATACTTTT | 31380 |
| mRNA | ------------------------------------------------------------ | |
| genome | TAGGGATTTCAGAGTATATAGCTGAAGGTGATATTTTATGTAAATATGTTTTATGGAAAC | 31440 |
| mRNA | ------------------------------------------------------------ | |
| genome | TTATTGCTCATCGCTGTTTCCTGTTAACTCTCCTAAAATATAATTAAACTTTTGGAACTT | 31500 |

FIG. 1 Z

| | | |
|---|---|---|
| mRNA | ------------------------------------------------------------ | |
| genome | TTTTATAGCTTTTGTGCTAGACTAATTTTTGTCTCTAATGAGGTTATATAAATGGCAGCT | 31560 |
| mRNA | ------------------------------------------------------------ | |
| genome | TCTGACGTTTTCAATGTAGGAAGTCATTTAAAACTTCATGTATATTGTGAAAATGTAGTC | 31620 |
| mRNA | ------------------------------------------------------------ | |
| genome | TGCTTTAAGCTCTCTAAAGTGGTCTAAGTTACTGGTTCCTAAGTATGGATGAGCATCAAA | 31680 |
| mRNA | ------------------------------------------------------------ | |
| genome | ATCATCTGGAAAATTTGTTAAAAATACAGTAATGAAGGCACCTCACTGTCCTTTTTCCCA | 31740 |
| mRNA | ------------------------------------------------------------ | |
| genome | AACATACTTCTGCATTCTGTTTGAGTAGGTAGGGACTACACATTTTTCACAAGTATCCTC | 31800 |
| mRNA | ------------------------------------------------------------ | |
| genome | TTGGGAATACCCAGGAATGCTTACTTGAGCAACCTCTTACTAATATGTACCTTGATAAGG | 31860 |
| mRNA | ------------------------------------------------------------ | |
| genome | TGGCTAGGTAAACATAAATATACAAAAATCCATAGATCTCCCATATATTAGCATAAATCA | 31920 |
| mRNA | ------------------------------------------------------------ | |
| genome | GCTAGAAAATATAACGTTTAAAGATCTAGTTCACAGTAGCACCAATATATCGAACTCTAA | 31980 |
| mRNA | ------------------------------------------------------------ | |
| genome | GGAATCGATAAATATGCAAAAACTTTATAAAAACTTCTGTTAATGTTTCTGAAAGATATA | 32040 |
| mRNA | ------------------------------------------------------------ | |
| genome | GGTGACCACTTTCTAGATAGGAAGATTTTATATTACTAAGTTGAATTTTCTCTAAATTAA | 32100 |
| mRNA | ------------------------------------------------------------ | |
| genome | CACAGAAATTTAAAATAATCTTGATCAAAATTCTAGTAGAGGTATTTTTGAACTTGTTCA | 32160 |
| mRNA | ------------------------------------------------------------ | |
| genome | CTGCAAGAATAAATACATAATTGCAAAGAATATCTCAAAATCATCACCAGGCCTGGTGTG | 32220 |
| mRNA | ------------------------------------------------------------ | |
| genome | GTGGCCCATGCCTGTAATCCCAGCACTTTGGGAGGCTGAGGCAGGCAGATCACCTGAGGT | 32280 |
| mRNA | ------------------------------------------------------------ | |
| genome | CAAGAGTTTGAGACCAGCTGGACCAGTGCGGTGAAACACTGCCTCTACTAAAAATACAAA | 32340 |
| mRNA | ------------------------------------------------------------ | |
| genome | AATTAGCTGGGTGTGGTGGTGCATGCCTGTAGTCCCAGCTACTTGGGAGGCTGAGGCAGG | 32400 |
| mRNA | ------------------------------------------------------------ | |
| genome | AGAATTGCTTGAACCCAGGAGGTACAGGTTGCGGTGAGCCTAGATCGCACCACTGCATTC | 32460 |
| mRNA | ------------------------------------------------------------ | |
| genome | CAGCCTGGGCGACAAGAGCAAAATTCTGTCTCAAGAAAAAGAGAAAAAAGAAAAAGAAA | 32520 |
| mRNA | ------------------------------------------------------------ | |
| genome | TCAACACTAATATGGTGAGACTTAATGTATGTGACATTAAAATAGTGATTGGATGTTAAA | 32580 |
| mRNA | ------------------------------------------------------------ | |
| genome | ACAGGTATAGAACAGAAAGAAGAGTGTATGTGTGTATCTGTATGAATTTATGATGGGTGT | 32640 |
| mRNA | ------------------------------------------------------------ | |
| genome | AACATATATGTATTAGGGAAATGAGGGAAATGATACATTTCTCTGACTTTGGGAGAACAT | 32700 |
| mRNA | ------------------------------------------------------------ | |
| genome | TATATCTCTACCTCATATTGCAAACAAACATAAAGTTCAGATTAATTACCTAAATGTGAA | 32760 |

FIG. 1 AA

| | | |
|---|---|---|
| mRNA | ------------------------------------------------------------ | |
| genome | AAAATGAAATAATTTCTTTAAAAAATGTAATCTTAGTTTGAGGAAGGTTAACATTATAAA | 32820 |
| mRNA | ------------------------------------------------------------ | |
| genome | GGAAAAAACTGTTTTGAGTGGAATATAGTTCAATATGTCAAAATCCACCTTCAACAAAAT | 32880 |
| mRNA | ------------------------------------------------------------ | |
| genome | TGAAAGTAAATTGAACTTGGGGAAAGTATTGACAGCATATAGATCAAAGGTTACTAGCCT | 32940 |
| mRNA | ------------------------------------------------------------ | |
| genome | GTGTAAAGAGCAGTTATAAATATCGTTAAGAAAAACACTGTCGACCTGTCGGCACCTTGT | 33000 |
| mRNA | ------------------------------------------------------------ | |
| genome | TCTCCGACTCCCAGCCTCCAGAACTGTGACGAGTAAGTGCTTATTGTTTAAACCACCCAG | 33060 |
| mRNA | ------------------------------------------------------------ | |
| genome | TCTGTATGTGGTATTTTGTTATAGAAACTCAAGCTGATTAGGACACTAGTAATCAGTAGA | 33120 |
| mRNA | ------------------------------------------------------------ | |
| genome | CTGAAACTGAAACAAAAATAAGAACCTTTTTTACCTGTCAAATTGGCAAACATTAAGAAT | 33180 |
| mRNA | ------------------------------------------------------------ | |
| genome | ATTCAGATTTTTGTCAGAGGTGATACAACCTTCTAAGAAGGCAATTTGGGAAAATATAAA | 33240 |
| mRNA | ------------------------------------------------------------ | |
| genome | GCTTTAGATTATTATATGTCTGACCTAGCAGTTTTACCTCTAGGGTGCTTACCCCTAGGA | 33300 |
| mRNA | ------------------------------------------------------------ | |
| genome | AAGTGTGTAATGATATTGGTGCAGTGCCCTTCATCCCATTAGAAAATTAAAAATAACCTT | 33360 |
| mRNA | ------------------------------------------------------------ | |
| genome | AATGGCCTACCACTAAAAGGGGATTGAAAATTTAAGATATATTTATTTATGTGTTTATTG | 33420 |
| mRNA | ------------------------------------------------------------ | |
| genome | AGATGGAGTCTTGCACTGTCCGCCTGGGCCAGAGTGCAATGGTGCGATCTCGGCTCACTG | 33480 |
| mRNA | ------------------------------------------------------------ | |
| genome | CAACCTCTGCTTCCCGGGTTCATGTGATTCTCCTGCCTCAGCCTCCTGAGTAGCTGGGAT | 33540 |
| mRNA | ------------------------------------------------------------ | |
| genome | TACAGGCTCACACCACCGCACCCGGCTAATTTTTTGTATTTTTAGTAGAGATGGGGTTTC | 33600 |
| mRNA | ------------------------------------------------------------ | |
| genome | ACTGTGTTGGCCAGACTGGTCTCGAACTCCTGACCTCATGATCCGCGCCCCTCGGCCTCC | 33660 |
| mRNA | ------------------------------------------------------------ | |
| genome | CAGTGTTGGGATTACAGGTGTGAGCCACTGCGCCTGGCCAGATACATTTATACAAGAGAA | 33720 |
| mRNA | ------------------------------------------------------------ | |
| genome | TGTTAGTTAACATTCATAGATATTTATATTTTGTTTACTTTTTATTAAAAAAATTTTTTT | 33780 |
| mRNA | ------------------------------------------------------------ | |
| genome | TAGAGACAGGATCTTACTCTGTCACCCAGGCAGGATGCAGTTGCACAATCATAGCCCACT | 33840 |
| mRNA | ------------------------------------------------------------ | |
| genome | GCAGCCTGAACTCCTGGGCTTAAGTGATCCTTCTGCCTCAGCCTTTTGAGTACCTGGGGG | 33900 |
| mRNA | ------------------------------------------------------------ | |
| genome | ACTTTAGGCAGTGCTACTATACCTGGCTAATTTTTAAATGTTTTATAGATGAGATCTTGC | 33960 |
| mRNA | ------------------------------------------------------------ | |
| genome | TGTATTGCCCAGGCTGGTCTAGAATTCCTGGGCCCAAGTGATCCTCCCACCTTGGCCTCC | 34020 |

FIG. 1 BB

| | | |
|---|---|---|
| mRNA | ------------------------------------------------------------ | |
| genome | CAAAGCGCTGAGATTACAGGCATGAGCCACCACTTCTGACCAATAGATATTTATATTTGT | 34080 |
| mRNA | ------------------------------------------------------------ | |
| genome | GACTGGAAAATATATTAACAATGTGTTAAAAAATTCAGTTAAAAAATAATGAAAGATTTT | 34140 |
| mRNA | ------------------------------------------------------------ | |
| genome | TGCTTCTGGCTAAGATAGAATAACAAGGACAGCATTTATCTTCTTGCCTTGAAATAGTTG | 34200 |
| mRNA | ------------------------------------------------------------ | |
| genome | AAAACGGAAGAAATATATGTAACAGTGGTTTTCAAGTTATTGGGCATCAGGCAAAGAAGA | 34260 |
| mRNA | ------------------------------------------------------------ | |
| genome | ATAGTTATCCCAGGAAAATGAATGTGGAGAGCCCTACAATTTCCTTACATTACTGCCTGG | 34320 |
| mRNA | ------------------------------------------------------------ | |
| genome | TCATGGCAAGAGGAAAAACTGAGAGGAGACTGAGGCTGAGCCAGTGGTTTGCTGGGTTGA | 34380 |
| mRNA | ------------------------------------------------------------ | |
| genome | GGAGGCAGAGCTGGGAGTGCAGAGATGCAAGGTGGTGAGAGCCCATATGGAAGAATACCA | 34440 |
| mRNA | ------------------------------------------------------------ | |
| genome | GGGAAGAGAGCTGCAGAGGGAGCTCCGGAGACCTGCACCCTGCCCTCTCAGTACCCTGTC | 34500 |
| mRNA | ------------------------------------------------------------ | |
| genome | ATGTGTGTAGCTGAGTACTGACGAGCACTTGCTTGTGCGGAAATGACCCAGGGCTGGAGG | 34560 |
| mRNA | ------------------------------------------------------------ | |
| genome | TAGAGCCACCTGAAAGGATTAGAAGGAACAGTTGCTGAAAGTCACACAGGGCCAGGAAGA | 34620 |
| mRNA | ------------------------------------------------------------ | |
| genome | ATTTCTAATCACACCAGTTGGAGTGGAAAACCTCAGCTCTCATAGAGCAGGTAGGGTACT | 34680 |
| mRNA | ------------------------------------------------------------ | |
| genome | CAGAAGGGTTTGCCCACCTAGCCCCAGACTAAGTTTCGTTACTCTGACCCTACCTAATAT | 34740 |
| mRNA | ------------------------------------------------------------ | |
| genome | TAAAAGAGATTAATTAAATTGTTCGCAACAAAAATAATATATTTCAGTGTTTGTAACAC | 34800 |
| mRNA | ------------------------------------------------------------ | |
| genome | GTAGAAGTGAATTGTATGACAATAGCATAAAGGCTGGAAGAGCAGAAATTGACATGTATT | 34860 |
| mRNA | ------------------------------------------------------------ | |
| genome | TGCGCTGGGCAGAATAATGCTCCCCTCTTTCCCCAAAAGATATCAAGTCCTAATCCCTGG | 34920 |
| mRNA | ------------------------------------------------------------ | |
| genome | AGCCTGTAAATATTACTTTATATGGAAAATTGTTTTATGATGTGATTAAATTCAGGATCT | 34980 |
| mRNA | ------------------------------------------------------------ | |
| genome | TGAGATGAGGGGGCTATCTTGGATGATCTGGGTAGGCACTAAATGCAATCACATATATAT | 35040 |
| mRNA | ------------------------------------------------------------ | |
| genome | AAAAGGAGGCAGAGGGAGATTTTACACACAGAGAGAAGGCCCTGTGAAGATGGAACAGA | 35100 |
| mRNA | ------------------------------------------------------------ | |
| genome | AAGATTTGAAGGTGCTGGCCTTGAAAATTGGAGTGATGAAGCTATAAGCCAAGGAATGCA | 35160 |
| mRNA | ------------------------------------------------------------ | |
| genome | GCAGCCACCAAAGCTGGAAGAGGCACGGAGCAGTTCTCATTTAGAGCCTACTCCAGAGGG | 35220 |
| mRNA | ------------------------------------------------------------ | |
| genome | AATGTGGTGCTGCCAATTCCTTTTTTTTTTTTTTTTTTAAGATATCATTTACCCCTTTAA | 35280 |

FIG. 1 CC

| | | |
|---|---|---|
| mRNA | ------------------------------------------------------------ | |
| genome | GTTGGTTTTTTTTTTTTTTTTTTTTTAGTATTTATTGATCATTCTTGGGTGTTTCTT | 35340 |
| mRNA | ------------------------------------------------------------ | |
| genome | GGAGAGGGGGATTTGGCAGGGTCATAGGACAATAGTGGAGGGAAGGTCAGCAGATAAACA | 35400 |
| mRNA | ------------------------------------------------------------ | |
| genome | TGTAAACAAAGGTCTCTGGTTTTCCTAGGCAGAGGGCCCTGCCACGTTCTGCAGTGTTTG | 35460 |
| mRNA | ------------------------------------------------------------ | |
| genome | TGTCCCTGGGTACTTGAGATTAGGGAGTGGTGATGACTCTTAACGAGTATGCTGCCTTCA | 35520 |
| mRNA | ------------------------------------------------------------ | |
| genome | AGCATCTGTTTAACAAAGCACATCTTGCACCGCCCTTAATCCATTTAACCCTTAGTGGAC | 35580 |
| mRNA | ------------------------------------------------------------ | |
| genome | ACAGCACATGTTTCAGAGAGCACGGGGTTGGGGGTAAGGTTATAGATTAACAGCATCCCA | 35640 |
| mRNA | ------------------------------------------------------------ | |
| genome | AGGCAGAAGAATTTTTCTTAGTACAGAACAAAATGGAGTGTCCTATGTCTACTTCTTTCT | 35700 |
| mRNA | ------------------------------------------------------------ | |
| genome | ACGCAGACACAGTAACAATCTGATCTCTCTTTCTTTTCCCACATTTCCTCCTTTTCTATT | 35760 |
| mRNA | ------------------------------------------------------------ | |
| genome | CGACAAAACTGCCACCGTCATCATGGACTGTTCTCAATGAGCTATTGGGTACACCTCCCA | 35820 |
| mRNA | ------------------------------------------------------------ | |
| genome | GATGGGGTGGCGGCCGGGCAGAGGGGCTCCTCACTTCCCAGATGGGGCGGCCGGGCAGAG | 35880 |
| mRNA | ------------------------------------------------------------ | |
| genome | GCGCCCCCCAACCTCCCAGACGGGGCGGCGGCTGGGCGGGGGCTGCCCCCCACCTCCCGG | 35940 |
| mRNA | ------------------------------------------------------------ | |
| genome | ACGGGGCGGGTGGCCGGGCGGGGGCTGCCCACCACCTCCCGGACGGGGCGGCTGGCCGGG | 36000 |
| mRNA | ------------------------------------------------------------ | |
| genome | CGGGGGCTGCCCCCCACCTCCCGGACGGGGCGGGTGGCCGGGCGGGGGCTGCCCCCCACC | 36060 |
| mRNA | ------------------------------------------------------------ | |
| genome | TCCCGGACGGGGCGGCTGGCCGGGCGGGGGCTGCCCCCCACCTCCCGGACGGAGCGGCTG | 36120 |
| mRNA | ------------------------------------------------------------ | |
| genome | CCGGGCGGAGGGGCTCCTCACTTCCCGGACGGGGCGGCTGCTGGGCGGAGGGGCTCCTCA | 36180 |
| mRNA | ------------------------------------------------------------ | |
| genome | CTTCTCAGACGGGGCGGCTGGTCAGAGACGCTCCTCACCTCCCAGACGGGGTGGCAGTGG | 36240 |
| mRNA | ------------------------------------------------------------ | |
| genome | GGCAGAGACATTCTTAAGTTCCCAGACGGAGTCACGGCCGGGCAGAGGTGCTCTTCACAT | 36300 |
| mRNA | ------------------------------------------------------------ | |
| genome | CTCAGACGGGGCGGCGGGGCAGAGGTGCTCCCCACTTCCCAGACGATGGGCGGCCGGGCA | 36360 |
| mRNA | ------------------------------------------------------------ | |
| genome | GAGATGCTCCTCACTTCCTAGATGGGATGACAGCCGGGAAGAGGCGCTCCTCACTTCCCA | 36420 |
| mRNA | ------------------------------------------------------------ | |
| genome | GACTGGGCAGCCAGGCAGAGGGGCTCCTCACATCCCAGACGATGGGCGGCCAGGCAGAAA | 36480 |
| mRNA | ------------------------------------------------------------ | |
| genome | CGCTCCTCACTTCCTAGACGGGGTGGCGGCTGGGCAGAGGCCGCAATCTTGGCACTTTGG | 36540 |

FIG. 1 DD

| | | |
|---|---|---|
| mRNA | ------------------------------------------------------------ | |
| genome | GAGGCCAAGGCAGGCGGCTGGGAGGTGAAGGTTGTAGTGACCCGAGATCACGCCACTGCA | 36600 |
| mRNA | ------------------------------------------------------------ | |
| genome | CTCCAGCCTGGGCAACACTGAGCACTGAGTGAGCGAGACTCCGTCTGCAATCCCGGCACC | 36660 |
| mRNA | ------------------------------------------------------------ | |
| genome | TCGGGAGGCCGAGGCTGGCAGATCACTTGCAGTCAGGAGCTGGAGACCAGCCCGGCCAAC | 36720 |
| mRNA | ------------------------------------------------------------ | |
| genome | ACGGCGAAACCCCGTCTCCACCAAAAAACACGAAAACCAGTCAGACATGGCGGTGCGTGC | 36780 |
| mRNA | ------------------------------------------------------------ | |
| genome | CTGCAATCCCAGGCACTTGGCAGGCTGAGGCAGGAGAATCAGGTAGGGAGGTTGCAGTGA | 36840 |
| mRNA | ------------------------------------------------------------ | |
| genome | GTAGAGATGGTGGCAGTACAGTCCAGCCTTGGCTCGGCATCAGAGGGAGACTGTGCGAGG | 36900 |
| mRNA | ------------------------------------------------------------ | |
| genome | GCGAGGGCGAGGGCGAGGGAATTCCTTAATTTCAGTTTAGTGATACTAATTTTGGACTCT | 36960 |
| mRNA | ------------------------------------------------------------ | |
| genome | GGCCTCTAAAACTGTGAAAGAAAAAATTTTTTGTTTGTTTGTTTCTTTTAAGCCACATAG | 37020 |
| mRNA | ------------------------------------------------------------ | |
| genome | TTTGTGGTAATTTGTTACAGCAGCTGCAGGAAACTAATTTATGCTGCATGTGAAATGGTG | 37080 |
| mRNA | ------------------------------------------------------------ | |
| genome | TAATAAGGTAGATTGTGATGAAGATACATAGTATAAACAATTAAGCAACAACTAAAAGCA | 37140 |
| mRNA | ------------------------------------------------------------ | |
| genome | CAACAAGGAATTATAGCTAATGAACCAAAAAAGGAGATTAGAATAATAAAAATGGTGAAT | 37200 |
| mRNA | ------------------------------------------------------------ | |
| genome | CCCAAAGAAGCCAGAAATAGGGGAAGAGGCAAATAAAGGAAAGAAAGAGCTTGATGGTAG | 37260 |
| mRNA | ------------------------------------------------------------ | |
| genome | ATTTCAACCTAACTATGTCAAAAAGGACATTACATGTAAAAGGCAGCGATTTTTCAGATT | 37320 |
| mRNA | ------------------------------------------------------------ | |
| genome | GAATGGAAAAGTAAGACTCGGTATATGCTGCTGCCTGCAAGAAACACATTCTAAATATAA | 37380 |
| mRNA | ------------------------------------------------------------ | |
| genome | AGGCAAAAATAACCTACAGGTAACAGAACGGAAAGAAGTTCACTGTGCTTACAAGAATTA | 37440 |
| mRNA | ------------------------------------------------------------ | |
| genome | GATGCAAGCTAGACTGGTTCTGTTAATATCAGACAAAGTGGATTTCAAAGCAAAGGCTCT | 37500 |
| mRNA | ------------------------------------------------------------ | |
| genome | TGCCCAGGATGAGATGGTCATTTCATAATGATGAAGGGGATTCGTTCATCAGCCTGGCAT | 37560 |
| mRNA | ------------------------------------------------------------ | |
| genome | AGCAAGCTGAAATGTTTATGCACCGGACTACAGAGCTAAAATACATGAAGCAAAGCCTGA | 37620 |
| mRNA | ------------------------------------------------------------ | |
| genome | CAGAACTACAAGTAGAAACAGACAAATCCACAGTGATAGAGATTTCAGTAGCCGCTCTCA | 37680 |
| mRNA | ------------------------------------------------------------ | |
| genome | ATGATTTGTAGAACACGTAGCCATAATATCTGGATCTAGAACACTTGACCAACACTGTCC | 37740 |
| mRNA | ------------------------------------------------------------ | |
| genome | CCTGTGCAACCTCATTGGCATTTACAGGACACTCCACCCAGCACCAGCAGAAGAGACACT | 37800 |

FIG. 1 EE

| | | |
|---|---|---|
| mRNA | ---------------------------------------------------------------- | |
| genome | CTCTCAAGTGCTCACAGAATGTTTGCCAAGATAGAGCAGATGCTGGGCCATAAAACAAGT | 37860 |
| mRNA | ---------------------------------------------------------------- | |
| genome | CTCTAAATTAAAAGCATTCAAATTATTCAGAGTATGTTTTCTGACCTCAGTATCATTAAG | 37920 |
| mRNA | ---------------------------------------------------------------- | |
| | rs7659144 | |
| genome | TTGGAATATATTATAGGAAGATAACCTGGAAAAGCCTCAGATATGTGGAAAAAC CCATTT | 37980 |
| mRNA | ---------------------------------------------------------------- | |
| genome | CCACATGGCCCATGGGTCAGAAGTGAAGTCAAAAGGGAAATTTGAAAGTCTTTTGGATTG | 38040 |
| mRNA | ---------------------------------------------------------------- | |
| genome | ACTGATATAAAAACAATAGATTTCTAAACTTGTGGGGTGCTGTTACAGCATAGTAAATGG | 38100 |
| mRNA | ---------------------------------------------------------------- | |
| genome | AAATTTCTAGCATTAAATGCCTGTTTTAGGAAAGAAAGATTTCAAATCAATGACCTCAGC | 38160 |
| mRNA | ---------------------------------------------------------------- | |
| genome | TTCTACCTTTGGAAACTTGAAAATGACAAGCAAATGGAATCCAGAGTTACCAGAAGGGCC | 38220 |
| mRNA | ---------------------------------------------------------------- | |
| genome | AGGTACGGTGGCTTATGCCTGCAGTTCTGCCACTTTGGGAGGCCGAGGCAGGTGGATTGT | 38280 |
| mRNA | ---------------------------------------------------------------- | |
| genome | TTGAGACTGGCAGTTGAAGACCAGCCTGGGCAGCCTAGGGAGACCCCATATCTACAAAAA | 38340 |
| mRNA | ---------------------------------------------------------------- | |
| genome | ACAAAAAAATTAGCCAGGTGTGGTGGCATGTGCCTGTAGTCCCAGCTAACCAGGAGTCTA | 38400 |
| mRNA | ---------------------------------------------------------------- | |
| genome | AGGTGGGAGGATTGCTTGAGTCTGGGAGGTTGAGGCTGCAGTGAACTGTGATTGTGCCAC | 38460 |
| mRNA | ---------------------------------------------------------------- | |
| genome | TGTGTTCCATCCTGGGCAACAGAATGAGACCCTGTCTCAAAAACAAAAACAGTTACTAGA | 38520 |
| mRNA | ---------------------------------------------------------------- | |
| genome | AGAATGGACATCATAAAGATAGGAGCAGAAGTCAGTAAAATAGAAAACAAAAATACATAG | 38580 |
| mRNA | ---------------------------------------------------------------- | |
| genome | GAAATCAATAAAACCAAAAGCTGGTTCATCAAGAACATCAATAAATTGGTAAAGCTGATA | 38640 |
| mRNA | ---------------------------------------------------------------- | |
| genome | GGAAAAACAGTGAAGTCACAAATTAGCAATATCAGGAATGAGGGAGATGACAGTAGTATA | 38700 |
| mRNA | ---------------------------------------------------------------- | |
| genome | GATTATATAGATATTAAAAGGACTGTATGAGGCAGGTGTGGTGGTTCACGCCTGTAATCC | 38760 |
| mRNA | ---------------------------------------------------------------- | |
| genome | CAGCACCTTGGGAGGCCGAGGTGGACAGATCACCTGAGGTCAGGAGTTTGGGACCAGCCT | 38820 |
| mRNA | ---------------------------------------------------------------- | |
| genome | GGCCAACATGGTGAAACTCTGTCTCTACTAAAAATACAAAAATTAGTTGGTCGTGGTGCT | 38880 |
| mRNA | ---------------------------------------------------------------- | |
| genome | GTGTGCCTGTAATCCCAGCTACTTGGGAGGCTGAGGCAGGAGAATTGCTTGAACCTGGGA | 38940 |
| mRNA | ---------------------------------------------------------------- | |
| genome | GGCGGAGGTTGCAGTGAGCTGAGATTGTGCCGTTGCACTCCAGCCTGGGTGACAGAGCAA | 39000 |
| mRNA | ---------------------------------------------------------------- | |
| genome | GACTCCATCTCAAAACAAATAAATAAATAAAAAGGACTATATGGTAATATTATGAACAAC | 39060 |

FIG. 1 FF

| | | |
|---|---|---|
| mRNA | ------------------------------------------------------------ | |
| genome | TTTATGCCAATAAATTTGACAACTTATAGATGAAATGGATGAGTTCCTTGAAAGACACAG | 39120 |
| mRNA | ------------------------------------------------------------ | |
| genome | AAACTATTAAAGCTCTCTCAAGAAGATATAGATAAGCTGATTAGCCCTATATCTATTTTA | 39180 |
| mRNA | ------------------------------------------------------------ | |
| genome | TTGAATTTAAATGTAAAAATCAATATTTAGTTACTGGAAAACTTTTAAGTGTGGTTGGAA | 39240 |
| mRNA | ------------------------------------------------------------ | |
| genome | ATGGTATACGAACTTTTTCAACTGAATTTTATGAAGTCTAATCACAGGTAAAGGTTTTCT | 39300 |
| mRNA | ------------------------------------------------------------ | |
| genome | GATGAAAATTTAGTGTCTGAATTGAGATATACTGTAAAAAATGTTATATATCTTAATTAT | 39360 |
| mRNA | ------------------------------------------------------------ | |
| genome | TTCTTCACATTAATTACATGTTGAAATAATACTTTGGGTGTATTGGGTTAAATTAAATAT | 39420 |
| mRNA | ------------------------------------------------------------ | |
| genome | TATGAAAATCTTGCCTGTTTTCTTTTTACTTTTGATGCGTCAGCTAGGAAATATAAAAGT | 39480 |
| mRNA | ------------------------------------------------------------ | |
| genome | GTAGCTCACATTCTGTTTCTGTTGACAGTACTGCTTTGGAGCACAGTGTTTGAATGATCT | 39540 |
| mRNA | ------------------------------------------------------------ | |
| genome | ATCATTTCAAAGACCTTTCCTCAGTTCGTTATTCATGGCTGTCTGTATTCCACATAGATA | 39600 |
| mRNA | ------------------------------------------------------------ | |
| genome | AGGTCTGAAATACTGCTAAGTGGCATGTTTTGTTTTATGCTTTTATAAGTTTGTTGATCA | 39660 |
| mRNA | ------------------------------------------------------------ | |
| genome | TTACTGATGTGGACTTTTGGTGCCTCTTAGGCTCATTGCTATCTTCCAACCATTGTTTGC | 39720 |
| mRNA | ------------------------------------------------------------ | |
| genome | AATTTTTACCTAGAGATAAAGAGAAAGAGACATTTGGTTTCAGAGTAGTTAGATTGGGAT | 39780 |
| mRNA | ------------------------------------------------------------ | |
| genome | CATGAAAGAGCAACCTCATTTTGATGCTTCAAAAATAGCACATCCCCCGTATTACTGGGA | 39840 |
| mRNA | ------------------------------------------------------------ | |
| genome | TTTGCTATTCTTGGGATTACTTCAAGAACATCCTTGTGTTACTGGTTTGGATGCTTCTGA | 39900 |
| mRNA | ------------------------------------------------------------ | |
| genome | ATGCTGTGAAGTCAGTTTCATGTACATGGCTCATCAGTTTAGCTCTCTCTTGGCTTTGTT | 39960 |
| mRNA | ------------------------------------------------------------ | |
| genome | TAGACAGTTGGAGCATGATGGCCTAAACAGCTTCTTTCAATTAAACATTTTAAAATAGTT | 40020 |
| mRNA | ------------------------------------------------------------ | |
| genome | TACAAATAGTAAACAAACTCCAGTTTTTGTGACTCTTTGTCTCGCACAACAAAAACACAA | 40080 |
| mRNA | ------------------------------------------------------------ | |
| genome | TCTGACCATGATCATCTGGCATCTTAGGGTGAAATATGGTTATACTTTGGCCCATACCGA | 40140 |
| mRNA | ------------------------------------------------------------ | |
| genome | AAGCAAGATTAAAAAGGGGCAGGAGAGATAGACTGCTGAACTGATTTTCAAGGTTCCAAG | 40200 |
| mRNA | ------------------------------------------------------------ | |
| genome | AATATTGTAGGTTAAGAGTAAAAGTAAACTTTTGGTAGAAAGCAGTGGGTTGTCTAGGAT | 40260 |
| mRNA | ------------------------------------------------------------ | |
| genome | TGAAGTATCTGAAGTTTTTAAACGAAAATTTAAAAAGAAAAATGAGAATTGCCTTACAAG | 40320 |

FIG. 1 GG

| | | |
|---|---|---|
| mRNA | ------------------------------------------------------------ | |
| genome | TACAATCTCTTCTTTTTAAAAAATAAACTTTATTTTGAAATAGTTTTAGATTTATAGAA | 40380 |
| mRNA | ------------------------------------------------------------ | |
| genome | AAAAATTAGATAGGGTAGGAAGTTTTCATATACCCTACATCCAGTTACCCCAGTTATTAT | 40440 |
| mRNA | ------------------------------------------------------------ | |
| genome | CATCCTAATTTAGTGTGAGACATTTTCATGTTTAATGAATCAATATTGATATGCTATTAA | 40500 |
| mRNA | ------------------------------------------------------------ | |
| genome | CTTAAGTCCAGACTTTATTCAGATTTTCTTAATTTCTATGTAATGTCCTTTTTCTGTTCC | 40560 |
| mRNA | ------------------------------------------------------------ | |
| genome | AGAATTCCATGCAGGACACCGGATACCTCATTACATTTCATTGTCATGTCACCTTAGGCT | 40620 |
| mRNA | ------------------------------------------------------------ | |
| genome | CCTCTTGACAGTTTCTCTTCTTTTTTGCTTAGAAATTCTCCAGAATTTCAGAAACTTCT | 40680 |
| mRNA | ------------------------------------------------------------ | |
| genome | GGGCATCGCTATGGAACTTTTCTGCTGTGCAGTGATGACGCAGAGTCAGATGTCAGGAT | 40740 |
| mRNA | ------------------------------------------------------------ | |
| genome | GGTGGCTGACGAATGCCTCAACAAAGTTATCAAAGTAAGAACCGTGTGGATGATGTTCTC | 40800 |
| mRNA | ------------------------------------------------------------ | |
| genome | CTCAGAGCTATCATTGTTGTAGGCTGAGAGAAGAAGCGATCATTGAGTGTTCTTCTGTTT | 40860 |
| mRNA | ------------------------------------------------------------ | |
| genome | TGAGTCCCTGAGGATGTCTGCACTTTTTTCCTTTCTGATGTATGGTTTGGAGGTGCTCTG | 40920 |
| mRNA | ------------------------------------------------------------ | |
| genome | TTGTATGGTTTGGAGGTGCTCTGTTGTATGGTTTGGAGGTGCTCTATTGTATGGTTTGGA | 40980 |
| mRNA | ------------------------------------------------------------ | |
| genome | GGTGCTCTGTTGTATGGTTTGGAGGTGCTCTTGTATGGTTTGGAGGTGCTCTTGTATGGT | 41040 |
| mRNA | ------------------------------------------------------------ | |
| genome | TTGGAGGTGCTCTGTTGTATGGTTTGGAGGTGGTCTTGTATGGTTTGCAGGTGCTCTATT | 41100 |
| mRNA | ------------------------------------------------------------ | |
| genome | GCATGGTTTGCAGGTGCTCTATTGTATGGTTTGGAAGTGCTCTTGTATGGTTTGGAGGTG | 41160 |
| mRNA | ------------------------------------------------------------ | |
| genome | CTCTTGTATGGTTTGGAGATGCTCTATTGTATGGTTTGCAGGTGCTCTATTGTATGGTTT | 41220 |
| mRNA | ------------------------------------------------------------ | |
| genome | GGAAGTGCTCTTGTATGGTTTGGAGGTGCTCTTGTATGGTTTGGAGGTGCTCTGTTGTAT | 41280 |
| mRNA | ------------------------------------------------------------ | |
| genome | GGTTTGGAGGTGCTCTGTTGTATGGTTTGGAGGTGCTCTTGTATGGTTTGGAGGTGCTCT | 41340 |
| mRNA | ------------------------------------------------------------ | |
| genome | ATTGTATGGTTTGGAGATGCTCTGGTATCTGCCTGCATTGCTTGCCACACCTGCCCGGTC | 41400 |
| mRNA | ------------------------------------------------------------ | |
| genome | AGAAGGCGCTATGTTGACAATTGTGCCTGCACGGTGCCTAGGTCAATGAAGGGAACCGAT | 41460 |
| mRNA | ------------------------------------------------------------ | |
| genome | GGTAGCCACTGGATGCTCCTGGGAAAATGTCACTACAGGCACCAGAGAAGCCAGAGCTAT | 41520 |
| mRNA | ------------------------------------------------------------ | |
| genome | GCCCAAATTTCTATGAGTCTCAGTTTTCTTAACCATAAAATGGGATCAATGTTTTTGTGG | 41580 |

FIG. 1 HH

| | | |
|---|---|---|
| mRNA | ------------------------------------------------------------ | |
| genome | CATGTGTATGAGTGTGTGTCTGTGTATGTGTGAGGATTAAATTGTGTATGTGTGAGGACT | 41640 |
| mRNA | ------------------------------------------------------------ | |
| genome | AATTGCCACTACTGGATCCTCAAAGTGGTAAGAAGTGTTCTTATTAATAATGACATCCTT | 41700 |
| mRNA | ------------------------------------------------------------ | |
| genome | ACACTCTTACCCAGCAAGATTGATGGGTGTGGCACTGCTTCTCTTTTTCCATCACATGGT | 41760 |
| mRNA | ------------------------------------------------------------ | |
| genome | TTCCATGGTATCCTTTTGCCCAGGGAATCTTTGCTTTGTGGCTAGCACTTTGTTGTTTGG | 41820 |
| mRNA | ------------------------------------------------------------ | |
| genome | CTAATCACGCTTTCTGTGGTCAGGACGCTGGCTTCTCTGGAGCCATGGGATTCTAGCTCC | 41880 |
| mRNA | ------------------------------------------------------------ | |
| genome | CTGTCTTGTCCCTAGAGTGGTCACTGTCTTCTCTCTCCGCTTGCAATTCCTGCTTTGCTC | 41940 |
| mRNA | ------------------------------------------------------------ | |
| genome | GCATCTCACTTATGCAGTGACGTATATCAGTTTCACCTTGTTCTCCGTGCCTGCTGATCA | 42000 |
| mRNA | ------------------------------------------------------------ | |
| genome | TTGGCACCACTTGCATGGTGCCATTTAGGGCCTGCTTCCAGTTAAGCTTGCTTCTCCACA | 42060 |
| mRNA | ------------------------------------------------------------ | |
| genome | GGCCTAAATATCCTTGCTTGCTTCTTTTATTCTCACTGGCAGGACCAGGGCGGTCTGTCT | 42120 |
| mRNA | ------------------------------------------------------------ | |
| genome | TTGCATGAGACAGGGTCTCGCTCAGTCACCCAGGCTGGAGTGCAGTGGCTGATCACGGCT | 42180 |
| mRNA | ------------------------------------------------------------ | |
| genome | CATTGCAGCCTTGAGCTACCGGGCTCAAGCTATCCTCCTGGCTTGGCCCCTTGAGTAGCT | 42240 |
| mRNA | ------------------------------------------------------------ | |
| genome | GGGACTACAGGCGTGCACCACCATGCCCAGCTAATTTTTAAAATTATTTGTAGAGATGGG | 42300 |
| mRNA | ------------------------------------------------------------ | |
| genome | ATCTCGCCAGGTTGCCCAGGCTGGTCTTGAACGCCTGGGCTCAAGTGATCCTCCCTCCTT | 42360 |
| mRNA | ------------------------------------------------------------ | |
| genome | GGTTTCCCAAAGTGCTGGGATCACAGGTGTGAGCCACTGTGCCTGGCCCTTGATGTTTCA | 42420 |
| mRNA | ------------------------------------------------------------ | |
| genome | GTTCTTGATATTTGATCCTCAGAGTCAGAAAATCTAAAAAGAGGGCTATCCCAGGTTGCC | 42480 |
| mRNA | ------------------------------------------------------------ | |
| genome | TTGGTTCATGGCAAATGGGACGTTAAGAGGGCAGAGAGAATATGAACAGAAACTGTTCTA | 42540 |
| mRNA | ------------------------------------------------------------ | |
| genome | ATATTGGTCATTTAATGTGTAAGTATTGTTCTTTTTAAACCTCCTTCATTTTTTTTCCA | 42600 |
| mRNA | ------------------------------------------------------------ | |
| genome | GGAATTGCTGGACACAGTGGCTTGGTGTGTGTCTGAGGACTGTAGGCCATGGCCCTAGGT | 42660 |
| mRNA | ------------------------------------------------------------ | |
| genome | TGTGGTTTTAGGTCTCAGGTGCTCTTCCTGGCTGTCTCCTTGCTTCTTTCCCATGTCCTC | 42720 |
| mRNA | ------------------------------------------------------------ | |
| genome | TTCTTTGTTTCCAGCCATTTCTCCCTTATGCTTAAGTTTGGTGCAGCAGGGTTTGGCTGC | 42780 |
| mRNA | ------------------------------------------------------------ | |
| genome | TCTCAGATTCCTGCTTCCTCAGATGCTGTAGTTGTCAGGCCCAGCGGGCTGGCAGCGGGA | 42840 |

FIG. 1 II

| | | |
|---|---|---|
| mRNA | ------------------------------------------------------------ | |
| genome | TCAGGATCTGGCTAGGTTTGCTCTCACTGTGGCAGAGTAGGGGGAGGCGTGGGAGAGCAC | 42900 |
| mRNA | ------------------------------------------------------------ | |
| genome | GTGTGACCCCAGGCCAGCTGTAGGGAGCATAGGCATGGTCACGTAGCCTTCAGGTCCTAG | 42960 |
| mRNA | ------------------------------------------------------------ | |
| genome | ACTTTGTCTTCTCATGAGTATGGCTGTGTGTGTATGGTGAAAACTAGGTTCTACTTAGCC | 43020 |
| mRNA | ------------------------------------------------------------ | |
| genome | CAAGAAAATGGGCACATTTTGCATGTGGTTTCTGTAGAGAAATGCACTGGGTATCTGACA | 43080 |
| mRNA | ------------------------------------------------------------ | |
| genome | TAGCCTGGCAGCATGCCTCCCTCAGGTAGGTTAGTCTCAGGCGGTGAAGCACGTGTGTCC | 43140 |
| mRNA | ------------------------------------------------------------ | |
| genome | AGCAAGAACTTCATATGTGGCATAAAGTCTCCGTTCTGTGAGGTGCTGGCAAATCACCAC | 43200 |
| mRNA | ------------------------------------------------------------ | |
| genome | CACCGTCAAGAGGCTGAAGTGATTTTTGTCTAGGGAGGCAGGAAAGGCTTCCTGGAGTCA | 43260 |
| mRNA | ------------------------------------------------------------ | |
| genome | GCAGCCAGTAGGTGAAAGAGTAGATTGGAGACCTTCTTAATCATCACCGCCTCTTGTCTC | 43320 |
| mRNA | ------------------------------------------------------------ | |
| genome | AAGGGGTGCCAGGAAGCTGTGGAGGCTGAACCCATCTTATGCTGCCAGAGAGTGGGACAC | 43380 |
| mRNA | ------------------------------------------------------------ | |
| genome | CATGAGGGTCAGGTCAAGGGGTTGTACCTTGTTTGGTAGAGAATTAGGGGCTCTTGAAGA | 43440 |
| mRNA | ------------------------------------------------------------ | |
| genome | CTTTGGATGTGGTCAGGGGAGTGTATCATTTAGGAAGAGTGACCCGGTGAGGACGTGGGG | 43500 |
| mRNA | ------------------------------------------------------------ | |
| genome | TAGAGGAGGACAGGTGGGAGGGAGTCCAGGTGGGAGTGAGTAGACCCAGCAGGAGTGCAG | 43560 |
| mRNA | ------------------------------------------------------------ | |
| genome | GGCCTCGAGCCAGGATGGTGGCAGGGCTGTGAGGAGAGGCAGCCACCTGTGTGTCTGCGG | 43620 |
| mRNA | ------------------------------------------------------------ | |
| genome | AAGCAGGGGCAAGAGGGAAGAGGCCAGCAGCGTGCTGCCATCACCCAGCGACTGGCGTAG | 43680 |
| mRNA | ------------------------------------------------------------ | |
| genome | ATTGTGAGAGACCATTCCCTGCTCTTAGGAGGGGCTGAGTTTTAGTTTTCTCTTGTTATA | 43740 |
| mRNA | ------------------------------------------------------------ | |
| genome | CAATAAGCTTGGTATTTGTTTACAAAACATTTGTAAAGCTAAATCAAGGTTTGATAAGGC | 43800 |
| mRNA | ------------------------------------------------------------ | |
| genome | TTCTAGTTTTATTTAAGAAGTAATGTTGAAATAAATGTTTGTCCAATTCGCTTTGCTCAT | 43860 |
| mRNA | ------------------------------------------------------------ | |
| genome | TTAAGGACTTTCAGTACAAACTGCAACAACAGGATTAGGATTTAAACGTTTCTGAGATGT | 43920 |
| mRNA | ------------------------------------------------------------ | |
| genome | TTTTACTCCTCAGAATTTCCCAGAATGTGATCTGGTTTTGATTTTCAAGCTTGCTGACCC | 43980 |
| mRNA | ------------------------------------------------------------ | |
| genome | AATAGGTTAACCCACAAGTTTTACGAAGACCATCTCAGTCCACTTACATCAACTGCCCAT | 44040 |
| mRNA | ------------------------------------------------------------ | |
| | rs16843804 | |
| genome | GC[C]ACGGTTAAAGAGATCATCGACTGATGTTTGGCACAGCTTCCTCCCTCTTGGGTGGGC | 44100 |

FIG. 1 JJ

```
mRNA      ------------------------------------------------------------
genome    AAGCATTTGGAAGAGAAGGCTCCTATGGGTGAGAGTGGGGCACCAAAGTCTTCCCTGTCC  44160
mRNA      ------------------------------------------------------------
genome    CATCCCCTAGCTTGAGAAGCCCTTCTCTAATGTGGACTTTGTGCCGTTAGCATCGTTACT  44220
mRNA      ------------------------------------------------------------
          rs2024115
genome    AGCTTGAAGTTGACCATCTGGACGTACTTTCTGGTTTAGCCTCACAAGTGAGCAAGGAGG  44280
mRNA      ------------------------------------------------------------
genome    GTTGAGAGATGTGCTGTGAGGAATGTGGGGCCCCAGCTGGCAGCAGGCTCTGGGTCAGGG  44340
mRNA      ------------------------------------------------------------
genome    GGGCAGGGACCACGGGCATACCTGACAGTGAGGAGGGGCCACACCTGCAGAAAAGGATGC  44400
mRNA      ------------------------------------------------------------
genome    AGGACTCCGCCTTGGGAAGTGTTCTAGGCCAGAGCGAGGGTCTGTGGTTTATAAGTACAC  44460
mRNA      ------------------------------------------------------------
genome    CCACAGTGCTCGGGACCCTGCAGATGTCCAGGGTGCCGTCTGAGCCCGTATCATCCAACA  44520
mRNA      ------------------------------------------------------------
genome    GAATGTTCTGCTAGTGAAGATTAAAGATTTACTCCAGGGGCTTTAGGATTTATTATATAT  44580
mRNA      ------------------------------------------------------------
genome    ATATAAATCCTATATATAATTTTTTTTTTTTTTTTTGAGATGGAGTTTCGCTCTT  44640
mRNA      ------------------------------------------------------------
genome    GTTGCCCAGGCTGGAGTGCAATGGCGTGATCTTGGCTCACTGCAACCTCCGCCTCCCGGG  44700
mRNA      ------------------------------------------------------------
genome    TTCAAACTATTCTCCTGCCTCAGCCTCTCGAGTAGCTGGGATTACAGGCGCCCACCACCA  44760
mRNA      ------------------------------------------------------------
genome    CACCCGGCTAATTTTTGTATTTTTTAGTAGAGACGGAGTTTCTCCATGTTGGTCAGGCTG  44820
mRNA      ------------------------------------------------------------
genome    GTCTTGAACTCCTGACCTCAGGTGATCTGCCCGCCTTGGCCTCCCAAAGTGCTGGGATTA  44880
mRNA      ------------------------------------------------------------
genome    CAGGCATGAGCCACCCCACCTGGCCAGGATTTATTGTATTTGAACCATCTACCATTTTAA  44940
mRNA      ------------------------------------------------------------
genome    TTTTGATGTTATGTAGTATTTGATGATAATGAAAGTTAAATTGTTTTCTTTCCATTTTT  45000
mRNA      ------------------------------------------------------------
genome    CTGTTTAAGTGAATGACCTGTATCTAGTTTATTCAGTAACTTCCTGCATATATTTGTTTC  45060
mRNA      ------------------------------------------------------------
genome    TTTCATTCTTAATGAATATATTCTTAATTTAGTTGCTATTATGTTTTGCTTTGCCCCAAA  45120
mRNA      ------------------------------------------------------------
genome    ATTGAAATCTTAGTTTCCTTTTAGCTCGTTTTAGAACTAGTGATGGGATGTGTCTTCCAT  45180
mRNA      ------------------------------------------------------------
genome    AAATCTCTTGTGATTTGTTGTAGGCTTTGATGGATTCTAATCTTCCAAGGTTACAGCTCG  45240
mRNA      ------------------------------------------------------------
genome    AGCTCTATAAGGAAATTAAAAAGGTGGGCCTTGCTTTTCTTTTTTAAAAATGTTTTAAAT  45300
mRNA      ------------------------------------------------------------
genome    TTTAAATTTTTATAGGTACACGTATTTTGTAGGTACATGTAAATGTATATATTTATGGGG  45360
```

FIG. 1 KK

| | | |
|---|---|---|
| mRNA | ------------------------------------------------------------ | |
| genome | TACATGAGATATTTTGATACAGGTATACAATACATAATAATCACACCATGGAAAGTTGGA | 45420 |
| mRNA | ------------------------------------------------------------ | |
| genome | TATCCATGCCCTCAAGCATTTATCCTTTGTGTTACAAACAATCCAGTTACATGCTTTACT | 45480 |
| mRNA | ------------------------------------------------------------ | |
| genome | TATTTTATTTTATTTTTGAGACAGAGTCTTGCTTTCACCCATGCTAGAGTACAGTGGCAT | 45540 |
| mRNA | ------------------------------------------------------------ | |
| genome | GACCTTGGCTCACTGCAACCTCCGCCTCCCGGGTTCAACCGAACTTTGGGCTGGTCTCAA | 45600 |
| mRNA | ------------------------------------------------------------ | |
| genome | ACTCCTGACCTCAGGTGATCCGCCCGCCTCGGCCTCCCAAAGTGTTGGGATTACAGGCGT | 45660 |
| mRNA | ------------------------------------------------------------ | |
| genome | GAGCCACTGTGCCGGGCCTGATTGTACATTTTAAAATAACTAAAACAGTCAGGGCACAGT | 45720 |
| mRNA | ------------------------------------------------------------ | |
| genome | GGCTCATGCCTGTAATCCCAGCATTTTGGGAGGCTGAGGCAGGTGATCACCTGAGATCAG | 45780 |
| mRNA | ------------------------------------------------------------ | |
| genome | GAGTTCGAGACCAGCCTGGCCAACATGGAGAAACCCTGTCTCTACTAAAAATACAAAAAT | 45840 |
| mRNA | ------------------------------------------------------------ | |
| genome | TAGCCAAGTGTGGTGGCGGGCGCCTGTAATCCTGGCTACTCGGGAGGCTGAGGTAGGGGA | 45900 |
| mRNA | ------------------------------------------------------------ | |
| genome | ATCGCTTGAACCTGGGGGTGGAGGTTGCAGTGAGCCGAGATCACGCCACTGCATTCCAGC | 45960 |
| mRNA | ------------------------------------------------------------ | |
| genome | CTGAGCGACAGAGTGAGACTTTGTCTCAAAAAATAAAAATGAAATAAAATTGGGCCGGGT | 46020 |
| mRNA | ------------------------------------------------------------ | |
| genome | GTGGTGGCTCACACCTTAGTCCCAGCACTTTGGGAACCTGAGGCAGGTGGATGCTTGAGA | 46080 |
| mRNA | ------------------------------------------------------------ | |
| genome | CCAGGAGTTTGAGACCAGCATGGGCAACATGGCAAAACGCTGTCTGTACAGAAATTAGCT | 46140 |
| mRNA | ------------------------------------------------------------ | |
| genome | GGGTGTGGTGGTGCACAACTATAGTCTCAGCTACTTGGGAGATTGAGGTGGGAGGATTAA | 46200 |
| mRNA | ------------------------------------------------------------ | |
| genome | TTGAGCCTGGAAGGTTGAATCTATAGGTAGCTGAGATTGTGCCACTGCCCTTCAGCCTGG | 46260 |
| mRNA | ------------------------------------------------------------ | |
| genome | GCGACCAAGTGAGACCCTGTCTCAAAAGAAAAACAAAAAAACAAAAAACAAACCACTATT | 46320 |
| mRNA | ------------------------------------------------------------ | |
| genome | ATCGACTATATATTATTGTCTATGATCCCTCTGCTGTGCTGTCGAATACCAGGTCTTGGG | 46380 |
| mRNA | ------------------------------------------------------------ | |
| genome | CCCTTATTTCCATCACTGAGCAAACTTCACTCTGTTAAGCAGCAGGTGTGGGATTTCATC | 46440 |
| mRNA | ------------------------------------------------------------ | |
| genome | GTTATTCAGTAATTCACAATGTTAGAAGGAAATGCTGTTTGGTAGACGATTGCTTTACTT | 46500 |
| mRNA | ------------------------------------------------------------ | |
| genome | TTCTTCAAAAGGTTACTCTTTATTAGATGAGATGAGAATTAAAAATGGTAACTTACTTTA | 46560 |
| mRNA | ------------------------------------------------------------ | |
| genome | TATCTTTATAATTGAAGCCCACTAGACCTTAAAGTAGTTACCAGATGTTTTATGCATTTA | 46620 |

FIG. 1 LL

| | | |
|---|---|---|
| mRNA | ------------------------------------------------------------ | |
| genome | AATGGCCTTTTCTCTAAAATTAGAAAGTAACAAGGAAAGAAAATGCTTCGTTTCTATGCA | 46680 |
| mRNA | ------------------------------------------------------------ | |
| genome | ACCCTCTTGGTGACTAGTATGTGACTCTTAATGCAACCCTCATTGCACCCCCTCAGAATG | 46740 |
| mRNA | ------------------------------------------------------------ | |
| genome | GTGCCCCTCGGAGTTTGCGTGCTGCCCTGTGGAGGTTTGCTGAGCTGGCTCACCTGGTTC | 46800 |
| mRNA | ------------------------------------------------------------ | |
| genome | GGCCTCAGAAATGCAGGTAAGTTGTACACTCTGGATGTTGGTTTTTGTCGGGGGCCAGCT | 46860 |
| mRNA | ------------------------------------------------------------ | |
| genome | GCTACTGATCCTTTATGTCTCAGCTCAGATGTCATTTCAAAAGTCTGCTCTGCCCTCTCC | 46920 |
| mRNA | ------------------------------------------------------------ | |
| genome | AAATTGCAGTCGACCTTGCCCTGTTTATGTTTCCCTCATAGCACTAATCCATGTCAGAAA | 46980 |
| mRNA | ------------------------------------------------------------ | |
| genome | TTGTCACGTACAGTCTATCTGTGTGCTTGTTTATTTTCTATCCCACCCTTCCGCAAGAGA | 47040 |
| mRNA | ------------------------------------------------------------ | |
| genome | CTTATGGGATGTGTGCCCCAGGACAGCAGGGGTCTTACTGTCTTATGCTCTGTTGCAGCC | 47100 |
| mRNA | ------------------------------------------------------------ | |
| genome | CAGCAGCGATAACAGTGTCTGCACATAGTACTTGCTTAAAAGATACTTGCCAAATTGTTG | 47160 |
| mRNA | ------------------------------------------------------------ | |
| genome | AAGGTTGAGGTACCAATTTCATTATTGCTGACTATAGGAGTTATAGCAAAATATCCATTT | 47220 |
| mRNA | ------------------------------------------------------------ | |
| genome | GTCTGTTACATGAGTTAAAAATATGGTTGTTGCACTGTGAATAGTTTGGTTTAGTCAAAA | 47280 |
| mRNA | ------------------------------------------------------------ | |
| genome | CAGTTGTATCTTAACGGATTGAGAAACAAAAGCAGGACCACTTTTCATCAGCTCCCTCCT | 47340 |
| mRNA | ------------------------------------------------------------ | |
| genome | TCTCCTTAACCAGCAATACATGCTGATGCTGATATCCCATAGACCCTCAGCTCCATCCTG | 47400 |
| mRNA | ------------------------------------------------------------ | |
| genome | AGTCACTGGGAATGTGGTCTAAACCCTCACTATTAATATGAACTGAGTTTCAATAAGAAT | 47460 |
| mRNA | ------------------------------------------------------------ | |
| genome | CTTATATGGGTCGGGCATAGTGGCTCATACCTTTGATCCCAGCACTTCAGGAGGCCAAGG | 47520 |
| mRNA | ------------------------------------------------------------ | |
| genome | CAGGTGGATTGCTTGACCCAGACTAGGCAACATGGTGAAACGCCGCCTCTACAAAAAATA | 47580 |
| mRNA | ------------------------------------------------------------ | |
| genome | CAAAACTTAGCCAGGCATGGTGGTGCGTGCCTGTGGTCACAGCCACTCGAGAGGCTGAGG | 47640 |
| mRNA | ------------------------------------------------------------ | |
| genome | TGGGAGGATCACTTGAGCCTGGGAGGTGGAGGTCGTGTTGAGCCAAGATCGCACCACTGC | 47700 |
| mRNA | ------------------------------------------------------------ | |
| genome | ACTCCAGCCTGGGCAACAGAGTGAGACCTGTCTCAAAAAAACCAAAATCCAGAAAAGAAC | 47760 |
| mRNA | ------------------------------------------------------------ | |
| genome | TTATATGGCTGCAGAGGTATAATCACTAAGGAAATTTCCTTTTGTATAATCTTTTTTCTT | 47820 |
| mRNA | ------------------------------------------------------------ | |
| genome | TTACTATCATTTAAAAAAATGTGTTATATTTCTGAAGCAACACATCCAGGTTCTGCACAT | 47880 |

FIG. 1 MM

| | | |
|---|---|---|
| mRNA | ------------------------------------------------------------ | |
| genome | AGCAGCCAAAGTGACCTTAAAGAATATAACTGGGTCTTGTCATTCCCTTATTTAAACTCT | 47940 |
| mRNA | ------------------------------------------------------------ | |
| genome | TGTACCCATTTCCCAGTGCCGTTTAGATAGAGATTCCAGACTCGTCAATGGCTCTGTCAC | 48000 |
| mRNA | ------------------------------------------------------------ | |
| genome | CTCAGACACCCTGCATTGACTCATTAGTCTGATTAGAGTCAGGTTTTTCTTCCTCCTGAT | 48060 |
| mRNA | ------------------------------------------------------------ | |
| genome | GGTTTTTTTTCCCCCTTAGTTCTCAGCGGAACAGTCACTTCCTTAGGGAGGTTTCCCCA | 48120 |
| mRNA | ------------------------------------------------------------ | |
| genome | GCCACCCTCTGAGGCCGTGCTTGTTGCCAGACTCTGCCACTAGAGGGCAGGGCTGCACCA | 48180 |
| mRNA | ------------------------------------------------------------ | |
| genome | CTCCTGGCACCTCGCACCCGGCCTGCCCTGTCACTCTGTGTGTTGGGTGAATTCCTGTGA | 48240 |
| mRNA | ------------------------------------------------------------ | |
| genome | TCTGTGACTCACTGCTCTGTGTCCTACACATTCGGCTTTTCTTCTCTCCCCACAACCCCA | 48300 |
| mRNA | ------------------------------------------------------------ | |
| genome | TTTTATAATTCTCCTTTTTCAGGAAAGCTTTATTCCCATTTAAAAATTTTTGTTTTTAAA | 48360 |
| mRNA | ------------------------------------------------------------ | |
| genome | ATGGTATTTCTTACACTTATTTTCTAATTAAAAATGAGTGTTTTAAGAAGTATTATGAT | 48420 |
| mRNA | ------------------------------------------------------------ | |
| genome | TTACTGCAAATAATTTTTAAACCCAGCCTTTTAGATCCTCTGTGATCATAAGAGAAATGA | 48480 |
| mRNA | ------------------------------------------------------------ | |
| genome | AGGATGTCTCCCAACACTTGAGCTTCATCCACATTTCATCCTCCTGTTCTTTCAGCTGAG | 48540 |
| mRNA | ------------------------------------------------------------ | |
| genome | TTTTCCCCATCCCATTAGGGACTGTTGGAATATAAAACTGGCTTTTCCCTAACAGGGAAT | 48600 |
| mRNA | ------------------------------------------------------------ | |
| genome | GAATTGCTTCTGTTTCTCCTGAAGGAGAGCTGGAAGAATGACTTGCGTTCTTTTGCATAC | 48660 |
| mRNA | ------------------------------------------------------------ | |
| genome | ACAGGCCTTACCTGGTGAACCTTCTGCCGTGCCTGACTCGAACAAGCAAGAGACCCGAAG | 48720 |
| mRNA | ------------------------------------------------------------ | |
| genome | AATCAGTCCAGGAGACCTTGGCTGCAGCTGTTCCCAAAATTATGGCTTCTTTTGGCAATT | 48780 |
| mRNA | ------------------------------------------------------------ | |
| genome | TTGCAAATGACAATGAAATTAAGGTATGATTGTTGCCTCAGGTCACAAACATGCGAGTGA | 48840 |
| mRNA | ------------------------------------------------------------ | |
| genome | TGCTGTGAGTGAGTCTGTGGAGGGTGAGGGCTTCTGAACAGGGAGTCCTGTGGGAGTGCT | 48900 |
| mRNA | ------------------------------------------------------------ | |
| genome | TCTTGGGGTATGTTGTATGTCGTAATTTAGACTACCATCATTTGTGTTATTTTTGAGGCA | 48960 |
| mRNA | ------------------------------------------------------------ | |
| genome | CCTAAGGACTTCTTTCCACTTCTCATTTCTTACTGTGGGGTGAAGAGTTGAATTGGGAGA | 49020 |
| mRNA | ------------------------------------------------------------ | |
| genome | TGGTTTCTAGATGCAAATTGAAAAGGCATTTTTCCAGAGCAGATTTGTTTTCGGCGTACT | 49080 |
| mRNA | ------------------------------------------------------------ | |
| | rs10015979 | |
| genome | AGAGTGACTCTTTAACCTAGCTGCGGGAAGATGACTGTGCCAAGACTGCAGGTAGGAGAA | 49140 |

FIG. 1 NN

| | | |
|---|---|---|
| mRNA | ------------------------------------------------------------ | |
| genome | AGCTCACTGACGAGGCCTTGTGGGTCTGAACGTCCTGCAGCTATCAGAGCCTGTTGGCTT | 49200 |
| mRNA | ------------------------------------------------------------ | |
| genome | CCTGTTGTGCATTCCAACAAATCATCTTCAAACCCACTTTAGTGTTTTGTTTATAATGTC | 49260 |
| mRNA | ------------------------------------------------------------ | |
| genome | CAGAAATAGTGACCCTGTCACATGCTCTACAGATTACAGGATTCTTAGCCTCTTCCTTTT | 49320 |
| mRNA | ------------------------------------------------------------ | |
| genome | TGGTAGGTCAGTCCTGGGTTTGAGCCCAAGTGACCCTCCTGGGAGGTGATGATACACACT | 49380 |
| mRNA | ------------------------------------------------------------ | |
| genome | GGGTAGAGTGGAATCAGATGGACTTGGATTAGAATTCTGTCCTCTTTACTAGTTATTTTC | 49440 |
| mRNA | ------------------------------------------------------------ | |
| genome | CTCTAGGCAAACTGCCCAACAGCTCTAAGCTATTTCCTTCGTATTCTGAAAAATAAGCCT | 49500 |
| mRNA | ------------------------------------------------------------ | |
| genome | TAATGGGACCCATATAGGGCAACTCTGAGAGTAAAATAAAGGAATATGTGTTAGAGTGTA | 49560 |
| mRNA | ------------------------------------------------------------ | |
| genome | GCATAGTCACCCACGGGAAGGGCTTAGATGTTAGCTGCTACTGCTCTTATTAGCTGAATG | 49620 |
| mRNA | ------------------------------------------------------------ | |
| genome | ATTTGGAATAAACTGTTAGCCTCTCTCATGTTTTTTCTCTTGAGCTTCGAAGTTTTCTTG | 49680 |
| mRNA | ------------------------------------------------------------ | |
| genome | TTAATACTAAGGAGATATTCAAACTAGTCATGGGGTTTTGGAATGACGAAGGGAGATGAT | 49740 |
| mRNA | ------------------------------------------------------------ | |
| genome | GAATCTAAAGAATTTAGTGTAATATTTCTTCATGCTCAGTAAATGGTAGTTTCTGCTGCT | 49800 |
| mRNA | ------------------------------------------------------------ | |
| genome | GTTATTTTTATTACCATCTCTTTGGAATGGGAGTAGGTGCTCCTTTGTGGTCAGAGGCTG | 49860 |
| mRNA | ------------------------------------------------------------ | |
| genome | TGAGAGCTCCACAGCGCCAGTTTGCCCATCTGTACACTGGGGTCTGTTGAAGGCAGTCCC | 49920 |
| mRNA | ------------------------------------------------------------ | |
| genome | CTCTGTGATATCTCTGGCTGTCAGAGCTCAGATGATAGATGGTATTTTGTACTCTTAGT | 49980 |
| mRNA | ------------------------------------------------------------ | |
| genome | TCTCATCATTTTCATGATTTCGATCACCATTTGAGTATGATGATGCTAACACTTTGTTGA | 50040 |
| mRNA | ------------------------------------------------------------ | |
| genome | ACGTAGAATCCGTTAATTACTTCCTTCCTGAACCTTTGGCATTAAAAAAAATCTATTCTG | 50100 |
| mRNA | ------------------------------------------------------------ | |
| genome | CTACCTCTCTGCTCATTTATGGTTATTCAAATTTATTATCAAGAGCCTGGTACAGTGGCT | 50160 |
| mRNA | ------------------------------------------------------------ | |
| genome | TGTGCCTATAATTGTAGCTACTTGGGAGGCTGAGGTAGGAGGATTGCTTGAGGCCAGGAG | 50220 |
| mRNA | ------------------------------------------------------------ | |
| genome | TTTGAGACCAGCCTGGGCAAGATAGTGAGACCCTATCTCTAAAAAAACTGAAAAAAAATT | 50280 |
| mRNA | ------------------------------------------------------------ | |
| genome | AGCTGGACATGATGGCATGTGCCTGTGGTCCTAGCTACTCAGGAGGCTGAGACAGGAGGC | 50340 |
| mRNA | ------------------------------------------------------------ | |
| genome | TCGGTTGAGCCCAGGAGTTGGAGTTCGAGGCTACACTGAGCTGTGATTGTGCCACCACAC | 50400 |

FIG. 1 OO

| | | |
|---|---|---|
| mRNA | ----------------------------------------------------------------- | |
| genome | TCCAGCATGGGTGGTAAAACAAGATGCCATTTCTTAAAAAAAAAAAATATATATATATAT | 50460 |
| mRNA | ----------------------------------------------------------------- | |
| genome | ATTATCAATGAAATTCAGTAGTACCAACAGGATTATAAACAAAGATAGTAGTTCCCTTCC | 50520 |
| mRNA | ----------------------------------------------------------------- | |
| genome | TACTTTTTCTCTTAATCCTTGTGTCTCACAGGCAAACATAACTCTTAGTATTTCTTCCAA | 50580 |
| mRNA | ----------------------------------------------------------------- | |
| genome | TATTTACTTTCATGTTTCTTTCTTTCTTTCTTTTTTTTCTTTGAGATGGAGTTTTGCTC | 50640 |
| mRNA | ----------------------------------------------------------------- | |
| genome | TTGTTGCCAAGGCTGGAGTGCAATGACGCAATCTTGGCTCACCACAACCTCTGTCTCCCG | 50700 |
| mRNA | ----------------------------------------------------------------- | |
| genome | GGTTCAAGCGATTCTCCTGCCTCAGCCTCCTAGTAGCTGGGATTACAGGCATGCATCACC | 50760 |
| mRNA | ----------------------------------------------------------------- | |
| genome | ACGCTCGGCTAATTTTGTACTTTTAGTAGAGATGGGGTTTCTCCGGGTTGGTCAGGCTGG | 50820 |
| mRNA | ----------------------------------------------------------------- | |
| genome | TCTCGAACTCCTGACCTCAGGTGATCCTCCCACCTCAGCCTCCCAAAGTGCTGGGATTAC | 50880 |
| mRNA | ----------------------------------------------------------------- | |
| genome | AGGCGTGAGCCACTGCGCCCAGCAACTTCCACATTTCTAAATAACATGCTTCTACTGCTA | 50940 |
| mRNA | ----------------------------------------------------------------- | |
| genome | TTTTTTTTTTCAATTTTAGACATTTTTTTACTTTCACTATAGTTCTATCAGAATTCAGTG | 51000 |
| mRNA | ----------------------------------------------------------------- | |
| genome | TGTACGTTATTATGCCTAAGTAAATAGTCATGGTTGCTTACGTATTATATTTCTTTGATT | 51060 |
| mRNA | ----------------------------------------------------------------- | |
| | rs7691627 | |
| genome | GT[G]TTTCTTATTTGATGAGAAAGCTGTGTTTTTTGCTCTGGGTTGAAACTGGAGAGAGGA | 51120 |
| mRNA | ----------------------------------------------------------------- | |
| genome | CCTGGGGAGGAGGAGGAGGACAGATGAAGTTGGTGACTGTACCTTCATGGCCATAGCTGG | 51180 |
| mRNA | ----------------------------------------------------------------- | |
| genome | GTTCTCAGCACCCGGGGATCTGCTGATCACCTACTCATAGGCCAGGCCCCTATCGAAGTT | 51240 |
| mRNA | ----------------------------------------------------------------- | |
| genome | CTAGGTGACCCAGTGCTGGGGACGGGGGGGCCACCTGCAAGGTCTAATCATGGAGGTGGG | 51300 |
| mRNA | ----------------------------------------------------------------- | |
| genome | GGCTACAGTGTTGGCTTGTGCTGGGGCCAGCATCCTTAGGAAGGCATCTTGGAGGTGGAG | 51360 |
| mRNA | ----------------------------------------------------------------- | |
| genome | GAGACAGCCGCCCACTTCTTGATTGGGGCCTTCAGCAGCACCAGCTTCTTGGGCAGGCTG | 51420 |
| mRNA | ----------------------------------------------------------------- | |
| genome | GTGCTGGCTTTCATCACCATGTCGTGTTCAATCTTCTTCCAGATCCTGACTTCTAGGTTC | 51480 |
| mRNA | ----------------------------------------------------------------- | |
| genome | AGCTTTCCTCAGACCCTGGTTCCTTTCAGAGGCCATTGCTGCTGCCTTGCTCTTTGCTGG | 51540 |
| mRNA | ----------------------------------------------------------------- | |
| genome | CTTGTGCCTTGATTATATGTCTTTGTACAACTTTTTGTTTTCCTGGAGTTAATCTTCACA | 51600 |
| mRNA | ----------------------------------------------------------------- | |
| genome | TCTGTTTTCTTGGAGTTAATCGTTACCTCTATATCGCTTGCTTATTATTCTTTGGCCTTT | 51660 |

FIG. 1 PP

| | | |
|---|---|---|
| mRNA | ------------------------------------------------------------ | |
| genome | TTGTCTTCTCACACCTTCCAACTTCTTTGTAATATGTGTTTAGTACAATTTTTCATGACA | 51720 |
| mRNA | ------------------------------------------------------------ | |
| genome | GGTAGTTTACTGAATCAGTTTTTCCCCAGTGTGGTCATCCAACTTGAGTTATCCAGCTCT | 51780 |
| mRNA | ------------------------------------------------------------ | |
| genome | CTGCCCCAGTCTGGGCAGGTTGATCTTCAGGTCTGTAGTACACTTGTATCCTAGGACTTC | 51840 |
| mRNA | ------------------------------------------------------------ | |
| genome | TCTTTGCCATTAGCCTGGAATTTCCTTTGCAGTTCTCCCGTTGGATGCCCAGTTCCTAGA | 51900 |
| mRNA | ------------------------------------------------------------ | |
| genome | TGCCATATGTTTTCTATCGTCTAGTAGCTTCCTGAGAGAAGATGAATGGGAGGGAAATT | 51960 |
| mRNA | ------------------------------------------------------------ | |
| genome | GTATGAGGTTTTGCATTCATAAAAATGCCATTTTTTTCCTGTACACTTGGCTGGGTATG | 52020 |
| mRNA | ------------------------------------------------------------ | |
| genome | GTGTTCTGGGGTAGAAATCATTTTCCCTCAGAAATGCAAAGTCTTTGCCCTGTTGTCTTA | 52080 |
| mRNA | ------------------------------------------------------------ | |
| genome | AAATCTCCAACGTGACCCGATTCCTTAACCTATGAATGTACTTTTCTTTGGAAGCTTTCC | 52140 |
| mRNA | ------------------------------------------------------------ | |
| genome | ATTTTTGGGGAGGTGAAGTGCTAGGTACTTAGTAGGCCTTTTAATTTGGAAACTTACATC | 52200 |
| mRNA | ------------------------------------------------------------ | |
| genome | CCTTCAGTTCTGGGAAAATTTTCTTAACATTTCTCTGAGAAGTTCTTGCCTTTTATTTTC | 52260 |
| mRNA | ------------------------------------------------------------ | |
| genome | TGTGTTCTCTCCTGAAATTGGTTAGTTGGATGTTGGTCCTCCTAGATTGACTCACATCTT | 52320 |
| mRNA | ------------------------------------------------------------ | |
| genome | ACCTTTTTCTTTTCTTTTTCTGGTACTTTTTAGATATCCATCTCAAACTCTTCTATTCAT | 52380 |
| mRNA | ------------------------------------------------------------ | |
| genome | TGTTATGTTTTTAACTTCTTTCTTTTCTTTGTCTCTTGATGGGGTCTTGCCCTGTTGCCC | 52440 |
| mRNA | ------------------------------------------------------------ | |
| genome | AGGTTGTGGTGCAGTGGTGCGATCATAGCTCACTGCAGCCTCAAATTCCTGGGCTCAAGC | 52500 |
| mRNA | ------------------------------------------------------------ | |
| genome | AGCTGTTCTGCCTCACCCTCCCAAGTAGTTGGGACTACAGGTATGCACCACCACGTCCAG | 52560 |
| mRNA | ------------------------------------------------------------ | |
| genome | CTATTTTCTTTACTTTTTTTTTTTTTTTTGAGATGGAGTCCTACTCTGTCGCCCAGGC | 52620 |
| mRNA | ------------------------------------------------------------ | |
| genome | TAGAGTGCGGTGGTGGGATTTTGGCTCACTTAAGCCTCTGCCTCCCAGGTTCAAGCAGTT | 52680 |
| mRNA | ------------------------------------------------------------ | |
| genome | CTCCTGCCTCAGCCTCTCAAGTAGCTGGGATTACAGGTGTGCACCACCATGCCCGGCTAA | 52740 |
| mRNA | ------------------------------------------------------------ | |
| genome | TTTTTGTATTTTTAGTAGAGCCAGAGTTTCACCATGTTGGCCAGGCTGGTCTCGAACGCC | 52800 |
| mRNA | ------------------------------------------------------------ | |
| genome | TGACCTCAGGTGATCCGCCTGCCTTGGCCTCCGAAAGTGCCGGGATTACAGGCGTGAGCC | 52860 |
| mRNA | ------------------------------------------------------------ | |
| genome | CATCATTAGATCTTTAAATACCAGTATCTATAAGTCTTTTCCTCTTGAGTCAGCTAGTAT | 52920 |

FIG. 1 QQ

| | | |
|---|---|---|
| mRNA | ------------------------------------------------------------ | |
| genome | CCCTGGAAGGAAATTACTCATTTTCCTGCTTGGAGGCTATAAGCTTGGCTATGTTTATCC | 52980 |
| mRNA | ------------------------------------------------------------ | |
| genome | TGCAACCGGGGACTGGAAGGGAGGGGACTGACAGTGTTGCTGGTCAGGGTGCCCTCTTAC | 53040 |
| mRNA | ------------------------------------------------------------ | |
| genome | TTTTTGTTTTCTGTGTGCATCTCACGTCTGTCCTCAGCCTATGTAAACACCTCTTGAGAT | 53100 |
| mRNA | ------------------------------------------------------------ | |
| genome | TATCCCTCTCAATCTTTGCCGGAGGTGGGGGAGGGGCTGCTTCCTGGGCTGCCTTGGATT | 53160 |
| mRNA | ------------------------------------------------------------ | |
| genome | GGAGGGAAGACCTCAGGTGAGTGGGTGGGAATTTGCCCAAGGAGCCATGAGACCAGCCAC | 53220 |
| mRNA | ------------------------------------------------------------ | |
| genome | TATTTCACCCTCTCCATCCCTCCACTTTCAGATGTATGTGGCGCCTCCAAAGCCCGAGCT | 53280 |
| mRNA | ------------------------------------------------------------ | |
| genome | CTTCTTGGCGTCTGTGGCTTCAATAAGCTTGCTTTTTGCTGGTATCCCTCCTACCCTCCC | 53340 |
| mRNA | ------------------------------------------------------------ | |
| genome | CTGTCCCCAGCAAAGCTTGCATTTGAACTTCTTCCTACGGGCTAACAAATCAGTCAGTTA | 53400 |
| mRNA | ------------------------------------------------------------ | |
| genome | TGTAGCTCTTGTTACTTTTTAGCTTCCGAAGTTTTGTTGACACCCGTAGTCTGCTAATGT | 53460 |
| mRNA | ------------------------------------------------------------ | |
| genome | CCCTGTTCTGTTCTTTCTGTTCGTGTAAATATATGCTTTATACAACTTCTTTACATGATT | 53520 |
| mRNA | ------------------------------------------------------------ | |
| genome | TTTGTGGGGTTTCTGGGTAGCAGAGCTTCACAAGTTCAATCCAGCGTGTTGGATTAGAAA | 53580 |
| mRNA | ------------------------------------------------------------ | |
| genome | TCTCCCACCCTCTGGTTTATTCTTATTCTCAAAATTACCTGCCAAACACTGATACTCCCT | 53640 |
| mRNA | ------------------------------------------------------------ | |
| genome | TGTTTTTCCTTTTCCTGACAGGAAATGTACATACCATACAGGACAGAAATCATTAGTGTA | 53700 |
| mRNA | ------------------------------------------------------------ | |
| genome | TCCCTTGGTGAATAACCACAAAGTGAACTTAACCCTTGTAACCGCCACCCAGGTCAAGAC | 53760 |
| mRNA | ------------------------------------------------------------ | |
| genome | AGAATATTACCAAGCACTCAGAAGCCTCTCCCCTATTCCCCCGTCACTGCTCCTGCCTTC | 53820 |
| mRNA | ------------------------------------------------------------ | |
| genome | CTCCCCAAGGTCATGACTGCTGGCTTCTAATTCCAGAGTCTGTTTTTAAATTCTGTGTAC | 53880 |
| mRNA | ------------------------------------------------------------ | |
| genome | ATAGACCATGGATTAAGTGTTCTTTTTGTCTGGTTTATTTTGGTCGACATTAAGTTCATG | 53940 |
| mRNA | ------------------------------------------------------------ | |
| genome | AGAGTCTTCTATATTATCGTGTGTATTAGTATTCCTGTAGTTTTAGGAGCTTCATAGCAT | 54000 |
| mRNA | ------------------------------------------------------------ | |
| genome | TCCATTGTAGGGATATACCACAGTTTATTCATTGTATTATCACTGGGTTGTTTCTAGTTC | 54060 |
| mRNA | ------------------------------------------------------------ | |
| genome | TTGGCTATTGCGAGCAGTGCTACTGTGACCACTCTTAGGTGTGTCTTTTGGAGTACATGT | 54120 |
| mRNA | ------------------------------------------------------------ | |
| genome | GCAGGTTTCCATCTTGCACAGCTAGAGGTGGAGTTGTTGGGTGATAGGGTGTGTGCATCT | 54180 |

FIG. 1 RR

| | | |
|---|---|---|
| mRNA | ------------------------------------------------------------ | |
| genome | CAGCTGCAGTAGAAACTGCCAAATAGCTTTCCTTGAGTGCTTGTACCAGCTCACCCTTTT | 54240 |
| mRNA | ------------------------------------------------------------ | |
| genome | GCCACTGTGTATGGGGATTCCAGGAGCTCTGGTCCTCGCTAGCACTTGGAATTGCTGATG | 54300 |
| mRNA | ------------------------------------------------------------ | |
| genome | CTTTTACTCTTAGCCTTCCTGATGGGTGTTTTCTGGAATCACATTATGATTTTAATTTCC | 54360 |
| mRNA | ------------------------------------------------------------ | |
| genome | ATTCCTTAAAGTACCCTTGGCTCTGAAGTTTAATGATTCATGCATCTCTTCCCTTTTGAA | 54420 |
| mRNA | ------------------------------------------------------------ | |
| genome | GTACTCTTACAGGTATGTTGTGCATGTGTTGAAAAGTGGCACTATCTATTCTAAAATACA | 54480 |
| mRNA | ------------------------------------------------------------ | |
| genome | GTAT[G]CCTCCTCTGTGTTTGAACAGTTGTAGCGTGGCCTTGGGGCCTCCTGTTAGCTGGC (rs2798235) | 54540 |
| mRNA | ------------------------------------------------------------ | |
| genome | TTGGAGAAGGGATTCTTGGGATTGTAGAGATTAGACCTGAGGAGGCCCCTTGGAGCTCTC | 54600 |
| mRNA | ------------------------------------------------------------ | |
| genome | TGACTAAATTTTATTCTTTATTATTCCAAACTATTTAAGCTCACCGTGTGCTGACTCATC | 54660 |
| mRNA | ------------------------------------------------------------ | |
| genome | ATAATAATGAGTAGCTCTCATTGTGCTTGTCTATTTGGACTCATACAATGATTTTTTTT | 54720 |
| mRNA | ------------------------------------------------------------ | |
| genome | TTTCTTTGAGACAGAGTCTTGCTCTGTTGCCTAGGCTGGAGTGCAGTGGCACAATCTCGG | 54780 |
| mRNA | ------------------------------------------------------------ | |
| genome | CTCACTGCAGCCTCCACCTCCCAGGTTCAAGTGATTCTTGTGCCTCAGCTTCTCAAGTAG | 54840 |
| mRNA | ------------------------------------------------------------ | |
| genome | CTGAGACTGCAGGTGCGTACCACCATGCCTGGCTAATGTTTGTATTTTTAGTAGAGACGG | 54900 |
| mRNA | ------------------------------------------------------------ | |
| genome | GGTTTCACCATGTTGGCCAGGTTGGTCTCAAACTCCTGACCTCAAGTGATCTGCCTTCTT | 54960 |
| mRNA | ------------------------------------------------------------ | |
| genome | CAGCCTCCCAAAGTGCTGGGATTACAGGTGTGAGCCACTGAGCTTGGCCAAAGTAGTTTT | 55020 |
| mRNA | ------------------------------------------------------------ | |
| genome | TTAAGATGTTAGTATCTTTTCTTGCAGCTAAAAAAGTTTGTCAGAGATGATTCTACTTTG | 55080 |
| mRNA | ------------------------------------------------------------ | |
| genome | TTCTCCAGGTGTTTTCTCAGGGAGAAATTGGAGGCAGTAAGCCACTGGGGGAGTCCTGTG | 55140 |
| mRNA | ------------------------------------------------------------ | |
| genome | GCTGGGGGTGGGGTAGTCCTGTGGCTCCTTGTCAGGGAGTCCTGTGGCTGGCAAGGAGA | 55200 |
| mRNA | ------------------------------------------------------------ | |
| genome | GAAGTCCTGTGGCTGGGTTGGGAGGGAGTCCTGTGGCTGGGGTCTCATCCTGTGCCTAAC | 55260 |
| mRNA | ------------------------------------------------------------ | |
| genome | AGTGTCCAGAGGTGCCGAGACCAGCTCAGTCGGGGAGACCCTAACCCAGCAGCGCTAGAG | 55320 |
| mRNA | ------------------------------------------------------------ | |
| genome | GAATTAAAGACACACACACAGAAATATAGAGGTGTGAAGTGGGAAATCAGGGGTCTCACA | 55380 |
| mRNA | ------------------------------------------------------------ | |
| genome | GCCTTTAGAGCTGAGAGCCCTGAACAGAGATTTACCCACATATTTATTAATAGCAAACCA | 55440 |

FIG. 1 SS

| | | |
|---|---|---|
| mRNA | ------------------------------------------------------------ | |
| genome | GTCATTAGCATTGTTTCTATAGATGTTAAATTAACTAAAAGTATCCCTTATGGGAAACGA | 55500 |
| mRNA | ------------------------------------------------------------ | |
| genome | GGGGATGGGCCGAATTAAAAGAAGAGGTTGGGCTAGTTAACCGCAGCAGGAGCATGTCCT | 55560 |
| mRNA | ------------------------------------------------------------ | |
| genome | TAAGGCACAGATCGCTCATGCTATTGTTTGTGGCTTAAGAATGCCTTTAAGCGGTTTTCC | 55620 |
| mRNA | ------------------------------------------------------------ | |
| genome | ACCCTGGGTGGGCCAGGTGTTCCTTGCCCTCATTCCTGTCAACCCACAACCTTCCAGTGT | 55680 |
| mRNA | ------------------------------------------------------------ | |
| genome | GGGCATTAGGGCCATTATGAACATGTTACAGTGCTTCAGAGATTTTGTTTATGGCCAGTT | 55740 |
| mRNA | ------------------------------------------------------------ | |
| genome | TTGGGGCCAGTTTATGGCCAGATTTTGGGGGGCCTGCTCCCAATACAGAGGTCTCGTGTA | 55800 |
| mRNA | ------------------------------------------------------------ | |
| genome | AATTCCCTGGGAGGCGATAAGCCTCTGAGAAACAGACTATGCTAACCACGCCATGAAAGA | 55860 |
| mRNA | ------------------------------------------------------------ | |
| genome | GAAACTTATTTATAAATCAGATGCCAGTTACTAGTTTACTGCTTATTTGCCCAGGCGTAG | 55920 |
| mRNA | ------------------------------------------------------------ | |
| genome | CTCTGACAGAGTCCCCGACTCATAGTGCTTGCTCAGTGCATGCTGAACAATGATTGGAAT | 55980 |
| mRNA | ------------------------------------------------------------ | |
| genome | CAAGTCATGGCTCAGAGCATAGTTTTGAATAATGGGAAATGGATGTTCTTAAGTAACATA | 56040 |
| mRNA | ------------------------------------------------------------ | |
| genome | GTCACCAAGATAATGCGACTAGCTGGGTCACCCCTTTTCAATTTTAGGATATTTTTATCA | 56100 |
| mRNA | ------------------------------------------------------------ | |
| genome | AGATTTAAATGGCCATCATTAGAGTTATAGCACTTTCTCCTTTGGATTGTCCTAGAGGCC | 56160 |
| mRNA | ------------------------------------------------------------ | |
| genome | CATGAGAAAGTATTCCCTAATTTCTTAGGAGAACAGTTTGTGGGTAGTATGCGGTCATGT | 56220 |
| mRNA | ------------------------------------------------------------ | |
| genome | CCAGTTAAATTGCAGATATTTCCGATCGAAGATGTTCCAGTCCTGAGAACTTCGTGACAT | 56280 |
| mRNA | ------------------------------------------------------------ | |
| genome | TAGCAGGACTTCTACAAGCCATCTCTTAGGGTGGGGCATTTACTGCAGTTGGCTAGTACT | 56340 |
| mRNA | ------------------------------------------------------------ | |
| genome | CTTTTCTCCTTAACTTTGTCATTTGTTGATTTTTTTTAACTGTCCCCAAATACTGTGGG | 56400 |
| mRNA | ------------------------------------------------------------ | |
| genome | CAGAGTGTATCTAGAATTGAGGCCTCCACCATTGCGGAGAGGACATGGATGCTGAGCAGT | 56460 |
| mRNA | ------------------------------------------------------------ | |
| genome | CCCCTGAGTGAAGGTTATAAAGAAGCAAATAGACTACACATGTCTGTAAACTGCTCTTGA | 56520 |
| mRNA | ------------------------------------------------------------ | |
| genome | GTGTCCCAAATTTGGGGTACTTCAGTTCAGCTGTAGGAAAAGCCTCAAACTGTTTATACT | 56580 |
| mRNA | ------------------------------------------------------------ | |
| genome | TTGCAAGAATTGGAAACTTCTAATTCACGTTAAGTTTTATGTAATACATGATAAGCTTCA | 56640 |
| mRNA | ------------------------------------------------------------ | |
| genome | TAGGAGCTTCATCTTTTATCTACTTGGACTTTTGCTTCCGTAGGTTTTGTTAAAGGCCTT | 56700 |

FIG. 1 TT

| | | |
|---|---|---|
| mRNA | ------------------------------------------------------------ | |
| genome | CATAGCGAACCTGAAGTCAAGCTCCCCCACCATTCGGCGGACAGCGGCTGGATCAGCAGT | 56760 |
| mRNA | ------------------------------------------------------------ | |
| genome | GAGCATCTGCCAGCACTCAAGAAGGACACAATATTTCTATAGTTGGCTACTAAATGTGCT | 56820 |
| mRNA | ------------------------------------------------------------ | |
| genome | CTTAGGTAAGGTGGAGGCATATGAGTGGAAGAGTCTCCAGCATGTACTCAAGATAGACCT | 56880 |
| mRNA | ------------------------------------------------------------ | |
| genome | TTGAAATAAATAAAACCAGATGATCCCTCAGCTTCTAGACCAGGCTATTTGGCACTGGTT | 56940 |
| mRNA | ------------------------------------------------------------ | |
| genome | GATTGAATGTGAACTGCACTGGGGCTGCTGTGAGCCCGCATGGGTCTCTGTGACCCTGCA | 57000 |
| mRNA | ------------------------------------------------------------ | |
| genome | GATGCAGCCGTGCCCAGGGACTGGGCAGTGGGTGTGGGCTGGTGTGAGCCCTGTCTGCCA | 57060 |
| mRNA | ------------------------------------------------------------ | |
| genome | CCCAGGGCCTGGCCCTCTGTCTGTGTCGGCCATGACTATGGTGAGTCTTGTAGGCTTGAG | 57120 |
| mRNA | ------------------------------------------------------------ | |
| genome | ACTGTGCCTCGGGTTCCTGCGGGTTCTCTGTAGGTCAGTTGACAGTTTCTCCTGTTGTTT | 57180 |
| mRNA | ------------------------------------------------------------ | |
| genome | GGGTAACTGTGGAAACGAACACTGGCAAGTGCTGAAGCGAGCATGTGGACGTGCGATATG | 57240 |
| mRNA | ------------------------------------------------------------ | |
| genome | AAATAACGACCTGGCTTTCAAAGGCAGTGAGGCTCTCTGGAAAGGACCTTGCTGAGCTAG | 57300 |
| mRNA | ------------------------------------------------------------ | |
| genome | GGATGTGGGTGTGTAGCCATTCCCAGTGGGCCTCATGGCGTACTCGTTCATGATCATGTT | 57360 |
| mRNA | ------------------------------------------------------------ | |
| genome | TGTGCCATCTTGATCTCTCAGGATCTCTTCTTTTTTAACAGATTAAGCCGGGAATCTCCA | 57420 |
| mRNA | ------------------------------------------------------------ | |
| genome | AACAGTGAGTCAGATGTTAAGATGTCTTGCTTCCACCCCCACAGGCTTACTCGTTCCTGT | 57480 |
| mRNA | ------------------------------------------------------------ | |
| genome | CGAGGATGAACACTCCACTCTGCTGATTCTTGGCGTGCTGCTCACCCTGAGGTATTTGGT | 57540 |
| mRNA | ------------------------------------------------------------ | |
| genome | GCCCTTGCTGCAGCAGCAGGTCAAGGACACAAGCCTGAAAGGCAGCTTCGGAGTGACAAG | 57600 |
| mRNA | ------------------------------------------------------------ | |
| genome | GAAAGAAATGGAAGTCTCTCCTTCTGCAGAGCAGCTTGTCCAGGTAGGAGCACAGGGTTT | 57660 |
| mRNA | ------------------------------------------------------------ | |
| genome | ACTCTAGGCCCTGCATGTGAATGACTGACATTCAAAGAACCGATTAATTTGGAAGAGAAG | 57720 |
| mRNA | ------------------------------------------------------------ | |
| genome | CGGCAGAACCGAGAGTTAGAGGTGTGGACTCTGGAGCTGCGCTGCTCGTTTCCAACCCTA | 57780 |
| mRNA | ------------------------------------------------------------ | |
| genome | GGTGCTGACCTCTAGCTGTCTTCCCTCTGTATGTCCCTGTCACCGTGAGTCAAATGCGGG | 57840 |
| mRNA | ------------------------------------------------------------ | |
| genome | TGATGCCTCCTCAGGTGCCGTGTTACCTAAGCCTCTCAGAGACCACTGCTACCCTGTTTC | 57900 |
| mRNA | ------------------------------------------------------------ | |
| genome | TAAAACCAGAGGTCACGATATGTGTTCATCCACCCAGTAAATACTGATTGAGCACCCACT | 57960 |

FIG. 1 UU

| | | |
|---|---|---|
| mRNA | ------------------------------------------------------------ | |
| genome | GTGTGCTAGGCTCTGGGATAGGGGCTGGGTATACAATGGTGAGTATTTCAGCTGCAGCTT | 58020 |
| mRNA | ------------------------------------------------------------ | |
| genome | CTGCCCCGTGGAGGCTGTGGCCTAGCACACTGGTCTAGGCACGGTGGTATATGCTCACTC | 58080 |
| mRNA | ------------------------------------------------------------ | |
| genome | AAGGAGATAGGGACGTGGTCGTTTGGGGTGTCGGAACAAAATGTCGGAACTTCTCTTTCC | 58140 |
| mRNA | ------------------------------------------------------------ | |
| genome | AATGCAGAGAAACCTTGCAGTAATTCTAATGTACTGTGATTGGCAGTTGACTTCAGTTCT | 58200 |
| mRNA | ------------------------------------------------------------ | |
| genome | TTGTAGCACGCTTACTCAGGTTATTTCACTAACTATGTAACCATGCAGCCTCATTTTAAG | 58260 |
| mRNA | ------------------------------------------------------------ | |
| genome | CAATTGGATTTTTTGAACTTTACTTAAAATGTTATGTCAGGGTTTTTATTGTGCTTAATG | 58320 |
| mRNA | ------------------------------------------------------------ | |
| genome | TGTGCCATTTAGCTAAGTTTTGTAGGATACGAAATTGTAAGTGGCTTAAAATGATTCTTA | 58380 |
| mRNA | ------------------------------------------------------------ | |
| genome | ATAGAATCATGAATTGAAGATAATGCTAATAATTTAAGCACTGAGTTAGGTAGTGTTTGT | 58440 |
| mRNA | ------------------------------------------------------------ | |
| genome | AAAATGCTTAGAATGCTTCCTGGCACATGTTAAGGCCATGTAAGTGCTGCGTGTTGATAA | 58500 |
| mRNA | ------------------------------------------------------------ | |
| genome | ACAGCTGAGCAAAAGTGGACTCTTAAGAAAGTATTGGGGCTGAGAGTTCTGTTCCAACCA | 58560 |
| mRNA | ------------------------------------------------------------ | |
| genome | GCTGCCCTTTGGTTATTTTCAGAATAAAAGCAGAGTCTCATGGGATATGACATTTATAT | 58620 |
| mRNA | ------------------------------------------------------------ | |
| genome | TTCCTTCACAAAAAACACTGCTGAGTGTTTTGTTGAGTAAAAAGGGTGTAGCCATGGTAA | 58680 |
| mRNA | ------------------------------------------------------------ | |
| genome | TAATACATTTAAAATATAGTTTATTTCATCTTTACCTTGCCTTGTTTTTTTTTAAGCTA | 58740 |
| mRNA | ------------------------------------------------------------ | |
| genome | GCTTTTTATTGAGAATTCCACACATACAAAAGTATCAACTCATGACCAGTTATATTTCAT | 58800 |
| mRNA | ------------------------------------------------------------ | |
| genome | TTATAATCCTACTTCTCCCTTTTTTATTATTTGAAAGCAAACCCCAATTATCCTCTTAT | 58860 |
| mRNA | ------------------------------------------------------------ | |
| genome | TTCATCTATAAGTATTTCAGTATCTCTATAGATGAGGACTCTTCTTTATTTTTAAAACTT | 58920 |
| mRNA | ------------------------------------------------------------ | |
| genome | TATTTTAAAATGATGGTCAGATGCAGTGTTCATGCCTGTAATCCCAGAACTTTGGGAGG | 58980 |
| mRNA | ------------------------------------------------------------ | |
| genome | CCAAGCTGGGCGGATCACTTGAACCTGGGAGTTTGAGACCAGCCCGGGAAACATGGCGAA | 59040 |
| mRNA | ------------------------------------------------------------ | |
| genome | ACCCCATGTCTTAAAGAAAAAAATCAGCCAAGTGTGGTGATGCATGCCTGTAGTCCCAGC | 59100 |
| mRNA | ------------------------------------------------------------ | |
| genome | TACTTGGGAGGCTGAGATGGGAGGGTCACATGAGCCTGGAAGATCAAGGCTGCAGTGATC | 59160 |
| mRNA | ------------------------------------------------------------ | |

FIG. 1 VV

| | | |
|---|---|---|
| genome | CATGATTGTACCACTGCACTCCATCCTGGGTGATGGAGCAAGATTCTGTCTCAAAAAAAC | 59220 |
| mRNA | ------------------------------------------------------------ | |
| genome | AAAACTGCAAAACAACGTCACAAAACAGTGCCATTGTTAGACCTGAAAATATTAAACATT | 59280 |
| mRNA | ------------------------------------------------------------ | |
| genome | TCCTACATCAAATACCCACCAACTCATTATCAATTTTTCTCTCTACTCTTTTGGAATCAG | 59340 |
| mRNA | ------------------------------------------------------------ | |
| genome | CATCTAAATAAAATTGGTCGATAAGGATTGTAAATCTCTTTGATGAACTGGTTCCCCTCC | 59400 |
| mRNA | ------------------------------------------------------------ | |
| genome | ATCCCAGTTTTTTTCCCTTAGAGTTCATTTATTGAGAAACCAGATTGTTTGTCTTCTAAG | 59460 |
| mRNA | ------------------------------------------------------------ | |
| genome | TTTTCCTGTGGTCTGATATACTGCTTCCATCTCCACTGTGTAAATTAACACCTTTTTCTC | 59520 |
| mRNA | ------------------------------------------------------------ | |
| genome | TTCTCTGTATTTCCTGTAAATCAATAATTGGAGGAAAAGCCTTGTCAGATTTAGTGTATA | 59580 |
| mRNA | ------------------------------------------------------------ | |
| genome | TTTTATATCTGAGTCCAGTATTTCTTATATAATATTTAAGATAAGTGTACTCTTTTAAA | 59640 |
| mRNA | ------------------------------------------------------------ | |
| genome | AAGTATTGAAACTATATGCTCAATTTTTTTTAACTGATGCTTTTAAGAAGGCTGCTTGAT | 59700 |
| mRNA | ------------------------------------------------------------ | |
| genome | CATAAAAGTTTAGAGATCATTGGTCTGATGGGAAAAGCAAATAATTACTAAACCGTTTAG | 59760 |
| mRNA | ------------------------------------------------------------ | |
| genome | CAAGGTTGAGGTGCACATGGTGGGGCCTGGAGAAGTTCAGTCATGAGCCGTCACTTATGG | 59820 |
| mRNA | ------------------------------------------------------------ | |
| genome | GCACGTGGAATCTGACCCGGCACAGAGTTGGGAGAAGACAGGAGCTTTATAGACAGAAAA | 59880 |
| mRNA | ------------------------------------------------------------ | |
| genome | TGTGGTCTTTGCTAAGTCCCAGGAGTGAAAGGGTGAGACAGTGCTCACAGCACACGAGTG | 59940 |
| mRNA | ------------------------------------------------------------ | |
| genome | TGGGTGCGTAGACAGAGCAAGGGTGGGTCCTGAAAAGGCCTGCAGGCTTTCTCATAGATT | 60000 |
| mRNA | ------------------------------------------------------------ | |
| genome | AGCAAGAGTGCTGGTTACGGAGGTTTCTAACATTTGTGAACAGATCGAAACTGTGTTAAA | 60060 |
| mRNA | ------------------------------------------------------------ | |
| genome | TTGGGATTGCAGTAATCCTGGAAGGACAGGGATAGAGGGTGAAGGGGAAAAAAGGGTATG | 60120 |
| mRNA | ------------------------------------------------------------ | |
| genome | GATGTGAGACTTAATTGCTGATTTTCTTAAGACCTTTCTCCAAAGTAAATAAATGATGTG | 60180 |
| mRNA | ------------------------------------------------------------ | |
| genome | GCACATTTTTGAACTGGCAAATTCTAAACTCTAGATATGATTATCTCTATAACATATCTT | 60240 |
| mRNA | ------------------------------------------------------------ | |
| genome | ACTCCATCTTCTTTTGACTAAAAACTGTTCTTAATTAAATTACCATGAGACGTTCAATTC | 60300 |
| mRNA | ------------------------------------------------------------ | |
| genome | AGCAAATGTAGTTTGGCTAACCATATTTAATTAGAATTTAATATAATCCTAGGCCTGGCC | 60360 |
| mRNA | ------------------------------------------------------------ | |
| genome | AAACTATTAAGCAAGTGTGGGCAAAATATTGATAATTTTAGATATGCAGGAACTTAGTTT | 60420 |
| mRNA | ------------------------------------------------------------ | |

FIG. 1 WW

| | | |
|---|---|---|
| genome | GCTTTCCATGTGTGCTTTTCGAAAAAGGAATAAATTGAAAAATAGAGGAAGCCCTGAAAT | 60480 |
| mRNA | ------------------------------------------------------------ | |
| genome | CCAAGAAGCAAACTCTCTCACCTAGGCATGCAGTAAAAGCAATTCTAGGATGATTGCTGT | 60540 |
| mRNA | ------------------------------------------------------------ | |
| genome | TTGGCGCGTAGTTCGTATTAGAAACCATTCTTCTTGAATAAATAGTATGTTTAAGAAGCT | 60600 |
| mRNA | ------------------------------------------------------------ | |
| genome | GGGCAGAGGGAAGGCATATGCATATATTATCAACAAGGAGGGAGAAAAAGGCAATTAGTA | 60660 |
| mRNA | ------------------------------------------------------------ | |
| genome | ACCATCCATAGGAGGGTCAGCAAGATTTATAAAGGAAATTTGTGATCCAAGTATGAAGCA | 60720 |
| mRNA | ------------------------------------------------------------ | |
| genome | AAATAAGGTGCAGAATAAATTTTAAGCAAGTAATAGATTAGAGTAAGAGAACCCATTTGA | 60780 |
| mRNA | ------------------------------------------------------------ | |
| genome | CCATTAACCTTGGGACATTCTCTTTCAAATGACATGGAGTAGTACTGAAATCTTTCTTTC | 60840 |
| mRNA | ------------------------------------------------------------ | |
| genome | TTTCTGAGTCTAGGTTATTGTGACTGGACTCAGAAAGAAATATTTCATTATTGCAGTGAA | 60900 |
| mRNA | ------------------------------------------------------------ | |
| genome | TAACATTTGTGAACATTATTGTTCATAAATTATGCAGTGAATAACATTTATGAACACGTG | 60960 |
| mRNA | ------------------------------------------------------------ | |
| genome | ATGTGTAAGATACATACTGTTTATTTTTAGTTAAGTTTTTTGGCTCAACTTCTAGGCAGA | 61020 |
| mRNA | ------------------------------------------------------------ | |
| genome | GAACATTAAATGTAAATAGTGTTACCTAGGAGCATGTAAATGGAAATCTCCATAGTATGA | 61080 |
| mRNA | ------------------------------------------------------------ | |
| genome | AAGCAGTGCTGTTGCTAACAGAATTTAGGAGGGGGCAGATGAGGTGAAGGAAATGTGGGT | 61140 |
| mRNA | ------------------------------------------------------------ | |
| genome | GCTGATTTCCTTATTACATTGAGAGGAGCCAGGAGATTCTTTGTTCAAAATGGATGGCTT | 61200 |
| mRNA | ------------------------------------------------------------ | |
| genome | AAGAAGTCAAAGTATAAGCTGATTACGTAGAGCAGGTACCCAAAAATGTTTTGTGTAAGG | 61260 |
| mRNA | ------------------------------------------------------------ | |
| genome | GGCCAGATAGTAAATATTTTCAGTCTTGCAGGCCATCCCAAGTCTGTGGCAGCTACTCAA | 61320 |
| mRNA | ------------------------------------------------------------ | |
| genome | CACTACCTTTGTAGCATGAAAGCAGCCACAGGCAGCCCATAAATGTGGCTCTGTTCCGGT | 61380 |
| mRNA | ------------------------------------------------------------ | |
| genome | GAAACTTTAGGTACAAAAGCAGGTGCAGGCCAGACCTGACCTGTGCACTGTGGTTTGCTG | 61440 |
| mRNA | ------------------------------------------------------------ | |
| genome | ACCTGGGATTCAGGGGTATAGAAGTTACCATCAGAAGAGCTAAAAGTGAGACTTTTTACT | 61500 |
| mRNA | ------------------------------------------------------------ | |
| genome | TTATACTCTTCTACACTGTCTGATTTTGAAAAAAAGAAACATGTATTTTATAATATTAAA | 61560 |
| mRNA | ------------------------------------------------------------ | |
| genome | GATAGGGTTGGCAAATAGCAAATAAAAATACAGAATACCAGTGAAATTTGAACTTCAGAT | 61620 |
| mRNA | ------------------------------------------------------------ | |
| genome | ACATTATGAGTAATTTTATGGTGTAAGTATATTCCAAATCATGTGGGACATACTTACACT | 61680 |
| mRNA | ------------------------------------------------------------ | |

FIG. 1 XX

| | | |
|---|---|---|
| genome | ACAAAATTATTTGTTGTTTGTTTACAGTTTAAATTTGAGTGCCTTGTATTTTATCTGGCA | 61740 |
| mRNA | ------------------------------------------------------------ | |
| genome | ACTGTAATTAAAGGGAAAAAGAATAAATTCATTATGTTCATATAATGTGATATAGCAGGG | 61800 |
| mRNA | ------------------------------------------------------------ | |
| genome | GTCCCCAACCCCCAGGCTGCAGAGTGGTACTGGTCCATGGGTCCCCAACCCCCAGGCTGC | 61860 |
| mRNA | ------------------------------------------------------------ | |
| genome | AGAGCGGTATTGGTCCATGGCCTGTTAGGAACCAGGCTGCCCAGCAGGAAGTGAGCAGCA | 61920 |
| mRNA | ------------------------------------------------------------ | |
| genome | GGTGAGCTGGCATTCCCACCTGAGCACCGCCTCCTGTCAGATCAGTGGCAGCATTAGATT | 61980 |
| mRNA | ------------------------------------------------------------ | |
| genome | CCCATAGGAGTGCAAACCCTATTGTGAACTGCACATGTGAGGGGTCTAGGTTGTGCGCTC | 62040 |
| mRNA | ------------------------------------------------------------ | |
| genome | CTTATGAGAATCTAATGCCTGATGATCTGAGGTGGAACAGTCTCGTCTTGAAACCATCCC | 62100 |
| mRNA | ------------------------------------------------------------ | |
| genome | CTGGCCCTGTGGAAAAATTGTCTCCCATGAAACCAGTCTCTGGTGCCAGAAAGGTTGGG[rs4690072]T | 62160 |
| mRNA | ------------------------------------------------------------ | |
| genome | AGCACTGTGATATAGTATTAAAAGTGCTAATAAATATGGCATACTGCCTTTAAAATGTCT | 62220 |
| mRNA | ------------------------------------------------------------ | |
| genome | GGTAGCTCTTTCTCAGTGGCACTCATAATAGTGTTTTTTGATTTTTAAATGTGTGTCAAG | 62280 |
| mRNA | ------------------------------------------------------------ | |
| genome | CTGACTCTCCCCTCCGTGTATGCTGGGCTTTATTTTCCCTTTCCTAGTCACCAGTTTTGG | 62340 |
| mRNA | ------------------------------------------------------------ | |
| genome | GAAATAGAGATCTTCATTCTCATGCTGCTCCTCTAGTGCAAGTGCTCCATTTATTTTTAA | 62400 |
| mRNA | ------------------------------------------------------------ | |
| genome | GGAATTAATATAACAAAAAATCATGGGAATTTAGAAAACAACATGGAAGCTAATGATCAC | 62460 |
| mRNA | ------------------------------------------------------------ | |
| genome | ATTGGTGGAAGTGATAGGGAAATATTTAGGGGGAGAAGTTAAGGTATAAACTTTGTCAAT | 62520 |
| mRNA | ------------------------------------------------------------ | |
| genome | GAAGTCCTATTAAAAACAACAAAAAAGTGAAGCTTAGGATGCATTTTATAAACTCTGACC | 62580 |
| mRNA | ------------------------------------------------------------ | |
| genome | AGAACACCTGTGTTTCTCTGTTTCTAGGTTTATGAACTGACGTTACATCATACACAGCAC | 62640 |
| mRNA | ------------------------------------------------------------ | |
| genome | CAAGACCACAATGTTGTGACCGGAGCCCTGGAGCTGTTGCAGCAGCTCTTCAGAACGCCT | 62700 |
| mRNA | ------------------------------------------------------------ | |
| genome | CCACCCGAGCTTCTGCAAACCCTGACCGCAGTCGGGGGCATTGGGCAGCTCACCGCTGCT | 62760 |
| mRNA | ------------------------------------------------------------ | |
| genome | AAGGAGGAGTCTGGTGGCCGAAGCCGTAGTGGGAGTATTGTGGAACTTATAGGCAAGTTA | 62820 |
| mRNA | ------------------------------------------------------------ | |
| genome | TTAGCAAGGTCTACTCTTACAATTAACTTTGCAGTAATACTAGTTACACTCTATTGATTA | 62880 |
| mRNA | ------------------------------------------------------------ | |
| genome | TGGGCCTGCCCTGTGCTAAGCAGTCTGCATTCCATCTTCCTTGCCAAAACTTATAATACA | 62940 |
| mRNA | ------------------------------------------------------------ | |

FIG. 1 YY

```
genome    AATTTCATCTTTATTTTATAAATAGGGGAGTTGGGCTGGGTGTGGTGGCTCACGCCTGTA  63000
mRNA      ------------------------------------------------------------ genome    ATTTCAGCACTTTGGAAGGATCGCTTCAGCCCAGGAGTTTGAGACAACCTGGCCAAGTGA  63060
mRNA      ------------------------------------------------------------ genome    GACCCTGTCTCTACAAAAAAAAAAAAAAAAAAAATTAGCTGGGCATGGTGGCACATGC   63120
mRNA      ------------------------------------------------------------ genome    CTGTAGTCCCAGCTGCTTTGGAGGCTGAGGTGGTAGGATTGCTTAAGCCCAAGAGGTTGA  63180
mRNA      ------------------------------------------------------------ genome    GGCTGCAGTGAATCTTGATGGCAGCTGCACTGAGCCTGGTGACAGAGCAAGATGCTGTCT  63240
mRNA      ------------------------------------------------------------ genome    CAAAATAAATTTAAAAATAAAATAAGAGAATTAAAGTTTAGCAGGTTGGGTGGCAAAATG  63300
mRNA      ------------------------------------------------------------ genome    AGGCCACACATTTAAAGCCCCTCCTCCTGATTCTTTTCTCTGCCTTGGCTGCCTCCTGTG  63360
mRNA      ------------------------------------------------------------ genome    GCATTTTAGGTGCTGAGAAATGAAAACAGTAGGGAAAATAGTTCCAGGATCCTCATGTTA  63420
mRNA      ------------------------------------------------------------ genome    ATTTGCCAGAAATGGCATCTTCAAGTCGTCAGAGGGATCTGAGAGTTCCTTCCTGGCCTG  63480
mRNA      ------------------------------------------------------------ genome    ACTTGAGAAAATCCGTCTGTCCCCAGCTCTGCGTCTGCCTCCACTGCCCAGTCACCTCCT  63540
mRNA      ------------------------------------------------------------ genome    CTCCATGCTCTTGGGGCTGGGCCCTACCCCACCATGCAGTGCTGCCCTGGAGCAGTGAGC  63600
mRNA      ------------------------------------------------------------ genome    TTGGTGGGTCCTGTCTGGCATGAGAGCTGCCTTTGGGAGCTGGATCCCAGCCTCTACCAC  63660
mRNA      ------------------------------------------------------------ genome    TGGGTCTGGTGCCTAGCAGGCTATGGATAAACTTCTGCTGACTCCGGCCTCTCCTAAGCC  63720
mRNA      ------------------------------------------------------------ genome    ACTGCAACGTGGTCGGTGTAGTGCACAGTGTGTGTGCAGCGTGGCCTTACTCACAGCCTC  63780
mRNA      ------------------------------------------------------------ genome    CACATTAGAGAGAATCTGACTGAAGTCTTACTGCTGCCTCGTGTGAACATAAATGTTTGC  63840
mRNA      ------------------------------------------------------------ genome    CAGAACCATGAGCAGGAAATGTTAATCTGCCTTGTTTCCTGTCCTTTACACGGAAGAATT  63900
mRNA      ------------------------------------------------------------ genome    TTTTTCTGTATGGAATGCGTGCCTTACAAATAATGAGTGGAAATACCCATCGCTAATGAA  63960
mRNA      ------------------------------------------------------------ genome    AAGTTATACTTGACTGTTAGTCAGCTAAATAATCTGAGATTTCTAATACTTTTAATTTGG  64020
mRNA      ------------------------------------------------------------ genome    CTTTTACAATGCAATTTATCTTAGCTTTTTTGATTTCTTAGGTCATATCTTTAGAACTAT  64080
mRNA      ------------------------------------------------------------ genome    ATATTTGAATGTTAATGTAATTTTCATATTGAAATTAAAATGTTGAACTGCGATGTTAAG  64140
mRNA      ------------------------------------------------------------ genome    TGTTTCCTGTGGAAAAACGTTCACATTTTCTCTAGTTTTAAAGTTGAATCAAGCTGTTTG  64200
mRNA      ------------------------------------------------------------
```

FIG. 1 ZZ

| | | |
|---|---|---|
| genome | AAGATTTTCACATTTCTTCTAGATTTTATCAGCTTGTTACTTTATCTGTCACTTTCTGTG | 64260 |
| mRNA | ------------------------------------------------------------ | |
| genome | ATTTGCAGCTGGAGGGGGTTCCTCATGCAGCCCTGTCCTTTCAAGAAAACAAAAAGGTGA | 64320 |
| mRNA | ------------------------------------------------------------ | |
| genome | TTATTTCAGAAATCAGAGTCTTGTGTTGAATCTTACTGATTTTCTTGTATTTCTGTAATG | 64380 |
| mRNA | ------------------------------------------------------------ | |
| genome | TAATGTATCTTGTATTTCTTGTAATACTGTATTGGACTCTGTGTATATCTCTTCTCAGAT | 64440 |
| mRNA | ------------------------------------------------------------ | |
| genome | GAGTGATTATATGTGTGAATGTTGCTGGAATCTGATAACCAGGCCTGAATAGTTTTGTAG | 64500 |
| mRNA | ------------------------------------------------------------ | |
| genome | GGTGGCTTTTAAAAATTACTTTCATATCAGAATTGCTTTGTCATAAATTTTGAACGCATC | 64560 |
| mRNA | ------------------------------------------------------------ | |
| genome | ATAAATTTCTAATGTTCGGGGTCAGCAGACTTTTTTTGTAAAGGGACAGAGTGTAAACAT | 64620 |
| mRNA | ------------------------------------------------------------ | |
| genome | CTTAGCTTTATGGGCCATATGGTCTCTTTTGCAACATTCAGCTCTGCCCTGTGACAGGAA | 64680 |
| mRNA | ------------------------------------------------------------ | |
| genome | TGCAGTTGTAAAGACATGAGCTACTGGCCAGCTATGTTCCAGTAGAACTTTACTTACAGA | 64740 |
| mRNA | ------------------------------------------------------------ | |
| genome | AACAGACAGGCTGTAGTTTGCCAATACCTGCCTTAGGGAATGTGTTGTTATATTTTGTGA | 64800 |
| mRNA | ------------------------------------------------------------ | |
| genome | GTTACCTTCTCAGTAAATTTTATTTAGTATTAGTCAGGAATATTATTAAGTAGCTTCTTT | 64860 |
| mRNA | ------------------------------------------------------------ | |
| genome | TCCAGCCTGGTCAACATAGTGAGACCCGGTCTCTACCAAAACAAAACAAAACAAAAAAAC | 64920 |
| mRNA | ------------------------------------------------------------ | |
| genome | AGCCACGCATGTGGCATGTGCCTGTAGCCTCAGCTGCTGCTCAGGGGGCTGAGGCAAGAG | 64980 |
| mRNA | ------------------------------------------------------------ | |
| genome | GATTGTTTGAGCCCAGGAGTTTGAGGTCACAGTGAGCTGTAGTCATGCCACTGCACTCCA | 65040 |
| mRNA | ------------------------------------------------------------ | |
| genome | GCCTAGGCAACAGAATGAGACCTTGTGTCTTAAAAAAAAAAAGTTTCCTTTGTTGGGTTA | 65100 |
| mRNA | ------------------------------------------------------------ | |
| genome | TTTTAATTTGGACCTGGTTATCATTTTTCAGCCATATTTAACTTTGTACATATCAGAATG | 65160 |
| mRNA | ------------------------------------------------------------ | |
| genome | TTCTGATAAAACTTAACTTTTATTAAAGTGTTTGTGATATAATCTGCTAGTTTTGGTACA | 65220 |
| mRNA | ------------------------------------------------------------ | |
| genome | CATTATCTTTTGCAATGCCAGTTATTTTCTTTTCCAGTGTGGGTTTGCATAGGAAAAGAA | 65280 |
| mRNA | ------------------------------------------------------------ | |
| genome | TTGCTGTCACTTTCTATTTTGAAATCTTAAAAGACTGATCCTTTTTTGTGTCATGATTTG | 65340 |
| mRNA | ------------------------------------------------------------ | |
| genome | AGTATTTAATTGAGAGCCTAATGCCTAATATTATTTGCAGTATTAAATGGGATCTTAACA | 65400 |
| mRNA | ------------------------------------------------------------ | |
| genome | GGAATAGCATTCTAGCCTTCATTGAATTAAGTAAACATTTCTTAAGAGAACTTGGAATCT | 65460 |
| mRNA | ------------------------------------------------------------ | |

FIG. 1 AAA

```
genome    ATAATATTTGCGTCATCATAGTATGAGATACTTAATCAAGTTTGAGATTTTAGTGAAACA  65520
mRNA      ------------------------------------------------------------ genome    TTGTTTAGAAGCCAAAAGGATTCTAGGAAAAATTAATGTCTATATTCTTGAATTAGGAGA  65580
mRNA      ------------------------------------------------------------ genome    GATTTTGGGACGTGTGACTAAGTTACGCTGACACTTGTTTGTTTCTTAGTCGCTTTTTCC  65640
mRNA      ------------------------------------------------------------ genome    AGTGGCGGTGAGAACGAAGATGACTGATTCACATTGCTCAGATGAGTTTATCCTCTTCTG  65700
mRNA      ------------------------------------------------------------ genome    GCTGGGACATGGGATATATCCTGTCTCTTTTAAGCCTTTTTGGTATTTTTCCCCCATTGA  65760
mRNA      ------------------------------------------------------------ genome    GAGCTGTGTCTTCAAACTCTTCTGTTATAGCTGGAAAATCCTTTTTAAGTGAAATCTGCC  65820
mRNA      ------------------------------------------------------------ genome    CAAATTATAAGACAGATGAAGGTAGAGTTGTGTTGGATATAGGATTAGGGTGAAAGTAGT  65880
mRNA      ------------------------------------------------------------ genome    GGGGGTGTCCTGGAGCCTCTCTTCTGGTGGCAGCCTAGCTCTTGTGCCTTTGAGGAAATT  65940
mRNA      ------------------------------------------------------------ genome    ACCCTGGGGACGGCTCTGTGGAACATATTTGCAAACCACTGATTTGGAAGATAGAGATGG  66000
mRNA      ------------------------------------------------------------ genome    CTTTTGTTAAGATCTGAATTCACCTTTTTGGCATTTTATTTGATTTCTCAAGGTAAAGAA  66060
mRNA      ------------------------------------------------------------ genome    CTTATTTTGTAATAAAGTTTCCTATTATTTAGTAGATAGGCCAAGTTGCTGTGTTAATTC  66120
mRNA      ------------------------------------------------------------ genome    CATGTAGATTTTGGGTTTCCTTTGCTCATTTTTTCACTCTTAATCTCACATCATTGTAAG  66180
mRNA      ------------------------------------------------------------ genome    TTTATGGAAGTTATCATACTTCTGACTTTTTCTTTGAAGAGCAGAAATTAGAAATTCCCA  66240
mRNA      ------------------------------------------------------------ genome    ATAATTATTTTGATAGTGTCATTTAATGACACTCACATGTGATGTAGCCACAAAGATTTA  66300
mRNA      ------------------------------------------------------------ genome    ATGAGTTCAGTTTTAAATCATATTAAGACTGTTGGTTTCATTTGTTCTCATTAATGTAAT  66360
mRNA      ------------------------------------------------------------ genome    TCTGAAGATGAACAATAAAATGTATTTTTAGAACTTTCAAATGAAATATTATTTCATCCT  66420
mRNA      ------------------------------------------------------------ rs6446723
genome    TCCAGATCATATAATGCTTAAGTTCTGATTGTTAATCATAAAGTCTAGAAAATTAAAAGA  66480
mRNA      ------------------------------------------------------------ genome    TAATAAAATGAAAGTGACTTTTAGGTATTAGAGTTTTATTATAAATTCTGGTGTGTCATT  66540
mRNA      ------------------------------------------------------------ genome    GGAGCTATGACATGAATATTTCAAAGGCCAATAGCATTGGATCTTTACAGTTATAACTTA  66600
mRNA      ------------------------------------------------------------ genome    CCATTTTTAAGTTTAAGTAGTAATATAGATTATTTAATAATCAAAATCAATAAATATTAA  66660
mRNA      ------------------------------------------------------------ genome    TTATTAAAATGTTTTGTGGTATAGTTTGAGAATCATTGCTTTTAACTTTTTCCATATAGG  66720
mRNA      ------------------------------------------------------------
```

FIG. 1 BBB

| | | |
|---|---|---|
| genome | TTTATTGACTTTAATAGCATTCTAAACATAACATCTCTACATTCTTTGTGTTTAATACTG | 66780 |
| mRNA | ------------------------------------------------------------ | |
| genome | TGGAGGTATAAAAATACTTATATATGATGATAAACTATATTAGAGTAAATTAAATATTCT | 66840 |
| mRNA | ------------------------------------------------------------ | |
| genome | TATGAGTTTCATTTTAGAGTGCATTTACTTAATTTTGAAGTCCTTATTTTTAGCAAACTA | 66900 |
| mRNA | ------------------------------------------------------------ | |
| genome | AAAGGAATGTTGGTACATTATTTACTAGGCAAAGTGCTCTTAGGAGAAGAAGAAGCCTTG | 66960 |
| mRNA | ------------------------------------------------------------ | |
| genome | GAGGATGACTCTGAATCGAGATCGGATGTCAGCAGCTCTGCCTTAACAGGTAGTTCTCAC | 67020 |
| mRNA | ------------------------------------------------------------ | |
| genome | TAGTTAGCCGCTGGTGTGGACCTTCACTGTCTGCCTTCCACCCCTTGCCCTTCCTGCTCG | 67080 |
| mRNA | ------------------------------------------------------------ | |
| genome | TCCCCCTGCACCTGGTGGACAGCACGACTGGGGGCAGCAGTGGAGCCAGGTTGCTTAAAT | 67140 |
| mRNA | ------------------------------------------------------------ | |
| genome | GGGGCATATTCGGGCTTCTTTTATAATACTTACTCTGAAGCTTGTGTGTCTGTGGTGTTT | 67200 |
| mRNA | ------------------------------------------------------------ | |
| genome | GCATCATATATTTGTTGTTTTCCATGGTTTAGGCTGTTTTAAAATTAGGTTTATGGCTTG | 67260 |
| mRNA | ------------------------------------------------------------ | |
| genome | AGCATAGGGCTTTGTGAGTAGGGGATGGCAGGTCGAAACATCTCATGAGTTGGATGGGTT | 67320 |
| mRNA | ------------------------------------------------------------ | |
| genome | ATGCTGGGGGTTGGGAAATGGGATGAAAAATTATGGGATGAAAAATTGCCTATGGATAGT | 67380 |
| mRNA | ------------------------------------------------------------ | |
| genome | TTAACTTGAAAGAATCTGCCTTTGTTTACAGATAGTTATCTTTTTTCTTTTTTGAGATAG | 67440 |
| mRNA | ------------------------------------------------------------ | |
| genome | AGTCTCACACTGTCACCCAGTGCAGATACCCAGTGTCACTGGAGTGCAGTGGTGTGCTCT | 67500 |
| mRNA | ------------------------------------------------------------ | |
| genome | TGGTGCACTGCAGCCTCCGCCTTCTGGGTTCCAGCGATTCTCCTGCCTCAGCCTCCCAAG | 67560 |
| mRNA | ------------------------------------------------------------ | |
| genome | TAGCTGGGACTACAGGTGCCCGCCACCACGCTTGGCTAATTTTTGTATTTTTTGTGGAG | 67620 |
| mRNA | ------------------------------------------------------------ | |
| genome | ACGGGTTTTTGCCATGTTGGTCAGGCTGGTCTTGAACTCCTGACCTCAAGTGATCTGCCT | 67680 |
| mRNA | ------------------------------------------------------------ | |
| genome | GCCTCAGCCTCCCACAGTGCCGGGATTACAGGAGTGAGCCACTGTGCCCGGCCAGTTACA | 67740 |
| mRNA | ------------------------------------------------------------ | |
| genome | GATACTTATCTAATGAAATTCTCTGTGTACTTTATAAAAGATGAGGATTAACTGAAGGTA | 67800 |
| mRNA | ------------------------------------------------------------ | |
| genome | CTAATAACTGGATTATATGAGGGTGGTTTTGGTTGTATAATCCTATCTAAAAGAATATTT | 67860 |
| mRNA | ------------------------------------------------------------ | |
| genome | TAGCTATAACTGAAAGTAAGACTTAAATATTTAGAGAGGAAAATCTGAATAATTCTAGTA | 67920 |
| mRNA | ------------------------------------------------------------ | |
| genome | GTAATTATTTATTTACAAAATAAAAATAGATTTTTTTTTGATTACACAAATTAAACAACA | 67980 |
| mRNA | ------------------------------------------------------------ | |

FIG. 1 CCC

| | | |
|---|---|---|
| genome | ATAAAACATCACAGCAATCCGGATACTATAAAGCTCACATGCTTACCGACCCAACTGCCC | 68040 |
| mRNA | ------------------------------------------------------------ | |
| genome | CAGGAGTGACCACTGCCAACAGCTTCATGTCGACCTTTTTGCCATAATTTTTATATAGCC | 68100 |
| mRNA | ------------------------------------------------------------ | |
| genome | TTTTTTGTTTTTAAATGGTAATTTAGAAAGTCAACTAGGAAAATGTGTTACAGGTTTATC | 68160 |
| mRNA | ------------------------------------------------------------ | |
| genome | TTCCAGGAGAATAGGACTGGAGTCGAGATCTTGAATGTGGCTTGGAAGAAGGCAAGCCCA | 68220 |
| mRNA | ------------------------------------------------------------ | |
| genome | CCCCAGAGAGATGAGTTGACAGTTGTTTCTGACCACTGCTTGCTTAGAGGGCCTGCGTGT | 68280 |
| mRNA | ------------------------------------------------------------ | |
| genome | CTGTGACCGCCTAGCTTTGCGCCCCTGACTAGGCTGCCCCTTAATTACAAATGTCTTTAT | 68340 |
| mRNA | ------------------------------------------------------------ | |
| genome | ATATTGCTCCAGCTAAGGCTTGGAGTAGTCGGTTAAGAACTTGAACTTCGGTTTTTGCAG | 68400 |
| mRNA | ------------------------------------------------------------ | |
| genome | TGAAACAGCATTTGAGAATATCACCTTCTGATAAGCCTTATTTTATAAGGTGGGTACTGT | 68460 |
| mRNA | ------------------------------------------------------------ | |
| genome | AGTGGGAGGCAGTGTGAGAGATGCTTGAAGGATGCACTGCTGTCCTGCATTTCAGCATCT | 68520 |
| mRNA | ------------------------------------------------------------ | |
| genome | TCAGGATGCTGTGCAGCTGAAACATTTGATAACGGTGGAACTGTTCGTTATTTTGCAAGC | 68580 |
| mRNA | ------------------------------------------------------------ | |
| genome | CTGTGATTCCCTATTGAATGTTTTCTCTCGCCATTTGACAAATGAGTGTTTCTCTGTCTT | 68640 |
| mRNA | ------------------------------------------------------------ | |
| genome | CAGCCTCAGTGAAGGATGAGATCAGTGGAGAGCTGGCTGCTTCTTCAGGGGTTTCCACTC | 68700 |
| mRNA | ------------------------------------------------------------ | |
| genome | CAGGGTCAGCAGGTCATGACATCATCACAGAACAGCCACGGTCACAGCACACACTGCAGG | 68760 |
| mRNA | ------------------------------------------------------------ | |
| genome | CGGACTCAGTGGATCTGGCCAGCTGTGACTTGACAAGCTCTGCCACTGATGGGGATGAGG | 68820 |
| mRNA | ------------------------------------------------------------ | |
| genome | AGGATATCTTGAGCCACAGCTCCAGCCAGGTCAGCGCCGTCCCATCTGACCCTGCCATGG | 68880 |
| mRNA | ------------------------------------------------------------ | |
| genome | ACCTGAATGATGGGACCCAGGCCTCGTCGCCCATCAGCGACAGCTCCCAGACCACCACCG | 68940 |
| mRNA | ------------------------------------------------------------ | |
| genome | AAGGGCCTGATTCAGCTGTTACCCCTTCAGACAGTTCTGAAATTGTAAGTGGGCAGAGGG | 69000 |
| mRNA | ------------------------------------------------------------ | |
| genome | GCCTGACATCTTTTTTTTTATTTTTTATTTGAGACAGAGTCTCACTCCATAGTGCAGTGG | 69060 |
| mRNA | ------------------------------------------------------------ | |
| genome | AGGCCGGGCACAGGGGCTCATGCCTGTAATCCCAGCACTTTGGGAGACTGAGGCAGGCGG | 69120 |
| mRNA | ------------------------------------------------------------ | |
| genome | ATCACTTGAGGTCAGGAGTTCGAGACCAGCCTGGCCAACATGGTGAAACCCTGTCTCTAC | 69180 |
| mRNA | ------------------------------------------------------------ | |
| genome | TAAAAATACAAAAATTAGTTGGGCGTGGTGGCACATGTCTGTAGTCCCAGCTGTTAGGGA | 69240 |
| mRNA | ------------------------------------------------------------ | |

FIG. 1 DDD

| | | |
|---|---|---|
| genome | GGCTGAGGCAGGAGAATTGCTTGAGCCTGGGAGGCAGAGGTTGCAATGAGCCGAGATCGT | 69300 |
| mRNA | ------------------------------------------------------------ | |
| genome | GACACTGCACTCCAGCCCGGGCAACAGAGCAAGACTCCATTTCAAAAAAAATAAAAAAAT | 69360 |
| mRNA | ------------------------------------------------------------ | |
| genome | AAAGTGCAGTGGCTCGTTCTCAGCCCACTGCAACTTCTGCCTCCCAGGCTCGAGCGATTC | 69420 |
| mRNA | ------------------------------------------------------------ | |
| genome | TCCCGCCTCAGCCTCCTGAGTAGGTGGGATTACAGGTGGGCACCACCACACTCAGCTAAT | 69480 |
| mRNA | ------------------------------------------------------------ | |
| genome | GTTTGTATTTTCAGTAGAGACAGGGTTTCACCATGTTGGCCAGGCTGGTCTCAAACTCCT | 69540 |
| mRNA | ------------------------------------------------------------ | |
| genome | GACCTTAGATGATCCACCCACCTTGGCCTCCTAAAGTATTGGGATTATAGTTGTGAGCCA | 69600 |
| mRNA | ------------------------------------------------------------ | |
| genome | CCATGCCCGGCCCTGCCACCTGCCATCTTTTGAGTTCTTCCCTGGAGACCTAGACCTGAA | 69660 |
| mRNA | ------------------------------------------------------------ | |
| genome | CCCTCCTGCTTGTTCTCTTGTTATCTAATACCCCTATTGACAGCGCAGCTTAGATCATTA | 69720 |
| mRNA | ------------------------------------------------------------ | |
| genome | ATGGAGAGCTTGACCTCATCTGATACCTTCACTGAAGGAAACAACTTAGTGTCTTTTGTG | 69780 |
| mRNA | ------------------------------------------------------------ | |
| genome | TTGAACACTGAGGTAAAAAATTGGAATAGTTGATTATATGAACTCTGCTAAAATTGAGTG | 69840 |
| mRNA | ------------------------------------------------------------ | |
| genome | CATTTTACATTTTTTAAGGCCTTGTTGGGCCCTGGTTAAATAATTATTTTTAAAAATCCT | 69900 |
| mRNA | ------------------------------------------------------------ | |
| genome | TAAGGAGCCTATTATAAACAGATCTGTGGTCTTAATGAAATGTGATTAATACTGTGCATT | 69960 |
| mRNA | ------------------------------------------------------------ | |
| genome | ATTTTAAGAACTTTTGACTTTTCAAAAAACTTTTACAACATTTCCCATTTGATAGCGGCA | 70020 |
| mRNA | ------------------------------------------------------------ | |
| genome | TAGGTTTAAGCACTTCTCATCTCTAAGTTAGTGGACAAAAAACCCTCATGGATAGTCTAA | 70080 |
| mRNA | ------------------------------------------------------------ | |
| genome | TAATGTTTGCTACAAGTCCATGTTGAGTTTTATACTCCATTTTATTTTCAGTTTTAAAAA | 70140 |
| mRNA | ------------------------------------------------------------ | |
| genome | CTGTGGTTAAATATGTGTAACATAAAATTTATGTTCTTAACCATTTTTTGCGTATACAGT | 70200 |
| mRNA | ------------------------------------------------------------ | |
| genome | TCGCTGGTATTAAATACATTTAAATAATGTCATGGAATCATTGCTACCACCCATCTCTGT | 70260 |
| mRNA | ------------------------------------------------------------ | |
| genome | AACCTTTTGATCATGTAACACTGAAGCTCTGTTCCCATTGAACTCTATTCCTCCTTTCCC | 70320 |
| mRNA | ------------------------------------------------------------ | |
| genome | GCCAAGTCCCTGGCAACCACGATTCTTCTTTCTGTCTTCTGAATTTGACTACTTTGGGTT | 70380 |
| mRNA | ------------------------------------------------------------ | |
| genome | CTCATATACTTTAGGAGTCACACAGTATTTGTTTTACTTAGCATAATGTCCCCAAAGCTC | 70440 |
| mRNA | ------------------------------------------------------------ | |
| genome | ATGCATGTTGTAGCCTATGTTAGAACTTCCTAATGTTTCAGGCCAAATACTATTCCATTG | 70500 |
| mRNA | ------------------------------------------------------------ | |

FIG. 1 EEE

| | | |
|---|---|---|
| genome | TATGGATAGGCCACATTTTGCTTTTCCATTCCTCTGTCCATGGACACTTGTATTGCTTCA | 70560 |
| mRNA | ------------------------------------------------------------ | |
| genome | TGTTTTAGCCATTGTGAATCATGCTGTTATGAACGTGGGTGTACAGATAGCTCCTGGAGA | 70620 |
| mRNA | ------------------------------------------------------------ | |
| genome | CTCTGCTTTCCATTTTTTGGCTAAATACCCAGAAATGGAGTTGCTTTTACATTCCAATT | 70680 |
| mRNA | ------------------------------------------------------------ | |
| genome | TTAATTTAAAACATTCATATCATTGAGTGTTTTACTTAATAGTATAGTAGTTAACAAACT | 70740 |
| mRNA | ------------------------------------------------------------ | |
| genome | TAATAAAATAGTATTTTGGTAATAATTTGCTGGTAGTCCATTGTTCAGTTTTTTAGGTA | 70800 |
| mRNA | ------------------------------------------------------------ | |
| genome | AATTACACAGGACATTTCAAGTGGACATGAAACATCTTGTGATGTGGAATCATGCCCCAA | 70860 |
| mRNA | ------------------------------------------------------------ | |
| genome | GCTGATGGCTAAACATATGAAATACCATACCCTAAATTTAGTAGATTAGTCTTTGCAAT | 70920 |
| mRNA | ------------------------------------------------------------ | |
| genome | TTAGGAGATAACCTGTTATATTGTTAGGTTTTTGTCGAAAAGCTTTGTCCTCATATTTCC | 70980 |
| mRNA | ------------------------------------------------------------ | |
| genome | AACTTGCTGTAAAATTTGTTTGTGAAGACAAATATTTTTGTATGGGTTTTTTCTTTTTCA | 71040 |
| mRNA | ------------------------------------------------------------ | |
| genome | TATTAAAAAGAAATGTCCACATTGGAATTTTTTGGAGTTTTTAGAGCTAATAGAGCTTT | 71100 |
| mRNA | ------------------------------------------------------------ | |
| genome | TCATAATGTAGTGGGAATGAGTGATCAGTAAGCTCTTAGCAGTTTCCATGCGTGCATTTC | 71160 |
| mRNA | ------------------------------------------------------------ | |
| genome | TGTGCCTTGAAATAAATGACAGATGAGTACATTTGTGTTCTGTGTGTAAAATGTGCTCTT | 71220 |
| mRNA | ------------------------------------------------------------ | |
| genome | TCCTCATTGCACTTCCATGTTGGAGGGCTTGTCTCTTGGTGATCACACTTCAAAATTCTC | 71280 |
| mRNA | ------------------------------------------------------------ | |
| genome | ACAGCCCCCCTTGAACCGTTTAGGTGTTAGACGGTACCGACAACCAGTATTTGGGCCTGC | 71340 |
| mRNA | ------------------------------------------------------------ | |
| genome | AGATTGGACAGCCCCAGGATGAAGATGAGGAAGCCACAGGTATTCTTCCTGATGAAGCCT | 71400 |
| mRNA | ------------------------------------------------------------ | |
| genome | CGGAGGCCTTCAGGAACTCTTCCATGGGTATGTGGACTACAGGTGATGCGCTACAAAGTG | 71460 |
| mRNA | ------------------------------------------------------------ | |
| genome | GTTTGTATTCAGACCTGGACATCTTAATTATATCTTTGCTTCCAAGAAGAAGTCCTTTGA | 71520 |
| mRNA | ------------------------------------------------------------ | |
| genome | TACTGTTTTCTGAGTTCTGAATAGCTGATGAAAATGACCAATTGAGGAATAATCATACTT | 71580 |
| mRNA | ------------------------------------------------------------ | |
| genome | TTTCTTGATCTAAATCTTATACTTTTGAGTTATCTTAGCATAAATGTATAATTGTATTTT | 71640 |
| mRNA | ------------------------------------------------------------ | |
| genome | AAGTGGAAATTTGTCACTTAATCTTGATTTCTCTGTTTTTAAAGCCCTTCAACAGGCACA | 71700 |
| mRNA | ------------------------------------------------------------ | |
| genome | TTTATTGAAAAACATGAGTCACTGCAGGCAGCCTTCTGACAGCAGTGTTGATAAATTTGT | 71760 |
| mRNA | ------------------------------------------------------------ | |

FIG. 1 FFF

| | | |
|---|---|---|
| genome | GTTGAGAGATGAAGCTACTGAACCGGGTGATCAAGAAAACAAGGTGAGGGACATAGGCTT | 71820 |
| mRNA | ------------------------------------------------------------ | |
| genome | GAGACGACTTGGTGTTTCTGAGCTTGTGTGAGGATTTAAAATCGCCCTGGCTACTGTCTA | 71880 |
| mRNA | ------------------------------------------------------------ | |
| genome | CTTTATTGCTTTCCCATCCCTGGGCCTTTAAATTTCCCCTTTAAATACCAGCTCTTCCCA | 71940 |
| mRNA | ------------------------------------------------------------ | |
| genome | GGCCTGTTGTTTTCTGCCTTTCCAGGTACTACCCACAGCCTTGAGAATTGCCTGAGTTCT | 72000 |
| mRNA | ------------------------------------------------------------ | |
| genome | GCCTCCTTTGAGAGTGTGCCCCAGACAAATCTATTCTGTACTGAATGTTTCCTTGTCTGA | 72060 |
| mRNA | ------------------------------------------------------------ | |
| genome | TTTCTTGGATCATTCATTTGATGGTTGCGTATGGCCTGCAACGTTTCTTGTTTTGGTTCT | 72120 |
| mRNA | ------------------------------------------------------------ | |
| genome | ACTGAACTGTTCTAAAAGTCTCTCTTCATATTATCTTTTTACATGTAAATGTAACTGTCT | 72180 |
| mRNA | ------------------------------------------------------------ | |
| genome | TCACTTTTAATTCCTCAAGGACAAGGAATAGCGTTTCACAGTTCGTCCCATCAATCAGAA | 72240 |
| mRNA | ------------------------------------------------------------ | |
| genome | TTATAGCCTTTGGCATCTCCCTATCTACCAGGCCCACTTCCTCTTAGATTTGGGCTTCCC | 72300 |
| mRNA | ------------------------------------------------------------ | |
| genome | CAGGCTGTTGCCTTTCCCCAAGTAGCTTCTGCTTGTCCTGTAGAAGACCTTTCATGCTTT | 72360 |
| mRNA | ------------------------------------------------------------ | |
| genome | GCTTCTGCAGCAGCCGTTCCTGAATGCCTAGTGTCAACTGCCTTCTTACCACGCCCACCC | 72420 |
| mRNA | ------------------------------------------------------------ | |
| genome | TCCCTGCATGCTGCATTTATCCCCTGCCACAGCCCTGTGACCCTGTGTCCTGCTGCCTCT | 72480 |
| mRNA | ------------------------------------------------------------ | |
| genome | GACTTGTCTGTTTCTGCTTGGCCATGGTCTCTGTGAGGTCAGGTGTGCATATGGGCACAA | 72540 |
| mRNA | ------------------------------------------------------------ | |
| genome | ACCAGGGCATCTCTTTATCCCCAGCACCTGGCTTAAGTGCTGCTCTGGAACTATCTGTTG | 72600 |
| mRNA | ------------------------------------------------------------ | |
| genome | AATGAACTAATGCATGAATGTATTGTTGAGTATGAGACAAACAAGTGTCATTGTCTCCTT | 72660 |
| mRNA | ------------------------------------------------------------ | |
| genome | TCTAGCCTTGCCGCATCAAAGGTGACATTGGACAGTCCACTGATGATGACTCTGCACCTC | 72720 |
| mRNA | ------------------------------------------------------------ | |
| genome | TTGTCCATTGTGTCCGCCTTTTATCTGCTTCGTTTTTGCTAACAGGGGGAAAAAATGGTG | 72780 |
| mRNA | ------------------------------------------------------------ | |
| genome | AGTACAAAAGGGGATGTGCACAGTTGAAGGAAATAACTAGGTTTCAGAGGTCAGCTTGGT | 72840 |
| mRNA | ------------------------------------------------------------ | |
| genome | GGCCTGTTTTTGCCTTGCGTGCAGCAGAGGAAGTAGAATCTGAGGATGAGTTTGGTTTTC | 72900 |
| mRNA | ------------------------------------------------------------ | |
| genome | ACTAGCCGAGGGGAGGGAGGGAAATGATGGGAGCAGGTAGGTTATTGGGTCTGGTTTTGTT | 72960 |
| mRNA | ------------------------------------------------------------ | |
| genome | CATTTGAAAACAATCTGTTGTTTGAGGCTGAAGGTGGCTTGGGTGATTTCTTGGCAGTGC | 73020 |
| mRNA | ------------------------------------------------------------ | |

FIG. 1 GGG

```
genome    TGGTTCCGGACAGGGATGTGAGGGTCAGCGTGAAGGCCCTGGCCCTCAGCTGTGTGGGAG 73080
mRNA      ------------------------------------------------------------ genome    CAGCTGTGGCCCTCCACCCGGAATCTTTCTTCAGCAAACTCTATAAAGTTCCTCTTGACA 73140
mRNA      ------------------------------------------------------------ genome    CCACGGAATACCCTGGTATGTTAAAAGTTCACATCTTATTTTCTCAGATTTAATCATTAT 73200
mRNA      ------------------------------------------------------------ genome    TGTAAAAACTATTTCAGTATTGACTATTTTAGTTTTAGAGCAGTAAGTGTTTTGAGTTCA 73260
mRNA      ------------------------------------------------------------
                                     rs363081
genome    TTTGGGATATTTGACCTGCGTTGTAGCTCTTCAGAAAACACATGAATAGTGAAGTTCTTT 73320
mRNA      ------------------------------------------------------------ genome    GTTTCATGGGTTCCCTTTAGATGAAACCCATAGAGGAGAAAAGTAGAAACCTCAGCACGT 73380
mRNA      ------------------------------------------------------------ genome    AAGAGCCAACATATATACACATCGGATTTAAACCTAAAGCACAAATTGTGCCTGGTCGCA 73440
mRNA      ------------------------------------------------------------ genome    GTGGCGCTGAGTCGCACTCAGCCAGGCCAGGCATTCACACTCAGGGTGAGTGGGAACCAG 73500
mRNA      ------------------------------------------------------------ genome    GACTGGCTGAGGCAGCAGTGGACCCAAGTCTCCATCGCGCCCATGCTTACTATGGAGCCT 73560
mRNA      ------------------------------------------------------------
            rs363080
genome    TCTCGTTCTCTCTTTTTCTTTGGGTGAGAGGGTACACTTGTGTTTTTGAATTTATATGAG 73620
mRNA      ------------------------------------------------------------ genome    GTAAGTGTGTAATAGGGTTTTTTCTAATCTTTTTTAAGTGGAATCTGGAATTTTAATCAG 73680
mRNA      ------------------------------------------------------------ genome    ATTTATTATCTGACAACCTAGAATTATAATCCAGAAAGTCTGTGGTATTGAGGACATATT 73740
mRNA      ------------------------------------------------------------ genome    GGCAATATGATGAATCTCTAATTCTTAAATCCTGAAACTTTTTTTTTTTAATCACTTAG 73800
mRNA      ------------------------------------------------------------ genome    GGTTATTATAGTGAAGTCATTTCTGAATTTGGATCTTCTCTTCACACCTCTTTTTCTCTT 73860
mRNA      ------------------------------------------------------------ genome    TCCTGAGAATTAAGCTTTTGTTTCGAGTTAGAAAGTTGATAGTAGGGAATTGTTCCATGG 73920
mRNA      ------------------------------------------------------------ genome    CTGAGCAATTTATCTCCACAGAGGAACAGTATGTCTCAGACATCTTGAACTACATCGATC 73980
mRNA      ------------------------------------------------------------ genome    ATGGAGACCCACAGGTTCGAGGAGCCACTGCCATTCTCTGTGGGACCCTCATCTGCTCCA 74040
mRNA      ------------------------------------------------------------ genome    TCCTCAGCAGGTCCCGCTTCCACGTGGGAGATTGGATGGGCACCATTAGAACCCTCACAG 74100
mRNA      ------------------------------------------------------------ genome    GTAACGGCCAGTTTTTCAGCTGTGTTTTTTCTAGTTATGCTTACTAAGGTTTAAGTTTAG 74160
mRNA      ------------------------------------------------------------ genome    ATGATGATGTTTGTTGCTTGTTCTTCTGGTTAGGAAATACATTTTCTTTGGCGGATTGCA 74220
mRNA      ------------------------------------------------------------ genome    TTCCTTTGCTGCGGAAAACACTGAAGGATGAGTCTTCTGTTACTTGCAAGTTAGCTTGTA 74280
mRNA      ------------------------------------------------------------
```

FIG. 1 HHH

```
genome    CAGCTGTGAGGGTGAGCATAATCTTCTGTGGAACCATTTCTTCACTTAGTGGACATTTTA  74340
mRNA      ------------------------------------------------------------ genome    TCATTGCTACAATTAAAATTGGAGCTTAATAGGAAATATTTCCATGCACTCTAAAGCTGT  74400
mRNA      ------------------------------------------------------------ genome    AACCAGTAATACCCACCATGTATCCATCTCTCAGCTTTAGAAAGAAAACGTTGCCAGTAA  74460
mRNA      ------------------------------------------------------------ genome    AGTTAATGCTTCATAAACTTCAGTTTAAGTTCTAATTCTCAGAATATTTGTTTGAAATAG  74520
mRNA      ------------------------------------------------------------ genome    ACCTCTTCCTAAAGGATATATTTAGAAATAACCTATCATTAAGTGTAAAGTCTGTTGAAT  74580
mRNA      ------------------------------------------------------------ genome    ATGCTGGGCACGGTGACTCACACCTGTAATCTGACCACTTTGGGAGGCCAAGGTGGAAGG  74640
mRNA      ------------------------------------------------------------ genome    ATTGCTTGAGCCCAGGAGTTCAAGACTATGGGCAACATAGTTGACCCTGTCCCTACAGAA  74700
mRNA      ------------------------------------------------------------ genome    AATTAAAAAAAAAAAAAAAAAAGTAGCTGGGTATGGTGGTGCATACCTGTAGTCTCAGC  74760
mRNA      ------------------------------------------------------------ genome    TACTCGGGAAGCTGAGGTGGAGGGGGGATTGCTTGAGCCCCAGAGATCAAGGCTGCAGTA  74820
mRNA      ------------------------------------------------------------ genome    AGGCGTGGTTACACCACTGCCCTCTAGCCTGGGCAACAGAGTGAGACTGTCTCAAAAATA  74880
mRNA      ------------------------------------------------------------ genome    ATAGTAATAATAATCAGTTGAATTAAAAAAAAAAAAAAAAAAACCACTGTGCTAGGCCCA  74940
mRNA      ------------------------------------------------------------ genome    TAGTATGGTAAGAGTTAAAGTGAGCCTTAGGGATTATTTACTCAACCTCTGTTTCTGTAT  75000
mRNA      ------------------------------------------------------------ genome    AAAGTGGAATAGGCTCAATTCTTTAAGTGATAGCATGTTGAACCTTTCCATACCAACTGG  75060
mRNA      ------------------------------------------------------------ genome    CTCATAAGTCACAACTGGCCAGTCAACAAGAGTAAAAATTAACTGGTAAAAATCAAAGCA  75120
mRNA      ------------------------------------------------------------ genome    AAAAACCTACAATTGTCAAATTTGTGGGATAACTCCCCCTTTTAAAATGTCATGCCTGAC  75180
mRNA      ------------------------------------------------------------ genome    AGTAATTTCTCTCTAGTTTCCAGGTTTTCAGTCAGTTGTGTCTTTTTGAGCAGAAGGAA  75240
mRNA      ------------------------------------------------------------ genome    GCATGCTAAGAGCTCAATCTTGTGGCTAGCTGGGGGTCTTTGTGTCAGCCATGCATGTGA  75300
mRNA      ------------------------------------------------------------ genome    TGGTGCCCCTGGGTGCTTGGGGCTGCAGGGGAGGGGTACAGCAGTAGGGGCCTGTTCTGT  75360
mRNA      ------------------------------------------------------------ genome    TCTCTCGTGCTGTGGAGTACATAGTGACATAGTGGGGTGGTCCTTGGTGTAGGTCCCTTG  75420
mRNA      ------------------------------------------------------------ genome    TTCCTACCCCTGGGTCTGAGATTTATTTAGAAGTGGTGTTGGGGCTGTGCGGCAGGCCCC  75480
mRNA      ------------------------------------------------------------ genome    TCTGTAACTGATCAATGTTTGTGAAGTTGCTGTTTGAGAGTTGAAACCATGACATAAGCA  75540
mRNA      ------------------------------------------------------------
```

FIG. 1 III

| | | |
|---|---|---|
| genome | GAAATGGAAGGAAGAAAGAACCAGTTATGTGAAAGGGACACATTTACTTTTAAGCTTGTA | 75600 |
| mRNA | ------------------------------------------------------------ | |
| genome | TTTACTGAGATAAAGTATTCTTAATCAATGTTCTTGAGAGGTGTGGGAAAAATGCAACAT | 75660 |
| mRNA | ------------------------------------------------------------ | |
| genome | CCTGGTTGCAGTTAAACCCAGAACATTGTGTGTTGAAGAGTGACGGTTCTCAAACCGTCA | 75720 |
| mRNA | ------------------------------------------------------------ | |
| genome | AGACGCGGGTACTGAGTGGGACTAACCTGCTGTCCTCTTGCCTTGGACCTTGTGTTCCAG | 75780 |
| mRNA | ------------------------------------------------------------ | |
| genome | AACTGTGTCATGAGTCTCTGCAGCAGCAGCTACAGTGAGTTAGGACTGCAGCTGATCATC | 75840 |
| mRNA | ------------------------------------------------------------ | |
| genome | GATGTGCTGACTCTGAGGAACAGTTCCTATTGGCTGGTGAGGACAGAGCTTCTGGAAACC | 75900 |
| mRNA | ------------------------------------------------------------ | |
| genome | CTTGCAGAGATTGACTTCAGGTAAGTGAGTCACATCCATTAGATTTCATGAACTAAGCTC | 75960 |
| mRNA | ------------------------------------------------------------ | |
| genome | AATTGAAAGTTCTGGGATCACTTGATGCAAGGAATGATGTTATCAAGTACCCTGTCCATC | 76020 |
| mRNA | ------------------------------------------------------------ | |
| genome | AGAAATCCGAGTGGTTTAGGTAGATGACAGTGATTTCTCCTCCCAGTGGCTTTTTGCTG | 76080 |
| mRNA | ------------------------------------------------------------ | |
| genome | AACTTTGCCCTATGCTTGGAATTTTATTTTATTTTATTATTTATTTAGAGACAAGATCTT | 76140 |
| mRNA | ------------------------------------------------------------ | |
| genome | GCTCTGTCGCCCAGGCTTGAATGCAGTAGCACAATCATAGCTCACTGAAGCTTTGAACTC | 76200 |
| mRNA | ------------------------------------------------------------ | |
| genome | TAGGACTCAAGTGGTCCTCCTGCCTCAGCCTCCCGATTAGCTAGGAGAATAGGTGTGTGC | 76260 |
| mRNA | ------------------------------------------------------------ | |
| genome | CGTCACACTGGCTAATATTTTTTGTAGAAATGGGGTCTTGCTATGTTGCCCAGGCTGGTC | 76320 |
| mRNA | ------------------------------------------------------------ | |
| genome | TCAAACTCCTGGGCTTGATTGATCCTCCATCTTGGCCTCCCAAAGTGCTGGGATTACAGG | 76380 |
| mRNA | ------------------------------------------------------------ | |
| genome | CATGAGCCACTGTGCCTGGCCTAGAATTTTAAAATATAAGTAGAAGAGTAGATTTTTTTT | 76440 |
| mRNA | ------------------------------------------------------------ | |
| genome | TTTGGTAGTCCTCGTCATTTAAGTATTCTGGATAGTGGGAATAAAAGAGCTTAGAATTTT | 76500 |
| mRNA | ------------------------------------------------------------ | |
| genome | TCATCTTTGTCTTAAACTTTTAAAAAAATGTAGCTTATATTAATTCTGCTTGTTTAAAAA | 76560 |
| mRNA | ------------------------------------------------------------ | |
| genome | GAATATACTCTTCATTATACTGAACCTAGGTAAGACAGCTGGTTTATATTTTGTTGCAAT | 76620 |
| mRNA | ------------------------------------------------------------ | |
| genome | TAAAAAACGTGAGCTGTGGTTGCAGTGAGCCAAGATTGTGGCCATTGCACTTCAGCCTGG | 76680 |
| mRNA | ------------------------------------------------------------ | |
| genome | CAACAGAGTGAGACTTGGCCTCAAAAAAAAAAAAATAACATGAGCTGTGTTGGCACTTTC | 76740 |
| mRNA | ------------------------------------------------------------ | |
| genome | ATTTTCTAAGAGTAGTTTTGGCTGGAGAAGTTTTCTTTCAGTACTTTCTTTTAGAAGGGA | 76800 |
| mRNA | ------------------------------------------------------------ | |

FIG. 1 JJJ

```
genome   AATTTTCCTTTATAATTTAGGGTTTGTTTTTTTTTTTCCAAGCCACCTTTTATAGAGCC  76860
mRNA     ------------------------------------------------------------ genome   CTTGTGGGTTATTTCATTTAATCCTTAGAATGTTTATAAATCTGGGCTTGTTCTCGGCTC  76920
mRNA     ------------------------------------------------------------ genome   CACCCACAGATAGGGACGCTGAGCGTGCATGAGTGGGCAGCAAGATAGCAGGTTATGGAG  76980
mRNA     ------------------------------------------------------------ genome   GGCCCAGCTCACCCCTTCTGTGGCTTGAGCCAATTTTATAGGGCACTTACAGAGTCTTTT  77040
mRNA     ------------------------------------------------------------ genome   GAAATAGTATTTATTTTGAAGAAAAAGAAAAACAGTTTACTGAGTACTGTCTTATTGAGT  77100
mRNA     ------------------------------------------------------------ genome   CTGGAATTGTGAGAGGAATGCCACCTCTATTTATTTAAAGCCATTGGCCTTTTTTGTTGT  77160
mRNA     ------------------------------------------------------------ genome   TTTGAGTAAGTGCTGCCCAAGGTCCTTCCAGGGCACCTGGATGAGCCTGCTCTGGAGCAA  77220
mRNA     ------------------------------------------------------------ genome   GCTGGCGGTAAGTGTTTACTGAGTAACTAAATGATTTCATTGTTAAATGTGCTCTTTTGT  77280
mRNA     ------------------------------------------------------------
                                                              rs363075
genome   TAGGCTGGTGAGCTTTTTGGAGGCAAAAGCAGAAAACTTACACAGAGGGGCTCATCATTA  77340
mRNA     ------------------------------------------------------------ genome   TACAGGGGTAAGCGGTTTATTTTTGTGAGATGCTGTTTTACCTTCAAGAAGGTGAAAGTG  77400
mRNA     ------------------------------------------------------------ genome   AGGCTTTCCTTGTGGAATTTCTCTAAATGCATTCGTCATGTTTTAGATGTTTATTTCACA  77460
mRNA     ------------------------------------------------------------ genome   GTTTATATCATGAAAGTTATAATCTTGTCATATGGATTTAAGTCTAGTAATGTTGAGTTC  77520
mRNA     ------------------------------------------------------------ genome   TTTCTCACTAGCTTTCCAAAATATCTTACCTAAAATTTAGTCAAATACAAGATTATGTTT  77580
mRNA     ------------------------------------------------------------ genome   ATTTTTATTATCCTTCTCTCTAAAGCTTTTAAAACTGCAAGAACGAGTGCTCAATAATGT  77640
mRNA     ------------------------------------------------------------ genome   TGTCATCCATTTGCTTGGAGATGAAGACCCCAGGGTGCGACATGTTGCCGCAGCATCACT  77700
mRNA     ------------------------------------------------------------ genome   AATTAGGTATTTACCAATATTTTATCTCTTTTCCTTTTTTGGTTGAAGTACTAAAAGATA  77760
mRNA     ------------------------------------------------------------ genome   CGAGAATGGAAAGAGAGGGAAGAATTCAAAGGATGTAGAGCAGTATTCCTGAATCTGAGC  77820
mRNA     ------------------------------------------------------------ genome   TCATTTCAGCCATTCTATTCTTAAACTATAATGAAAAAAAAATCCAAAAAAGTCTAAAAT  77880
mRNA     ------------------------------------------------------------ genome   TATAATTAAAAAAACAACAAAATACTAACTGTCCATTGTAAAAAGTAATGCACTTTCATT  77940
mRNA     ------------------------------------------------------------ genome   GTAAAAATTTTGGACTATAGAGAATAGTACTAAGAAGAAAAAAAAAATCACCTTCAATTC  78000
mRNA     ------------------------------------------------------------ genome   TGCTGCCACCTGGAGGTAATCACTGTTAATATTTTGCTATATACTCTATGAGTTTCTTGT  78060
mRNA     ------------------------------------------------------------
```

FIG. 1 KKK

```
genome    TCAAAATCAGGTCAAAATTACATGCAATTTTGTAATCTGACAATTTCCACTTAATATTTT  78120
mRNA      ------------------------------------------------------------ genome    ATTAGCATTTTCCTGTTATGAAACAGTAATTTTAGTTATGGGTCGTTGTTTTGCTATGCG  78180
mRNA      ------------------------------------------------------------ genome    GTTGGGATAAAATTTTATATACTTTTTTTGGCAATTACTTATTATACATAAATGTTTGTG  78240
mRNA      ------------------------------------------------------------ genome    TATAGTTTTCTTTTTCTGAGAATTCCTGGAAGTTGAGTTACCAGGCCCGGCTTTGAATTT  78300
mRNA      ------------------------------------------------------------ genome    TTTTTTTTATTTTTTTTTGAGACAGAGTCCTGCTCTATTGTCCAGGTGCTATCTCGGCT   78360
mRNA      ------------------------------------------------------------ genome    CACTGCAACCTCTGTCTCCCTGGTTCAAGCGATTCTCCTGCCTCAGCCTCCCGAGTAGCT  78420
mRNA      ------------------------------------------------------------ genome    GGGATTACAGGGGCACACCACCACGCCCAATTAATTTTTGTATTTTTAGTAGAGACAGGG  78480
mRNA      ------------------------------------------------------------ genome    TTTCACGATATTGGCCAGGCTGGTCTCGAACTTCTGACCCCGTGATCCACCTGCATTGGC  78540
mRNA      ------------------------------------------------------------ genome    CTCCCAAAGTGCTGGGATTACAGGCGTGAGCCATGGCGCCTGGCCAGGCTTTAAATTTAA  78600
mRNA      ------------------------------------------------------------ genome    AACAAATCTTCTAATAGCTTTATGGAGGTTATAATTTACATTTCTTGAAATGTACTCACT  78660
mRNA      ------------------------------------------------------------ genome    TTGAGTGTATAGTAAACTCCAATTTTATCACATTTCTGTCACCCCAAATGTATCCTTGTG  78720
mRNA      ------------------------------------------------------------ genome    CCCATTTGCTGTAACCTCCGGTTCCTGCCCCAACTCCTAGGCAGCCACTCATCTATTTTC  78780
mRNA      ------------------------------------------------------------ genome    TGTCCCTTAAGATTTGTGTTTTCGCCAGGCGCTCATGCCTGTAATCCCAGCACTTTGGGA  78840
mRNA      ------------------------------------------------------------ genome    GGCCGAGGTTGGTGGATCACTTGAGGTCAGGAGTTCGAGACCAGCCTGGCCAACATGGTG  78900
mRNA      ------------------------------------------------------------ genome    AAACCTTGTCTCTACTAAAAATACAAAAATTAGTCGGATGTGGTGGCACACGCCTGTAAT  78960
mRNA      ------------------------------------------------------------ genome    CCCAGCTACTCGGGAGGCTGAGGCAGGAGAATCACTTGAACCTGGGAGGCGGAGGTTGCA  79020
mRNA      ------------------------------------------------------------ genome    GTGAGCAGAGATCGCGCCACTGCCTTCCAACCTGGGCAACAGAGAGAGACTGTCTCAAAA  79080
mRNA      ------------------------------------------------------------ genome    CAAACAAAGATTTGTATTTTCTGGACATTTTATAGTACTGGGGTCATAGTATAGATGGAC  79140
mRNA      ------------------------------------------------------------ genome    TTTTGCATTTGGCTTCTTTTACTTAATTGTGAGATTGGTTCTTGTTGTAGCATGTATCAG  79200
mRNA      ------------------------------------------------------------ genome    TAGTTTGTTCATTTTTATTGGCGAAAGTATTCTATTATATGAATAATACCATATTTTATC  79260
mRNA      ------------------------------------------------------------ genome    TATCCATCAGATGGATATTATAGAGTTCATGTTTTGGCTAATTTATGAATTATGGTACTG  79320
mRNA      ------------------------------------------------------------
```

FIG. 1 LLL

| | | |
|---|---|---|
| genome | TGAACATTTGCCTGCAAGATTTTGTGTAGACATGTCTTCATTTCTCTTGAGTAGATCACC | 79380 |
| mRNA | ------------------------------------------------------------ | |
| genome | TAGAAGTGGATTTTTAAATAATTTTGGTACTTACTGTGAAACTGCTCTTCAAAAACATAC | 79440 |
| mRNA | ------------------------------------------------------------ | |
| genome | CATTGTTCCTTCCTTCCTTCCTTCCTTCCTTCCTTCCTTCTTTCCTTCCTCCCTTCCTCC | 79500 |
| mRNA | ------------------------------------------------------------ | |
| genome | CTCCCTTCCCTACTTCCCTCTCCCTTTCCCTTTCCCTTCCCCTTTTCCCTTCCCCTTCCC | 79560 |
| mRNA | ------------------------------------------------------------ | |
| genome | GCCTGCCTGCCTGCCTGCCTTCCTTCCTTCCTTCCTTCGTTTCTTTCTACATATACACAT | 79620 |
| mRNA | ------------------------------------------------------------ | |
| genome | TTTTTTAAATTTCAATGGTTTTTGGGGTACAAGTGGTTTTTGGTTACATGGCTGAATTTT | 79680 |
| mRNA | ------------------------------------------------------------ | |
| genome | GGTTACATGGTGAAGTCTGAGATTTTAGTACACCTGTCACCCGAGTAGTGTACCTTGTAC | 79740 |
| mRNA | ------------------------------------------------------------ | |
| genome | CCAATATGTAGTTTTTTGTCCCTCACCTTCCAGCCTTCCGCCTTGTGAGTCTCCAATGTC | 79800 |
| mRNA | ------------------------------------------------------------ | |
| genome | CATTATACCACACTGTATGCCCTTGCGTACCCACAGCTCAGCTCCCACTTCTGAGAACAT | 79860 |
| mRNA | ------------------------------------------------------------ | |
| genome | ATAGCAGAAACATGCCAAAGTATACTCCCACTACCAGAATGTGATTGTGCCTGATTCTTC | 79920 |
| mRNA | ------------------------------------------------------------ | |
| genome | TCACCAGTACAAATATTTCAAAAAAAGTTAAATATGTATCAGTTTTTTGGGCAGAAGTTG | 79980 |
| mRNA | ------------------------------------------------------------ | |
| genome | ATACTTCTCTTTATTTATTTATTTTTTTGAGATAGGGTCTCATTCTATGATGCCCAGGC | 80040 |
| mRNA | ------------------------------------------------------------ | |
| genome | TGGAGTGTGGTGGTGCGATCTCGGCTCACTGCAGTCTCTGCCTCCCAGGTTCAAGTGATT | 80100 |
| mRNA | ------------------------------------------------------------ | |
| genome | CCCACGTCAGCCTCCCAGGAAGCTGGAATTACAGGCGAGGGCCACCACTGCCAGCTAATT | 80160 |
| mRNA | ------------------------------------------------------------ | |
| genome | TTTGTATTTTTTGGTAGAGATGGGGTTTCACCATGTTGGCCAGACTGGTCTCAAGCTCCT | 80220 |
| mRNA | ------------------------------------------------------------ | |
| genome | GACCTCAAGTGATCCACCTGCCTTGGCCTTCCAAAGTGCTGGGATTACAGGCGTGAGCTA | 80280 |
| mRNA | ------------------------------------------------------------ | |
| genome | CCACACCCGGCTGATATTTCTTTTTAAAATAACTTACCTTCTTTTGAAAGTAATACATGT | 80340 |
| mRNA | ------------------------------------------------------------ | |
| genome | TTAATGAACAGAATTTAAGGAAAATATAAAAAAACGAAATAATCTTTGTAATCAAACTAC | 80400 |
| mRNA | ------------------------------------------------------------ | |
| genome | TGAAAAGAAAACCAAAGTTACATTTTGGTGCATATTCTTTTTCATTTTCATCATTGTAAT | 80460 |
| mRNA | ------------------------------------------------------------ | |
| genome | TTGCATTTCTTTGATTACTTGTGAGACACTCCTTTCATTTACTTAATAGGTTTATATGAC | 80520 |
| mRNA | ------------------------------------------------------------ | |
| genome | TTGCCTATTCAGAGATTTTGCAGCTTTACCATTTTCTGCAAATGATAGCAACTTCTTTTT | 80580 |
| mRNA | ------------------------------------------------------------ | |

FIG. 1 MMM

```
genome      GTTTGTTTGTTTGTGGAGACAGAGTCTCGCTCTGTCACTCAGGCAGGAATGCAGTGGTGG  80640
mRNA        ------------------------------------------------------------ genome      AATCTTGGCTCATTGCAACTATTGCCTCCTGGGTTCAAGCGATTTTCCTGCCTCAGCCTC  80700
mRNA        ------------------------------------------------------------ genome      CCAAGTAGCTGGGATTACAGGAGTGTGCCACCATGCCCGGCTAATTTTTGTATCTTTAGT  80760
mRNA        ------------------------------------------------------------ genome      AGAGATGGGGTTTTGCCATGTTGGCCGGGCTGATCTTGAACTCCTGGCCTCAAGCGGTCC  80820
mRNA        ------------------------------------------------------------ genome      CCCTGTCTCGGCCTCCCAAAGTGCTGGGATTACAGGCGTGAGCCACCGTACCCAGCCAGT  80880
mRNA        ------------------------------------------------------------ genome      AGTTACTTCTTATATTCTAGAAAAAATTCTACTCATGATCAAGTCTCCATGAGGAAAGAG  80940
mRNA        ------------------------------------------------------------ genome      ACTTTAATTGAAGATCATGGGGCTTGCAGACCAATATGATAAAATAGTTCATTGTTTCTA  81000
mRNA        ------------------------------------------------------------ genome      AAAGTATTACTGAGTGTTGATGGCAGATATGAACCCTTTTGTTTTTGTAGGAAAATGTTA  81060
mRNA        ------------------------------------------------------------
                       rs363064
genome      CCCGTATTCTCCATTTGAATTCAGTTTAGATTTGTTAGGAATCGCAGCTTAAGCTTTGCC  81120
mRNA        ------------------------------------------------------------ genome      ATCTGGGAGTGTTTGGGACAGTTTTGCAGACAAAATTGCAAAAGTGCCTAAGGAATGCAG  81180
mRNA        ------------------------------------------------------------ genome      CTGGCATTCAGACCTGCTCTGTGCTCAGTACTCTGTGGACAGACACTGTTCAGCACTTGT  81240
mRNA        ------------------------------------------------------------ genome      TGATCAGAAGGTTTAGAAAGAGAACTTTCAAAGTTGGTTTTTAATTAAAGCATTTAATAG  81300
mRNA        ------------------------------------------------------------ genome      TGTAAATAGAAAGGGATTAAATTTTATGACAGACAAAAGAAAGTACAGCACCCAGCTGGG  81360
mRNA        ------------------------------------------------------------ genome      CGTGGGGGCTCACGCCTGTAATCCAGCACTATGGGGGGCTGAGGTGGGTGGATCACGAGG  81420
mRNA        ------------------------------------------------------------ genome      TCAGGAGTTCAAGAGTTCAAGAACAGCCTGGCCAAGGTGATGAAACCCTGTCTCTACTAA  81480
mRNA        ------------------------------------------------------------ genome      AACTACAAAAATTAGCCGGGCGCGGTGGCAGGCGCCTGTAATCCCAGCTACTCAGGAGGC  81540
mRNA        ------------------------------------------------------------ genome      TGAGGCAGGAGAATCACTTGAACCTGGACGGCAGAGGTTGCAGTGAGCCAAGATTGCACC  81600
mRNA        ------------------------------------------------------------ genome      ATTGTACTCCGGCCTGGGCCACAGAGTGACATTCTGTCTCAAAAAAAAAAAAAAGAAA  81660
mRNA        ------------------------------------------------------------ genome      AAAAGAAAGTACAGCACCCAGTTATGTCCGAGTGGGTGCATGAGAGTGACCCTGAGATTG  81720
mRNA        ------------------------------------------------------------ genome      GAGACAACGCTGTCACGTGCTTGAAGAACGCCACCTGAGAAGGGGGCGAGAAGTGGTGT  81780
mRNA        ------------------------------------------------------------ genome      CCGCTGGTAACCAGAGGTGTTGGCTTAGCCATCTGCAGGGAGGAGGGTGGTCTATCACAG  81840
mRNA        ------------------------------------------------------------
```

FIG. 1 NNN

| | | |
|---|---|---|
| genome<br>mRNA | GTGAGTTTCATCTACTTTCTTAAGCAAATTAACCTTACTTTTGTGTTAGGCTTGTCCCAA<br>------------------------------------------------------------ | 81900 |
| genome<br>mRNA | AGCTGTTTTATAAATGTGACCAAGGACAAGCTGATCCAGTAGTGGCCGTGGCAAGAGATC<br>------------------------------------------------------------ | 81960 |
| genome<br>mRNA | AAAGCAGTGTTTACCTGAAACTTCTCATGCATGAGACGCAGCCTCCATCTCATTTCTCCG<br>------------------------------------------------------------ | 82020 |
| genome<br>mRNA | TCAGCACAATAACCAGGTATGCTGACCCAGTGGCATCTTCACATTGTCGGGAAAATGCCC<br>------------------------------------------------------------ | 82080 |
| genome<br>mRNA | TTTCCTGATGCCTTTCTTTAGGCTTTAATTGAAAACATTTTATTTTCTAGAAAAAAGCTT<br>------------------------------------------------------------ | 82140 |
| genome<br>mRNA | CAGCTCAGGATGTTTGAGTGTAGGTCAGTCCTTTGATAGGATATTATCATTTTGAGGATT<br>------------------------------------------------------------ | 82200 |
| genome<br>mRNA | GACCACACCACCTCTGTATTTAAGCTCTGCCACAATCACTCAGCTGTGACACTGTAAATC<br>------------------------------------------------------------ | 82260 |
| genome<br>mRNA | TCTTAATAGTTTATTACATTCCATGTGCTGACAGTTGTATTTTTGTTTGTGACACTTACG<br>------------------------------------------------------------ | 82320 |
| genome<br>mRNA | TATTATCTGTTAAAACATTTTCACTTTAGTTGTGTTACCTTTAAAGAGGATTGTATTCTA<br>------------------------------------------------------------ | 82380 |
| genome<br>mRNA | TCATGCCTGTTGATTTTTTGGTGAGCGGGCTATTAAAGTCAGTGTTATTTAGGGTTATCC<br>------------------------------------------------------------ | 82440 |
| genome<br>mRNA | ACTAGTTCAGTGATTTGCGAGATTATCATTCACATTTATTGTGGAGCTTTTGAATATCGT<br>------------------------------------------------------------ | 82500 |
| genome<br>mRNA | GTCAAATGGCCACATATATCCCATTCTTATCTGCTTCTTAGGTGAGTGGGACACAGTGCT<br>------------------------------------------------------------ | 82560 |
| genome<br>mRNA | TTAATGAAGCTATAATCTTCAGAATTCTAGCTTGCAGAGAAGATTGCAGAAGTGATAAGA<br>------------------------------------------------------------ | 82620 |
| genome<br>mRNA | CTTGTGCTTTTTAATTTTGTCTTTTAAATGTTATTTTAAAAATTGGCTTTATATGATACT<br>------------------------------------------------------------ | 82680 |
| genome<br>mRNA | CTTTTTTTCTGCTGAGTAACAGTGTTTTACAAAACTTGGACTAAATGACTTCTAAGCTTA<br>------------------------------------------------------------ | 82740 |
| genome<br>mRNA | AATGATCACTTGATGCTTTTTTTCTGAATTAGGAACTCAGCTTATCAAATATCAAAGTCA<br>------------------------------------------------------------ | 82800 |
| genome<br>mRNA | TAATTCCTGAATAAATAACGTCTTTTTTCATGTAAAGACTGCTTTAAAAAACACATGGAA<br>------------------------------------------------------------ | 82860 |
| genome<br>mRNA | GGCTGGGTGCGGTGGCTCACGCCTGTAATCCTAACACTTTGGGAGGCCCAGGTGGGCAGG<br>------------------------------------------------------------ | 82920 |
| genome<br>mRNA | TCGCTTGAGCTCAGGGGTTCAAGACCACCCAGGGCAACATGGCAAAACCCACCTCTACTC<br>------------------------------------------------------------ | 82980 |
| genome<br>mRNA | AAATACAAAAAATTAGCCAGGCGTGGTGGCGGGCCCCTGTAATCCCAGCTACTCGGGAGG<br>------------------------------------------------------------ | 83040 |
| genome<br>mRNA | CTGAGGGATGAGAATCACTTGAGCCCCGGAGGCAGAGGTTGCAGTGAGCCAAGATTGTGC<br>------------------------------------------------------------ | 83100 |

FIG. 1 OOO

```
genome    CATTGCACTCCCAGCTTGGGCTACAGAGTGAGACTCTGTCTCAAAAAAAGACACACACAC   83160
mRNA      ------------------------------------------------------------ genome    AAACAAAAAAAACATGGAGACATTTTTTTGGCCACCTTAATATTTCCCCTCAGATAATTT   83220
mRNA      ------------------------------------------------------------ genome    CCTTTGTTTAAACTCAGAACTGGCATTTTCTCTCTTGGAGAAGATTCAGGACAAATACTC   83280
mRNA      ------------------------------------------------------------ genome    CTTTAAGATAAGTAGAAGCAGTGAAAGAGGATTTGATTATCAGGAATTTGATAAGCTTAG   83340
mRNA      ------------------------------------------------------------ genome    AATAAATTGTTGCTTCTTAATGTCATTTCAGAAGATGAATATTTATTAATAGATGCCAAC   83400
mRNA      ------------------------------------------------------------
                                          rs3025849
genome    TGAGATATCATTAAAATTGATTACTAACTACTACTTGGAAAAGTCTCCCAGTTCCAAACT   83460
mRNA      ------------------------------------------------------------ genome    TCAGCAGGCCTCTTGACAATTCAGCTGTGGTCAATTGGGTCTTGCGTGATAGATACAATG   83520
mRNA      ------------------------------------------------------------ genome    ACCAATTGTGCAGCAGAGTGTGCTGCTTAGCTGCCTATTCTGTTAGCATTCATGTGTTAA   83580
mRNA      ------------------------------------------------------------ genome    CTTAAAATCATAATCTCCTTAGTTTTGTTGAGTGTCTCCGTGGACAAGACACTGTGAGGG   83640
mRNA      ------------------------------------------------------------ genome    ATACAAAATCAGATTGGCTTTATTCAAACCACTGGGGTATTATAATTCATTTATAATTTA   83700
mRNA      ------------------------------------------------------------ genome    TTTTATTTTTTGCCTTTTTTCCATGTGTTCTAAAGGAATTAGAGTTTGTATATAACTATA   83760
mRNA      ------------------------------------------------------------ genome    ATGGGGGATAGAAATTGACATGTGCCATGAAGGGAATGCAAAAAAGTGCCGTGGGAGATG   83820
mRNA      ------------------------------------------------------------ genome    AGAAGTGGAGAAAGGAATTTCTTTTTTCTTGGAAGCAGGAATAACTTCATGAAGCATGTA   83880
mRNA      ------------------------------------------------------------ genome    TTTCAACTTAAACAGATAGTAGGCAACGCTGTAAGGGGAGTATGGCTGCAGCAAAAGTGT   83940
mRNA      ------------------------------------------------------------ genome    TCGGGGCAGACTGGGAGGAAGGGAGGGAATAAATTCAGCCATTGTTATGGAATAATGATC   84000
mRNA      ------------------------------------------------------------ genome    AAAATTTATTTTCAGCCCGTTTCACTTAAAAGTTGAGACTGCTTAACTTTTTTTAATCTT   84060
mRNA      ------------------------------------------------------------ genome    TAATCTTAAACTTTTAAATGCCATTTGATCTTTAAAAATATATGTTTTAATAGTGTATTT   84120
mRNA      ------------------------------------------------------------ genome    TAAGTCTCTATATTTTTGTTATTAGAATATATAGAGGCTATAACCTACTACCAAGCATAA   84180
mRNA      ------------------------------------------------------------ genome    CAGACGTCACTATGGAAAATAACCTTTCAAGAGTTATTGCAGCAGTTTCTCATGAACTAA   84240
mRNA      ------------------------------------------------------------ genome    TCACATCAACCACCAGAGCACTCACAGTAAGTCTCTTTCTTGATCGGTCTTACTGACATT   84300
mRNA      ------------------------------------------------------------ genome    GTAATAGTTTTTGGTAGCTTGTATGGCCAGTTAGTTGTATGGTCATCTTACGGTGAGGTG   84360
mRNA      ------------------------------------------------------------
```

FIG. 1 PPP

| | | |
|---|---|---|
| genome | CTTGTCTTACAGCTCTTACTTATCCATGAGGCTTGCTAAGAAATTGTGCTTCTGTGAAAA | 84420 |
| mRNA | ------------------------------------------------------------ | |
| genome | GAATCTCAGCTTACTCCAGGAATGTAAATGACTATGTTTTTTCTGATTATTAAAGTAATA | 84480 |
| mRNA | ------------------------------------------------------------ | |
| genome | CACGCCCAAAATAAAAAAATTCAGCCAATTTAGGAAGACACAACAATTAAAATAAGCCAG | 84540 |
| mRNA | ------------------------------------------------------------ | |
| genome | GCATGGTGGCTCATGCCTGTAATCCCAGCACTTTGGGAGGCCAAGGTTGGGGGCTCACTT | 84600 |
| mRNA | ------------------------------------------------------------ | |
| genome | GAGGTCAGGAGTCGGATACCAGCCTGGCCAACGTGGTGAAACCCCATCTCTACTAAAAAT | 84660 |
| mRNA | ------------------------------------------------------------ | |
| genome | ACAAAAATTAGCTGGGCGTGGTGGCGGGCGCCTGTAATCCCAGCTACTCAGGAGGCTGAG | 84720 |
| mRNA | ------------------------------------------------------------ | |
| genome | GCAGGAGAATCGCTTGAACCTGGGAGGTAGAGGTTGCAGTGAGCTGAGGTCAAGCCACTG | 84780 |
| mRNA | ------------------------------------------------------------ | |
| genome | CACTCCAGCCTGTGCAATAGAGCGAGACTCTGTCTCAAAAAAAAAAAAAAAAAAAGAAAA | 84840 |
| mRNA | ------------------------------------------------------------ | |
| genome | GAAAAAAGTAAACTACTGTCACCTGCATTGGTAATGTATCAGAAGTTTAAAATGTCTAGA | 84900 |
| mRNA | ------------------------------------------------------------ | |
| genome | TTATAATTAACTCAGTGACCTGGTAATATATACTAAGGGAAAAATATTTATAATTTACAT | 84960 |
| mRNA | ------------------------------------------------------------ | |
| genome | TTTTACATTTTTATTTTTTAATTTTATTATTTTTTTTTGAGACAGAGTTTTGCTCTTG | 85020 |
| mRNA | ------------------------------------------------------------ | |
| genome | TTGCCCAGGCTGGAGTGCAATGGCATGATCTCAGCTCACCACAACCTCCACCTCCCGGGT | 85080 |
| mRNA | ------------------------------------------------------------ | |
| genome | TCAAGCAATTCTCCTGCCTCAGCCTCCTGAGTAGCTGGGATTACAGGCATGCACCACCAT | 85140 |
| mRNA | ------------------------------------------------------------ | |
| genome | GCCCGGCTAATTTTGTATTTTTAGTAGAGACAGGGTTTCTCCATGTTGGTCAGGCTGGTC | 85200 |
| mRNA | ------------------------------------------------------------ | |
| genome | TCAAACTCCCAACCTCAGGTGATCCGCCCTCCTCGACCCCCCAAAGTGCTGGGATTACAG | 85260 |
| mRNA | ------------------------------------------------------------ | |
| genome | GTGTGAGCCACCATGCCTGGCCTTACATTTTTATAATAAGAATTTATGTTGCTGACATTA | 85320 |
| mRNA | ------------------------------------------------------------ | |
| genome | GAAAAGAACCATAATATCCAAGAATCCAAGAATAATTAAATTATGTACATATGCTAGTAT | 85380 |
| mRNA | ------------------------------------------------------------ | |
| genome | ATAGTGTGATGCTTTGGAGAATTTTTAACAATATGGAGATGTATAATCTGGATTGTAATA | 85440 |
| mRNA | ------------------------------------------------------------ | |
| genome | TTGAGTGAAAAAAGGCAGAATACAAACCTGGTGGGGGTATAGTCGGATTTCAGTTAAGAA | 85500 |
| mRNA | ------------------------------------------------------------ | |
| genome | AAATAATATTTACATATATACATTTCTCACACTGGCAGATAATCACCAAGATAAATTTTG | 85560 |
| mRNA | ------------------------------------------------------------ | |
| genome | GGATTGTGGATGATTTTTTTCTTCTTTATATTTTTCAGATATTCTCAAATTTTCTAAAAT | 85620 |
| mRNA | ------------------------------------------------------------ | |

FIG. 1 QQQ

| | | |
|---|---|---|
| genome | GAGCAAGTATAACTTTGTTATCAGAAAAAAATAATATACAAAAGTAATGTTAATTTGCT | 85680 |
| mRNA | ------------------------------------------------------------ | |
| genome | GGTGACCAGGTTAAACCTTTTTATTTTTATTTTTTGAGATGGAATCTCACTCTGTTGCCC | 85740 |
| mRNA | ------------------------------------------------------------ | |
| genome | AGGCTAGAGCACAGTGGCATGATCTTGGCTCACTGCAGCCTCCGCTTCCTGGGTTCAAAT | 85800 |
| mRNA | ------------------------------------------------------------ | |
| genome | GATTCTCTGGCCCCAGCCTCCTGAGTGGCTGGAATTACAGGCGTGTGGCACCACACCTGG | 85860 |
| mRNA | ------------------------------------------------------------ | |
| genome | CTAATTTTTGTATTTTTAGTAGAGGTAGGGTTTCACCAGGTTGGTCAGGCTGGTCTCGAA | 85920 |
| mRNA | ------------------------------------------------------------ | |
| genome | CTCCTGACCTCGTGATCCACCCACCTCGGCCTCCCAAAGTGCTGGGATTACAGGCGTGAG | 85980 |
| mRNA | ------------------------------------------------------------ | |
| genome | CTACTGCGCCCAGCCAGACCTTTTTATTTTATTTGACAAAAGAAATACTTCCATGTTATA | 86040 |
| mRNA | ------------------------------------------------------------ | |
| genome | GAAGACTAAATATTGTTTGGGCTGTCTGCAGTATGGTCTTCCCTTGATTTGTTCAAAATA | 86100 |
| mRNA | ------------------------------------------------------------ | |
| genome | TCGTAAACTTTGCTTATTTATTTTTATTGTGGCCGACTGTGTCGGGCACTGTTGTAGGCT | 86160 |
| mRNA | ------------------------------------------------------------ | |
| genome | TGGGATGGAAAAACAGGATTCCTGCCCTTAGGGTTTCTGCAGGCTGGTCAGGGAGACGAT | 86220 |
| mRNA | ------------------------------------------------------------ | |
| genome | GTGGTAAGCTGGAGCTCAGCTCCTAAGGATGTGCAGGGGCAGTTGAGAGGCGGAAGGGTG | 86280 |
| mRNA | ------------------------------------------------------------ | |
| genome | GGAGATCATTCCAGGGTGTGGGCAGCACAGGAACCTCTCTTCATTGGGATATAATTGCCA | 86340 |
| mRNA | ------------------------------------------------------------ | |
| genome | TTCTGATAACACGTGTTTGAGGTGTCTAAAGTAGGAAGTTGTACCATGGTGGGACAGATA | 86400 |
| mRNA | ------------------------------------------------------------ | |
| genome | TCCTGTGGTTATCATACACAGATCTCAGTTTTCTTCTCATTGTTTGTACTTTTTATAAAG | 86460 |
| mRNA | ------------------------------------------------------------ | |
| genome | GGTAACAGGAGATATAATTCAATAAACCTTTGTGGTGTTTGGGTGTGATTTTATTGTTTC | 86520 |
| mRNA | ------------------------------------------------------------ | |
| genome | TTTCTTCTCAGTTTGGATGCTGTGAAGCTTTGTGTCTTCTTTCCACTGCCTTCCCAGTTT | 86580 |
| mRNA | ------------------------------------------------------------ | |
| genome | GCATTTGGAGTTTAGGTTGGCACTGTGGGTATGTATTTTCCTCAGTATATATTAATAGTT | 86640 |
| mRNA | ------------------------------------------------------------ | |
| genome | GTCTACAACAGTATGACATAAACATAGTTATTAGGATGCCCTTTTTCTTTCTTTTTAAGT | 86700 |
| mRNA | ------------------------------------------------------------ | |
| genome | CTTTTATCAATTTGGCTTTTTGGAAAAATATCTGATGGAATACTTGTTTCTGCTATATTA | 86760 |
| mRNA | ------------------------------------------------------------ | |
| genome | GCTGTGTGAGACTAGTGACAGGAGCTGTGGGAAATGAATGCCAAATGTTCTTAGGCATTG | 86820 |
| mRNA | ------------------------------------------------------------ | |
| genome | ATGGGAATTTCAGGGTGTGGTCTTCAAGTTCATTTAAGGGAATTTTCATATGCTGGCAAA | 86880 |
| mRNA | ------------------------------------------------------------ | |

FIG. 1 RRR

```
genome      AGGCTTTTCTCATTAGCTTGACTCTTTCCAAAATTATTTGCTGTGAATTAGAAGTTTAGG 86940
mRNA        ------------------------------------------------------------ genome      AACCTTTTTCACTTAATTGTGACCTAGCATACGAAATGGTGATGATTAGGAACTACTG  87000
mRNA        ------------------------------------------------------------ genome      TTCTTGTATTAACAGCTTTTATTTAAAAATGATTTTCCTCCAGTAGATGGCCCTACTAGC 87060
mRNA        ------------------------------------------------------------ genome      ATCTGGGAAATAATTTCAAGTCTTCTCCAGCATTCAGGAATAGGCTTTCATTTTGTGTAT 87120
mRNA        ------------------------------------------------------------ genome      CAATTACTGAGAATGATTTTGGTGACTCACATCACATTTGAGAAGTAAACCTGCAGATTT 87180
mRNA        ------------------------------------------------------------ genome      CTTGTGTGTGTCAGCAAATGACCAACTGATATTTGCTTGAAGTGGATTACATTATCTGCT 87240
mRNA        ------------------------------------------------------------ genome      CTAGAATGATTGCTTTCCCACCTTCCTCACATACAGACTGAGCAGCTACGGTTTCTAATC 87300
mRNA        ------------------------------------------------------------ genome      ATAGGTCTGGCACTAGACTTCACTTCTGGGCAACTTTGGCATTGGAGTAAAATGTATTAA 87360
mRNA        ------------------------------------------------------------ genome      TTTAAAGAAAGTTAAAAATCCGTTCAAGTAAACATACAGTTCTAATACTTTTTACAATTT 87420
mRNA        ------------------------------------------------------------ genome      AAAATATAGATTTAAATGATAAAATAAAAAAGAAAATATGGGTAGACACCATAATCCTCG 87480
mRNA        ------------------------------------------------------------ genome      TTTCTGCATCTGTTCACAAGGGGTTGATATTTATGAGTTCTATTCTCCATATCCATTCTA 87540
mRNA        ------------------------------------------------------------ genome      TGTTCTCTTAATGCTCAGTCAGCACCTCAGGTGGTTGGAGTTCAATGCTTGGTAGTTTGA 87600
mRNA        ------------------------------------------------------------ genome      CTTACACTGTCTTTTCTAGGGGATTGAGCCCTGGGTAGTCCTGCTTATTTGAGGTTGCAA 87660
mRNA        ------------------------------------------------------------ genome      TTTGTCTTTCAATAACTTTTACTACAAGATATGGCGTGTTAAAGGATACCATTGGGGAAC 87720
mRNA        ------------------------------------------------------------ genome      CAACATAATAATATCAGGAAAACTAACCACGTCAGACCTGCCCCATTGTGTATCAAGTAC 87780
mRNA        ------------------------------------------------------------ genome      ACTATTTTTCCATAGTAATAAAGAGTTCACCCCAGCCAATTCTCTTTTATTTTGTGCCTG 87840
mRNA        ------------------------------------------------------------ genome      TTTACTCAATGGCATTAACATGCCCAAATGTCTGGGTAGCTGTCTCATCTCCAGTTCAGC 87900
mRNA        ------------------------------------------------------------
                                              rs6855981
genome      AGAACCATTGTCATATGCCCTAGTAAAAGCATTCCTTCATTGGACACTTAGGCCCCAATA 87960
mRNA        ------------------------------------------------------------ genome      CTTTCATTCAGATCTACTACCTGATTTCATTTCTCAAATGATTTTTATGGAGCTCTGATT 88020
mRNA        ------------------------------------------------------------ genome      TATAGGAAAGATGTTAGTTGATTAAAAATAAAACAATTTCTGAGCTGGTATAAAATGTAT 88080
mRNA        ------------------------------------------------------------ genome      TGTGACATGCCTTCCTCTTGGAATTGCAAGAGAAAGGAAGACTGTTGTTTGCTTAAAAAT 88140
mRNA        ------------------------------------------------------------
```

FIG. 1 SSS

```
genome    TGTCTATAATTTGACTTTGCAAATGTCTGCTTCCAGAGTGCCTCCACTGAGTGCCTCAGA 88200
mRNA      ------------------------------------------------------------ genome    TGAGTCTAGGAAGAGCTGTACCGTTGGGATGGCCACAATGATTCTGACCCTGCTCTCGTC 88260
mRNA      ------------------------------------------------------------ genome    AGCTTGGTTCCCATTGGATCTCTCAGCCCATCAAGATGCTTTGATTTTGGCCGGAAACTT 88320
mRNA      ------------------------------------------------------------ genome    GCTTGCAGGTACTGGTACTGAGTTGAAACAGGGACTCCAGGACTTGGATTTTGATTTCCT 88380
mRNA      ------------------------------------------------------------ genome    TAGGGGGAATGGGGGTGGTGAGCATATGAGGGGAAAATACTATAAGGTCATTGCCAGTGA 88440
mRNA      ------------------------------------------------------------ genome    TGGCTTGTCCCTTTAGTCAAATTTCAGATGTTACCTATATGCATAAACACATGCAGTTGG 88500
mRNA      ------------------------------------------------------------ genome    CAGCTGTTCTGTGCTGAGTATTTTAAAGTAGCCTCTTCCCAATATAGCCCCTCAGTTAAC 88560
mRNA      ------------------------------------------------------------ genome    TACAAGTAAACTCATTTTGAATTTCATTTTAATGGGCACCATATGCCAGTACTCCCTCGG 88620
mRNA      ------------------------------------------------------------
                                                              rs363102
genome    GCACTGGGATGTTAAGAAAGTATAATGTATGGACTTCATTCTCAAGTTAGTTTTAGATTA 88680
mRNA      ------------------------------------------------------------ genome    GAGGGGGATACACGTAAACAAAAGTGCAGTGGTCACACAGAGTGGCCCTAATCACTCTCC 88740
mRNA      ------------------------------------------------------------ genome    TTGGGCAGATTTATGGGCTGGTAGGAAAGAGCACAACACGGAGAGGGTGTAGCACCTTGG 88800
mRNA      ------------------------------------------------------------ genome    CGATGATAATGGAGGATGTGGCCAGCAAGGAAGACGGAGTCCATTGAAATTGATTTTGGG 88860
mRNA      ------------------------------------------------------------ genome    AGAAGTTGCCAATCTCCATGAAAGAATTGGGGCCTGTGCTATTTGCTTCAGGGGGCTATA 88920
mRNA      ------------------------------------------------------------ genome    GGAGAGTTTCGTGAAAGGGACTAAAAGATGAGTATTTTAATAAGATCATTCATCCAACTT 88980
mRNA      ------------------------------------------------------------ genome    GAACATGGGCTGGAGGAGAAGGTAGGGAGACTCAGGAGATTAATGTTGATGCTAAGGCAA 89040
mRNA      ------------------------------------------------------------ genome    GATAATGGCTTTGGGACTGTAGGGAAGACACTGATTGTAAGAGAATGAAGGAGGCAGAAT 89100
mRNA      ------------------------------------------------------------ genome    TGCCAGGCCTGGTTCACCAACTGAACTTCGGTTGTGAAGACAAAGAAACCTGGGATGACT 89160
mRNA      ------------------------------------------------------------ genome    TCACATCCTGGGCAGGTGTGTGGTGGTGACAGTCATGGAAATTGGGAACACAGATTTGTG 89220
mRNA      ------------------------------------------------------------ genome    CGGGAAACATCAGTTTCAGTTTGAGTTTGGCTTATCAGTTGAATATCAGGCACAGATGTC 89280
mRNA      ------------------------------------------------------------ genome    TGGCCAACTCTCAACATAGGGTCTTAAATGACTTCAGTTCCCCAAGCAATTTGTCCTTCC 89340
mRNA      ------------------------------------------------------------ genome    CATGCTATTGGGGTGGAGAGGTAATGTCTGTGCCCATATCACAGCCAGTGCTCCCAAATC 89400
mRNA      ------------------------------------------------------------
```

FIG. 1 TTT

| | | |
|---|---|---|
| genome | TCTGAGAAGTTCATGGGCCTCTGAAGAAGAAGCCAACCCAGCAGCCACCAAGCAAGAGGA | 89460 |
| mRNA | ------------------------------------------------------------ | |
| genome | GGTCTGGCCAGCCCTGGGGGACCGGGCCCTGGTGCCCATGGTGGAGCAGCTCTTCTCTCA | 89520 |
| mRNA | ------------------------------------------------------------ | |
| genome | CCTGCTGAAGGTGATTAACATTTGTGCCCACGTCCTGGATGACGTGGCTCCTGGACCCGC | 89580 |
| mRNA | ------------------------------------------------------------ | |
| genome | AATAAAGGTAATGTCCCACTTGGGTGCTGGATTCATACAGCCTTAATGACTATGGGTTTC | 89640 |
| mRNA | ------------------------------------------------------------ | |
| genome | CAGACTACCTTTGTTTAGTAATCTGTCCCTTCTTTATTCTCTTTTTGCTTTAAATGAACA | 89700 |
| mRNA | ------------------------------------------------------------ | |
| genome | AAATTGCTCAGATTGTGACACTAAATTTAACATCAAAATGTGACCATGTGGATGGGTGCA | 89760 |
| mRNA | ------------------------------------------------------------ | |
| genome | GTGGCTCGTGCCTGTTATTCCAGCACTTTGGGAGACTGAGGCAAGTGGATCACTTGAGGC | 89820 |
| mRNA | ------------------------------------------------------------ | |
| genome | CAAGAGTTCGAGACCAGCCTGGGCAACATCACGAAACCCCCTCTCTACTAAAAATACAAA | 89880 |
| mRNA | ------------------------------------------------------------ | |
| genome | AAATTAGATGGGTTGGGCCGGGCGTGGTGGCTCAAGCCTGTAATCCCAGCACTTTGGGAG | 89940 |
| mRNA | ------------------------------------------------------------ | |
| genome | GCCGAGGTGGGCGGATCACGAGGTCAAGAGATCAAGACCATCCTGGCTAACACAGTGAAA | 90000 |
| mRNA | ------------------------------------------------------------ | |
| genome | CCCCGTCTCTACTAAAAATACAAAAAAATTATCTGAGCATGGTGGCGGGCGCCTGTAGTC | 90060 |
| mRNA | ------------------------------------------------------------ | |
| genome | CCAGCTGCTCGGGAGGCTGAGGCAGGAGAATGGCGTGAATCCGGGAGGCGGAGCTTGCAG | 90120 |
| mRNA | ------------------------------------------------------------ | |
| genome | TGAGCCGAGATCGTGCCACTGCACTCCAGCCTGGGTGACAGAGCGAGACTCCGTCTCAAA | 90180 |
| mRNA | ------------------------------------------------------------ | |
| genome | AAAAAATTAGATGGGCATGGTGGTGCGTGCCTGTAATCCCAGCTACTTGGGAGGCTGAG | 90240 |
| mRNA | ------------------------------------------------------------ | |
| genome | GCAAGAGAGTTGCTTGAACCTGGGAGGCGGAGTTTGCAGTAAGCCTTGATTGTGCCGCTG | 90300 |
| mRNA | ------------------------------------------------------------ | |
| genome | CACTCCAGCCTGGGTGACAGAGTCAGACTCTTTCCAAAAGAAGAAAAAAATGTGACCATG | 90360 |
| mRNA | ------------------------------------------------------------ | |
| genome | TGTTTTATAGCTCTTTTAGTATCATCAGTCACTGTTATCCCTAAGAGGGAAATACCTAGC | 90420 |
| mRNA | ------------------------------------------------------------ | |
| genome | TTTAGTTTTAGGTTTCCAGCATTAGCCAAGAAAGCTCAGAATTGATGTTCCTGGCCAAGT | 90480 |
| mRNA | ------------------------------------------------------------ | |
| genome | ACCTCATTGCTGTCTCCTTAAATCTTGGTTAATGGCTACTGTCCTGGCTAGCATAGTTAT | 90540 |
| mRNA | ------------------------------------------------------------ | |
| genome | GGAGCATTTCCATGGTTGTAGAATGTTCTGCCAATCTCAGGGACAGTTTTGCTTTTCTGT | 90600 |
| mRNA | ------------------------------------------------------------ | |
| genome | GAAGCAATAAAATCAACTTCAAAACAAATGTTAACTATTTGTACAATGGATTTAAGATAG | 90660 |
| mRNA | ------------------------------------------------------------ | |

FIG. 1 UUU

```
genome    ACCAGTTCACATACTTTTTTTTTTTTTTTTTTGAGATGGAGTTTCATTCTTGTTGCCT  90720
mRNA      ---------------------------------------------------------- genome    GGGCTGGAGTGCAATGGTGTGATCTCAGCTCACTGCAACTTCTGCCTCCTGGGTTCAAAC  90780
mRNA      ------------------------------------------------------------ genome    GATTCTTCTGCCTCAGCCTCTCGAGGCAGATTACAGCTGGGATTACAGGCATGCACCACC  90840
mRNA      ------------------------------------------------------------ genome    ACACCCAGCTAATTTTTTTGTAGTTTTAGTAGAGACGGGGTTTCACCATGTTGGTCAGGT  90900
mRNA      ------------------------------------------------------------ genome    TGGTCTCAAACTCCTGACCTGAAGTGATCTATCCGCTTCGGCCTCCCAAAGTGTTGGGAT  90960
mRNA      ------------------------------------------------------------ genome    TACGGGCATGAGCCACCACGCCCAGCCTAAGATAGACCAGTTCACTTACTGTTTATATCT  91020
mRNA      ------------------------------------------------------------ genome    GATTACTCTCTCTTTGCCTTGTCTTCTACCTTTAAAAATCTCCCTACTAACTTCCCATTC  91080
mRNA      ------------------------------------------------------------ genome    TCCTTTAGCTGCCATCAGTCTTCTCCCTTCTCTGCAAACATCTCTGGAGAGTCCCAGCCT  91140
mRNA      ------------------------------------------------------------ genome    CAGCCCACAGAGCTTCCCACTGCTCTGAGGTGGACCTTGTTTGCAAGGCTTCTTTGGCTC  91200
mRNA      ------------------------------------------------------------ genome    TCTTGGCCTGGACCCTGTCTACTACTTCAGCCATCCTTCCTTAACCCCTGCTGGTGGTTT  91260
mRNA      ------------------------------------------------------------ genome    CTGTTGCCACACTCCATAGCAGCGTTTCCCGCCCAGATCATGTCTTTACATCTCTGGGCA  91320
mRNA      ------------------------------------------------------------ genome    CTGCTCTGGTCCTGCCTGCCTTTCCCTCTTTGTATCCTGCAGGCTGCTACCCCCATCTTG  91380
mRNA      ------------------------------------------------------------ genome    AGTGTCCTCTTCAGTTGGCTTTCAGAGGGCCTCCTGGGTGTTCCCTTACCCACTTGCCAC  91440
mRNA      ------------------------------------------------------------
                                              rs11731237
genome    TCCCCAGTCACTGGGTTCAGTCCTTCCTGCCCACCAGCACATGCTTTCTAGGCTCTGTCC  91500
mRNA      ------------------------------------------------------------ genome    TAGGCCGTCTTCTCTCTTTGTAGTCTCTGGGCCAGTGCTGTTCTAGAGAGTGGCAGAATT  91560
mRNA      ------------------------------------------------------------ genome    TTCTATAACCATGGCAGTGCTCCATAGCTATGCCAGGCAAGACAGTAGCCACTAAACACA  91620
mRNA      ------------------------------------------------------------ genome    TATAGCTGTTGAGCCCTTGAAATGCAGCTAGTGTGACTGAAGAACTGAACCCCGATTCGG  91680
mRNA      ------------------------------------------------------------ genome    TTTAATTTTCATTAAATTTAAATTTAAATAACCTTATGTGGGTAGTGGCTCCAGTATTGG  91740
mRNA      ------------------------------------------------------------ genome    GCAGGGCAGCCTGAGAGTCGGGGCTGTTCTCCTGTCTTCAGTGTCTAGATGAGGGACCTC  91800
mRNA      ------------------------------------------------------------ genome    AGAGGACCTGTCTCTGGAGCTGCAGTTCAATGTAGCCAGCTGCCCCGTGACACTTACATA  91860
mRNA      ------------------------------------------------------------ genome    TAGCTGATTTGTGGATATGTCAGACACGGTGTGATGAGCTCAGCTTTCTGTCCTCCTCCC  91920
mRNA      ------------------------------------------------------------
```

FIG. 1 VVV

```
genome      CACATCTGCCCCTGCCCCATTTACCCCACTTTGTGTCTTATCAAGCTAGAAACAGGTCAC  91980
mRNA        ------------------------------------------------------------ genome      CACAAGTCTTCATTTCCACTCACCAAGTCTTTTGTTTCCCCTACTAAATATTTTGCGAGA  92040
mRNA        ------------------------------------------------------------ genome      AGAAAGTGTGTACCTTTGTATTCACATACATGTACATGCACATATACATGCACATATGCA  92100
mRNA        ------------------------------------------------------------ genome      GGGGTCCCCAACCTCTGTTAAAAACCGGACTGCAGGCCGTGCGTGGTGGCTCACGCCTGT  92160
mRNA        ------------------------------------------------------------ genome      AATTCCAGAACTTTGGGAGGCCGAGACCAGTGCATCACAAGGTCAGGAGATCGAGACCAT  92220
mRNA        ------------------------------------------------------------ genome      TCCGGCTCACACGGTGAAACCCCGTCTCTACTAAAAATACAAAAAAAAATTAGCCGGGTG  92280
mRNA        ------------------------------------------------------------ genome      TGGTGGCGGGCGCCCATAGTCCCAGCTACCTGGGAGGCTGATGCAGGAGAACGGCGTGAA  92340
mRNA        ------------------------------------------------------------ genome      CCTGGGAGGCGGAGCTTGCAGTGAGCCGAGATTGTGCCATTGCACTCCAGCCTGGGCGAC  92400
mRNA        ------------------------------------------------------------ genome      AGAGCGAGACTCTGTCTCAAAAACAAAACAAAACAAAAAAAAAAAAAAACCAGGCTGCACA  92460
mRNA        ------------------------------------------------------------ genome      GGAAGAAGTGAGCAAGCATTACCATCTGAGCTCTATCTCCTCTCAGGCCAGTGGTGGCAT  92520
mRNA        ------------------------------------------------------------ genome      TAGATTCTCATAGGAGCGTGTATGAGTTCGTTCTCACACTTCTGTAAAGACATACCTGAG  92580
mRNA        ------------------------------------------------------------ genome      ACATATAAAGAAAAGAGGTTTAATTGGCTCACAGTTCTGCAGGCTGTACAGGCTTCTGTT  92640
mRNA        ------------------------------------------------------------ genome      TCTGGGAAGGCCTCAGGAAACTTGCAGTCATGGCAGAAGGTGAAGGGGAAGTAGGCACAT  92700
mRNA        ------------------------------------------------------------ genome      CTTCACATGGCCCACAGGAAAAGAGAGAAGGAGAGAGAGAGAGAGACAGAGAGAGAGAG  92760
mRNA        ------------------------------------------------------------ genome      AGAAAAGAAAGATTGAGAGGGAGAGAGGAGGGAGAAAGGAGAGTGCCTGTAGGGGGAGT  92820
mRNA        ------------------------------------------------------------ genome      TGCTACACAAAGGAGCACCAGGGGGATGGTGCTCAACCATTAGAAACTACCCCCATGATC  92880
mRNA        ------------------------------------------------------------ genome      CAATCACCTCCCACCAGGCCCCACCTCCGACACTGGAGATTACAATTCAGCATGAGATTT  92940
mRNA        ------------------------------------------------------------ genome      GGGTGGGGACACAGAGCCAAACCATATCAGAGCATGAACCCTATTGTGAACTGCACATTT  93000
mRNA        ------------------------------------------------------------ genome      GAGGGATCTAGGTTGCATGCTCCTTATGAGAATCTAATGCCTGATGATGATTTGAGGTGG  93060
mRNA        ------------------------------------------------------------ genome      AACAGTTTCATCCCGAAACCATCCCCCGCCAACCCTGGTTTGTGGAAAAATTGTCTTCCA  93120
mRNA        ------------------------------------------------------------ genome      CAGAACCGGTCCCTGGTGCCAAAAAGTTTGGGGACCTCTGCACATATGCATGCACCTGTA  93180
mRNA        ------------------------------------------------------------
```

FIG. 1 WWW

| | | |
|---|---|---|
| genome | CATGGACACATAATACATGTACATATGCATACTTTATATTCTCTGCCACTTCTGGTCCAG | 93240 |
| mRNA | ------------------------------------------------------------ | |
| genome | ACTGATATACTATCTCATTTGGATTACTGCACTAGCCTTTTGTTTTGGAAACAGCATTTT | 93300 |
| mRNA | ------------------------------------------------------------ | |
| genome | TTAAAAAATTTAATTTAATTTTTTTGAGATAGGGTGTCATTCTGTTGCCCAGCTTGGAGT | 93360 |
| mRNA | ------------------------------------------------------------ | |
| genome | GCAGTGTCATGATCATAGCTCACTGCGGCCTCGATCTCCCAGGCTCAAGTGATCCTTCTG | 93420 |
| mRNA | ------------------------------------------------------------ | |
| genome | CCTCAGCCTTCTCAGTAGTTGGGACTACAGGCATACCCACCATGCCCAGCTAATTTTTTG | 93480 |
| mRNA | ------------------------------------------------------------ | |
| genome | ATTTTTTTTTTTTTTGAGACAGAGTCTCAGCCTGTCGCCCAGGCTGGAGTGGGTTGGCG | 93540 |
| mRNA | ------------------------------------------------------------ | |
| genome | CGATCTCAGCTCACTGCAACTTCTGCCTCCCAGGTTCAAGTGATTCTCCTGCCTCAGCCT | 93600 |
| mRNA | ------------------------------------------------------------ | |
| genome | CCCGAGTAGTTGGGATTACAGGCGCCTGCCACCACACCCAGCTAACTTTTTGTATTTTTA | 93660 |
| mRNA | ------------------------------------------------------------ | |
| genome | GTAGAGACGGGGTTTCACCATGTTGGCCAGGCTGGTCTCGAACTTGTGACCTCGTGATTA | 93720 |
| mRNA | ------------------------------------------------------------ | |
| genome | GCCCGCCTCGGCCTCCCAAAGTGCTGGGATTACAGGCGTGAGCTACCGCTCCCAGCCAGG | 93780 |
| mRNA | ------------------------------------------------------------ | |
| genome | AAACAGCATTCTTGAGATAATTCATATAATTCACCCATTTAAAGTATATAATTCATTCTC | 93840 |
| mRNA | ------------------------------------------------------------ | |
| genome | TTTAGTATGCCCACAGAGTTGTACAGCCATCACCAGAATCAGTTTTAGAACCCATAAAGG | 93900 |
| mRNA | ------------------------------------------------------------ | |
| genome | AACTCTGTACTCTTTACCCAAAACCTCCATGCCTCCAGCTGCAGGCAGCCACTAACCTGC | 93960 |
| mRNA | ------------------------------------------------------------ | |
| genome | CTTCTGTCTCTGTGACTCTACGTCTTCTGGACATTACTGTGGATGGGCTCATACAGTCAG | 94020 |
| mRNA | ------------------------------------------------------------ | |
| genome | TGAGCTTGTGACTGGTGCCTTCTACCAAGCAGGGTTTTCAGTGTAGCAGCCTCTCTGTTT | 94080 |
| mRNA | ------------------------------------------------------------ | |
| genome | TTCTTTTTTTTTTTAAATTGTGACGGAACTTCTGCCTCCCGGGTTCAAGCGATTCTCCTGC | 94140 |
| mRNA | ------------------------------------------------------------ | |
| genome | CTCAGCCTCCCGAGTGGCTGGGACTACAGGCCCATGTCACCATGCCTGGCTAATTTTTTT | 94200 |
| mRNA | ------------------------------------------------------------ | |
| genome | TTTTTTTTTTTTTAGTAGAGATGGGGTTTCAACATGTTAGCCAGGGTGGTCTCGATCTCCT | 94260 |
| mRNA | ------------------------------------------------------------ | |
| genome | GACTTCATGATCCGCCTGCCTCGGCCTCCCAAAGTGCTGGGATTACAGGCGTGAGCCACC | 94320 |
| mRNA | ------------------------------------------------------------ | |
| genome | ATGCCCGGCTAACCTTTCATTTACTGTCTGCATTTCTTCCCTGATGCCTTCCAGTCCATG | 94380 |
| mRNA | ------------------------------------------------------------ | |
| genome | CACCCGATTGTAGCCATTCATCCTATTATGGTTTAAGGTGACTGTCTTAGTCAGCATGGG | 94440 |
| mRNA | ------------------------------------------------------------ | |

FIG. 1 XXX

| | | |
|---|---|---|
| genome | TTGCCATAACAAAATACCATAGCCTGGGTGGCTTCAACAACAGAATTTACTTCTCACACT | 94500 |
| mRNA | ------------------------------------------------------------ | |
| genome | TCTGGAGGTTGGGAAGTCCAAGATCCAGGACTTTCGCCTTGCCCTCATGTGGTGAGGGGG | 94560 |
| mRNA | ------------------------------------------------------------ | |
| genome | TGAGGAAGCTCTGTGGGGCCTCTTATATATGGATGCTAATCTCATTCATGAGGGGTCTGC | 94620 |
| mRNA | ------------------------------------------------------------ | |
| genome | CCTCATGACCCAGTCACCTCCCAAAGGCCCCACCTCCTAATACCATCACCCTGGTAATTA | 94680 |
| mRNA | ------------------------------------------------------------ | |
| genome | AGTTTCAGTGTATAAATTTGGGGGACTATAGACATTGAAACCATAACAAGCACTTTTCTA | 94740 |
| mRNA | ------------------------------------------------------------ | |
| genome | AGATCAGGGAGTGAGTAAGTAGCAGAGCTAGGACCTCAATTCCACATGTCAGTCATCTTG | 94800 |
| mRNA | ------------------------------------------------------------ | |
| genome | CCTTCACTCTGCTCCATGATGGCTGCCTCCTAGAGCATTGGGAGTCTCGATGTTCTATAT | 94860 |
| mRNA | ------------------------------------------------------------ | |
| genome | GCTCTCATGTGTTGTGTATTGGAGATAGTTGAGGCTTTATGAATACATCTGGATTTGTTG | 94920 |
| mRNA | ------------------------------------------------------------ | |
| genome | ACTTCTAGCTTTGCTGGTAACCAGCTGTGACCTTGAATAAGTTACTTCATCTCTGAGCCT | 94980 |
| mRNA | ------------------------------------------------------------ | |
| genome | GTTTCCTCTTTTAGAAACAGGAGTTTAAAATGCTGCTTTGGGTTGGGCACGGTGGCTCAT | 95040 |
| mRNA | ------------------------------------------------------------ | |
| genome | GCCTGTAATTCCAGCACTTTGGGAGGCTGAGATGGGAGGATCACTGGAGCTTGGAGTTCG | 95100 |
| mRNA | ------------------------------------------------------------ | |
| genome | AGACCAGCCTGGGCATCATAGTGTGAGATCCTGTCTCCTCAAGAAATTAAAAAATTAGCT | 95160 |
| mRNA | ------------------------------------------------------------ | |
| genome | GGGTGATGTGGCGTGTGCCTGTGGTCCCATCTACTCTGGAGGCTGAGGTGGGAGGATTGC | 95220 |
| mRNA | ------------------------------------------------------------ | |
| genome | TTGAGCCCAGGAGGTTGAGGCTACAATGAAATATGATTGCACCCCATCCTGGGTGACGAG | 95280 |
| mRNA | ------------------------------------------------------------ | |
| genome | TGAGACCCTGTCTCAAAAAAGAAAAAAAAAATGCTGCTTTGTACCCCTTTCATGTCATGG | 95340 |
| mRNA | ------------------------------------------------------------ | |
| genome | CGTCATGGCCAACATAGAATGCCCTGGTTGTTTGCTGTTGGAGGGCATGGGCCTGGGGGC | 95400 |
| mRNA | ------------------------------------------------------------ | |
| genome | TCCCTGAGGGCTCCTTCCATCTTCAACTCATTCTCTGTGCACCTGTTAGGAAGTTGTGGG | 95460 |
| mRNA | ------------------------------------------------------------ | |
| genome | CCAGTCCCTACCATGTATCATTGTGTGGGTAAAAGTAAATAAAATGTGTACAGTGTCTGA | 95520 |
| mRNA | ------------------------------------------------------------ | |
| genome | ACTGTACATATCAGGGTCCAAGAACAAAATGAGTGACATGGGTTAGCTCTTTTTAATAAA | 95580 |
| mRNA | ------------------------------------------------------------ | |
| genome | TGGTAAAACCAAATATTCTAATTTTCAGTTTTGTTATACTTCCATCACATGTTTTTGTTT | 95640 |
| mRNA | ------------------------------------------------------------ | |
| genome | TTTTGTTTTTTGTTTTTGTTTTTCTATTTTAGGCAGCCTTGCCTTCTCTAACAAACCCCC | 95700 |
| mRNA | ------------------------------------------------------------ | |

FIG. 1 YYY

```
genome      CTTCTCTAAGTCCCATCCGACGAAAGGGGAAGGAGAAAGAACCAGGAGAACAAGCATCTG  95760
mRNA        ------------------------------------------------------------ genome      TACCGTTGAGTCCCAAGAAAGGCAGTGAGGCCAGTGCAGGTAGGAAACAGCGTGGGGAAG  95820
mRNA        ------------------------------------------------------------ genome      GGAGGGACATGAGTGCAGCATCTGTCATGTAGAAACATAGGATTTAAGTAACTTGGTGTT  95880
mRNA        ------------------------------------------------------------ genome      TTAGAGAAATAAATATAATACACATCAGTAAAGTGAGAGAAAGTTTCTCCAGGTGCGGTT  95940
mRNA        ------------------------------------------------------------ genome      CAAGATATTAGAAACTAATGACTGATGTACACAGACCACCTTTTGGTCTGAAGCATTTCT  96000
mRNA        ------------------------------------------------------------ genome      AAGTGCCACTGGCTGACATGCAGCCCCTACAGCCTCCAGGCTTCCAGCCCTAGCATGGAG  96060
mRNA        ------------------------------------------------------------ genome      CATCACTCTCCTATGCTTCCCTGGTTGCAGGTGATGGCTGGAGAGGCCTCCTGATTTTCA  96120
mRNA        ------------------------------------------------------------ genome      GTAAGGGAAGTGGTGTAGATGCTTAGGAATAGATGTAGTGAGTGAAAAAACTGATTCTGA  96180
mRNA        ------------------------------------------------------------ genome      TATGTCAAAAATTCTGATTGGAAATGGAATATTTACATTTGGAAGAGCTAAAGGCGAGAG  96240
mRNA        ------------------------------------------------------------ genome      AAAGTGGGGATAAAGTCATCTGAGTTGGAGGAGCTTAAACCATTCACAAGTTTGGAGGAC  96300
mRNA        ------------------------------------------------------------ genome      CTTTTTTTACCCATGAAAAGGTCAGAACAGAAGGGGCTAGGATTTAGGTGTGACTGCAGT  96360
mRNA        ------------------------------------------------------------ genome      TTATTGAATTCCCATCCATACTGCTCTCGGTGGGCAGTGGCAGGGGCAGGAGAGGAGCCT  96420
mRNA        ------------------------------------------------------------ genome      GGCAAAGCATGAAGTGACTGCTGCTGCCTCTGCTATCTGGGACGCCTGGCCACCTGTCTG  96480
mRNA        ------------------------------------------------------------ genome      TACAGTCTCCCTCCAGACCCATTCTCACGCTGTCTCTTGGCACCCAGGGGCCAGTGATGG  96540
mRNA        ------------------------------------------------------------ genome      TTCTCCCATTTGTTTTGTGTATATAGCATTTATATCAAGGCTATTTATTTATTTATTTAT  96600
mRNA        ------------------------------------------------------------ genome      TTTATTTATTTATTTTTTGAGACAGAGTCTCACTCTGTCACCCAGGCTGGAGTGCAGTG  96660
mRNA        ------------------------------------------------------------ genome      GTGCAATCTCGGCTCAGTGCAAGCTCTGCCTCCTGGGTTCAAGCAATTCTCCTGCCTCAG  96720
mRNA        ------------------------------------------------------------ genome      CCTCCTGAGTAGCTGGGACTACAGGTGTGCACCACCACACCTGGCTAATTTTTTGTATTT  96780
mRNA        ------------------------------------------------------------ genome      TTTATTAGTGGAGACGGGGTTTCACCTTGTTGGCCAGGATGGTCTTGATCTCCTGACCTC  96840
mRNA        ------------------------------------------------------------ genome      GTGATCCGTCCACCTCAGCCTCTCAAAGTGCTGGGATTACAGGCATGAGTCACTGTACCC  96900
mRNA        ------------------------------------------------------------ genome      GGCCTATTTATTTATTTTTAATTGACAAAATTGTATATATCTGTAATATACAACATGATG  96960
mRNA        ------------------------------------------------------------
```

FIG. 1 ZZZ

| | | |
|---|---|---|
| genome | TTTGAAATATGTGTACATTGGCCAGGCGTGGTGGCTCACACCTGTAATCCCAGCACTTTG | 97020 |
| mRNA | ------------------------------------------------------------ | |
| genome | GGAGGCTGAGGTGGGCGGATCACGAGGTCGGGAGTTCAAGACCAAACTGGCCAGCATGGT | 97080 |
| mRNA | ------------------------------------------------------------ | |
| genome | GAAATCCTGTCTCTACTAAAAATACCACAAAAAAAAAAAAAAAAAAAAAAGCCGGGCAT | 97140 |
| mRNA | ------------------------------------------------------------ | |
| genome | GGTGGCTCGCGCCAGTCGTCCCAGCTACTTGGGAGGCTGAGGCAGGAGAATTGCTTGAAT | 97200 |
| mRNA | ------------------------------------------------------------ | |
| genome | CTGGCAGGTGGAGGTTGCAGTGAGCTGAGTTCATGCCACTGCACTCTAGCCTGGGCGATA | 97260 |
| mRNA | ------------------------------------------------------------ | |
| genome | GAGCGAGACTCCGTCTCAAAAAAAAAAAAAAAAGAAGAAATACATATGCATTGTGGAATG | 97320 |
| mRNA | ------------------------------------------------------------ | |
| genome | GCTAATTAACCTGTGCATCACCTCACGTATCATTGTTTTGTGGTGAGAACACTTAAAATC | 97380 |
| mRNA | ------------------------------------------------------------ | |
| genome | TACTCTTTCAGTGATTTTCTTGCATATGGTACATTGCTATTAACTGCAGTCACCATGCTA | 97440 |
| mRNA | ------------------------------------------------------------ | |
| genome | TACAGTAGATCTCTTGAACTCATTCCTCCTGTCTATAAATGAAATTTTGTATCCTTGACC | 97500 |
| mRNA | ------------------------------------------------------------ | |
| genome | AACACATTCAAGGTTTTTTTTGAGATGGAGTCTTCTTCACCCAGGCTGGAGTACCATGGC | 97560 |
| mRNA | ------------------------------------------------------------ | |
| genome | ACGATCTCATCTCACTGCAACCTCCGCCTCCCAGGTTCAAGCAATTCTCCTGCCTCAGCC | 97620 |
| mRNA | ------------------------------------------------------------ | |
| genome | TCCTGAGTAGCTGGGATTACAGGCACATGCTACTGCACCTGGCTAATTTTGTATTTTTA | 97680 |
| mRNA | ------------------------------------------------------------ | |
| genome | GTAGAAGTGGAGTTTCACCATGTTGGCCAGGCTGGTCTCGAACTCCTGACCTCAAGTGAT | 97740 |
| mRNA | ------------------------------------------------------------ | |
| genome | CCGCCTGCCTTGGCCTGCCAAAGTGCTGGGATTACAGGTGTGAGCCACTGCACCCGGCCT | 97800 |
| mRNA | ------------------------------------------------------------ | |
| genome | CAAGCGTTTTAAAAGATGCTCTTTTCTAAGGATTGACTGTAGTACAGGAGGAAGATTGAC | 97860 |
| mRNA | ------------------------------------------------------------ | |
| genome | CTGTTGAAAAGCCTCAGCCTTTACAAGTGTAAAATTATCAGTATATTACTATCATCTTTC | 97920 |
| mRNA | ------------------------------------------------------------ | |
| genome | TGATGAATTAAATAAACTAAGGACTCCAAGTCAAAAGTCTTCAAACTGAAGTAGAATAGT | 97980 |
| mRNA | ------------------------------------------------------------ | |
| genome | TGTATATAGTGCTTGGCACTTTAATATTTAGTATCGGTTTAATGATAATGTTTGTGCCTT | 98040 |
| mRNA | ------------------------------------------------------------ | |
| genome | TGCCGTCTTTAAAACATTTTTACATCATCCCTGTTTGATTACTTGGTGTGCTCATGAAGT | 98100 |
| mRNA | ------------------------------------------------------------ | |
| genome | TGTTGGCCACTAAGGAATCTTAGGCTCAGAGAGGTTCTGGAATTGGCCAGTGGTCCTTGA | 98160 |
| mRNA | ------------------------------------------------------------ | |
| genome | ATCAGCTGCTCCTATGATTCTCTAACTGATTTCTCACAAAGCAAACAAGCAATCATAACA | 98220 |
| mRNA | ------------------------------------------------------------ | |

FIG. 1 AAAA

```
genome   AAACAACTGTGCACACTGCTCTTCTTATTTTGTTATTTAAAAAGTACTTAGGCTCTACTT 98280
mRNA     ------------------------------------------------------------ genome   ATGTTTGTTAGTCAATTTCTCATTACTTCTAGTTAATCAAAAGGTCAGAGGAAATACTTG 98340
mRNA     ------------------------------------------------------------ genome   AATATTTTCATACTAGAATACTTTAAAAAATCATGATTTCCAGTAATCTCTTTAAAACTT 98400
mRNA     ------------------------------------------------------------ genome   GGCAAGTTATTTTGATCTAAAAGTTTATCTTTTGTGTGCATATTTTTAAAGCTTCTAGAC 98460
mRNA     ------------------------------------------------------------ genome   AATCTGATACCTCAGGTCCTGTTACAACAAGTAAATCCTCATCACTGGGGAGTTTCTATC 98520
mRNA     ------------------------------------------------------------ genome   ATCTTCCTTCATACCTCAAACTGCATGATGTCCTGAAAGCTACACACGCTAACTACAAGG 98580
mRNA     ------------------------------------------------------------ genome   TATGGGCCTCTGCATCTTTTAAAAATATATATGCACACATACTTACGTCTAATGGATAGT 98640
mRNA     ------------------------------------------------------------ genome   TGATGTTTTTCTTATGATTTGTAGGATGTATAAGCCCTTTGAGATATGAGTTACATTTAG 98700
mRNA     ------------------------------------------------------------ genome   TTTTTTCAAGTTTGTTTGTCTTTCAGCTTTGTTTATGATAGCTTCTATCATACAGGTGTT 98760
mRNA     ------------------------------------------------------------ genome   TTGGATTTTCATATTGTTTGTACTCACAGCTAAGATTGATTACAGTGACAGAGCTAGGAT 98820
mRNA     ------------------------------------------------------------ genome   GTGCAGCCAGGTTATAGGGGGAAGTGGCCCTGGTGGAGTCTGGAGGGATCCGTGTACAGG 98880
mRNA     ------------------------------------------------------------ genome   CTTCCTTCCCTCCCGTGAGGCTCACACAAAAATACAGCAACATGCTGGTCCTGCAGGTAC 98940
mRNA     ------------------------------------------------------------ genome   CCTCTGCCTAACATGAGCCACAATTCCAGACTCACAGAAGAAAAGCAGGTGTTCGGCATA 99000
mRNA     ------------------------------------------------------------ genome   AACCATGTGTTTCAAATAGTCTGGGCATGGTGAGCCACTTGTTATCAGCTAGGGAAAGTT 99060
mRNA     ------------------------------------------------------------ genome   TATGTCAGCGTAAGAAACTGTTCACCAGATACCCCCAAGAGCCAGCCTTTCTGTCTAGGG 99120
mRNA     ------------------------------------------------------------ genome   ATGTTTTAGTTTTTTAGTTCATTTTTTTTTTTAACTTTAAAATTTTCTGTTCATCTGCAA 99180
mRNA     ------------------------------------------------------------ genome   TTTGTTAGATATGAAGTATGTGTCTAATTTAATTTTTGTTTTTGGTTGTCCCCAATAATG 99240
mRNA     ------------------------------------------------------------ genome   TTTACAGAAGAATTTTTCTGCACTAATTGGCTTGAGTTACTTACATTCTCATAGTTCTCT 99300
mRNA     ------------------------------------------------------------ genome   AGTTTCAGTAGTTTCATTTATTATTTTGTTATATCAATCTATCTGTCTGCTCATCTATTA 99360
mRNA     ------------------------------------------------------------ genome   GAAGCATCCTTGTTTTTTTTTTTCTTTTTTAGACAGAGTCTTGCTCTGTCCCCAGGTTG 99420
mRNA     ------------------------------------------------------------ genome   GAGTGCAGTGGTGCAACCATGCCTCCCTGCAGTCTCAGGGCTCAAGTGATCCTCCCACCT 99480
mRNA     ------------------------------------------------------------
```

FIG. 1 BBBB

| | | |
|---|---|---|
| genome | CAGCTCCTGAGTACCTGGGACTACCGGCATGTGCCACCACACCCAGCTAATTTTTACATT | 99540 |
| mRNA | ------------------------------------------------------------ | |
| genome | TTTTGTAGAGACAGGGTCTCCCTAAGTTGCCTGGGCTGGTCTCAAGCTCCTGGCTTAAGT | 99600 |
| mRNA | ------------------------------------------------------------ | |
| genome | AATCCTCCCTCCTTGGCCTCCCAAAGTGCTGGGATTACAGGTGTGAGCAACTGCACCCGG | 99660 |
| mRNA | ------------------------------------------------------------ | |
| genome | CTACAAGTATACTTCTTAATTATTGTAGCTTAATGGTATTTATGAGGGGATCAGTTCCCC | 99720 |
| mRNA | ------------------------------------------------------------ | |
| genome | TGTTGTTCTTTAGAATTTTCTGGATATTCTTCTTTATTGATTTTGGGATGTGAACAATAG | 99780 |
| mRNA | ------------------------------------------------------------ | | rs4690073

| | | |
|---|---|---|
| genome | AATCAACTTCTACTTGTAGATTGATTTAGGGAGAACTTATACCTCAGATGTTAAGTCACC | 99840 |
| mRNA | ------------------------------------------------------------ | |
| genome | CTGTCCAGAATGTGGGATGCTTTCCTATTTGTTCAGAACTTTTTAAATTACCTCAGAAGC | 99900 |
| mRNA | ------------------------------------------------------------ | |
| genome | ACATGAAATTTAAAGGATTTTAAAAAAAACTTAAAGATTATTTCACATAGCTCTTGCACA | 99960 |
| mRNA | ------------------------------------------------------------ | |
| genome | TTTCTTGATAAATGAATCCTCAGGTATTCCTCTGTTTTGTTACTAATAGTTACTTCTTA | 100020 |
| mRNA | ------------------------------------------------------------ | |
| genome | TGGGTTTTTTTTCCCCTGAAAATCATTTATCAAACGTATGTGGCTTATTTTCTGAAGGAT | 100080 |
| mRNA | ------------------------------------------------------------ | |
| genome | GTTTGATAATTTTGGAAGATATGAAAGTCTTCATATTTTACAAGGTTTGAGGTCTCTTTA | 100140 |
| mRNA | ------------------------------------------------------------ | |
| genome | AGCTGCATGGTTCTCATGTCAGCTCCCAAAGCAGAAGACGGCATGTTGAAAAATGCCGTA | 100200 |
| mRNA | ------------------------------------------------------------ | |
| genome | GAGAAGATACTTCTTTTCCACCTGTTTTCAACTCATATCATCTTGAATTTCAGGGCACCT | 100260 |
| mRNA | ------------------------------------------------------------ | |
| genome | TTCCATGCTCCTAGTGCTTGCTATCTGTTTATTATTTTCCTTCCTGAATACCCTGAACTC | 100320 |
| mRNA | ------------------------------------------------------------ | |
| genome | CAGCATGTTCTGCTGTAATTCTGGCCTCCCTGGCATCTTGGACTCCTGTTTCCTTTGCTC | 100380 |
| mRNA | ------------------------------------------------------------ | |
| genome | TGTCATCCCCGCGGTCAGCTCCTGCTGCGCAGCTTCTCAGCTGAAGTGCGTTTGGAGTGC | 100440 |
| mRNA | ------------------------------------------------------------ | |
| genome | CTGGCGTGTCTTGCTGGATCTTTGAGTATTGCCTCTGGTTTCCTTGGTTCCTTCTGCTGA | 100500 |
| mRNA | ------------------------------------------------------------ | |
| genome | GTTGCTCAGCGTCTCCACTCCCCATTTCTTGTGTGGCCCTTCCTGCACTCCTCTGATTCC | 100560 |
| mRNA | ------------------------------------------------------------ | |
| genome | TTTTGTCTTCCCTGGTTTCTTGCTTTGGTTTCGAGTCTCCACAGAACTTTTGCAGCTCTT | 100620 |
| mRNA | ------------------------------------------------------------ | |
| genome | CTGAAGACCTGGAAGCTTTTTCATCTTAATTCTCATCTCATGACCTCTTTTCCCTTCTTT | 100680 |
| mRNA | ------------------------------------------------------------ | |
| genome | GAGAGCTAGAACTTCCCATGGTGAACTTCTCTTTCCAGAATTCCATGCCTTCTTTTCCCT | 100740 |
| mRNA | ------------------------------------------------------------ | |

FIG. 1 CCCC

```
genome      CCCACTTACCTGTTGTCCAGGAGAGGTCAGATTGCTGTGCATATTGGAGGAGAACCCTTT  100800
mRNA        ------------------------------------------------------------ genome      CTTCCCTGGGCTCTTCATCTCACATGACATCACCACATCACCTCGTTCCTTGGACCCTCA  100860
mRNA        ------------------------------------------------------------ genome      GTGGTGTCACTGCTGGATTTTTCTTTCCTTTGGCTGGCCTTAGGGCACACCCAGGTTGAC  100920
mRNA        ------------------------------------------------------------
                                            rs363144
genome      TAGCGTAGTCATGGTATTTAGATCCACTCACATTTTCAGTTTCTGTGTCTGTCTCTTGCC  100980
mRNA        ------------------------------------------------------------ genome      TGCTTCTGACTTCGCCCAGAGAAAGCTTCTCTTTCACAAGGGTTCTTAGATTTATGTTCA  101040
mRNA        ------------------------------------------------------------
                                                                    rs3025838
genome      CTGAGCACCTTCTTTTCTGAGGCAGTGTTTTACCAATATTTATTTTCCTAGTCAGTCTCG  101100
mRNA        ------------------------------------------------------------ genome      CCTTACCTTTCTTGTTATGCATGTCTTTGGTCCTGACCCATTCTCTGAGTCTGTAAAATA  101160
mRNA        ------------------------------------------------------------ genome      GAATTGCTGTATAATTTAATTACATGAAATCCTTTAGAATCTTAACACATCTTACACCTG  101220
mRNA        ------------------------------------------------------------ genome      ATTTAATATTTTATTGTATCCAAATTGAACCAACCCTATGTGAATTTGACAGTGATTTCT  101280
mRNA        ------------------------------------------------------------ genome      CCCAGGGATCCTAGTGTATAAGGAATAGGACTTAGTATTTTCTATTTTTTGATATACCAC  101340
mRNA        ------------------------------------------------------------ genome      ATACCAGATACTGATTATGATGGACATTTAACCCTTTTTTCTCATTATGAAAGAAAGTTA  101400
mRNA        ------------------------------------------------------------ genome      GGAATTATTTCTTCCAGTAGCGCCAGTGTAACCTGAAAGCCTTTGAAAGAGTAGTTTTTG  101460
mRNA        ------------------------------------------------------------ genome      TATAGCTATCTGAAAGGAATTTCTTTCCAAAATATTTTTCCAGTGCTGACAACAAACACG  101520
mRNA        ------------------------------------------------------------ genome      CAGACACACCCTGCAAGGTGAGTGTACGGCGCCGCACAGTGGAGGCATCTGCTGCAGCCG  101580
mRNA        ------------------------------------------------------------ genome      TCGATGTTTGTGTCTTTGGTTGTACATTATGAGATCGTGACAGGGCCAGTAACCGTGTGT  101640
mRNA        ------------------------------------------------------------
                                                            rs34315806
genome      TCTCTCCTTCACCTTCCCAAGGTCACGCTGGATCTTCAGAACAGCACGGAAAAGTTTGGA  101700
mRNA        ------------------------------------------------------------
                   rs363099
genome      GGGTTTCTCCGCTCAGCCTTGGATGTTCTTTCTCAGATACTAGAGCTGGCCACACTGCAG  101760
mRNA        ------------------------------------------------------------ genome      GACATTGGGAAGGTTTGTGTCTTGTTTTTTCTCCTTGGGTTGTGGCTGGCACACTTGATG  101820
mRNA        ------------------------------------------------------------ genome      TGCGTCTTCTGGGCTGAGTTCATCTAGGATGGAGCCTGGTTCTCCAGGGTGCCTCCGGGA  101880
mRNA        ------------------------------------------------------------ genome      GACTCCTCCCTGCCCCACGTGCTTGCGTCACAGGACCCAAGTCTGACTCTGCCTTAGCCA  101940
mRNA        ------------------------------------------------------------
```

FIG. 1 DDDD

| | | |
|---|---|---|
| genome | TGAAGTTTAGGGGGAAGTTTCTATTTGTATTCTATTTTTGTCTGTTATCATGTATTAGCT | 102000 |
| mRNA | ------------------------------------------------------------ | |
| genome | TAGACCCAGTTTAGTTTGGAAAATCAGTGGGTTTCAAAATGTGTTTGTAGAGTCCTTTAT | 102060 |
| mRNA | ------------------------------------------------------------ | |
| genome | TTCTTAACTTGACCTTTTCAAGTGGAAAGGGGCAAAACAGACGGGTAAGGGGCGGGGCG | 102120 |
| mRNA | ------------------------------------------------------------ | |
| genome | GGAGGTGTGACTTGCTCTTTTGTGCCTGAGGAAGTAACAGAGCTGGGGTTGACAGTCATA | 102180 |
| mRNA | ------------------------------------------------------------ | |
| genome | TTCTCTGACACAGATAGTCTCTGACTTATCTCACAGAAAGTCAGCGGCAGAGCCTGAGTT | 102240 |
| mRNA | ------------------------------------------------------------ | |
| genome | AAAAGTCTCGTAGATTTTCTTTTTCTTTTTTTGGTGGCTAATTTCAGTTTTATTTATAT | 102300 |
| mRNA | ------------------------------------------------------------ | |
| genome | TTGTTTATTTATTTATTATACTTTAAGTTCTGGGTTACATGTGCAGAATGTGCAGTTTTG | 102360 |
| mRNA | ------------------------------------------------------------ | |
| genome | TTACATAGGTATACACGTGCCATGATGGTTTGCTGCACCCATCAACCCATCACCTACATT | 102420 |
| mRNA | ------------------------------------------------------------ | |
| genome | AGGTATTTCTCCTAATGTTATCCCTCCCCCAGTCCCCTCACTCCCCATGGGCCCCGGTGT | 102480 |
| mRNA | ------------------------------------------------------------ | |
| genome | GTGATGTTCTCCTCCCTGTGCCCATGTGTTCTCATTGTTCAATTTCCACTTGTGAGTGAG | 102540 |
| mRNA | ------------------------------------------------------------ | |
| genome | AACATGCGGTGTTTGGTTTTCTGATCTTGTGATAGTTTGCTGAGAATGATGGTTTCCAGC | 102600 |
| mRNA | ------------------------------------------------------------ | |
| genome | ATCATCCATGTGCCTGCAAAGGACATGAACTCATCCTTTTTTATGGCTGTATAGTATTCC | 102660 |
| mRNA | ------------------------------------------------------------ | |
| genome | ATGGTGTATATGTGCCACATTTTCTTAATCCAGTCTATCATTGATGGACATTCGGGTTGG | 102720 |
| mRNA | ------------------------------------------------------------ | |
| genome | TTCCAAGTCTTTGCTATTGTGACTAGTGCCACAATAAACATACATGTGCATGTGTCTTTA | 102780 |
| mRNA | ------------------------------------------------------------ | |
| genome | TCGTAGAATGATTTATAATCCTTTGGGTATATGCCCAGTAATGGGATTGCTGGGTCAAAT | 102840 |
| mRNA | ------------------------------------------------------------ | |
| genome | GGTATTTCTAGTTCTAGACCTTTGAGGAATCGCCAGACTGTCTTCCACAATAGTTGAACT | 102900 |
| mRNA | ------------------------------------------------------------ | |
| genome | AATTTACACTCCCACCAACAGTGTAAAAGTGTTCCTATTTTTCCACAACCTCTCCAGCAT | 102960 |
| mRNA | ------------------------------------------------------------ | |
| genome | CTGTTGTTTCGTGACTTTTTAACGATCGCCATCCTAACTGGCGTGAGATGGTATCTCATT | 103020 |
| mRNA | ------------------------------------------------------------ | |
| genome | GTGATTTTGATCTGCATTTCTCTAATGACCAGTGGTGATGAGCATTTTTTCGTATGTCTG | 103080 |
| mRNA | ------------------------------------------------------------ | |
| genome | TTGGCTGCATAAATGTCTTCTTTTGCGAAGTGTCTGTTCATATCCTTTGTCCATTTTTTG | 103140 |
| mRNA | ------------------------------------------------------------ | |
| genome | ATGGGGTTGTTTGCTTTTTTTTCGTAAATTTGTTTAAGTTCTTTGTAGATTCTGGATGTT | 103200 |
| mRNA | ------------------------------------------------------------ | |

FIG. 1 EEEE

| | | |
|---|---|---|
| genome | AATCTTTTGTCAGATGGGTAGATTGCAAAAATTTTATCCCATTCTGTAGGTTGCCTGTTC | 103260 |
| mRNA | ------------------------------------------------------------ | |
| genome | ACTCTGATGATAGTTTCTTTTGCTATGCAGAAGCTCTTTAGTTTAATTAGATCCCGTTTG | 103320 |
| mRNA | ------------------------------------------------------------ | |
| genome | TCAATTTTGGCTTTTGTTGCCATTGCTTTTGGTGTTTTAGACATGAAGTCTTTGCCTATG | 103380 |
| mRNA | ------------------------------------------------------------ | |
| genome | CCTATGTCCTGAATGTTATGGCCCAGGTTTTCTTCTAGGATTTTTATGGTCCTAGGTCTT | 103440 |
| mRNA | ------------------------------------------------------------ | |
| genome | ATGTTTAAGTCTTTGATCCATCTTGAGTTGATTTTTGTGTAAGGTATAAGGAAGGGGTCC | 103500 |
| mRNA | ------------------------------------------------------------ | |
| genome | AGTTTCAGTTTTCTGCATGTGGCTAGCCAGTTTTCCCAACACCATTTATTAAATAGGGAA | 103560 |
| mRNA | ------------------------------------------------------------ | |
| genome | TCTTTTCCCCATTGCTTATGTGTGTCAGGTTTGTCAAAGATCAGATGATTGTAGATGTGT | 103620 |
| mRNA | ------------------------------------------------------------ | |
| genome | GGTGGTATTTCTGAGGCCTCTGTTCTGTTCCATTGGTCTATATATCTGTTTTGGTACCAG | 103680 |
| mRNA | ------------------------------------------------------------ | |
| genome | TACCATGCAGTTTTGGTTACTGTAGTGTTGTAGTATAGTTTGAAGTCAGGTAGTGTGATG | 103740 |
| mRNA | ------------------------------------------------------------ | |
| genome | CCTCCAGCTTTGTTCTTCTAGCCCAGGATTGTCTTGGCTATGCAGGCTCTTTTTTGGTTC | 103800 |
| mRNA | ------------------------------------------------------------ | |
| genome | CATATGAAGTTTAAAATAGTTTTTTCCAATTCTGTGAAGAAAGTCAGTGATAGCTTGATG | 103860 |
| mRNA | ------------------------------------------------------------ | |
| genome | GGGGGATAGCATTGAATCTATAAATTACTTTGGGCAGCAAGGCCATTTTCACGATATTGA | 103920 |
| mRNA | ------------------------------------------------------------ | |
| genome | TTCGTCCTATCCATGAACATGGAATGTTTTCTATTTGTTTGTGTCCTCTCTTATTTCCT | 103980 |
| mRNA | ------------------------------------------------------------ | |
| genome | TGAGCAGTGGTTTGTAGTTCTCCTTGAAGAGGTCCTTCACATCCCTTGTAAGTTGTCTTC | 104040 |
| mRNA | ------------------------------------------------------------ | |
| genome | CTAGGTGTTTCATTCCCTTAGTAGCATTTGTGAATGGGAGTTCACTCATGATTTGGCTCT | 104100 |
| mRNA | ------------------------------------------------------------ | |
| genome | CTGTTTGTCTGTTATTGGTGTATAGGAATGCTTGTGATTTTTGCACATTGATTTTGTATC | 104160 |
| mRNA | ------------------------------------------------------------ | |
| genome | CTGAGACTTTGCTGAAGTTGCTAATCAGCTTAAGGAGATTTTGAGCTGAACCAATAGGGT | 104220 |
| mRNA | ------------------------------------------------------------ | |
| genome | TTTCTAAATATACAATCATGTCATCTGCAAACAGGGACAGTTTTACTTCCTCTCTTCCTA | 104280 |
| mRNA | ------------------------------------------------------------ | |
| genome | TTTGAATACCCTTTATTGCTTTCTCTTGCCTGATTGCGCTGGCCAGAACTTCCAATACTA | 104340 |
| mRNA | ------------------------------------------------------------ | |
| genome | TGTTGAATAGGAGTGGTGAGAGAGGGCATCCTTGTCTTGTGCCGGTTTTCGAAGGGAATG | 104400 |
| mRNA | ------------------------------------------------------------ | |
| genome | CTTCCAGTTTTTGCCCATTCAGTATGATATTAGCTGTGGGTTTGTCATAAATAGCTCTTA | 104460 |
| mRNA | ------------------------------------------------------------ | |

FIG. 1 FFFF

| | | |
|---|---|---|
| genome | CTATGTTGAGATACGTTCCATCGATACCTAGTTTATTGAGAGTTTTTAGCATGAAAGGCT | 104520 |
| mRNA | ------------------------------------------------------------ | |
| genome | GTTGAATTTTGTCAAAGGCCTTTTCTGCATCTGTTGAGATAATCATATGGTTTTTGTTGT | 104580 |
| mRNA | ------------------------------------------------------------ | |
| genome | TGGTTCTGTTTATGTGATGGATTACGTTTATTGATTTGCGTATGTTGAACCAGCCTTGCA | 104640 |
| mRNA | ------------------------------------------------------------ | |
| genome | TTCCAGGGATGAAGCTGACTTGATTGTGGTGGATAAGCTTTTTGATGTGCTGCTGGATTC | 104700 |
| mRNA | ------------------------------------------------------------ | |
| genome | AGTTTGCCAGTATTTTATTGAGGATTTTCACATCGATGTTCATCAGGGATATTGGCCTAA | 104760 |
| mRNA | ------------------------------------------------------------ | |
| genome | AATTCTCTTTTTTGTTGTGTCTCTGCCAGGCTTTGGTATCAGGATGATGCTGGCCTCAT | 104820 |
| mRNA | ------------------------------------------------------------ | |
| genome | AAAATGAGTTAGGGAGGATTCTCTCTTTTTCTATTGATTGGAATAGTTTCAGAAGGAATG | 104880 |
| mRNA | ------------------------------------------------------------ | |
| genome | GTACCATCTCCTCTTTGTACCTCTGGTAGAATTCGGCTGTGAATCCATCCTGGACTTTTT | 104940 |
| mRNA | ------------------------------------------------------------ | |
| genome | TTGGTTAGTAGGCTATTAACTATTGCCTCAAGTTTAGAACCTGTTATCAGTCTATTCAGA | 105000 |
| mRNA | ------------------------------------------------------------ | |
| genome | GATTCAGCTTTTTTCTGGTTTAGTCTTGGGAGGGTGTATGTGTCCAGGAATTTATCCATT | 105060 |
| mRNA | ------------------------------------------------------------ | |
| genome | TCTTCTAGATTTTCTAGTTTATTTGGGTAGAGATGTTTATAGTATTCTCTGATGGTAGTT | 105120 |
| mRNA | ------------------------------------------------------------ | |
| genome | TGTATTTCTGTGGGATCGGTGGTGATATCCCCTTTATCGTTTTTATTGAGTCTATTTGAT | 105180 |
| mRNA | ------------------------------------------------------------ | |
| genome | TCTTCTCTCTTTTCTTCTTTATTAGTCTTGCTAGCGGTCTACCTATTTTATTGATCTTTT | 105240 |
| mRNA | ------------------------------------------------------------ | |
| genome | CAAAAAACCAGCACCTGGATTCATTGATTTTTTTGGAGGGTTTTTTTCGTGTCTCTAT | 105300 |
| mRNA | ------------------------------------------------------------ | |
| genome | CTCCTTCAGTTCTGCTCTGATCTTAGTTATTTTTTGTCTTCTGCTAGCTTTTGAATTTGT | 105360 |
| mRNA | ------------------------------------------------------------ | |
| genome | TTGCTCTTGCTTTTCTAGTTCTTTTAATTGTGATGTTAGGGTGTTAATTTTAGATCTTTT | 105420 |
| mRNA | ------------------------------------------------------------ | |
| genome | CTGCTTTCTCTTGTGGGCATTTAGTGCTATAAATTTCCCTCTACACACTGCTTTAAATGT | 105480 |
| mRNA | ------------------------------------------------------------ | |
| genome | GTCCCAGAGATTCTGGTATGTTGTGTCTTCGTTCTCATTGGTTTCCAAGAAAATTTTTAT | 105540 |
| mRNA | ------------------------------------------------------------ | |
| genome | TTCTGCCTTCATTTCGTTATTTACCCAGTAGTCATTCAAGAGCAGGTTGTTCAGTTTCCA | 105600 |
| mRNA | ------------------------------------------------------------ | |
| genome | TGTAGTTGTGTGGTTTTGAGTGAGATTCTCAATCCTGAGTTCTAATTTGATTGCACTGTG | 105660 |
| mRNA | ------------------------------------------------------------ | |
| genome | GTCTGACAGACAGTTTGTTGTGATTTCTGTTCTTTTACATTTGCTGAGGAGTGTTTTACT | 105720 |
| mRNA | ------------------------------------------------------------ | |

FIG. 1 GGGG

| | | |
|---|---|---|
| genome | TCCAACTATGTGGTCAGTTTTAGAATAAGTGCAATGTGGTGCTGAGAAGAATGTATGTTC | 105780 |
| mRNA | ------------------------------------------------------------ | |
| genome | TGTTGATTTGGGGTGCAGAGTTCTGTAGATGTCTATTAGGTCCGCTTGGTCCAGTGCTGA | 105840 |
| mRNA | ------------------------------------------------------------ | |
| genome | GTTCAAGTCCTGGATATCCTTGTTAATTTTCTGGCTCATTGATCTGCCTAATATTGACAG | 105900 |
| mRNA | ------------------------------------------------------------ | |
| genome | TGGGGTGTTAAAGTCTCCCACTATTACCGGGTGGGAGTCTCTTTGTAGGTCTCTAAGAAC | 105960 |
| mRNA | ------------------------------------------------------------ | |
| genome | TTGCTTCATGAATCTGGGTGCTCCTGTATTGGGGGCGTGTATATTTAGGATAGTTAGCTC | 106020 |
| mRNA | ------------------------------------------------------------ | |
| genome | TTCTTGTTGAATTGATCCCTTTACCATTATGTAATGGCCTTCTTTGTCTCCTTTGAACTT | 106080 |
| mRNA | ------------------------------------------------------------ | |
| genome | TGTTGATTTAAAGTCTGTTTTATCAGAGACTAGGATTGCAATCCCTGCTTTTTTTTGCT | 106140 |
| mRNA | ------------------------------------------------------------ | |
| genome | TTCCATTTGCTTGTTAGATCTTCCTCCATCCCTTTATTTTGAGCCAATGAGTGTCTTTGC | 106200 |
| mRNA | ------------------------------------------------------------ | |
| genome | ATGTGAGATGGGTCTCCTGAATACAGCACACCAATGGGTCTTGACTCTTTATCCAATTTG | 106260 |
| mRNA | ------------------------------------------------------------ | |
| genome | CCAGTCTGTGTCTTTTAATTGGGGCATTTAGCCCATTTACATTTAAGGTTAATATTGCTA | 106320 |
| mRNA | ------------------------------------------------------------ | |
| genome | TGTGTGAATTTGATCCTGTCATTATGATCCTAGTTGGTTATTTTGCCCGTTAACTGATGC | 106380 |
| mRNA | ------------------------------------------------------------ | |
| genome | AGTTTCTTCATAGCGTCAGTAGTCTTTACAATTTGGCATGTTTTTGCAGTGGCTGGTACT | 106440 |
| mRNA | ------------------------------------------------------------ | |
| genome | GGTTGTTCCTTTCCATGTTTAGTGCTTCCTTCAGGAGCTCTTGTAAGGCAGGCCTGGTGG | 106500 |
| mRNA | ------------------------------------------------------------ | |
| genome | TGACAAAATCTCTGCATTTGCTTGTCTGTAAAGGATTTTATTTCTCGTTCACTTATGAAG | 106560 |
| mRNA | ------------------------------------------------------------ | |
| genome | CTTAGTTTGGCTGGATATGAAATTCTGGGTTGAAAATACTTTTTTAAAGAATGTTGAAT | 106620 |
| mRNA | ------------------------------------------------------------ | |
| genome | ATTGGCTCCCACTCTTTTCTGGCTTGTAGGATTTCTGCAGAGAGATCTGCTGTTAGTCTG | 106680 |
| mRNA | ------------------------------------------------------------ | |
| genome | ATGGGCTTCCCTTTGTGGGTAACCCGACCTTTCTCTCTGGCTGCCCTTTCCTTCATTTCA | 106740 |
| mRNA | ------------------------------------------------------------ | |
| genome | ATCTTGGTGGATCTGATGATTATGTGTCTTGGGGTTGCTCTTCTCGAGGAGTATCTTTGT | 106800 |
| mRNA | ------------------------------------------------------------ | |
| genome | GGTGTTCTCTGTATTTCCTGAATTTGAATGTTGGTCTGCCTTGCTAGGTTGGGGAAGTTC | 106860 |
| mRNA | ------------------------------------------------------------ | |
| genome | TCCTGGATAATATCCTGAAGAGTGTTTTCTAACTTGGTTCTATTCTCCCCATCACTTTCA | 106920 |
| mRNA | ------------------------------------------------------------ | |
| genome | GGTACACCAATCAAACGTAGATTTGGTCTTTTCACATAGTCCCATATTTCTTGGAGGCTT | 106980 |
| mRNA | ------------------------------------------------------------ | |

FIG. 1 HHHH

| | | |
|---|---|---|
| genome | GGTTCATTTCTTTTCACTCTTTTTTCTCTAATCTTGTCTTCTCGCTTTATTTCATTAATT | 107040 |
| mRNA | ------------------------------------------------------------ | |
| genome | TGATCTTCAATCACTGATATCCTTTCTTCTGCTTGATTGAATCGGCTGTCGAAGCTTGTG | 107100 |
| mRNA | ------------------------------------------------------------ | |
| genome | TATACTTCACAAAATTCTCGTTCTGTGGTTTTTAGCTCCATCAGGTCATTTAAGCTCTTC | 107160 |
| mRNA | ------------------------------------------------------------ | |
| genome | TCTACACTGGTTATTCTAGCCATTAGTCTAACATTTTTTTCAAGGTTTTTAGCTTCCTTG | 107220 |
| mRNA | ------------------------------------------------------------ | |
| genome | TGATGGGTTAGAACATGCTCCTTTAGCTCGGAGAAGTTTGTTATTACCGACCTTCTGAAG | 107280 |
| mRNA | ------------------------------------------------------------ | |
| genome | CCTACTTCTGTCAATTCATCAAACTCATTCTCCATCCAGTTTTGTTCCCTTGCTGGTGAG | 107340 |
| mRNA | ------------------------------------------------------------ | |
| genome | GAGTTGTGATCCTTTGGAGGAGAAGAGGTGTTCTGGTTTTTGGAATTTTCAGCCTTTCTG | 107400 |
| mRNA | ------------------------------------------------------------ | |
| genome | CTATGGTTTCTCCCCATCATTGTGGTTTTATCTACCTTTGGTCTTTGATGTTGGTGACCT | 107460 |
| mRNA | ------------------------------------------------------------ | |
| genome | ACGGATGGGGTTTTGGTGTGGGTGTCCTTTTGTTGATGTTGATGCTATTCCTTTCTGTT | 107520 |
| mRNA | ------------------------------------------------------------ | |
| genome | TGTTAGTTTTCCTTCTAACAGACAGGCCCCTCAGCTGCAGGTCTGTTGGAGTTTGCTGGA | 107580 |
| mRNA | ------------------------------------------------------------ | |
| genome | GGTCCACTCCAGGCCCTGTTTGCCTGGGCATCACCAGCAGAGGCTGCAGAACAGCAAATA | 107640 |
| mRNA | ------------------------------------------------------------ | |
| genome | TTGCTGCCTGATCCTTCCTCTGGAAACATCGTCCCAGAGCACGAAGGTGTCTGCCTGTAT | 107700 |
| mRNA | ------------------------------------------------------------ | |
| genome | GAGGTGTTTGTTGGCCCCTACTGGGAGGTGTCTCCCAGTCAGGCTACATGGGGGTCAGGG | 107760 |
| mRNA | ------------------------------------------------------------ | |
| genome | ACCCACTTGAGGCAGTCTGTTCATTATCGGAGCTTGAATGCCGTACCGGGAGAACCACTG | 107820 |
| mRNA | ------------------------------------------------------------ | |
| genome | CTCTCTTCAGAGCTGTCAGGCACGTATGTTTAAATCTGGAGAAGCTGTCTGCTGCCTTTT | 107880 |
| mRNA | ------------------------------------------------------------ | |
| genome | GTTCAGATGTGCCCTTCCCCCAGAGGTGGAATCTAGAGAGGCAGTAGGCCTTGCTGAGCT | 107940 |
| mRNA | ------------------------------------------------------------ | |
| genome | GCAGTGGGCTCTGCCCAGTTCGAGCTTCCCTGCTGCTTTGTTTACACTGTGAGCATAGAA | 108000 |
| mRNA | ------------------------------------------------------------ | |
| genome | CCACCTACTCTAGCCTCAGCAGTGGTGGACACCCCTCCCCCAGCCAAGCTCCTGCATCCC | 108060 |
| mRNA | ------------------------------------------------------------ | |
| genome | AGGTCGATTTCAGAGTGCTGCGCTAGCAGTGAGCAAGGCCCCATGGGCGTGGGACCCGCT | 108120 |
| mRNA | ------------------------------------------------------------ | |
| genome | GAGCCAGGCACAGGAGAGAATCTCCTGGTCTGCTGGTTGTGAAGACTGTGGGAAAAGTGC | 108180 |
| mRNA | ------------------------------------------------------------ | |
| genome | AGTATTTGGGCAGGAGTGTACTGCTCCTTCAGGTACAGTCACTCATGGCTTCCTTTGGCT | 108240 |
| mRNA | ------------------------------------------------------------ | |

FIG. 1 IIII

| | | |
|---|---|---|
| genome | TGGAAAGGGAAGTCCCCCGACCCCTTGTGCTTCCCAGGTGAGGCAACACCCCGCCCTGCT | 108300 |
| mRNA | ------------------------------------------------------------ | |
| genome | TCGGCTTGCCCTCCGTGGGCTGCACCCACTGTCCAGCAAGTCCCAGTGAGATGAACTAGG | 108360 |
| mRNA | ------------------------------------------------------------ | |
| genome | TACCTCAGTTGGAAATGCAGAAATCACCTGTCTTCTGTGTCGATCTCACTGGGAGCTGTA | 108420 |
| mRNA | ------------------------------------------------------------ | |
| genome | GACTGGAGCTGTTCCTATTCGGCCATTTTGGAAGCATCCCTTGTTTTTGAGGTGGAGTC | 108480 |
| mRNA | ------------------------------------------------------------ | |
| genome | TTGCTCTGTCGCCCAGGCTGACGTGCATCGGCACAATCTCGGCCCACTGCAACCTTTGCC | 108540 |
| mRNA | ------------------------------------------------------------ | |
| genome | TCCTGGTTTCAAGCGATTCTCCTACCTCAGCCTCCGGAGTAGCTGGGATTACAGGCACCT | 108600 |
| mRNA | ------------------------------------------------------------ | |
| genome | GCCACCATGCCTGGCTAATTTTTTGTATTTTTAGTGGAGATGGGGTTTCACCACATTGGC | 108660 |
| mRNA | ------------------------------------------------------------ | |
| genome | CAGGCTAGTCTCGAACTCCTGACCTTGTGATCCACCCACCTCAGCCTCCTAGAGTGCTGG | 108720 |
| mRNA | ------------------------------------------------------------ | |
| genome | GATCACAGGTGTCAGCCACCACGCCCAGCCATATTTTCAGATCTCCCTCTCTTTGCCCTA | 108780 |
| mRNA | ------------------------------------------------------------ | |
| genome | AACCACTGTGCTTAATAAGTAGTTTTTAGTGGCCAGCAGTCTCCATGTATAACACATTTT | 108840 |
| mRNA | ------------------------------------------------------------ | |
| genome | AGCAAAATGGAAAATACTATATGTTTTAAATTTGAACGTGAGATTATACTGAAATAAAAA | 108900 |
| mRNA | ------------------------------------------------------------ | |
| genome | TCATCTAACTGGGATTCTTTAAATAGTAAGATTTTCTTTTTTGTATGTGGGTTTTTTTTT | 108960 |
| mRNA | ------------------------------------------------------------ | |
| genome | AACCTTATTATTATGACTGTCATATATAGAAATGGCTGTTTTTCAGTTACAGTCAGTGAA | 109020 |
| mRNA | ------------------------------------------------------------ | |
| genome | TGTATCAAATGCTGCCTTATCCAAATAATAAAAGTAAATTATTAATAAGTCACAATTTAA | 109080 |
| mRNA | ------------------------------------------------------------ | |
| genome | TGAAGATTGATGTTAGTTGATCTTTATATTCTTGAAATCAGCCATATGGTTGTGTGTGTA | 109140 |
| mRNA | ------------------------------------------------------------ | |
| genome | TGTATATATTTTTAAAGGTACATAAAGATAATAAGCTCATCTCTGAAAATTTTTACATTT | 109200 |
| mRNA | ------------------------------------------------------------ | |
| genome | GGCATAAGAATAACTGGATAATTAAGCATCTTATTCTCTGGCCTGTGTCTTTACAGTTAA | 109260 |
| mRNA | ------------------------------------------------------------ | |
| genome | AGGTAGATTTACTCACCTCTCCTTTTTGTTTTTCTAAGTTCATCTTTTTGCTGTTTCA | 109320 |
| mRNA | ------------------------------------------------------------ | |
| genome | AGACAGAGGCCCATTTTAGCTTTCTCGCATATCCTTTTGTTTGTACTTTGGAAGCCTCAC | 109380 |
| mRNA | ------------------------------------------------------------ | |
| genome | CTGCTTAATTGTTGAGTTTTTATCCGTGGTCTTTTAGAGGGGGATATGTAGGGTAGAAGC | 109440 |
| mRNA | ------------------------------------------------------------ | |
| genome | TTTCACAGGTTCTTGTTTGCACTTGGCCCCTGACTGTTTTGAGGAATCTCCCTCACTGAC | 109500 |
| mRNA | ------------------------------------------------------------ | |

FIG. 1 JJJJ

| | | |
|---|---|---|
| genome | TCACAGCATGGCAAGGTTTCAGATCTCTTTCTGCCACACAGCAGTTCTGAGGCAGCTGGA | 109560 |
| mRNA | ------------------------------------------------------------ | |
| genome | AAGATATCCAGATGCTTAGATTGTCAGGCCAGGCTTGAGATATACAAACTATTGAGCCTT | 109620 |
| mRNA | ------------------------------------------------------------ | |
| genome | ATCTGTGACCTTGCTTAGGTGAAGGCATCAGAGCCCCTGCACCAACATGCATAGGCCTCT | 109680 |
| mRNA | ------------------------------------------------------------ | |
| genome | GCATGTGTGCGGGGCTGGGTGTTGAGGTCTGAGCACAAGTGTAGCTGGAGAGGTGAGCTT | 109740 |
| mRNA | ------------------------------------------------------------ | |
| genome | GATGTGGCGACGGGTATGAGCAGGTTTTCTTCAGACTTCTGTGAGTTTACCTAGTTCCAG | 109800 |
| mRNA | ------------------------------------------------------------ | |
| genome | GATTTAAAGGCACAGAGACTTTAGAATTAAAATAGAATCATTTTCTTTTTCTAAATAGCA | 109860 |
| mRNA | ------------------------------------------------------------ | |
| genome | ACACTAGGAATAAAAAATAATAATTCCACATTCTTGACAGGTAATGTTTTTTCTTGTCTT | 109920 |
| mRNA | ------------------------------------------------------------ | |
| genome | CTAATCCTTATTTATTCCATACTCATTTTTATACATAATTGAAATGTATTATGCATTGGA | 109980 |
| mRNA | ------------------------------------------------------------ | |
| genome | TTTTTCTTTTGCATTATATTATAGACGATTTTTCATGTAACTCCTTACTGTTCCATTTTA | 110040 |
| mRNA | ------------------------------------------------------------ | |
| genome | TATGTTTTGTCTGGTTTAAGACTTTATCTGCAAACCGGGAAACTGTCTCTACAAAAAGAA | 110100 |
| mRNA | ------------------------------------------------------------ | |
| genome | AAACAAAAATAGTTGGCCGCAGTGGCATGCGTCTGTGGTCCCAGCTACTCGGGGCTGAGG | 110160 |
| mRNA | ------------------------------------------------------------ | |
| genome | TGGGAGGATTGCTTGAGCCTTGGGAGGTTGAGGCTGCAAAGAGCCATGATCATGCCATTG | 110220 |
| mRNA | ------------------------------------------------------------ | |
| genome | CACTCCAGCATGGGTGACAGACTTTATACTGTCTGTTTTGGGTGATTTGATAATGATATG | 110280 |
| mRNA | ------------------------------------------------------------ | |
| genome | CCCTGATGTAGTTTTTTTATATCTTGTGTTTCTTGTGCCTGGGTTTATTGAGGTTGGGTC | 110340 |
| mRNA | ------------------------------------------------------------ | |
| genome | TGTGGCTTCATAGTATTTTTAAAGTTTGGAAAATTTTAGGCCATTCTTTCTTTCTTTCTT | 110400 |
| mRNA | ------------------------------------------------------------ | |
| genome | TCTTTTTTTTTTTTTGAGACAGTGTCTCGCTCTGTCGCCTGCGTTGGAGTGCAGTGACA | 110460 |
| mRNA | ------------------------------------------------------------ | |
| genome | CTATCTTGGCTCACTGCAAGCTCTGCCTCCTGGGTTCACGCCATTCTCCTGCCTCAGCCT | 110520 |
| mRNA | ------------------------------------------------------------ | |
| genome | CCTGAGTAGCTGGGACTACAGGCGCCTGCCACCACGCCTGGCTAATTTTTTGTATTTTTA | 110580 |
| mRNA | ------------------------------------------------------------ | |
| genome | GTAGAGACGAGGTTTCACTGTGTTAGCCAGGATGGTCTCAATCTCCTGACCTCGTGATCT | 110640 |
| mRNA | ------------------------------------------------------------ | |
| genome | GCCCGCCTGGGCCTCCCAAAGTGCTGGGATTACAGGCGTGAGCCACTGCACCCAGCTAGG | 110700 |
| mRNA | ------------------------------------------------------------ | |
| genome | CCATTATTTCTTCAAAGATTTTTTTTCTGCCCTGCCTCCCTCCTTTTTTCCCTCTCTTAA | 110760 |
| mRNA | ------------------------------------------------------------ | |

FIG. 1 KKKK

| | | |
|---|---|---|
| genome | AGGGGCTGTGATTTCCTGAATGATTGCTTAGTGTTGTCCCATAGCTTACTGATGCTCTTT | 110820 |
| mRNA | ------------------------------------------------------------ | |
| genome | TCAGTGTTTGATTGTTTTATGTGTTTTCTGTTTTGTATAGTTTCTATTATTGTGTTTTCA | 110880 |
| mRNA | ------------------------------------------------------------ | |
| genome | AGTTCTCTGATCTTTTCTTCTACAGTGTCTACTCTGTTGTTAATCTGTTAATCTGTTGTT | 110940 |
| mRNA | ------------------------------------------------------------ | |
| genome | AATCCTGTCCAGCGTATTTTTTTTTTGTTTTTGAAACAGTCTCACTCTGTTGCCCAGGC | 111000 |
| mRNA | ------------------------------------------------------------ | |
| genome | TGGAGTTTAGTGGTGCGATATCAGCTCACTGCAACCTCCACCTCCCAGGCTCAAGCAATT | 111060 |
| mRNA | ------------------------------------------------------------ | |
| genome | CTTCTGCCTCAGCCTCCCGAGTAGCTGGGACTATAGGCACGTGCCACCACACCTGGCTAA | 111120 |
| mRNA | ------------------------------------------------------------ | |
| genome | TTTGTGTATTTTTATTAGAGATGGGGTTTCACCATGTTGGCCAAACTGGCCTTGAACTCC | 111180 |
| mRNA | ------------------------------------------------------------ | |
| genome | TGACCTCAGGTGATTCATCCGCCTCGGTCTCCCAAAGTGTTGGGATTATAGGCATGAGCC | 111240 |
| mRNA | ------------------------------------------------------------ | |
| genome | ACCGTGTCTGGCCCCTGTTCAGTGTATATCACTAATTTTGTTTTTATCTCTAGAAGTTTG | 111300 |
| mRNA | ------------------------------------------------------------ | |
| genome | ATTTAGGTCTTTTAAAAATGTCTCCCTGTGTTTCTGTTTAGCTTTGTGAACACAATTGTA | 111360 |
| mRNA | ------------------------------------------------------------ | |
| genome | ATAACTGTTTTAATATCCTTCTCTGCTAGTTCTAAGATCTTCTAATAACTTCCCAGTTCT | 111420 |
| mRNA | ------------------------------------------------------------ | |
| genome | TGGTGTTTCTCATTGGTTGATTGATACTCCTCGTTTTGGGTTGTATTTTCCTGCCTCTTT | 111480 |
| mRNA | ------------------------------------------------------------ | |
| genome | GTATGGCTGCCAATTTTTTATTGGATGCCCAACCTTGTGAATTTTACTTTGTTGGATGCT | 111540 |
| mRNA | ------------------------------------------------------------ | |
| genome | ATATATTTTGTGTTCCCATAGATCTTCTTGAGCTTTGTTCTGAGGTTAGTTGAGTTACA | 111600 |
| mRNA | ------------------------------------------------------------ | |
| genome | TATAGATGGTTTACTCTTTTGGGTCTTGCTTTATAATTTGTCAGATGGGTTGGAGCAGTG | 111660 |
| mRNA | ------------------------------------------------------------ | |
| genome | CTTAGTTTAGGACTAATTTTTTTTTGGACTAATTATTCCTCTTTAGGAATAATTAGGTA | 111720 |
| mRNA | ------------------------------------------------------------ | |
| genome | CCATGCTTAGGAGGCAAGACCATCCTGAGTACTCTACCTAATGAACCAGAAAGTTTGGGT | 111780 |
| mRNA | ------------------------------------------------------------ | |
| genome | TTTCCAGTCCGCCTGCTGAGAACAGTGACTTTCTAGCCCTGTGTGAGCGCTGAGCTCTGC | 111840 |
| mRNA | ------------------------------------------------------------ | |
| genome | TCCTTCTAATCCTTTCCAATGCTTCTTTCCCTGGCCTCAGGGAGTTTTCTCACACACATA | 111900 |
| mRNA | ------------------------------------------------------------ | |
| genome | TCTCTGCTGAGTACTCGAGAGGGACCTTCCCCAGATCTCCAGAGCTCTCTCTGTCTTGTT | 111960 |
| mRNA | ------------------------------------------------------------ | |
| genome | TTCTCTTCTCTGGTGCTCTGTCTTATGAACTGTGGCTGTCTTGGTCTCCTTAGATTCTCA | 112020 |
| mRNA | ------------------------------------------------------------ | |

FIG. 1 LLLL

| | | |
|---|---|---|
| genome | GCACCTCTTCAATTCAGAGGGTTGCCTGTCCCTCCTCCTTGTGCCACAGCCTAGGAACTC | 112080 |
| mRNA | ------------------------------------------------------------ | |
| genome | TCTCAAAGCAGCGAGTTGGGGCAGCCATAGGGCTGACTTAGTCTCTCGTCTCCCAGGGAT | 112140 |
| mRNA | ------------------------------------------------------------ | |
| genome | CACTGTCCTTCATTGCTCATGTCCAGTGTCTTGAGGACTCTGGGTTTTGTCTGTTTTGTT | 112200 |
| mRNA | ------------------------------------------------------------ | |
| genome | TTTTGGTTTGCTTTGGTTGTCTCAGGCAGGAGGGTAAACCCAGTCCCTCACCCTCATTGT | 112260 |
| mRNA | ------------------------------------------------------------ | |
| genome | GCTCAGTAGTGGAAGTCTCACTCTATTACATTAGATATTAGTATTTGTAGCAGAGCCCTG | 112320 |
| mRNA | ------------------------------------------------------------ | |
| genome | GTTCCCTGGTACTTGGGGAGCTCTTGAAAGGCCAGAAACAGCATGCTTTCTCACCTTTTC | 112380 |
| mRNA | ------------------------------------------------------------ | |
| genome | CAGGGCTTCAGTTTCTGGTGCACATCAAGCATTCCATACACATTTGTTAAAGTCCTTTGT | 112440 |
| mRNA | ------------------------------------------------------------ | |
| genome | TAGACAAGTAGTGATTCACAGGTTCTATTTGTAATTTTTTCAGTTAACATGTATTGGGTA | 112500 |
| mRNA | ------------------------------------------------------------ | |
| genome | TCTGCTGGGAGCTAGTAAAAACAAAAAGTGGTGTGTGACAAATTCAATTCTGACAAGAAC | 112560 |
| mRNA | ------------------------------------------------------------ | |
| genome | AACCTTAAACACTTAGAATATACTTTGAGCATATCAGAATTTTAAAAATGTGTGGCCCTT | 112620 |
| mRNA | ------------------------------------------------------------ | |
| genome | GAGTATTTGAAACCAACAAGAATCTATTGCTTATTAGTAGAGGATATTTGTTAAACAAG | 112680 |
| mRNA | ------------------------------------------------------------ | |
| genome | TGGAGAGAGAGGCATTTTCAGTCTAATTGGTGTTGGCTTTTAGCAGCTGATGGAAACCAG | 112740 |
| mRNA | ------------------------------------------------------------ | |
| genome | TTCGTGATTAGCCAGGCAGTGGTGAAACAGGCTGTGCATTCTGAATGCCTAGGTATCTAG | 112800 |
| mRNA | ------------------------------------------------------------ | |
| genome | GCATTCAGAATGGTGGCGCTCTTTGAGTTAGCATCTTCTTCTTTCTTGATTCTTTTTTTT | 112860 |
| mRNA | ------------------------------------------------------------ | |
| genome | TTTTTTTTGAGATGGACTTTCGCTCTTGTTGCCCAGGTAACAACTCCAGTGCAATGGCGC | 112920 |
| mRNA | ------------------------------------------------------------ | |
| genome | CATCTCGGCTCACTGTAACCTCTGCCTCCCTGGTTCAAGCGATTCTCCTGCCTCAGCCTC | 112980 |
| mRNA | ------------------------------------------------------------ | |
| genome | TCAAGTAGCTGGGATTACAGGTGTGCGCCACCACGCCTGGCTAATTTTGTATTTTTGGTA | 113040 |
| mRNA | ------------------------------------------------------------ | |
| genome | GAGATGGGGTTTCACTATATTGGTCAGGCTGGTCTTGAACTCCTGACCTCAAGTGATGCA | 113100 |
| mRNA | ------------------------------------------------------------ | |
| genome | CCTGCCTCGATCTCCCAAAATGCTGGGATTACAGGCGTGAGCCACCACTCCCAGCCCCTT | 113160 |
| mRNA | ------------------------------------------------------------ | |
| genome | CTTGATTCTTGAAAAGGACATTGGGTGCTGTACATCTCGTTATAGATGTTGATAAAAATG | 113220 |
| mRNA | ------------------------------------------------------------ | |
| genome | CTTGTGAGAAGAGTAACATTAAGGTAGTTATTTGGTCATTTTTGCAGATTATTTTAAGAC | 113280 |
| mRNA | ------------------------------------------------------------ | |

FIG. 1 MMMM

| | | |
|---|---|---|
| genome | AATTCTAGGACTGATTTGTGGTAAATCACACATTGCTGTATCATAGTTGTGTTCACTGAA | 113340 |
| mRNA | ------------------------------------------------------------ | |
| genome | CATATTCAGGGGCTCTACAGATGCAGGGCTCTTAGCTGCTTTGCACACTTCTGAATTCCT | 113400 |
| mRNA | ------------------------------------------------------------ | |
| genome | GCCCTGCGAACAGGACTGGATACCTAATAGACAACAGGTACTTGATAACAGTTTATTGAA | 113460 |
| mRNA | ------------------------------------------------------------ | |
| genome | TTAATGAGTGAATGAACAGATACATAAATGCATGAAAGAATGGTTGTAATGTATATAACT | 113520 |
| mRNA | ------------------------------------------------------------ | |
| genome | TGGATTTCAAGACTTTTTACTGACTGTTCAAAATAAGAAATTGAAAACTTTCCTCTGATT | 113580 |
| mRNA | ------------------------------------------------------------ | |
| genome | TTCCTCTACTATTTACACAATTTAAATGGAAGTTATCTTGTACCTTCAATTTCTGTCTAG | 113640 |
| mRNA | ------------------------------------------------------------ | |
| genome | GATTCGTACAATAACGGGTCATCTCTGAGTCGCTTAATGTCTCACTTGTCTTTCTACAGT | 113700 |
| mRNA | ------------------------------------------------------------ | |
| genome | GTGTTGAAGAGATCCTAGGATACCTGAAATCCTGCTTTAGTCGAGAACCAATGATGGCAA | 113760 |
| mRNA | ------------------------------------------------------------ | |
| genome | CTGTTTGTGTTCAACAAGTAAGAGCTTCATTCTTTTCCTCTTCTGTTAAGACGTTCGGGT | 113820 |
| mRNA | ------------------------------------------------------------ | |
| genome | ATGACAGCAAAACGCTGCTACTCCTTAAGAGGCAGGCGCTGTTGGCATAATCAGCTGGGA | 113880 |
| mRNA | ------------------------------------------------------------ | |
| genome | GGATTGTGGGGTCCAGCGCAGCACTTTTTGGCTCAGTCCATGATTGAGCCAAGAGGCCAT | 113940 |
| mRNA | ------------------------------------------------------------ | |
| genome | CCTTCCCTTCACTCCCCAGGAGGACGAGGTCTGTCACTGTGGAGGGCAGAGGACACCAGA | 114000 |
| mRNA | ------------------------------------------------------------ | |
| genome | AGCTCCTCTGCAACCTCGCTAGTTAACTTCCAGTCCCTCGGAGTTTCTGTTTAGAATGCT | 114060 |
| mRNA | ------------------------------------------------------------ | |
| genome | CAATCTCATTTAGAATTGCAAGGAAACCCAAAACGCCTATTTAAGGTACAAACAGCACTT | 114120 |
| mRNA | ------------------------------------------------------------ | |
| genome | CATACAATATCTCATGAGGTATTAATAGTGATTCACAGGAAGAATTTCACGCTGTGAGTC | 114180 |
| mRNA | ------------------------------------------------------------ | |
| genome | TTTGCTAACATATCCAGTTATTTACAGATGGATTTGATATTTGTGTGGGAGATTCTTAAA | 114240 |
| mRNA | ------------------------------------------------------------ | |
| genome | AGTGTTGTTCACGCCACATTGTTGATGCCTCATTTTTTTCACTGTAGTTGTTGAAGACTC | 114300 |
| mRNA | ------------------------------------------------------------ | |
| genome | TCTTTGGCACAAACTTGGCCTCCCAGTTTGATGGCTTATCTTCCAACCCCAGCAAGTCAC | 114360 |
| mRNA | ------------------------------------------------------------ | |
| genome | AAGGCCGAGCACAGCGCCTTGGCTCCTCCAGTGTGAGGCCAGGCTTGTACCACTACTGCT | 114420 |
| mRNA | ------------------------------------------------------------ | |
| genome | TCATGGCCCCGTACACCCACTTCACCCAGGCCCTCGCTGACGCCAGCCTGAGGAACATGG | 114480 |
| mRNA | ------------------------------------------------------------ | |
| genome | TGCAGGCGGAGCAGGAGAACGACACCTCGGGGTAACAGTTGTGGCAAGAATGCTGTCGTT | 114540 |
| mRNA | ------------------------------------------------------------ | |

FIG. 1 NNNN

```
genome    GGTGGAAGCACGAAAGAGCAAGCAGGAAATACTTTGTAAAAGAATAAAAACGAAAAATGT  114600
mRNA      ------------------------------------------------------------ genome    TAGCGAACATCTTCTAATAGTCTGCTGTATTCAGAGAACTCTAGGAGATATATATGGTTG  114660
mRNA      ------------------------------------------------------------ genome    ATGCAAAGATGATTTAAGGCATAGCCCGGCCTTCCAAGAAGTGTGTGGCCAGTGAGTGAG  114720
mRNA      ------------------------------------------------------------ genome    ATGGGCTTGGGACTTACACATCTCAGAGGTGGGGGTAGAGGAGGAGGAACACTGAGTGGG  114780
mRNA      ------------------------------------------------------------ genome    CTGAGAAGCAGCCAGCTCTCATTGCCAAAGTGTGTCAGCAAACCAGAATGCAGTTCATAA  114840
mRNA      ------------------------------------------------------------ genome    TGTCCCCACCCATTCAAAGCACAGGACCTGTAGAGTGGTGTGGCATGTGTTGGTGGCACT  114900
mRNA      ------------------------------------------------------------ genome    TTTCAGGCCTGTAACAAGGATGAAAGAACAGCTTCATAGCAGCACAGTAGTGCTGGTGTT  114960
mRNA      ------------------------------------------------------------ genome    CAGAGGTGTGTGAAGGCCATAGAAGCATCTTGGATATATTACCTTGTGTTTTGTCAGCTT  115020
mRNA      ------------------------------------------------------------ genome    TATGACTAGAAGTCTCTTTTCACTTAAATTTGTTTTTTTTTTTTGAGACGGAGTCTTG    115080
mRNA      ------------------------------------------------------------ genome    CTCTGTCGCCCAGGCTGGAGTGCAGTGGTGCAATCTCAGCTCACTGCAAGCTCTGCATCC  115140
mRNA      ------------------------------------------------------------ genome    TGGGTTCATGCCATTCTCCTGCCTCAGCCTCCCGAGTAGCTGGGACTACAGGCGCCTGCC  115200
mRNA      ------------------------------------------------------------ genome    ATCACGCCTGGCTAACTTTTTTTTGTATTTTTAGTAGAGACGGGGTTTCACCATGTTAGC  115260
mRNA      ------------------------------------------------------------ genome    CAGGATGGTCTCGATCTCCTGACCTCGTGATCTGCCCGTCCCGGCCTCCCAAAGTGCTGG  115320
mRNA      ------------------------------------------------------------ genome    GATTACAGGCGTGAGCCACCGCGCCCGGCCTCTTTTCACTTAAATTTATGTTTGTGTTTT  115380
mRNA      ------------------------------------------------------------ genome    TAATGCCTAGTATACAGGACTTCTTAAATTGCCTTAAGTATGAACAGGTATTTGAGTTGC  115440
mRNA      ------------------------------------------------------------ genome    TAATCTGTATAGTAGCAATAATAGAATCCCTTGTTTTCCTTTTATAAATTTAGCGATTA   115500
mRNA      ------------------------------------------------------------ genome    AATAGCTACAATTAAAACACTAGAGTCAGGAGTCAAGGAAAATACCCATGTTCCAGGCTG  115560
mRNA      ------------------------------------------------------------ genome    TATGTTAGTGATGTACTTACTATATATTGGAGTTTCAGGAGTAAGTCTGTTTCAATGCTT  115620
mRNA      ------------------------------------------------------------ genome    TCTGTAACCATTTGGGGTATTAATAAGCATGTGAGTGTGTGCATGTTTGGGTTAATTTCA  115680
mRNA      ------------------------------------------------------------ genome    TATATGTTTCTTAGAAGGGATATCATTGATGTAAATATTTTAAAGGCTTGTCCTCCAAAA  115740
mRNA      ------------------------------------------------------------ genome    AAATCATGTAATTTCTTCTAAATTACTGATCTTTTAAATGACCTTCACCTTTCTCTCAAA  115800
mRNA      ------------------------------------------------------------
```

FIG. 1 OOOO

| | | |
|---|---|---|
| genome | TCTCACTTAAGACTGGGCTGAGTAGTCAGTTTCCTGTAGCAGAAAAAAGCTCAGACTTGA | 115860 |
| mRNA | ------------------------------------------------------------ | |
| genome | GTAGCCTTCTGCGAGTGAGGAGACTTGATGGCTGTCAGGCAGCTGTAAACTCTAAATAGA | 115920 |
| mRNA | ------------------------------------------------------------ | |
| genome | GTGTCATTATCTGAAGAGGGCGATGCTGCCACACTGAGTGGCCTTTCAAGTTGTTTCTCA | 115980 |
| mRNA | ------------------------------------------------------------ | |
| genome | ATCTGACACGTTCTGATCGTGTGAATGTGAAATTGGTTTGAGCAGGAGTATATCTGAGTG | 116040 |
| mRNA | ------------------------------------------------------------ | |
| genome | CAGAGGAGATTATTTAAAGATATTCTCATTCTCTGCTTCCCTTTTATTCCCATTTGGCAG | 116100 |
| mRNA | ------------------------------------------------------------ | |
| genome | ATGGTTTGATGTCCTCCAGAAAGTGTCTACCCAGTTGAAGACAAACCTCACGAGTGTCAC | 116160 |
| mRNA | ------------------------------------------------------------ | |
| genome | AAAGAACCGTGCAGATAAGGTAAATGGTGCCGTTTGTGGCATGTGAACTCAGGCGTGTCA | 116220 |
| mRNA | ------------------------------------------------------------ | |
| genome | GTGCTAGAGAGGAAACTGGAGCTGAGACTTTCCAGGTATTTTGCTTGAAGCTTTTAGTTG | 116280 |
| mRNA | ------------------------------------------------------------ | |
| genome | AAGGCTTACTTATGGATTCTTTCTTTCTTTTTTTCTTTTTTATAGAATGCTATTCATAAT | 116340 |
| mRNA | ------------------------------------------------------------ | |
| genome | CACATTCGTTTGTTTGAACCTCTTGTTATAAAAGCTTTAAAACAGTACACGACTACAACA | 116400 |
| mRNA | ------------------------------------------------------------ | |
| genome | TGTGTGCAGTTACAGAAGCAGGTTTTAGATTTGCTGGCGCAGCTGGTTCAGTTACGGGTT | 116460 |
| mRNA | ------------------------------------------------------------ | |
| genome | AATTACTGTCTTCTGGATTCAGATCAGGTTTGTCACTTTTATCTTTCATCCATCATACCT | 116520 |
| mRNA | ------------------------------------------------------------ | |
| genome | GTTCCTAATTTAGTACAAATTACCCTAAAAGACACTGAAATCTACTTTAAAGAAATGTGG | 116580 |
| mRNA | ------------------------------------------------------------ | |
| genome | TCTGCATGTTTCCCTCATCAGTTGCTGCTGCTTATCTTTTTCATGCACCTAGCTGGTGCA | 116640 |
| mRNA | ------------------------------------------------------------ | |
| genome | GAAGGCCTGGGGCATAGCCAGCCTCAGCAAGTCAGCATCCTTGCCCCAGCTCCCTGGACT | 116700 |
| mRNA | ------------------------------------------------------------ | |
| genome | CAAGGCTAACCTGGGGTTGGCTGTTAGGGATTTCCAAAGGTTTGTCCCATCCACTTGCCT | 116760 |
| mRNA | ------------------------------------------------------------ | |
| genome | CCCCTCCAAAATAAGTTTGAATTTAAATTGTGAGATACAATTAAGATTTATTGTTTGGGG | 116820 |
| mRNA | ------------------------------------------------------------ | |
| genome | AACATTTTGCAAAATCTAGAGTTAGTTTAAACAGATTATCAATTATTACCATAATTGAT | 116880 |
| mRNA | ------------------------------------------------------------ | |
| genome | CATCTGCAGTTTCAAGCTATCTAACAGGTTCACTTACCTCTTTAAAAAGGAATGGAATTT | 116940 |
| mRNA | ------------------------------------------------------------ | |
| genome | AGCAGGACAGTAACTGAGACCCGTGCTCCTGGAGTCCATGTGGGAGCTGTGTGGCTCTGC | 117000 |
| mRNA | ------------------------------------------------------------ | |
| genome | ACAAGCATTTGCACGCTTCCCCTCTTGACTGCATTACCTTCCTCCTATAGTTGCTGTGGG | 117060 |
| mRNA | ------------------------------------------------------------ | |

FIG. 1 PPPP

| | | |
|---|---|---|
| genome | CACCAGATTCTGGCTAGTCCTGTCCCTTCATGATGCACATTTTCCTCAAGATTCGTCCCA | 117120 |
| mRNA | ------------------------------------------------------------ | |
| genome | GTTAAATCACTGCAGATGAAACTGCCTTTTCATCGTCAAAATTTAACTGTCATTTTTGAG | 117180 |
| mRNA | ------------------------------------------------------------ | |
| genome | CCGTGATCTTGGGCTACTTTCTTATGTGGGGTAGGAATATTTGTGAGTTAGAAATATTAC | 117240 |
| mRNA | ------------------------------------------------------------ | |
| genome | ACTTCTCTATTTCCTTCTAGACGTAAATCTGTTAATCCTGTCAGCACTGTTACTCACCTG | 117300 |
| mRNA | ------------------------------------------------------------ | |
| genome | AAAGGGTCTGTTTCCCTAGGAGAACTGAGGGCACTCGGTCAACACTGATTTTCCACAGTG | 117360 |
| mRNA | ------------------------------------------------------------ | |
| genome | GGTATTGGGGTGGTATCTGCTTGTTTTTTTGTTGTTGTTGTTTGTTTTTTTTTGTTTTT | 117420 |
| mRNA | ------------------------------------------------------------ | |
| genome | TTTTTGAGATGGAGTCTCGCTCTGTCACCCAGGCTGGAGTGCAGGGGTGCGATCTCGGCT | 117480 |
| mRNA | ------------------------------------------------------------ | |
| genome | CACTGCCAGCTCCGCCTCAGAGGTTCACGCCATTCTCCTGCCTCAGCCTCCCGAGTAGCT | 117540 |
| mRNA | ------------------------------------------------------------ | |
| genome | GGGACTACAGGCACCCACCACTACGCCAGGCTAATTTTTTGTATTTTTAGTAGAGACGAG | 117600 |
| mRNA | ------------------------------------------------------------ | |
| genome | GTTTCACTGTGTTAGCCAGGATGGTCTCCATCTCCTGACCTCGTGATCTGCCCGCCTCGG | 117660 |
| mRNA | ------------------------------------------------------------ | |
| genome | CCTCCCAAAGTGCTGGGATGACAGGCGTGAGCCACCGCGCCCGGCCTGGGGTCTGCTTTT | 117720 |
| mRNA | ------------------------------------------------------------ | |
| genome | AATGAAGGAGGCATCAAGGGGTGGGCTTTGCGTTGGCCTGATGCTTTCATCTTTCTTTCA | 117780 |
| mRNA | ------------------------------------------------------------ | |
| genome | CAAAACCTGTCCGAAGAAAATCCGTCTAAATGGGCCATTGCTCTCCTCAGGAAATAGTCA | 117840 |
| mRNA | ------------------------------------------------------------ | |
| genome | TTGGGAACTTCTTTTCCTTTCCTTTGACACTAGGAGGCTGACTGGGGAGAAGCCCTGGTC | 117900 |
| mRNA | ------------------------------------------------------------ | |
| genome | TATGGCTGTGGGCAGCAGGGGCTGAGAGGAGCAGGCTCTCAGGGGGGCACGGGTACCCCA | 117960 |
| mRNA | ------------------------------------------------------------ | |
| genome | AGGGAAGCCAGAGCCCTGATTTGTTCCATTCTAGTAAGAACAAAGACTGCTCTGGTTTCA | 118020 |
| mRNA | ------------------------------------------------------------ | |
| genome | TGTTTGTTCTGATTGCCTTTCATCAACCGGTCCCCTTTCTCCCAGTTCTTAAGATTCAGT | 118080 |
| mRNA | ------------------------------------------------------------ | |
| genome | ACAGTGACAGTTTTATGAACAAGAATAGAACACTAGAACAGACAAACCATTGAACTCTAT | 118140 |
| mRNA | ------------------------------------------------------------ | |
| genome | GCTGATAAAGATTTATTGAGCTCCTGCTGTATGTTTGCATTCTGCCCAGAGGCTCTGAGA | 118200 |
| mRNA | ------------------------------------------------------------ | |
| genome | AAACCAGGCCATATGCTCCATGCTTTATCCATGGAAGCTCCCCGTCAGGTTGGGAAAGCT | 118260 |
| mRNA | ------------------------------------------------------------ | |
| genome | GACAGCTGCAGGGAATACAGTGTGACACAAAACTGGCTCCCATGCAGCCCTTACGTGTCG | 118320 |
| mRNA | ------------------------------------------------------------ | |

FIG. 1 QQQQ

| | | |
|---|---|---|
| genome | CCTCTCAGATGGTTGGGGGACGAAGGTCGACTCCTTTGGGTATCTTATTACTAAACCAGT | 118380 |
| mRNA | ------------------------------------------------------------ | |
| genome | TTCAGGGAATCTGTGCCACCCTATCTGCCATTAACGTGAACAGATGAGTCCCCAAGGTGT | 118440 |
| mRNA | ------------------------------------------------------------ | |
| genome | AATTTTGGGTATTGTCTGATGTCTCTTGGAATTTATTATTTGTTTTTCCAATGAGATTTC | 118500 |
| mRNA | ------------------------------------------------------------ | |
| genome | ACCTCAGGGTATAGTAAAGTTGTTGAGGGGATTCCTGGATGTGTTCTGCAATTATCTAGG | 118560 |
| mRNA | ------------------------------------------------------------ | |
| genome | CTGATTTCAGAATAGAGTTATGCTTATAGTCAAATTTATCAGCTGTCAAGAATTTTATTT | 118620 |
| mRNA | ------------------------------------------------------------ | |
| genome | AAAATTTATGCAGATAAGCAGGAGGAAAAGAAGCCTGGTTTTTACATTTTAATCCTATTA | 118680 |
| mRNA | ------------------------------------------------------------ | |
| genome | TTGATGTGAAATTTTATTTTCCTTCCTGTAGGTGTTTATTGGCTTTGTATTGAAACAGTT | 118740 |
| mRNA | ------------------------------------------------------------ | |
| genome | TGAATACATTGAAGTGGGCCAGTTCAGGTAATAGCATTTTATTATTTTAGATTTTTTTCT | 118800 |
| mRNA | ------------------------------------------------------------ | |
| genome | TCTTCTTGTGTACTTACATGTAATTTAGGTTATTAAGTGAATGTTTAAACTACTGTTAGG | 118860 |
| mRNA | ------------------------------------------------------------ | |
| genome | CATTTTTGCTGTTTTCTTTAAATGGAAATCTGACTAACATACTGTGCATTTTTGCTTCTC | 118920 |
| mRNA | ------------------------------------------------------------ | |
| genome | TTAAAAATTAATGTATATCTCAAGACTTGTTTGGAAGTAGTTATGTATCTGAAAATTCCA | 118980 |
| mRNA | ------------------------------------------------------------ | |
| genome | TATGTTGTCAGTATTCATTGCACATTTCAAAGCATTTAATTGTGTTGACAGATGGTGGAA | 119040 |
| mRNA | ------------------------------------------------------------ | |
| genome | TGAAATCTTGTGGTGGAGCACTAGTTTTTAAATCTTCTTAGAGAAAGCAGTTTTATATAA | 119100 |
| mRNA | ------------------------------------------------------------ | |
| genome | TGTTGTCTTTAGTAATTATTATGCATTTGTATTCTCTGCAGCTTTTTCTTGCTAGATGTT | 119160 |
| mRNA | ------------------------------------------------------------ | |
| genome | GAGGTTTTAATACTTCTTGCTAGTCCATTACAGGTTTATAATTATTAAAAGTTAAAATTC | 119220 |
| mRNA | ------------------------------------------------------------ | |
| genome | TTTTAGTACCTAAAATGCTTAATAAACATTGTAATTAGGAAAATTTAGTGCAGAAGGAAA | 119280 |
| mRNA | ------------------------------------------------------------ | |
| genome | GTGTTCCCAGATTCCCTGGGGTCTGGAAACATAGTGTTTATTCTAATTACATGACACCTC | 119340 |
| mRNA | ------------------------------------------------------------ | |
| genome | CACTGTGTTTTGGGGCAAGTTACTGTTTCTCTTTTGAGTTTCAATTTCTTCAAGAGCAAA | 119400 |
| mRNA | ------------------------------------------------------------ | |
| genome | GAGGCAGAGGAGAGCTAGGAAGATCGTAGCTGCTGTGCCCCTGTGCCGTCGGGTGCCTTC | 119460 |
| mRNA | ------------------------------------------------------------ | |
| genome | TACCTGCTGCCTCCGAACCTTTACACATGTCCCTGCTCTGCGCGAGGGCACAGATGGGAT | 119520 |
| mRNA | ------------------------------------------------------------ | |
| genome | GCACTGTGGCAGGGGTGGGGTTAGAGTAGATCACGGACACCTGTTAGCTTGATGTGTGCT | 119580 |
| mRNA | ------------------------------------------------------------ | |

FIG. 1 RRRR

| | | |
|---|---|---|
| genome | TGCTGTCAAGGTTGAATCATGAATTATTTTATGTTGCTTATATTGATATGTATCTTAATT | 119640 |
| mRNA | ------------------------------------------------------------ | |
| genome | TTAAAAGAAAGGTCTAAATGGATGTTTTTGTTTTTAGGGAATCAGAGGCAATCATTCCAA | 119700 |
| mRNA | ------------------------------------------------------------ | |
| genome | ACATCTTTTTCTTCTTGGTATTACTATCTTATGAACGCTATCATTCAAAACAGATCATTG | 119760 |
| mRNA | ------------------------------------------------------------ | |
| genome | GAATTCCTAAAATCATTCAGCTCTGTGATGGCATCATGGCCAGTGGAAGGAAGGCTGTGA | 119820 |
| mRNA | ------------------------------------------------------------ | |
| genome | CACATGGTAACGGGACACACCTTTCACTGTCGTCTTCGGTGTCGTGATGTGCTTGGCAGT | 119880 |
| mRNA | ------------------------------------------------------------ | |
| genome | GTTCGTTTTCATATACCCACTTTGAACGTTGTCAGTGGCAGCCATGTGCTTCTCAGGCTC | 119940 |
| mRNA | ------------------------------------------------------------ | |
| genome | TGCATGTGTGTCTGTGTATGTGAAGGTACTGGTTAGAGACGTTTCAAAAGAGAAGAGAGC | 120000 |
| mRNA | ------------------------------------------------------------ | |
| genome | ATATTCTTTACTCTCAGCAATTTGTAATCTTCTCAGGGAAAAAAATTCAAGAAACAGTAA | 120060 |
| mRNA | ------------------------------------------------------------ | |
| genome | GATAACCTAAGGTACAGATAGATTCTGAATATAAAGTTCCTGTTCATTCACATGAAACGC | 120120 |
| mRNA | ------------------------------------------------------------ | |
| genome | TAAAAGTTCTTCACTTGATCTTAGCCAAAAGGCCAAGAAGCGATGCAACACTAAAAATTC | 120180 |
| mRNA | ------------------------------------------------------------ | |
| genome | TTAAATCGAACTTGCCGTGAATTAAATTTTGATCTCTCATCCAGTGGTATTGGAGATATA | 120240 |
| mRNA | ------------------------------------------------------------ | |
| genome | GTTTGACTTGGGTTCAGGGCTTTCTGTTTTGCCTGATGATTTTGCTGGAGCTTAAATAAG | 120300 |
| mRNA | ------------------------------------------------------------ | |
| genome | GAACCCAGGAGATGGCCAGCTGTGCAAGCCCCCAGCCTGTGGAAGGAGCTAGTGTGGTTT | 120360 |
| mRNA | ------------------------------------------------------------ | |
| genome | TATGAATGAGTTGCAAATCTTTCTTTGAGCTTTTTGAACTGATCTTCCAGCATTGCCCTA | 120420 |
| mRNA | ------------------------------------------------------------ | |
| genome | TTGACCCCTCCCTGACTCCTTTGCTGGAATCTGTAGGCTTTTGAACTTTGACAGGGACAC | 120480 |
| mRNA | ------------------------------------------------------------ | |
| genome | ATCCTAAGACCCTTGCAAACTCCCAGATGTGAGAATGGCACTACTACTTAGAGTCTTTTC | 120540 |
| mRNA | ------------------------------------------------------------ | |
| genome | GACTCAGCGTGTGTGCAGAAGAGCATCAACCGGGCTGTGTTGCGAGGCAGGGCCTTGGCT | 120600 |
| mRNA | ------------------------------------------------------------ | |
| genome | GACCTCTCAGTGTTTACATAGCTAAGCCAGTTAGTGTTTGCCACGGCCTCACAAGGGCTT | 120660 |
| mRNA | ------------------------------------------------------------ | |
| genome | CAGATTCACACAGCCAAAGTATAGATTATTAAAGGCATAGGTGTTTGGTTTCCTGGACTT | 120720 |
| mRNA | ------------------------------------------------------------ | |
| genome | GGAGGGTCTTTGGACAGAAAATCAGTAGGCAACCACACCCAGTACTTTGTGCTGGGAAGC | 120780 |
| mRNA | ------------------------------------------------------------ | |
| genome | TTGGTCATCTGTGAGAGGGTCAGAGAGTATACCCATGCGTGCATGCCACCGAAGGGTCAG | 120840 |
| mRNA | ------------------------------------------------------------ | | rs363096 marks the boxed T in the second row.

FIG. 1 SSSS

| | | |
|---|---|---|
| genome | TGAGTATTCCTGTGTGTGCATGTCTCAGGGCCGGAGAGAGTATGTGTCACTGAGAGGTCA | 120900 |
| mRNA | -------------------------------------------------------- | |
| genome | GAGTGTTTGTGTGTGTGTCAAAGAGGGTTGCATTGTGCCCTTCACTGAGGGGTCAGAGGG | 120960 |
| mRNA | -------------------------------------------------------- | |
| genome | TGCCTCGCGTGTGTGTGTGTACGTGTGTGTGTCACTGAGGGGTCAGAGTGTGCCTG | 121020 |
| mRNA | -------------------------------------------------------- | |
| genome | TGTGTGTGCTTGTGTGTGCGTACATGTCACTGAGGGGTCAGAGTGTGCCTCTGTGTGTGT | 121080 |
| mRNA | -------------------------------------------------------- | |
| genome | GCTCATGTGTGTGCATACGTGTCACTGAGGGGTCAGAGTGTGCCTCTGTGTGTGCTCATT | 121140 |
| mRNA | -------------------------------------------------------- | |
| genome | TGTGAGCGTATGTGTCACTGAGGGGGTCAGAGTGTGCCTCTGTGTGTGTGCTCATGTGTG | 121200 |
| mRNA | -------------------------------------------------------- | |
| genome | AGCGTATGTGTCACTGAGGGGGTCAGAGTGTGCCTCTGTGTGTGTGCTCATGTGTGAGCG | 121260 |
| mRNA | -------------------------------------------------------- | |
| genome | TATGTGTCACTGAGGGGTCAGTGTTCCTATGTGCTCATGACATTGAGGGTCAGAGTGTGC | 121320 |
| mRNA | -------------------------------------------------------- | |
| genome | CTGTGTGCCAATGAAAGGCATTTCTTATATTTTTTATATGTGGTCATAGTAGACCAGTT | 121380 |
| mRNA | -------------------------------------------------------- | |
| genome | AATTTATTTTGACTCCTGTGTTAGACCAAAATAAGACTTGGGGGAAAGTCCCTTATCTAT | 121440 |
| mRNA | -------------------------------------------------------- | |
| genome | CTAATGACAGAGTGAGTTTACTTAAAAAAGCATAATAATCCAGTGGCTTTGACTAAATGT | 121500 |
| mRNA | -------------------------------------------------------- | |
| genome | ATTATGTGGAAGTCTTTATTGTCTTTTCAGATGAATCAAGTAGATTATTCTTGAGACCAG | 121560 |
| mRNA | -------------------------------------------------------- | |
| genome | GAATGTTGCTGTTTTGGTTATTTGGAAAGTTTTATCATTTTCAAATTGACTTTTGAATTT | 121620 |
| mRNA | -------------------------------------------------------- | |
| genome | GAGTCACCTTTTTTCAGAAGTGGTGTTAAATTATAGGAGCCCTAGGTTTTTTTTCTTTTT | 121680 |
| mRNA | -------------------------------------------------------- | |
| genome | TTAGAAGTCATCACAAAATGATCAGTGTTCAGAGGAAGAGCTTTGACCTTCCACATGGTA | 121740 |
| mRNA | -------------------------------------------------------- | |
| genome | TAATGATTGATAACCTTAATTCATCTCTTACCATAAACCAAGTATGTGTAAGGGTTTTCT | 121800 |
| mRNA | -------------------------------------------------------- | |
| genome | TTATTTCTTGAAAGCATTTTGTAGATGTTGAGAGCAGTTTTCCAAATGTAATTTCCATGA | 121860 |
| mRNA | -------------------------------------------------------- | |
| genome | AATGCCTGATAAGGGTACCCTTTTGTCCCCACAGCCATACCGGCTCTGCAGCCCATAGTC | 121920 |
| mRNA | -------------------------------------------------------- | |
| genome | CACGACCTCTTTGTATTAAGAGGAACAAATAAAGCTGATGCAGGAAAAGAGCTTGAAACC | 121980 |
| mRNA | -------------------------------------------------------- | |
| genome | CAAAAGAGGTGGTGGTGTCAATGTTACTGAGACTCATCCAGTACCATCAGGTAAGAGGA | 122040 |
| mRNA | -------------------------------------------------------- | |
| genome | ATGTATGTTGGAACTGTCGTGGATACTTTATTGACCCGTGCAGATGGAAGGAAGTGCCAT | 122100 |
| mRNA | -------------------------------------------------------- | |

FIG. 1 TTTT

| | | |
|---|---|---|
| genome | GTGGTAACGCTCACTGTTAACTGTGTTACTTTGAACCAGGTTTGGGCTTTCTGGGGCCTG | 122160 |
| mRNA | ------------------------------------------------------------ | |
| genome | GGTAGATGCCGGTGCAGGGGGATGGGGAGGGAGGCGGGGGGTGGGGGGGTGTGGTGGAGT | 122220 |
| mRNA | ------------------------------------------------------------ | |
| genome | TGGGGAGGTGCAGTGGCAGGAGGTGTTGTTGGTGTGTATCCTTTTTTTTTTTTGAGATG | 122280 |
| mRNA | ------------------------------------------------------------ | |
| genome | GAGTCTCTCTCCGTCGCCCAGGCTGGAGTGTGGTGGCACGATCTTGGCTCATTGCAAGCT | 122340 |
| mRNA | ------------------------------------------------------------ | |
| genome | CCACCTCCCGGGTTTAAGCAATTCTCCTGCCTCCACCTCCCGAGTAGCTGGGATTACAGG | 122400 |
| mRNA | ------------------------------------------------------------ | |
| genome | CATGCACCACCATGCCCAGCAAATTTTTTTTTTGTATTTTTAGTAGAGATGGGGTTTCA | 122460 |
| mRNA | ------------------------------------------------------------ | |
| genome | CCATGATGGCCAAGCTGTTTCGAACTCCTGACCTCAAGTGATCCTCCTGCCTTGGCCTCC | 122520 |
| mRNA | ------------------------------------------------------------ | |
| genome | CAAAGTGCTAGGATTACAGGCGTGAGCCACCATGCCCAGCCTGGTGTTTATCTTTAAAGT | 122580 |
| mRNA | ------------------------------------------------------------ | |
| genome | GGGCACAGCCACAGGAGTTCACCTGACTCCTGGTCTGAGAGTCACGAGATCGTTCAAGAT | 122640 |
| mRNA | ------------------------------------------------------------ | |
| genome | AGTGAGGCCCTCTTTTCCAAAACGAGGACCAAAAATCAATTGACAGTGTTGGTCAAGATG | 122700 |
| mRNA | ------------------------------------------------------------ | |
| genome | GTAGAAACCTTAAAATGATAGAAATCTCAACTCTGAAATAAAAACTTTATTTGTATATTT | 122760 |
| mRNA | ------------------------------------------------------------ | |
| genome | ATTTACCACTATTTTGACATAGGGCTAAGGTCTTTTTCTTTGAGCTGATTTCTGGTTTTG | 122820 |
| mRNA | ------------------------------------------------------------ | |
| genome | TTTTCTTAAAGTGGCATAAGAATTCAAAGACATTTTGAGGAAGGCTGAGTGCAGAAATCT | 122880 |
| mRNA | ------------------------------------------------------------ | |
| genome | CTCTTTTTAAATGACTTCTCCTTTCTTTTAACTTGCACTGTTGTCTAGCCCTCACTTATT | 122940 |
| mRNA | ------------------------------------------------------------ | |
| genome | TTGTCAATTCTTTTTAGCTGTTTGTCTTTGAATCTTCATAAAGCCATAGCTTTTCTCATA | 123000 |
| mRNA | ------------------------------------------------------------ | |
| genome | AGAAGCAGCACTTTCTTTGTTCATTCATATTTTAATGAACCCCTGTAGTATTTAATTAAA | 123060 |
| mRNA | ------------------------------------------------------------ | |
| genome | TACTTAATGCCTAATTAAATCACATAATTGCAATGCAAAAGTACATGTATCATAAAGAGG | 123120 |
| mRNA | ------------------------------------------------------------ | |
| genome | TCTGAAAATGAGCAACTGGCAAGCAGGTGGTGGCAGGCAGAGCTGCTTGGGTGGGTGGGT | 123180 |
| mRNA | ------------------------------------------------------------ | |
| genome | GTCATGGAGAGGAGTTCATCAGCCACATGTTCAGTGAGCTCTGGATATGTCTGTTTAGAA | 123240 |
| mRNA | ------------------------------------------------------------ | |
| genome | ATGATCACTAATAAACTTGTGCTCAACCATGTATACCTCTGGGAAGCAGGTGCTCTTCAG | 123300 |
| mRNA | ------------------------------------------------------------ | |
| genome | TAGATTGCCTCTGCAGAGAACACAGAATTGAAGTGAATGTCCACAAAGGCAATGAGCCAC | 123360 |
| mRNA | ------------------------------------------------------------ | |

FIG. 1 UUUU

| | | |
|---|---|---|
| genome | CTGCAGAATAGTTTAGTCAAGGCTGTGTTTGAAGTTTGCCAAAGATTAATATACATTTGA | 123420 |
| mRNA | ------------------------------------------------------------ | |
| genome | TTTTCATGTTGTGCCTTTTCTCTGATTGTGAAATATTACAAATTCTATACAAATAACAAT | 123480 |
| mRNA | ------------------------------------------------------------ | |
| genome | GATGGCAAATCCTCCTGAGCAAAGTGTGCACCTTGTATGTGCCCTAGAGGAACTTGTGTT | 123540 |
| mRNA | ------------------------------------------------------------ | |
| genome | TCGTTCTGATTCCCCTACATTTCTCATGTCATAGAGTGGGGGTTGCATTAGTGTCCCCCT | 123600 |
| mRNA | ------------------------------------------------------------ | |
| genome | GTCCTCGCTGGGATCACATCTGTTTGGATCCTAGAGTCTTCCAGCTGAACTGGGACAAGT | 123660 |
| mRNA | ------------------------------------------------------------ | |
| genome | ATAACAGACGGACACGTAGGGGTGGAAAGGCGTCTCTTGGCAGCAGACTTTCTAATTGTG | 123720 |
| mRNA | ------------------------------------------------------------ | |
| genome | CACGCTCTTATAGGTGTTGGAGATGTTCATTCTTGTCCTGCAGCAGTGCCACAAGGAGAA | 123780 |
| mRNA | ------------------------------------------------------------ | |
| genome | TGAAGACAAGTGGAAGCGACTGTCTCGACAGATAGCTGACATCATCCTCCCAATGTTAGC | 123840 |
| mRNA | ------------------------------------------------------------ | |
| genome | CAAACAGCAGGTTTGTCCCCGCAGCCTTGGCTTGTTGTTGCATAGTGATGGTAGCTTAAG | 123900 |
| mRNA | ------------------------------------------------------------ | |
| genome | GTCCTTGTGAAAGGTGGGTGGCTGGAATCAGCTCTTCCTTCAGTCCTAATCTGTGCCTTG | 123960 |
| mRNA | ------------------------------------------------------------ | |
| genome | ATAGCAGTTCTCCGTGCTAGTCATGGGACAGCTGACTTCATTTCTTCTCACAATGCCATC | 124020 |
| mRNA | ------------------------------------------------------------ | |
| genome | TCAGGTTGGTATTGCCCACCTACTTTACAGGGGGGATCCCACAGCTCCGAGAGGTTATGG | 124080 |
| mRNA | ------------------------------------------------------------ | |
| genome | AGGTGATCAGGCAGCACACAGCTTTAGAGTGCTGGGGTGAGGGCGGGCCAAGGCTAACTC | 124140 |
| mRNA | ------------------------------------------------------------ | |
| genome | TAAAGCCCGAACCCTTACCTCCTACACTGCCTCCTGCATTCTGGTCAACCCAGTGTTTTA | 124200 |
| mRNA | ------------------------------------------------------------ | |
| genome | TTTGGTGGTTAGATTTTTGTTTTTGTTACCTTACTGCTTGTAATTTAGCAGTTTTCCTTT | 124260 |
| mRNA | ------------------------------------------------------------ | |
| genome | CCTTTCCCTTCCTTTCCTTTCCGACAGGGTCTCACTCTGTCACCCAGGCTAGAGTGCAGT | 124320 |
| mRNA | ------------------------------------------------------------ | |
| genome | CGTGTAATCTCACTGCAACAACCTCTGCCTCCCAGGTTCAACCAATTCTCCCACCTCAGC | 124380 |
| mRNA | ------------------------------------------------------------ | |
| genome | CTCCTGAGTAGCAAGGACCACAGGTGTGCACCACTACGCCTGGCTAGTTTTTTGTATTTT | 124440 |
| mRNA | ------------------------------------------------------------ | |
| genome | TAGTAGAGATGAGGTCTCGCTGTGTTGCCCAGGCTGGTTTTAAACTCCTGGGCGCAAGTG | 124500 |
| mRNA | ------------------------------------------------------------ | |
| genome | ATCCACCAACCTTGGCCTGCCAAAGTGCTGGCATTACAGGTGTGAGCCACCTCGCCTGGC | 124560 |
| mRNA | ------------------------------------------------------------ | |
| genome | CTATTCATCACTAATCAGAATTTCTATGATCAAATGACATGAATCATTGTTTCCACAACT | 124620 |
| mRNA | ------------------------------------------------------------ | |

FIG. 1 VVVV

```
genome    GCAGTGGAAGGAAATGGCCTGGCAGTGCCAGTTTCAGAAGCAGCCTGCCCCCAGTCAGGC  124680
mRNA      ------------------------------------------------------------ genome    ACAGGCCACTGTGCCCCCAGTGTAGCAGCACCTCTGTAGCTCACAGAGAAGGGTGGTGGG  124740
mRNA      ------------------------------------------------------------ genome    GACCTCCTTGAGGCAGCTCTGCCAGAAAATCTCATGAGCTGCCTGGCACAGCTTGAGGTT  124800
mRNA      ------------------------------------------------------------ genome    GCCTTTTAAGTGGACTCAGCAAATACATGTTTGTTCATCTTGATTATACACAATAAACAA  124860
mRNA      ------------------------------------------------------------ genome    CTACTCTGTATAGTACGAGTAGTCCGTGGTTTTTGGCATTTGATTTAAACTTAGAGGCAT  124920
mRNA      ------------------------------------------------------------ genome    GTGATATTGATGTTACTGCCTTCATGACTGCACCCCCATTCTGATTTCATAATGGAATGT  124980
mRNA      ------------------------------------------------------------ genome    TATCTTGAGACCAGTTAGACAACAGGACAGGGATCTTGGCTTCTGGTGAGATTGACAGCA  125040
mRNA      ------------------------------------------------------------ genome    GTTTTAGTGTGGTCAGGGTCTCCCTGCCTACAGATGGTTTTAGAATGGTGCCCTGGAAGC  125100
mRNA      ------------------------------------------------------------ genome    TTTATCCCATTCTTTTCTGTGCGTAATCTGAGTAGAGTGGAGATCGAAGGCCTGAATACA  125160
mRNA      ------------------------------------------------------------ genome    TAGTAAATACCTGACTTAATATCTGCCGCAATGGAAATTGTGTGATACAACATTTATGAA  125220
mRNA      ------------------------------------------------------------ genome    ACGCTTAGTGCAGCACCTGCCAGGTAGCTCACCACAGGTGCATGTTGCATTCAGAAGTAG  125280
mRNA      ------------------------------------------------------------ genome    TGCTAGATACTATCCTGTTACTGGCAGTGCATACATCAGTGATCAAAGCAGATTAAAGAA  125340
mRNA      ------------------------------------------------------------
                                                                 rs2298967
genome    AGACCCCCTGCCTTCTTGGAGTGAAGATTTTGTTGGGATGCGGGTAAGGGACAGACAAT   125400
mRNA      ------------------------------------------------------------ genome    AGAAAAGCAAGTGAGTGAAGTCTATACCATGGCGGCTGATCAGGAACACCGTACAGAAGA  125460
mRNA      ------------------------------------------------------------ genome    ATCCAGGAGGGAAGAGAGTTAGGTGGTGTCTGCGGTGGGAGTGGCATTGTTCAGCTGGTG  125520
mRNA      ------------------------------------------------------------ genome    ATGAGAAGAAGCTTTGGTGATCTGGTGACATTTGAGTGAATTTGCAGAAAGGAAAGATAC  125580
mRNA      ------------------------------------------------------------ genome    AAGCCTAGGAGATACCTGGGGAAGGAACATTCCAGGCAGAGCAAATAGCAGTGCAAAGGC  125640
mRNA      ------------------------------------------------------------ genome    CCTGGCGGGGGCGGACATGCTGTTAGGGTACAAGCAATGAGGGTGGAGGAGTGGGGCAG   125700
mRNA      ------------------------------------------------------------ genome    CCATGGGGAGGGAAGGGAGTGAGGCCTGGTGGGGTGAGGCCAGTGTGGAGGAGCCTTGAG  125760
mRNA      ------------------------------------------------------------ genome    AGGGTTTGCGCTGATGTGGTGTAGGTTTTAGCAGGATCATTCTTATTCCTGAGTTGAGAA  125820
mRNA      ------------------------------------------------------------ genome    TAGCCTTGAGGGGGAGGTGAGGGCAGAGCAGGGCCACCCATGTGAGACCCGGCACTGGAG  125880
mRNA      ------------------------------------------------------------
```

FIG. 1 WWWW

```
                    rs2298969
genome   TGGAATGGCCCAAGTCAGCATCCCTTGGCAGCATGAAAGCAAAACCAGCAAGGTTTGCTG  125940
mRNA     ------------------------------------------------------------ genome   GTGGCTTAGATGTGGCATGTGAGAGAGAGCAGGGCTTTGGGGGTGATTTCAGGGTGAGGA  126000
mRNA     ------------------------------------------------------------ genome   CAGGGTGGCTGTGGACAAGGTAGGGCAGACATTGGGGGCAGCAGGAGGTCAGAGCCTGTC  126060
mRNA     ------------------------------------------------------------ genome   TGGATGTAGCAGTTGAGACCCCATAGGTGCCTAATGAGGTGAGGCCAGCATCAGGTGTAT  126120
mRNA     ------------------------------------------------------------ genome   GAGCCTGGAGTTGTCGAGAGACTGTGGGGCAGGGGGTCAGCATCTGAGATGTCCACTCAC  126180
mRNA     ------------------------------------------------------------ genome   AGTGGACCCAGACTGGCTGGAGAGGAGGAGGAGCTTGAATACCGAGCCTGCTGAGTCCCA  126240
mRNA     ------------------------------------------------------------ genome   GCTCCAAGGTCAGGTAGGTGAGGGGAGCCAGTGCTGGGGCAGGGGGAGTAGGCAGGTGTG  126300
mRNA     ------------------------------------------------------------ genome   GGGTTCCTAAAGCCAAGATTTTTTTTAAGGCATTTTGTGCAGGAGGGCGACATCTGCTGT  126360
mRNA     ------------------------------------------------------------ genome   CAGCACCTTGGGAACTTGGCCCAGGTTTGGCAGCACCGAGGGCACTGATGAGTGCTTTTG  126420
mRNA     ------------------------------------------------------------ genome   GAGGAGCAAAGGGAGCCAAACCCTAATGGGAATGTGTTCCTGAAAGGACAGGAGAGAGAC  126480
mRNA     ------------------------------------------------------------ genome   TTGGGAAAAGGTTTTACTTGAAGAGGGAACGGAGAAATAGGGCAGTAGCCAGAGGAGGAG  126540
mRNA     ------------------------------------------------------------ genome   AGGAGTCGGCAATGGGTTAAGTTGGCAGAAATGAAGGCCTGTTTACGCACTGAGGGCAGA  126600
mRNA     ------------------------------------------------------------ genome   AGCAACAGGGAGGATCAGTTCATGACACAGGAGACACAAATCGCCGTTGTGGTGTTCACA  126660
mRNA     ------------------------------------------------------------ genome   GACATGGGTTAGGATTGGCTGCATGGATGACAGAGCACTGTGGGTTCTCCCAGAGTTGCT  126720
mRNA     ------------------------------------------------------------ genome   GGGGAGGAGGCAGAGTTGGTGAGCACAGGCGAGGGTCCAGGATGCAGGAATCCTGGAGCT  126780
mRNA     ------------------------------------------------------------ genome   CAAGTCAGTTGTTCCCTTGTTGTAAGATGTGGCCAGTGTTGTGAGCTTCACATCTGTGCC  126840
mRNA     ------------------------------------------------------------ genome   TTGAAAAACACCACATCTGTTTGCAGAGTTGTTTACTATGTATACACACTCAGTAGAAAC  126900
mRNA     ------------------------------------------------------------ genome   AAAAATTGGAAACAGTCAGTGCCCACCATCAATAAGTAATGGTTGAACACACTGTGGTAT  126960
mRNA     ------------------------------------------------------------ genome   AAGCTTAGACTATTTTAGCTTGGGCTATTTTGCATGATTAAAAATGTTCTGGCCAGGTGT  127020
mRNA     ------------------------------------------------------------ genome   GGTGGCTCATGCCTGTAATCCCAGCACTTTGGGAGGCCAAGGCAGGCAGATTGCTTGAGC  127080
mRNA     ------------------------------------------------------------ genome   TCAGGAGTTTGAGACCAGCCTGGGCAACATGGTGAAACCCTGTCTCTACTAGAAATACAA  127140
mRNA     ------------------------------------------------------------
```

FIG. 1 XXXX

| | | |
|---|---|---|
| genome | AAAGTAGCTGGGTGTGGTGGTGTGCGCCTGTAGTCCTGGCTAACTCAGGAGGCTGAGGTG | 127200 |
| mRNA | ------------------------------------------------------------ | |
| genome | GGAGGATCACTTGAGCCCATTCGTGCGCCACTGCACTCCTGGGGCACAGAGTGAGACTCT | 127260 |
| mRNA | ------------------------------------------------------------ | |
| genome | GTTAGAAAGAGAGAGAGAGAAAGAAGAGAGAGGGAGGGAGGAAGGAAGGAAGGAAATAAA | 127320 |
| mRNA | ------------------------------------------------------------ | |
| genome | TGGAAGAAATGGAAGGGAGGAAGGGGAGGGAGGAAGGAAGAAAGGAAGTTCAGCCAGTTG | 127380 |
| mRNA | ------------------------------------------------------------ | |
| genome | CCTTGGGAGTTCTCCATTGCACTGGGTTAAGTGAGAAGAGCAGAGACGTTTATGATTTTT | 127440 |
| mRNA | ------------------------------------------------------------ | |
| genome | CAAAACAACTAAAACAAAACCTCTGTGGGTGAGGGGGCAAGGATATGGCTATAGGAACAT | 127500 |
| mRNA | ------------------------------------------------------------ | |
| genome | GGGGCAGATTAAGAAAGGGATATACACACACCACTTAGCATTTGTTACAACTGTTGTGGG | 127560 |
| mRNA | ------------------------------------------------------------ | |
| genome | AGGGATGGAGTGCAGAAAAAGAAAAAAAAAAGTGCACACCATCCCATGTATGTGTATACA | 127620 |
| mRNA | ------------------------------------------------------------ | |
| genome | AAGGGACGCTTGGAAGACTGGTCCCCAAAATGTTGGTAATGATTGTGTCAGGGTGCTGCA | 127680 |
| mRNA | ------------------------------------------------------------ | |
| genome | GTGCTAGTTGATTTTTTTTCACACTTTTGTATATTTGAGTCTTTTACAGAAAGCATTTAT | 127740 |
| mRNA | ------------------------------------------------------------ | |
| genome | TATTTATGTAATAAAAATCTAAATGACAAGATTTCTGTTATGGGAAAAATGTAGCTATAC | 127800 |
| mRNA | ------------------------------------------------------------ | |
| genome | AGTGTTGTTGTAAAAATGTTTGCTTGGTTCACCACTGAACTTAAAATGCTTTTAAATGAG | 127860 |
| mRNA | ------------------------------------------------------------ | |
| genome | GGAAGGTGACGATGAGATGATTATGATGATTTGCCCTTGAGTTACATAGCTGGTGTACAG | 127920 |
| mRNA | ------------------------------------------------------------ | |
| genome | GAAGCTGTCGTTTCTTTTGGCTTACGTAGAAATGTTTGTGGTGTCTAATTCCACAGATGC | 127980 |
| mRNA | ------------------------------------------------------------ | |
| genome | ACATTGACTCTCATGAAGCCCTTGGAGTGTTAAATACATTATTTGAGATTTTGGCCCCTT | 128040 |
| mRNA | ------------------------------------------------------------ | |
| genome | CCTCCCTCCGTCCGGTAGACATGCTTTTACGGAGTATGTTCGTCACTCCAAACACAATGG | 128100 |
| mRNA | ------------------------------------------------------------ | |
| genome | TGAGTCTCTCGCCTGGCTCAGCAGATGAATCTGGACGGCTTGTTCAGGCTCTGATTACTG | 128160 |
| mRNA | ------------------------------------------------------------ | |
| genome | GGACCACCCCCAGAATGTCTGAGTCAGTCAGTTTGGGTAGGGCTTCTTGAGAGTTTGCTT | 128220 |
| mRNA | ------------------------------------------------------------ | |
| genome | TTTTTTTTTTTTTTTTTTGGTGTGGGGGTGGTGCGGAACAGAGTCTCACTCTGTCGCC | 128280 |
| mRNA | ------------------------------------------------------------ | |
| genome | CAGGCTGGAGTACAGTGTCATGATCTCGGCTCACTGCAAGCTCTGCCTTCCAGCTTCACA | 128340 |
| mRNA | ------------------------------------------------------------ | |
| genome | CCATTCTCCTGCCTCAGCCTCCCGAGTTGCTGGGACTACAAGCGCCCACCACCACGCCCG | 128400 |
| mRNA | ------------------------------------------------------------ | |

FIG. 1 YYYY

| | | |
|---|---|---|
| genome | GCTAATTTTTTGTATTTTTAGTAGAGATGGGGTTTCACCGTGTTAGCCAGGATGGTCTT | 128460 |
| mRNA | -------------------------------------------------------- | |
| genome | GATCTCCTGACCTCGTGACCCGCCCATCTCAGCCTCCCAAAGTGCTGGGATTACAGGCGT | 128520 |
| mRNA | -------------------------------------------------------- | |
| genome | GAGCCACCGCACCCGGCCTTTTTATTTTTTTGGAGATGGAGCCTTGCTCTGTCACCCAG | 128580 |
| mRNA | -------------------------------------------------------- | |
| genome | GCTGGAGTACAGTGGCGCTACCTCGACTCACTGCAACCTCCGCCTCCCGGGTTCAAGCAA | 128640 |
| mRNA | -------------------------------------------------------- | |
| genome | TTTTCCTGCCTCAGCCTCCCGAGTAGCTGGGACTACAGGTGCGTGCCACTGTGCCCGGCT | 128700 |
| mRNA | -------------------------------------------------------- | |
| genome | AATTTTTGTATTTTTAGTAGAGACGGGGTTTCACTGTGTTAGCCAGGATGGTCGCGATC | 128760 |
| mRNA | -------------------------------------------------------- | |
| genome | TCCTGACCTTGTGATCCGCCCGCCTCGGCCTCCCAAAGTGTTGGGATTACAGGTGGCTCT | 128820 |
| mRNA | -------------------------------------------------------- | |
| genome | CGCACCAAGCCAAGAGTTTGCATTTTTAGCAAATTCCCAGGTGAAACTAATGCCTGCTTT | 128880 |
| mRNA | -------------------------------------------------------- | |
| genome | TCTGGGAGCACACTTTGGGACTCAGTGATAGAGAGGTTTATTGGTAGGATAGTAAAATAG | 128940 |
| mRNA | -------------------------------------------------------- | |
| genome | GAGTTATTTTCTTTCACAAAATTGGCAATTGGGGGAAATTTAATCTTCCTTTTTTCTTCA | 129000 |
| mRNA | -------------------------------------------------------- | |
| genome | GCTGTGACTTATGTATTATGTTTATTTTAGGCGTCCGTGAGCACTGTTCAACTGTGGATA | 129060 |
| mRNA | -------------------------------------------------------- | |
| genome | TCGGGAATTCTGGCCATTTTGAGGGTTCTGATTTCCCAGTCAACTGAAGATATTGTTCTT | 129120 |
| mRNA | -------------------------------------------------------- | |
| genome | TCTCGTATTCAGGAGCTCTCCTTCTCTCCGTATTTAATCTCCTGTACAGTAATTAATAGG | 129180 |
| mRNA | -------------------------------------------------------- | |
| genome | TTAAGAGATGGGGACAGTACTTCAACGCTAGAAGAACACAGTGAAGGGAAACAAATAAAG | 129240 |
| mRNA | -------------------------------------------------------- | |
| genome | AATTTGCCAGAAGAAACATTTTCAAGGTATGCTTTCTATCTGAGCCTATAACTAACCCAT | 129300 |
| mRNA | -------------------------------------------------------- | |
| genome | GCCTTTTGGGAAGTCACGTGATGTTTCACAGTCAGTAAGTCTGGAATAATACCTGGTCTT | 129360 |
| mRNA | -------------------------------------------------------- | |
| genome | GCTTCACTTCTGAGTTGGGTAAAGAAGTCTGTATCAGTGTAATTTTCTAATCCGTCCTGC | 129420 |
| mRNA | -------------------------------------------------------- | |
| genome | ATTATCTATGGCTCTTGGTTCATACCTGTCTTGAAGTTCTGTCATGTTCTGTCTCTTGTC | 129480 |
| mRNA | -------------------------------------------------------- | |
| genome | CTCAGTAGAGATGCTACAGCAGTGGCTCGCCTCAGGCAGGGCAGGGCAGTGGGGTGGCTG | 129540 |
| mRNA | -------------------------------------------------------- | |
| genome | TCCTGGGGGCAGGCAGTAGGGGCACGCTGACGTCAGGGAAGTTGAAACCCAAGAGAAGCC | 129600 |
| mRNA | -------------------------------------------------------- | |
| genome | AGTAAAAGTGAGTCTCAGATTGTCACCATGTGCTGGCAGTTTTACACGCTGTCAGTAATA | 129660 |
| mRNA | -------------------------------------------------------- | |

FIG. 1 ZZZZ

```
genome    AAAGTCTTCTCCCTGCAGGGCAGCCTGCCTCCAATAAATACGTGTAGTATCAAATCCTGT 129720
mRNA      ------------------------------------------------------------ genome    CTTCCCTCATAAATTGTTTGGAAGCTCCCCAAGGACAGTGATGAGGCACTCGTAAGTGCT 129780
mRNA      ------------------------------------------------------------ genome    TGCTGCCTAGATGGGTCCCTCTCCACCTTTGCTAGATTCTGAGCATTCACTGAGTTAGAG 129840
mRNA      ------------------------------------------------------------ genome    CTGCTTCTGCAAATGTGCTGCTTCTGCTAAGTGGCTGTGACTTCATGCAGCCTTCACTTG 129900
mRNA      ------------------------------------------------------------ genome    GTTTGTCATCAGTGGAGATGCCCTGTGTTGTCGAAGGAGATAAGCCCAGTAAGCCTGCTG 129960
mRNA      ------------------------------------------------------------ genome    GGCACCTTTTGGTTTGCAGGTTCAGCAGGCAGCCCATGGCTTTCCTGTGTCGCATTGAA  130020
mRNA      ------------------------------------------------------------ genome    GCAGCTGGCTAAAATTGATGATACATTAAATTCCTGTGACAGATGATCAGCTTGTATTTG 130080
mRNA      ------------------------------------------------------------
                                                             rs6844859
genome    TGTAATGGTGTACAGTTCACAAAGCTTAAAAAAATGCTACCTGCCATTTCATCCTCAGTG 130140
mRNA      ------------------------------------------------------------ genome    AGGAAGGTGATACACAGAGAGACCAAGTGACTGTGTCCACGGCGACGGCGCTCTGCATTT 130200
mRNA      ------------------------------------------------------------ genome    CACTTTAGCGGTTAATGTACTCTACCTATATTTTTACTTTATATTTACCATATATCTTTT 130260
mRNA      ------------------------------------------------------------ genome    CATGTATACTTGGCGTAAGTGCTTTATAGTAGTCACCTAATTCACTGTCATCTTTTTTGT 130320
mRNA      ------------------------------------------------------------ genome    TTCTTGGAAGGTTTCTATTACAACTGGTTGGTATTCTTTTAGAAGACATTGTTACAAAAC 130380
mRNA      ------------------------------------------------------------ genome    AGCTGAAGGTGGAAATGAGTGAGCAGCAACATACTTTCTATTGCCAGGAACTAGGCACAC 130440
mRNA      ------------------------------------------------------------ genome    TGCTAATGTGTCTGATCCACATCTTCAAGTCTGGTAGGTGAATCACATTAGTCTTCCTGG 130500
mRNA      ------------------------------------------------------------ genome    AGTGTCTCGTTCCCCATTCTGCACTATACACTCTCAGAGTGTAGGAGCTGTGCTGCCCGG 130560
mRNA      ------------------------------------------------------------ genome    TAGAAACTCTGCCTTGCCCAGTGTGCCAGTTGAAAATATTTGTTGCTGTAAGAGTACACC 130620
mRNA      ------------------------------------------------------------ genome    TGATACCATGTGACCCAGCAGTTCCACTCTTGGGTATATACCCAAAAGAATGGAAAGCAG 130680
mRNA      ------------------------------------------------------------ genome    GGTGGTGAAAAGATATTTGCATGCCAGCATTCATAGCAGCATTATTCACGATAGCTAAAA 130740
mRNA      ------------------------------------------------------------ genome    TGTGGAACCAACTGAAGTGTCCCTCGATGGATGAATGGATAAGCAAAATCTGGTGTATAT 130800
mRNA      ------------------------------------------------------------ genome    TTACAGTGGAATATTATTCAGCCTTAAAAAAGGACATTCTGACACATGCTACAACATGG  130860
mRNA      ------------------------------------------------------------ genome    GTGACCCTTAAGGACATTATGCTAAATGAAATAAGCCAGTCACAAAAGGACAAATACTAT 130920
mRNA      ------------------------------------------------------------
```

FIG. 1 AAAAA

| | | |
|---|---|---|
| genome | GTGATTCCACTTACATGAGGGACCTGGAGTAGTTAATTCATAGATATAGAAAGTAGAATG | 130980 |
| mRNA | ------------------------------------------------------------ | |
| genome | GTGGTTGCCAGGGGCTGCAGGGGAGGGGAGTTATTTTTACAAGATGAAGAGAGTTATTCT | 131040 |
| mRNA | ------------------------------------------------------------ | |
| genome | AGAAATGAATGGTGGTGATGGTTGTATAACATTATGAATGTACTTAATGCTACTGAACTG | 131100 |
| mRNA | ------------------------------------------------------------ | |
| genome | TACAGTTAAAAATAGTTAAGAGGACCAGGTGTCATGGCTCATGCCTGAAATCCAAGCACT | 131160 |
| mRNA | ------------------------------------------------------------ | |
| genome | TTGAGAGGCCAAGGCAGGAGGATTGCTTGAGCCAAGGAGTTTGAGACCAGCCTCAGCAAC | 131220 |
| mRNA | ------------------------------------------------------------ | |
| genome | ATGGTAGGACCCCATCTGTACAAACAAACTAGCCGGGGATAGTGGTGTGCATGTGGTCCC | 131280 |
| mRNA | ------------------------------------------------------------ | |
| genome | AGCTACTCAGGAGACTGAGGCTGGAGGATCGCTTGAGCCCAGGAGGTTAAGTCTCTAGTG | 131340 |
| mRNA | ------------------------------------------------------------ | |
| genome | AGATGTGTTCATGCCACTGCACTCCAGCCTCGGCTATAGAGTAAGACCCTGCCTCAAAAA | 131400 |
| mRNA | ------------------------------------------------------------ | |
| genome | AACAAAACAAAACAAGACAAGAGCCAAAAATGGTTAAGATGGGCCAATCACAGTGGCTTA | 131460 |
| mRNA | ------------------------------------------------------------ | |
| genome | TGCCTGTAATCCCAACACTTTGGGAGGTCAAGGTAAAAGGATCACTTGAAGCCAGGAGCT | 131520 |
| mRNA | ------------------------------------------------------------ | |
| genome | TGGGACCAGCCTGAGCAACATATCGAGACCCCTATCTCTACAAAGAAAATCAAAAACTAG | 131580 |
| mRNA | ------------------------------------------------------------ | |
| genome | CTAGATATGGTGGGCACATGCCTGTAGTCCCAGCTACTTGGGAGGCTGAGGTGGGAGGAT | 131640 |
| mRNA | ------------------------------------------------------------ | |
| genome | CTCTTGAGCTCAGGAGTTCGAGGCTGCAGGGAGCTATTATTGCACTCCAGCCTGGGCTAC | 131700 |
| mRNA | ------------------------------------------------------------ | |
| genome | AGAATGATACCCTGCCTCTTATTAAAAAAAAATCCAAAAAAAAAAAAAAGTAAACCTGAG | 131760 |
| mRNA | ------------------------------------------------------------ | |
| genome | AGCTTCCTCCTCCTGTGTTAAATTTGGAGGCCAAGATGTTTTGTTACTTTTACAAATGA | 131820 |
| mRNA | ------------------------------------------------------------ | |
| genome | TCAAGGACGGTGAAGGTTGGGCATGGTAGCTCACACCTGAAATCCCAGCACTTTGGGAGG | 131880 |
| mRNA | ------------------------------------------------------------ | |
| genome | CTGAGGCGGGGTGATCGCTTGAGCTTGAGACCAGCCTGGACAACATAGCAAGAGACCCCA | 131940 |
| mRNA | ------------------------------------------------------------ | |
| genome | TCTCCACAAAAATAAAAAAATAAAAAAAAATAGCCAGGAGTAGTGGCATGAGCCTGAGCC | 132000 |
| mRNA | ------------------------------------------------------------ | |
| genome | CAGGAGGTCAAGCTGTAGTGAGCCATGATCATGCCACTGCACTCCAGCCTGGGCGAGATC | 132060 |
| mRNA | ------------------------------------------------------------ | |
| genome | GAGACCATGTCTCTAGAGAAAGAAAATGACAAGGACAGTGAACCCAAGAAAGTCATAAGA | 132120 |
| mRNA | ------------------------------------------------------------ | |
| genome | TGCCAGCTGTGCAGCAAGCATGGAAAGCAGCCAGTCCAAATTAGGACAGTGTGTTTTCCA | 132180 |
| mRNA | ------------------------------------------------------------ | |

FIG. 1 BBBBB

| | | |
|---|---|---|
| genome | AGAAGAACGATCGTTTGTAATGAGAATGCTTTGCTTTAAATAAATGACTAAATAGCTAGA | 132240 |
| mRNA | ------------------------------------------------------------ | |
| genome | AGCCTAGTTCTAGGGGATAGGCACGTCTTTCTTCTCTCAAGAAAATAGAAAGGCAATTCT | 132300 |
| mRNA | ------------------------------------------------------------ | |
| genome | AATTTCTAGTAACAGCAAACAGCATTAAGTCATGGTCCAAATATGAGGCAAACCAAAATG | 132360 |
| mRNA | ------------------------------------------------------------ | |
| genome | TGGCTTGATTGTTCAGCAGTTGATCTGTTGGAAGCCCTTGATATTAAAAAGGTTCTCCTT | 132420 |
| mRNA | ------------------------------------------------------------ | |
| genome | TAAGCGGCTTAGGAGTCACGATCAAAGACCTATAGAAAGAGATGCCATCCTTCTAGGATC | 132480 |
| mRNA | ------------------------------------------------------------ | |
| genome | CTTGGCTCTCTTGGGAACTAGATTCAGATAGTCATAATGTAAATACTGCTTGAGCTTTCT | 132540 |
| mRNA | ------------------------------------------------------------ | |
| genome | TTCTTTCTTTCTTTCTTTTTTTTTGAGACAGAGTTTCACTCTTGTTGCCCATCC | 132600 |
| mRNA | ------------------------------------------------------------ | |
| genome | TGGAGTGCAATGGTGCCATCTCGGCTCACCGCAACCTCTGCCTCCCAGGTTCAAGCAATT | 132660 |
| mRNA | ------------------------------------------------------------ | |
| genome | CTCCTGCCTCAGCCTCCCGAGTAGCTGGGATTACGGGCATGCACCACCACGCCTGGCTAA | 132720 |
| mRNA | ------------------------------------------------------------ | |
| genome | TTTTTTGTATTTTTAGTAGAGACAGGGTTTCTCCATGTTGAGGCTGGTCTCGAACTCCTG | 132780 |
| mRNA | ------------------------------------------------------------ | |
| genome | ACCTCAGGTGATCCACCCGCCTCGGCCTCCCAAAGTGCTGGGATTACAGGTGTGAGCCAC | 132840 |
| mRNA | ------------------------------------------------------------ | |
| genome | CGCACCCGGCCCGAGCTTTCATTTTTGAAATCAATGTATGACTGAAACACTGAAGACTTA | 132900 |
| mRNA | ------------------------------------------------------------ | |
| genome | CTGACTTAATTATGGTTTCAGAACAGAATGAAAATGTCTTCGGTTCTGATGAATATAAAA | 132960 |
| mRNA | ------------------------------------------------------------ | |
| genome | GGAAAACTAACCAAGTTAATTTGGCAAGTAGATGGTAGAGATAGAGGTGGGGAGTGGAAG | 133020 |
| mRNA | ------------------------------------------------------------ | |
| genome | GGGAACTAAAATCTTCACCTAGCATTGTTGGGATTATATGGTTACATCATCTGAAGTTGA | 133080 |
| mRNA | ------------------------------------------------------------ | |
| genome | CAGACCAAAATATAGAGGCTTCAGAGGTCTCCAAATAGAACTAAACATGTAATTCAGATT | 133140 |
| mRNA | ------------------------------------------------------------ | |
| genome | GTTAGGAGGTAGTATAAATGAGCTAAATCTCATCTTTATTACGGTAGAGTTAATGGGTGA | 133200 |
| mRNA | ------------------------------------------------------------ | |
| genome | TGTCTAAAGTTGTCTGAAGTCTATAAATCATGACAAATTATGATGTGGTGATTGTATTCA | 133260 |
| mRNA | ------------------------------------------------------------ | |
| genome | ACAGTCTTTCAGTTGCAGGGATAAAACCCCAGTTTAAACTAGAGTAAGAGAAAGAATGTG | 133320 |
| mRNA | ------------------------------------------------------------ | |
| genome | TTGGTTTAAGCTCCTGGAAAGTGCAGGCAAGGGTAGTTGGTAGGACTGCATCTAGTGTTG | 133380 |
| mRNA | ------------------------------------------------------------ | |
| genome | TAATTCTGTGGTCTGCATTGTATATTTATGCATCTCAGCTCTGCTTTCTTCTTTTCATTT | 133440 |
| mRNA | ------------------------------------------------------------ | |

FIG. 1 CCCCC

| | | |
|---|---|---|
| genome | ATATAATTTTTAAATTTTATTTTAAAGATAGGGTCTCACTTTGTCGCCTAGGCTGAAGTG | 133500 |
| mRNA | ------------------------------------------------------------ | |
| genome | CAGTGGCATGAAGTGCAGTGCGAGGCTCACTCTAGCCTCGAACTCCTGGGCTCTAGAGTT | 133560 |
| mRNA | ------------------------------------------------------------ | |
| genome | CTTCCTGCCTCAGCCTTCTAAGTAGCTGAGACAATAGGCATGTACCAACATGCCTGGATA | 133620 |
| mRNA | ------------------------------------------------------------ | |
| genome | GGTTTTAAAATTTTTTGTAGAAATGGAAGTCTTGCTGTGTTGCCCAGGCGGGTCTTTAA | 133680 |
| mRNA | ------------------------------------------------------------ | |
| genome | CTCTTAGCTTCAGGCGATCCTCCTGCCTCTGCCTCCCAAAATGCTGAGGTTATAGGTGTC | 133740 |
| mRNA | ------------------------------------------------------------ | |
| genome | ACCCACCACGCCCAGTCTCATCTCTGCTTCCTGTGTTAGTTTTGTTCTCTGGTGGGCTGT | 133800 |
| mRNA | ------------------------------------------------------------ | |
| genome | TTTCACATGACCGAAGATGACCTCTAGCAGGCTGTGTTCTCAGCCCCTCAAGTAGGCCTA | 133860 |
| mRNA | ------------------------------------------------------------ | |
| genome | TGTGATTGGCCTTGCATGAGTAATATGGGTGACCATAAACCCCTGAATGCTCTGGTCCAC | 133920 |
| mRNA | ------------------------------------------------------------ | |
| genome | ATGGGCCAAATGGGAGACTGGACAGCATTCCATTGATGAGGAGGTGGGGCTGGTCTCCGG | 133980 |
| mRNA | ------------------------------------------------------------ | |
| genome | GAGTAAGGGAGAGGAGCACATGCAGTAACTGATGGTCTGCTGCAAGGGATAGCAGCACAG | 134040 |
| mRNA | ------------------------------------------------------------ | |
| genome | CAGTTAGAATTTTGGAGGTAACTACCAGAACTGAAAACAGAAATGATAACAAGTAGTTGC | 134100 |
| mRNA | ------------------------------------------------------------ | |
| genome | CTTAAAAGGGATGGGAGCAGGGTGCTTTTGTGATCAAAGCTCCTTTCTCTTACTGGATT | 134160 |
| mRNA | ------------------------------------------------------------ | |
| genome | TTTGTACACATTTTGCATACATATCTTAGAGTAAAAGATAGCATTTTCAGCCTTGGTCCA | 134220 |
| mRNA | ------------------------------------------------------------ | |
| genome | TTTGAGGATACTCTTGGCGTGGCCCGCCTCCATGCTAGCAGGCTCTGGTTGTGCCAAGTT | 134280 |
| mRNA | ------------------------------------------------------------ | |
| genome | CAGTTGAGCATCCTGGCTCTTGCCTGCACGGAACTTCCAGTCAGTGCGTCAGTATCACAA | 134340 |
| mRNA | ------------------------------------------------------------ | |
| genome | GTCTTGATATTTCCTATGAAGAAGAACAGTAGTGCAGTGACAGACGAAATGGGTGGGCAG | 134400 |
| mRNA | ------------------------------------------------------------ | |
| genome | GCAGAGGCAGGATTTCTGAGGGAGAGAAGTAGCTAGCTTTTTGCAGAGAAGAGTTCCGGC | 134460 |
| mRNA | ------------------------------------------------------------ | |
| genome | ACCCAAGAGAGCAGCTGAGAGTACAGGCAGGCAGGCAGGATGCCGGTAGGGCCCGGCCGC | 134520 |
| mRNA | ------------------------------------------------------------ | |
| genome | ACGGCGCCACAGAATCCTGGAGAAAGGGGCCTCTTCATGGCCTCTGCATTCAGCTGCTGT | 134580 |
| mRNA | ------------------------------------------------------------ | |
| genome | CACCCTCCGCACAGGCCATGGCCAAAATTTAATTTTCATAGTGGACTCTAGTTTTTGAGC | 134640 |
| mRNA | ------------------------------------------------------------ | |
| genome | CTTACTTGCTATTATTGAAATAATTTTCTTGTTTCTTTTTAAAGATCTTCGGATTATGCT | 134700 |
| mRNA | ------------------------------------------------------------ | |

FIG. 1 DDDDD

```
genome    TCACTGACCACTGTAATAAGTTTAAAGTTGAGAAAATATGGCTTGTTAATGAATGATAGG 134760
mRNA      ------------------------------------------------------------ genome    TCAATTTTAGTATGTTGGTCATTTTAATATTTTGCCACCAGTTGGTTTGGATTTGATGCC 134820
mRNA      ------------------------------------------------------------ genome    AGGAGGAGACAGCCTCATTTCTAAGGACTAGTCTTGCCTTTGTGGGATAAGGGTGGTGTG 134880
mRNA      ------------------------------------------------------------ genome    TTCTGTGTCCTTCTACATGTCCGAGCGATCTCTGTGCAGCTCAAATGTGGTCACTGTCTT 134940
mRNA      ------------------------------------------------------------ genome    ATTGCGCTGATTTCCTCTCCTTCCATCTCACAATTGAGGCAAAATATTGTTACTGTTGAA 135000
mRNA      ------------------------------------------------------------ genome    GTGTTGTCCAATAGGACTTCCAGCAGAGACAGGATGTCTGCACTGTCTAATTTAGTTGCC 135060
mRNA      ------------------------------------------------------------ genome    TTTAGCCACATGTGGTGTTCTGTACCTGAAATGTGGCTGGTCTGATTGGATAGCTTAATT 135120
mRNA      ------------------------------------------------------------ genome    TATAATTTTATTTAATTTTAATTAACTTAAATTTAAACAGCTCTGTGTGGATAGTGGCTC 135180
mRNA      ------------------------------------------------------------ genome    CTGTATGAGACAGTGCAGGTCTGTTGAGAAGCAGCTTTACTGGTGGGAGTGGAGGGCTTG 135240
mRNA      ------------------------------------------------------------ genome    GAGAGGGCACGTGGGTTTCCTGCTGGTATCTTTTGACCTTATTTAATCTGCCCAACATTT 135300
mRNA      ------------------------------------------------------------ genome    GCAAGTAAGTTGTGTGTGTGTATATATAAATGTGTGTTTCTGTCTTCTTGTTTCCTTT 135360
mRNA      ------------------------------------------------------------ genome    GACTGCATTTATTTGAAAGACACTAGGTGGCAGAATTACTGTATTTGATTGGTTTCAAGA 135420
mRNA      ------------------------------------------------------------ genome    TAAGAGTTGAAATAATTCATCTCGTGTTTTTATATAAGTAAGGTGTGTTTAGCATGTAAA 135480
mRNA      ------------------------------------------------------------ genome    ATTGGTAATATGTATTCACGTACTGCTTAAACAAAGGCTATGAATTCCACCCATAAACCG 135540
mRNA      ------------------------------------------------------------ genome    AAAATGAAGACCTTTAAATTTGTCCATTTCAGGCGTGGGTACTTCTTAAATAATACCTGG 135600
mRNA      ------------------------------------------------------------ genome    TTCAGGAACTAGTCAGAATGGCACCCTTGACTTTTTGTTTCCTGCTTTTCCTCTTGTTGG 135660
mRNA      ------------------------------------------------------------
                                            rs363092
genome    GAGAGGAGGGTATTCATCCCAAGTGGTTTGCCTATTTCACATTCCATCTAGGATAAGCA 135720
mRNA      ------------------------------------------------------------ genome    GAATAGCCAAGAAAGATAGCTGTCCTCCTGTTTACAACATTTGGGGTAACCAGCATCCCT 135780
mRNA      ------------------------------------------------------------ genome    CTCTTTTGGTCCAAGATAGACTGGTTTAGAAACAGATGATGGCACCAGAGGCCCAGGAGG 135840
mRNA      ------------------------------------------------------------ genome    TGGAAACATCAGCTTTGTTTGTTGTCCATGTGGCTGAATTAGAGCTGTCTGGCCTTGTAG 135900
mRNA      ------------------------------------------------------------ genome    CCTCAACACGGCCTTCCAGCTTTGCTCACCGTGATTTTCAAGGACACATCTTGTGCTCTT 135960
mRNA      ------------------------------------------------------------
```

FIG. 1 EEEEE

```
genome      CCCTGCCTGCCATCCAGACTATACCCAGTCAGGGTGGCAGGAGCTGCTGCCCCTTCCTCC  136020
mRNA        ------------------------------------------------------------ genome      CTGAGTCCTGGTCGTGGGTGGTGGAGATGTGCCATGACGCTCACGGAGGCATGCTCACCC  136080
mRNA        ------------------------------------------------------------ genome      CTTCCTCTGTGGCAGAGGGGATGGCTGCACGACAGCTCTTCCCTGTCCTTTCCAAAGCGT  136140
mRNA        ------------------------------------------------------------ genome      CTGTGGTTCCACTTTTTGGGGCAAAGCAGGAATACTGGAAGAGAGAGAAAGTGGTCCTTT  136200
mRNA        ------------------------------------------------------------ genome      CTATAGTAATAAAGTTGACATTGATTCAAGTTCATGCTTGGGGAAAGGACAGGGCTACTA  136260
mRNA        ------------------------------------------------------------ genome      ACAATTATAATGCTGGGAGCAATGGAATTTTCTCATGGGTATGTGGTAGGTTTAATTTTA  136320
mRNA        ------------------------------------------------------------ genome      ATTATCCCAGTTAATTCTTAGAACTGCTCTGTGAAGTATTTCCCGCTTTGTGCTTAAGTT  136380
mRNA        ------------------------------------------------------------ genome      CTAAAAGATCCTGTGCCAAAACCAAGAATGAAAACCCAAGCATTCTTTCTTGCCCATCGA  136440
mRNA        ------------------------------------------------------------ genome      TCTTTCTCTCATCAGGCCACTTCTTGGGTTGATAGTGGTGAGTGTAGCCGCTGCCACTTT  136500
mRNA        ------------------------------------------------------------ genome      CAGAATACCCACCATGGGCCCCAGTCACTGTGTGGCGTGGAGAAGAGATGGTTCTCTCTG  136560
mRNA        ------------------------------------------------------------ genome      TGTCATAGCTGAACAAGCCCAGCCCAGAGAGGTTTCTGCCCTAGGAGCTCTCGATGGTGG  136620
mRNA        ------------------------------------------------------------ genome      AATTGGGATGCGATCCCACATCCTGCCTGTTTTGAAAACAGCATTCTTTATTTCCAATTC  136680
mRNA        ------------------------------------------------------------ genome      CTGCTTCCATTGTTCCTTTTAATATTTCTTTGTTTAGCTCACAAAAACACGGCTTGCGGA  136740
mRNA        ------------------------------------------------------------ genome      GCTGCTGCGTGCAGCTGTAGCTGTTTCTCTGGGTGCAGCCTGCATCCGCCTTCCTGCCCG  136800
mRNA        ------------------------------------------------------------ genome      CCTCCTTTCCTGCACTGCCATCGTGGTCTCCGGGCACTTGGTCCCTTTCTCTTCCCCTGA  136860
mRNA        ------------------------------------------------------------ genome      GTCCCTTTGGCTCCCCTGTGCCACCCTTGTGATCCACAGGCTCTGCCTTCTTTCTGTCTC  136920
mRNA        ------------------------------------------------------------ genome      AGACTGCTGCTCATCACTACTCGGGACCCTAGGAAGGGAGGTTCCACCGAGAAGCATCTT  136980
mRNA        ------------------------------------------------------------ genome      CTCATCTCAGCCACGTTCTCAGTGCCACTGTTGTCTTTGTTAGGTAATGGTAGCTACTGT  137040
mRNA        ------------------------------------------------------------ genome      AACAAATAAACCAACATTTCCATGGCTTCACACCAGAGAAGGTTGTTTCTTGGTTTTATG  137100
mRNA        ------------------------------------------------------------ genome      ACAATGTATTGAGGGTGTTCTTGGTTCACGGATGGTTTTCCTCCATGTGGGAATTCGGGG  137160
mRNA        ------------------------------------------------------------ genome      ACCCAGGCTCCTTTCCTTCTTTTGGTTCTGTTCTCCAGGCCTTCACATCCTCTGTGTCTG  137220
mRNA        ------------------------------------------------------------
```

FIG. 1 FFFFF

| | | |
|---|---|---|
| genome | GTTGGGGACAAGGAGAGGGAAGGTAAAGAAGGCTTTGTGGCCTTGGATAAGTGACAGGCA | 137280 |
| mRNA | | |
| genome | TGCCTTTGCTGGTGTTCTCTCGTGGTGACAGGTCACAGCCCCACCCTGTAAAAGGGGACT | 137340 |
| mRNA | | |
| genome | GAGAGACGTCGTCCTGCTGCTTCCCAGCAGCAGCACTGTGGTCTCTGATGTGTTTTCTGT | 137400 |
| mRNA | | |
| genome | GAGGATAAAAACAGGTGATTCCAGGATGAGGAAAGTCAGGGAAACCCTTGGAAGGAGGGG | 137460 |
| mRNA | | |
| genome | ACCAGGCGGGTGTCACCATGGGATTAGTGGTGGCTTCAGAATGAGCTGCAGCGAGTGCCA | 137520 |
| mRNA | | |
| genome | TGCCTTCTAAAGCTTTTGCTATTCTGATATGCCCACACCATGCCCAGCAGGTGTCTGCCT | 137580 |
| mRNA | | |
| genome | TGCTCTCCGCAGAGAGTGATGAATCCTTCTCATGAGCCTCTGTCCAGTTGTTCCTCCC | 137640 |
| mRNA | | |
| genome | TCCACCTGGAAGGGACCCTGGGTTCCTCATAACATCCCAGCGGAACAGGGGACCTTCTAT | 137700 |
| mRNA | | |
| genome | CCTGTCCCCAAGTTCATCCTCATCCTCCTGCCGGCTTCCTGGCCCCTCTTATGTCTGCTT | 137760 |
| mRNA | | |
| genome | CCTGACGCCACATCCTTCTGGATTCTCTGGAATTGAATTTTGCCTTTGATGCTTATTTAA | 137820 |
| mRNA | | |
| genome | AAATATCCATTGCAGGCCAGGTGTGGTGGCTCACACCTGTAATCCTGTGCACTTTGGGAA | 137880 |
| mRNA | | |
| genome | GCCAAGGTGGGCAGATTGCTTGAGCCCAGGAGTTTGAGATTAGCCTGAGCAACATGTTGA | 137940 |
| mRNA | | |
| genome | AATCCTGTTTCTATAGAAAATACAAAAATTAGCTGGGCATGGTGGCGCACACCTATACTC | 138000 |
| mRNA | | |
| genome | CCAGCTACTCAGGAACCTGAGACAGGAGGATCAATTGAGCCCCGGAGGCCAAAGCTACAG | 138060 |
| mRNA | | |
| genome | TGGGCTGTGATCGTGCCACTGTACTCCAGTCTGGTCAAACAGAGTGAGACCCTGTCTGAA | 138120 |
| mRNA | | |
| genome | AAAAAAAAAAAATCCATTGCATACTTCACCGTAGCGAAACATGTATGTCTTACCTTTCC | 138180 |
| mRNA | | |
| genome | TTTCCTGCCTGTAGCTGCTCTTTTACACTTAACAGCCACACTAAGCCAGCCTTAAATGAA | 138240 |
| mRNA | | |
| genome | AAACAAACCAGCACTTCCTGTGCCCTCCTGCTTCCTTCATGAGGGGTCCCTCCCTCTGTG | 138300 |
| mRNA | | |
| genome | TACACTCCATTCTCATTGCCCATGGTGGTTTGTTTCCCTCTTGTTTCTCAAGCCATGGCA | 138360 |
| mRNA | | |
| genome | GCCTGCCTCTTGCCCTCTTTACTAAAAAGGCCTTTGCAGAGGCTGCCTGTGTTCTTTCTT | 138420 |
| mRNA | | |
| genome | TCTAGGTCTCTCTCATCCTAGGCCCTCCAGCTTGATTCTGTGGAGCTGCCCTCTTGTCAC | 138480 |
| mRNA | | |

FIG. 1 GGGGG

| | | |
|---|---|---|
| genome | TCAGTAGCTTGTGGGGTCTTCTCTGTCTAGCCACTTAATTGATTGTGTTCCTCGAGTTGC | 138540 |
| mRNA | ------------------------------------------------------------ | |
| genome | TGTCCATGGTCTCTCGTTACTGTTTTCTCTGTGTTTCTGCCTCTCTCCTTGGCCTTGGTA | 138600 |
| mRNA | ------------------------------------------------------------ | |
| genome | GGTCCATCCCCTTTGTGACCTTGGCTGTTGCTCTCATGGACAACTTTCTCTTGCTGGTCC | 138660 |
| mRNA | ------------------------------------------------------------ | |
| genome | TTGTAGTCCTGGCATCCAGCTTCTCGACACGGGACTTGTCCTGCCAGTACCTCAGACTTG | 138720 |
| mRNA | ------------------------------------------------------------ | |
| genome | CACTTAAAATTGAACTAGCACCACTGTCACTCTCCAGGGCCTCTTCTTGTTAATTAGATC | 138780 |
| mRNA | ------------------------------------------------------------ | |
| genome | ATTAGGGATGTTCAGAATCCCAGCATCATAGTATGTTCCTCCTCCCGCTACCCCAGGAAC | 138840 |
| mRNA | ------------------------------------------------------------ | |
| genome | CCTAACCTTACCTCCTCCTCTCTATCTACTAGGAGGTGGCCCTCAGAGTCCGTCTCATCT | 138900 |
| mRNA | ------------------------------------------------------------ | |
| genome | TCCACCTGAACTTCCCTAATAGGCTCCAGCAGCTGCCACCCCGGGGGCTGAGTACTTCCT | 138960 |
| mRNA | ------------------------------------------------------------ | |
| genome | CCATGCCTTGTGCAGTGCTGAGCCCTTTACCTGGGTTCTCCTGTTTGCTCCTTATTACAG | 139020 |
| mRNA | ------------------------------------------------------------ | |
| genome | CCCTGCGAACAGATACTGCTCTTAATTCCATCTTACACCTAAGGAAGCTGAGGCCCCAGG | 139080 |
| mRNA | ------------------------------------------------------------ | |
| genome | TAAGGTGCATCCAAGGTCACCCAGGTAGTAGACAGTAGAGCCACGATCTGAACCAGGCAG | 139140 |
| mRNA | ------------------------------------------------------------ | |
| genome | TCTGATTCAGAGCCTGTGTTGACACTCAGCCACCTAGAACACAGCTTGGATTGTGGGTTT | 139200 |
| mRNA | ------------------------------------------------------------ | |
| genome | CTATTACCTGTTCAAAACCCCTACATCCCGGGTCTGTCCCTGCACGTGCTCTGTGGCCTG | 139260 |
| mRNA | ------------------------------------------------------------ | |
| genome | GCTGCATCTTCCTTGAAGGCAGTGCATGCCTCTTCACTCAGGGGGCCCATGCAGGAACAG | 139320 |
| mRNA | ------------------------------------------------------------ | |
| genome | AGGGCCCCACAGAAGGATGAGGCCAGTGCAGAATGGGCTGGAGGGGACAATGCTGACCAG | 139380 |
| mRNA | ------------------------------------------------------------ | |
| genome | GAAGCAAGTGTAGAGAAATCCCAGGAAACCTGGAGGAGCCAGAGACAAGGCATTAGAACT | 139440 |
| mRNA | ------------------------------------------------------------ | |
| genome | CCTCGTCGTGACCTGGTCTGCATTCTCTGAGTGTGCTGCTTCTGTTAGCTCGCTTCCTTG | 139500 |
| mRNA | ------------------------------------------------------------ | |
| genome | GTCTCAGGTTATAGTTTAAGGCATTGTGGAGCCCTAAAAAGCCTGTACTCTGTTTTTACC | 139560 |
| mRNA | ------------------------------------------------------------ | |
| genome | TGTTTTAGGACCCTTTCACTTTGGGGATGTGTTGATTTTTTTTTTTTTTTTTTTTT | 139620 |
| mRNA | ------------------------------------------------------------ | |
| genome | TTTGAGATAGAGTCTCGCTCCATTGCCCAGGCTAGAGTGCAGTGGCACGATCTTGGCCAC | 139680 |
| mRNA | ------------------------------------------------------------ | |
| genome | TGCTGCCCCTGCCTCCTGGGTTCAAGCAATTCTTGTGCTCCCGCCTCCCAAATACCTGGG | 139740 |
| mRNA | ------------------------------------------------------------ | |

FIG. 1 HHHHH

| | | |
|---|---|---|
| genome | ATTACAGGCACCCGCCACCACACTCGGCCAATTTTTGTATTTTTAGTGGAGACAGGGTTT | 139800 |
| mRNA | ------------------------------------------------------------ | |
| genome | TACCATGTTGGTCAGGCTGGTCTCGAACTCCTGACCTCAAGTGATCTGCCCACCTTGGCC | 139860 |
| mRNA | ------------------------------------------------------------ | |
| genome | TCCCAAAGTGCTGTGATTATAGGCGTGAGCCACCACACCCGGCCTGAAATTTAAATCAGA | 139920 |
| mRNA | ------------------------------------------------------------ | |
| genome | AATAAAATTTTGATCCCAACAGTGATGCCAGGCAGCCCAGATCTGGGGGAGAGGGTGGCC | 139980 |
| mRNA | ------------------------------------------------------------ | |
| genome | TTGGCCAGCTGGGCCTTTCTCTGTTTCCCAAGTCTTGCTGCCTCTCCCTGCTGGGCTTTG | 140040 |
| mRNA | ------------------------------------------------------------ | |
| genome | CAGCCTGTGCATGTCTCTGTGCCTTTGACCTTGTTTATCCAAAGGAGAGGATAGAATGAA | 140100 |
| mRNA | ------------------------------------------------------------ | |
| genome | GTCATGATTCCTGGAGCCCTGAGAAGGATGCTGTGGAGAAATTTGCCGGTAGAATCTAGC | 140160 |
| mRNA | ------------------------------------------------------------ | |
| genome | TGAGTGTGTTGCTGAGGTGCCAGCATTGTGTGTGGGGAGGCTGACCGCTTGGCCTGCCTA | 140220 |
| mRNA | ------------------------------------------------------------ | |
| genome | GGCCCAGGATGCTCCATGGCCGGGCACAGAGGCCACTTGGCTGTCAGGTGTCAGGAGCCT | 140280 |
| mRNA | ------------------------------------------------------------ | |
| genome | GCAGAGGGCACACAGAGCCTGGACCGCAGGGGGGTCCTGCTTTCTCACCTGGCCTCCTTC | 140340 |
| mRNA | ------------------------------------------------------------ | |
| genome | AGCATTTCTGTCCCTCAGTCCTTAGCAAGCCCAGGAGCTGTTGAGTTTGGCAGGTGCCGA | 140400 |
| mRNA | ------------------------------------------------------------ | |
| genome | GTGCTGTTCCTGCCTGTGTAGCTGTGGCTCAGTCCTGTGGGGGCCCCGCTGTGGCCCGAG | 140460 |
| mRNA | ------------------------------------------------------------ | |
| genome | TGCAGTGATTCGAGGCGCTGAGTGTTCCCTGACTCCTTCTCCAGGAGCTGTGTTCAGACT | 140520 |
| mRNA | ------------------------------------------------------------ | |
| genome | TTCGCAGCTCTTGGCTTGGAGCTCCTGGAGGGCTTGGCATTGCCGACCAATGTGGAGGTC | 140580 |
| mRNA | ------------------------------------------------------------ | |
| genome | GACAGTGAGAGAGGAGGAATGCTAGCTTTCTTGACCAGTCCATTAAATAAGTGGGATATT | 140640 |
| mRNA | ------------------------------------------------------------ | |
| genome | GGCCAGGCACGGCGGCTCACGCCTTAATCCCAGCACTTTGGGAGGCTGAGGCGGGTGGAT | 140700 |
| mRNA | ------------------------------------------------------------ | |
| genome | CACGAGCTCAGGAGTTCAAGACCAGCCTGGCCAACATGGTGAAACCCCCTCTATACTAAA | 140760 |
| mRNA | ------------------------------------------------------------ | |
| genome | AATACAAATATTAGCTGGGCGTGGTGGCAGGCGCCTGTAATCCTAGCTACTTGGGAGGCT | 140820 |
| mRNA | ------------------------------------------------------------ | |
| genome | GAGGCAGGAGAACAGCTTGAAACCGGAAGGTGGAGTTTGCAGTGAGCCAAGATTGCGCCA | 140880 |
| mRNA | ------------------------------------------------------------ | |
| genome | CTGCACTCCAACCTGGGCAACAAGAGCAAAACTCTATCTCAAAAAAAAAAAAAAGTAG | 140940 |
| mRNA | ------------------------------------------------------------ | |
| genome | GATATCTGTTTCTGCTTAGAAAAATCAGAATTTTCTAAATGCCAGGTGTTCTGAATACGT | 141000 |
| mRNA | ------------------------------------------------------------ | |

FIG. 1 IIIII

| | | |
|---|---|---|
| genome | AAGTATGGGAGACGACTCAGCCTGTTTCATTTTTATGTAAAATCTTCGCGTAGCCATGTG | 141060 |
| mRNA | ------------------------------------------------------------ | |
| genome | GCACTGGACCGAGATGAAAGCAAAGACATTTCTCCTTAACTTTGTTTCTAGGAATGTTCC | 141120 |
| mRNA | ------------------------------------------------------------ | |
| genome | GGAGAATCACAGCAGCTGCCACTAGGCTGTTCCGCAGTGATGGCTGTGGCGGCAGTTTCT | 141180 |
| mRNA | ------------------------------------------------------------ | |
| genome | ACACCCTGGACAGCTTGAACTTGCGGGCTCGTTCCATGATCACCACCCACCCGGCCCTGG | 141240 |
| mRNA | ------------------------------------------------------------ | |
| genome | TGCTGCTCTGGTGTCAGATACTGCTGCTTGTCAACCACACCGACTACCGCTGGTGGGCAG | 141300 |
| mRNA | ------------------------------------------------------------ | |
| genome | AAGTGCAGCAGACCCCGAAGTAGGTTCATAATGCCCCACAGCCCAGGGCGCCAGCCCAGC | 141360 |
| mRNA | ------------------------------------------------------------ | |
| genome | ACCCTGTCCTGAGACTCCCAGTAACCTGAGCTTTGGCCACCGTTAAAGCATTTTCATTTT | 141420 |
| mRNA | ------------------------------------------------------------ | |
| genome | CCATTTTTGTGAGGGCTTGTGAAATTTCTGCTGCATATTAATATTCCTTTCATGGACAG | 141480 |
| mRNA | ------------------------------------------------------------ | |
| genome | CATATTATTGGGACAAACATGCGGTCCAGCTAAAGGCATTCAAAATAGCAGTTGCTTTCT | 141540 |
| mRNA | ------------------------------------------------------------ | |
| genome | AAATGCGATTTTCTTTGGCAGGTTCTTTGACACCATTGCATCTTGTGGGATATGCTTGTC | 141600 |
| mRNA | ------------------------------------------------------------ | |
| genome | ATGCTCTGTGGCTCCTACTAAGTTCTAGTCCTTAAATTGGTTCCATAGCCAGACATGTTG | 141660 |
| mRNA | ------------------------------------------------------------ | |
| genome | CAATGTCTTAACCTCATTATAAAGTAAATGTGGTTCTGGTTATCCTTAGATAATGAAGTA | 141720 |
| mRNA | ------------------------------------------------------------ | |
| genome | ACAGTGTAGCAAATTTCAAAACCTCTTGGAAATGTTATTTTACCATTCAAAAAGGCTTAC | 141780 |
| mRNA | ------------------------------------------------------------ | |
| genome | TAAGGTTCTCGTTATGGGTGGCCCTCTTTTTGCAAAAGGTTTTCAGGCTTAAGCTCCATT | 141840 |
| mRNA | ------------------------------------------------------------ | |
| genome | TCTAGGTGCTCCAACACTCCATTATTTGTATATGTATGGAAATAAAAGCTGTGACCACCC | 141900 |
| mRNA | ------------------------------------------------------------ | |
| genome | CCAACCCTGGCCCCCGCCCAGCTGAATCCTCAGCACAGTATTTCTGGAAGGCTCAAGATC | 141960 |
| mRNA | ------------------------------------------------------------ | |
| genome | CCACGCTGGGGAAAAGAAGTTCTGGAGACAAAAGAGGGCAGGTGCTGCCGTGCCTCTCTG | 142020 |
| mRNA | ------------------------------------------------------------ | |
| genome | CTCAGTATGGATACTGGACCTTGTGCTGCCAGGGCTCCCAGTAGGGCCAGTTCATGGCAC | 142080 |
| mRNA | ------------------------------------------------------------ | |
| genome | TCAGCTGGAAAGTCCACTGTTGGGAGGCATTCTTAACCATCCACTCTGTGCCGTATGTAG | 142140 |
| mRNA | ------------------------------------------------------------ | |
| genome | TGGGGTCTGGTCATTCTGTTGGAGGAGACAGACCAGTGACGACATTTGAAATGCTTGGTG | 142200 |
| mRNA | ------------------------------------------------------------ | |
| genome | GATGTCTTAGGCCTGTTACGATGACTGAGCACTGTGGGGGCAGGAGACAGAAAGTCAGTG | 142260 |
| mRNA | ------------------------------------------------------------ | |

FIG. 1 JJJJJ

| | | |
|---|---|---|
| genome | TCTCCTAGTTCTGTGCTGCTTTAACGTGCATAGAAATCAGCTGCGGATTCAGCAGATCAC | 142320 |
| mRNA | ------------------------------------------------------------ | |
| genome | TCCTTTTCTGACAGATGGGCCTGCTTACTCTGATGTTATATCAGAAAGCTCTGAATCTGG | 142380 |
| mRNA | ------------------------------------------------------------ | |
| genome | GAATTGTGTCCCCTGAATTGGAGTAACAGAAATGCTTAGATGATGAGTGTTTAAAAGAAA | 142440 |
| mRNA | ------------------------------------------------------------ | |
| genome | TAAACCAAAGGTAAATTTAGTTTGGAATTCAGCAAGCGTCTTCATTCAGCCCTCTGAGGG | 142500 |
| mRNA | ------------------------------------------------------------ | |
| genome | CAAACTACAGCTTTTTGTAAATGTAGGTAAATTCTGTGACTGTTTCGTGACCCCCTCTGA | 142560 |
| mRNA | ------------------------------------------------------------ | |
| genome | TCCAGTTTTCCTTTATAACCTTCTGTATTGTTCCTTCTATTATCCTGAAATAACATTAAT | 142620 |
| mRNA | ------------------------------------------------------------ | |
| genome | AGATTAGGCTGGGCGTGGTGGCTCATGCCTATAATCCCAGCACCTTGGGAAGCCAAGGCG | 142680 |
| mRNA | ------------------------------------------------------------ | |
| genome | GGCAGATCACCTGAGGCCAGGACTTCGAGACCAGCCTGGCCAACATGATGAAATGCTGTC | 142740 |
| mRNA | ------------------------------------------------------------ | |
| genome | TCTACTGAAAATAACAAAAATTAGCCGAGCATGGTGACAGGTGCCTGTAGTCCCTGCTAC | 142800 |
| mRNA | ------------------------------------------------------------ | |
| genome | TCAGAAGGCTGAGGCGGGAGAATCGCTTGAACCTAGGAGGAAAAGGTTGCAGTGAGCTGA | 142860 |
| mRNA | ------------------------------------------------------------ | |
| genome | GATCGCGCCACTGCACTCTAGCCTGGGTGACAGAGTGAGACTCCATCTCAAAAAAAAAAA | 142920 |
| mRNA | ------------------------------------------------------------ | |
| genome | AAAAAAAAAAAAATTAATGGATCAATGGATTTTTAACCTAATAATTAAATTTCAAAAAAT | 142980 |
| mRNA | ------------------------------------------------------------ | |
| genome | ATCGTTCTTTAATGGTAATGTAAAGGTAAAATTAAGATAATATGTAACAAGCATGTGAGT | 143040 |
| mRNA | ------------------------------------------------------------ | |
| genome | GTCTAAGGTGTCCCCGTGGTGGAAGGAAAAAATAAATCCCCATAAGTGTCCAAGATGCCC | 143100 |
| mRNA | ------------------------------------------------------------ | |
| genome | ATAGAGAGCAGAGCTGTTCTGGTTTAAACCCCTGCTCTTAGCACTGTGTTTTTCCAGCTG | 143160 |
| mRNA | ------------------------------------------------------------ | |
| genome | TGGGTGGTGGGGGATGAGTATCTTTTTATTTCCATGAGATGAGAAAAATGAATTACTAGA | 143220 |
| mRNA | ------------------------------------------------------------ | |
| genome | AGTGTGAAATACAAAACACAGCTGCTCTTTTTTTAGCCATAGACTCAGCAGCCATAAAAT | 143280 |
| mRNA | ------------------------------------------------------------ | |
| genome | TGCTGTATCCAGTTGCAGAAATTCCTGCTGCTTACTCTTGACCCTCTCTCGGTTTGTGTG | 143340 |
| mRNA | ------------------------------------------------------------ | |
| genome | CATCTCCTCTCAGGCTGGCTCCCAGATGGGAGCTGGCTCCAGGCGACACTGGGTGCTCTG | 143400 |
| mRNA | ------------------------------------------------------------ | |
| genome | CTCCAGGAGGTCCTTATGTGGGTCCTGCCCTAGCCTAGCCCCTCTCTTATGGACTCTGTC | 143460 |
| mRNA | ------------------------------------------------------------ | |
| genome | ACTGTGGGTTTATGATTCACTCTCAATCTGTCTTACCTCTTGGTGAACTGTTAGAGTCCT | 143520 |
| mRNA | ------------------------------------------------------------ | |

FIG. 1 KKKKK

| | | |
|---|---|---|
| genome | GCCTATACTTTGGCGCTTGTGGGTGTGTTGTGGTACACATGATGTGTTGGTCACTTCCCA | 143580 |
| mRNA | ------------------------------------------------------------ | |
| genome | GCTCATCTTGTTCTGAGTCACCCTAGATTTGGGACATTCATTCGCCACCAGTACCGGGCG | 143640 |
| mRNA | ------------------------------------------------------------ | |
| genome | GTGTATGGCCTGAGATTTGGGGGGGCTTGTGCTGCTACAAATTGGGGCTGAATTTGAGTT | 143700 |
| mRNA | ------------------------------------------------------------ | |
| genome | GACAGTGGACCTTCTTTATGTCTACTGCTCATATTTGAATTGCAAATACTGCCTCTTCTC | 143760 |
| mRNA | ------------------------------------------------------------ | |
| genome | TTTCAGAGGCTCATTACCCTATAGCTGTATTATTGCAAAGTGCACAATTACAGCTTGAGT | 143820 |
| mRNA | ------------------------------------------------------------ | |
| genome | GTAAGTCACACTGCGCTGGCAGGACGGCCCACTGAGAAAGGGCACGTTTCCTGTTCGTTA | 143880 |
| mRNA | ------------------------------------------------------------ | |
| genome | GTTTTCACATTGACACATAATTTACAATACAGTAAAATGTACTTTTCTATCAACTGTAGT | 143940 |
| mRNA | ------------------------------------------------------------ | |
| genome | CAGTAACAGCCCCCCTCCCCCAACCACATCAAGATATAGAGGAGTGCTGTCACTTCAAAC | 144000 |
| mRNA | ------------------------------------------------------------ | |
| genome | AGTTCCCTCTTCCTCTGCCACATCCTGCCCCTCCCCAGGTCTAACCACCAATCCGTGCTC | 144060 |
| mRNA | ------------------------------------------------------------ | |
| genome | TGTCCCTCTGTTCAGCCCATTGCAGAAGGCCATAGAAATAGAATCTATAGGCTAGGTGTG | 144120 |
| mRNA | ------------------------------------------------------------ | |
| genome | GTGGCTCATGCCTGTAATCCCAGTATTTTGAGAGGCTGAAGTGGGAGGATGACTTGAGGC | 144180 |
| mRNA | ------------------------------------------------------------ | |
| genome | TGGGAGTTCAAGACTAGCCTGGGCTGCCTAGCAAGACCCCATCTCCAGAAAAAAAAAATT | 144240 |
| mRNA | ------------------------------------------------------------ | |
| genome | TAAAAATTACAATCACGTCCCTGTAGTTCAGCTGCTTGGGAGGCTGAGGCAGGAGGATCA | 144300 |
| mRNA | ------------------------------------------------------------ | |
| genome | CTTGAGCTCAGGAGTTAGAGGTTACAGTGAGCTATGATCGTGCCACTGTGCTCCAGCCTA | 144360 |
| mRNA | ------------------------------------------------------------ | |
| genome | GGTGACACAGCAAGACGTTGTCTCTGGGGAAAAAAGAAAGAAACGGAACCACGCGGTGTG | 144420 |
| mRNA | ------------------------------------------------------------ | |
| genome | CAGCCTTCTGAGTCTGGCCCCTTTCGGTGAGCAGTGTCTAAAGTTCTGTCGCGTGTTGCC | 144480 |
| mRNA | ------------------------------------------------------------ | |
| genome | CACGCGTCGGTGGCTCGCTCCTTGCAACTGCTGAGCATTGTATGGCTAGGCTGTAGTTTG | 144540 |
| mRNA | ------------------------------------------------------------ | |
| genome | TTTTCACTTCACCAGTTGGGAAACAGAGAAAAGGCACTTTTTAAAAAGTTTAAATCTGTA | 144600 |
| mRNA | ------------------------------------------------------------ | |
| genome | GAATTTTGGTTTTTACCAGTTCTCTTCTAAATCCTGAGGGATTACAGGAAAAGTTGTTGT | 144660 |
| mRNA | ------------------------------------------------------------ | |
| genome | ATTTCAGAATATTCTTAGCTTGATGTGACCTCTGTCCCCGTTAAGGCCCTTTGCCGCAAT | 144720 |
| mRNA | ------------------------------------------------------------ | |
| genome | GGGAAGGACGTCGCTCGGTCAGACCCTGAAGGTCAGAGGGGCAGTTTGGGAGTGTGTCAA | 144780 |
| mRNA | ------------------------------------------------------------ | |

FIG. 1 LLLLL

```
genome    CATTTTAACTGTATGGACTAGAGCCAAGAGTCTCAAGGTTTATAATTCCCACGTATTCAA  144840
mRNA      ------------------------------------------------------------ genome    AAAGAAAAAAACAATAAAGTGAGAAGTCAGTGTAGAGTGAAATAACCTGTGTTAGTGGGG  144900
mRNA      ------------------------------------------------------------ genome    AAGAAGTGTTTTTAAACAGGATTTCCATAACGTATAACATCAACATGTTTAGAGTGGTGA  144960
mRNA      ------------------------------------------------------------ genome    TGTTTCATTGGGAAACGAACAGTAAAACATGAAAGCAGGGAGGTTTTCATTCTGGCAGTT  145020
mRNA      ------------------------------------------------------------ genome    GGCAACTTTCACGGCAGATGGAGAATTTCAAAAGCAATTGCTCAATTATCAAACATAGCC  145080
mRNA      ------------------------------------------------------------ genome    AGTGTGAGTTCTGAAATAAAGGTGCTGATTGAATGTGCAGCTTTATGGTGGATTTTGCTA  145140
mRNA      ------------------------------------------------------------ genome    TTCAGGCAAGCATTTTAATTTTCTGCCTGTTAAATTCTGTTTTCTTTAGTTTTTCATATG  145200
mRNA      ------------------------------------------------------------ genome    TGGTTTATTGTAGCTTAGGAATAGATAACTGAGAGTATATATTACACATACAACATTCTG  145260
mRNA      ------------------------------------------------------------ genome    ATATGGCAATATTTAAAACAACTTGTCTGTTTTAGAACTAGAATTAAACATAATCATCTT  145320
mRNA      ------------------------------------------------------------ genome    CAGTATTTTGCAAATAAGCTCACTGCCATCCAGAAACATTGTCAATGCATCTGTTGCTCC  145380
mRNA      ------------------------------------------------------------ genome    TTCTAGAAGACACAGTCTGTCCAGCACAAAGTTACTTAGTCCCCAGATGTCTGGAGAAGA  145440
mRNA      ------------------------------------------------------------ genome    GGAGGATTCTGACTTGGCAGCCAAACTTGGAATGTGCAATAGAGAAATAGTACGAAGAGG  145500
mRNA      ------------------------------------------------------------ genome    GGCTCTCATTCTCTTCTGTGATTATGTCGTAAGTTTGAAATGCCTGTAAACGGGGTTGAG  145560
mRNA      ------------------------------------------------------------ genome    GGAGGTGGGGACCAGGAGAACATCCTGTGTAGATGACACTTGCATGGACCCTCTGGAACC  145620
mRNA      ------------------------------------------------------------ genome    CAGACCGCCCGGTGTCCTGCCAAGCTCCATCGAAACTAAATCTAGAATGAATGTTTACTT  145680
mRNA      ------------------------------------------------------------ genome    CTGCTGTGACATATAATTGGAGACCAGGCCTGGCCTTCCAGTCACTGGATTCTAAGTTGG  145740
mRNA      ------------------------------------------------------------ genome    ACTGTGAGAGTTTTTGCAGCTGACTCATTTATCAAATGCCCGGCTATTGGCTCACGCCTA  145800
mRNA      ------------------------------------------------------------ genome    CATGATGCTGGGTATGTTTGTTAATTTGAGGGAAGCAATGGAATAATAATAACTAATGAT  145860
mRNA      ------------------------------------------------------------ genome    TTAAAAAACAAAGTAAGTGCATTGACTGTAGTGGGGTTCTGATTTTAAATTTTTTAAAA  145920
mRNA      ------------------------------------------------------------ genome    ATTAATACCAGGAGCAGTGGCTTATGCCTAAATTCCAGCAACTCGAGAGGCTGAGGTAGG  145980
mRNA      ------------------------------------------------------------ genome    AAGATCACTTGAGCCCAGGAGTTTGAGACAAGCCTGGGCTATGGTGTGAGACACCCATCT  146040
mRNA      ------------------------------------------------------------
```

FIG. 1 MMMMM

| | | |
|---|---|---|
| genome | CTAAAAAAATAAAAAATAAAAAATTATCCAAGTGTGGTGGCTCGTGCCTGTAATCACAGC | 146100 |
| mRNA | ------------------------------------------------------------ | |
| genome | TCTTTGAGAAGCTGAGGGCGGAGGATGGCTTGAGCCTGGGAGTTCGAGACCAGCCTGGCA | 146160 |
| mRNA | ------------------------------------------------------------ | |
| genome | ACACAGAGAAACCCTGCCTCTACCAAAAAAGAAAGAGAGGAAGAAAGAAAAATTAGCCT | 146220 |
| mRNA | ------------------------------------------------------------ | |
| genome | GGCGTGGTGGTGCATGCCTGTGGTCCCAGCCACCTGAGAGACTGAGAAGGGAGGATTGCT | 146280 |
| mRNA | ------------------------------------------------------------ | |
| genome | TGAGCCCAGAAGTTTGAGGCTGCAGTGAGCTGTGACTGTGTCACTGCACTCCGGCCTGGG | 146340 |
| mRNA | ------------------------------------------------------------ | |
| genome | TGACAAGGCGAGACCCCTGCTCTAAAATAATTTTTTTAAGTTAATTTGTAGAAAAGGTGT | 146400 |
| mRNA | ------------------------------------------------------------ | |
| genome | TAGATGTTCTTTGTCACATTTTATGATGGATTCCTGTTTAAATGCCGTTCTCTTTAAAGA | 146460 |
| mRNA | ------------------------------------------------------------ | |
| genome | AAAAAAAATAACTTGTGGGAGTTTTTAACCATAAAACTAGCATCACATATTTACCATGGA | 146520 |
| mRNA | ------------------------------------------------------------ | |
| genome | GAATTTACAAAAAAACAAATAAACGGAGGAAAATAAAACCTCCTGTAATCATACTACTCA | 146580 |
| mRNA | ------------------------------------------------------------ | |
| genome | GAGATAACTTGCTGTTAGATTTTGGTCTAGATTTAATACTTTTTCTATATTTATATTAAA | 146640 |
| mRNA | ------------------------------------------------------------ | |
| genome | AATATTTAAAACATATGCATTTCTTTGTCACAAACATGGTATCTTATAGATACTACTGTC | 146700 |
| mRNA | ------------------------------------------------------------ | |
| genome | ACATAGCAAAACAGTGTTAAATATTCTGAATCAGAAAAGGAAGCCGACTCTCCAACTGAA | 146760 |
| mRNA | ------------------------------------------------------------ | |
| | rs7685686 | |
| genome | AGAGGTGTTATCCTAGAGACTTTTTCTGGTGATGACAATTTATTAATAGTCACTTTTTGC | 146820 |
| mRNA | ------------------------------------------------------------ | |
| genome | TTTACTTTCTCTATTGAAGTAGTTTTTCTATTTTGTTCTACTTTTAAGGATAATATAATT | 146880 |
| mRNA | ------------------------------------------------------------ | |
| genome | TATAATGCTGTTTTTCACAGAAATATAAGAAAAAAGATACTAATTTTATAAGTTAATAAA | 146940 |
| mRNA | ------------------------------------------------------------ | |
| genome | GTTTGATCATCCCAAATCCAAAAATCTGAAATCCAAAATGCTCCAAATTCTGAAGCTTTT | 147000 |
| mRNA | ------------------------------------------------------------ | |
| genome | TGAGTGCTGACATTATGTTCAAAGGAAATGTTCATTGGAAGGTTTCAGATTTTCGGATTT | 147060 |
| mRNA | ------------------------------------------------------------ | |
| genome | AGGGAGCTCAACAAATAAGTATAATGCACATATTTCAAAACCTGAAAAAAATCCTAAATT | 147120 |
| mRNA | ------------------------------------------------------------ | |
| genome | CAGAATACTTCTGATCCCAAACATTTCAGATAAGGGTTATTCAACCTGTACTGTCAGATG | 147180 |
| mRNA | ------------------------------------------------------------ | |
| genome | ATCCCAAATGAAAAATATTAATCGTTAACCAAATATCAAGGAATTGATCACATTTTACAG | 147240 |
| mRNA | ------------------------------------------------------------ | |
| genome | TTTCTGCCTAGGATTATGAATCAAGATGAAAAGGCTCTGCATGTTTAAAAATATATATTT | 147300 |
| mRNA | ------------------------------------------------------------ | |

FIG. 1 NNNNN

```
genome      TTATTTTCTTATAAATCTTAAATATCTACACTTAAGATTTATTTGATATGTGGGATCCAT 147360
mRNA        ------------------------------------------------------------ genome      TCATATTTTGGATTCAACAGTTCTGTCAAAACTGTGGCAGTGATAGGGGATTCTTTTTTT 147420
mRNA        ------------------------------------------------------------ genome      CCCACTGAACTATCACAAAATTGGAAAAAGAGTAATTGGAGAACCCCACTGGCTTAGCCG 147480
mRNA        ------------------------------------------------------------ genome      GCCCGAAGCCCGGGAGAGGGCAGGCAGTGCTGTGGATGGGGTCATCCCAGCGCAACGCTG 147540
mRNA        ------------------------------------------------------------ genome      CCCCTGCTACCTGCGGATCTCGCTGAGGCCTGCCTTTGTCCTTTGACCCTTGGCCATTTG 147600
mRNA        ------------------------------------------------------------ genome      TTAGTGTCTCTGAGAGCTGGACTGCTGTACCCTACTTCCCCAGGGGGCCTAACTTCACAC 147660
mRNA        ------------------------------------------------------------ genome      AGCCTCTGCCGCAGTGCGTGGTTGGAGGTGACGGCCTTGGTAAATCGAGTTTCCTACCTC 147720
mRNA        ------------------------------------------------------------ genome      CTCAATTATTTGTGCTCATACACTGTATATTTTTAGTGAGGTTTATATTTGGGATGTGTT 147780
mRNA        ------------------------------------------------------------ genome      TTCTCCTTCTTACCCTTTCTGGCCTTTCTATGGCATTAATACCTGGTCTCTTCTTGTGTA 147840
mRNA        ------------------------------------------------------------ genome      CTTGAAAATGAATCTCTCATCATATTTTTCCTTAGTGTCAGAACCTCCATGACTCCGAGC 147900
mRNA        ------------------------------------------------------------ genome      ACTTAACGTGGCTCATTGTAAATCACATTCAAGATCTGATCAGCCTTTCCCACGAGCCTC 147960
mRNA        ------------------------------------------------------------ genome      CAGTACAGGACTTCATCAGTGCCGTTCATCGGAACTCTGCTGCCAGCGGCCTGTTCATCC 148020
mRNA        ------------------------------------------------------------ genome      AGGCAATTCAGTCTCGTTGTGAAAACCTTTCAACTGTACGTCTTCATCCTGCCGACTATT 148080
mRNA        ------------------------------------------------------------ genome      GCCAGTTGCAGTTTTCCCTGCCTTAAAAATGGAGTATTGAAATTTTTAACTTTAATTTCT 148140
mRNA        ------------------------------------------------------------ genome      GATTTGCAAAATAGTCATCTTTTGTTCTTTTCCTTCTTGCTGTTAGCCAACCATGCTGAA 148200
mRNA        ------------------------------------------------------------ genome      GAAAACTCTTCAGTGCTTGGAGGGGATCCATCTCAGCCAGTCGGGAGCTGTGCTCACGCT 148260
mRNA        ------------------------------------------------------------ genome      GTATGTGGACAGGCTTCTGTGCACCCCTTTCCGTGTGCTGGCTCGCATGGTCGACATCCT 148320
mRNA        ------------------------------------------------------------ genome      TGCTTGTCGCCGGGTAGAAATGCTTCTGGCTGCAAATTTACAGGTATTGGGAAGAGAAAC 148380
mRNA        ------------------------------------------------------------ genome      CCTGATATTGATTTATATTGAAAATTTAGCAGGCCAAGCAAAACAGGTGGCTGGCTTTTT 148440
mRNA        ------------------------------------------------------------ genome      CCTCCGTAAGTATGGTCTTGACATGGTCACCGATAGAAACATGGAAACATCTGCAAACTT 148500
mRNA        ------------------------------------------------------------ genome      GCCGTTACTCGTGTGTCCGATCTGACTGTTTCTTGTATTTTTTCTAGTCTGCCCTTACT 148560
mRNA        ------------------------------------------------------------
```

FIG. 1 OOOOO

```
genome      AGGATGAACTGTACACATCAGTTCATCCTTTTTAAATGAGCATGAGGTTATTTTGGGTTG  148620
mRNA        ------------------------------------------------------------ genome      TTAGGTGTTACAAACACACTAATGTGTTTTTGTCTATTAGAGCAGCATGGCCCAGTTGCC  148680
mRNA        ------------------------------------------------------------ genome      AATGGAAGAACTCAACAGAATCCAGGAATACCTTCAGAGCAGCGGGCTCGCTCAGAGGTA  148740
mRNA        ------------------------------------------------------------ genome      ATGCTGGAAACACAGGTCGTCCTTGTGTTAGGACAACCCAGGATATAAAGGATATAGATT  148800
mRNA        ------------------------------------------------------------ genome      TGTACGGGAATAAATTCACAGGACAAGAAATCGATGTGCCTTATAGGTGGGTTTACTGCA  148860
mRNA        ------------------------------------------------------------ genome      GAAGTGCCATAATAGAACCTTCCTACTTTTAAAACAACCAGATCTCACTTTCTAAAGAGT  148920
mRNA        ------------------------------------------------------------ genome      AAAGGATGACCGGCAGGATCACGTCTGTGACGTGAGTGGAGGCAGTTTGCACTCCTGGTG  148980
mRNA        ------------------------------------------------------------ genome      GCTGTTTGAGAGGTAGCATTTAGAATGCCTGTATTCACTGTCCTGTGATGAGTGGGAAAA  149040
mRNA        ------------------------------------------------------------ genome      TAGGTTATCAGGTTTATCTTAGCAAAATCAAAGCATGTCATCTAATTGCTAAACAAGAGT  149100
mRNA        ------------------------------------------------------------ genome      TGGCAAATCTGAGAGACATTACTCAATCCTTGGCATGCAGGACTTACATCTGCATCCTGT  149160
mRNA        ------------------------------------------------------------ genome      TGCCATTTTATGTCTTCAAAGCATTTAATCATTTAGTTGTGTTTGCAAAGTCTTTGAGAA  149220
mRNA        ------------------------------------------------------------ genome      GCCTTTGTCAGAAATCCCTACATCTCCTATGTGAGTGTATTTCCATGACTGCAGAATAAG  149280
mRNA        ------------------------------------------------------------ genome      TTAAACTTTTACCTTTTTCCTTCCCTTGCGGGGCGGGTGGGGGCAGGGATTGTGTGTG    149340
mRNA        ------------------------------------------------------------ genome      TGAGAGGGAGAGAGAGACAGCAGAGAAGGAGAATATAATTATCATGCTGTGTACTTTGAG  149400
mRNA        ------------------------------------------------------------ genome      CTGAAACTGCAAAAAAGGAAAAACACACAAAAATTATTATGCTTTTCAGTCTTTAGAGTA  149460
mRNA        ------------------------------------------------------------ genome      CCTTGTCTATTATGCTTTTCAGTCTTTAGAGTACCTTGTTGATGGTGTTTTTAAATGGGA  149520
mRNA        ------------------------------------------------------------ genome      TTGGGCACAATTAGGTGGACAGTTTGGGATGATTTTTCAGTCTGTAGGGCCAAGCTCTTT  149580
mRNA        ------------------------------------------------------------ genome      TGTAATTTGCATTATGAAGTTGTCACTCTCATAGCAGATGGCGGGAGATAAACTATTATT  149640
mRNA        ------------------------------------------------------------ genome      ACTTTTTGACCCTAGACTTAGTCTTCAGTCCAGATGAGGGAGATTAAAAGATTATAAATA  149700
mRNA        ------------------------------------------------------------ genome      TCTTGTGCCAGATGAGGTGATTTTATTTTGAAATGACCATGAATTCCTATCAGTTGTCTT  149760
mRNA        ------------------------------------------------------------ genome      ACTGGGATATTTGATAGTGGAATTTGTGCATTTGAGTCTTAGATGATCTGTTTTACATTT  149820
mRNA        ------------------------------------------------------------
```

FIG. 1 PPPPP

```
genome    ATTAAGAAAGCCTTTATTAGCTTTTATACTGTGTATTGCCTGTTGCAGTGTTTGAGTATA  149880
mRNA      ------------------------------------------------------------ genome    AATGAAATTTCTGGAAAATATTAATGGAGTACAAACTGTGATACTTAAAAGTAAACTAGG  149940
mRNA      ------------------------------------------------------------
                                                       rs363088
genome    GCCTGCATTTGTATCATGACCTGTTTGAGTATTGATGAGAAGATAGCTGTGAAGAAAAAG  150000
mRNA      ------------------------------------------------------------ genome    GTTTAAACAAGTGTATTTTCCTTTAAGAAGCCACTAATAGTGCATCTCCTTAGAGTGTAT  150060
mRNA      ------------------------------------------------------------ genome    ATTTCTAGAATCCTAGTGTGCAGAGTTTAGACTAAGACTAAAAAAAAAAAAAAACAAATT  150120
mRNA      ------------------------------------------------------------ genome    ATACTGTAATTTCATTTTTATTTGTATTTTAGACACCAAAGGCTCTATTCCCTGCTGGAC  150180
mRNA      ------------------------------------------------------------ genome    AGGTTTCGTCTCTCCACCATGCAAGACTCACTTAGTCCCTCTCCTCCAGTCTCTTCCCAC  150240
mRNA      ------------------------------------------------------------ genome    CCGCTGGACGGGGATGGGCACGTGTCACTGGAAACAGTGAGTCCGGACAAAGTAAGTGTC  150300
mRNA      ------------------------------------------------------------ genome    CAGCGTGTCTGCATGGGAGGCACAGGGCGCTGAGTGCCTCTGTCACCTGTGGCAGATACA  150360
mRNA      ------------------------------------------------------------ genome    GAGAGTGCAGAGGAGGTGCCGTGGACCCAAGGAGTTCTGGCGCTCGGCTCGGCTCAGTGA  150420
mRNA      ------------------------------------------------------------ genome    AGCTGTGGTTAGAGACGTGGGGGGCCATCAAGGTCTGAGGGAGCCAAGCAGTGCTGATGT  150480
mRNA      ------------------------------------------------------------ genome    GGGACCCTTTTGGTAGGAGTGTGGGGTGAGTAGTTAGTGGGTGAATCAAGGAATAGTCGG  150540
mRNA      ------------------------------------------------------------ genome    CCGTGGCCTGCAGGCCCCTGACTGCACAGGCCTTCAAGCACATGTCAATGCCGTTAGCCT  150600
mRNA      ------------------------------------------------------------ genome    CCCTCCATCTCCTCATACCTTCTGGCCACCTGTGAGTTGCACTGCCACTGCCAGCCATTC  150660
mRNA      ------------------------------------------------------------ genome    TGGTATGTTGTCAGCACCTCCACTGCTCATACCTCATGGTTAGGGACCACCTGGAGCCTT  150720
mRNA      ------------------------------------------------------------ genome    GGTAGAGCCTTGGTAGAGCCTTGGTACTCTACTTTCCTGGACAAAGTTCAGCTTATGAAT  150780
mRNA      ------------------------------------------------------------ genome    ATGAATTTAGATTTCAAAAACCAGCAGCCCAAGTATAAGAAAGCGAAGGTTCAGTCCTGC  150840
mRNA      ------------------------------------------------------------ genome    CTTCTTAGGCTCTATTCGCTAAGCACCTGCCCTGCCCTGGTTGCTGGGGAGAGATGAGTA  150900
mRNA      ------------------------------------------------------------ genome    AAGCAGACAACCCAGGAGAGGATGGCAAAGGGGCCGCTAACCCTTAGTGGTTTAGCTATA  150960
mRNA      ------------------------------------------------------------ genome    TTTGGAAGGCCTATTGGAAGTTCACCAGGTGAAGGGGGAGGCTGTGAGGGTGCCCAGGCA  151020
mRNA      ------------------------------------------------------------ genome    GGTAACAGAAGTCCAAAGGGGAAAACCTGTGGTGTGGTGAGCCGTATAGCCACAGCCTGC  151080
mRNA      ------------------------------------------------------------
```

FIG. 1 QQQQQ

| | | |
|---|---|---|
| genome | CGGCCGGCAGCCCTCTCAGCCTAGTGCGGTGTTCCCAAGCACTGGCCTAGGCCTGTAGCT | 151140 |
| mRNA | ------------------------------------------------------------ | |
| genome | CCAGGGATGTGAAGTCCCCTTGAACGCCGCCCATCATGTTCCCCTTATCCATTTTTTTCT | 151200 |
| mRNA | ------------------------------------------------------------ | |
| genome | TCCCAGGACTGGTACGTTCATCTTGTCAAATCCCAGTGTTGGACCAGGTCAGATTCTGCA | 151260 |
| mRNA | ------------------------------------------------------------ | |
| genome | CTGCTGGAAGGTGCAGAGCTGGTGAATCGGATTCCTGCTGAAGATATGAATGCCTTCATG | 151320 |
| mRNA | ------------------------------------------------------------ | |
| genome | ATGAACTCGGTACGGGGGGAGCAGTGGAGGCAAGGAATCCTCAGCTTTTCTTGTGACTTC | 151380 |
| mRNA | ------------------------------------------------------------ | |
| genome | CAAGTGGGATTTGTCTCATCATCATGTGACCCACTTGTTGACAACACATGTTGGGGACTC | 151440 |
| mRNA | ------------------------------------------------------------ | |
| genome | CAGTCTGGGCAGGGACGGGATGTCGGAGAGACTCCACTCTGAATGGGGCCGGGAAGTGGG | 151500 |
| mRNA | ------------------------------------------------------------ | |
| genome | GAGGACTCCATTTCAGATGGGGTCGGGACATGGGGGTTATGCTGATCGAGACAGAAAAGC | 151560 |
| mRNA | ------------------------------------------------------------ | |
| genome | ACATTGTTTCAGCCACATTAGAATCCACGGAGGTGTTGTTTTGAAATCCAGCTGGCCCCA | 151620 |
| mRNA | ------------------------------------------------------------ | |
| genome | AGGCTGGGTGTATGGTTTGGGATGAGAACTATCTGGCCTCCACTGGAGGAACAAACACAG | 151680 |
| mRNA | ------------------------------------------------------------ | |
| genome | GATGTTATCATCTAAGCTCCATGGCCAAGACAGAATGGAAGTCAAGGTTGCGTATTTGCC | 151740 |
| mRNA | ------------------------------------------------------------ | |
| genome | GTAGACTTCAACACAGTGTCGTAATGCGTGACGTCAATAACTTGTTTCTAGTGTCTTGGA | 151800 |
| mRNA | ------------------------------------------------------------ | |
| genome | AGTTGATCTTTAGTCGTAAAAGAGACCCTTGGATGCAGCGAGATTTCCTCTACTCACACC | 151860 |
| mRNA | ------------------------------------------------------------ | |
| genome | TCTGTTAGATGTAGTGAGGTTCTTCACCCCCCAACCCCAGATGTCAGAGGGCACCCTGCG | 151920 |
| mRNA | ------------------------------------------------------------ | |
| genome | CAGAGCTAGGAGGCCATGCAAAGCCTTGGTGTCCCTGTCCCTCACCCGTGGGCAGGTCCT | 151980 |
| mRNA | ------------------------------------------------------------ | |
| genome | GTGAGCAGTGGGGGGCCACCTCTTGGGTATGGTGCAGCCATGGCCCAAGCAGGGCTTCT | 152040 |
| mRNA | ------------------------------------------------------------ | |
| genome | TCTCAGACCTACTAGGACGGGAGAAACCTCCTGGTGCTTTAGCCCTGCGTTGATATGCAG | 152100 |
| mRNA | ------------------------------------------------------------ | |
| genome | CAAATGGGAGGGAAGTGGGCACCTGGGAGGACAAATGCCTGTAGAGGCCGGGAGTGACGG | 152160 |
| mRNA | ------------------------------------------------------------ | |
| genome | CAGGTGTTCATGAAAAGAGACCTTGTGGGGAGGGCAACACAACAGTGTGTTCTGATGTAC | 152220 |
| mRNA | ------------------------------------------------------------ | |
| genome | TGAAGAGCTCAACTGAAAACAACAGGAGAATTAGCCCAAAATCCATTTACTAAAATTGTT | 152280 |
| mRNA | ------------------------------------------------------------ | |
| genome | TATCTTTTTTTTTTTTTTGAGACAAAGTCTCGCTGTTGTCCCCAGGCTGGAGTGCAAT | 152340 |
| mRNA | ------------------------------------------------------------ | |

FIG. 1 RRRRR

| | | |
|---|---|---|
| genome | GGCGCTATCTTGGCTCACTGCAACCTCCGCCTCCTGGGTTCATACGATTCTCCTGCCTCA | 152400 |
| mRNA | ------------------------------------------------------------ | |
| genome | GCCTCCCAAATAGCTGGTATTAACAGGCATGCACCACCACGCCCGGCTAATTTTTGTATT | 152460 |
| mRNA | ------------------------------------------------------------ | |
| genome | TTTAGTAGAGACGGGATTTCACCATGTTGGCCAGGCTGGTCTCAAACTCCTGACCTCAGG | 152520 |
| mRNA | ------------------------------------------------------------ | |
| genome | TGATCCGCCCACCTCGGCCTCCCAAAGTGCTGGGATTATAGGCCTGAGCCACCACGCCCG | 152580 |
| mRNA | ------------------------------------------------------------ | |
| genome | GCCTAAAATTGTTTATCTTAAGATTCATGCAGTGAAAGCTAACTTACTGAGTGATAAATT | 152640 |
| mRNA | ------------------------------------------------------------ | |
| genome | TGCTTAGTGATCTGTTTATTAGGTTTTCCAAATTTGCTAATTGGGCTTTGAACAGCTGTA | 152700 |
| mRNA | ------------------------------------------------------------ | |
| genome | AAAGTTCTGACTGTAAAAGAAAGCTTCAACTTTTGGCATTCATGATGCTTTTCTGAGTAT | 152760 |
| mRNA | ------------------------------------------------------------ | |
| genome | TAAACTAAGATAGATGTTTTACCTGAAGGATCGGCCACCAATCTTTAAATGGCTAAACAA | 152820 |
| mRNA | ------------------------------------------------------------ | |
| genome | AAGGGTTGCTAAAACATAATCCAAATTGACATAAGAAATACCATTTTTCCAACCAAAATT | 152880 |
| mRNA | ------------------------------------------------------------ | |
| genome | TTGGCATTCATATGGCTACTTTTACGTATTTCAGCTGCATTTGAACATCTTTTTCAAACT | 152940 |
| mRNA | ------------------------------------------------------------ | |
| genome | TTAGGGTGGTTGGTGTATCACTGAGGTCTTGGATGACACTTTAGCTTTGATTTTGTTTTT | 153000 |
| mRNA | ------------------------------------------------------------ | |
| genome | ATGAATTAAAATTGTCATACCAAAATTTTTATTTCAAGCAAATCCAAGAGCATAAAAAAT | 153060 |
| mRNA | ------------------------------------------------------------ | |
| genome | TAAAATATTACTTAAAATACTAAGAGAGAACAGATATATATTTTACTAAGCATATGTTGA | 153120 |
| mRNA | ------------------------------------------------------------ | |
| genome | ATGAAATTGTTCAAATATTTATAACAGGCATAGAGTAGAATTTTCTTAAAAATATTTTTG | 153180 |
| mRNA | ------------------------------------------------------------ | |
| genome | ATGGTATACCAATTTGTATTTTCTCAGAAACATTTGCCTTATTCTTTTTTCTGTTGTGTT | 153240 |
| mRNA | ------------------------------------------------------------ | |
| genome | TTTCTTACCTGATTGAAAGCTCATAATCTGTTGTTATTGTTTGTTAACCTTTAATGCTCT | 153300 |
| mRNA | ------------------------------------------------------------ | |
| genome | GATTTCAGGAGTTCAACCTAAGCCTGCTAGCTCCATGCTTAAGCCTAGGGATGAGTGAAA | 153360 |
| mRNA | ------------------------------------------------------------ | |
| genome | TTTCTGGTGGCCAGAAGAGTGCCCTTTTTGAAGCAGCCCGTGAGGTGACTCTGGCCCGTG | 153420 |
| mRNA | ------------------------------------------------------------ | |
| genome | TGAGCGGCACCGTGCAGCAGCTCCCTGCTGTCCATCATGTCTTCCAGCCCGAGCTGCCTG | 153480 |
| mRNA | ------------------------------------------------------------ | |
| genome | CAGAGCCGGCGGCCTACTGGAGCAAGTTGAATGATCTGTTTGGTAATTAAAATTAAAATT | 153540 |
| mRNA | ------------------------------------------------------------ | |
| genome | TATCTTATTTTTAAAAAGCATTCCAGGGCCAGTATAGTACTTTGCACCAAGTAAATGTAC | 153600 |
| mRNA | ------------------------------------------------------------ | |

FIG. 1 SSSSS

| | | |
|---|---|---|
| genome | AATAAAGGCAGTGGATCTAATACATTGAAAGCGTTTACAGAGGTAGCTAAAGAGCAGCAC | 153660 |
| mRNA | ------------------------------------------------------------ | |
| genome | GGGTGTCCTCGGCTCAGAATTTCTTCCTGTGTGTTTGCCACTTTGCCATTCATTGACATG | 153720 |
| mRNA | ------------------------------------------------------------ | |
| genome | GTCATGGACATAGGGCTCTAAGCCCTTGAGGAAGGCTGGGCCAGACCTCAGGGGAGATGC | 153780 |
| mRNA | ------------------------------------------------------------ | |
| genome | AGCCCCAAACCACGTGCAGTCCTGTGGACGGATGTGTAGATGTGCCACTGAGGAACAATG | 153840 |
| mRNA | ------------------------------------------------------------ | |
| genome | TCTTGAGCTTTCATCAGATTCTCAGAGAATTGCTTGACTGCCTTTCGAAGTTGATGCATC | 153900 |
| mRNA | ------------------------------------------------------------ | |
| genome | TGTGCTCACGTTTGCACCCACCCACGAGGTCCTTCTGTTTCAGGGGATGCTGCACTGTAT | 153960 |
| mRNA | ------------------------------------------------------------ | |
| genome | CAGTCCCTGCCCACTCTGGCCCGGGCCCTGGCACAGTACCTGGTGGTGGTCTCCAAACTG | 154020 |
| mRNA | ------------------------------------------------------------ | |
| genome | CCCAGTCATTTGCACCTTCCTCCTGAGAAAGAGAAGGACATTGTGAAATTCGTGGTGGCA | 154080 |
| mRNA | ------------------------------------------------------------ | |
| genome | ACCCTTGAGGTAAGAGGCAGCTCGGGAGCTCAGTGTTGCTGTGGGGAGGGGCATGGGGC | 154140 |
| mRNA | ------------------------------------------------------------ | |
| genome | TGACACTGAAGAGGGTAAAGCAGTTTTATTTGAAAAGCAAGATCTCTGACCAGTCCAGTC | 154200 |
| mRNA | ------------------------------------------------------------ | |
| genome | ACTTTTCCATCTCAGCCTGGCAGTAAGTCTTGTCACCGTCAAGTTATTGTAGCCATCCTT | 154260 |
| mRNA | ------------------------------------------------------------ | |
| genome | CACCCTCACCTCGCCACTCCTCATGGTGGCCTGTGAGGTCAGCCAGGTCCCCTTCTCATC | 154320 |
| mRNA | ------------------------------------------------------------ | |
| genome | TGCACCTACCATGTTAGGTGGATCCTAATTTTAGAGACATGAAAAATAATCATCTGGAAG | 154380 |
| mRNA | ------------------------------------------------------------ | |
| genome | TACTTTATGTCTTAAGTTGGCCTGGACATGTCAGCCAAGGAATACTTACTTGGTTTGTGT | 154440 |
| mRNA | ------------------------------------------------------------ | |
| genome | TAGTGCTTGTAATTCGCCCCCAGAATGTGTACACGTTCTGGATGCATTAAAGTCTGGCCT | 154500 |
| mRNA | ------------------------------------------------------------ | |
| genome | GTATCCTTAAAGGGCCATCGCTGTGCTGCCTGCCCTCAGCAAGGACACACTTTGCAGACC | 154560 |
| mRNA | ------------------------------------------------------------ | |
| genome | CACAGAGGCTCCGCCTCCACCTCACACCAAAGAAAGGGAGGAGTCCAAAGGGCATCAGTG | 154620 |
| mRNA | ------------------------------------------------------------ | |
| genome | CCATTACTCACAAAATGATAAATACACCCTTATTCTGAACCACGTGGAGTCATATGGTTT | 154680 |
| mRNA | ------------------------------------------------------------ | |
| genome | GTGATCCCTGTCCTTCAGGTTTCAGCTTAGTGGGGAAGTGGGAAAGTCAGCGTGTGATCA | 154740 |
| mRNA | ------------------------------------------------------------ | |
| genome | CAGCACAGGGTGATTGCTGCTGATTATATTATGTGCCTGCTGTATGCAGGATGAAATACT | 154800 |
| mRNA | ------------------------------------------------------------ | |
| genome | TTATATGCGTCATCTTATTTGACTCTCACAACCCCCTGTGAGATAGGCTCTGTTACTCCC | 154860 |
| mRNA | ------------------------------------------------------------ | |

FIG. 1 TTTTT

```
genome      ATTTGACAGGTGAGGAAAGCAAGGCTTAGAGAATTTCAGTGACTTGCCCAGGTCCTCTGA  154920
mRNA        ------------------------------------------------------------ genome      GCTAGGAAGTAGCCATTCTGGCATTTGAACCCAAGGCCTGCTATCCCTAGAACCCACGCT  154980
mRNA        ------------------------------------------------------------ genome      CTCAAATTCAACCTATGACAGAGGCAAGCCCTGGTGCTGTGGGAGCCCCAAGGAAGAGCC  155040
mRNA        ------------------------------------------------------------ genome      TCTGGCCTGGTGGCCACGTAGCCCAGGAGAGATTTCTACAGGAGCCCACAGCGCTGAAGG  155100
mRNA        ------------------------------------------------------------ genome      AGAGAGAGGCAGCAGAGTAAGGGGGCTTTGTGGCAGAGAGGGGACTGGCACTTTGGGGAA  155160
mRNA        ------------------------------------------------------------ genome      TAGGTGGGTCAGGACTGAATGTAATGGAGCCATGTCAGAGCTGTCCTTCTGGAAGGGCAA  155220
mRNA        ------------------------------------------------------------ genome      GGGCACCTGGACGCGCTGCCCCTCAGTGCTTTGGACGGTTCCACAACTGTGATTCACACG  155280
mRNA        ------------------------------------------------------------ genome      GCTTCCCCAAACGAAGGTACACGAGTGGGCATTCTGTGACTCGGTACTTCCCTTTAGGCC  155340
mRNA        ------------------------------------------------------------ genome      CTGTCCTGGCATTTGATCCATGAGCAGATCCCGCTGAGTCTGGATCTCCAGGCAGGGCTG  155400
mRNA        ------------------------------------------------------------ genome      GACTGCTGCTGCCTGGCCCTGCAGCTGCCTGGCCTCTGGAGCGTGGTCTCCTCCACAGAG  155460
mRNA        ------------------------------------------------------------
                                                rs362331
genome      TTTGTGACCCACGCCTGCTCCCTCATCTACTGTGTGCACTTCATCCTGGAGGCCGGTGAG  155520
mRNA        ------------------------------------------------------------ genome      TCCCCGTCCATGAACGGTGGGTTCCTATCATAGTTCCTGTCTGCTTCACCATGTTTTTAT  155580
mRNA        ------------------------------------------------------------ genome      TTTGTGCTGCCTGTTTGCCAGGTACTAAGCTAGGAATTGGGGATGGAGAGGTAGATAAAA  155640
mRNA        ------------------------------------------------------------ genome      TATGCATCAGGAAGGGCTGGGCCCCATCTCTTACTCTCCAATATATTGGAGTCTACACTG  155700
mRNA        ------------------------------------------------------------ genome      GAATTTAACTGGAATTTGCTTTTTTAGTCATTTTATTTAGATTTTGAAGTTTCAGCTTTC  155760
mRNA        ------------------------------------------------------------ genome      ATCAAAAATACCTCTAAACTTTATGTCTCTGTGATCTTTGGTCTTAGCTGTTTTATGTAT  155820
mRNA        ------------------------------------------------------------ genome      TTAGTCTTATATGATCATAAGATTAATAACATTACATTCAGAAGATTATTTGTTTTCTGT  155880
mRNA        ------------------------------------------------------------ genome      CAGAGTTAAAATGTTTGTTTTTATACTGCATTGTAATATTAACGTACTGTAAAATAAAAG  155940
mRNA        ------------------------------------------------------------ genome      TGGCTTGTTCTTTTCAAGGAACAGTATCCTCAACAAGGGTCATTAGCCACAATTTTTAAA  156000
mRNA        ------------------------------------------------------------ genome      AAATTGGACGTCATAGTTTACATGTTAGAGGGCGTTTTGAAGCTTTGTATTTTTAAATTA  156060
mRNA        ------------------------------------------------------------ genome      AATGTTATAGAGTGATGTTTTCATGTTTCATAATTGTTTTCATCTGTGCATTTGTAGCCA  156120
mRNA        ------------------------------------------------------------
```

FIG. 1 UUUUU

```
genome      ACTTGAAAACAAAGATCCAGGGATTACTACTTAAAAGCCAGACTTCTTGGAGGTTATAGT 156180
mRNA        ------------------------------------------------------------ genome      GATGATTTTGATAGTATCTTGAGCCGTCTCATAATAACCTCAGGGTGAGAGATGGCCAAC 156240
mRNA        ------------------------------------------------------------ genome      AGGAGACAGTCGAGGGACTTAGAAATCTGAATGAAATCTGAAGTTCAAATCTTCAGACAT 156300
mRNA        ------------------------------------------------------------ genome      ATACCACTAACCAAGAGATTGGTACCTCAGTCTAGTATTGTCTGTTTGTCTAAAATTGGT 156360
mRNA        ------------------------------------------------------------ genome      TCTAAGGAATCTAGGCTAGTCTGTCTATCCCTTTCAACTTTTGTGAGGCTGCACAAATGT 156420
mRNA        ------------------------------------------------------------
                                                          rs916171
genome      AAAATGTTGAATAAAAAGCACTGATGGAAGTGTGTAGAAATTCTTCTCTTTGTTCTGTTG 156480
mRNA        ------------------------------------------------------------ genome      TAATTTTAGTTGCAGTGCAGCCTGGAGAGCAGCTTCTTAGTCCAGAAAGAAGGACAAATA 156540
mRNA        ------------------------------------------------------------ genome      CCCCAAAAGCCATCAGCGAGGAGGAGGAGGAAGTAGATCCAAACACACAGAGTAAGTCTC 156600
mRNA        ------------------------------------------------------------ genome      AGGACCCATTTTTTCTTACATGTTGTTCCTCCAGGACTTAAAAATCATTCACAGAGACG 156660
mRNA        ------------------------------------------------------------ genome      TGCACCGCGGTGAGTGTGGACTCCTGGAAGCGCACCGTAGCTCCGCTGTGTCCTGCTGCT 156720
mRNA        ------------------------------------------------------------ genome      CCTCCCTAGCTGTCAGGGAGGCTGTAGTCCATTGCTTTGCCAGCTCTTTTGTTTCCGAGT 156780
mRNA        ------------------------------------------------------------ genome      GAACACCTTATCCGTACACATGCGGCTGTCTCTGACCCTACAGACCAGCTGGGATGCCAC 156840
mRNA        ------------------------------------------------------------ genome      TGGGGGAGCGCTCCCTTCCCCCCGCACTTCCCACACTCTGCAGTTATTCTGAGATCCTTG 156900
mRNA        ------------------------------------------------------------ genome      AGGGCAGGGAACAGGTTTGTCTTCTTTGTGTTCTCAGAAATTAATGCTCGGCCTCTGGTC 156960
mRNA        ------------------------------------------------------------ genome      AGCAAGCAACAACCTTTTGTTGAGTGATAATGAATAAATAAATGTTTCCCACATGAGTAT 157020
mRNA        ------------------------------------------------------------ genome      TCAGTAACCTCAGTGTCAGGTTCAGCCATCTGTTTTGGTGGATATTTAAAAGAAAATTCC 157080
mRNA        ------------------------------------------------------------ genome      GCTTTTCCTACAGAAAAAAAAAAAAATCCAAATCCCAGTGATTTAAGCCAGTTATAGACT 157140
mRNA        ------------------------------------------------------------ genome      TAGACATATACTACGGCTTTTCATGCACTTTCCTCCCAATTCTAGAGTAGGTATTTTACT 157200
mRNA        ------------------------------------------------------------ genome      AGGAAAATGGTGGCAGTGCCTGTTGGGAGGAAGATTCTTTGGCCAAGTGTCTTTTGTTCT 157260
mRNA        ------------------------------------------------------------ genome      TGCCAGGGCCCCTAGGCTGCTGGGGTGCTTCAGCTTCTTTAGCCCAGTGTCTGGTGGGGA 157320
mRNA        ------------------------------------------------------------ genome      ATGGCCCCTGTTGCCTGTCCCACAGAGGTGGGGGTGCCTCACCTGGAGCCTGTCCACACA 157380
mRNA        ------------------------------------------------------------
```

FIG. 1 VVVVV

```
genome    TTTTACACAGCACGCTTACCTGGAGCATCAGGCATCTTTTCCATGCTCTGTGGCTCAGGA  157440
mRNA      ------------------------------------------------------------ genome    AACACGCCTTTTCAATCATGAGTGCACCAGTGCTTTTGGGCTTTTTCTCCCCGCTTTTGT  157500
mRNA      ------------------------------------------------------------ genome    GCAATCCTGGTTGTGGATGGAGTTTTCCTGTCTTTAGTCTTCTGCATAGTACTTTTCTCT  157560
mRNA      ------------------------------------------------------------ genome    TCTGGTTCCCGGTTCAAGGTTTTGTAATTAGAGAATGACCCAGAAGCAATGGCATTTTAA  157620
mRNA      ------------------------------------------------------------ genome    TGCACAGCCAAGGACTTCTCTGAATTTGTATCTCAAACCTCTGTGGGTCCTTCAGGCTTC  157680
mRNA      ------------------------------------------------------------ genome    AGTTTGTGATTTCATGATTTCTTGTTGCTACCTAAGGAATATGAAAACACCCACCTCCCT  157740
mRNA      ------------------------------------------------------------ genome    ACTCTGCATCTTCCAGCCGAGTGGCACCTCAGGCTGTGGATCCTGTGCTTCTGTGGTGAG  157800
mRNA      ------------------------------------------------------------ genome    GATAAGAATAGTGCCAACCGTGTGGATTGAAATCAATCAGTTAATCCCTCCATGTAAAGC  157860
mRNA      ------------------------------------------------------------ genome    ACCTGGAACGGATGACAGTCTTGTTATGAATACTCAACAAATGCTATCATGATTTTAGT  157920
mRNA      ------------------------------------------------------------ genome    TAGATTTCCATTGCTTTAAAACAGTTGAGACATCTTGGCGGTTTGAGTTAGAGCAACGGG  157980
mRNA      ------------------------------------------------------------ genome    CCCTGAAGTGGGTTCTGTTTGGGTGAAGATGATTATGCTTATTCCCCATGGCCCTCTTTA  158040
mRNA      ------------------------------------------------------------ genome    GGCAAGAGTGGGAAGCTTTCTTTGTTTTTTTAATCACCTCGATAGGACGTTACTTCTTAA  158100
mRNA      ------------------------------------------------------------ genome    AGGTCATCCAATAAATATTAATAGGCCGGGCGCGGTGGCTCACGCCTGTAATCCCAGCAC  158160
mRNA      ------------------------------------------------------------ genome    TTTGGGAGGCCGAGGCGGGCGGATCACGAGGTCAGGAGATCGAGACCATCCCAGCTAAAA  158220
mRNA      ------------------------------------------------------------ genome    CGGTGAAACCCCGTCTCTACTAAAAATACAAAAAATTAGCCGGGCGTAGTGGCGGGCGCC  158280
mRNA      ------------------------------------------------------------ genome    TGTAGTCCCAGCTACTTGGGAGGCTGAGGCAGGAGAATGGCGTGAACCCGGGAGGCGGAG  158340
mRNA      ------------------------------------------------------------ genome    CTTGCAGTGAGCCGAGATCCCGCCACTGCACTCCAGCCTGGGCGACAGAGCAAGACTCCG  158400
mRNA      ------------------------------------------------------------ genome    TCTCAAAAAAAAAAAAAAATATTAATAAAGCCAACTCGTTAGCGTGGGGCTTAATTGCTT  158460
mRNA      ------------------------------------------------------------ genome    AAGTCCAATGAGAAGTCCTTCTCTATCCTAGGAAGTTGCCCAAACTGTAGAATCTCGTGG  158520
mRNA      ------------------------------------------------------------ genome    CCTGTGGGTAATAGCCACGTAATACACACTCACTGCCTCAACAAATCATATTTTAGTAGG  158580
mRNA      ------------------------------------------------------------ genome    TATGATATTCTAGACTCAAGACACCATTCTGTGGATCTTCCCAAGGGTGTGAAGTGTCCA  158640
mRNA      ------------------------------------------------------------
```

FIG. 1 WWWWW

| | | |
|---|---|---|
| genome | CAGCGTCTGCCTTGGGAGTTTCCATGCCCACCAGAACCATGCCCCAAGCCCCTCAAGCAC | 158700 |
| mRNA | ------------------------------------------------------------ | |
| genome | TCTGACCTAGGAAAGCCAGTGAAGCAAGGATGACAACATGGCCCTTTGATACTAGCTGAG | 158760 |
| mRNA | ------------------------------------------------------------ | |
| genome | GGACAGACACAGGTCCTGGGAGACCAGAGAAAGACGAGGGGCAGAGGAGGTGTCCTAAAG | 158820 |
| mRNA | ------------------------------------------------------------ | |
| genome | GAAGTCTGAGGCTGAGGAGCCACAGGATGGCTTCCAGCTGTCACAGGCTGCTGCTGGCCT | 158880 |
| mRNA | ------------------------------------------------------------ | |
| genome | TATCACAGAGAGTGGGCCAGAGGGCTGGGAACCAAGGCCAGAGCTCAGGTTCAGGACCAT | 158940 |
| mRNA | ------------------------------------------------------------ | |
| genome | TCCAGCAATCCCAGCAGAAAATGGGGAGAATTGTATGGTATAGGCGGATATGAAGGTAGA | 159000 |
| mRNA | ------------------------------------------------------------ | |
| genome | ATCTGCAGGCCTTCAGTGGCCAACTCAGAGTCTAAGTGGATTCCACAGTTACAGCTTGAG | 159060 |
| mRNA | ------------------------------------------------------------ | |
| genome | CAGCTGGTTGTAGGTCATGCTTTCTACACTGGGCATATAGGATGTGTTTTTAAAAAGTC | 159120 |
| mRNA | ------------------------------------------------------------ | |
| genome | CTCTCTTAACCGTTGCTTGTTTAGATCCTAAGTATATCACTGCAGCCTGTGAGATGGTGG | 159180 |
| mRNA | ------------------------------------------------------------ | |
| genome | CAGAAATGGTGGAGTCTCTGCAGTCGGTGTTGGCCTTGGGTCATAAAAGGAATAGCGGCG | 159240 |
| mRNA | ------------------------------------------------------------ | |
| genome | TGCCGGCGTTTCTCACGCCATTGCTAAGGAACATCATCATCAGCCTGGCCCGCCTGCCCC | 159300 |
| mRNA | ------------------------------------------------------------ | |
| genome | TTGTCAACAGCTACACACGTGTGCCCCCACTGGTGAGTCTGCTCGTTCCTTGCAGAAGAC | 159360 |
| mRNA | ------------------------------------------------------------ | |
| genome | CAAGTACGGTGAAAGGCACCGGTAGGCCCTGGGCTGGGCACACGTGAGAGGGCGGGACAG | 159420 |
| mRNA | ------------------------------------------------------------ | |
| genome | AATCCCCGCAGCCCAGAGGCTGCCTGCTGTGGTTCTGGTGCCCACTGTGGTTCTGGTGCC | 159480 |
| mRNA | ------------------------------------------------------------ | |
| genome | AGGCTGCTTTCCTCAGGCACCACGTGTGGAGGTCGCTAGTAGAAATACTGGGTTTTCTAA | 159540 |
| mRNA | ------------------------------------------------------------ | |
| genome | AATGAACTGAGGCCCTACATCCCTAAGAGATTAGTGTTAGACCTGATTCTAGAGCAACTA | 159600 |
| mRNA | ------------------------------------------------------------ | |
| genome | GACCACTTTGCTTAATAGCAGACCAGAAACCACACCCCCTCGAGTGAGTGAGATTTTCCT | 159660 |
| mRNA | ------------------------------------------------------------ | |
| genome | TTGGAGATAATTCATGTTTTTCTACACAGTTTTGCAGTTGTCTTCAGAATTGGTTTAAAG | 159720 |
| mRNA | ------------------------------------------------------------ | |
| genome | TAGGTGTTATTGCCAGGCGCAGTAGCTCATGCCTGTAATCCCAGCACTTTGGGAAGCCAA | 159780 |
| mRNA | ------------------------------------------------------------ | |
| genome | GGTGGGCGGATCACTTGAGGTCAGGATTTCGAGACCAGCCTGGCCAACATGGTGAAACCC | 159840 |
| mRNA | ------------------------------------------------------------ | |
| genome | CATCTCTACTAAAAATATAAAAATTAGCCAGGTGTGGTGGTGTACGCCTGTAATCCCAGC | 159900 |
| mRNA | ------------------------------------------------------------ | |

FIG. 1 XXXXX

```
genome    TACTCAGGAGACTGAGACAGGAGAATCGCTTGAACCCAGGAGGCGAAGGTTGCAGTAAGC  159960
mRNA      ------------------------------------------------------------ genome    CGAGATCGCGCCACTGCACTCTAGCCTGGGCAACAGAGCAAGACTCCGTCTCAAAAAAAA  160020
mRNA      ------------------------------------------------------------ genome    AAAAGGTAGGTGTTATTGATCAGAACCCTTGTTTCAGATAACATGAGGAGCTTAGCTTGA  160080
mRNA      ------------------------------------------------------------ genome    GGAGAGTGAGGGTTGATGGAGGGGGACTGACTTCTGCCCAGTGAAATGGCATCATCTCCC  160140
mRNA      ------------------------------------------------------------ genome    ACCAGCCCGCTGAAATAAGATGATGGGGCCTGTTCCTTAGGGCCTGCAGCATCCTCAGGC  160200
mRNA      ------------------------------------------------------------ genome    AGGAAAGAAAGGCCGACCTGGCAGGGTGTGAGCCAGCAGGTGTAGGTCAGGGAGAATGGA  160260
mRNA      ------------------------------------------------------------ genome    GCCAGGTCCCAGGGAAGAGGCTTGTGGCTGCCTGAGAAGGGTGCGTGCCTGCCTGTGTGT  160320
mRNA      ------------------------------------------------------------ genome    GTGTGTGCACGTGTGTGTATGTATGCTGGAGAGTCTAGGGAGGCTTGCTCCAAGGACGCA  160380
mRNA      ------------------------------------------------------------ genome    GTATTGTTTGATCCTGAGAGATAAGGATTCTGCCGCAGGGAATGAAGGTATTCCAGATGG  160440
mRNA      ------------------------------------------------------------ genome    CGGGCTTATTCCGAAGAAGAGGCCAGTGCCTGGCGGTGCTGGAAGCAGTTGCAGAACAGG  160500
mRNA      ------------------------------------------------------------ genome    GAGTTGTAGGCTTTCCTGGGAAGAGAGCAGCAGGGGTGCTGGAGAAGCAGGCCACACTTG  160560
mRNA      ------------------------------------------------------------ genome    CTGCATGGGGTTGCTCTCGGCCCCACTCTTGGTGCACAGCGAGTCACTGTGGGTTCATTA  160620
mRNA      ------------------------------------------------------------ genome    GCATCTGGTTATGAGACAGTAACTGCTCCTTTGGAGGGGCTCGTGGAGACCATGCAGGAG  160680
mRNA      ------------------------------------------------------------ genome    GGCACGGTCTTGAGGTCATGCCGTCCAGAGCACACCTGAGGATAGGCCAGGACGGGCTGC  160740
mRNA      ------------------------------------------------------------ genome    ACGCTGTAGGTAAAATTCCTCCAGCAAGCTCTTCACTGGCATTGAGGAGTTCCCTGAGTG  160800
mRNA      ------------------------------------------------------------ genome    CGGTCATCTGGAAGGCAGCTGTAACAGGCACTGCAGTCTCTCCCTGGGTGGGTACCAGAG  160860
mRNA      ------------------------------------------------------------ genome    AGGAGCATAGGGGAGCATAACCGATTTAAAGAGAGGGCTTTCCTGTGGTGAGGTAAGAGA  160920
mRNA      ------------------------------------------------------------ genome    TTAGCTGGTCATTATCATAGAGCCCCCTCTGCCTTTGTGCAGATGGGCTGTGGGAATCCT  160980
mRNA      ------------------------------------------------------------
                                                          rs362322
genome    GGGGTTCCGTTGGGTCCTTTGTCACCTCACTGAAGGC[A]GTAAGCTGAGCTGGCCAGACC  161040
mRNA      ------------------------------------------------------------ genome    GTGAGCTGATCCTGCCACTTGAACAGCATCAAGCCTGCCTCTGGATTCTTCTGTGCATGG  161100
mRNA      ------------------------------------------------------------ genome    CACTTGTCTGAGCACCTCACGCACAGAGAACTGGACTTCAGAGTTTACAGAAATAAGCTG  161160
mRNA      ------------------------------------------------------------
```

FIG. 1 YYYYY

```
genome    TATGGTTCATTTTCATGCCTGCTTGCCAATAAACATATCTGAGCTGAACCTCATTGAACG  161220
mRNA      ------------------------------------------------------------ genome    CCTGCCTTTATTCTAGCACAGCACCTGCTGTTTGTGGGCGAGGGGTGCTGTCTCTAACTC  161280
mRNA      ------------------------------------------------------------ genome    CTGCCTGCTTCTCCCAGCACTCCCTGAGTGGGGTGTGCCAGCAGCCTCAGGATGAGGACA  161340
mRNA      ------------------------------------------------------------ genome    GGAAGTGGGAGGGCAGAGCAGATTTGGGAGGGCCACTTGATGGGGAAGGAAGTCCCAGGA  161400
mRNA      ------------------------------------------------------------ genome    AGCAGTTGGAGCTGTTTTCTGGGGGAGAAGGTGCCAGCTCTGGGACAGTGTTGGGGTAGT  161460
mRNA      ------------------------------------------------------------ genome    GAGGAGGGAGCCCAGTGGAGAGAAGTCGGGCTTCCTGCTTCCTCACAGTATGTCTGTCCT  161520
mRNA      ------------------------------------------------------------ genome    GACTCAACTCGGATGATGTCACTTCCTTTTCATCTTCTCAGGTGTGGAAGCTTGGATGGT  161580
mRNA      ------------------------------------------------------------ genome    CACCCAAACCGGGAGGGGATTTTGGCACAGCATTCCCTGAGATCCCCGTGGAGTTCCTCC  161640
mRNA      ------------------------------------------------------------ genome    AGGAAAAGGAAGTCTTTAAGGAGTTCATCTACCGCATCAACACACTAGGTACTCTTGGGG  161700
mRNA      ------------------------------------------------------------ genome    CCTCTCCTTCAGGTCACCATTGTCGGACATCTACCGGGAGGAAATCCAGAGCCCCCAGTA  161760
mRNA      ------------------------------------------------------------ genome    CTGGGATCTTCTCATTTGACTCCAGAAAAGATTTAAGCATGATAATAATACAAACCTATG  161820
mRNA      ------------------------------------------------------------ genome    TGAATACATTTTGCAGTGTTGGCAAAACTCCTTTTATACTGAGAAAATAGATCCCAGTTC  161880
mRNA      ------------------------------------------------------------ genome    CTGTGTTTTGTGGCTTGAATCCCAGCTTTGTGTATTCCGGGCTTGTTTGAAGTCAGGAAA  161940
mRNA      ------------------------------------------------------------ genome    GGTTCATGTGTAGTGGACAACGTGAGACCAAATTCTGCCTTAGATTTTGCATTTAGGCTA  162000
mRNA      ------------------------------------------------------------ genome    AACAGTGGCAGCACTTGTCTCAGAATGTTTTCTTGTGTTCACCAGTCTGATCCTGTTGTG  162060
mRNA      ------------------------------------------------------------ genome    TCTCAGTGGTCCATTTTCTCATATGGGAACAAGCAGACGGGAGCAGATGGAGTCAGGTTT  162120
mRNA      ------------------------------------------------------------ genome    CTTGGCACTCGCCTTCCCCAGAGCCTAGAGGCAGCATGGGGAGAAAGCAGGCTTGGGGCT  162180
mRNA      ------------------------------------------------------------ genome    CAGACAGTCCTGGTCTGCTTCCAGCCCTCCTACCTGAGCAGCGCAGGGCAAGTCCGTCTA  162240
mRNA      ------------------------------------------------------------ genome    ACCTCTAGAGACCCTCAGTTTTGTCATATGTAAAATGGGGGTCGTGTCTATTTCATAGAA  162300
mRNA      ------------------------------------------------------------ genome    TTGTTGCAGATTTAGAAATTACATTTCTAAACAAATGTTACCCCTTATTTCTAAATAAGT  162360
mRNA      ------------------------------------------------------------ genome    GTCTAAATGAATAAGTCACCACTTTTGCCCCTATTTGATGGCAAGAGGTGTGATCTTGTG  162420
mRNA      ------------------------------------------------------------
```

FIG. 1 ZZZZZ

| | | |
|---|---|---|
| genome | GTGGGACTGTAATCAGTCAGTTCTCAGTGACTGTGCCCTGCTGTGGTGTTTCCTGGAATG | 162480 |
| mRNA | ------------------------------------------------------------ | |
| genome | TTCCTGTCTTGTCCTAGAAAGTCTGGCAGGGGCACCCTGACTCCACTGTCCAGTCCTCTC | 162540 |
| mRNA | ------------------------------------------------------------ | |
| genome | CCCAGTCCCTCGGGCTTCTGCAGATTTGAGGCTTGTTTGGATCCCAGAAGGTTGTGGCAG | 162600 |
| mRNA | ------------------------------------------------------------ | |
| genome | GAGACACCTTGCCTCTACTTTCCCCTTTATAATTCAATGTCCAAAGAGAGCCCTGAGCAG | 162660 |
| mRNA | ------------------------------------------------------------ | |
| genome | GTACCTCACGCCAGCTGCCTCACGGAGCTCCTCCTCTTCCTGGCTGTGAGGATCGGTATC | 162720 |
| mRNA | ------------------------------------------------------------ | |
| genome | AGTGGCCTCCTGCTCTCTCCCCCTTGCCTAACACGAGCACCTTTGCTTACTTGGGTGCCC | 162780 |
| mRNA | ------------------------------------------------------------ | |
| genome | TTGCTCTTGAACTGCCCATCGGACGTGCGTGACCCAAGACTGTGCCGCAGTCCTTGCCTT | 162840 |
| mRNA | ------------------------------------------------------------ | |
| genome | GTCTGTGCTCATTTTCTTTGTTCATTTTTTCCCTGTAACGTAAATTGTTATATTTGTCT | 162900 |
| mRNA | ------------------------------------------------------------ | |
| genome | GTATCTGTGTCTGAATCAGTCCTGCACGCTCTCCTTCTCTCTGTCTCTTGTTCTTTCTTT | 162960 |
| mRNA | ------------------------------------------------------------ | |
| genome | ACCCCGTTTATCACGGGGACCCCGATGTCCATTGCTCTAGTTCTCCTGTCCTAAGCACCC | 163020 |
| mRNA | ------------------------------------------------------------ | |
| genome | CATCCCGTCTCTCTGGCCTTACCACAAGTGGCGTGGCTGCCTCAGACATCATGATGGGGA | 163080 |
| mRNA | ------------------------------------------------------------ | |
| genome | CATGAAGCACAGCTGTCAGAAACAACTGTTCGTTAGATACACTCGAATGCAGCTCATCAA | 163140 |
| mRNA | ------------------------------------------------------------ | |
| genome | TAGGGATGGAGGGTCTGTCGGATGTATTTTCACTGAATCCCCGTTCCTACCTTGATACAC | 163200 |
| mRNA | ------------------------------------------------------------ | |
| genome | TCTTTTTAATCTATTCTTCTAGACAGGTCAGAGGAACCATTACTTTGACTTTTAAATTTT | 163260 |
| mRNA | ------------------------------------------------------------ | |
| genome | TAGCAGCTTTATTGAGGTAGAATTCACATACTACAGATTTCACCCACTCTAAGCGGACAG | 163320 |
| mRNA | ------------------------------------------------------------ | |
| genome | CTTGGTGGCCATTAGTTTTATCCACAGAGTTGTGCAGCCAGCTGCACAGTCTCAGGGCTG | 163380 |
| mRNA | ------------------------------------------------------------ | |
| genome | GACTCCAGGGAAGATTTTAGCCCATTTAGTGAGTGGGGCAGAAGTGGCCCTGGCCCTGCA | 163440 |
| mRNA | ------------------------------------------------------------ | |
| genome | CGAGGTTGCCTGCATGGGCGTCCCTGCCCTGTCCCTGTGTCTGCTCCACTGGGGGTTGAC | 163500 |
| mRNA | ------------------------------------------------------------ | |
| genome | CAGGCTGCCAGGGCCGACTTGGGCCTGTGCCACCTGCCTCTCATGTGTCTCGGACAGTGC | 163560 |
| mRNA | ------------------------------------------------------------ | |
| genome | AGCCGATGTCTATACTTCGGTTTCCTCAATGATGAAATGGAGGGGATAGTGTTCCCCGCA | 163620 |
| mRNA | ------------------------------------------------------------ | |
| genome | TCATAGAACTGTGTGAGGTTTAAGGGACTCACTGCCCTTGGCGTGGAGCCTTCTCCAGGG | 163680 |
| mRNA | ------------------------------------------------------------ | |

FIG. 1 AAAAAA

```
genome    GCCGTGCTGTGTCGGCGTAGCTGTCAGCTCTCCGTTACAGGCTTGAGAAGGGTTGACACT  163740
mRNA      ------------------------------------------------------------ genome    CTCTCATGTAACATTTATATTTCTAGGCTGGACCAGTCGTACTCAGTTTGAAGAAACTTG  163800
mRNA      ------------------------------------------------------------ genome    GGCCACCCTCCTTGGTGTCCTGGTGACGCAGCCCCTCGTGATGGAGCAGGAGGAGAGCCC  163860
mRNA      ------------------------------------------------------------ genome    ACCAGAAGTAAGGCCACACCCTGTGCTGGTTGGCACATGGGCAGTTATGGCCGCTTGCAG  163920
mRNA      ------------------------------------------------------------ genome    GCCTTTGGTGGGGAATAAAATAAGGCAGCAAGCTGGTGTTCTTTTTTTCTCTTACCTTAT  163980
mRNA      ------------------------------------------------------------ genome    TTTTGAAAGAGTAGCTGAATGGTGTCTTGACTGATATTCCAGAGCAGGGACAAAGCCTGC  164040
mRNA      ------------------------------------------------------------ genome    TGAGGTCTGGGGGCTGCGATTACCAATGGCTGGAATGCATTTTATTACGGTGCATTCCAT  164100
mRNA      ------------------------------------------------------------ genome    GTTAAGGATCAATACGATTGTGCCCTTTCTGGAAAATATCTTTTAGTTTATCAATATTCA  164160
mRNA      ------------------------------------------------------------ genome    GAGGAGTGTAGGTTGAATTAAAATGAAAAGGCACTTTATAAAGGCCATGAGTAGTACCTG  164220
mRNA      ------------------------------------------------------------
                                                  rs362275
genome    GTTTCATTTTTCTAATGTCTTGCAGAGATTTTATCAGGCTTCTTGAAGTGTTCACGTACA  164280
mRNA      ------------------------------------------------------------ genome    TTACGCTAACACGATATTAATAATAACTGTGCTCTGGTACAGCGGAGCCAGCAGAATGGG  164340
mRNA      ------------------------------------------------------------ genome    AAGTTGTGGAATGCAGGCCCTTGATTCTGATAGAAGGTGTGGTTTGAACTCACAGAAATG  164400
mRNA      ------------------------------------------------------------ genome    ACAGTTTGGAGGGTAGACATATGTCACAAGTCATCAAGATTGTCTTTAAATTCATGCATA  164460
mRNA      ------------------------------------------------------------ genome    GAAGCTAACAGGGTGTCATAAGCAAGGCCTGTAAAATGTATGAGGGAATTCAAAGATAAT  164520
mRNA      ------------------------------------------------------------ genome    TTATTAAAAAGTAATTCATGTTTGGAGTTTTGTGCCCAAAGGAGTCCTTGATTTGAAAAA  164580
mRNA      ------------------------------------------------------------ genome    TGGGCTTTTGCCCATCAGATTGTTTCAGGGCCCGTGTGTGCGGAGGCCCTGCCTTGTGCC  164640
mRNA      ------------------------------------------------------------ genome    CCGTGAGCTCAGCCTGACAGAAATCCTTTGGTAGCACTTAAGGCTCCTCTTCCTCCCATT  164700
mRNA      ------------------------------------------------------------ genome    GAGGCAGGGAAGACTCTGGGTTCTGCAGGCAGAGGTGGTTGTGGGTGTCTTGCTGCTCTT  164760
mRNA      ------------------------------------------------------------ genome    GTTGACATGTGGGCTCTCCTTCCAGGAAGACACAGAGAGGACCCAGATCAACGTCCTGGC  164820
mRNA      ------------------------------------------------------------ genome    CGTGCAGGCCATCACCTCACTGGTGCTCAGTGCAATGACTGTGCCTGTGGCCGGCAACCC  164880
mRNA      ------------------------------------------------------------ genome    AGCTGTAAGCTGCTTGGAGCAGCAGCCCCGGAACAAGCCTCTGAAAGCTCTCGACACCAG  164940
mRNA      ------------------------------------------------------------
```

FIG. 1 BBBBBB

| | | |
|---|---|---|
| genome | GTTTGCTTGAGTTCCCACGTGTCTCTGGGACATAGCAGGTGCTGGGGACAGTGGGTTCCC | 165000 |
| mRNA | ------------------------------------------------------------ | |
| genome | CGCTGAAGCGTCCAGCAGCTTCAACCAGGCCGTTTTCCTTCATTGCTAGAATTGAAAACA | 165060 |
| mRNA | ------------------------------------------------------------ | |
| genome | CCGTCCGTGTGGCCTGTGCAGGAGATGCAGACCCAAAGGTGGCCTCCTGGTCAGTGAGAA | 165120 |
| mRNA | ------------------------------------------------------------ | |
| genome | GCTGGAAACGTGACAGGAACTGACGTGGGGTTATTGAGCATTTAGGGGAAGACGTTAGCA | 165180 |
| mRNA | ------------------------------------------------------------ | |
| genome | GAGCAGGAATGAGCAGGCAACTAGTAGAACACCCACTTAAGGGCTCACGGACAGGTGCTC | 165240 |
| mRNA | ------------------------------------------------------------ | |
| genome | ACTTAGGAAGTGAGTTTCATTTGGTATTACACCAGGTTCCTTTAGGCAAAGCGGAGGGAA | 165300 |
| mRNA | ------------------------------------------------------------ | |
| genome | AGTTCTGGTGTTTTTCACTTGTAAGATTTTGAAGGAAACAAAACACTCTTTACCTTTTTT | 165360 |
| mRNA | ------------------------------------------------------------ | |
| genome | CTAAAATGTAGGTTTGGGAGGAAGCTGAGCATTATCAGAGGGATTGTGGAGCAAGAGATT | 165420 |
| mRNA | ------------------------------------------------------------ | |
| genome | CAAGCAATGGTTTCAAAGAGAGAGAATATTGCCACCCATCATTTATATCAGGCATGGGAT | 165480 |
| mRNA | ------------------------------------------------------------ | |
| genome | CCTGTCCCTTCTCTGTCTCCGGCTACTACAGGTACCTGAGGGAAAGGGTGCGGGGGAGCG | 165540 |
| mRNA | ------------------------------------------------------------ | |
| genome | GTTGTACTTGGGCTAGAATGAGAGAAGACTGGCATGCTCACCACACCAGTGATGCGGGAA | 165600 |
| mRNA | ------------------------------------------------------------ | |
| genome | GACCTGAGTGTGGTCTGAGTTGGAGGCTGTGGTGCTAAATACGCTGCCCCTTTCATAAGC | 165660 |
| mRNA | ------------------------------------------------------------ | |
| genome | AGGAGTCTTAGTCAGGCCCAGGGAGGAAGTAAAATCTGGAAATGAATGAGAAGCATTCTC | 165720 |
| mRNA | ------------------------------------------------------------ | |
| genome | TCCTGCCAGTCAAGAAATGAGAAGCGAAAGAATTCTCACGGGCTGTAAGACCAGCAGGAT | 165780 |
| mRNA | ------------------------------------------------------------ | |
| genome | TTAAAAGTTGAATTAGTTGCTTATGTTAAGAACTCAACCAAGTTCATCTACACAAGCTGA | 165840 |
| mRNA | ------------------------------------------------------------ | |
| genome | ATCTCCAGCTTTTCCTAAGAAACCATGTGTGGCAGTGGCTGCAGGGCAGGGCACAGCTGG | 165900 |
| mRNA | ------------------------------------------------------------ | |
| genome | GCCTGAGCACCCCGCTCCCTGCACCTCTCCCCTCCCTGGGCCCTGCCTGTCACTGCCCAC | 165960 |
| mRNA | ------------------------------------------------------------ | |
| genome | TCTCCCACCAAGCCTTCCGGTTGTGTGCCTGCCCTATCACAGGCATCGGAGCTTGTCACC | 166020 |
| mRNA | ------------------------------------------------------------ | |
| genome | TGGTTTAAAAGAAGAGAGTTGTGTGGGGATTTGGGATGCACGTTTTTCACTCAAAAGTAT | 166080 |
| mRNA | ------------------------------------------------------------ | |
| genome | TTTAGCGTAGAGCTCTGTGATTCCGTAGCTATTTAGGAGTTTAAGCACCTTGAAGGCTTT | 166140 |
| mRNA | ------------------------------------------------------------ | |
| genome | AATTGCAGAAAGTTCTATGTGGACGTGCAATGTGTTATACGCAGTGTCTATGAGACTCAA | 166200 |
| mRNA | ------------------------------------------------------------ | |

FIG. 1 CCCCCC

| | | |
|---|---|---|
| genome | ATGTTTATTAGGGCGTTGAAGTAAACTGAGCACTTGGAGGGCCATGGATCCAGCCTTCAA | 166260 |
| mRNA | ------------------------------------------------------------ | |
| genome | GGAGCTCATAAGTCAGGAGGACCCAGGAGCAATGACCTGTCATAGAAGGCAGAAAAGAGG | 166320 |
| mRNA | ------------------------------------------------------------ | |
| genome | GGCACAGAGGTGGGTGGGAGGCATACACAGGCAGCTCCTGGAGCTCCAAGGGGAGCAAGT | 166380 |
| mRNA | ------------------------------------------------------------ | |
| genome | GCTTCCAGGGAAGGGGGCGTGGAGGCCCCTTTGGAGGAGGCAAGTTGATCTGGGGTCTGG | 166440 |
| mRNA | ------------------------------------------------------------ | |
| genome | CAGAGGGTTAGCTGGGGACATTTAGCGGGAGGCTGGTGCCCGGGAATTGGGGGGATGCCC | 166500 |
| mRNA | ------------------------------------------------------------ | |
| genome | AGCAGAAAGACATGAGGAGGCTGGCCTGGGGCGTGGGGGGGTGTGAAAGGTTAAGTGGGG | 166560 |
| mRNA | ------------------------------------------------------------ | |
| genome | GCATTATCCTGCTCCCGCTCCTGCCGGCTGTATCTGGTCAGCCTGGGCACCGAGGTGGGG | 166620 |
| mRNA | ------------------------------------------------------------ | |
| genome | TTCTGGAAGGCACTGTTCACCAAAATGCTTATCTGGGTCCCCCAGAGAGCTTGCCTGCCT | 166680 |
| mRNA | ------------------------------------------------------------ | |
| genome | GGACTGTCGGCTCGCCTGCAACTGCTGACTCCTAAGCTTTTGCAGCTCAGCCCACAACCA | 166740 |
| mRNA | ------------------------------------------------------------ | |
| genome | GTTCCTATTCACAGAGGTGGGAGCTGAGGGGTGACAAGTGACTGCTGCAGTCTTATTTGT | 166800 |
| mRNA | ------------------------------------------------------------ | |
| genome | CATAGAGAAAAAGTGACAGAGTCCAGCTTGCCCACTGGCCCTGCCAGCTTAACTGGTTAT | 166860 |
| mRNA | ------------------------------------------------------------ | |
| genome | AAAGTGACAAATCCCCAAGACCCACAGGGCTCTGCACAACCTGGGCCCTCCTGCCAGTGG | 166920 |
| mRNA | ------------------------------------------------------------ | |
| genome | CGGCGAGGGCAGGTGGCTCACGGCTGGGTGCCTGTCTGGGCAGGAGCTGGGCTGGTATGG | 166980 |
| mRNA | ------------------------------------------------------------ | |
| genome | GGTGGGCCTGCGGCCCTGCCCCCCTGTGCAGATCAAGACTCAGGGTGCTGGTGTTCACAG | 167040 |
| mRNA | ------------------------------------------------------------ | |
| genome | GTGCCCTCATCAGCCACGAGAAGCTGCTGCT[A]CAGATCAACCCCGAGCGGGAGCTGGGGA | 167100 |
| mRNA | ------------------------------------------------------------ | |
| genome | GCATGAGCTACAAACTCGGCCAGGTCAGTCTCGCGCCCCCGCCGCCTGGCCTCTGTCCGT | 167160 |
| mRNA | ------------------------------------------------------------ | |
| genome | TTCTGTCCTCAGACTTTGGCGCTTGACACACCCAGGAGAAAAGCTCAGTGCACTTTTTAA | 167220 |
| mRNA | ------------------------------------------------------------ | |
| genome | ATGAAAGGAAGTTTTCCTTTTTTTTAAAAAAAAATTTAATGTTCATTGTTTTTATCTGTT | 167280 |
| mRNA | ------------------------------------------------------------ | |
| genome | TTATTCCTAGGTCCCGCAAGCAGAGGAAGCATTAGTTTTGTTTTTATTTATGTTCTGTAT | 167340 |
| mRNA | ------------------------------------------------------------ | |
| genome | TCCAGAAAGTAGTTAAGAGACCTCACATGTAGCGATAGAGATGTGTGTAAGAGACAGTGA | 167400 |
| mRNA | ------------------------------------------------------------ | |
| genome | GAGGGCGTGACTTGGACTTAAGCAAGGACCGTGAGACACAAAAAGGGGGGTGAGGACAGA | 167460 |
| mRNA | ------------------------------------------------------------ | |

(rs362273 marked above the [A] in the row ending 167100)

FIG. 1 DDDDDD

| | | |
|---|---|---|
| genome | GTGGAGTCAGCTGAAATGCTCAGGAGGAAGTAGACGCCATGAAGGGCCATGGTATGGGGG | 167520 |
| mRNA | ------------------------------------------------------------ | |
| genome | GCCGCAGGCGTGGCCGTGAGTGTCCCTGGGGCCAGCTCTTGGGGGGCTCCCTGAGTGTCC | 167580 |
| mRNA | ------------------------------------------------------------ | |
| genome | CTGTCCCTGTGGCCAGTTCTGGGTGGGAGCCCCGTGTGCAGGCAGACAGCTCGGCCACTT | 167640 |
| mRNA | ------------------------------------------------------------ | |
| genome | CCTAGCAGGTCACATTGGTCTGTGCTTCTGTTTCCTCCTCAGATAAGTGAAGGGATTCAA | 167700 |
| mRNA | ------------------------------------------------------------ | |
| genome | GGGTCTGGGTGTGGTGGCTAACACCTGTAATCTATAACATTTTAGGAGGCTGAGGCAGGA | 167760 |
| mRNA | ------------------------------------------------------------ | |
| genome | GGCTTACCTGAGCTCAGGAGGTTGAGGCTGCAGTGAGCCATGATTGCACCACTGCACTCC | 167820 |
| mRNA | ------------------------------------------------------------ | |
| genome | AGCCTGGGCAACAGACCAGTACTCTGTCCCTTAAAAAAAAATGTAAACAGAAACGTAGGG | 167880 |
| mRNA | ------------------------------------------------------------ | |
| genome | CCATTTGCATATGATGGCACATGGCGTGGAGCCCTACAGGTGTATGCTGGGCGGGGCCCG | 167940 |
| mRNA | ------------------------------------------------------------ | |
| genome | GCTGTGCTGGCCGACTTGCACCTTTCCCTCCACCCCGGTGCTGTGTCTTTCGCTCACCGG | 168000 |
| mRNA | ------------------------------------------------------------ | |
| genome | GTTCCTGATTTAGTGAAAGCAGTTGTGCAGGACAGTTCTCTTTGTAGCTTTTGTTTCTGT | 168060 |
| mRNA | ------------------------------------------------------------ | |
| genome | GGAAATGGGTCAGAATATGGTGTTTAGAAACACTTATGAGCTCTGAGAGTTTCCTCTTCT | 168120 |
| mRNA | ------------------------------------------------------------ | |
| genome | GAGTTCCTGGCCTGCAGCCTTCACAGCAGAAACCCTGTGATGTCACAAGCCTGTTTCTGT | 168180 |
| mRNA | ------------------------------------------------------------ | |
| genome | TCCCTGCTCTCTGCCTGTACTGTCCTGTTTTGTGCCTGCCGGTTTCAGTGACAGGAAGCA | 168240 |
| mRNA | ------------------------------------------------------------ | |
| genome | GGGAGCTACTGGACCAGCCTGTATTTTTCTAGACATAGTTGGAAAAAGAAGTCCCACTCT | 168300 |
| mRNA | ------------------------------------------------------------ | |
| genome | TCTGTCCTTTCACCTTTGACAGATGTTTCCACCCCAAGATAAGTGAAAATGACCAATAGG | 168360 |
| mRNA | ------------------------------------------------------------ | |
| genome | ATGCACTGTATTTTTCATGAAAGTGTTTCTGAAGGGCAGGCTGAGAGTGAGAGGCCTGGG | 168420 |
| mRNA | ------------------------------------------------------------ | |
| genome | GCTCACTGGGTGCCTCTGGCCTTGTCCTGGGCCCAGGGACACTGGTCTGTGCCCGAGGTA | 168480 |
| mRNA | ------------------------------------------------------------ | |
| genome | TTCCCTATCCCCCCAACCCCGCTGCATTTGGCCACATCCTTCAATGTTTGCGTTGTGTCC | 168540 |
| mRNA | ------------------------------------------------------------ | |
| genome | AGCGTCCGCAAACCAACTGTCATGGGATCATACTGGGGCTGAAGTACGGTCCCACCCCTG | 168600 |
| mRNA | ------------------------------------------------------------ | |
| genome | CCCTGTCTGGGGCTGAAGTACAGTGCCACCCCTGCCCTGTCTGGGGCTGAAGGACAGTGC | 168660 |
| mRNA | ------------------------------------------------------------ | |
| genome | CACCCCTGCCCTGTCTGGGGCTGAAGTACAGTGCCACCCCTGCCCTGTCTGGGGCTGAAG | 168720 |
| mRNA | ------------------------------------------------------------ | |

FIG. 1 EEEEE

```
genome      GACAGTGCCACCCCTTCCCTGTCTGGGGCTGAAGGACAGTGCCACCCCTGCCCTGTCTGG  168780
mRNA        ------------------------------------------------------------ genome      GGCTGAAGGACAGTGCCACCCCTGCCCTGTCTGGGGCTGAAGGACAGTGCCACCCCTGCC  168840
mRNA        ------------------------------------------------------------ genome      CTGTCTGGGGCTGAAGGACAGTGCCACCCCTGCCCTGTCTGGGGCTGAAGGACAGTGCCA  168900
mRNA        ------------------------------------------------------------ genome      CCCCTGCCCTGTCTGGGGCTGAAGGACAGTGCCACCCCTGCCCTGTCTGGGGCTGAAGGA  168960
mRNA        ------------------------------------------------------------ genome      CAGTGCCACCCCTGCCCTGTCTGGGGCTGAAGGACAGTGCCACCCCTGCCCTGTCTGGGG  169020
mRNA        ------------------------------------------------------------ genome      CTGAAGGACAGTGCCACCCCTGCCCTGTCTGGGGCTGAAGGACAGTGCCACCCCTGCCCT  169080
mRNA        ------------------------------------------------------------ genome      GTCTGGGGCTGAAGGACAGTGCCACCCCTGCCCTGTCTGGGGCTGAAGGACAGTGCCACC  169140
mRNA        ------------------------------------------------------------ genome      CCTGCCCTGTCTGGGGCTGAAGGACAGTGCCACCCCTGCCCTGTCTGGGGCTGAAGGACA  169200
mRNA        ------------------------------------------------------------ genome      GTGCCACCCCTGCCCTGTCTGGGATGTTTAGCCCCTAGATGCCACTGGACTGAGCCGCTA  169260
mRNA        ------------------------------------------------------------ genome      CTTGCTTTTGGGAAAGAGGGGTGGGGGTTAGGGGTCTGGGCGAGGGGAGTGCAGGGGCTC  169320
mRNA        ------------------------------------------------------------ genome      CTCCTTGGCCTGAGAGCTGTTCATACAGACTCCTCGCCCACTCCCTGCAGGGTGCTGGGT  169380
mRNA        ------------------------------------------------------------ genome      CCCAGGGGGGAAATGGCCCTTGGTGCCAAGAACGTGAGTTGGGGCTAGTGCCAGTGATGA  169440
mRNA        ------------------------------------------------------------ genome      TGGAGAACAGCTTTTTATGGGCACACAGCCCACAGCACTGTGCCAAGTGCTCGAGGCTTC  169500
mRNA        ------------------------------------------------------------ genome      CCGAGAACCAGGCAGAAAGGAGGACAGTCGAGGTGTGCTGACTGCGTGGTGGCTGCGTGA  169560
mRNA        ------------------------------------------------------------ genome      TCTAGAGCGCGGGTCACAAAGGCGCGAGGGAGCTCTGGCCTTGGGTTTACCGCAATGACT  169620
mRNA        ------------------------------------------------------------ genome      GCCAGTGCGGGAGACTGGAAAAGGAATCTCACGTATTGGTTCCGTGTTTTGGGGACTCCA  169680
mRNA        ------------------------------------------------------------ genome      TTCAGATGTCACTTAGGAGTGAAAGCATCCCTTCGTAGAGCCTCTTTCTGTGTCACCCTC  169740
mRNA        ------------------------------------------------------------ genome      CTCAGCTGCTCCTGGGGTTGACTGGCCCCTGATTCATGCCTTTAGCATGTGCTGGAGCTT  169800
mRNA        ------------------------------------------------------------ genome      CCCAGCAGCTGTCCAGCCCCTGCCCCACCCTCTCTGTGGGCTCCCTTGCCCGTAACCTGG  169860
mRNA        ------------------------------------------------------------ genome      GGTGTCTGAACGACCCTTGCTAAGGGGCAGACTGTTAGACGGTAGGCATGTGCTGAGTCC  169920
mRNA        ------------------------------------------------------------ genome      CAGTGGCCACACCCACCCACCAGGAGCCTGGCACTGTGGCCGCAGCACTGAGCAGTGCCC  169980
mRNA        ------------------------------------------------------------
```

FIG. 1 FFFFFF

```
genome      CGTTTCTGTGGCAGGTGTCCATACACTCCGTGTGGCTGGGGAACAGCATCACACCCCTGA  170040
mRNA        ------------------------------------------------------------ genome      GGGAGGAGGAATGGGACGAGGAAGAGGAGGAGGAGGCCGACGCCCCTGCACCTTCGTCAC  170100
mRNA        ------------------------------------------------------------ genome      CACCCACGTCTCCAGTCAACTCCAGGTTTTCCAATGGCCTTTTTCTTTTTAACAGAAATT  170160
mRNA        ------------------------------------------------------------ genome      TGAAATTTCTTATCAGTCATTTGATTTGTTTGAGGTGCTTCTTGAAATGAGCCTCTCATC  170220
mRNA        ------------------------------------------------------------ genome      TCATGTACTTGGAAAATACCCATCTCGCATATTCCACAGGAAACACCGGGCTGGAGTTGA  170280
mRNA        ------------------------------------------------------------ genome      CATCCACTCCTGTTCGCAGTTTTTGCTTGAGTTGTACAGCCGCTGGATCCTGCCGTCCAG  170340
mRNA        ------------------------------------------------------------ genome      CTCAGCCAGGAGGACCCCGGCCATCCTGATCAGTGAGGTGGTCAGATCCGTAAGTGAGCC  170400
mRNA        ------------------------------------------------------------ genome      TTCCCATTCCCCTCACACCTGCACGTGCCACACGCACCACACACGCCACACACCCCACAC  170460
mRNA        ------------------------------------------------------------ genome      ACACACACCGCCCACACACATGCCACTTGCACACACACCCCTCATGCATGCAACACACAC  170520
mRNA        ------------------------------------------------------------ genome      ACAGGCCACACGCACCATAGACACCACACACACATGCCACATGCACACACATACACGGCA  170580
mRNA        ------------------------------------------------------------ genome      TGCACCATACACACAACACACACAGCACACATGCCACACACACACGCCACACCACATGCA  170640
mRNA        ------------------------------------------------------------ genome      CCACACACATGCCACATGCACACACACTCCACATGCATGCACCACACACACACACACACA  170700
mRNA        ------------------------------------------------------------ genome      CCACACACACCACATGCACCACACCACACAGGTTACATGCACACAACACACACATGCCAC  170760
mRNA        ------------------------------------------------------------ genome      GTGCACACACCCCACACACCACATGTATGTGCCACACACACAGCACACAACCACACACATGC  170820
mRNA        ------------------------------------------------------------ genome      ACCACACACATGCCACATGTGCATGCACCAGACACATGGCACACACTACACACACGCCAC  170880
mRNA        ------------------------------------------------------------ genome      GTGCACACACCCCACACACATGTACGCACCACACACATGCCACACACACATGCACCACAC  170940
mRNA        ------------------------------------------------------------ genome      ACATGCCACATGTACACACATGTATATACACACCCCACACCACACACACACCACTTGCAC  171000
mRNA        ------------------------------------------------------------ genome      ACCACGCACACACACCACATGCGCACACACACACCACATACGCCACATGTACACACCATA  171060
mRNA        --------------------------------GCTGCCGGGACGGGTCCAAGATGGA    25
                                            *   **  **  ** **        *
genome      CACACACCATACATGCACCACGTGTACCACGCACCCACACAGACACAGCACACGCATACA  171120
mRNA        CG---GCCGCTCAGGTTCTGCTTTTACC-TGCGGCC-CAGAGCCCCA-TTCATTGCCCCG  79
            *     **   ** *   * * ****   **  ** ** **  *     **       *
genome      CCACACACACACGCACACATGCGTCCCGCACAGTAATGTCTCTTGGGTGTAAGAACACGA  171180
mRNA        GTGCTGAGCGGCGCCGCGAGTCGGCCCGAGGCCTCCGGGGACTGCCGTGCCGGGCGGGAG  139
            *  *   ***   *  ** ****          *   *   **   ***   *
genome      CTTGCCAGTAGTAGCGTTCTGGATGCGTTGCCTGGATTCTAACAGCGCGATTCTCCCCTT  171240
mRNA        ACCGCCA-TGGCGAC--CCTGGAAAAGCTGATGAAGGCCT------TCGAGTC-CCTCAA  189
```

FIG. 1 GGGGGG

```
             ****  *  *    *  *****   *   **          **      ***  **  ** *
genome   GCCCTCCTGGTTTTCCACATCTCCAGCTTCTAGTGGTCTCAGACTTGTTCACCGAGCGCA 171300
mRNA     GTCCTTCCAGCAG-CAGCAGCAGCAGCAGC-AGCAGCAGCAGCAGCAGCAGC--AGCAGC 245
         * ***  *      *   ** *  **** * **  *          ***        *  ***
                        rs2276881
genome   ACCAGTTTGAGCTGATGTATGTGACGCTGACAGAACTGCGAAGGGTGCACCCTTCAGAAG 171360
mRNA     AGCAGCAGCAGCAGCAACAGCCGCCACCGCCGCCGCCGCCGCCGCCGC-CTCCTCAGCTT 304
         *  ***      *** *        *  *   *  *  *       *   **  * ****
genome   ACGAGATCCTCGCTCAGTACCTGGTGCCTGCCACCTGCAAGGCAGCTGCCGTCCTTGGGA 171420
mRNA     CCTCAGCCGCCGCCGCAGGCACAGCCGCTGCTGCCTCAGCCGCAGCCGCCCCCGCCGCCG 364
            *     *  ***     *     *    ****  ***    *****  ***  *   *
genome   TGGTAAGTGACAGGTGGCACAGAGGTTTCTGTGCTGAAGCCACGGGGGCCCATCTGCCTT 171480
mRNA     CCCCCGCCGCCACCCGGCCCGGCTGTGGCTGAG---GAGCCGCTGCA-CCGACCAAAGAA 420
         *  **  ***  *** *  **   *** *    ****  *   **  ** * *
genome   GGGACCTGGTGTTGGCCAGAGGTGCCGGGTGCGGCTGCCTCCTTCCAAGAGTTGACCCGA 171540
mRNA     AGAACTTTCAGCTACCAAGAAAGACCGTGTG-AATCATTGTCTGACAATATGTGA---AA 476
          * **     * *  *** *** *** **      **    ***  ***  *
genome   ACCGGACTCCACGGCCCACGTGAG---CTGCAGTGCTTCTCAGATGGAGGGGGTTCAGCG 171597
mRNA     ACATAGTGGCACAGTCTGTCAGAAATTCTCCAGAATTTCAGAAACTTCTGGGCATC-GCT 535
         **        *** * *         **     ** ***    ***  *     ***  ** **
genome   ACGGTCAGTGCCATTCACAGGTCACTG-TGATGTGGGTTGTGGCGGCCAAGCCATGGTTT 171656
mRNA     ATGG--AACTTTTTCTGCTGTGCAGTGATGACGCAGAGTCAGATGTCAGGATGGTGGCTG 593
         * **     *       *  * **  **    *   *    *    **        *** *
genome   GGGGTCCCGTATCCCTGGGCTTATGACATCATTGTAGTAGCCCATCCCCACAGAACCACG 171716
mRNA     ACGAAT--GCCTCAACAAAGTTATCAAAGCTTTGATGGATTCTAATCTTCCAAGGTTACA 651
              *   * **    ****  *  *  ***   *   *   *   **     **
genome   GTGTGTGGTGGCGCTGAGGCATCGTAGATGGTGGAAATGCTACTGGCTTCCCCATGCTCT 171776
mRNA     GCTCG-AGCTCTATAAGGAAATTAAAAAGAATGGTGCCCCTCGGAGTTTGC----GTGCT 706
         *  *     *  *  *   **  * *    ***   * *  **  *   **     **
genome   GCCCTGAGGCCTGACTGCCTCACTCCCCTTCTCAGTTATGTTCCAGGCCCCCCGAGCTTC 171836
mRNA     GCCCTGTGGAG-GTTTGCTGAGCTGGCTCACCTGGTTCGGCCTCAGAAATGCAGGCCTTA 765
         ****** **   *  ***    ** *      *    ***    ***      *  ***
genome   CTGGCTGGACAGCTTCTCTCCTGGGGGCCGTTTTGTCACAGTGACCCTGTGTTTCTAGTC 171896
mRNA     CCTGGTGAACCTTCTGCCGTGCCTGACTCGAACAAGCA-AGAGACCCGAAGAATC-AGTC 823
         *  *  ** **           *    **          ** ** *****    *  ** ****
                        rs3121419
genome   CCAAATCTGGGTGCTATAGTCTCTTTTTAGCGTGGTGGTTGTCTTAGTCTTTTTTGGCTG 171956
mRNA     CAGGAGACCTTGGCTGCAG-CTGTTCCCAAAATTATGGCT---------TCTTTTGGCAA 873
         *  *       ***  ** ** **         *   *** *              *  *******
genome   CTACCACAAGTTACCTTAGACTGGGTAATTTATAAACAGTGGAAATTTACTTCTCACCGT 172016
mRNA     TT-TTGCAAATGACAATGAAATTAAGGTTTTGTTAAAGGC---------CTTCATAGCGA 923
          *    *** * ****  *    *  *   *** * **  *         ****   * **
genome   TCTGGGGGCTGGAAGTTTTCATGGTCAAGGTGCCAGCAGATTTGGTGTGTGATGAGGGCT 172076
mRNA     ACCTGAAGTCAAGCTCCCCCACCATTCGGCGGACAGC-GGCTGGATCAGCAGTGAGCATC 982
          *  *     ** ** *    **  ** **    ****  *     **    *   ****
genome   GCTCTCTGCTTCATAGATGGCATCTTCTGGCTGGGTCCTCACGGTGGAAGGAGTGAACAA 172136
mRNA     TGCCAGCACT-CAAGAAGGACACAATATTTCTATAGT-TGGCTACTAAATGTGCTCTTAG 1040
          *    ** **      *  ** **   * * **    * *     ** * *     *
genome   GCTCCCTCAGGCCTTTTAGAAGGGCCCCAATCCACAAGGGCTCTCCCATCATGACCTCAT 172196
mRNA     GCTTACTC-GTTCCTGTCGAGGATGAACACTCCACTCTG-CTGATTCTTGGCGTGCTGCT 1098
         ***  *** *  *  ***  *   * ** *  * *****  * *    *   *   *
genome   CACCTCCCAAGGCCCCACCTTCTTGTACTGTGGCACTGCAAATTAGGTGTCAGTGTAGGA 172256
mRNA     CACC--CTGAGGTATTTGGTGCCCTTGCTGCAGCA--GCAGGTCA------AGGACACAA 1148
         ****  *  ***       *  *  *  ***  ***  ***   **      * *  *
genome   GTTTCAGGAGGGATAGAAACATTCAGACCATCCCAGCGGTCAAGTGTTCATCCTCTTGAG 172316
mRNA     GCCT---GAAAGGCAGCTTCGGAGTGACAAGGAAAGAAATGGAAGTCTCTCCTTCTGCAG 1205
         *  *     ** *  *   *  *  **     ***  * *  ** *  **  * *  ***
genome   TTCCTCCTTATTCTGCTTCTGGTTTATCAGGATTCAGCCAGTGCAGCAT-GGTACCTGTA 172375
mRNA     AGCAGCTTGTCCAGGTTTATGAACTGAC--GTTACATCATACACAGCACCAAGACCACAA 1263
           *  *    *  * ** **   *    *   * * * *   *****     ***  *
genome   TTCTGTGGCACATCACCACATGGTATTTGC--CAAGTATCCATCACCTGCACACGTGAAA 172433
mRNA     TGTTGTGAC-CGGAGCCCTGGAGCTGTTGCAGCAGCTCTTCAGAACGCCTCCACCCGAGC 1322
```

FIG. 1 HHHHHH

```
              *  ****  *  *      **          *      ****  **    *  **  **        ***  **
genome        TCATTGCCCGTGGGTCCCGACATCTGGCGAAGCATATTCAAGGATGGCAGAACTGTCAGA 172493
mRNA          T-----TCTGCAAACCCTGACCGCAGTCGGGG-GCATT-GGGCAGCTCACCGCTGCTAAG 1375
                   *  *        **  ***      **  ***        ***    **        *  **
genome        GCTGGCACCTCTGGTTCCTTGTCAT-GTGGCATTACCTAGTAATCCATTTTATGATAGCA 172552
mRNA          GAGGAGTCTGGTGGC-CGAAGCCGTAGTGGGAGTATTGTGGAAC-----TTATAGCTGGA 1429
                *    *      ***      *  *  * ****  *   **        ****      *  *
genome        ATGGAAACTCATTTCTTCAACAAACACCTGAGTGGCTGCCGTGTGCCAGCCGTCTGGGGC 172612
mRNA          GGGGG-------TTCCTCATGCAGC-CCTGTCCTTTCAAGAAAACAAAAAGGCAAAGTGC 1481
                **        ***  ***      *    * ****                *        *  **
genome        CCTTGGTGAGAATGGCATGGTGGTGCCCATCAGGGCCTGCCTAGCCCGTGCTCTGG-ACG 172671
mRNA          TCTTAG-GAGAA------GAAGAAGCCTTGGAGGATGACTCTGAATCGAGATCGGATGTC 1534
              ***  *  *****          *    *  ***          ***          **          **  *  **  *
genome        GGCTCCTGTGTGTCAGGAACGACAATGCTGTCATGACGGTGAATGATTTTTTTTTTTGCC 172731
mRNA          AGCAGCTCTGCCTTAACAGCCTCAGTGAAGG-ATGA-GATCAGTGGAGAGCTG----GCT 1588
               **    **  **  **      *    *    **  **          ****  **    *          **
genome        ATCACTCCAGCCGCTAACATTTGCGGAGCTCTTCCTCCCGCACCCCCACCTGACAAGGCC 172791
mRNA          GCTTCTTCAGGGGTTTCCACT--CCAGGGTCAGCAGGTCATGACATCATCACAGAACAGC 1646
                 ***  ***      *    **  *    *                *      *  **  *  ***        *
genome        AAGGGTGACCTTGGCCCCACCCTAGGCGGCCAAGGTCAGAGGTTAGCTGGCTTGTCTGGG 172851
mRNA          CACGGTCACAGCA--CACACTGCAGGCGGAC----TCAGTGGAT--CTGGCCAGCTGTGA 1698
                 *  ***  **    *  ***    ******  *          ****  **      ****  *
genome        TCACACAAAATGCAGCAGAGGTTGAGGTGAGCACATGTCCGTGACCTGGAGCCTGACTCC 172911
mRNA          CTTGACAAGCTCTGCCACTGATGGGATGAGGAGGATATCTTGAGCCACAGCTCCAG-CC 1757
                  ****          *        **      *    *  ****    *                *  ***      ***        *    **
genome        CTCTCTGCGA-GTCTTGACTGCTCTTGCCTAGACTCTGTCCTCCCCGAGCCCAAACGCCA 172970
mRNA          AGGTCAGCGCCGTCCCATCTGACCCTGCCATGGACCTGAA-TGATGGGACCCAGGCC--- 1813
                **  ***  ***        ***      *  ****  **  *  ****          *  ****  *
genome        GTCATCTTCCCTTGTGGGTGTCCTTCAGCCTGGTGCCATGCTGG-TGACTCAGCAG---- 173025
mRNA          -TCGTCGCCCATCAGCGACAGCTCCCAGACCACCACCGAAGGGCCTGATTCAGCTGTTAC 1872
                **  **    **  **          *        *    ***  **          **      *  ***  ****** *
genome        CCGTCCAGGGAGTGGAAACAATTGAGTGTGTGGGTTCCCTGTGTGGGCATCTC--TCTTC 173083
mRNA          CCCTTCAGACAGTTCTGA-AATTGTGTTAGACGGTACCGACAACCAGTATTTGGGCCTGC 1931
                **  ***    ***        *  *****  **    *  ***  **        *  ***  *          * *
genome        ACGGCGAACACCCTCTGGGTGTTGCCCACACGATGTCAAAGCGGCTCTTGGAAGGGGTCC 173143
mRNA          AGATTGGACAGCCCCAGGATGAAGATGAGGAAGCCACAGGTATTCTTCCTGATGAAGCCT 1991
                  *      *  ***  **  *  **  **      *      *              **        **          **  *  *  *
genome        TTCTCCTTTGTGGGAAGTTTCAGCTGCTGGGCTAACTTGAATTGTAACTGTGGTTTTGTG 173203
mRNA          CGGAGGCCTTCAGGAACTCT----TCCATGGCC--CTTCAACAGGCACA-----TTTATT 2040
                   *        *  ****  **        *    *  ***      ****        ***  **
genome        CTCAGGCCCAGATCCCCCTAGGCAAGTGTTGTGCCATCAGTAATCAAATGAGAAATAATC 173263
mRNA          GAAAAACATGAGTCACTGCAGGCA-GCCTTCTGACAGCAGTGTT-----GATAAATTTGT 2094
                 *  *        **  *    *****  *  **  **  **  ****  *        **  ****
genome        ATTTTGAAAAGCAGATCCTAAGGCAGGATGGTCATGGACACTCACTCCCAGCTCTTTGTG 173323
mRNA          GTTGAGAGATGAAGCTACTGAA-CCGGGTGATCAAGAAAAC--------AAGCCTTGCCG 2145
                **  **    **  **  *      *  *  **  **  ***  **    *  *        *        *    ***
genome        CACTCATGCTTTCTGGAAGATGGCCATCCTCTG-TGAAGGTTTTCAGCGCGTCATGCTTG 173382
mRNA          CATCAAAGGT----GACATTGGACAGTCCACTGATGATGACTCTGCACCTCTTGTCCATT 2201
              **    *    * *          *        *        *  ***  ***  ***  *    *        *          *  *  * *
genome        GTACCCACGTATCCAGAGCATGTCGTTTTGAGGTATTTGCCCACCGTTGTGAAATCCGTG 173442
mRNA          GTGTCCGCCTTTT------ATCTGCTTC----GTTTTTGCTAACAGGGGGAAAAAATGTG 2251
              **    **  * *      **    **            **  *  **        **  *  *****  **    *    ***    ***
genome        CCACCCGAGAGCAGGTCCTGATGTGGGCTTTCAGAAGTGGGACCTGGGGCCGTACGCAG 173502
mRNA          CTGGTTCCGGACAGG----GATGTGAGGGT--CAGCGTGAAGGCCCTGGCCCT----CAG 2301
                *            *  ****        ******  **    ***              *  **    **  **            ***
genome        TCCTTAGGGAGGGGCCGTGTGGCGTTGTGCGTGTGAGGGGATAGCACAGGGTGAGGTGGG 173562
mRNA          CTGTGTGGGAGCAGC--TGTGGCCCTCCACCCGGAATCTTTCTTCAGCAAACTCTATAAA 2359
                       *  *****  **  ******  **    *    *        *          *
genome        GGCCC----AAGAAGGAAGTGACCCACAAAGAACAGCCTCCTCTTTTGGTCCTTGTTCCT 173618
mRNA          GTTCCTCTTGACACCACGGAATACCCTGAGGAACAGTATG-TCTCAGACATCTTGAAC-T 2417
                  *  **        *  *        *    **        *  ******  *    ***          ****  *  *
genome        GGGATGGCTGGGAGTGGCTTCTGTGTCGTCCGGCCATTTCCCCTG-CGGAGAGGCTCCTA 173677
mRNA          ACATCGATCATGGAGACCCACAGGTTCGAGGAGCCACTGCCATTCTCTGTGGGACCCTCA 2477
```

FIG. 1 IIIIII

```
genome   CCACTGCCGAGAACCTCATCATTCCACAAAAACAAGAGGCCGCCTGGCCATCCAGCGCTC 173737
mRNA     TCTGCTCC---ATCCTCAGCAGGTCCCGCTTCCACGTGGGAGATTGGAT-----GGGCAC 2529
          *   **   * *****  **  * *   ** ** **  *  ***     *  ** *
genome   CATGGGAATTCTGTGTCCCCATAGTCTTGGGCTGAAGGAGGGTGA-CATTCCTTGCTGA- 173795
mRNA     CATTAGAACCCTCACAGGAAATACATTTTCTTTGGCGGATTGCATTCCTTTGCTGCGGAA 2589
          ***   ***    **       **      ***  *   * **  **** ***  **
genome   ----CTTCTGCAGGGGTCTCCTCACTGTTAAAGAGCAGATTGAAA----GTGAAGAAC-G 173846
mRNA     AACACTGAAGGATGAGTCTTCTGTTACTTGCAAGTTAGCTTGTACAGCTGTGAGGAACTG 2649
             **    * * * **** **    **  *   ** ***  *    **** **** *
genome   TGGGCTAAGTGTTTAGGTCGATATTTAACCCTGCTAGGTTTTGGATACTAAGTGAAATTG 173906
mRNA     TGTCATGAGTCTCTGCAGCAGCAGCTA---CAGTGAG--TTAGGACTGCAGCTGA--TCA 2702
          **  *  ***  * *   *  *   **  *  **  **  ***     *  *** *
genome   AGGCCATTTTGGTTGAAGTTGACAGAAACCACTATCAGGGATCCCCAAGACTACCCCAGG 173966
mRNA     TCGATGTGCTGACTCTGAGGAACAGTTCCTATTGGCTGGTGAGGACAGAGCTTCTGGAAA 2762
             *   * **  *     ****   *  *  **      **   ** **   *
genome   CTTTTCTAGAAA--GACTCTCAGCTAAGATGTGTTATGGTAAAAGCACACAAAACAAAAT 174024
mRNA     CCCTTGCAGAGATTGACTTCAGGCTGGTGAGCTTTTTGG-----------AGGCAAAAG 2810
          *  **   *** *  ****    ***    *  ** ***        *  *****
genome   CAGCAAAGAAAATTAGCAAGGGCAGAGGCCCATGGGGCGATGTCCCGAGGACACCAGGCT 174084
mRNA     C-----AGAAAACTTACACAG--AGGGGCTCAT----CATTATAC--AGGGCTTT----T 2853
          *     ******  ** **   ** *** ***      *  *  ***    *
genome   TGAGCTTCCAGAATCCTCTCCCAGCGGGGTCGTGCAGGACGCACTTAACTCCCCGCACAG 174144
mRNA     AAAACTGCAAGAACGAGTGCTCAATAATGTTGTCATCCATTTGCTTGGAGATGAAGACCC 2913
            ** * ****   * **    ** **   *   ***          **
genome   TGAGCCGTGACAGCGCGTGTGCAGTGTCGTCGCCAGGAAAGCACACTAGAGACTCGGTGC 174204
mRNA     CAGGGTGCGACA---TGT-TGCCGCAGCATCACTAATTAGGCTTGTCCCAAAGCTGTT-T 2968
          *  **** **   ** *** * **  * **    ***     *  *  *
genome   CAGGGTTTTTACTGGGGGCTGGGCACATGGGCACCCTCTGCCTGCCTCGTGCCCAGACTC 174264
mRNA     TATAAATGTGACCAAGGACAAGCTGATCCAGTAGTGGCCG--TGGCAAGAGATCAAAGCA 3026
          *   * ** ****  *  *      * *    * ** ** *  * *  ** *
genome   TGGACTCCCGGAGGGAAGGCAAGTTCTCA-GCACCAACCCTGGTGCCCA-CACAAGCAGC 174322
mRNA     GTGTTTACCTGA-------AACTTCATGCATGAGACGCAGCCTCCATCTCATTTCTC 3078
          *  * **  **         ** ****** **   * *    ****  *
genome   TGAGCACAGGGAGCCCCTCCTCAGTGAGGATGGTGGGCACCGTCCCAACACCAGCCAGGG 174382
mRNA     CGTCAGCACAATAACCAGAATATATAGAGGCTATAACCTACTACCAAGCATAA--CAGAC 3136
          *    **    **   *   *    *    *    *    ** * ***  *   ***
genome   GCCAGCCTTGCACACAGGCCTCTCAGGATGGTCTCCGGCCTGCTGTGTAGTCTCTTCTGC 174442
mRNA     GTCACTATGGAAAATAACCTTTCAAGAGTTATTGCAGCAGTTTCTCATGAACTAATC-AC 3195
          * *   ** *  ***  **       * * *** ** **  *  * * *  ** **
genome   ACACAAGCGTGAGGGCAGCGCCCCCGCCTCGGCTGTGGGGAGGAGCCACTGGGACGTGAG 174502
mRNA     AT-CAACCACCAGAGCA----CTCACATTTGGATGCTGTGAAG---CTTTGTGTC-TTCT 3246
          *  *** *  ** ***     *  *   * ** * ** * **      * ** * *
genome   CTCTGGTGGCATGCAGCAGCTTTTGTCTGTGTGTGCCTAGGACAAGGCCGTGGCGGAGCC 174562
mRNA     TTCCACTGCCTTCC--CAGTTTGCATTTG---GAGTTTAGGTTGGCACTGTG---GAGTG 3298
          **    **  ***    *** **  *** *    * ****   *** ***    ***
genome   TGTCAGCCGCCTGCTGGAGAGCACGCTCAGGAGCAGCCACCTGCCCAGCAGGGTTGGAGC 174622
mRNA     CCTCCACTGAGTGCCTCAGATGA-GTCTAGGAAGAGCTGTACCGTTGGGATGGCCACAAT 3357
          **  *  ***  ***  * *    **** ***            *  **       *
                          rs362272
genome   CCTGCACGGCGTCCTCTATGTGCTGGAGTGCGACCTGCTGGACGACACTGCCAAGCAGCT 174682
mRNA     GATTCTGACCCTGCTCT---CGTCAGCTTGGTTCCCATTGGATCTCTCAGCCCATCAAGA 3414
          *  *      * * ****   *     *  *    **** *  *     * *** * **
genome   CATCCCGGTCATCAGCGACTATCTCCTCTCCAACCTGAAAGGGATCGCCCAGTGAGTGGG 174742
mRNA     TGCTTTGATT-TTGGCCGGAAACTTGCTTGCAGCC----AGTGCTC-CCAAATCTCTGAG 3468
          *   *   *  **    * **  * **  **      ** **** **  **  ** **
genome   AGCCTGGCTGGGG-CTGGGGCGGGGGTC---TCAGAATGAGCTGTGAAGGAAGCAGCATC 174798
mRNA     AAGTTCATGGGCCTCTGAAGAAGAAGCCAACCCAGCAGCCACCAAGCAAGAGGAGGTCTG 3528
          *   *  ** *  *      *  *   *   ***     *  *    **   **  **
genome   ACCCTCTCCAAGTGCCCAGGCTCCTGGCCAGATGGCAGGCCAGGTATCAGTGGGAACCC- 174857
mRNA     GCCAGCCCTGGGGGACCGGGCCCTGGTGCCCATGGTGGAGCAGCTCTTCTCTCACCTGCT 3588
          **   *    *   * ** ***  *   * *** *** ** ** * *  *  *       *
genome   --AGGTGGGTGCCAT----GGCTGAGGTCAGTGAGACGCAAGAGCACAGGTGCGTCCTAG 174911
```

FIG. 1 JJJJJ

```
mRNA      GAAGGTGATTAACATTTGTGCCCACGTCCTGGATGACGTG-GCTCCTGGACCCGCAATAA 3647
          *****  *  ***      *  *    *   * *   ****   *  *    *  **   **
genome    AGGCTTCCTCGGGCACCTCCAGCGAGCTGGAGCTCTCGCCTCTGCTGCTGTCTCATGTGG 174971
mRNA      AGGCAGCCTTGC-CTTCTCTAACAAACC----CCCCTTCTCTAAGTCCCATCCGACGAAA 3702
          ****  ***  **  * ***  ***  *      *  *   *    *   *   **
genome    CGCTTAGCACACTCTCCCACGTGCCCATTCCTGACTCTGCTCTCGAGGCCATCGGCTCTC 175031
mRNA      GGGGAAGGAGAAAGAACCAGGAGAACAAGCAT--CTGTACCGTTGAGTCCCAAGAAAGGC 3760
            *   ** * *    ***  ***  *  * *  ** *   *  ***  **   *     *
genome    ATTCTCTGCTCCCAGAACCCTGTTATTACCCAGGCTAGCCTCCTCTCTGCACCTTCCCCG 175091
mRNA      AGT----GAGGCCAGTGCA--GCTTCTAGACAATCTGATAC---CTCAGGTCCTGTTAC- 3810
          * *      ***  *     *  **  *   *  **   **    *** *  ***    *
genome    CCCTGGCCCAGTACCTCCCTCTTGTTTCCACTGTGATTCCGACCTCACCTTAT-CTTAAA 175150
mRNA      -----AACAAGTAAATCCTCATCACTGGGGA-GTTTCTATCATCTTCCTTCATACCTCAA 3864
               * ****  ***   *   *    **    *  * ***   **   ** * **
                                   rs362271
genome    GCTGCTGGACGGCAGGTTCT[G]TACACACGTGTCCTTGACAAAGCACGGCTGGTGCCGCAA 175210
mRNA      ACTGCATGATGTCCTGAAAGCTACACACGCTAACT--ACAAGGTCACGCTGGATCTTCAG 3922
            ****  **  **  *  *  ********   **   ****  *****   **   * *
genome    CCCCTCAGCGAGCAAGTCA-AGCTCTTCACAGCGATGTCTTACAAGCGCAGAGGGCTCTG 175269
mRNA      AACAGCACGGAAAAGTTTGGAGGGTTTCTCCGCTCAGCCTTGGATGTTC-------TTTC 3975
            *   **  **   *   *    **   ***  **   * ***  *  *        * *
genome    TGACACCCTGGTCTCACCGCCACTCTTCCAAA-GTCGCAGAGGCTTTAGCAGAGATGGGC 175328
mRNA      TCAGATACTAGAGCTG--GCCACACTGCAGGACATTGGGAAGTGTGTTGAAGAGAT---C 4030
          *  *   **  **    ***** **  *    *   *  **   *   *  ******    *
genome    CCAGCCTCTCTGAGTCATAGGCTTCTGCACACGGGAGCTGTCTTTAGAGGGAGGGTGGAA 175388
mRNA      CTAGGATACCTGAA----ATCCTGCTTTAGTCGAGAACCAA--TGATGGCAACTGTTTGT 4084
          * **  *  ****        *  ** **   *  ** **    *   *  *    **
genome    TTTCATCAGCCACCCACATGGGGGAGTTGAGGGCAAGAATTAGGAGCAAAGATGGGAAGG 175448
mRNA      GTTCAACAATT-------------GTTGAAGACTCTCTTT-GGCACAAACTTGGCCTCC  4129
           ****  **              ***** *  *         ** **  *     *
genome    GGTCTGGGAGGAATGGCCAGTGATCCCCTTTGACAAGTGGGCAGGAAACGGGGGCTAGGT 175508
mRNA      CAGTTTGATGGCTTATCTTCCAACCCCAGCAAGTCACAAGGCCGAGCACAGCGCCTTGGC 4189
             *  **   *   *      * ***        *   *** *   **  *  ** **
genome    CAAAGTTGAGTGGAAGACCTGGAGGGAGACGGGAAGGTCTCTGTAGGCACAGTTCAGACA 175568
mRNA      TCC--TCCAGTGTGAGGCCAGGCTTGTACCACTACTGCTTCA--TGGCCCCGTACACCCA 4245
            *   ****  **   ** **  **  *  *  **        *** *  *   **   **
genome    GGAGGGAGGTGTGAGCCAGGGCACATGCCGGTGGCCGTCTGGCAGGATTTGGGACATGCT 175628
mRNA      C---------TTCACCCAGGCCCTCGCTGACGCCAGCCTGA-GGAACATGGTGCAGGC-  4293
                     *   **  *** **  *    *    ***    *   *   ***  **  **
genome    GGAGCAGGGACAGCGGCTCATCAGGGGCCATTGCCCTCATCCAGGCCAGAGTGTCACAAG 175688
mRNA      GGAGCAGGAG-AACGACACCTCGGGATGGTTTGATGTCCTCCAG---AAAGTGTCT---A 4346
          ********    *  ** * ** **    ***   ***   ** ***    * ******
genome    CCCGTGGGGAGGCCCTTCTCGCCTGTCATCCTTGCTGGGCAGTGGGTGCTGTGCTAGCAG 175748
mRNA      CCCAGTTGAAGACAAACCTCACGAGT----------GTCACAAAGAACCGTGC-----A  4390
          ***     *  * *   ***  *  **             *  **     *   * ****
genome    GACAGGCGGACGGCTGGCAACTGTCTCTGCATCCCTGGAGCCTGGCATAGGGCCAAGTCA 175808
mRNA      GATAAGAATGCTATTCATAATCACATTCGT-TTGTTTGAACCTCTTGTTATAAAAGCTTT 4449
           ** *   * *         *   *     * **  * ***  ***  *    *
genome    CACGGGGCACAGGCCTGCAAATCAGGCACATATGTTGGTGCAGTGACGTGATTTTGGGGG 175868
mRNA      AAAACAGTACACGACTACAA------CATGTGTGCAGTTACAGAAGCAGGTTTTAGATTT 4503
            *     * ***  *  ***        *   *  *   *****  *   *    * ****
genome    GCAGCCCCAGAACAGGCCCCAGACACAGGCCAAAGCCCTGCCTGTGCTGGTGTGTTGGGC 175928
mRNA      GCTGGCGCAG--CTGGTTC-AGTTACGGGTTAAT-TACTGTCTTCTGGATTCAGATCAGG 4559
          ** *  ***    ** ***       *** **  ***         **     *   *
genome    TGTTCTATGGCTCTTGCTGTGGGCATGGAGGACTCAGGGAAGGAGAGTTGAGGTGGTCCA 175988
mRNA      TGTTTATTGGCTTTT--------GTATTGAAA---CAGTTTGAATACATTGAAGTGGGCCA 4608
          ****  ***** *         *  ** ***    ****   ****  ***
genome    GGAGTTGCGTTTGGGATGCAGAGAGCTTGTGGCATCCAGGTAGAAATGGTGCGTGGGGCT 176048
mRNA      G-------------TTCAGGGAATCAGAGGCAATCATTCCAAA------CATCTTTTT   4647
          *              *  *** ** ****  **    **   ** * *
genome    GACCTCAGCACCATGGGCAGAGGGGCCGTGTCACGTGCCTCCGAGGTGGAGGTGGGACCA 176108
mRNA      CTTCTTGGTATTACTATCTTATGAACGCTATCAT-----TCAAAACAGATCATTGGAATT 4702
           **    *    *   *  *  *   * *  ***     **   *     *   ***
```

FIG. 1 KKKKKK

```
genome  CGTGGTGACAGATATACGCATCACTGGGCACGTTTTTGTGGGTGTTGGGGGGCATCGTAT  176168
mRNA    CCT------AAAATCATTCAGCTCTGTG-ATGGCATCATGGCCAGTGGAAGGAA------  4749
         * *          *  * *** *   * * ** * genome  TGGCTCCTCTGTTCACAGTGGCCACTCATTCAGTCCCTGGCTACCAGGTCCTCACTGTGC  176228
mRNA    -GGCTGTGACACATGCCATACCGGCTC-TGCAGCCCATAGT--CCACGACCTCTTTGTAT  4805
         ****      *  *   *** * *   *   *   *** * **  * genome  CATGGGGAAGGCCGGCGCTGTCGGGGGATCACAGAAGGCAGCACGTCATGATGGCATGTG  176288
mRNA    TAAGAGGAA------------------CAAATAAAGCTG---------------------  4826
         * * **                    *   * genome  CCATGAAGGAAAAGCACAGGGCACTCAGGAAGTAGAGGGGACTGGCCTGGGGTGTGGGAA  176348
mRNA    --ATGCAGGAAAAGAGCTTGAAACCCAAAAAG-AGGTGGTGGTGTCAATGTTACTGAGAC  4883
           * ******   *       *          * genome  TC-TAGGGCCTCGTTGAGGGACAGAGAGAGGAAGTGTGTGGTGGCCAGCATGGAGGTGGC  176407
mRNA    TCATCCAGTACCATCAGGTGTTGGAGATGTTCATTCT----TGTCCTGCA--GCAGTG-C  4936
        ** *   *   * *        **  * *     *  *    * * genome  CACAGGGGAGGCTGAGTTAGGCCGAGAGGGCAGGGCGTTGGGGAGGTAGACGGGCTCAGC  176467
mRNA    CACAAGGAGAATGAAGACAAGTGGAAGCGACTG---TCTCGACAGATAGCTGACATCATC  4993
        **        **  * *   *  *  * *   *   *  *    *** * genome  CACTCAGGGAGTGGTCAAGCAGAGGCTGAAGGGTCAGGCCAGGTTGCAGGGGCCTGGGGG  176527
mRNA    CTCCCAATGT-TAGCCAAACAGCAGATGCACATTGACTC----TCATGAAGCCCTTGGAG  5048
        *      *    *   * *  *    * *       *  *   *  * genome  AGCCACTCAGGGTAGGCGCTCCCGGGAGCCCGCCTGGCCCATAGCTCTACACTCCCGCGT  176587
mRNA    TGTTAAATACATTA------TTTGAGATTT----TGGCCCCTTCCTC----CCTCCGTCC  5094
         *    *    **       * **     *    ****** *  ***      * *** genome  GGGGCCGGACATGCTGTGAAGCCCTCTCCACGTTGGATGGGGGTGGCTGAGCCTGGATGC  176647
mRNA    GG---TAGACATGCT----------TTTACGGAGTATGTTCGTCACTC--CAAACACAA  5138
            ******            *  *** * *    **  *      * genome  TGTCTCCCGTTTTCAGCTGCGTGAACATTCACAGCCAGCAGCACGTACTGGTCATGTGTG  176707
mRNA    TGGCGTCCGTGAGCA-CTGTTCAACTGTGGATATCGGGAATTCTGGCC--ATTTTGAGGG  5195
        ** *  **      *   *  *   *  *  *    * **    * * genome  CCACTGCGTTTTACCTCATTGAGAACTATCCTCTGGACGTAGGGCCGGAATTTTCAGCAT  176767
mRNA    TTCTGATTTCCCAGTCAACTGAAGATATTGTTCTTTCTCGTATTCAGGAGCTCTCCTTCT  5255
           *    *   *    *   *  ***     *   * *  *** *   *   * genome  CAATAATACAGGTGAGTGGGCCCTGGCTGTCTTCCTCTGCACACGGGGAGTGGGCTTCCC  176827
mRNA    C-----TCCGTATTTAATCTCCTGTACAGTAATTAATAGGTTAAGAGATGGGACAGTAC  5310
        *       *   *  *    *    *   *   *  * *   * *** genome  TTCTCTTTTCCTTGCAGGATCATACCAGTGGGCCAGTTTTGACTTGGTCGGGAGGAGGCA  176887
mRNA    TTCA----ACGCTAGAAGAACACAGTGAAGGGAAACAAATAAAGAATTTGCCAGAAGA--  5364
        ***       *  ** * **  *   * **   *    *    *  * **  * genome  TGAACACCTGAGACTGTGCAGCGATTCTTTGACACAGAGGCCTTTCTCCCTGTGCAGATG  176947
mRNA    --AACATTTT--------CAAGGTTTCTATTACAACTGGTTGGTATTCTTTTAGAAGACA  5414
          **** *             ** * **  *  *  *   *     * genome  TGTGGGGTGATGCTGTCTGGAAGTGAGGAGTCCACCCCCTCCATCATTTACCACTGTGCC  177007
mRNA    T-TGTTACAAAACAG-CTGAAGGTG-GAAATGAGTGAGCAGCAACATA---CTTTCTATT  5468
          * **    *  *    *  * *** * *   *   * *   *    *   * * genome  CTCAGAGGCCTGGAGCGCCTCCTGC-TCTCTGAGCAGCTCTCCCGCCTGGATGCAGAATC  177066
mRNA    GCCAGGAACTAGGCACACTGCTAATGTGTCTGATCCACATCTTCA----AGTCTGGAAT-  5523
          ***   *  **  *  **  *   * * ****** *  **  *       **** genome  GCTGGTCAAGCTGAGTGTGGACAGAGTGAACGTGCACAGCCCGCACCG--GGCCATGGCG  177124
mRNA    ----GTTCCGGAGAATACACAGCAGCTGCCACTAGGCTGTTCCGCAGTGATGGCTGTGGCG  5579
             **   * **  *  *   *      *****  *   *  *** genome  GCTCTGGGCCTGATGCTCACCTGCATGTACACAGGTGAGCATGTACACGGTGCCCATAAG  177184
mRNA    GCAGTTT-CTACACCCTGGACAGCTTGAACTTGCGGGCTCGT-TCCATGATCACCACCCA  5637
                  **  *    * * **   *  ***  *  ***    * *** genome  GCCAGCCCAAGTCCTGTTCAAGGGAGGCAGGAGCATGCTCACTCAAGGGACCTCGACTAG  177244
mRNA    CCCGGCCCTGGTGCTGCTC--TGGTGTCAGATACTGCTGCTTGTCAACCACACCGACTA-  5694
                    *  *    *  *  * genome  GTGCCCTCTGATTT-CACACTTCTGGTGTTGCCCCAAGCCGGCCCCATC-ACCTTGCAAG  177302
mRNA    ----CCGCTGGTGGGCAGAAGTGCAGCAG-ACCCCGAAAAGACACAGTCTGTCCAGCACA  5749
              *  *    *     *  *   **** *    * *  *  *  ** * genome  AAAGGCTCTGGAGCCCCCAGGGCTGGAGTACCTGGTCAGGGTTGACCGTCCCTGTGGTCA  177362
mRNA    AAGTTACTTAGTCCCCAGATGTCTGGAGAA---GAGGAGGATT--CTGACTTGGCAGCCA  5804
        **       * *  *** * * ******     *** **  **    *  ** ** ***
```

FIG. 1 LLLLLL

```
genome  CTCATCCCATGTGGCTGAGCTGGGCTGGGTCCTGGGCAAGCAAGGGGCTGATATCACCTG 177422
mRNA    AACTTGGAATGTGC---AATAGAG--AAATAGTACGAAGAGGGGCTCTCATTCTCTTCTG 5859
         * *  *****    *  * *     * * * *   *           *  ** ***
genome  CTTTCAGATCTCCAGGGACTCACTGGACCCCTGTGTACAAAGCACTGTCTACAGAGCCTA 177482
mRNA    TGATTATGTCTGTCAGAACCTCCATGACTCC-GAGCACTTAACGTGGCTCATTGTAAATC 5918
         * *   ***     * **   * *** ** ** **  * *      *  *   *
genome  TTGGGTTGTATAGAGGTAACCTTCGTACTGAACACTTTTGTTACAGGAAAGGAGAAAGTC 177542
mRNA    ACATTCAAGATCTGATCAGCCTTTCCCACGAGC-------CTCCAGTACAGGACTTCATC 5971
          **      * ****       ** *          * *** * ****       **
genome  AGTCCGGGTAGAACTTCAGACCCTAATCCTGCAGCCCCCGACAGCGAGTCAGTG-ATTGT 177601
mRNA    AGTGCCGTTCA---TCGGAACTCTGCTGCCAGCGGCCCTGTTCATCCAGGCAATTCAGTCT 6028
        *** * * *     *   ** **  * *   * **    ** ** ** **  *   * *
genome  TGCTATGGAGCGGGTATCTGTTCTTTTTGATAGGTAAGAAGCGAAGCCC-CATCCCTCAG 177660
mRNA    CGTTGTGAAA-----ACCTTTCAACTCCAACCATGCTGAAGAAAACTCTTCAGTGCTTGG 6083
         * ** *       * **  *       *  *    ****  ** ** **   **  *
genome  CCGTTAGCTTCCCTAGAACTTTGGCCTGAAGCTGTGCTTTTG-TGTGTGTCTGCTGATCC 177719
mRNA    AGGGGATCCATCTCAG----CCAGTCGGGAGCTGTGCTCACGCTGTATGTGGACAGGCTT 6139
           *  *   *  **      *  * *********  * *** ***    *  *
genome  CCTGGCGCTGTTGCTGGAGTCCTGCCAGTGATTCCCCACCACAGCCTGACCATGGGCTGC 177779
mRNA    CTGTGCACCCCTTTCCGTGTGCTGGC---------------TCGCATGGTC---GACATC 6181
         *   ** *  *   * ** *** *              ** **  *    * * *
genome  CTTGGCTCAGGGTTCCACTGGCAGCCGAGCTGGTGGTCCTTGGACCCCAGCACTCAGGTGTAGC 177839
mRNA    CTTGCTT---------GTCGCCGGGTAGAAATGCTTCTGGCTGCAAATTTACAGAGCAGC 6232
        ****  *         *  ** * *     *   * *  * **  *      * * ***
genome  GTTGACCAGTTCCAAGGTTGTCCCAGTGCCTGCCCATCTCTCCTGAGGGCTCAGGGACAG 177899
mRNA    ATGGCCCAGTTGC---------CAATG---GAAGAACTCAAC--AGAATCCAGGAATAC 6277
         *  * ****** *           **  *    *   * **   **    **** *  *
genome  TACCTGGCAGTTGGGGGTGTGGCAGGGGGCAGGAATGACCAGCCTCTGGGAGGGTGGGGC 177959
mRNA    --CTTCAGAGCAGCGGGCTCGCTCAGAGACACCAAAGGCTCTATTCCCTGCTGGACAGGT 6335
          *  *   **  * ***  *     * *   ** *    **   * ***  * **  **
genome  AGAAGCCTGTACAGTGAGGAGGAGCTGGCTCAGCCTGGCTGCCTATCGTGAGAGGGGAGC 178019
mRNA    TTC-GTCTCTCCACCATGCAAGA-CTCACTTAGTC------CCTCTCCTCCAGTCTCTTC 6387
         *  ** **   * **  **  *  **  **         *** ** *     *
genome  CCACGGGGCTGTGGGAGGGGGGCCGTGGTGCCTGTGAGCAGGGTGAGGAGCAGCGGCAGG 178079
mRNA    CCAC----CCGCTGGACGGGGATGG--GCACGTGTCACTGGA------AACAGTGA-GTC 6434
        ****     * * *** ****       * *  ***  *            * *** *
genome  AGGATGAAGGTGGAACCCACACATGCATCTT-TGAGACCCGTGTGGTCAGTGGCTTCTGC 178138
mRNA    CGGACAAAG-----ACTGGTACGTTCATCTTGTCAAATCCCAGTGTTGGACCAGGTCAG- 6488
         *** ***       ** *  ****** *  * * *   *** *   **  *    *
genome  CCCCCACCACCCCCCACTGCTGTGCGTGCATAGAATTGGCTTCCCTCACCTGCTCTGGAA 178198
mRNA    --------ATTCTGCACTGCTG-GAAGGTGCAGAGCTGGTGAATCGGATTCCTGCTGAAG 6539
                 *  * ********  *    *** ***   * *       *** *
genome  GTGGGTTAGGAGCTTGGTAGGGCTTTTTCTCAAGGACAAGGGCCCCTGATTTGCTCTCAG 178258
mRNA    AT--ATGAATGCCTTCATGATGAAA----CTCGGAGTTCAA---CCTAAGCCTGCT----A 6586
         *  *    **   *  *    *      *** *   ** *   **   * ****
genome  GCCTCAGTCCTGGCGACATGGTGGATCTGGAGCCTTGTTGCACTGCCTTGCCTGTGCTCT 178318
mRNA    GCTCCATGCTTAAGCCTAGGGATGAGTGAAATTTCTGGTG----GCCAGAAGAGTGCCCT 6642
        ** **  *   *    *  **  **    *   * **  ***          **** **
genome  CCAATCAGGGTGGCCAGTGGGGAGCCATTTGGCTTTTCTCAAGAGCATACT-CAGGTGGA 178377
mRNA    TT--TTGAAGCAGCCCGTGAGGTGAC-TCTGGCCCGTGTGAGCGGCACCGTGCAGCAGCT 6699
          *       *** *** **  * *   ***   *    **   * ***  * *** *
                                          rs3775061
genome  CCTTGCT--CCACTGT-TTGACCAGATGAGGC[A]TTCTGAACAGCCAAGCCTGTGCTGGTC 178434
mRNA    CCCTGCTGTCCATCATGTCTTCCAGCCCGAGCTGCCTGCAGAGCCGGCGGCCTACTGG-- 6757
        ** **** ***  *  * *    **** **  *  ** *** **  *  ***  * ***
genome  TGTTTTCATGTTGATTTTTTTTTTCTTTTCTTTTTGAGATGGAGTTTTTCCCTTGTCAC 178494
mRNA    ----AGCAAGTTGAATGATCTGTTTGGGGATGCT---GCACTGTATCAGTCCCTGCCCAC 6810
            ** ****** * * * ***     *   *      *  *  *  *****   ***
genome  CCAGGCTGGAGTGCAATGGTGTGATCTCGGCTCACTGCAACCTCCGCCTCCCGGGTTCAA 178554
mRNA    TCTGGCCCGGGCCC--TGGCACAGTACC---TGGTGGTGGTCTTCCAAACTGCCCAGTCAT 6865
         * *** * ***    *** **  * **   * *  *  ** ****  ** *** * *
genome  GTGATTCTCCTGCCTCAGCCTCCCTAGTAGCTGGGATTACAGGCACACACCACCATGCCC 178614
mRNA    TTGCACCTTCCTCCTGAGA------AAGAGAAGGACATTGTGAAATTCGTGGTGGCAACC 6919
```

FIG. 1 MMMMMM

```
              **   ** *  *** **       *   **  **     *     *     *  *         **
genome    AGCTAATTTTTGTGTTTTAGTAGAGACGGGGTTTCACCGTGTTGGCTGGGCTGGTCTCG 178674
mRNA      CTTGAGGCCCTGTCCTGGCATTTGA---------TCCATGAGCAGATCCCGCTGAGTCTG 6970
              *   ***  *** *   * **         **    *     ****   *
genome    AACTCCTGAACTCAAGTGATCCACC-CTCCTTGGCCTCCCAAAGTGCTGGGATTGCAGGC 178733
mRNA      GATCTCCAGGCAGGGCTGGACTGCTGCTGCCTGGCCCTGCAGCTGCCTGGCCTCTGGAGC 7030
               *    *    *    **    *    ** *****   **     ****  *      **
genome    GTGAGCCACTGCGCCCGGCCCCCATGTCGATTTTTAAATGCACCTCTGCATCGTTCTTCA 178793
mRNA      GTGGTCT----------CCTCCACA--GAGTTTGTGACCCACGCCTGC----TCCCTCA 7073
              *** *         ** *** ** *** *    * *** ****     *  ***
genome    GTCCCCATATGCTCACTGAGCACCACTGCGACTGGCAGACGGGCACAGGGAGGCGCCACG 178853
mRNA      TCTACTGTGTGC------------ACTTCATCCTGGAGGCCGTTGCAGTGCAGCCTGGAG 7121
              *  * ***           ***    *     * ** *    *** * **         *
genome    ACCAGTCCTGGCCTTCAAGGGGCTTGTGGTCTAGTGGGCCCAATGCTAGGTGGCGAGTGC 178913
mRNA      AGCAGCTTCTTAGTCCAGAAAG---AAGGACAAATACCCCAAAAGCCAT-CAGCGAG--- 7174
              * ***    * **         *       ** * **      ** **  **  *       *****
genome    TCCAAAGAGTGTGGTGCACGCCTTCCGCTTGACCGCTCTCCAGACGCCACAGGGAGGCAC 178973
mRNA      ---GAGGAGGAGGAAGTAGATC--CAAACACACAGAATCCTAAGTATATCACTGCAGC-- 7227
                 * ***   *    *   * *       *    **   *  *     **   *  **
genome    CTCGCAGCTGACCACAGATTTCTCTCTGTGGAGCAGTGTCTTCAGAGCG-GCTGCCATGC 179032
mRNA      CTGTGAGATGGTGGCAGAA-------ATGGTGGAGTCTCTGCAGTCGGTGTTGGCCTTG 7279
              ** ** **   ****        *** *** ***  *     * ** ** *
genome    CACTGCTGGGCGAGGGTCTGCGGGCGGGTAGAGCCAGGAGCACCTGTGAGGAAGTGCACT 179092
mRNA      GGTCATAAAAGGAATAGCGGCGTGCCGGCGTTTCTCACGCCATTGCTAAGGAACATCATC 7339
              **      * *** ** **      *        **     * *****     **
genome    GCCATTTTCGTAGCTGCTTCCCGTGTGTCT-CAGTTACACACGGCTGGCATGTGTGCACT 179151
mRNA      ATCAGCCTGGC--CCGCCTGCCCCTTGTCAACAGCTACACACG-----TGTGCCCCCACT 7392
              **   *   * ** * **  ****  *** *******      **     ****
genome    GATGAGACGGGAACGTGATGGTTGCTTTTCAGCACTGAAAGGGATACTGCTCAGGGGGCG 179211
mRNA      GGTG---TGGAAGCTTG--GATGGTCACCCAAACCGGGAGGGGATTTTGGC---ACAGCA 7444
              * **      ** **  **   * **       **    * * *****  **      **
genome    TGTTTCAGGATCTGGTTAGGGAAGAAGCAGCGAGAGCACAGATGGGGCCCTGTGTGGTAA 179271
mRNA      TTCCCTGAGATCCCCGTGGAGTTCCTCCAGGAAAAGGA-AGTCTTTAAGGAGTTCATCTA 7503
              *    ****  *  * *    *** *    *** **                 *    *
genome    CAAGAAAAAGTCCTGGTTGACAACAGTGCCACGAAGCGTTAGAACACATAGGGATGTTT 179331
mRNA      CCGCATCAACACACTAGGCTGGACCAGTCGTACTCAGTTTGAAGAAACTTGGGCCACCCT 7563
              *   *   **    **  *    * ****   **    **   * *   * ** **         *
genome    GTGGAGCATTTGCATGTGGAAAGCAGCAAAAACATAATGGGAACGGGTTCTTTTGTTATG 179391
mRNA      CCTTGGTGTCCTGGTGACGCAGCCCCTCGTGATGGAGCAGGAGGAGAGCCCACCAGAAGA 7623
              *  *  *  *  * *  *   *  *   *          *    *    *  *   *
                                                                ┌─────────┐
                                                                │rs362310 │
                                                                └─────────┘
genome    ATTTTTAAAAATCTCTTTTGT-AACATCCTTCCCGC-TG C GCCGTTTCTGCA-TATTCCT 179448
mRNA      AGACACAGAGAGGACCCAGATCAACGTCCTGGCCGTGCAGGCCATCACCTCACTGGTGCT 7683
              *       * * *   *     * ***  ****  ***   *** ***  *  *** *   **
genome    TTATGTAGCTTTCAAACTCCTCTTAGGAGTTCTGGTCCCTACAGGGCGTGGGAGCCCAGG 179508
mRNA      CAGTGCAATGACTGTGCCTGTGGCCGGCAACCCAG-CTGTAAGCTGCTTGGAGCAGCAGC 7742
                ** *         *         * *   ** *         *   ** ***         ***
genome    CTTTACGTAGCTTTCAAACTCCTCTTAGGAGTTCTGGTCCCTACAGGGTGTGGG----AG 179564
mRNA      CCCGGAACAAGCCTCTGAAAGCTCTCGACA--CCAGGTTTGGGAGGAAGCTGAGCATTAT 7800
              *       *   **   ****     *   * ***      *     **  *
genome    CCCAGGGCCTGTGCCGAGCAGCCTGCCTCCACGAGCTAGACAGAGGAAGGGCTGGGGTTT 179624
mRNA      CAGAGGGATTGTGGAGCAAGAGATTCAAGCAATGGTTTCAAAGAGAGAGAA-TATTGCCA 7859
              *  ****  ****    *   **   *   **  *  * **** **   **   *
genome    TGCCTTTTTAGTCTCAAAATTCGTACTCCAGTTGCTTAGGCTCTGACTTTCCCCACTTGG 179684
mRNA      CCCATCATTTATATCAGGCATGGGA-TCCTGTCCCTT---CTCTGTCTCCGGCTACTACA 7915
              *  *  **  * ***    * * *** **  ***   *****  **   * ***
genome    AAAGTCCCTCACGGCCGAGGGTCCCTCCCAGCCCTGATTTCACATCGGCATTTTCCCCAG 179744
mRNA      GGTGCCCTCATCAGCCACGAGAAGCTGCTGCTACAGATCAACCCCGAGCGGGAGCTGGGG 7975
              * **    * ***   **   **    *    **        *       *
genome    TATTAGAGCCAAGGCCCTCCGCGGGCAGGTGGGGCAGCTGTGGGAGCTGGTGCCAGTCTC 179804
mRNA      AGCATGAGCTACAAACT----CGGCCAGGTGT-----CCATAC-ACTCCGTGT-GGCTGG 8024
              ****  *        *** ******     *   *    ***  *
genome    TGACCTGCGTCCCTCCTCCCAGGATCAGGAAAGGCTTTCCTTGTGAAGCCAGAGTGGTGG 179864
```

FIG. 1 NNNNNN

```
mRNA     GGAACAGCATCACACCCCTGAGGGAGGAGGAATGGGACGAGGAAGAGGAGGAGGAGGCCG 8084
         *  *  **  **  *  **    *      *  ** *       *    * **  *
genome   CCAGGATCCTGCCCCAGTTTCTAG--ACGACTTCTTCCCACCCCAGGACATCATGAACAA 179922
mRNA     ACGCCCCTGCACCTTCGTCACCACCCACGTCTCCAGTCAACTCCAGGAAAC-----ACCG 8139
            *    **    **   *  *    *** **  *   * ** ****** *     **
genome   AGTCATCGGAGAGTTTCTGTCCAACCAGCAGCCATACCCCCAGTT-CATGGCCACCGTGG 179981
mRNA     GGCTGGAGTTGACATCCACTCCTGTTCGCAGTTTTTGCTTGAGTTGTACAGCCGCTGGAT 8199
            *  **    *  *  ***      ****   *   **** *   *** * *
genome   TGTATAAGGTGAGGTTGCATGTGGGATGGGGATGGAGTGGGAAAGCCTGGAGGTGGAGTT 180041
mRNA     CCTGCCGTCCAGCTCAGCCAGGAGGACCCCGGCCATCCTGATCAGTGAGGTGGTCAGATC 8259
             *        **   *  ***     *        *    **   **  ***     *
genome   GCCTCCGACTTCCCAGCAGATTCGCCAGCAGAGCCCAGCTCCTCCGCTTTAAAGCA-GCA 180100
mRNA     CCTTCTAGTGGTCT--CAGACTTGTTCACCGAGCGCAACCAGTTTGAGCTGATGTATGTG 8317
          *  **         *  ****  *  *       *  **** ** *    *   *  *
genome   ATGCCTCTGGCCCCCACCCCACCCCCGCCACCCAGGCGCAGCAGGTGCTTCCCGTCCCCC 180160
mRNA     ACGCTGACAGAACT-GCGAAGGGTGCACCCTTCAGAAGACGAGATCCTCGCTCAGTACCT 8376
          * **       *  *    *      *  **    *** *  *        * *   **
genome   CAGCCCTGACACTCAGGCACCTGCTTGCTCCTTGCAGGTGTTTCAGACTCTGCACAGCAC 180220
mRNA     GGTGCCTGCCACCTGCAAGGCAGCTGCCGTCCTTGGGATGGACAAGGCCGTG-GCGGAGC 8435
            ****  ***     * ***    * **  *  **    **      **   **
genome   CGGGCAGTCGTCCATGGTCCGGGACTGGGTCATGCTGTCCCTCTCCAACTTCACGCAGAG 180280
mRNA     CTGTCAGCCGCC--TGCTGGAGAGCACGCTCAGGAGCAGCCACCTGCCCAGCAGGGTTGG 8493
         *  *  ***  ** ** * *    *  *  *  *  * ***  *    *  *  **   *
genome   GGCCCCGGTCGCCATGGCC-ACGTGGAGCCTCTCCTGCTTCTTTGTCAGCGC-GTCCACC 180338
mRNA     AGCCCTGCACGGCGTCCTCTATGTGCTGGAG-TGCGACCTGCTGGACGACACTGCCAAGC 8552
          ****   **  **   *  * ***   *     *  *   *  **  *  * *
genome   AGCCCGTG--GGTCG-CGGCGA-TGTATCCTCTCTGGGTCCCTGGTGCTGGCCCCGTTTC 180394
mRNA     AGCTCATCCCGGTCATCAGCGACTATCTCCTCTCCAA---CCTGAAA--GGGATCGCCCA 8607
         ***  *     ****  *  **** * * *******    ****   **   **
genome   CCTTGTCAACACCGA-GGCTCATGTTTCATGATAAGGTTTTGAAAC-CTAACCTTTGCAA 180452
mRNA     CTGCGTGAACATTCACAGCCAGCAGCACGTACTGGTCATGTGTGCCACTGCGTTTTACCT 8667
         *   **  ****    *  **        *  *   *  ** *  *  *    *** *
genome   AAACCCCACAGATGCCAGGGTGACAGGCCCTCAGCCCCAGGGAAGTAAAATGCTGACAGG 180512
mRNA     CATTGAGAACTATCCTCTGGACGTAGGGCCGGAATTTTCAGCATCAATAAT----ACAGA 8723
          *    *    *  **   **    ***  **    * ***   * *         ****
genome   GGTACAGAAAGGAGCACGTCCAGACATTTGCTGACCAGGGCCTCTCAGAGGGGCCGGTGT 180572
mRNA     TGTGTGGGGTGATGC-TGTCTGGAAGTGAGGAGTCCACCCCCTCCATCATTTACCACTGT 8782
          **    *   *  *   *     **   **  *  *   ****     *   **  ***
genome   ATGGCAGGAGGGTCGCAGCTGAGGGGCCTTTCTGTGGAGGGCCTGGGTGAGGGGAGCGAG 180632
mRNA     GCCCTCAGAGGCCTGGAGCGCCTCCTGCTCTCTGAGCAGCTCTCCCGCCTGGATGCAGAA 8842
          ****  * ***    **     **   ** **** *  *     *    *  **   **
genome   GGTGGGCGGTGGTCTCTGCAGACGTCCCGCCCACTCGCGGGCTCTGTGTGGCTGGGCTTC 180692
mRNA     -----------TCGCTG-----GTCAAGCTGA---GTGTGGACAGAGTGAACGTGCACA 8882
                    ** ***      ***  **  *      * *  * * ***     * **
genome   TCCTGACACTGCTTCTCATTAGCTTTGGTCATTGTGCCTCGATCGCCCTCTCGGGGAAAG 180752
mRNA     GCCCG-CACCGGGCCATGGCGGCTCTGGGCCTGATGC-----TCACCTGCATGTACACAG 8936
          *  * ***  *      *** *** * **  * *         *  *   *   *  **
genome   GCTTAAGTAAAGATCCAGTTCCCACCCCCAGATGCTGGCTGCCAGGAGTTTCCCTTTCCA 180812
mRNA     GA--AAGGAGAAAGTCAGT--------CCGGGTA--GAACTTCAGA---CCCTAATCCTG 8981
         *    *** *  *  ****         * *    * * *  *      ** * * *
genome   CAGCCCTTCCCCAAGACAGACCACAAGAGCCTCCAAGCAGCACAGTTGTCCTGGTGCTGA 180872
mRNA     CAGCCCCCGAC--AGCGAGTCAGTGATTGTTGCTATGGAGCGGGTATCTGTTCTTTTTGA 9039
         ******     *   **  ** **        *       * *  * *   *    ***
genome   CAGCACAGCCTTGCCCGGCGTGCCTGGCACGGCTCTGCCCTCACTGCATTGGAGCAGGGC 180932
mRNA     TAG---GATCAGGAAAGGCTTTCCTTGTGAAGC--------CAGAGTGGTGGCCAGGATC 9088
          **      *   ***  *****  **       **       **    ***     *
genome   TAGTGGAGGCCAGCGGAAGCACCGGCCACCAGCGCTGCACAGGAGCCAGGCCAGGTGAGT 180992
mRNA     CTGCCCCAGTTTCTAGACG-ACTTCTTCCCACCCCAGGACATCA--TGAACAAAGTCA-- 9143
          *          * **   *  ** **  *     ***  * *   * ** * *
genome   GCTGCCGAGTGGGTGCCCTGCCTGCAGGGCATCCAGCCAGCCAAGGGTTGCAGGAATGGA 181052
mRNA     -TCGGAGAGTTTCTGTCCAACCAGCAGC-CATACCCCCAGTTCATGGCCACCGTGGTGTA 9201
          *  ****   **  **  **** ***  ****   *   * ***  *    *   **
genome   GGTGGAGGCGCTGATGCAGCTGGAGGCATCCAGGTGGCCCTTCCGGGGCTCTG-CTCGCT 181111
```

FIG. 1 OOOOOO

```
mRNA      TAAGGTGTTTCAGACTCTGC--ACAGCA-CCGGGCAGTCGTCCATGGTCCGGGACTGGGT 9258
           ** *   * **  * **    *** ** **  * * *  ** *   * ** * *
genome    C-TCCAGGCTCCCTGGACCCCTTTGTAGACTGTTTCAGGAGAGGAACTCCCAGGTGAGGA 181170
mRNA      CATGCTGTCCCTCTCCAACTTCACGCAGAGGGCCCCGGTCGCC--ATGGCCACGTGGAGC 9316
           * * * * **  * *     * *** *   *         *
genome    CAGGGAGGCAGCATTCCC--CTCATTTGCCGGCCTTTTTCCTTAACTCCTGCACCAGCCT 181228
mRNA      CTCTCCTGCTTCTTTGTCAGCGCGTCCACCAGCC------CGTGGGTCGCG-GCGATCCT 9369
           *    ** * **   *  * **  ** ***    * *  **  *  * * ***
genome    CCCACATGTCATCAGCAGGATGGGCAAGCTGGAGCAGGTGGACGTGAACCTTTTCTGCCT 181288
mRNA      CCCACATGTCATCAGCAGGATGGGCAAGCTGGAGCAGGTGGACGTGAACCTTTTCTGCCT 9429
          ************************************************************
genome    GGTCGCCACAGACTTCTACAGACACCAGATAGAGGAGGAGCTCGACCGCAGGGCCTTCCA 181348
mRNA      GGTCGCCACAGACTTCTACAGACACCAGATAGAGGAGGAGCTCGACCGCAGGGCCTTCCA 9489
          ************************************************************
genome    GTCTGTGCTTGAGGTGGTTGCAGCCCCAGGAAGCCCATATCACCGGCTGCTGACTTGTTT 181408
mRNA      GTCTGTGCTTGAGGTGGTTGCAGCCCCAGGAAGCCCATATCACCGGCTGCTGACTTGTTT 9549
          ************************************************************
genome    ACGAAATGTCCACAAGGTCACCACCTGCTGAGCGCCATGGTGGGAGAGACTGTGAGGCGG 181468
mRNA      ACGAAATGTCCACAAGGTCACCACCTGCTGAGCGCCATGGTGGGAGAGACTGTGAGGCGG 9609
          ************************************************************
                                           rs362307
genome    CAGCTGGGGCCGGAGCCTTTGGAAGTCTGCGCCCTTGTGCCCTGCCTCCACCGAGCCAGC 181528
mRNA      CAGCTGGGGCCGGAGCCTTTGGAAGTCTGCGCCCTTGTGCCCTGCCTCCACCGAGCCAGC 9669
          ************************************************************
genome    TTGGTCCCTATGGGCTTCCGCACATGCCGCGGGCGGCCAGGCAACGTGCGTGTCTCTGCC 181588
mRNA      TTGGTCCCTATGGGCTTCCGCACATGCCGCGGGCGGCCAGGCAACGTGCGTGTCTCTGCC 9729
          ************************************************************
genome    ATGTGGCAGAAGTGCTCTTTGTGGCAGTGGCCAGGCAGGGAGTGTCTGCAGTCCTGGTGG 181648
mRNA      ATGTGGCAGAAGTGCTCTTTGTGGCAGTGGCCAGGCAGGGAGTGTCTGCAGTCCTGGTGG 9789
          ************************************************************
genome    GGCTGAGCCTGAGGCCTTCCAGAAAGCAGGAGCAGCTGTGCTGCACCCCATGTGGGTGAC 181708
mRNA      GGCTGAGCCTGAGGCCTTCCAGAAAGCAGGAGCAGCTGTGCTGCACCCCATGTGGGTGAC 9849
          ************************************************************
                                                   rs362306
genome    CAGGTCCTTTCTCCTGATAGTCACCTGCTGGTTGTTGCCAGGTTGCAGCTGCTCTTGCAT 181768
mRNA      CAGGTCCTTTCTCCTGATAGTCACCTGCTGGTTGTTGCCAGGTTGCAGCTGCTCTTGCAT 9909
          ************************************************************
genome    CTGGGCCAGAAGTCCTCCCTCCTGCAGGCTGGCTGTTGGCCCCTCTGCTGTCCTGCAGTA 181828
mRNA      CTGGGCCAGAAGTCCTCCCTCCTGCAGGCTGGCTGTTGGCCCCTCTGCTGTCCTGCAGTA 9969
          ************************************************************
genome    GAAGGTGCCGTGAGCAGGCTTTGGGAACACTGGCCTGGGTCTCCCTGGTGGGGTGTGCAT 181888
mRNA      GAAGGTGCCGTGAGCAGGCTTTGGGAACACTGGCCTGGGTCTCCCTGGTGGGGTGTGCAT 10029
          ************************************************************
genome    GCCACGCCCCGTGTCTGGATGCACAGATGCCATGGCCTGTGCTGGGCCAGTGGCTGGGGG 181948
mRNA      GCCACGCCCCGTGTCTGGATGCACAGATGCCATGGCCTGTGCTGGGCCAGTGGCTGGGGG 10089
          ************************************************************
                          rs362303
genome    TGCTAGACACCCGGCACCATTCTCCCTTCTCTCTTTTCTTCTCAGGATTTAAAATTTAAT 182008
mRNA      TGCTAGACACCCGGCACCATTCTCCCTTCTCTCTTTTCTTCTCAGGATTTAAAATTTAAT 10149
          ************************************************************
genome    TATATCAGTAAAGAGATTAATTTTAACGTAACTCTTTCTATGCCCGTGTAAAGTATGTGA 182068
mRNA      TATATCAGTAAAGAGATTAATTTTAACGTAACTCTTTCTATGCCCGTGTAAAGTATGTGA 10209
          ************************************************************
genome    ATCGCAAGGCCTGTGCTGCATGCGACAGCGTCCGGGGTGGTGGACAGGGCCCCCGGCCAC 182128
mRNA      ATCGCAAGGCCTGTGCTGCATGCGACAGCGTCCGGGGTGGTGGACAGGGCCCCCGGCCAC 10269
          ************************************************************
genome    GCTCCCTCTCCTGTAGCCACTGGCATAGCCCTCCTGAGCACCCGCTGACATTTCCGTTGT 182188
mRNA      GCTCCCTCTCCTGTAGCCACTGGCATAGCCCTCCTGAGCACCCGCTGACATTTCCGTTGT 10329
          ************************************************************
genome    ACATGTTCCTGTTTATGCATTCACAAGGTGACTGGGATGTAGAGAGGCGTTAGTGGGCAG 182248
mRNA      ACATGTTCCTGTTTATGCATTCACAAGGTGACTGGGATGTAGAGAGGCGTTAGTGGGCAG 10389
          ************************************************************
```

FIG. 1 PPPPPP

```
genome    GTGGCCACAGCAGGACTGAGGACAGGCCCCCATTATCCTAGGGGTGCGCTCACCTGCAGC  182308
mRNA      GTGGCCACAGCAGGACTGAGGACAGGCCCCCATTATCCTAGGGGTGCGCTCACCTGCAGC  10449
          ************************************************************
genome    CCCTCCTCCTCGGGCACAGACGACTGTCGTTCTCCACCCACCAGTCAGGGACAGCAGCCT  182368
mRNA      CCCTCCTCCTCGGGCACAGACGACTGTCGTTCTCCACCCACCAGTCAGGGACAGCAGCCT  10509
          ************************************************************
genome    CCCTGTCACTCAGCTGAGAAGGCCAGCCCTCCCTGGCTGTGAGCAGCCTCCACTGTGTCC  182428
mRNA      CCCTGTCACTCAGCTGAGAAGGCCAGCCCTCCCTGGCTGTGAGCAGCCTCCACTGTGTCC  10569
          ************************************************************
genome    AGAGACATGGGCCTCCCACTCCTGTTCCTTGCTAGCCCTGGGGTGGCGTCTGCCTAGGAG  182488
mRNA      AGAGACATGGGCCTCCCACTCCTGTTCCTTGCTAGCCCTGGGGTGGCGTCTGCCTAGGAG  10629
          ************************************************************
genome    CTGGCTGGCAGGTGTTGGGACCTGCTGCTCCATGGATGCATGCCCTAAGAGTGTCACTGA  182548
mRNA      CTGGCTGGCAGGTGTTGGGACCTGCTGCTCCATGGATGCATGCCCTAAGAGTGTCACTGA  10689
          ************************************************************
genome    GCTGTGTTTTGTCTGAGCCTCTCTCGGTCAACAGCAAAGCTTGGTGTCTTGGCACTGTTA  182608
mRNA      GCTGTGTTTTGTCTGAGCCTCTCTCGGTCAACAGCAAAGCTTGGTGTCTTGGCACTGTTA  10749
          ************************************************************
genome    GTGACAGAGCCCAGCATCCCTTCTGCCCCCGTTCCAGCTGACATCTTGCACGGTGACCCC  182668
mRNA      GTGACAGAGCCCAGCATCCCTTCTGCCCCCGTTCCAGCTGACATCTTGCACGGTGACCCC  10809
          ************************************************************
genome    TTTTAGTCAGGAGAGTGCAGATCTGTGCTCATCGGAGACTGCCCCACGGCCCTGTCAGAG  182728
mRNA      TTTTAGTCAGGAGAGTGCAGATCTGTGCTCATCGGAGACTGCCCCACGGCCCTGTCAGAG  10869
          ************************************************************
genome    CCGCCACTCCTATCCCCAGGCCAGGTCCCTGGACCAGCCTCCTGTTTGCAGGCCCAGAGG  182788
mRNA      CCGCCACTCCTATCCCCAGGCCAGGTCCCTGGACCAGCCTCCTGTTTGCAGGCCCAGAGG  10929
          ************************************************************
genome    AGCCAAGTCATTAAAATGGAAGTGGATTCTGGATGGCCGGGCTGCTGCTGATGTAGGAGC  182848
mRNA      AGCCAAGTCATTAAAATGGAAGTGGATTCTGGATGGCCGGGCTGCTGCTGATGTAGGAGC  10989
          ************************************************************
genome    TGGATTTGGGAGCTCTGCTTGCCGACTGGCTGTGAGACGAGGCAGGGGCTCTGCTTCCTC  182908
mRNA      TGGATTTGGGAGCTCTGCTTGCCGACTGGCTGTGAGACGAGGCAGGGGCTCTGCTTCCTC  11049
          ************************************************************
genome    AGCCCTAGAGGCGAGCCAGGCAAGGTTGGCGACTGTCATGTGGCTTGGTTTGGTCATGCC  182968
mRNA      AGCCCTAGAGGCGAGCCAGGCAAGGTTGGCGACTGTCATGTGGCTTGGTTTGGTCATGCC  11109
          ************************************************************
genome    CGTCGATGTTTTGGGTATTGAATGTGGTAAGTGGAGGAAATGTTGGAACTCTGTGCAGGT  183028
mRNA      CGTCGATGTTTTGGGTATTGAATGTGGTAAGTGGAGGAAATGTTGGAACTCTGTGCAGGT  11169
          ************************************************************
genome    GCTGCCTTGAGACCCCCAAGCTTCCACCTGTCCCTCTCCTATGTGGCAGCTGGGGAGCAG  183088
mRNA      GCTGCCTTGAGACCCCCAAGCTTCCACCTGTCCCTCTCCTATGTGGCAGCTGGGGAGCAG  11229
          ************************************************************
genome    CTGAGATGTGGACTTGTATGCTGCCCACATACGTGAGGGGGAGCTGAAAGGGAGCCCCTC  183148
mRNA      CTGAGATGTGGACTTGTATGCTGCCCACATACGTGAGGGGGAGCTGAAAGGGAGCCCCTC  11289
          ************************************************************
genome    CTCTGAGCAGCCTCTGCCAGGCCTGTATGAGGCTTTTCCCACCAGCTCCCAACAGAGGCC  183208
mRNA      CTCTGAGCAGCCTCTGCCAGGCCTGTATGAGGCTTTTCCCACCAGCTCCCAACAGAGGCC  11349
          ************************************************************
genome    TCCCCCAGCCAGGACCACCTCGTCCTCGTGGCGGGGCAGCAGGAGCGGTAGAAAGGGGTC  183268
mRNA      TCCCCCAGCCAGGACCACCTCGTCCTCGTGGCGGGGCAGCAGGAGCGGTAGAAAGGGGTC  11409
          ************************************************************
genome    CGATGTTTGAGGAGGCCCTTAAGGGAAGCTACTGAATTATAACACGTAAGAAAATCACCA  183328
mRNA      CGATGTTTGAGGAGGCCCTTAAGGGAAGCTACTGAATTATAACACGTAAGAAAATCACCA  11469
          ************************************************************
genome    TTCCGTATTGGTTGGGGGCTCCTGTTTCTCATCCTAGCTTTTTCCTGGAAAGCCCGCTAG  183388
mRNA      TTCCGTATTGGTTGGGGGCTCCTGTTTCTCATCCTAGCTTTTTCCTGGAAAGCCCGCTAG  11529
          ************************************************************
genome    AAGGTTTGGGAACGAGGGGAAAGTTCTCAGAACTGTTGGCTGCTCCCACCCGCCTCCCG  183448
mRNA      AAGGTTTGGGAACGAGGGGAAAGTTCTCAGAACTGTTGGCTGCTCCCACCCGCCTCCCG  11589
          ************************************************************
genome    CCTCCCCCGCAGGTTATGTCAGCAGCTCTGAGACAGCAGTATCACAGGCCAGATGTTGTT  183508
mRNA      CCTCCCCCGCAGGTTATGTCAGCAGCTCTGAGACAGCAGTATCACAGGCCAGATGTTGTT  11649
          ************************************************************
```

FIG. 1 QQQQQQ

```
genome    CCTGGCTAGATGTTTACATTTGTAAGAAATAACACTGTGAATGTAAAACAGAGCCATTCC  183568
mRNA      CCTGGCTAGATGTTTACATTTGTAAGAAATAACACTGTGAATGTAAAACAGAGCCATTCC  11709
          ************************************************************
genome    CTTGGAATGCATATCGCTGGGCTCAACATAGAGTTTGTCTTCCTCTTGTTTACGACGTGA  183628
mRNA      CTTGGAATGCATATCGCTGGGCTCAACATAGAGTTTGTCTTCCTCTTGTTTACGACGTGA  11769
          ************************************************************
genome    TCTAAACCAGTCCTTAGCAAGGGGCTCAGAACACCCCGCTCTGGCAGTAGGTGTCCCCCA  183688
mRNA      TCTAAACCAGTCCTTAGCAAGGGGCTCAGAACACCCCGCTCTGGCAGTAGGTGTCCCCCA  11829
          ************************************************************
genome    CCCCCAAAGACCTGCCTGTGTGCTCCGGAGATGAATATGAGCTCATTAGTAAAAATGACT  183748
mRNA      CCCCCAAAGACCTGCCTGTGTGCTCCGGAGATGAATATGAGCTCATTAGTAAAAATGACT  11889
          ************************************************************
genome    TCACCCACGCATATACATAAAGTATCCATGCATGTGCATATAGACACATCTATAATTTTA  183808
mRNA      TCACCCACGCATATACATAAAGTATCCATGCATGTGCATATAGACACATCTATAATTTTA  11949
          ************************************************************
genome    CACACACACCTCTCAAGACGGAGATGCATGGCCTCTAAGAGTGCCCGTGTCGGTTCTTCC  183868
mRNA      CACACACACCTCTCAAGACGGAGATGCATGGCCTCTAAGAGTGCCCGTGTCGGTTCTTCC  12009
          ************************************************************
genome    TGGAAGTTGACTTTCCTTAGACCCGCCAGGTCAAGTTAGCCGCGTGACGGACATCCAGGC  183928
mRNA      TGGAAGTTGACTTTCCTTAGACCCGCCAGGTCAAGTTAGCCGCGTGACGGACATCCAGGC  12069
          ************************************************************
genome    GTGGGACGTGGTCAGGGCAGGGCTCATTCATTGCCCACTAGGATCCCACTGGCGAAGATG  183988
mRNA      GTGGGACGTGGTCAGGGCAGGGCTCATTCATTGCCCACTAGGATCCCACTGGCGAAGATG  12129
          ************************************************************
genome    GTCTCCATATCAGCTCTCTGCAGAAGGGAGGAAGACTTTATCATGTTCCTAAAAATCTGT  184048
mRNA      GTCTCCATATCAGCTCTCTGCAGAAGGGAGGAAGACTTTATCATGTTCCTAAAAATCTGT  12189
          ************************************************************
genome    GGCAAGCACCCATCGTATTATCCAAATTTTGTTGCAAATGTGATTAATTTGGTTGTCAAG  184108
mRNA      GGCAAGCACCCATCGTATTATCCAAATTTTGTTGCAAATGTGATTAATTTGGTTGTCAAG  12249
          ************************************************************
genome    TTTTGGGGGTGGGCTGTGGGGAGATTGCTTTTGTTTTCCTGCTGGTAATATCGGGAAAGA  184168
mRNA      TTTTGGGGGTGGGCTGTGGGGAGATTGCTTTTGTTTTCCTGCTGGTAATATCGGGAAAGA  12309
          ************************************************************
genome    TTTTAATGAAACCAGGGTAGAATTGTTTGGCAATGCACTGAAGCGTGTTTCTTTCCCAAA  184228
mRNA      TTTTAATGAAACCAGGGTAGAATTGTTTGGCAATGCACTGAAGCGTGTTTCTTTCCCAAA  12369
          ************************************************************
genome    ATGTGCCTCCCTTCCGCTGCGGGCCCAGCTGAGTCTATGTAGGTGATGTTTCCAGCTGCC  184288
mRNA      ATGTGCCTCCCTTCCGCTGCGGGCCCAGCTGAGTCTATGTAGGTGATGTTTCCAGCTGCC  12429
          ************************************************************
genome    AAGTGCTCTTTGTTACTGTCCACCCTCATTTCTGCCAGCGCATGTGTCCTTTCAAGGGGA  184348
mRNA      AAGTGCTCTTTGTTACTGTCCACCCTCATTTCTGCCAGCGCATGTGTCCTTTCAAGGGGA  12489
          ************************************************************
genome    AAATGTGAAGCTGAACCCCCTCCAGACACCCAGAATGTAGCATCTGAGAAGGCCCTGTGC  184408
mRNA      AAATGTGAAGCTGAACCCCCTCCAGACACCCAGAATGTAGCATCTGAGAAGGCCCTGTGC  12549
          ************************************************************
genome    CCTAAAGGACACCCCTCGCCCCCATCTTCATGGAGGGGGTCATTTCAGAGCCCTCGGAGC  184468
mRNA      CCTAAAGGACACCCCTCGCCCCCATCTTCATGGAGGGGGTCATTTCAGAGCCCTCGGAGC  12609
          ************************************************************
genome    CAATGAACAGCTCCTCCTCTTGGAGCTGAGATGAGCCCCACGTGGAGCTCGGGACGGATA  184528
mRNA      CAATGAACAGCTCCTCCTCTTGGAGCTGAGATGAGCCCCACGTGGAGCTCGGGACGGATA  12669
          ************************************************************
genome    GTAGACAGCAATAACTCGGTGTGTGGCCGCCTGGCAGGTGGAACTTCCTCCCGTTGCGGG  184588
mRNA      GTAGACAGCAATAACTCGGTGTGTGGCCGCCTGGCAGGTGGAACTTCCTCCCGTTGCGGG  12729
          ************************************************************
genome    GTGGAGTGAGGTTAGTTCTGTGTGTCTGGTGGGTGGAGTCAGGCTTCTCTTGCTACCTGT  184648
mRNA      GTGGAGTGAGGTTAGTTCTGTGTGTCTGGTGGGTGGAGTCAGGCTTCTCTTGCTACCTGT  12789
          ************************************************************
genome    GAGCATCCTTCCCAGCAGACATCCTCATCGGGCTTTGTCCCTCCCCCGCTTCCTCCCTCT  184708
mRNA      GAGCATCCTTCCCAGCAGACATCCTCATCGGGCTTTGTCCCTCCCCCGCTTCCTCCCTCT  12849
          ************************************************************
genome    GCGGGGAGGACCCGGGACCACAGCTGCTGGCCAGGGTAGACTTGGAGCTGTCCTCCAGAG  184768
mRNA      GCGGGGAGGACCCGGGACCACAGCTGCTGGCCAGGGTAGACTTGGAGCTGTCCTCCAGAG  12909
          ************************************************************
```

FIG. 1 RRRRRR

```
genome   GGGTCACGTGTAGGAGTGAGAAGAAGGAAGATCTTGAGAGCTGCTGAGGGACCTTGGAGA 184828
mRNA     GGGTCACGTGTAGGAGTGAGAAGAAGGAAGATCTTGAGAGCTGCTGAGGGACCTTGGAGA 12969
         ************************************************************
genome   GCTCAGGATGGCTCAGACGAGGACACTCGCTTGCCGGGCCTGGGCCTCCTGGGAAGGAGG 184888
mRNA     GCTCAGGATGGCTCAGACGAGGACACTCGCTTGCCGGGCCTGGGCCTCCTGGGAAGGAGG 13029
         ************************************************************
genome   GAGCTGCTCAGAATGCCGCATGACAACTGAAGGCAACCTGGAAGGTTCAGGGGCCGCTCT 184948
mRNA     GAGCTGCTCAGAATGCCGCATGACAACTGAAGGCAACCTGGAAGGTTCAGGGGCCGCTCT 13089
         ************************************************************
genome   TCCCCCATGTGCCTGTCACGCTCTGGTGCAGTCAAAGGAACGCCTTCCCCTCAGTTGTTT 185008
mRNA     TCCCCCATGTGCCTGTCACGCTCTGGTGCAGTCAAAGGAACGCCTTCCCCTCAGTTGTTT 13149
         ************************************************************
genome   CTAAGAGCAGAGTCTCCCGCTGCAATCTGGGTGGTAACTGCCAGCCTTGGAGGATCGTGG 185068
mRNA     CTAAGAGCAGAGTCTCCCGCTGCAATCTGGGTGGTAACTGCCAGCCTTGGAGGATCGTGG 13209
         ************************************************************
genome   CCAACGTGGACCTGCCTACGGAGGGTGGGCTCTGACCCAAGTGGGGCCTCCTTGTCCAGG 185128
mRNA     CCAACGTGGACCTGCCTACGGAGGGTGGGCTCTGACCCAAGTGGGGCCTCCTTGTCCAGG 13269
         ************************************************************
genome   TCTCACTGCTTTGCACCGTGGTCAGAGGGACTGTCAGCTGAGCTTGAGCTCCCTGGAGC 185188
mRNA     TCTCACTGCTTTGCACCGTGGTCAGAGGGACTGTCAGCTGAGCTTGAGCTCCCTGGAGC 13329
         ************************************************************
genome   CAGCAGGGCTGTGATGGGCGAGTCCCGGAGCCCCACCCAGACCTGAATGCTTCTGAGAGC 185248
mRNA     CAGCAGGGCTGTGATGGGCGAGTCCCGGAGCCCCACCCAGACCTGAATGCTTCTGAGAGC 13389
         ************************************************************
genome   AAAGGGAAGGACTGACGAGAGATGTATATTTAATTTTTTAACTGCTGCAAACATTGTACA 185308
mRNA     AAAGGGAAGGACTGACGAGAGATGTATATTTAATTTTTTAACTGCTGCAAACATTGTACA 13449
         ************************************************************
genome   TCCAAATTAAAGGAAAAAAATGGAAACCATCAGTTGTTGCTGTGTGAGGCTTGCTTTGCT 185368
mRNA     TCCAAATTAAAGGAAAAAAATGGAAACCATCA---------------------------- 13481
         ********************************
genome   TCATGAGAACCTAGACCTTGCTGAGCTGGAGTCTTAGGAAGCAGTCTCCTAAGTGCTTCT 185428
mRNA      ------------------------------------------------------------ genome   CCAGCAGGGGCAGAAACTGTCCCACCAGCTAACATCTGGCATTATGGAGGGTCCCCCAGG 185488
mRNA      ------------------------------------------------------------ genome   CAGCTGCCAGCAGGGACAGGCCCCGTGTTTTCTGTAGCCAGGGATGAGGAAGTGGCCCCA 185548
mRNA      ------------------------------------------------------------ genome   GGGCATGGGCCTGGCTGGGTGCTTCTGCAAGGGCCTTCCCAAACCACAGTACAGGTGGTC 185608
mRNA      ------------------------------------------------------------ genome   TTCCTGCCCTGCAGATGGGAGCTGTGGGAGCTGCTGGAGCTGCTGGAGCCTTCATGGTCA 185668
mRNA      ------------------------------------------------------------ genome   AGTGACATCATAAGCTTATATGACATACACAAGCCTCAGGACTTGGCCCATGGCACTGAA 185728
mRNA      ------------------------------------------------------------ genome   GCAGGTCATCAGGCCCAGCACAGAGACTAGAGCTGTGTTCTCACAGGGCCCACCACCCTT 185788
mRNA      ------------------------------------------------------------ genome   CCACCTCCTTGGCCATTGACACCTGCGTCCCTGGCCCAGCTGCTCCCAGGTAACCCCCAA 185848
mRNA      ------------------------------------------------------------ genome   AGCAGCTGGCACATCCCACCTCTGGTGTGGCCGGGGCTGCTGTGTGTCCGCAGGGCCTGC 185908
mRNA      ------------------------------------------------------------ genome   CCCGTCTATTCTAGCTTGTTTGTCCTGTCTGAACCAGCGCCTACTCCAAGAAGCCTCTGC 185968
mRNA      ------------------------------------------------------------ genome   TCAGCCCAGCGGGGATGCTTCTAAGCTCCGGACGAGCCTCTCGGAAGCCTTGGTGATTGG 186028
mRNA      ------------------------------------------------------------
```

FIG. 1 SSSSSS

| | | |
|---|---|---|
| genome<br>mRNA | TGGTGTAGTCATCTTGGGATGCAGATGTCTTACCAACCTGCAAGAACAAAAACCCTGTGG | 186088 |
| genome<br>mRNA | CTTCCTCTGGTGCAGGGTATTTAGTCAATGTTTGCTGAGGTCCCGTCTGGTTCTGGCTAA | 186148 |
| genome<br>mRNA | TTGGCAGGGGTCGTCCACCCATTCTTTCCCTGCTCTGCTGTCTGTGCCAGGAGAGACGGG | 186208 |
| genome<br>mRNA | GGCCAGTCGGCCAAGGGGCCAGCTCCTGCTGCCTGCTCCTCTTGGGCACGTGCGGGGGCC | 186268 |
| genome<br>mRNA | CCCTTTCTCTGAGCAGGGATAGGGATCAGTCTGCCGGAGGGATGTGGTGGACAGGCCTAA | 186328 |
| genome<br>mRNA | AGCATTTGGGGCGGGGCATGCCACTTGAGCTCCCTAAATCTGTCTCCTCATAGGTGACAC | 186388 |
| genome<br>mRNA | CGCTCCAGGGCCCCCCAGTGGCCTCTCCTTTCAGAGCTACCTAAATTCTGGTCACTTCAG | 186448 |
| genome<br>mRNA | AGAAATGGAGCACCCCCTTCTCCCTGGTCCAGGTGTGGACAGCCTGGCACACTGAGCACA | 186508 |
| genome<br>mRNA | CCTGGCATGGCTGGTAATTTCAGAAAGAAGAGGGGCCGGGGTCCAGTGGGAAGCAGCGGT | 186568 |
| genome<br>mRNA | GAACCCCTCGTGAGTGGGCTTTGCAGTCCCTCCCCATGCCACGGCAGAGCTGCCCTCAAC | 186628 |
| genome<br>mRNA | ACAGCCTTCCTCTTCCTCATCGGAGAGCACA`[C]`CCTGTCCCCTTGCCGAGCTGTGCCCTGT  (rs362296) | 186688 |
| genome<br>mRNA | GCCTTCGGTGGTATTTGATTTTGGCTGCTACTGGCTTTGTTGGGATCTGGAAGTCGCTTC | 186748 |
| genome<br>mRNA | CCCTGCGTGGTGCGTGGAGCACTGTAAGTCAGATGAGGGAAGTAGCCAGGGTGAGGTGAG | 186808 |
| genome<br>mRNA | TACCGGGTGGAGCCGCCACTGAAGGGACTGGGTAGGGGGCCTTGCCTCTACATGATGTG | 186868 |
| genome<br>mRNA | ACACAGCCAACCGAGGACAGAGGAAGCCCCGTTCCTGGGGGTGTGGGGTGCACCCCTCAG | 186928 |
| genome<br>mRNA | GGAAGCCTGCAGTGGGGCCTGAGGAAAGGCATCCTCCGCGAGCCCACGAGTCTGGTCCAT | 186988 |
| genome<br>mRNA | GAGCACCGTGACAGTGTCTGTGGGTAGAGGTGGACCCGGCCTTGTGTCATCACCAGGACC | 187048 |
| genome<br>mRNA | TCTTTTGGGAAACCATGTGGACATCGCTTGCGGGTCCCCCAGGCTCTGCAGCCCCAGCAG | 187108 |
| genome<br>mRNA | CCTGGCTGCCTTTTGGGCAAGTGGCTTGAGCCACAGAGGACCCAGTCCTGTTGCAGCCAC | 187168 |
| genome<br>mRNA | ATCCTCTGGGGGGCCCGCCAGTGTGGCCGGCTTTCTCCACCCTACACCAGGCCTCCAGG | 187228 |
| genome<br>mRNA | TGTCCTGGTCGGGGGTGTCTGGGCCCTGGGTGGGCCCTGTGGACCTGTGAGGTCAGGGTC | 187288 |

FIG. 1 TTTTTT

| | | |
|---|---|---|
| genome | AGGGCATCACTGGAGGCAGAGGGCTGAAGTTGTGGGTCTGGGTTCCCCTTGTGTGCACAG | 187348 |
| mRNA | ------------------------------------------------------------ | |
| genome | GCCCCTGCCCTCCATGCTTGGTCAGGCAGCTACCCCCAAAACTGCTAGGACAGGCTGGTC | 187408 |
| mRNA | ------------------------------------------------------------ | |
| genome | CTGAGGTGGATCCTGGCCCCTGTACCCTCTGGACAGCCCACCCGCCCAACCTTCTACCCT | 187468 |
| mRNA | ------------------------------------------------------------ | |
| genome | GCCCCAGCGGCGGCAGTGTTGGCCACATCCTTCCCCTCCTGGCCCCAATTGCTCTGGGGA | 187528 |
| mRNA | ------------------------------------------------------------ | |
| genome | AGTCCAGGCTCCGGAGCCTGCCCAGGGGCCCCCCGTGATTTGGGCCCAGGACTCCACGTG | 187588 |
| mRNA | ------------------------------------------------------------ | |
| genome | GTTCTCTGCCTTCACCCAAGCCCTGAACTCCTCAGCTGCCAAATCCCCACCCATCTGCAC | 187648 |
| mRNA | ------------------------------------------------------------ | |
| genome | AGGCTGTGCTCACCACTGCTGCTCCTGGAAGGTGCCCCTCAGTGGGACGCCCACCTCCTC | 187708 |
| mRNA | ------------------------------------------------------------ | |
| genome | TCTGGGCTTCTGTGTTTGGGAGCCCTGCTGCCCCCACCCTTGGTCAGTCCCCATGTCCTG | 187768 |
| mRNA | ------------------------------------------------------------ | |
| genome | CTGGCCTGTCAGGCAGGGCAGAAAATCCACCCAGAAATGCTGAGCAGGATGAGAGTCTAG | 187828 |
| mRNA | ------------------------------------------------------------ | |
| genome | TTGGGCCCAGCCTCATTATTTAGAAGGGATGGAGGCCTAGGGAGCATGCTTCTAGCCTGA | 187888 |
| mRNA | ------------------------------------------------------------ | |
| genome | GCCCAGCAGGGCCCCGCCCATGTCCCAGGTCTGCACCAGGGACAGCTCCTGCCGAGGCCT | 187948 |
| mRNA | ------------------------------------------------------------ | |
| genome | GACCTGCCCCTTCTCCCTCAGGTGCTGCTGGTTGACCAGCCTCTGGCCCTAGGAGACCCC | 188008 |
| mRNA | ------------------------------------------------------------ | |
| genome | GTAGCGACTGAGGGTCCCAGCAGGCCATGCAGCTTTGCCAAGGTACGAGCCCCTCCCCAG | 188068 |
| mRNA | ------------------------------------------------------------ | |
| genome | CAGGGGACAGATGTGGGGACCCTCCCAGGCAGGAGCAGCTGGGTGCCTGGTGCTGCCATC | 188128 |
| mRNA | ------------------------------------------------------------ | |
| genome | TGCTGCCTGCCTGGTTCTTGTCCTCACATTGGAGGTCAGTGTGAGGGCTCTGCCTCGGGA | 188188 |
| mRNA | ------------------------------------------------------------ | |
| genome | AAGGCCATGGAGCTTGCCCTGTCCAGGGCCTCCCATGTGCACTGAGCCTGGGAAGAGAGG | 188248 |
| mRNA | ------------------------------------------------------------ | |
| genome | GTTGGAGTTGAGCCTTTTACCCTGGGAATGCTGCCTGGAGGATGGTGCGGGTGTGGGGTG | 188308 |
| mRNA | ------------------------------------------------------------ | |
| genome | GCACCCTGCCAGGCAGGGCCCTGCCTCCCTGCGCCCACTGGAACTCGGGCAGGCAGGGGT | 188368 |
| mRNA | ------------------------------------------------------------ | |
| genome | GTAGGTGCCTCCTCTAGAGCCGTCCGGTGGGGGCCCCCGGCAGTGGTGGTGGTGTCCACT | 188428 |
| mRNA | ------------------------------------------------------------ | |
| genome | GGCCAGCAGCTGCCCCTTCAGCCAGGACAGTAGGCCTGACGCTGTCCCCAGCAGCTCCAA | 188488 |
| mRNA | ------------------------------------------------------------ | |
| genome | GGTGGATTTGTGGAAGGGGGTAGAGGGCACGTAGAGGCCCCATGACCTCCCCAGGGTTCT | 188548 |
| mRNA | ------------------------------------------------------------ | |

FIG. 1 UUUUUU

| | | |
|---|---|---|
| genome | GGGAGGGCTGTGCCCCCTTAGCCAGCACCATGCTGGGTGATATAGTCAGATCCTGTTACC | 188608 |
| mRNA | ------------------------------------------------------------ | |
| genome | CCTGTTGTGGAGGTGAGGAAACAGGTTAGTGGGGAGGACATGACTAAGGTCCATGCTGAG | 188668 |
| mRNA | ------------------------------------------------------------ | |
| genome | TCGCTAGAGCTGCACCCAGAACCACTGCTGGGACCCCATGCCTTTCTGCTTACCCCTTGT | 188728 |
| mRNA | ------------------------------------------------------------ | |
| genome | GCCGGGAGATGCCAAGAGATGCTGGGAGCCAGCCCCACCTCTGCCCTTGGAGTCATGGCT | 188788 |
| mRNA | ------------------------------------------------------------ | |
| genome | ACGGAAAGGGCATTCGGACCGGTCCCTGACCTCACCGGGGAGGGCCGAACCCTGTTCCTG | 188848 |
| mRNA | ------------------------------------------------------------ | |
| genome | AGGAGCCAGGGCTTCCTAGAGGAGGTAGGCCTTCTAGTCACTCCTTCATCTGCAGGCACT | 188908 |
| mRNA | ------------------------------------------------------------ | |
| genome | CCACAGAGCTCTCTGTGCCAGCCCCCAGCACGGAGGGCTGACCTTAGTCGAGTGGAGATG | 188968 |
| mRNA | ------------------------------------------------------------ | |
| genome | CCCCAGTGCCAGGCAGTAGGGATGATGTCTCCTGAGGCCCAGATGGAAGGGACTGGACTA | 189028 |
| mRNA | ------------------------------------------------------------ | |
| genome | GTCTCATGGGGCTGATGGTGGGGCCAGGCCTTGACCAGGGACCCAGTGTAGGGGGTGCAG | 189088 |
| mRNA | ------------------------------------------------------------ | |
| genome | AGACCCTCTGAGTTCCTCACACATCCCTGGGGCCCTCCCCATACACTTCCTATCCTGAC | 189148 |
| mRNA | ------------------------------------------------------------ | |
| genome | TGCGGGCAAGAGGGAGCCCCAGTTCGCCTTCCCTATGCTGGGCACCCACAGTGGGGCTGG | 189208 |
| mRNA | ------------------------------------------------------------ | |
| genome | GCACCCCGCCATGCCCCTGCCCTGTCCTTCCCCTGAGAGCCTCGGTCCCACCTCCAAGG | 189268 |
| mRNA | ------------------------------------------------------------ | |
| genome | TGCCTCAGAGGACAGCAGGGGCAGCGGGCAGAGGCCGAGATGCCTCCTCATTCCAGGCTC | 189328 |
| mRNA | ------------------------------------------------------------ | |
| genome | AGCTGCCCTTCTTGGGGCAGCCCACACCTGAGAGTCTCCTGCAGTTGGTCAGGCCTGAGG | 189388 |
| mRNA | ------------------------------------------------------------ | |
| genome | AGGGCAGGGGGTGCCTGCTGTCCCTCTGCTGACCACAGTGGCATTTAGCCTGGGCACCG | 189448 |
| mRNA | ------------------------------------------------------------ | |
| genome | CGCCCAGCACAGTCCATGCTGCACAGGTGCCGTGGGCTCCACAGAGCCCTGCCTGACATG | 189508 |
| mRNA | ------------------------------------------------------------ | |
| genome | CATGTGTTACGTTTCGGGTGCCGATGCCCTTGGGCGGCACTTCTCCGGGCAGAACCCCCA | 189568 |
| mRNA | ------------------------------------------------------------ | |
| genome | GGCCACCGCTCCGGTTCCGGTTCCGCTGCATCTGGGGCTCTCGGCAGGCTGTGGTCCTCC | 189628 |
| mRNA | ------------------------------------------------------------ | |
| genome | GGCCAGCCTGGGGGCATCTCAGTCCCTCAGCCCCACAGGGGCCTGCCCCGCAGCCTGGGC | 189688 |
| mRNA | ------------------------------------------------------------ | |
| genome | CTCGAGCCCCGTCTCCGCACGCTGTGCCGAATCTGGCTGCCCATCAGCTCCCTGCGTACC | 189748 |
| mRNA | ------------------------------------------------------------ | |
| genome | CAGACTGTGCCCTGCCATGCCCGTGGCTCTTCCCAGGAGTGCCCTGTGGCCTCCCCCTGG | 189808 |
| mRNA | ------------------------------------------------------------ | |

FIG. 1 VVVVVV

| | | |
|---|---|---|
| genome | CTTGCTGGGCTGATTCCCTCCTGTGTCTCAAACAGAGCTCACCTTTGCCATCACTGCTGT | 189868 |
| mRNA | ------------------------------------------------------------ | |
| genome | CCTCACCGGCCGGTGCCAGAGGCCCGTGTCTGTGTACCCTGTGTCTGCACCTCTGGGCAG | 189928 |
| mRNA | ------------------------------------------------------------ | |
| genome | GGCCTGGCTCTGACCAACCCGGGCTTCCAGTGTCCACAGACCTAAGGCCCAGGGCGCCTG | 189988 |
| mRNA | ------------------------------------------------------------ | |
| genome | GGGGCTGGAGCAAGAGAAGCAAAAGGAGCCAAGGGTGGGGGTTTGGGGTTCTTGTGAGGG | 190048 |
| mRNA | ------------------------------------------------------------ | |
| genome | CCCAGCCCCAGGACCCCAGGACCAGGACACCCAGGAGCCCCAGGGCCCAGCCCCAGTTCA | 190108 |
| mRNA | ------------------------------------------------------------ | |
| genome | GAAGGCAGGGGCCTTCTGAGGGAGCTTAAGGGTCCCACAGCCCAGGACCCCCACCAGGGC | 190168 |
| mRNA | ------------------------------------------------------------ | |
| genome | CAGTGGCCAGCGTTGGGGGACTCAGCCTCCTCGTCGCTCGTCCTCTCTGTTTCTCCCACC | 190228 |
| mRNA | ------------------------------------------------------------ | |
| genome | TTTTGCCCCCTTTCTCCTTGCCTGTTCCCACCCGAGGCCCCCTCTTGGCCTGCGTGAGCC | 190288 |
| mRNA | ------------------------------------------------------------ | |
| genome | GGGGCGGCACTGAACTGGGGGCCGATCCGCCTGGGCGGCGGTGAGAGGCAGGGCCGGGAG | 190348 |
| mRNA | ------------------------------------------------------------ | |
| genome | CCGGGCCGCTGGGTTTGGGCCTGGCCCGCTCGCCGCAATATTGATGGCCCGTCAGTGCAG | 190408 |
| mRNA | ------------------------------------------------------------ | |
| genome | CCCTGATTCCTGTGCTTTCAGTTAAAAGGTTTCTGTTGTTGTAGCTTATGCAGTTGCTCT | 190468 |
| mRNA | ------------------------------------------------------------ | |
| genome | GTTGCTATGGAAACGTGACATCAAAATGACGTTTCCCGTTTAAAAGCTTTTAACTAAATT | 190528 |
| mRNA | ------------------------------------------------------------ | |
| genome | CCTGCCTGTCAGATGTAGGCCCCATTTTGAGCGTGGAGCTGCCTTCGAGCGAGCGTGAGC | 190588 |
| mRNA | ------------------------------------------------------------ | |
| genome | GGCGCCTCCCGCCCATGGTGCGTGGGGCCGGGCCGGGGCCCTCGCTGAGCGCGCTCTCTC | 190648 |
| mRNA | ------------------------------------------------------------ | |
| genome | ACCCCACAGGCGCCTCCGGCATGGCGGCGGCCGAGGGGCCCGGCTACCTCGTGTCTCCCC | 190708 |
| mRNA | ------------------------------------------------------------ | |
| genome | AGGCGGAGAAGCACCGGCGGGCCCGCAACTGGACGGACGCCGAGATGCGCGGCCTCATGC | 190768 |
| mRNA | ------------------------------------------------------------ | |
| genome | TGGTCTGGGAGGAGTTCTTCGACGAGCTCAAGCAGACCAAGCGCAACGCCAAGGTGTACG | 190828 |
| mRNA | ------------------------------------------------------------ | |
| genome | AGAAGATGGCCAGCAAGCTCTTCGAGATGACCGGCGAGCGCAGGCTGGGCGAGGAGATCA | 190888 |
| mRNA | ------------------------------------------------------------ | |
| genome | AGATCAAGATCACCAACATGACCTTCCAGTACAGGTGGGCGAGCGGGCAGTGTGGGCCCC | 190948 |
| mRNA | ------------------------------------------------------------ | |
| genome | ACCAGGACGGGCGGGCCCGGGCGTGGCGGGCCGCTCCTGACTTTCTTGGAGCTCTGAGTC | 191008 |
| mRNA | ------------------------------------------------------------ | |
| genome | GGGACGATGTGTGGGTCGTGGCCTGCCTGTCGGTCTCCTCTGGCCGGGTATGGGCAGAAC | 191068 |
| mRNA | ------------------------------------------------------------ | |

FIG. 1 WWWWWW

| | | |
|---|---|---|
| genome | CCCACGGGGTGAGACGGGGCCCACGGAAACCGTGTGTGCAGCCTTCCATTGGGGAAGTGG | 191128 |
| mRNA | ------------------------------------------------------------ | |
| genome | GGAAACTGAGGCCCAGCAAGGGCAGGAAACCAGTCTAAGAGCTGAGGGGTAGCAGGGGTG | 191188 |
| mRNA | ------------------------------------------------------------ | |
| genome | GGGCTGGTGCTGGGCAGAGGCCAGGATGGCTCCCAGGACGTATGGGCGGTCTGGGCACTG | 191248 |
| mRNA | ------------------------------------------------------------ | |
| genome | TCCCTCGGAGGCAGCAACACTCATGGTGGTGCCCACTGACCTCACACCCTGCTCCCCCAT | 191308 |
| mRNA | ------------------------------------------------------------ | |
| genome | AGGGAGGCGGCGGCTGCCAGTGCCCTCCCCACCACCAAGCTCCCAAGCTCAGCAGGGGTT | 191368 |
| mRNA | ------------------------------------------------------------ | |
| genome | TCAGGGGCCTACTGCGTCATTGGGGAAATTGAGACTGCAAGTGAGAAGGAGGCTCAGTGC | 191428 |
| mRNA | ------------------------------------------------------------ | |
| genome | TCTGCGACTTGGAGCATCCACTGAGCCTCTGCCATGAGCCGGTGAGCCCCACTGGGGCTG | 191488 |
| mRNA | ------------------------------------------------------------ | |
| genome | GCCCTAGGGTCACGGTGGGGTATTTCCAGAAATCACCAGGTGAGGTGCAGGACCAGCCAG | 191548 |
| mRNA | ------------------------------------------------------------ | |
| genome | CGCATGGGTGGGGCTTACGGTGCGAAGAAGAAAGAGGTGGAGGCCTGCCCTGGCCCAGGA | 191608 |
| mRNA | ------------------------------------------------------------ | |
| genome | CTCCCAGCGTGGGGGCTCCCGGCCTGGCCCCACCTCTGCTCCTGCTACATGGCAGGTGGG | 191668 |
| mRNA | ------------------------------------------------------------ | |
| genome | CCCTTCCTGCCCTGGCAACCTGCAGGGAAGGCCGGAGGGGACCACCCAGCCAGGGAGATG | 191728 |
| mRNA | ------------------------------------------------------------ | |
| genome | TTGGCGTCTAGGAGGGGACAGGTGTGGTCCCACACACCCAGCATCTTAAAGTGCGTGGGT | 191788 |
| mRNA | ------------------------------------------------------------ | |
| genome | CCCCAGCCCATTAGGACAGGGTCCCGGGTGGGCAGGGGTCATGGTGGGGTGAAGGTCTCA | 191848 |
| mRNA | ------------------------------------------------------------ | |
| genome | GGCACAGGCAAGGTCACAGGTGCGGTGAGGGTCTTGCAGGGTGTGAAGGTCATAGGTGTG | 191908 |
| mRNA | ------------------------------------------------------------ | |
| genome | CGGTGAAGGTCACAGGTGTGGGGTGATGGTTTTGGGTGTGGGGAGGGTCTTGCACGGAGC | 191968 |
| mRNA | ------------------------------------------------------------ | |
| genome | GAGGGTGGCAGCAAGAGCTGGAAGCTGCAGGGGGAGAATGGCAGCAGAGAGCACCCGGCC | 192028 |
| mRNA | ------------------------------------------------------------ | |
| genome | CTGTGGGCGGCCTGGACAGGGCTGGGCCTGGGGCTGCCGGAGAGCCTGTCAGCTTCCAGG | 192088 |
| mRNA | ------------------------------------------------------------ | |
| genome | ATGGGAGTGGCCTCACTCAGCTGCTCCACCTCCGGGTCAGGCAGGTGAGCCTGGGGCAGA | 192148 |
| mRNA | ------------------------------------------------------------ | |
| genome | GAGGCTGAGAGCACCTGAGCCACTTGTGGGAGAGGCCACCCCCACTGCCCCCCTCAGGCG | 192208 |
| mRNA | ------------------------------------------------------------ | |
| genome | AGGAGCCGGCCTCCAGCACAGCAGAAGGGAACCCCCAGTCCCCAGCCCTAGTGGGAGTGG | 192268 |
| mRNA | ------------------------------------------------------------ | |
| genome | GGAAGAGGCCCAGCAAGGCCCCGGACAGACCGCCAGCCTGTGAGGTCTCCGCTTTCAGTT | 192328 |
| mRNA | ------------------------------------------------------------ | |

FIG. 1 XXXXXX

| | | |
|---|---|---|
| genome | GCGTTGATTTGATTTTTTCTGAGCCTTGAAGGAGGGGTCCGGGGCCTGGCCCTGCCCAAA | 192388 |
| mRNA | ------------------------------------------------------------ | |
| genome | GGCCCCTAGGCAGGCCCCAAAGCCGGGACCTAGGGTGCTGAGCATGACGGATGTTGGGTT | 192448 |
| mRNA | ------------------------------------------------------------ | |
| genome | TGAGCGGCTGGCTTGCGACGTGAGGGCTGAGGTGTGAGCCTGGGTATCTTCAGAGGTTCG | 192508 |
| mRNA | ------------------------------------------------------------ | |
| genome | GTGGACACAGGCAGCTGCCCGCGGCCCCACTGTTCCCGTGGCCTCCTAGTCCTGCTCAGG | 192568 |
| mRNA | ------------------------------------------------------------ | |
| genome | CACCTGGTGAGGAAGGGACGCAGAGGGCAGTGGGAGGTGGCCACGACTGTTCCAGCAGGC | 192628 |
| mRNA | ------------------------------------------------------------ | |
| genome | TCCCCTCTGACTCAGGAATTCACGGGCACCACCTCCCTGGCTGGCTCTGGTTGGTGTCTG | 192688 |
| mRNA | ------------------------------------------------------------ | |
| genome | GCCAGGTTATTCATTATTTATGCTGAAAGCCTCTTCAGAGTCCCAGGGGAGGGTTTCTGT | 192748 |
| mRNA | ------------------------------------------------------------ | |
| genome | CTCCATTCCTGGAGGCTGAGAGATGAGGGTGCAGCAGAGTGGGGGCCTCCACTCCAGACC | 192808 |
| mRNA | ------------------------------------------------------------ | |
| genome | CTGCAGTCTGGGCTGGCCAAGGGCTGCACCGGTGCACTGCACGTCATGGCTGATGAAGCA | 192868 |
| mRNA | ------------------------------------------------------------ | |
| genome | CTTCCACACCGCAGCCCCTCAGAGCTGCCACAGTCAGCCTTAGTTCACCGAGGGGAAGC | 192928 |
| mRNA | ------------------------------------------------------------ | |
| genome | TGAGGCCCAGAGCATGAGAGGGACTTGCCCAGGGCCACATAGTCCTTAGCAGAGGAAGCT | 192988 |
| mRNA | ------------------------------------------------------------ | |
| genome | GTGGCTGGGTGACTCGATCTTTGTCCTTTTTCTTTATACCCGCAGTCTCCCCATAGCAGA | 193048 |
| mRNA | ------------------------------------------------------------ | |
| genome | GGCTTTTCTTTTTTTTTCTTTTTCTTTTTTTTTTTTACAAGAACTCTTTATATATTA | 193108 |
| mRNA | ------------------------------------------------------------ | |
| genome | AGGCTGTTGGGCTGAAGAAGCCTGAGAGGGTGGCTGGTTCTGTGGAGCATGGTTTGTTGA | 193168 |
| mRNA | ------------------------------------------------------------ | |
| genome | AGTACAGTTTGGGGGCCTCCTACACTGAGAATAGGCCTTTTCTCGTTTCTCCAAAGAGTG | 193228 |
| mRNA | ------------------------------------------------------------ | |
| genome | GGCTGGCTCAAGTAGGGCAGAGAGAGAAGCCTGGGGCAGAGGTTAGGGATGGGCACCCAG | 193288 |
| mRNA | ------------------------------------------------------------ | |
| genome | CGCCTGCCCTCACACGCTCTGTGCTGGTGTCTTCACAGCCACGTGCCACCCTGGGCAGCA | 193348 |
| mRNA | ------------------------------------------------------------ | |
| genome | TCCCCTGCTCACCATCTGGCTGTGCCTGTTTGCTGGGGGCACCTCATTCAGAATCCAGCT | 193408 |
| mRNA | ------------------------------------------------------------ | |
| genome | TATTGTTTCCAACGGCCAATGGCCACACCCTGGCAGGTAGCAAGAGTAGGAGAGAGGAGA | 193468 |
| mRNA | ------------------------------------------------------------ | |
| genome | CACCCACTCCGAGCACAGGTTGGGTTTGGAGCCCGGCCTTGGGGCACTCTGTCACTCAAA | 193528 |
| mRNA | ------------------------------------------------------------ | |
| genome | GGCAGAGTGGGGAGTGGGCACTGGGCCTTAGGAGGTACTGGGTCCAGTGAGGCAGAGATG | 193588 |
| mRNA | ------------------------------------------------------------ | |

FIG. 1 YYYYYY

```
genome      CCCCTGCCCCACCCCCACCTTGTGGCTTCTTCCCTGGCCTGGCCAGAGCTGTCTGGCCGC  193648
mRNA        ------------------------------------------------------------ genome      CATGGGGCCCTGTGTCTCCTGCCTTGACCTCCCAGAGGGCAGCCGAGGCCCAGGGGAGGC  193708
mRNA        ------------------------------------------------------------ genome      CTGGGGACTTAGCCTCTCAGGGCAGGACCTGTCTGCAGGAGTAGGTGGGTGCTGGGGGTC  193768
mRNA        ------------------------------------------------------------ genome      CCAGTGGTAATGAGGCATCAGGCAGTGTGGGAAGGGGCCCATCCGGCCCACCCCAGGGCC  193828
mRNA        ------------------------------------------------------------ genome      TCTGGGCAGGTTGCAGGTTGTAGCGCTGGATCTAGGCTCCTGCCCAGACTGTAGGTTCAA  193888
mRNA        ------------------------------------------------------------ genome      CCAAGAATGGCATGGGAGCCCAGCCTGCTGTTTGCTTTATTAAATCTGCCCTGTAGCTGG  193948
mRNA        ------------------------------------------------------------ genome      GGGAGGGGCTTACTTTGATCATCACTATGTCATTGATATAAAAATAGAGGCTCAGAGAGG  194008
mRNA        ------------------------------------------------------------ genome      TGAATGAACCTGCCCAAAGTCACACAGCAAAGTGTGGAGATGAGATACTGACTCAGGGCT  194068
mRNA        ------------------------------------------------------------ genome      GTGGACACTGAAGCCTGTGCTCTAACGCCAGTGGCTGTCGCTCCCTGAGGCATTCTCTCC  194128
mRNA        ------------------------------------------------------------ genome      CGAACAACACAGTTATTATATTACAAAATATTATCACTATATTTATATATCTTATAATAC  194188
mRNA        ------------------------------------------------------------ genome      CTTATTATTACAATAAAACCTTATTACTCTACCTTTCAAAATGAATTATTTAAAAAGCAG  194248
mRNA        ------------------------------------------------------------ genome      TATTTGCTCATTGCAGAGAGTCTAGAAACTATAGAAAAGCAAGGGAAAAGCAATAGGACC  194308
mRNA        ------------------------------------------------------------ genome      AGCCCCAAGGTCCCAGCATGCACAGATAACCTTAGTAATACTGGGACGTGTGCTTCCTTT  194368
mRNA        ------------------------------------------------------------ genome      TTAACATCTGAGCCCGTGTAGGTCCTGAAGCCCAGCTTCTTTCTAAGTCCATTGTCATCT  194428
mRNA        ------------------------------------------------------------ genome      TGACCCTGGAGCCTGGCCGATTTTGCTGGGGAGGCCCTTGCCAGCCGAGAGCGGCTCCTG  194488
mRNA        ------------------------------------------------------------ genome      CCTGTGCCGGCGTGGCGCGCCCCTCTGCTGAGGCTGGGCAGGACAGGGGCTGGGCCAGCT  194548
mRNA        ------------------------------------------------------------ genome      CTGTTTCTCACCCTTGGCTCTTGTGTCTCTCGTTTCAGGAAATTAAAATGCATGACAGAT  194608
mRNA        ------------------------------------------------------------ genome      AGCGAGTCCGCCCCGCCCGACTGGCCCTATTACCTAGCCATTGATGGGATTCTGGCCAAG  194668
mRNA        ------------------------------------------------------------ genome      GTCCCCGAGTCCTGTGATGGCAAACTGCCGGACAGCCAGCCGCCGGGGCCCTCCACGTCC  194728
mRNA        ------------------------------------------------------------ genome      CAGACCGAGGCGTCCCTGTCGCCGCCCGCTAAGTCCACCCCTCTGTACTTCCCGTATAAC  194788
mRNA        ------------------------------------------------------------ genome      CAGTGCTCCTACGAAGGCCGCTTCGAGGATGATCGCTCCGACAGCTCCTCCAGCTTACTG  194848
mRNA        ------------------------------------------------------------
```

FIG. 1 ZZZZZZ

| | | |
|---|---|---|
| genome | TCCCTTAAGTTCAGGTAGTGTGTCTGCTTGTCCTTCCCCTGCCCTGGGGTATCTCAGCCC | 194908 |
| mRNA | ------------------------------------------------------------ | |
| genome | CCACCATTTAGAGAAAGGGACTGGGAGTGGCAAGGCCGGCGGCGGCGGCCACAGTGGTTG | 194968 |
| mRNA | ------------------------------------------------------------ | |
| genome | CAGAGGCCGTGGCTGCGGGCAGCGCCTCCAGGGACAGGCGGCCTCAGACCAGGGAGGGCT | 195028 |
| mRNA | ------------------------------------------------------------ | |
| genome | TTAGTGTCCACAGGCAGACCGAGTTTGTCTCCCAGCTCCATCACTTTTGAGCTGCACGGA | 195088 |
| mRNA | ------------------------------------------------------------ | |
| genome | AAGTTCCTTGACTTCTCTGGCCTCAGTCTCCCTCCTATAAAATGGGGGTAAATCAGTACC | 195148 |
| mRNA | ------------------------------------------------------------ | |
| genome | TTTCTCAGAGGGTGGCTGGGAGCATCACAGGAGAGAAGACGCAGCATGGGGCCCGGCACA | 195208 |
| mRNA | ------------------------------------------------------------ | |
| genome | CGGAGGGAGACCAAGCCCCAGACCCCAGAATGCGCCCCCTGGCCTCCCTTAGCCCACACA | 195268 |
| mRNA | ------------------------------------------------------------ | |
| genome | GACCCCACCCTCACAGGCTAGCTGCCCTCTCAGCACTGGGGAGGGTGTCGGGCTGCACCT | 195328 |
| mRNA | ------------------------------------------------------------ | |
| genome | CATCACGTGTTGCCGTGGGCATGACCCGTCCCCTCTGCCATCCATCCCACACCTCAGACC | 195388 |
| mRNA | ------------------------------------------------------------ | |
| genome | CGTCCCGTGCTGGCCACGTGACTGTGCCTGCAAGATGCTCACAGGGCAGCCGGGAGCCAG | 195448 |
| mRNA | ------------------------------------------------------------ | |
| genome | GCAGCATGCAGGACAGACACCTGCGGGGTGGGCCTGGGGAGCCCAGAGAAGGTGCTTTTG | 195508 |
| mRNA | ------------------------------------------------------------ | |
| genome | AGGAGGGGACATTTGGGGTGGGCTTTCAAGGTAAAATAGAAGTTGGCCATTTGGAGGCAA | 195568 |
| mRNA | ------------------------------------------------------------ | |
| genome | GAACAGGAAGATTGTGGATTTGAGTCACAGCTTCTCCCCTGCCCTGGTCTTCAAGTCTTT | 195628 |
| mRNA | ------------------------------------------------------------ | |
| genome | CTGACAGGAGGTGTCAGAAAAGTATCTTTAGTAGAGAAGGCGTCTCCGAGGAGGGTCCCT | 195688 |
| mRNA | ------------------------------------------------------------ | |
| genome | CTCATGCCGGGGGCCGCTGCTTGACTCAGGATTTCTCATTGAAGACCTGAGACAAAAACG | 195748 |
| mRNA | ------------------------------------------------------------ | |
| genome | CTTTTGCTGGCAGCTAGAAGGAACCAGCAGGAGGCCTGAGATTTGTGGCTGTTGTTCCCG | 195808 |
| mRNA | ------------------------------------------------------------ | |
| genome | TGGACTGAGCCCAGTTCTCAGACTCAGCTGCCTGGGGCCTTGCACAGGACTGGGGCGTGG | 195868 |
| mRNA | ------------------------------------------------------------ | |
| genome | GGGCTGCCCTCCCTGATCAGGCCCAAAGCGCGGATCTCACGCCCCTGAGGTTGGCTGTAC | 195928 |
| mRNA | ------------------------------------------------------------ | |
| genome | CCTCTCAGCTCAGAGCAGAGTGTGGGCCAGGGATGAGCAGGCACTGGAGCAGGGCCCTGG | 195988 |
| mRNA | ------------------------------------------------------------ | |
| genome | GGTCTGTGGGTTTTGGCAGCTCCCTGCCCTTCAGGGAGGTCTGCTGAGACCACGGGTGGC | 196048 |
| mRNA | ------------------------------------------------------------ | |
| genome | CCCTACCCCAGCAGCAGAGCTCTCAGGAGGCGCCCACAGGGCTGGACTGCCTTTACTCAC | 196108 |
| mRNA | ------------------------------------------------------------ | |

FIG. 1 AAAAAAA

| | | |
|---|---|---|
| genome | CACCTCTACCAGAGCTCTGAGGTCCTGGGGAGAGAGCCCAGGCCTCTTGTGGGCCCCACA | 196168 |
| mRNA | ------------------------------------------------------------ | |
| genome | CCCTCTAGGTGCCTGTCCTTCTGCCTCTCTACCAAGGTGTGCCGGCCCCATTTCTAGGCC | 196228 |
| mRNA | ------------------------------------------------------------ | |
| genome | GCCGGGAGATAAGGGGGCTCACATCTCAGGCCCTTCCTTCTGGGACCTCAGTTTCCCCAT | 196288 |
| mRNA | ------------------------------------------------------------ | |
| genome | CTGCCTAAGGCCGGGTGGGGCTGGTGGTCTTGGCTTCCCTACAGGGGTCCTGAGTACTCT | 196348 |
| mRNA | ------------------------------------------------------------ | |
| genome | GCACTACCCAGCACCCCCCACCCCTGCCTTCATCTCTCCCTGGGGGTGGTCTCTCCACCC | 196408 |
| mRNA | ------------------------------------------------------------ | |
| genome | CTGGCCCCCAACTGGGGCTGAGCCCCCACCTGCCCAGTTTGGTGGGTGAAGGGTGCTCCC | 196468 |
| mRNA | ------------------------------------------------------------ | |
| genome | TGGCAGGATATGCCCCTCTGCAGCCCAGAACATCCCACCCTTTCCAGACCGAAGGGGTGT | 196528 |
| mRNA | ------------------------------------------------------------ | |
| genome | GGATTGTCCTGGGACCCTGGTCATTGGGGTCATCCGCTAGTCGCAAAGGACGGCAATGCC | 196588 |
| mRNA | ------------------------------------------------------------ | |
| genome | TGTGGCCTCTCTTTCTTTCTTTTTCTTTTTTTTTTTTTGAGACGGAGTCTCGCTCTTG | 196648 |
| mRNA | ------------------------------------------------------------ | |
| genome | TGCAGAGAGCAGTGGCGCGATCTTGGCTCACTGCAACCTCCGCCTCGTGGGTTCAAGCGA | 196708 |
| mRNA | ------------------------------------------------------------ | |
| genome | TTCTCCTGCCTCAGCCTCCCGAGTAGCTGGGATTACAGGCACCCGCCACAACGCCTGGCT | 196768 |
| mRNA | ------------------------------------------------------------ | |
| genome | AATTTTTGTATTTTTAGTAGAGATGGGGTTTCACCATGTTGGCCAGGCTGGTCTTGAACT | 196828 |
| mRNA | ------------------------------------------------------------ | |
| genome | CCTGACCTCAGGTGATCCACCTGCCTCTGCCTCCCAAAGTGCTGGGATTACAGGCATAAG | 196888 |
| mRNA | ------------------------------------------------------------ | |
| genome | CCTCCACACCCGGCCACCCCTGTTACTTTCTGTCAAAGGCGGTGGGTTCTGGCCCCTCCT | 196948 |
| mRNA | ------------------------------------------------------------ | |
| genome | TTGCACATGGAATATGAGACCCTGAGTAAGTGACCTGACTCCCTGGGGCCTCAGTTTCCC | 197008 |
| mRNA | ------------------------------------------------------------ | |
| genome | CATTTGCCCAGTAGGATTGTCGGGAGGGTCCGGTGAGGCCCCTGGTGTGCCCAGGCTCTG | 197068 |
| mRNA | ------------------------------------------------------------ | |
| genome | TGGCCAGCACGTCCACAGCCGGCACTGTCCTTCCAGGTCGGAGGAGCGGCCGGTGAAGAA | 197128 |
| mRNA | ------------------------------------------------------------ | |
| genome | GCGCAAGGTGCAGAGCTGCCACCTGCAGAAGAAGCAGCTGCGGCTGCTGGAGGCCATGGT | 197188 |
| mRNA | ------------------------------------------------------------ | |
| genome | GGAGGAGCAGCGCCGGCTGAGCCGCGCCGTGGAGGAGACCTGCCGCGAGGTGCGCCGCGT | 197248 |
| mRNA | ------------------------------------------------------------ | |
| genome | GCTGGACCAGCAGCACATCCTGCAGGTGCAGAGCCTGCAGCTGCAGGAGCGCATGATGAG | 197308 |
| mRNA | ------------------------------------------------------------ | |
| genome | TCTGCTGGAGAGGATCATCACCAAGTCCAGCGTCTAGGCCAGCAGGCGGCGGCGGCGGCG | 197368 |
| mRNA | ------------------------------------------------------------ | |

FIG. 1 BBBBBBB

| | | |
|---|---|---|
| genome | GGGCCGGGCGGCTGGTGGTACTGCTCAGGCCACCCAGGGCAGGCCACTCAGGCCAGGCGG | 197428 |
| mRNA | ------------------------------------------------------------ | |
| genome | GCAAGGGGCCGCCCCGCGAGCGGAGACCGCCTTCCACCTGGCCTCTGGCAGGATGTCCC | 197488 |
| mRNA | ------------------------------------------------------------ | |
| genome | TTCTGAGGGGTATTTTGAGGAACCCCCAGGCCCTGGGGACCGTGAGGCTCCAGTCTCCAG | 197548 |
| mRNA | ------------------------------------------------------------ | |
| genome | CATGAATGCCCTTCCTCGGACACAGGCCAGGGCCTCTGGGGTTCACTCCGAGTAAGAACG | 197608 |
| mRNA | ------------------------------------------------------------ | |
| genome | TCCTAGAGCCACTCTCCAGTGTCGTTACTATCAATGATACTTGACGTGGCTTTGATATTA | 197668 |
| mRNA | ------------------------------------------------------------ | |
| genome | AACGTATACTTTTTCATTCTTGCCTGGAACGCACAGTTTGCTGTTGCTGGCTTGGTGAGG | 197728 |
| mRNA | ------------------------------------------------------------ | |
| genome | ATGCCCTGATTGATGGATCCCGAAAATGAAAGCAGATGGAAACGGGTTGGGGCAGGCTGG | 197788 |
| mRNA | ------------------------------------------------------------ | |
| genome | AGCTGGGGGAGCTCTCTCCTGAAGGGAACCCTGTGTCCTCCCTCACCAGGACCTCTGCGT | 197848 |
| mRNA | ------------------------------------------------------------ | |
| genome | CTCTCCTTAAATGGCCTCTGACGCCTGATGAAAACCCCAGCGACCTTCCAGGAGGCTTTT | 197908 |
| mRNA | ------------------------------------------------------------ | |
| genome | ATTCAGCTCTGTTTGGAGCATCAGGTGTTTCCACTGCCTCCTTAGCAATGACACTAATAA | 197968 |
| mRNA | ------------------------------------------------------------ | |
| genome | AAGTCGTAACACCTGTTCACATGCACAGCCCTGTTGAGTGTTCTGGGTGCTGGAGATATC | 198028 |
| mRNA | ------------------------------------------------------------ | |
| genome | ATGGTGGATGACACAAAGGCCCTGGCCTCTTGGAGCTTATGCTCCCATGCGGGGAAGACA | 198088 |
| mRNA | ------------------------------------------------------------ | |
| genome | CATGGGTCAGTAGAGAAATGGTTGCAGGTTGTGATAAGTGCTGGAAGGGAGGGGTTGGCC | 198148 |
| mRNA | ------------------------------------------------------------ | |
| genome | TGAGGACACGGAGGCAGACATACGTGGAGCTGGGAACAGTGGCCACACAGGGAACGGCCA | 198208 |
| mRNA | ------------------------------------------------------------ | |
| genome | GTGCGAAGGCCCAGAGGCAGAGGACACTGGAGCAAGCCCAGGAGCAGCTAGGAGGCTGGT | 198268 |
| mRNA | ------------------------------------------------------------ | |
| genome | GGCCAGCAGCCAGGCCACGGAAGCCCGTGCAGCCCGTGGGGAGGAGTGTTCATGCTTTTC | 198328 |
| mRNA | ------------------------------------------------------------ | |
| genome | AAGCTTAGTGGGAGTCTTTTGGCCAGTGCAGCTCTGGGTCTGACATCGGTGGGGACAGA | 198388 |
| mRNA | ------------------------------------------------------------ | |
| genome | GGGGTGGTGGAGCGGCCACAGCTGCAAGCTCACCTCACTGCCGGCCCTTCCACCAGTTTC | 198448 |
| mRNA | ------------------------------------------------------------ | |
| genome | AAACTCTTTCTAGAAGCTCCAGCTTTCCCAAAGCTGAATTCTCTATGAGCCTCCTTGGCC | 198508 |
| mRNA | ------------------------------------------------------------ | |
| genome | GGGACTCGGGCGTCTGGTTGCCCTGGCTGCAAAGGAGGCTGGGGCCAGGTGTGTTTGAGT | 198568 |
| mRNA | ------------------------------------------------------------ | |
| genome | CACCTCCTGGAATTAGGCAAGTTGCTGCCCAAATAGAAGGTTGTTGGCAGGTGGGTCAGC | 198628 |
| mRNA | ------------------------------------------------------------ | | rs1006798 (marked at position with A in the sequence AAGTCGTAACACCTGTTCACATGCACAGCCCTGTTGAGTGTTCTGGGTGCTGGAGATATC)

FIG. 1 CCCCCCC

```
genome    AGGTGAACAGCATGGTTTGACTCAGGGTTCAGAAAAATCTCCCTCTGGCTGCCAAGCGAG  198688
mRNA      ------------------------------------------------------------ genome    CAGGCCGTGGAGACAGGTGCAGAGGCAGGTGTGGCAGCAGGCATCCTGCCAGGCAGTGCT  198748
mRNA      ------------------------------------------------------------ genome    GCAGTCATCCTGCGACAAGCAGCAGCAGCTCATCCTACCCTCTAGGGGGTCTTGAGGTCA  198808
mRNA      ------------------------------------------------------------ genome    GCCAGGCAAGAGAGCAGCTTGGACTCCACTGGGTGTGGGACCAGCCTGTGGACCATGGTG  198868
mRNA      ------------------------------------------------------------ genome    GTGTGGAGGGTGCCCTCGGCCTGCCTGTGTGAAGGAGAGGCCGGCGTGTTCTGTGGAGCC  198928
mRNA      ------------------------------------------------------------ genome    CAAAGGGGAGCTGGGCAAGCAGGATTCACTTCACTCTGAGGGTCCTGGAGCTCCCACCCT  198988
mRNA      ------------------------------------------------------------ genome    CCTCAGCCATCTCCCCAGAGCCTGTGTGCCGAGGACTCGGCCCATGTTGCTGTGGGATGA  199048
mRNA      ------------------------------------------------------------ genome    GAGGCAGAGTGTCGTGAGGGTGTAAGGAGCGGCGGCAGTGGTGGGAGGAGGGAGCAGCAG  199108
mRNA      ------------------------------------------------------------ genome    CCAGCGCTACGGTGCCAGTTTCCAGCTGCCAGATGACGCCGCTGACCCTGTGGTTGAGAA  199168
mRNA      ------------------------------------------------------------ genome    GAGATGCACAGAGCCAGCTCTTGCAAGCCAGTGTGGCTGCCATAGCACCTGCCGAGAAGC  199228
mRNA      ------------------------------------------------------------ genome    AGAAGGAAGGGTGGCCCCAGGAGGACAGAGGATGCGGGCACATCTGATGCGGGCCTGAGT  199288
mRNA      ------------------------------------------------------------ genome    TTTGGGAGCTTTTGCTCTAGCCAGTTTCCAGCTCCGGGACCCACCCGCCTCGTAGGCAAG  199348
mRNA      ------------------------------------------------------------ genome    ACACCACCCAAGAAATCATTTGCTTAACAAACACACTGGGCTCCAACTGGACACCTGTGC  199408
mRNA      ------------------------------------------------------------ genome    CACCCTAGATGCTGGGAACCCAGCCATGACACAGGCACCTGCCCCCAGCTGCTGACCACT  199468
mRNA      ------------------------------------------------------------ genome    GAGGCTGGCTAGCAGCTCCCATGGGGCCAGTGTGGGGTTCCCCAGCCTCCTAACAGGGAG  199528
mRNA      ------------------------------------------------------------ genome    CCAGTCACAAGCCCTCGAGAGGGAAGGGTGCCCGCGGCCCTGGCAGGAAGGTTAGGCTGG  199588
mRNA      ------------------------------------------------------------ genome    ACGCTCCCACAAGACATAACAGATGGAGGTTCTAAATGATGTAGCAACTTCTTCACCCTG  199648
mRNA      ------------------------------------------------------------ genome    AAACTGCTGTAGAGTCAGCCATGACGCACCGGTACTTCAGTAACTGCCAGGCATCCGGGA  199708
mRNA      ------------------------------------------------------------ genome    CAGCACACCGCGAGTCGCTGCTGTGCTTGGGTTAGAAGTGGTTTGGTCTGTTTTCTTCTC  199768
mRNA      ------------------------------------------------------------ genome    GCCCTCTCTAATCAGAGTCAGTGATTCATGCCCTTCCATCACCTTAGAGAAGGGCAGGC  199828
mRNA      ------------------------------------------------------------ genome    GCTGCCCGACCTTCTCCAGGCTGGAGCAGCATCGCCTCATGTCAGCAGAACTCAGCTGTA  199888
mRNA      ------------------------------------------------------------
```

FIG. 1 DDDDDDD

| | | |
|---|---|---|
| genome | GAATATCGTGGGGTTGGTGCCTTTCATCAGCAGCATGTCCTTAACAACTTTCTGATTTCT | 199948 |
| mRNA | ------------------------------------------------------------ | |
| genome | TCCTTAGTTGTTGGTCCATTAAGGAGAAAAAAAATGATCTCAGCCATTGCTAAAATATTT | 200008 |
| mRNA | ------------------------------------------------------------ | |
| genome | GATAAGATTCAGCAAAGCAGCATGTTAACATTGAAAACTAGAATCAGGAGCCAGGCAGAT | 200068 |
| mRNA | ------------------------------------------------------------ | |
| genome | GTGCTTGCTTTTCACCTGTAGTATTTCATGTTGTTTTGACGTTTTTAGCTAATGCATTAA | 200128 |
| mRNA | ------------------------------------------------------------ | |
| genome | GATAAATAAACAAAAGCCGGGCACGGTGGTTCACGCCTGTAATCCCAGCACTTTGGGAGG | 200188 |
| mRNA | ------------------------------------------------------------ | |
| genome | CTGAGGCGGGAGGATCCTCTGAGGTCAGGAGTTCAAGACCAGCCTGACCAACATGGAGAA | 200248 |
| mRNA | ------------------------------------------------------------ | |
| genome | ACCTCGTCATTACTAAAAATACAAAATTAGCTGGGCGTGGTGGTGCATGCCTGTAATCCC | 200308 |
| mRNA | ------------------------------------------------------------ | |
| genome | AGCTACTTGGGAGGCTGAGGCAGGAGAATCGCTTGAACCCGGGAGGCGGAGGTTGCAGTG | 200368 |
| mRNA | ------------------------------------------------------------ | |
| genome | AGCTGAGATTGCACCACTGCACTCCAGCCTGGGTGACAGTGAAACTCGGTCTCAAAAAAA | 200428 |
| mRNA | ------------------------------------------------------------ | |
| genome | AAAAAAAATTAAAAAAAGATAAATAAAATAAGCAGGATAAGAAATGAAGAAAGTAGAGTT | 200488 |
| mRNA | ------------------------------------------------------------ | |
| genome | ACCTTTGTTTTCAGATTTCATTTTTGTATACCCAGAAAGCCAAATGTACAAAAGACTGGG | 200548 |
| mRNA | ------------------------------------------------------------ | |
| genome | AGCTCTTTAAACCAGCTTAAACTTGTTGAAAATGAGGATGAAGAAATATCCCATTCAGAG | 200608 |
| mRNA | ------------------------------------------------------------ | |
| genome | TTGGAATGAATTTAACCCAGAAGGAACAGGACCTCTACTGAAGAGAACTATGCAGTCTTA | 200668 |
| mRNA | ------------------------------------------------------------ | |
| genome | CTGAAAAATCTAAATAATACCTGAGCGCTGGAGAAACTTCGCACACTCCTGAAAGCTCCA | 200728 |
| mRNA | ------------------------------------------------------------ | |
| genome | AAGTCAATGTCATCATTTTATTAATGTCATTCCAAACATAGTCTCAATAATATCACTTCT | 200788 |
| mRNA | ------------------------------------------------------------ | |
| genome | TGGTTTTGACATGGACGCGATGATGTTTAAATTCATATGAAAAAAGAACGGGGCCAAAAG | 200848 |
| mRNA | ------------------------------------------------------------ | |
| genome | TCCAAGGCCAGTCAGCGTGAGAAGACCGCTCGGCCTCCCTCGGAGTCGGGGAGTTGGAAC | 200908 |
| mRNA | ------------------------------------------------------------ | |
| genome | CGCAGACTGAGATCATGTGGCTGCTGGAGGCCAGGACGAACGTCGGGAAATGGAGACTCC | 200968 |
| mRNA | ------------------------------------------------------------ | |
| genome | TGCGTTGCTGGTGGGATGTGGTGCAGCCGCTTCCAGGAGCAATTTGGTGTCCCGTCCTAA | 201028 |
| mRNA | ------------------------------------------------------------ | |
| genome | AGCTGAAGAAACGCATTTCCTCTGGTCAGTGCCACTCCTAGACAGGCCACCCTGCGGCAG | 201088 |
| mRNA | ------------------------------------------------------------ | |
| genome | CCGTCCTCAAACTGGTCTGAGGACCCCTCAACGCTCTTAAAAATCATTAAAAGTGGGCCA | 201148 |
| mRNA | ------------------------------------------------------------ | |

FIG. 1 EEEEEEE

| | | |
|---|---|---|
| genome | GGTGCGGTGGCTCACACCTGTAATCCCAGCACTTTGGGAGGCCAAGACAGGCGGATCACG | 201208 |
| mRNA | | |
| genome | AGGTCAGGACATTGAGATCATCCTGGCTAACACGGTGAAACCCCGTCTCTACTAAAAATA | 201268 |
| mRNA | | |
| genome | CAAAAAATTAGCCGGGCGTGGTGGCGGGCGCCTGTAGTCCCAGCTACTTGGGAGGCTGAG | 201328 |
| mRNA | | |
| genome | CCAGGAGAATGGCGTGAACCCAGGAGGTGGAGCTTGCAGTGAGCTGAGATCACTCCACTG | 201388 |
| mRNA | | |
| genome | CACTCCAGCCTGGGCAGCAGAGCGAGACTCTGTCTCAAAAAAAAATAATAAATAAATAAA | 201448 |
| mRNA | | |
| genome | TAAAAATAAAATAAAATAAAATTCATTAAAAGTGCCAAAGAACTTTTGCTTATGTGAGTT | 201508 |
| mRNA | | |
| genome | CTAATGACCAATATTAATACACATTAGAATATCTTATTAGAAATTAAACCTGAGACCTTT | 201568 |
| mRNA | | |
| genome | AGAAAACATGTATTCATTTCAAAATAGCAATAAACCCATGACATATTAACATAAATAACA | 201628 |
| mRNA | | |
| genome | ATTGTATGAAAAATATATTTTCCAAAACAAAAAGTTTTCGGGAGAAGTGTGGCATAGTTT | 201688 |
| mRNA | | |
| genome | TACATGGTCGTAAATCTCTGGCTTAAGAGAAGCCCACTGGCCTCTCAGCAGGCTCTGGGT | 201748 |
| mRNA | | |
| genome | CCGTCCACTTTGGGGGTGTTTTGGTTGTGAAGTATAGGAGTGAATGGAGAAGCTCATTCT | 201808 |
| mRNA | | |
| genome | TACCCAGATGTGTATTTGAAAAGAAAAGGAACATTTTAATAACCTTTGCAAATAATCGGT | 201868 |
| mRNA | | |
| genome | ATATTCTTCCGTGATCCTATTCCAACACTGGACAGGTGGTGGTTTGTTTTTTTTTTTTGG | 201928 |
| mRNA | | |
| genome | AGACGGAGTCCCGCTCTGTCACTCAGGCTGGAGTGCAGTGGCGCGATTTCAGCTCACTGC | 201988 |
| mRNA | | |
| genome | AAGCTCCGCCTCC | 202001 |
| mRNA | | |

_US 8,957,040 B2_

SELECTIVE REDUCTION OF ALLELIC VARIANTS

CROSS REFERENCED TO RELATED APPLICATIONS

This application is a U.S. National Phase filing under 35 U.S.C. §371 claiming priority to International Serial No. PCT/US2011/024103 filed Feb. 8, 2011, which claims priority to U.S. Provisional Application No. 61/371,635, filed Aug. 6, 2010, and U.S. Provisional Application No. 61/302,469, filed Feb. 8, 2010, each of which is incorporated herein by reference in its entirety.

SEQUENCE LISTING

The present application is being filed along with a Sequence Listing in electronic format. The Sequence Listing is provided as a file entitled BIOL0124USASEQ.TXT, created Aug. 6, 2012, which is 322 Kb in size. The information in the electronic format of the sequence listing is incorporated herein by reference in its entirety.

FIELD OF THE INVENTION

Embodiments of the present invention provide methods, compounds, and compositions for selectively reducing expression of an allelic variant of a gene containing a single nucleotide polymorphism (SNP). Such methods, compounds, and compositions are useful to treat, prevent, or ameliorate diseases.

BACKGROUND OF THE INVENTION

Genetic diseases are caused by abnormalities in genes or chromosomes. Such abnormalities may include insertions, deletions, and expansions. Huntington's Disease (HD) is one example of a genetic disease caused by an expansion. HD is a progressive neurodegenerative disorder that is inherited in a dominant fashion and results from a mutation that expands the polymorphic trinucleotide (CAG) tract in the huntingtin gene (HTT). The average CAG tract size in the general population is 17-26 repeats (wild type allele), however, in HD patients the CAG tract has expanded to 36 repeats or more (mutant allele) (Huntington's Disease Collaborative Research Group 1993. Cell 72(6):971-83). The HTT gene encodes the HTT protein and the expanded CAG tract results in a pathological increase in the polyglutamine repeats near the N-terminal of the protein. Individuals carry two copies of the HTT gene and one mutant allele is sufficient to result in HD.

HTT protein appears to have a role during development of the nervous system and a protective role in cells. In mouse models, constitutive knockout of the HTT gene is lethal during embryonic development (Nasir et al 1995. Cell 81(5): 811-23), while adult inactivation of the HTT gene leads to progressive cell death in the brain and the testes (Dragatsis et al 2000. Nat. Genet. 26:300-306). Reduction of huntingtin expression from the wild type allele may, therefore, have negative consequences.
BIOL0124WO Like HD, there are disorders for which a strategy of selective reduction of a mutant allele would be beneficial. Thus, there remains an unmet need to selectively reduce expression of mutant allelic variants like that of HTT, which are causative of disease, over the wild type variant, which appears to be necessary for normal cellular processes.

BRIEF DESCRIPTION OF THE INVENTION

FIG. 1 provides the mRNA (SEQ ID NO: 2) and genomic (SEQ ID NO: 1) HTT sequence showing SNP positions.

SUMMARY OF THE INVENTION

Provided herein are methods, compounds, and compositions for selectively reducing expression of an allelic variant of a gene containing a single nucleotide polymorphism (SNP). Such methods, compounds, and compositions are useful to treat, prevent, or ameliorate diseases. SNPs may be associated with a mutant allele, the expression of which causes disease. In certain embodiments, the expressed gene product of a mutant allele results in aggregation of the mutant proteins causing disease. In certain embodiments, the expressed gene product of a mutant allele results in gain of function causing disease.

In certain embodiments, selective reduction of mRNA and protein expression of a mutant allele is achieved by targeting a SNP located on the mutant allele with an antisense compound. In certain embodiments, the antisense compound is an antisense oligonucleotide In certain embodiments, antisense compounds designed to selectively reduce an allelic variant of a gene containing a SNP are created based on potency and selectivity of the antisense compound as well as population genetics.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"Active pharmaceutical agent" means the substance or substances in a pharmaceutical composition that provide a therapeutic benefit when administered to an individual. For example, in certain embodiments an antisense oligonucleotide targeted to an allelic variant is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Allele" is one member of a pair of genes or one member of a series of different forms of a DNA sequences that can exist at a single locus or marker on a specific chromosome. For a diploid organism or cell or for autosomal chromosomes, each allelic pair will normally occupy corresponding positions (loci) on a pair of homologous chromosomes, one inherited from the mother and one inherited from the father. If these alleles are identical, the organism or cell is said to be 'homozygous' for that allele; if they differ, the organism or cell is said to be 'heterozygous' for that allele. "Major allele" refers to an allele containing the nucleotide present in a statistically significant proportion of individuals in the human population. "Minor allele" refers to an allele containing the nucleotide present in a relatively small proportion of individuals in the human population. "Wild type allele" refers to the genotype typically not associated with disease or dysfunction of the gene product. "Mutant allele" refers to the genotype associated with disease or dysfunction of the gene product.

"Allelic variant" refers to one of the pair of genes or DNA sequence existing at a single locus. For example, an allelic variant may refer to either the major allele or the minor allele.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two ring atoms. A bicyclic sugar is a modified sugar.

"Bicyclic nucleoside" means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Differentiating polymorphism" means a variation in a nucleotide sequence that permits differentiation between a wild type and a mutant allele of a nucleic acid sequence. Differentiating polymorphisms may include insertions or deletions of one or a few nucleotides in a sequence, or changes in one or a few nucleotides in a sequence. A differentiating polymorphism or polymorphic allele can be in linkage disequilibrium with one or more other polymorphisms or polymorphic alleles.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Gap-widened" means a chimeric antisense compound having a gap segment of 12 or more contiguous 2'-deoxyribonucleosides positioned between and immediately adjacent to 5' and 3' wing segments having from one to six nucleosides.

"Gene product" refers to a biochemical material, such as RNA or protein, resulting from expression of a gene.

"Haplotype" means a set of alleles of closely linked loci on a chromosome that are generally inherited together. For example, a polymorphic allele at a first site in a nucleic acid sequence on the chromosome may be found to be associated with another polymorphic allele at a second site on the same chromosome, at a frequency other than would be expected for a random associate (e.g. "linkage equilibrium"). These two polymorphic alleles may be described as being in "linkage disequilibrium." A haplotype may comprise two, three, four, or more alleles. The set of alleles in a haplotype along a given segment of a chromosome are generally transmitted to progeny together unless there has been a recombination event.

"High-affinity sugar modification" is a modified sugar moiety which when it is included in a nucleoside and said nucleoside is incorporated into an antisense oligonucleotide, the stability (as measured by Tm) of said antisense oligonucleotide: RNA duplex is increased as compared to the stability of a DNA:RNA duplex.

"High-affinity sugar-modified nucleoside" is a nucleoside comprising a modified sugar moiety that when said nucleoside is incorporated into an antisense compound, the binding affinity (as measured by Tm) of said antisense compound toward a complementary RNA molecule is increased. In certain embodiments of the invention at least one of said sugar-modified high-affinity nucleosides confers a A™ of at least 1 to 4 degrees per nucleoside against a complementary RNA as determined in accordance with the methodology described in Freier et al., Nucleic Acids Res., 1997, 25, 4429-4443, which is incorporated by reference in its entirety. In another aspect, at least one of the high-affinity sugar modifications confers about 2 or more, 3 or more, or 4 or more degrees per modification. In the context of the present invention, examples of sugar-modified high affinity nucleosides include, but are not limited to, (i) certain 2'-modified nucleosides, including 2'-substituted and 4' to 2' bicyclic nucleosides, and (ii) certain other non-ribofuranosyl nucleosides which provide a per modification increase in binding affinity such as modified tetrahydropyran and tricycloDNA nucleosides. For other modifications that are sugar-modified high-affinity nucleosides see Freier et al., Nucleic Acids Res., 1997, 25, 4429-4443.

"Hybridization" means the annealing of complementary nucleic acid molecules. In certain embodiments, complementary nucleic acid molecules include an antisense compound and a target nucleic acid.

"Immediately adjacent" means there are no intervening elements between the immediately adjacent elements.

"Individual" means a human or non-human animal selected for treatment or therapy.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nuclease resistant modification" means a sugar modification or modified internucleoside linkage which, when incorporated into an oligonucleotide, makes said oligonucleotide more stable to degradation under cellular nucleases (e.g. exo- or endo-nucleases). Examples of nuclease resistant modifications include, but are not limited to, phosphorothioate internucleoside linkages, bicyclic sugar modifications, 2'-modified nucleotides, or neutral internucleoside linkages.

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage (P=S) is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Selectively reducing expression of an allelic variant" means reducing expression of one allele more than the other, differing allele among a set of alleles. For example, a mutant allele containing a single nucleotide polymorphism (SNP) may be reduced more than a wild type allele not containing the SNP.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single nucleotide polymorphism" or "SNP" means a single nucleotide variation between the genomes of individuals of the same species. In some cases, a SNP may be a single nucleotide deletion or insertion. In general, SNPs occur relatively frequently in genomes and thus contribute to genetic diversity. SNPs are thought to be mutationally more stable than other polymorphisms, lending their use in association studies in which linkage disequilibrium between markers and an unknown variant is used to map disease-causing mutations. The location of a SNP is generally flanked by highly conserved sequences. An individual may be homozygous or heterozygous for an allele at each SNP site. A heterozygous SNP allele can be a differentiating polymorphism. A SNP may be targeted with an antisense oligonucleotide, meaning that the SNP anneals to (or aligns with) position 1, 2, 3, 4, 5, 6, 7, 8, 9, 10, 11, 12, 13, 14, 15, 16, 17, 18, 19, or 20 of the antisense oligonucleotide. The remainder of the antisense oligonucleotide bases must have sufficient complementarity to the SNP site to facilitate hybridization.

"Single nucleotide polymorphism position" or "SNP position" refers to the nucleotide position of the SNP on a reference sequence.

"Single nucleotide polymorphism site" or "SNP site" refers to the nucleotides surrounding a SNP contained in a target nucleic acid to which an antisense compound is targeted.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. For example, for the purposes of this patent application, the target segment may be within the SNP site. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. (3-D-ribonucleosides) or a DNA nucleotide (i.e. (3-D-deoxyribonucleoside).

CERTAIN EMBODIMENTS

Embodiments of the present invention provide methods, compounds, and compositions for selectively inhibiting mRNA and protein expression of an allelic variant of a gene or DNA sequence. In certain embodiments, the allelic variant contains a single nucleotide polymorphism (SNP). In certain embodiments, the SNP is a differentiating polymorphism. In certain embodiments, a SNP is associated with a mutant allele. In certain embodiments, a SNP is in linkage disequilibrium with another polymorphism that is associated with or is causative of disease. In certain embodiments, a mutant allele is associated with disease. In certain embodiments, mRNA and protein expression of a mutant allele is associated with disease.

In certain embodiments, the expressed gene product of a mutant allele results in aggregation of the mutant proteins causing disease. In certain embodiments, the expressed gene product of a mutant allele results in gain of function causing disease. In certain embodiments, genes with an autosomal dominant mutation resulting in a toxic gain of function of the protein are the APP gene encoding amyloid precursor protein involved in Alzheimer's disease (Gene, 371: 68, 2006); the PrP gene encoding prion protein involved in Creutzfeldt-Jakob disease and in fatal familial insomnia (Nat. Med. 1997, 3: 1009); GFAP gene encoding glial fibrillary acidic protein involved in Alexander disease (J. Neurosci. 2006, 26:111623); alpha-synuclein gene encoding alpha-synuclein protein involved in Parkinson's disease (J. Clin. Invest. 2003, 111: 145); SOD-1 gene encoding the SOD-1 protein involved in amyotrophic lateral sclerosis (Science 1998, 281: 1851); atrophin-1 gene encoding atrophin-1 protein involved in dentato-rubral and pallido-luysian atrophy (DRPA) (Trends Mol. Med. 2001, 7: 479); SCA1 gene encoding ataxin-1 protein involved in spino-cerebellar ataxia-1 (SCA1) (Protein Sci. 2003, 12: 953); PLP gene encoding proteolipid protein involved in Pelizaeus-Merzbacher disease (NeuroMol. Med. 2007, 4: 73); DYT1 gene encoding torsinA protein involved in Torsion dystonia (Brain Res. 2000, 877: 379); and alpha-B crystalline gene encoding alpha-B crystalline protein involved in protein aggregation diseases, including cardiomyopathy (Cell 2007, 130: 427); alpha1-antitrypsin gene encoding alpha1-antitrypsin protein involved in chronic obstructive pulmonary disease (COPD), liver disease and hepatocellular carcinoma (New Engl J. Med. 2002, 346: 45); Ltk gene encoding leukocyte tyrosine kinase protein involved in systemic lupus erythematosus (Hum. Mol. Gen. 2004, 13: 171); PCSK9 gene encoding PCSK9 protein involved in hypercholesterolemia (Hum Mutat. 2009, 30: 520); prolactin receptor gene encoding prolactin receptor protein involved in breast tumors (Proc. Natl. Assoc. Sci. 2008, 105: 4533); CCL5 gene encoding the chemokine CCL5 involved in COPD and asthma (Eur. Respir. J. 2008, 32: 327); PTPN22 gene encoding PTPN22 protein involved in Type 1 diabetes, Rheumatoid arthritis, Graves disease, and SLE (Proc. Natl. Assoc. Sci. 2007, 104: 19767); androgen receptor gene encoding the androgen receptor protein involved in spinal and bulbar muscular atrophy or Kennedy's disease (J Steroid Biochem. Mol. Biol. 2008, 108: 245); CHNIP4B gene encoding chromatin modifying protein-4B involved in progressive childhood posterior subcapsular cataracts (Am. J. Hum. Genet. 2007, 81: 596); FXR/NR1H4 gene encoding Farnesoid X receptor protein involved in cholesterol gallstone disease, arthrosclerosis and diabetes (Mol. Endocrinol. 2007, 21: 1769); ABCA1 gene encoding ABCA1 protein involved in cardiovascular disease (Transl. Res. 2007, 149: 205); CaSR gene encoding the calcium sensing receptor protein involved in primary hypercalciuria (Kidney Int. 2007, 71: 1155); alpha-globin gene encoding alpha-globin protein involved in alpha-thallasemia (Science 2006, 312: 1215); httlpr gene encoding HTTLPR protein involved in obsessive compulsive disorder (Am. J. Hum. Genet. 2006, 78: 815); AVP gene encoding arginine vasopressin protein in stress-related disorders such as anxiety disorders and comorbid depression (CNS Neurol. Disord. Drug Targets 2006, 5: 167); GNAS gene encoding G proteins involved in congenital visual defects, hypertension, metabolic syndrome (Trends Pharmacol. Sci. 2006, 27: 260); APAF1 gene encoding APAF1 protein involved in a predisposition to major depression (Mol. Psychiatry. 2006, 11: 76); TGF-beta1 gene encoding TGF-beta1 protein involved in breast cancer and prostate cancer (Cancer Epidemiol. Biomarkers Prev. 2004, 13: 759); AChR gene encoding acetylcholine receptor involved in congenital myasthenic syndrome (Neurology 2004, 62: 1090); P2Y12 gene encoding adenosine diphosphate (ADP) receptor protein involved in risk of peripheral arterial disease (Circulation 2003, 108: 2971); LQT1 gene encoding LQT1 protein involved in atrial fibrillation (Cardiology 2003, 100: 109); RET protooncogene encoding RET protein involved in sporadic pheochromocytoma (J. Clin. Endocrinol. Metab. 2003, 88: 4911); filamin A gene encoding filamin A protein involved in various congenital malformations (Nat. Genet. 2003, 33: 487); TARDBP gene encoding TDP-43 protein involved in amyotrophic lateral sclerosis (Hum. Mol. Genet. 2010, 19: 671); SCA3 gene encoding ataxin-3 protein involved in Machado-Joseph disease (PLoS One 2008, 3: e3341); SCAT gene encoding ataxin-7 protein involved in spino-cerebellar ataxia-7 (PLoS One 2009, 4: e7232); and HTT gene encoding huntingtin protein involved in Huntington's disease (Neurobiol Dis. 1996, 3:183); and the CA4 gene encoding carbonic anhydrase 4 protein, CRX gene encoding cone-rod homeobox transcription factor protein, FSCN2 gene encoding retinal fascin homolog 2 protein, IMPDH1 gene encoding inosine monophosphate dehydrogenase 1 protein, NR2E3 gene encoding nuclear receptor subfamily 2 group E3 protein, NRL gene encoding neural retina leucine zipper protein, PRPF3 (RP18) gene encoding pre-mRNA splicing factor 3 protein, PRPF8 (RP13) gene encoding pre-mRNA splicing factor 8 protein, PRPF31 (RP11) gene encoding pre-mRNA splicing factor 31 protein, RDS gene encoding peripherin 2 protein, ROM1 gene encoding rod outer membrane protein 1 protein, RHO gene encoding rhodopsin protein, RP1 gene encoding RP1 protein, RPGR gene encoding retinitis pigmentosa GTPase regulator protein, all of which are involved in Autosomal Dominant Retinitis Pigmentosa disease (Adv Exp Med. Biol. 2008, 613:203)

In certain embodiments, selective reduction of mRNA and protein expression of a mutant allele is achieved by targeting a SNP located on the mutant allele with an antisense compound. In certain embodiments, the antisense compound is an antisense oligonucleotide. In certain embodiments, the antisense compound is not a ribozyme, a double stranded siRNA, or an shRNA. In certain embodiments, the antisense oligonucleotide may have one or more modified sugar(s), nucleobase(s), or internucleoside linkage(s). In certain embodiments, the antisense oligonucleotide is complementary to the SNP site. In certain embodiments, the antisense oligonucleotide is at least 65%, 70%, 75%, 80%, 85%, 86%, 87%, 88%, 89%, 90%, 91%, 92%, 93%, 94%, 95%, 96%, 97%, 98%, or 99% complementary to the SNP site. In certain embodiments, the antisense oligonucleotide is 100% complementary to the SNP site. In certain embodiments, the SNP site is 12, 13, 14, 15, 16, 17, 18, 19, 20, 21, 22, 23, 24, 25, 26, 27, 28, 29, or 30 nucleobases in length. In certain embodiments, the SNP anneals to position 1, 2, 3, 4, 5, 6, 7, 8, 9, 10, 11, 12, 13, 14, 15, 16, 17, 18, 19, or 20 of the antisense oligonucleotide.

In certain embodiments, antisense compounds designed to selectively reduce an allelic variant of a gene containing a SNP are created based on potency and selectivity of the antisense compound as well as population genetics.

In certain embodiments, selective reduction of mRNA and protein expression of an allelic variant of a gene containing a SNP occurs in a cell or tissue. In certain embodiments, the cell or tissue is in an animal. In certain embodiments, the animal is a human.

In certain embodiments, described herein are compounds comprising a modified antisense oligonucleotide consisting of 12 to 30 linked nucleosides targeted to a single nucleotide polymorphism site, wherein the modified oligonucleotide comprises a wing-gap-wing motif with a 5' wing region positioned at the 5' end of a deoxynucleoside gap, and a 3' wing region positioned at the 3' end of the deoxynucleoside gap, wherein position 5, 6, 7, 8, 9, 10, 11, 12, 13, 14, or 15 of the modified oligonucleotide, as counted from the 5' terminus of the modified oligonucleotide, or positions 1, 2, 3, 4, 5, 6, 7, 8, or 9 of the modified oligonucleotide, as counted from the 5' terminus of the gap, aligns with the single nucleotide polymorphism.

In certain embodiments, the single nucleotide polymorphism site is on a mutant allele that is associated with a disease. In certain embodiments, the single nucleotide polymorphism site contains a differentiating polymorphism.

In certain embodiments, the modified antisense oligonucleotide consists of 12 to 20 linked nucleosides. In certain embodiments, modified antisense oligonucleotide consists of 15 to 20 linked nucleosides. In certain embodiments, the modified antisense oligonucleotide consists of 15 to 19 linked nucleosides.

In certain embodiments, position 8, 9, or 10 of the modified oligonucleotide, as counted from the 5' terminus of the modified oligonucleotide, or positions 4, 5, or 6 of the modified oligonucleotide, as counted from the 5' terminus of the gap, aligns with the single nucleotide polymorphism.

In certain embodiments, the gap region is 7-11 nucleosides in length, the 5' wing region is 1-6 nucleobases in length and the 3' wing region is 1-6 nucleobases in length.

In certain embodiments, the wing-gap-wing motif is any one of the group consisting of 5-10-5, 2-9-6, 3-9-3, 3-9-4, 3-9-5, 4-7-4, 4-9-3, 4-9-4, 4-9-5, 4-10-5, 4-11-4, 4-11-5, 5-7-5, 5-8-6, 5-9-3, 5-9-5, 5-10-4, 5-10-5, 6-7-6, 6-8-5, and 6-9-2. In certain embodiments, the wing-gap-wing motif is any one of the group consisting of 2-9-6, 4-9-5, and 4-11-4.

In certain embodiments, at least one internucleoside linkage is a modified internucleoside linkage. In certain embodiments, each internucleoside linkage is a phosphorothioate internucleoside linkage.

In certain embodiments, at least one nucleoside comprises a modified nucleobase. In certain embodiments, the modified nucleobase is a 5'-methylcytosine.

In certain embodiments, at least one nucleoside of at least one of the wing regions comprises a modified sugar or sugar surrogate. In certain embodiments, each of the nucleosides of each wing region comprises a modified sugar or sugar surrogate. In certain embodiments, the sugar or sugar surrogate is a 2'-O-methoxyethyl modified sugar.

In certain embodiments, at least one of the wing regions comprises a 4' to 2' bicyclic nucleoside and at least one of the remaining wing nucleosides is a non-bicyclic 2'-modified nucleoside.

In certain embodiments, the non-bicyclic 2'-modified nucleoside is a 2'-O-methoxyethyl nucleoside.

In certain embodiments, the 4' to 2' bicyclic nucleoside is 4'-CH(CH3)-O-2' bicyclic nucleoside.

In certain embodiments, the modified antisense oligonucleotide consisting of 17 linked nucleosides and wherein position 9 of the modified oligonucleotide, as counted from the 5' terminus of the modified oligonucleotide, aligns with the differentiating polymorphism. In certain embodiments, the wing-gap-wing motif is 2-9-6.

In certain embodiments, described herein are compounds comprising a modified oligonucleotide consisting of 18 linked nucleosides and 90% complementary to a differentiating polymorphism, wherein the modified oligonucleotide comprises a wing-gap-wing motif, wherein position 9 of the modified oligonucleotide, as counted from the 5' terminus of the modified oligonucleotide, aligns with the differentiating polymorphism; wherein each nucleoside of each wing segment comprises a 2'-O-methoxyethyl sugar; and wherein the wing-gap-wing motif is 4-9-5.

In certain embodiments, described herein are compounds comprising a modified oligonucleotide consisting of 19 linked nucleosides and 90% complementary to a differentiating polymorphism, wherein the modified oligonucleotide comprises a wing-gap-wing motif, wherein position 10 of the modified oligonucleotide, as counted from the 5' terminus of the modified oligonucleotide, aligns with the differentiating polymorphism; wherein each nucleoside of each wing segment comprises a 2'-O-methoxyethyl sugar; and wherein the wing-gap-wing motif is 4-11-4.

In certain embodiments, described herein are compounds comprising a modified oligonucleotide consisting of 15 to 19 linked nucleosides and fully complementary to a differentiating polymorphism, wherein the modified oligonucleotide comprises a wing-gap-wing motif, wherein position 6, 7, 8, 9, 10, 11, 12, 13, or 14 of the modified oligonucleotide, as counted from the 5' terminus of the modified oligonucleotide, aligns with the differentiating polymorphism; and at least one high-affinity sugar modification. In certain embodiments, the modified oligonucleotide is 100% complementary to the single nucleotide polymorphism site.

In certain embodiments, at least one of the wing regions comprises a high-affinity sugar modification. In certain embodiments, the high-affinity sugar modification is a bicyclic sugar. In certain embodiments, the bicyclic sugar comprises a 4'-CH(CH3)-O-2' bridge.

In certain embodiments, at least one of positions 2, 3, 6, 9, 10, 11, 13, or 14 of the modified oligonucleotide, as counted from the 5' terminus of the modified oligonucleotide, comprises the at least one high-affinity sugar modification.

In certain embodiments, at least one of positions 2, 3, 13, and 14 of the modified oligonucleotide, as counted from the 5' terminus of the modified oligonucleotide, comprises the at least one high-affinity sugar modification.

In certain embodiments, each of nucleoside positions 2, 3, 13, and 14 of the modified oligonucleotide, as counted from the 5' terminus of the modified oligonucleotide, comprise the at least one high-affinity sugar modification.

In certain embodiments, the high-affinity sugar modification is a bicyclic sugar. In certain embodiments, the bicyclic sugar comprises a 4'-CH(CH3)-O-2' bridge.

In certain embodiments, the wing-gap-wing motif is any of the group consisting of 3-9-3, 4-9-4, and 5-9-5.

In certain embodiments, described herein are compounds comprising a modified oligonucleotide consisting of 15, 17, or 19 linked nucleosides and fully complementary to a differentiating polymorphism, wherein the modified oligonucleotide comprises a wing-gap-wing motif, wherein position 6, 8, 10, or 14 of the modified oligonucleotide, as counted from the 5' terminus of the modified oligonucleotide, aligns with the differentiating polymorphism; and at least one high-affinity sugar modification.

In certain embodiments, at least one of positions 2, 3, 6, 9, 10, 11, 13, or 14 of the modified oligonucleotide, as counted from the 5' terminus of the modified oligonucleotide, comprises the at least one high-affinity sugar modification.

In certain embodiments, the high-affinity sugar modification is a bicyclic sugar. In certain embodiments, the bicyclic sugar comprises a 4'-CH(CH3)-O-2' bridge.

In certain embodiments, the wing-gap-wing motif is any of the group consisting of 3-9-3, 4-9-4, and 5-95.

In certain embodiments, described herein are compounds comprising a modified oligonucleotide consisting of 15 linked nucleosides and 90% complementary to a differentiating polymorphism, wherein the modified oligonucleotide comprises a wing-gap-wing motif, wherein position 8 of the modified oligonucleotide, as counted from the 5' terminus of the modified oligonucleotide, aligns with the differentiating polymorphism; and at least one high-affinity sugar modification. In certain embodiments, the modified oligonucleotide is 100% complementary to the differentiating polymorphism.

In certain embodiments, each of nucleoside positions 2, 3, 13, and 14 of the modified oligonucleotide, as counted from the 5' terminus of the modified oligonucleotide, comprise the at least one high-affinity sugar modification.

In certain embodiments, the high-affinity sugar modification is a bicyclic sugar. In certain embodiments, the bicyclic sugar comprises a 4'-CH(CH3)-O-2' bridge.

In certain embodiments, the wing-gap-wing motif is 3-9-3.

In certain embodiments, described herein are methods of selectively reducing expression of an allelic variant of a gene containing a single nucleotide polymorphism in a cell, tissue, or animal, comprising administering to the cell, tissue, or animal a compound comprising a modified oligonucleotide complementary to a differentiating polymorphism, wherein the modified oligonucleotide comprises a wing-gap-wing motif and wherein position 5, 6, 7, 8, 9, 10, 11, 12, 13, 14, or 15 of the modified oligonucleotide, as counted from the 5' terminus of the modified oligonucleotide, aligns with the differentiating polymorphism. In certain embodiments, the modified oligonucleotide is 90% complementary to the single differentiating polymorphism. In certain embodiments, the modified oligonucleotide is 95% complementary to the single nucleotide polymorphism site. In certain embodiments, the modified oligonucleotide is 100% complementary to the single nucleotide polymorphism site.

In certain embodiments, the single nucleotide polymorphism site is from 12 to 30 nucleobases in length. In certain embodiments, the single nucleotide polymorphism site is from 15 to 25 nucleobases in length. In certain embodiments, the single nucleotide polymorphism site is from 17 to 22 nucleobases in length. In certain embodiments, the single nucleotide polymorphism site is 17 nucleobases in length. In certain embodiments, the single nucleotide polymorphism site is 18 nucleobases in length. In certain embodiments, the single nucleotide polymorphism site is 19 nucleobases in length. In certain embodiments, the single nucleotide polymorphism site is 20 nucleobases in length.

In certain embodiments, the allelic variant is associated with disease. In certain embodiments, the disease is Huntington's Disease.

In certain embodiments, the modified oligonucleotide is a single-stranded oligonucleotide.

In certain embodiments, at least one internucleoside linkage is a modified internucleoside linkage. In certain embodiments, each internucleoside linkage is a phosphorothioate internucleoside linkage.

In certain embodiments, at least one nucleoside comprises a modified nucleobase. In certain embodiments, the at least one modified nucleobase is a 5'-methylcytosine.

In certain embodiments, at least one nucleoside comprises a modified sugar. In certain embodiments, the modified sugar is a high-affinity sugar modification. In certain embodiments, the high-affinity sugar is a bicyclic sugar. In certain embodiments, each bicyclic sugar comprises a 4'-CH(CH$_3$)—O-2' bridge.

In certain embodiments, at least one of nucleoside positions 2, 3, 13, and 14 of the modified oligonucleotide, counting from the 5' terminus of the modified oligonucleotide, comprises a nucleoside having a bicyclic sugar wherein the bicyclic sugar comprises a 4'-CH(CH$_3$)—O-2' bridge.

In certain embodiments, each of nucleoside positions 2, 3, 13, and 14 of the modified oligonucleotide, counting from the 5' terminus of the modified oligonucleotide, comprises a bicyclic sugar wherein the bicyclic sugar comprises a 4'-CH (CH$_3$)—O-2' bridge.

In certain embodiments, the at least one modified sugar comprises a 2'-O-methoxyethyl. In certain embodiments, each nucleoside positioned in a wing segment of the modified oligonucleotide comprises a 2'-O-methoxyethyl modification.

In certain embodiments, the wing-gap-wing motif is any of the group consisting of 2-9-6, 3-9-3, 3-9-4, 3-9-5, 4-7-4, 4-9-4, 4-9-5, 4-10-5, 4-11-4, 4-11-5, 5-7-5, 5-8-6, 5-9-3, 5-9-5, 5-10-4, 5-10-5, 6-7-6, 6-8-5, and 6-9-2.

In certain embodiments, the modified oligonucleotide is not a ribozyme, a double stranded siRNA, or an shRNA.

In certain embodiments, the single nucleotide polymorphism site is on a mutant allele that is associated with disease. In certain embodiments, the single nucleotide polymorphism site contains a differentiating polymorphism.

In certain embodiments, the modified antisense oligonucleotide consists of 12 to 20 linked nucleosides. In certain embodiments, the modified antisense oligonucleotide consists of 15 to 19 linked nucleosides.

In certain embodiments, the gap region is 7 to 11 nucleosides in length, the 5' wing region is 1 to 6 nucleobases in length and 3' wing region is 1 to 6 nucleobases in length.

In certain embodiments, wherein at least one nucleoside of at least one of the wing regions comprises a modified sugar or sugar surrogate.

In certain embodiments, each of the nucleosides of each wing region comprises a modified sugar or sugar surrogate. In certain embodiments, the sugar or sugar surrogate is a 2'-β-methoxyethyl modified sugar.

In certain embodiments, at least one of the wing regions comprises a 4' to 2' bicyclic nucleoside and at least one of the remaining wing nucleosides is a non-bicyclic 2'-modified nucleoside.

In certain embodiments, the non-bicyclic 2'-modified nucleoside is a 2'-O-methoxyethyl nucleoside.

In certain embodiments, 4' to 2' bicyclic nucleoside is a 4'-CH(CH3)-O-2' bicyclic nucleoside.

In certain embodiments, described herein are methods of selectively reducing expression of an allelic variant of a gene containing a single nucleotide polymorphism in a cell, tissue, or animal, comprising administering to the cell, tissue, or animal a compound comprising a modified oligonucleotide complementary to a differentiating polymorphism, wherein the modified oligonucleotide comprises a wing-gap-wing motif and wherein position 5, 6, 7, 8, 9, 10, 11, 12, 13, 14, or 15 of the modified oligonucleotide, as counted from the 5' terminus of the modified oligonucleotide, aligns with the differentiating polymorphism.

In certain embodiments, described herein are methods of selectively reducing expression of an allelic variant of a gene containing a single nucleotide polymorphism in a cell, tissue, or animal, comprising administering to the cell, tissue, or animal a compound comprising a modified oligonucleotide consisting of 12 to 30 linked nucleosides and complementary to a differentiating polymorphism, wherein the modified oligonucleotide comprises a wing-gap-wing motif and wherein position 5, 6, 7, 8, 9, 10, 11, 12, 13, 14, or 15 of the modified oligonucleotide, as counted from the 5' terminus of the modified oligonucleotide aligns with the differentiating polymorphism; and wherein the allelic variant is a mutant allele.

In certain embodiments, the mutant allele is associated with any disease from the group consisting of Alzheimer's disease, Creutzfeldt-Jakob disease, fatal familial insomnia, Alexander disease, Parkinson's disease, amyotrophic lateral sclerosis, dentato-rubral and pallido-luysian atrophy DRPA, spino-cerebellar ataxia, Torsion dystonia, cardiomyopathy, chronic obstructive pulmonary disease (COPD), liver disease, hepatocellular carcinoma, systemic lupus erythematosus, hypercholesterolemia, breast cancer, asthma, Type 1 diabetes, Rheumatoid arthritis, Graves disease, SLE, spinal and bulbar muscular atrophy, Kennedy's disease, progressive childhood posterior subcapsular cataracts, cholesterol gallstone disease, arthrosclerosis, cardiovascular disease, primary hypercalciuria, alpha-thallasemia, obsessive compulsive disorder, Anxiety, comorbid depression, congenital visual defects, hypertension, metabolic syndrome, prostate cancer, congenital myasthenic syndrome, peripheral arterial disease, atrial fibrillation, sporadic pheochromocytoma, congenital malformations, Machado-Joseph disease, Huntington's disease, and Autosomal Dominant Retinitis Pigmentosa disease.

In certain embodiments, described herein are methods of treating Huntington's Disease, comprising selectively reducing expression of an allelic variant of a gene containing a single nucleotide polymorphism in a cell, tissue, or animal, comprising administering to the cell, tissue, or animal a compound comprising a modified oligonucleotide consisting of 12 to 30 linked nucleosides and complementary to differentiating polymorphism, wherein the modified oligonucleotide comprises a wing-gap-wing motif and wherein position 5, 6, 7, 8, 9, 10, 11, 12, 13, 14, or 15 of the modified oligonucleotide, as counted from the 5' terminus of the modified oligonucleotide, aligns with differentiating polymorphism; and wherein the allelic variant is associated with Huntington's Disease.

In certain embodiments, position 8, 9, or 10 of the modified oligonucleotide, as counted from the 5' terminus of the modified oligonucleotide, or positions 4, 5, or 6 of the modified oligonucleotide, as counted from the 5' terminus of the gap, aligns with the single nucleotide polymorphism.

Single Nucleotide Polymorphisms (SNPs)

Single-nucleotide polymorphisms (SNPs) are single base-pair alterations in the DNA sequence that represent a major source of genetic heterogeneity (Gene. 1999, 234:177). SNP genotyping is an important tool with which to investigate these genetic variants (Genome Res. 2000, 10:895; Trends Biotechnol. 2000, 18:77). In certain embodiments, antisense compounds designed to selectively reduce an allelic variant of a gene containing an SNP were selected based on potency, selectivity and population genetics coverage.

Potency

In certain embodiments, antisense compounds designed to selectively reduce an allelic variant of a gene containing a SNP are created based on potency of the antisense compound. Potency generally refers to how amenable the targeted sequence area is to antisense inhibition. In certain embodiments, specific SNP sites may be particularly amenable to antisense inhibition. Certain such highly amenable SNP sites may be targeted by antisense compounds for selectively reducing an allelic variant of a gene. Potency is demonstrated by the percent inhibition of mutant mRNA achieved by the antisense oligonucleotides targeting a SNP compared to the percent inhibition of mutant mRNA achieved by the benchmark oligonucleotide.

Selectivity

In certain embodiments, antisense compounds designed to selectively reduce an allelic variant of a gene containing a SNP are created based on selectivity of the antisense compound. Selectivity generally refers to antisense compounds comprising a particular sequence, motif, and chemical modification(s) that preferentially target the one or more differentiating polymorphisms (SNPs) in the RNA encoding a mutant HTT protein compared to the RNA encoding a wild type HTT protein. In certain embodiments, specific sequences, motifs, and chemical modification(s) are particularly selective in reducing an allelic variant of a gene containing a SNP. Certain such sequences, motifs, and chemical modification(s) are utilized to selectively reduce an allelic variant of a gene. Selectivity is demonstrated by the ability of the antisense oligonucleotide targeting a SNP to inhibit expression of the major allele or mutant allele preferentially compared to the minor allele or wild type allele.

Population Genetics

In certain embodiments, antisense compounds designed to selectively reduce an allelic variant of a gene containing an SNP are created based on the population genetics of a population afflicted with disease. Population genetics means the frequency at which the SNP appears in the disease chromosome of patients afflicted with a particular disease. In certain embodiments, the disease is Huntington disease. Where potency and selectivity amongst antisense compounds is equal, SNP targets that have higher population genetics coverage are favored over SNPs that have a weaker association with disease chromosomes.

Antisense Compounds

Oligomeric compounds may include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound is an antisense oligonucleotide. In certain embodiments, the antisense compound is not a ribozyme, a double stranded siRNA, or an shRNA.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, antisense compounds are 12 to 30 subunits in length. In other words, such antisense compounds are from 12 to 30 linked subunits. In other embodiments, the antisense compound is 8 to 80, 12 to 50, 15 to 30, 18 to 24, 19 to 22, or 20 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to a nucleic acid may be shortened or truncated. For example, a single subunit may be deleted from the 5' end (5' truncation), or alternatively from the 3' end (3' truncation). A shortened or truncated antisense compound targeted to a nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

However, selective reduction of expression of an allelic variant is optimized when the SNP contained in the target nucleic anneals to a complementary base in the antisense compound and not a mismatched base. Moreover, selectivity in general is increased when there are fewer mismatches between the SNP site and the antisense compound. However, a certain number of mismatches may be tolerated.

Antisense Compound Motifs

In certain embodiments, antisense compounds targeted to a nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In the case of an antisense oligonucleotide for selectively reducing expression of an allelic variant of a gene containing a SNP, the SNP anneals to a nucleobase within the gap segment.

In certain embodiments, the SNP anneals or is complementary to a nucleobase at position 5, 6, 7, 8, 9, 10, 11, 12, 13, or 14 of the antisense oligonucleotide, wherein position refers to the orientation of a nucleobase within the antisense oligonucleotide counting from the 5' terminus of the antisense oligonucleotide. For example, the 5' most nucleobase within the antisense oligonucleotide is in the first position of the antisense oligonucleotide. In certain embodiments, the SNP anneals or is complementary to a nucleobase at position 6, 7, 8, 9, or 10 of the antisense oligonucleotide (counting from the 5' terminus). In certain embodiments, the SNP anneals or is complementary to a nucleobase at position 9 or 10 of the antisense oligonucleotide (counting from the 5' terminus).

In certain embodiments, the SNP anneals to a nucleobase at position 1, 2, 3, 4, 5, 6, 7, 8, 9, or 10 of the gap segment, wherein position refers to the orientation of a nucleobase within the gap segment counting from the 5' terminus of the gap segment. For example, the 5' most nucleobase within the gap segment is in the first position of the gap segment. In certain embodiments, the SNP anneals to a nucleobase at position 4, 5, 6, or 7 counting from the 5' terminus of the gap segment. In certain embodiments, the SNP anneals to a nucleobase at position 4 or 5 beginning from the 5' terminus of the gap segment.

In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH$_2$)n-O-2' bridge, where n=1 or n=2). The bicyclic moiety may be a cEt having the formula 4'-CH(CH$_3$)—O-2.'

The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In certain embodiments, Y is between 8 and 15 nucleotides. In certain embodiments, Y is comprised of deoxynucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers of the present invention include, but are not limited to, for example 1-10-1, 1-18-1, 2-8-2, 2-9-6, 2-10-2, 2-13-5, 2-16-2, 3-9-3, 3-9-5, 3-10-3, 3-14-3, 4-8-4, 4-9-5, 4-10-5, 4-11-4, 4-12-3, 4-12-4, 5-8-5, 5-9-5, 5-10-4, 5-10-5, or 6-8-6.

In certain embodiments, the antisense compound has a "wingmer" motif, having a wing-gap or gap-wing configuration, i.e. an X-Y or Y-Z configuration as described above for the gapmer configuration. Thus, wingmer configurations of the present invention include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compounds targeted to a nucleic acid possess a 2-9-6 gapmer motif or a 6-9-2 gapmer motif.

In certain embodiments, antisense compounds targeted to a nucleic acid possess a 3-9-3 gapmer motif.

In certain embodiments, antisense compounds targeted to a nucleic acid possess a 3-9-5 gapmer motif or 5-9-3 gapmer motif.

In certain embodiments, antisense compounds targeted to a nucleic acid possess a 4-9-5 gapmer motif or 5-9-4 gapmer motif.

In certain embodiments, antisense compounds targeted to a nucleic acid possess a 4-10-5 gapmer motif or 5-10-4 gapmer motif.

In certain embodiments, antisense compounds targeted to a nucleic acid possess a 4-11-4 gapmer motif.'

In certain embodiments, antisense compounds targeted to a nucleic acid possess a 5-9-5 gapmer motif.

In certain embodiments, antisense compounds targeted to a nucleic acid possess a 5-8-6 gapmer motif or a 6-8-5 gapmer motif.

In certain embodiments, antisense compounds targeted to a nucleic acid possess a 6-7-6 gapmer motif.

In certain embodiments, antisense compounds targeted to a nucleic acid possess a 6-8-5 gapmer motif or a 5-8-6 gapmer motif.

In certain embodiments, antisense compounds targeted to a nucleic acid possess a 3-9-4 gapmer motif or a 4-9-3 gapmer motif.

In certain embodiments, antisense compounds targeted to a nucleic acid possess a 5-7-5 gapmer motif.

In certain embodiments, antisense compounds targeted to a nucleic acid possess a 4-7-4 gapmer motif.

In certain embodiments, antisense compounds targeted to a nucleic acid possess a 5-10-5 gapmer motif.

In certain embodiments, an antisense compound targeted to a nucleic acid has a gap-widened motif.

Certain Mixed Wings

In certain embodiments, the invention provides gapmer compounds wherein at least one nucleoside of one wing is differently modified compared to at least one other nucleoside of the same wing. Such antisense compounds are referred to as mixed wing antisense compounds (see WO 2008/049085). In certain embodiments, the modifications (or no modification) of one or more nucleosides of the 3' wing are different from those of one or more other nucleosides of the 3' wing. Such antisense compounds may be referred to as 3' mixed wing gapmers. In certain embodiments, the modifications (or no modification) of one or more nucleosides of the 5' wing are different from those of one or more other nucleosides of the 5' wing. Such antisense compounds may be referred to as 5' mixed wing gapmers. In certain embodiments, the modifications (or no modification) of one or more nucleosides of the 3' wing are different from those of one or more other nucleosides of the 3' wing and the modifications (or no modification) of one or more nucleosides of the 5' wing are different from those of one or more other nucleosides of the 5' wing. Such antisense compounds may be referred to as 3', 5' mixed wing gapmers. In such embodiment, the modifications and combination of modifications at the 3' wing and at the 5' wing may be the same or they may be different.

In certain embodiments, mixed wing compounds have desirable properties. Certain nucleoside modifications confer on the antisense compound a desirable property, for example increased affinity for a target or nuclease resistance, but also confer an undesirable property, for example increased toxicity. Incorporation of certain other nucleoside modifications results in antisense compounds with different profiles of properties. In certain embodiments, one may combine modifications in one or both wings to optimize desirable characteristics and/or minimize undesirable characteristics. In certain embodiments, the wings of a mixed wing antisense compound comprise one or more nucleoside comprising a first modification that increases affinity of the antisense compound for a target nucleic acid compared to an antisense compound comprising unmodified nucleosides; and one or more nucleoside comprising a second modification that results in reduced toxicity compared to an antisense compound with wings comprising nucleosides that all comprise the first modification.

In certain embodiments, an antisense compound comprises at least one wing comprising at least one MOE substituted nucleoside and at least one high affinity modification. In certain such embodiments, the at least one MOE substituted nucleoside and the at least one high affinity are in the 3' wing.

In certain such embodiments, the at least one MOE substituted nucleoside and the at least one high affinity are in the 5' wing.

In certain embodiments, an antisense compound comprises 1, 2 or 3 high affinity modifications in the 5' and/or 3' wings.

Target Nucleic Acids, Target Regions and Nucleotide Sequences

In certain embodiments, an allelic variant of huntingtin is selectively reduced. Nucleotide sequences that encode huntingtin include, without limitation, the following: GEN-BANK Accession No. NT_006081.18, truncated from nucleotides 1566000 to 1768000 (replaced by GENBANK Accession No. NT_006051), incorporated herein as SEQ ID NO: 1, and NM_002111.6, incorporated herein as SEQ ID NO: 2.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for huntingtin can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels of a particular allelic variant. In certain embodiments, the desired effect is reduction of levels of the protein encoded by the target nucleic acid or a phenotypic change associated with a particular alleleic variant.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

Cell Lines

In certain embodiments, the GM04281, GM02171, and GM02173B cell lines are used in experiments described herein below. The GM04281 cell line has a wild-type HTT allele that contains 17 repeats and a mutant HTT allele that contains 69 repeats. The cell line was derived from a patient both of whose parents were also affected by the disease. The GM02171 cell line was chosen as a counter screen control to the GM04281. This cell line was derived from the daughter of parents, only one of whom had the disease. The daughter had not developed HD but was considered to be at risk. The GM02173B cell line was also patient-derived and was used as a haplotype test control.

Table 1 provides SNPs found in the GM04281, GM02171, and GM02173B cell lines. Also provided are the allelic variants found at each SNP position, the genotype for each of the cell lines, and the percentage of HD patients having a particular allelic variant. For example, the two allelic variants for SNP rs6446723 are T and C. The GM02171 cell line is homozygous CC, the GM02173 cell line is heterozygous TC, and the GM04281 cell line is homozygous TT. Fifty percent of HD patients have a T at SNP position rs6446723.

TABLE 1

Allelic Variations for SNPs Associated with HD

| SNP | Variation | GM02171 | GM02173 | GM04281 | TargetPOP | allele |
|---|---|---|---|---|---|---|
| rs6446723 | T/C | CC | TC | TT | 0.50 | T |
| rs3856973 | A/G | AA | AG | GG | 0.50 | G |
| rs2285086 | A/G | GG | AG | AA | 0.50 | A |
| rs363092 | A/C | AA | AC | CC | 0.49 | C |
| rs916171 | C/G | GG | GC | CC | 0.49 | C |
| rs6844859 | T/C | CC | TC | TT | 0.49 | T |
| rs7691627 | A/G | AA | AG | GG | 0.49 | G |
| rs4690073 | A/G | AA | AG | GG | 0.49 | G |
| rs2024115 | A/G | GG | AG | AA | 0.48 | A |
| rs11731237 | T/C | CC | TC | TT | 0.43 | T |
| rs362296 | A/C | AC | AC | AC | 0.42 | C |
| rs10015979 | A/G | AA | AG | GG | 0.42 | G |
| rs7659144 | C/G | CG | CG | CC | 0.41 | C |
| rs363096 | T/C | CC | TC | TT | 0.40 | T |
| rs362273 | A/G | AG | AG | AA | 0.39 | A |
| rs16843804 | T/C | TC | TC | CC | 0.38 | C |
| rs362271 | A/G | AG | AG | GG | 0.38 | G |
| rs362275 | T/C | TC | TC | CC | 0.38 | C |
| rs3121419 | T/C | TC | TC | CC | 0.38 | C |
| rs362272 | A/G | — | AG | GG | 0.38 | G |
| rs3775061 | A/G | AG | AG | AA | 0.38 | A |
| rs34315806 | T/C | TC | TC | CC | 0.38 | C |
| rs363099 | T/C | TC | TC | CC | 0.38 | C |
| rs2298967 | T/C | TC | TC | TT | 0.38 | T |
| rs363088 | A/T | TA | TA | AA | 0.38 | A |
| rs363064 | T/C | TC | TC | CC | 0.35 | C |
| rs363102 | A/G | AA | AA | AA | 0.23 | G |
| rs2798235 | A/G | GG | GG | GG | 0.21 | A |
| rs363080 | T/C | CC | CC | CC | 0.21 | T |
| rs363072 | A/T | TA | AA | AA | 0.13 | A |
| rs363125 | A/C | AC | CC | CC | 0.12 | C |
| rs362303 | T/C | TC | CC | CC | 0.12 | C |
| rs362310 | T/C | TC | CC | CC | 0.12 | C |
| rs10488840 | A/G | AG | GG | GG | 0.12 | G |
| rs362325 | T/C | TC | TT | TT | 0.11 | T |

TABLE 1-continued

Allelic Variations for SNPs Associated with HD

| SNP | Variation | GM02171 | GM02173 | GM04281 | TargetPOP | al-lele |
|---|---|---|---|---|---|---|
| rs35892913 | A/G | GG | GG | GG | 0.10 | A |
| rs363102 | A/G | AA | AA | AA | 0.09 | A |
| rs363096 | T/C | CC | TC | TT | 0.09 | C |
| rs11731237 | T/C | CC | TC | TT | 0.09 | C |
| rs10015979 | A/G | AA | AG | GG | 0.08 | A |
| rs363080 | T/C | CC | CC | CC | 0.07 | C |
| rs2798235 | A/G | GG | GG | GG | 0.07 | G |
| rs1936032 | C/G | CC | CC | CC | 0.06 | C |
| rs2276881 | A/G | GG | GG | GG | 0.06 | G |
| rs363070 | A/G | AA | AA | AA | 0.06 | A |
| rs35892913 | A/G | GG | GG | GG | 0.04 | G |
| rs12502045 | T/C | CC | CC | CC | 0.04 | C |
| rs6446723 | T/C | CC | TC | TT | 0.04 | C |
| rs7685686 | A/G | GG | AG | AA | 0.04 | G |
| rs3733217 | T/C | CC | CC | CC | 0.03 | C |
| rs6844859 | T/C | CC | TC | TT | 0.03 | C |
| rs362331 | T/C | CC | TC | TT | 0.03 | C |

Hybridization

In some embodiments, hybridization occurs between an antisense compound disclosed herein and a SNP site. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

In certain embodiments, the antisense compounds provided herein are specifically hybridizable with the nucleic acid of a particular allelic variant.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., selective reduction of a gene product of an allelic variant).

Non-complementary nucleobases between an antisense compound and a target nucleic acid may be tolerated provided that the antisense compound remains able to specifically hybridize to a target nucleic acid. Moreover, an antisense compound may hybridize over one or more segments of a target nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a target nucleic acid, a target region, target segment, SNP site, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, a SNP site, target region, target segment, or specified portion thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, SNP site, or specified portion thereof.

In certain embodiments, antisense oligonucleotides that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, SNP site, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Chemically modified nucleosides may also be employed to increase selectivity in reducing expression the gene product of an allelic variant.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioate. Methods of preparation of phosphorous-containing and non-phosphorous-containing linkages are well known.

In certain embodiments, antisense compounds comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, increased selectivity for an allelic variant, or some other beneficial biological property to the antisense compounds. In certain embodiments, nucleosides comprise a chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or C(R1)(R)2 (R=H, C1-C12 alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH3 and 2'-O(CH2)2OCH3 substituent groups. The substituent at the 2' position can also be selected from allyl, amino, azido, thio, O-allyl, O—C1-C10 alkyl, OCF3, O(CH2)2SCH3, O(CH2)2-O—N(Rm)(Rn), and O—CH2-C(=O)—N(Rm)(Rn), where each Rm and Rn is, independently, H or substituted or unsubstituted C1-C10 alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides wherein the bridge comprises a 4' to 2' bicyclic nucleoside. Examples of such 4' to 2' bicyclic nucleosides, include but are not limited to one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., *J. Org. Chem.*, 2009, 74, 118-134); and 4'-CH$_2$—C(=CH$_2$)-2' (and analogs thereof see published International Application WO 2008/154401, published on Dec. 8, 2008). See, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); U.S. Pat. Nos. 7,053,207; 6,268,490; 6,770,748; 6,794,499; 7,034,133; and 6,525,191; Elayadi et al., *Curr. Opinion Invens. Drugs,* 2001, 2, 558-561; Braasch et al., *Chem. Biol.,* 2001, 8, 1-7; and Orum et al., *Curr. Opinion Mol. Ther.,* 2001, 3, 239-243; and U.S. Pat. No. 6,670,461; International applications WO 2004/106356; WO 94/14226; WO 2005/021570; U.S. Patent Publication Nos. US2004-0171570; US2007-0287831; US2008-0039618; U.S. Pat. No. 7,399,845; U.S. patent Ser. Nos. 12/129,154; 60/989,574; 61/026,995; 61/026,998; 61/056,564; 61/086,231; 61/097,787; 61/099,844; PCT International Applications Nos. PCT/US2008/064591; PCT/US2008/066154; PCT/US2008/068922; and Published PCT International Applications WO 2007/134181. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:
x is 0, 1, or 2;
n is 1, 2, 3, or 4;
each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is, —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-Methyleneoxy (4'-CH$_2$—O-2') BNA, (B) β-D-Methyleneoxy (4'-CH$_2$—O-2') BNA, (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, and (F) Methyl(methyleneoxy) (4'-CH(CH$_3$)—O-2') BNA, (G) methylene-thio (4'-CH$_2$—S-2') BNA, (H) methylene-amino (4'-CH2-N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) ethylene carbocyclic (4'-CH$_2$—CH$_2$-2') (carba LNA or "cLNA") as depicted below.

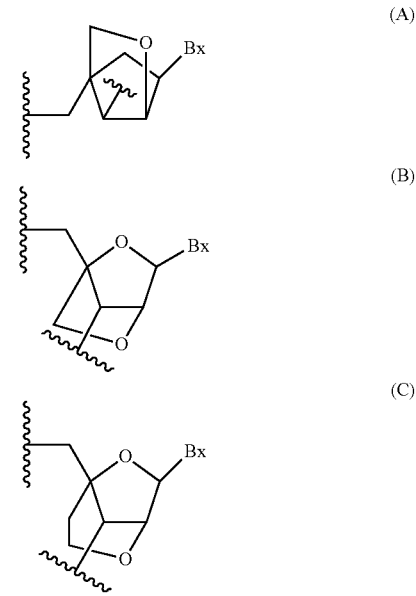

-continued (D)
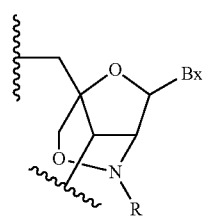

(E)
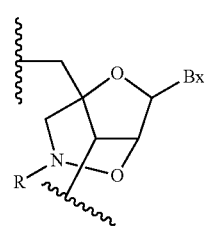

(F)
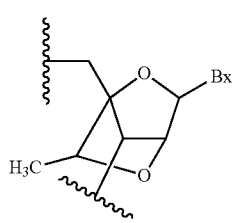

(G)
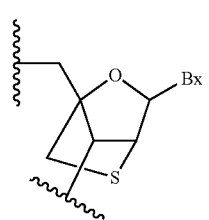

(H)
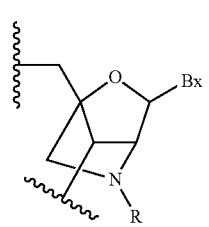

(I)
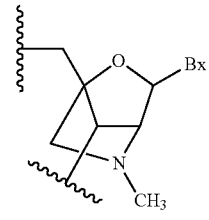

(J)
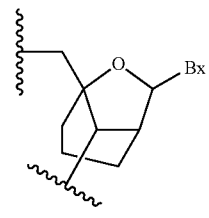

-continued (K)
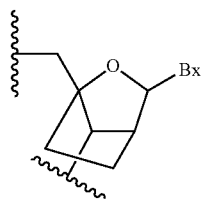

wherein Bx is the base moiety and R is independently H, a protecting group or $C_1$-$C_{12}$ alkyl.

In certain embodiments, bicyclic nucleoside having Formula I:

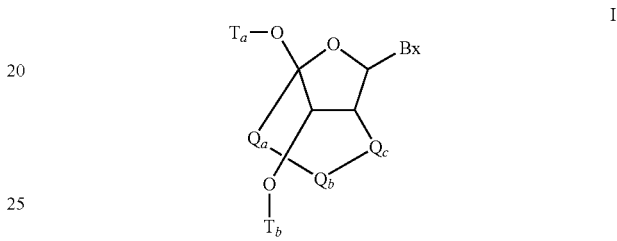

I wherein:
Bx is a heterocyclic base moiety;
-$Q_a$-$Q_b$-$Q_c$- is —$CH_2$—$N(R_c)$—$CH_2$—, —$C(=O)$—$N(R_c)$—$CH_2$—, —$CH_2$—O—$N(R_c)$—, —$CH_2$—$N(R_c)$—O— or —$N(R_c)$—O—$CH_2$;
$R_c$ is $C_1$-$C_{12}$ alkyl or an amino protecting group; and
$T_a$ and $T_b$ are each, independently H, a hydroxyl protecting group, a conjugate group, a reactive phosphorus group, a phosphorus moiety or a covalent attachment to a support medium.

In certain embodiments, bicyclic nucleoside having Formula II:

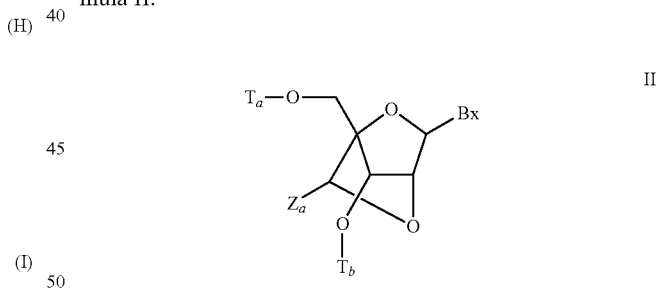

II wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups, is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_cC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleoside having Formula III:

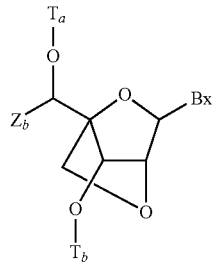

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleoside having Formula IV:

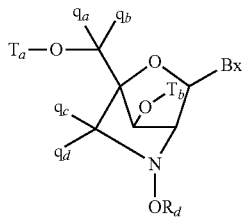

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleoside having Formula V:

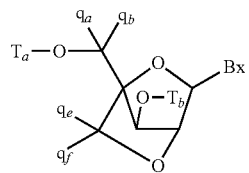

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;
or $q_e$ and $q_f$ together are =C($q_g$)($q_h$);
$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA, methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-Amino- and 2'-methylamino-BNA's have been prepared and the thermal stability of their duplexes with complementary RNA and DNA strands has been previously reported.

In certain embodiments, bicyclic nucleoside having Formula VI:

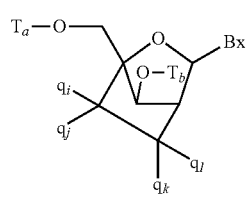

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and
$q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-substituent groups can also be selected from: C$_1$-C$_{12}$ alkyl, substituted alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., J. Biol. Chem., 1997, 272, 11944-12000). Such 2'-MOE substitution have been described as having improved binding affinity compared to unmodified nucleosides and to other modified nucleosides, such as 2'-O-methyl, 0-propyl, and O-aminopropyl. Oligonucleotides having the 2'-MOE substituent also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, C J. *Bioorg. & Med. Chem.* (2002) 10:841-854), fluoro HNA (F—HNA) or those compounds having Formula X:

Formula X:

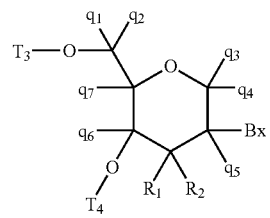

wherein independently for each of said at least one tetrahydropyran nucleoside analog of Formula X:

Bx is a heterocyclic base moiety;

T$_3$ and T$_4$ are each, independently, an internucleoside linking group linking the tetrahydropyran nucleoside analog to the antisense compound or one of T$_3$ and T$_4$ is an internucleoside linking group linking the tetrahydropyran nucleoside analog to the antisense compound and the other of T$_3$ and T$_4$ is H, a hydroxyl protecting group, a linked conjugate group or a 5' or 3'-terminal group;

q$_1$, q$_2$, q$_3$, q$_4$, q$_5$, q$_6$ and q$_7$ are each independently, H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl; and one of R$_1$ and R$_2$ is hydrogen and the other is selected from halogen, substituted or unsubstituted alkoxy, NJ$_1$J$_2$, SJ$_1$, N$_3$, OC(=X)J$_1$, OC(=OX)NJ$_1$J$_2$, NJ$_3$C(=X)NJ$_1$J$_2$ and CN, wherein X is O, S or NJ$_1$ and each J$_1$, J$_2$ and J$_3$ is, independently, H or C$_1$-C$_6$ alkyl.

In certain embodiments, the modified THP nucleosides of Formula X are provided wherein q$_m$, q$_n$, q$_p$, q$_r$, q$_s$, q$_t$ and q$_u$ are each H. In certain embodiments, at least one of q$_m$, q$_n$, q$_p$, q$_r$, q$_s$, q$_t$ and q$_u$ is other than H. In certain embodiments, at least one of q$_m$, q$_n$, q$_p$, q$_r$, q$_s$, q$_t$ and q$_u$ is methyl. In certain embodiments, THP nucleosides of Formula X are provided wherein one of R$_1$ and R$_2$ is F. In certain embodiments, R$_1$ is fluoro and R$_2$ is H; R$_1$ is methoxy and R$_2$ is H, and R$_1$ is methoxyethoxy and R$_2$ is H.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O-C$_1$-C$_{10}$ alkyl, —OCF$_3$, O—(CH$_2$)$_2$—O—CH$_3$, 2'-O(CH$_2$)$_2$SCH$_3$, O—(CH$_2$)$_2$—O—N(R$_m$)(R$_n$), or O—CH$_2$—C(=O)—N(R$_m$)(R$_n$), where each R$_m$ and R$_n$ is, independently, H or substituted or unsubstituted C$_1$-C$_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-OCH$_3$" or "2'-O-methyl" each refers to a nucleoside comprising a sugar comprising an —OCH$_3$ group at the 2' position of the sugar ring.

As used herein, "MOE" or "2'-MOE" or "2'-OCH$_2$CH$_2$OCH$_3$" or "2'-O-methoxyethyl" each refers to a nucleoside comprising a sugar comprising a —OCH$_2$CH$_2$OCH$_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also know in the art that can be used to modify nucleosides for incorporation into antisense compounds (see for example review article: Leumann, J. C, *Bioorganic & Medicinal Chemistry*, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleotides having modified sugar moieties. In certain embodiments, the modified sugar moiety is 2'-MOE. In certain embodiments, the 2'-MOE modified nucleotides are arranged in a gapmer motif. In certain embodiments, the modified sugar moiety is a cEt. In certain embodiments, the cEt modified nucleotides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity, increased selectivity for an allelic variant, or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds comprise one or more modified nucleobases. In certain embodiments, gap-widened antisense oligonucleotides comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution, increased selectivity for an allelic variant, or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression target nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes. Illustrative cell lines include GM04281, GM02171, and GM02173B cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides are mixed with LIPOFECTIN in OPTI-MEM 1 (Invitrogen, Carlsbad, Calif.) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Reduction, inhibition, or expression of a target nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to target nucleic acids. Methods for designing real-time PCR probes and primers are well known in the art, and may include the use of software such as PRIMER EXPRESS Software (Applied Biosystems, Foster City, Calif.).

Analysis of Protein Levels

Reduction, inhibition, or expression of target nucleic acids can be assessed by measuring target protein levels. Target protein levels can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of mouse, rat, monkey, and human proteins are commercially available.

In Vivo Testing of Antisense Compounds

Antisense compounds, for example, antisense oligonucleotides, are tested in animals to assess their ability to selectively reduce or inhibit expression of target gene product and produce phenotypic changes, such as, amelioration of a disease symptom. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA or protein is isolated from tissue and changes in target nucleic acid or protein expression are measured.

Administration

In certain embodiments, the compounds and compositions described herein may be administered in a number of ways depending upon whether local or systemic treatment is desired and upon the area to be treated. Administration may be topical (including ophthalmic, vaginal, rectal, intranasal), oral, pulmonary (including by inhalation or insufflation of powders or aerosols, including by nebulizer; intratracheal, intranasal, epidermal and transdermal) or parenteral, for example, by intravenous drip, intravenous injection or subcutaneous, intraperitoneal, intraocular, intravitreal, or intramuscular injection.

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

In certain embodiments, methods of specifically localizing a pharmaceutical agent, such as by bolus injection, decreases median effective concentration (EC50) by a factor of 20, 25, 30, 35, 40, 45 or 50. In certain embodiments, the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

In certain embodiments, an antisense oligonucleotide is delivered by injection or infusion once every month, every two months, every 90 days, every 3 months, every 6 months, twice a year or once a year.

Certain Compounds and Indications

Provided herein are compounds and methods that provide potent inhibition and increased selectivity for a mutant allele. Potency is demonstrated by the percent inhibition of mutant mRNA achieved by the antisense oligonucleotides targeting a SNP compared to the percent inhibition of mutant mRNA achieved by the benchmark oligonucleotide. Selectivity is demonstrated by the ability of the antisense oligonucleotide targeting a SNP to inhibit expression of the major allele or mutant allele preferentially compared to the minor allele or wild type allele. The usage of three cell lines with different genotypes at each SNP position have facilitated the determination of design rules that provide for potent and selective SNP targeting antisense oligonucleotides.

In certain embodiments, the compounds are antisense oligonucleotides as further described herein. The antisense oligonucleotides preferentially target a SNP or differentiating polymorphism. Oligonucleotides of various lengths were tested and certain lengths were determined to be beneficial for the targeting of SNPs.

In certain embodiments, the antisense oligonucleotides have a sequence that is 12-30 nucleobases in length. In certain embodiments, the antisense oligonucleotides have a sequence that is 12-25 nucleobases in length. In certain embodiments, the antisense oligonucleotides have a sequence that is 12-21 nucleobases in length. In certain embodiments, the antisense oligonucleotides have a sequence that is 12-20 nucleobases in length. In certain embodiments, the antisense oligonucleotides have a sequence that is 13-20 nucleobases in length. In certain embodiments, the antisense oligonucleotides have a sequence that is 14-20 nucleobases in length. In certain embodiments, the antisense oligonucleotides have a sequence that is 15-20 nucleobases in length. In certain embodiments, the antisense oligonucleotides have a sequence that is 12-19 nucleobases in length. In certain embodiments, the antisense oligonucleotides have a sequence that is 13-19 nucleobases in length. In certain embodiments, the antisense oligonucleotides have a sequence that is 14-19 nucleobases in length. In certain embodiments, the antisense oligonucleotides have a sequence that is 15-19, nucleobases in length. In certain embodiments, the antisense oligonucleotides have a sequence that is 16-19 nucleobases in length. In certain embodiments, the antisense oligonucleotides have a sequence that is 17-19 nucleobases in length. In certain embodiments, the antisense oligonucleotides have a sequence that is 12, 13, 14, 15, 16, 17, 18, 19, 21, 22, 23, 24, 25, 26, 27, 28, 29, 30 nucleobases in length.

For oligonucleotides of various lengths, the position of the nucleoside complementary to the SNP position was shifted within the gap and the wings and the effect was tested. Certain positions within the antisense oligonucleotide are shown to be beneficial for targeting SNPs.

In certain embodiments, the antisense oligonucleotide is at least 12, at least 13, at least 14, at least 15, at least 16, at least 17 at least 18 or at least 19 nucleobases in length and the SNP is complementary to positions 6-15 counting from the 5' terminus of the antisense oligonucleotide and/or positions 1-9 counting from the 5' end of the gap. In certain embodiments, the antisense oligonucleotide is at least 12, at least 13, at least 14, at least 15, at least 16, at least 17 at least 18 or at least 19 nucleobases in length and the SNP is complementary to positions 8-14 counting from the 5' terminus of the antisense oligonucleotide and/or positions 1-9 counting from the 5' end of the gap.

In certain embodiments, the antisense oligonucleotide is at least 12, at least 13, at least 14, at least 15, at least 16, at least 17 at least 18 or at least 19 nucleobases in length and the SNP is complementary to positions 8-14 counting from the 5' terminus of the antisense oligonucleotide and/or positions 4-7 counting from the 5' end of the gap. In certain embodiments, the antisense oligonucleotide is at least 12, at least 13, at least 14, at least 15, at least 16, at least 17 at least 18 or at least 19 nucleobases in length and the SNP is complementary to positions 8-10 counting from the 5' terminus of the antisense oligonucleotide and/or positions 4-6 counting from the 5' end of the gap.

In certain embodiments, the SNP is complementary to position 8, 9, or 10 counting from the 5' terminus of the oligonucleotide or position 4, 5, or 6, counting from the 5' end of the gap. For oligonucleotides of various lengths, the effect of the length of the gap, 5' wing, and 3' wing was tested.

Certain wing-gap-wing combinations were shown to be beneficial for a SNP targeting antisense oligonucleotide. In certain embodiments the gap is 7-11 nucleobases in length and each wing is independently 1-6 nucleobases in length. In certain embodiments the gap is 7-11 nucleobases in length and each wing is independently 2.6 nucleobases in length. In certain embodiments the gap is 8-11 nucleobases in length and each wing is independently 2-6 nucleobases in length. In certain embodiments the gap is 9-11 nucleobases in length and each wing is independently 2-6 nucleobases in length. In certain embodiments the gap is 9 nucleobases in length and each wing is independently 2-6 nucleobases in length. In certain embodiments the gap is 10 nucleobases in length and each wing is independently 2-6 or 4-5 nucleobases in length. In certain embodiments the gap is 11 nucleobases in length and each wing is independently 2-6, or 4-5 nucleobases in length. In certain embodiments, the wing-gap-wing configuration is one of 4-7-4, 5-8-6, 6-8-5, 6-7-6, 5-7-5, 6-8-5, 5-8-6, 3-9-4, 4-9-3, 2-9-6,6,9,2, 3-9-3, 3-9-5, 5-9-3, 5-9-4, 4-9-5, 5-9-5, 4-11-4, 4-10-5 and 5-10-4.

For oligonucleotides of various lengths, the effect of certain chemistries was tested. Certain chemistry modifications were shown to be beneficial for a SNP targeting antisense oligonucleotide. In certain embodiments, each nucleoside of each wing of the modified antisense oligonucleotide has a 2'-MOE modification. In certain embodiments, each nucleoside of each wing of the modified antisense oligonucleotide has a high affinity modification. In certain embodiments, the antisense oligonucleotide is a mixed wing gapmer. In such embodiment, the modifications and combination of modifications at the 3' wing and at the 5' wing may be the same or they may be different. In certain embodiments, the antisense oligonucleotide has one or more 2'-MOE modifications in the wings and/or one or more high affinity modifications in the wings. In certain embodiments, the high affinity modification is a cEt modification. In certain embodiments, the antisense oligonucleotide has a high affinity modification at positions 2, 3, 13, and 14 of the antisense oligonucleotide (counting from the 5' terminus). In certain embodiments, the antisense oligonucleotide has one, two, three, or four high affinity modifications in at least one of the wings. In certain embodiments, the antisense oligonucleotide has one, two, three, or four high affinity modifications in each of the 5' and 3' wings independently. In certain embodiments, the antisense oligonucleotide has a high affinity modification at positions 2 and 3 in one or both of the 5' and 3' wings (counting from the 5' terminus of the 5' wing and the 3' terminus of the 3' wing). In certain embodiments, the antisense oligonucleotide has a high affinity modification at positions 2, 3 and 4 in one or both of the 5' and 3' wings (counting from the 5' terminus of the 5' wing and the 3' terminus of the 3' wing). In certain embodiments, the antisense oligonucleotide has a high affinity modification at positions 1 of the 5' and/or 3' wings (counting from the 5' terminus of the 5' wing and the 3' terminus of the 3' wing). In certain embodiments, the antisense oligonucleotide has a high affinity modification at positions 1 of the 5' and 3' wings (counting from the 5' terminus of the 5' wing and the 3' terminus of the 3' wing) and at least one other position in the wing. In certain embodiments, the antisense oligonucleotide has alternating 2'-MOE and high affinity modification in at least one of the 5' and 3' wings.

In certain embodiments, the compound comprises an antisense oligonucleotide incorporating one or more of the design rules provided above.

In certain embodiments, the compound comprises a modified antisense oligonucleotide consisting of 12 to 30 linked nucleosides, fully complementary to a single nucleotide polymorphism site, wherein the modified antisense oligonucleotide comprises a wing-gap-wing motif, wherein the single nucleotide polymorphism aligns with any one of positions 6-15 beginning from the 5' terminus of the antisense oligonucleotide or positions 1-9 beginning from the 5' end of the gap of the modified antisense oligonucleotide; and wherein each nucleoside of each wing has a modified sugar or sugar surrogate. In certain embodiments the single nucleotide polymorphism site contains a differentiating polymorphism. In certain embodiments, the single nucleotide polymorphism site is on a mutant allele. In certain embodiments, the mutant allele is associated with disease. In certain embodiments, the wing-gap-wing motif is any one of the group consisting of 4-7-4, 5-8-6, 6-8-5, 6-7-6, 5-7-5. 6-8-5, 5-8-6, 3-9-4, 4-9-3, 2-9-6,6,9,2, 3-9-3, 3-9-5, 5-9-3, 5-9-4, 4-9-5, 5-9-5, 4-11-4, 4-10-5 and 5-10-4.

In certain embodiments, the compound comprises a modified antisense oligonucleotide consisting of 12 to 20 linked nucleosides, fully complementary to a single nucleotide polymorphism site, wherein the modified antisense oligonucleotide comprises a wing-gap-wing motif, wherein the single nucleotide polymorphism aligns with any one of positions 6-15 beginning from the 5' terminus of the antisense oligonucleotide or positions 1-9 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5. 6-8-5, 5-8-6, 3-9-4, 4-9-3, 2-9-6,6,9,2, 3-9-3, 3-9-5, 5-9-3, 5-9-4, 4-9-5, 5-9-5, 4-11-4, 4-10-5 and 5-10-4.

In certain embodiments, the compound comprises a modified antisense oligonucleotide consisting of 12 to 20 linked nucleosides, fully complementary to a single nucleotide polymorphism site, wherein the modified antisense oligonucleotide comprises a wing-gap-wing motif, wherein the single nucleotide polymorphism aligns with any one of positions 8-14 beginning from the 5' terminus of the antisense oligonucleotide or positions 1-9 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5. 6-8-5, 5-8-6, 3-9-4, 4-9-3, 2-9-6,6,9,2, 3-9-3, 3-9-5, 5-9-3, 5-9-4, 4-9-5, 5-9-5, 4-11-4, 4-10-5 and 5-10-4.

In certain embodiments, the compound comprises a modified antisense oligonucleotide consisting of 12 to 20 linked nucleosides, fully complementary to a single nucleotide polymorphism site, wherein the modified antisense oligonucleotide comprises a wing-gap-wing motif, wherein the single nucleotide polymorphism aligns with any one of positions 8-14 beginning from the 5' terminus of the antisense oligonucleotide or positions 4-7 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5. 6-8-5, 5-8-6, 3-9-4, 4-9-3, 2-9-6,6,9,2, 3-9-3, 3-9-5, 5-9-3, 5-9-4, 4-9-5, 5-9-5, 4-11-4, 4-10-5 and 5-10-4.

In certain embodiments, the compound comprises a modified antisense oligonucleotide consisting of 12 to 20 linked nucleosides, fully complementary to a single nucleotide polymorphism site, wherein the modified antisense oligonucleotide comprises a wing-gap-wing motif, wherein the single nucleotide polymorphism aligns with any one of positions 8-10 beginning from the 5' terminus of the antisense oligonucleotide or positions 4-6 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5. 6-8-5, 5-8-6, 3-9-4, 4-9-3, 2-9-6,6,9,2, 3-9-3, 3-9-5, 5-9-3, 5-9-4, 4-9-5, 5-9-5, 4-11-4, 4-10-5 and 5-10-4.

In certain embodiments, the compound comprises a modified antisense oligonucleotide consisting of 12 to 19 linked nucleosides, fully complementary to a single nucleotide polymorphism site, wherein the modified antisense oligonucleotide comprises a wing-gap-wing motif, wherein the single nucleotide polymorphism aligns with any one of positions 8-10 beginning from the 5' terminus of the antisense oligonucleotide or positions 4-6 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5. 6-8-5, 5-8-6, 3-9-4, 4-9-3, 2-9-6,6,9,2, 3-9-3, 3-9-5, 5-9-3, 5-9-4, 4-9-5, 5-9-5, 4-11-4, 4-10-5 and 5-10-4.

In certain embodiments, the compound comprises a modified antisense oligonucleotide consisting of 13 to 19 linked nucleosides, fully complementary to a single nucleotide polymorphism site, wherein the modified antisense oligonucleotide comprises a wing-gap-wing motif, wherein the single nucleotide polymorphism aligns with any one of positions 8-10 beginning from the 5' terminus of the antisense oligonucleotide or positions 4-6 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5. 6-8-5, 5-8-6, 3-9-4, 4-9-3, 2-9-6,6,9,2, 3-9-3, 3-9-5, 5-9-3, 5-9-4, 4-9-5, 5-9-5, 4-11-4, 4-10-5 and 5-10-4.

In certain embodiments, the compound comprises a modified antisense oligonucleotide consisting of 14 to 19 linked nucleosides, fully complementary to a single nucleotide polymorphism site, wherein the modified antisense oligonucleotide comprises a wing-gap-wing motif, wherein the single nucleotide polymorphism aligns with any one of positions 8-10 beginning from the 5' terminus of the antisense oligonucleotide or positions 4-6 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5. 6-8-5, 5-8-6, 3-9-4, 4-9-3, 2-9-6,6,9,2, 3-9-3, 3-9-5, 5-9-3, 5-9-4, 4-9-5, 5-9-5, 4-11-4, 4-10-5 and 5-10-4.

In certain embodiments, the compound comprises a modified antisense oligonucleotide consisting of 15 to 19 linked nucleosides, fully complementary to a single nucleotide polymorphism site, wherein the modified antisense oligonucleotide comprises a wing-gap-wing motif, wherein the single nucleotide polymorphism aligns with any one of positions 6-15 beginning from the 5' terminus of the antisense oligonucleotide or positions 1-9 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5. 6-8-5, 5-8-6, 3-9-4, 4-9-3, 2-9-6,6,9,2, 3-9-3, 3-9-5, 5-9-3, 5-9-4, 4-9-5, 5-9-5, 4-11-4, 4-10-5 and 5-10-4.

In certain embodiments, the compound comprises a modified antisense oligonucleotide consisting of 15 to 19 linked nucleosides, fully complementary to a single nucleotide polymorphism site, wherein the modified antisense oligonucleotide comprises a wing-gap-wing motif, wherein the single nucleotide polymorphism aligns with any one of positions 8-10 beginning from the 5' terminus of the antisense oligonucleotide or positions 4-6 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5. 6-8-5, 5-8-6, 3-9-4, 4-9-3, 2-9-6,6,9,2, 3-9-3, 3-9-5, 5-9-3, 5-9-4, 4-9-5, 5-9-5, 4-11-4, 4-10-5 and 5-10-4.

In certain embodiments, the compound comprises a modified antisense oligonucleotide consisting of 15 to 19 linked nucleosides, fully complementary to a single nucleotide polymorphism site, wherein the modified antisense oligonucleotide comprises a wing-gap-wing motif, wherein position 6, 8, 9, 10, 11, or 14 beginning from the 5' terminus of the modified antisense oligonucleotide aligns with the single nucleotide polymorphism; and wherein each nucleoside of each wing segment modified sugar or sugar surrogate. In certain embodiments, the wing-gap-wing motif is any one of the group consisting of 2-9-6, 3-9-3, 3-9-5, 4-9-5, 4-11-4, and 5-10-4.

In certain embodiments, the compound comprises a modified antisense oligonucleotide consisting of 15 to 19 linked nucleosides, fully complementary to a single nucleotide polymorphism site, wherein the modified antisense oligonucleotide comprises a wing-gap-wing motif, wherein position 1, 4, 5, 6, 7, or 9 of the gap segment aligns with the single nucleotide polymorphism; and wherein each nucleoside of each wing segment has a modified sugar or sugar surrogate. In certain embodiments, the wing-gap-wing motif is any one of the group consisting of 2-9-6, 3-9-3, 3-9-5, 4-9-5, 4-11-4, and 5-10-4.

In certain embodiments, the compound comprises a modified antisense oligonucleotide consisting of 15 to 19 linked nucleosides, fully complementary to a single nucleotide polymorphism site, wherein the modified antisense oligonucleotide comprises a wing-gap-wing motif, wherein position 6, 7, 8, 9, 10, 11, or 12 of the modified antisense oligonucleotide aligns with the single nucleotide polymorphism; and positions 2 and 3 of the 5' and 3' wing segments comprise a 4'-CH(CH$_3$)—O-2' bridge. In certain embodiments, the wing-gap-wing motif is any one of the group consisting of 2-9-6, 3-9-3, 3-9-5, 4-9-5, 4-11-4, and 5-10-4.

In certain embodiments, the compound comprises a modified antisense oligonucleotide consisting of 15 to 19 linked nucleosides and fully complementary to a single nucleotide polymorphism site, wherein the modified antisense oligonucleotide comprises a wing-gap-wing motif, wherein position 3, 4, 5, 6, 7, 8 or 9 of the gap segment aligns with the single nucleotide polymorphism; and positions 2 and 3 of the 5' and 3' wing segments comprise a 4'-CH(CH$_3$)—O-2' bridge. In certain embodiments, the wing-gap-wing motif is any one of the group consisting of 2-9-6, 3-9-3, 3-9-5, 4-9-5, 4-11-4, and 5-10-4.

A compound comprising a modified antisense oligonucleotide consisting of 15 to 19 linked nucleosides and fully complementary to a single nucleotide polymorphism site, wherein the modified antisense oligonucleotide comprises a wing-gap-wing motif, wherein position 6, 7, 8, 9, 10, 11, or 12 of the modified antisense oligonucleotide aligns with the single nucleotide polymorphism; and positions 2, 3, 13, and 14 of the antisense oligonucleotide comprise a 4'-CH(CH₃)—O-2' bridge. In certain embodiments, the wing-gap-wing motif is any one of the group consisting of 2-9-6, 3-9-3, 3-9-5, 4-9-5, 4-11-4, and 5-10-4.

A compound comprising a modified antisense oligonucleotide consisting of 15 to 19 linked nucleosides and fully complementary to a single nucleotide polymorphism site, wherein the modified antisense oligonucleotide comprises a wing-gap-wing motif, wherein position 3, 4, 5, 6, 7, 8, or 9 of the gap segment aligns with the single nucleotide polymorphism; and positions 2, 3, 13, and 14 of the antisense antisense oligonucleotide comprise a 4'-CH(CH₃)—O-2' bridge. In certain embodiments, the wing-gap-wing motif is any one of the group consisting of 2-9-6, 3-9-3, 3-9-5, 4-9-5, 4-11-4, and 5-10-4.

In certain embodiments, the compound comprise a modified antisense oligonucleotide consisting of 17 to 19 linked nucleosides, fully complementary to a single nucleotide polymorphism site, wherein the modified antisense oligonucleotide comprises a wing-gap-wing motif, wherein position 8, 9, or 10 of the modified antisense oligonucleotide aligns with the single nucleotide polymorphism; and wherein each nucleoside of each wing segment comprises a 2'-O-methoxyethyl sugar. In certain embodiments, the wing-gap-wing motif is any one of the group consisting of 2-9-6, 3-9-3, 3-9-5, 4-9-5, 4-11-4, and 5-10-4.

In certain embodiments, the compound comprises a modified antisense oligonucleotide consisting of 17 to 19 linked nucleosides, fully complementary to a single nucleotide polymorphism site, wherein the modified antisense oligonucleotide comprises a wing-gap-wing motif, wherein position 5, 6, or 7 of the gap segment aligns with the single nucleotide polymorphism; and wherein each nucleoside of each wing segment comprises a 2'-O-methoxyethyl sugar. In certain embodiments, the wing-gap-wing motif is any one of the group consisting of 2-9-6, 3-9-3, 3-9-5, 4-9-5, 4-11-4, and 5-10-4.

In certain embodiments, the compound comprises a modified antisense oligonucleotide consisting of 17 to 19 linked nucleosides, fully complementary to a single nucleotide polymorphism site, wherein the modified antisense oligonucleotide comprises a wing-gap-wing motif, wherein position 8, 9, or 10 of the modified antisense oligonucleotide aligns with the single nucleotide polymorphism; and positions 2 and 3 of the 5' and 3' wing segments comprise a 4'-CH(CH₃)—O-2'bridge. In certain embodiments, the wing-gap-wing motif is any one of the group consisting of 2-9-6, 3-9-3, 3-9-5, 4-9-5, 4-11-4, and 5-10-4.

In certain embodiments, the compound comprises a modified antisense oligonucleotide consisting of 17 to 19 linked nucleosides and fully complementary to a single nucleotide polymorphism site, wherein the modified antisense oligonucleotide comprises a wing-gap-wing motif, wherein position 5, 6, or 7 of the gap segment aligns with the single nucleotide polymorphism; and positions 2 and 3 of the 5' and 3' wing segments comprise a 4'-CH(CH₃)—O-2' bridge. In certain embodiments, the wing-gap-wing motif is any one of the group consisting of 2-9-6, 3-9-3, 3-9-5, 4-9-5, 4-11-4, and 5-10-4.

A compound comprising a modified antisense oligonucleotide consisting of 17 to 19 linked nucleosides and fully complementary to a single nucleotide polymorphism site, wherein the modified antisense oligonucleotide comprises a wing-gap-wing motif, wherein position 8, 9, or 10 of the modified oligonucleotide aligns with the single nucleotide polymorphism; and positions 2, 3, 13, and 14 of the antisense antisense oligonucleotide comprise a 4'-CH(CH₃)—O-2' bridge. In certain embodiments, the wing-gap-wing motif is any one of the group consisting of 2-9-6, 3-9-3, 3-9-5, 4-9-5, 4-11-4, and 5-10-4.

A compound comprising a modified antisense oligonucleotide consisting of 17 to 19 linked nucleosides and fully complementary to a single nucleotide polymorphism site, wherein the modified antisense oligonucleotide comprises a wing-gap-wing motif, wherein position 5, 6, or 7 of the gap segment aligns with the single nucleotide polymorphism; and positions 2, 3, 13, and 14 of the antisense oligonucleotide comprise a 4'-CH(CH₃)—O-2' bridge. In certain embodiments, the wing-gap-wing motif is any one of the group consisting of 2-9-6, 3-9-3, 3-9-5, 4-9-5, 4-11-4, and 5-10-4.

In a certain embodiment, the antisense oligonucleotide is 11 to 20 linked nucleosides in length and has, independently, 2 to 5 linked nucleosides in the 5' and 3' wings and 7 to 11 linked nucleosides in the gap. The SNP is complementary to position 5, 6, 7, 8, 9, 10, 11, 12, 13, or 14 of the antisense oligonucleotide (counting from the 5' terminus of the antisense oligonucleotide) or position 1, 2, 3, 4, 5, 6, 7, 8, 9, or 10 counting from the 5' terminus of the gap segment.

In a certain embodiment, the antisense oligonucleotide is 15 to 19 linked nucleosides in length and has, independently, 2 to 5 linked nucleosides in the 5' and 3' wings and 7 to 11 linked nucleosides in the gap. The SNP is complementary to position 6, 7, 8, 9, or 10 of the antisense oligonucleotide (counting from the 5' terminus of the antisense oligonucleotide) or position 4, 5, 6, or 7 counting from the 5' terminus of the gap segment.

In a certain embodiment, the antisense oligonucleotide is 17 linked nucleosides in length and has, independently, 2 to 5 linked nucleosides in the 5' and 3' wing segments and 9 to 11 linked nucleosides in the gap segment. The SNP is complementary to position 8, 9, or 10 of the antisense oligonucleotide (counting from the 5' terminus of the antisense oligonucleotide) or position 5, 6, or 7 (counting from the 5' terminus of the gap segment).

In a certain embodiment, the antisense oligonucleotide is 18 linked nucleosides in length and has, independently, 2 to 5 linked nucleosides in the 5' and 3' wing segments and 9 to 11 linked nucleosides in the gap segment. The SNP is complementary to position 8, 9, or 10 of the antisense oligonucleotide (counting from the 5' terminus of the antisense oligonucleotide) or position 5, 6, or 7 (counting from the 5' terminus of the gap segment).

In a certain embodiment, the antisense oligonucleotide is 19 linked nucleosides in length and has, independently, 2 to 5 linked nucleosides in the 5' and 3' wing segments and 9 to 11 linked nucleosides in the gap segment. The SNP is complementary to position 8, 9, or 10 of the antisense oligonucleotide (counting from the 5' terminus of the antisense oligonucleotide) or position 5, 6, or 7 (counting from the 5' terminus of the gap segment).

In certain embodiments, the invention provides methods of treating an individual comprising administering one or more pharmaceutical compositions described herein. In certain embodiments, the individual has an allelic variant associated with a disease or disorder. The pharmaceutical compositions provided herein preferentially target a SNP. In certain embodiments, the SNP is a differentiating polymorphism.

Methods have been described for determining whether a SNP is specific to a disease associated allele and more specifically whether a SNP variant of an allele of a heterozygous patient is on the same allele as a disease-causing mutation that is at a remote region of the gene's mRNA (WO 2008/147930 and WO 2008/143774).

Diseases associated with SNPs have been described for certain genes. In certain embodiments, the gene and associated disease are any of the following: APP gene encoding amyloid precursor protein involved in Alzheimer's disease (Gene, 371: 68, 2006); the PrP gene encoding prion protein involved in Creutzfeldt-Jakob disease and in fatal familial insomnia (Nat. Med. 1997, 3: 1009); GFAP gene encoding glial fibrillary acidic protein involved in Alexander disease (J. Neurosci. 2006, 26:111623); alpha-synuclein gene encoding alpha-synuclein protein involved in Parkinson's disease (J. Clin. Invest. 2003, 111: 145); SOD-1 gene encoding the SOD-1 protein involved in amyotrophic lateral sclerosis (Science 1998, 281: 1851); atrophin-1 gene encoding atrophin-1 protein involved in dentato-rubral and pallido-luysian atrophy (DRPA) (Trends Mol. Med. 2001, 7: 479); SCA1 gene encoding ataxin-1 protein involved in spino-cerebellar ataxia-1 (SCA1) (Protein Sci. 2003, 12: 953); PLP gene encoding proteolipid protein involved in Pelizaeus-Merzbacher disease (NeuroMol. Med. 2007, 4: 73); DYT1 gene encoding torsinA protein involved in Torsion dystonia (Brain Res. 2000, 877: 379); and alpha-B crystalline gene encoding alpha-B crystalline protein involved in protein aggregation diseases, including cardiomyopathy (Cell 2007, 130: 427); alpha1-antitrypsin gene encoding alpha1-antitrypsin protein involved in chronic obstructive pulmonary disease (COPD), liver disease and hepatocellular carcinoma (New Engl J. Med. 2002, 346: 45); Ltk gene encoding leukocyte tyrosine kinase protein involved in systemic lupus erythematosus (Hum. Mol. Gen. 2004, 13: 171); PCSK9 gene encoding PCSK9 protein involved in hypercholesterolemia (Hum Mutat. 2009, 30: 520); prolactin receptor gene encoding prolactin receptor protein involved in breast tumors (Proc. Natl. Assoc. Sci. 2008, 105: 4533); CCL5 gene encoding the chemokine CCL5 involved in COPD and asthma (Eur. Respir. J. 2008, 32: 327); PTPN22 gene encoding PTPN22 protein involved in Type 1 diabetes, Rheumatoid arthritis, Graves disease, and SLE (Proc. Natl. Assoc. Sci. 2007, 104: 19767); androgen receptor gene encoding the androgen receptor protein involved in spinal and bulbar muscular atrophy or Kennedy's disease (J Steroid Biochem. Mol. Biol. 2008, 108: 245); CHMP4B gene encoding chromatin modifying protein-4B involved in progressive childhood posterior subcapsular cataracts (Am. J. Hum. Genet. 2007, 81: 596); FXR/NR1H4 gene encoding Farnesoid X receptor protein involved in cholesterol gallstone disease, arthrosclerosis and diabetes (Mol. Endocrinol. 2007, 21: 1769); ABCA1 gene encoding ABCA1 protein involved in cardiovascular disease (Transl. Res. 2007, 149: 205); CaSR gene encoding the calcium sensing receptor protein involved in primary hypercalciuria (Kidney Int. 2007, 71: 1155); alpha-globin gene encoding alpha-globin protein involved in alpha-thallasemia (Science 2006, 312: 1215); httlpr gene encoding HTTLPR protein involved in obsessive compulsive disorder (Am. J. Hum. Genet. 2006, 78: 815); AVP gene encoding arginine vasopressin protein in stress-related disorders such as anxiety disorders and comorbid depression (CNS Neurol. Disord. Drug Targets 2006, 5: 167); GNAS gene encoding G proteins involved in congenital visual defects, hypertension, metabolic syndrome (Trends Pharmacol. Sci. 2006, 27: 260); APAF1 gene encoding APAF1 protein involved in a predisposition to major depression (Mol. Psychiatry. 2006, 11: 76); TGF-beta1 gene encoding TGF-beta1 protein involved in breast cancer and prostate cancer (Cancer Epidemiol. Biomarkers Prev. 2004, 13: 759); AChR gene encoding acetylcholine receptor involved in congential myasthenic syndrome (Neurology 2004, 62: 1090); P2Y12 gene encoding adenosine diphosphate (ADP) receptor protein involved in risk of peripheral arterial disease (Circulation 2003, 108: 2971); LQT1 gene encoding LQT1 protein involved in atrial fibrillation (Cardiology 2003, 100: 109); RET protooncogene encoding RET protein involved in sporadic pheochromocytoma (J. Clin. Endocrinol. Metab. 2003, 88: 4911); filamin A gene encoding filamin A protein involved in various congenital malformations (Nat. Genet. 2003, 33: 487); TARDBP gene encoding TDP-43 protein involved in amyotrophic lateral sclerosis (Hum. Mol. Genet. 2010, 19: 671); SCA3 gene encoding ataxin-3 protein involved in Machado-Joseph disease (PLoS One 2008, 3: e3341); SCAT gene encoding ataxin-7 protein involved in spino-cerebellar ataxia-7 (PLoS One 2009, 4: e7232); HTT gene encoding huntingtin protein involved in Huntington's disease (Neurobiol Dis. 1996, 3:183); and the CA4 gene encoding carbonic anhydrase 4 protein, CRx gene encoding cone-rod homeobox transcription factor protein, FSCN2 gene encoding retinal fascin homolog 2 protein, IMPDH1 gene encoding inosine monophosphate dehydrogenase 1 protein, NR2E3 gene encoding nuclear receptor subfamily 2 group E3 protein, NRL gene encoding neural retina leucine zipper protein, PRPF3 (RP18) gene encoding pre-mRNA splicing factor 3 protein, PRPF8 (RP13) gene encoding pre-mRNA splicing factor 8 protein, PRPF31 (RP11) gene encoding pre-mRNA splicing factor 31 protein, RDS gene encoding peripherin 2 protein, ROM1 gene encoding rod outer membrane protein 1 protein, RHO gene encoding rhodopsin protein, RP1 gene encoding RP1 protein, RPGR gene encoding retinitis pigmentosa GTPase regulator protein, all of which are involved in Autosomal Dominant Retinitis Pigmentosa disease (Adv Exp Med. Biol. 2008, 613:203)

In certain embodiments, the disease is a neurodegenerative disorder. In certain embodiments, the neurodegenerative disorder is Huntington's Disease. In certain embodiments, the targeted SNP is one or more of: rs6446723, rs3856973, rs2285086, rs363092, rs916171, rs6844859, rs7691627, rs4690073, rs2024115, rs11731237, rs362296, rs10015979, rs7659144, rs363096, rs362273, rs16843804, rs362271, rs362275, rs3121419, rs362272, rs3775061, rs34315806, rs363099, rs2298967, rs363088, rs363064, rs363102, rs2798235, rs363080, rs363072, rs363125, rs362303, rs362310, rs10488840, rs362325, rs35892913, rs363102, rs363096, rs11731237, rs10015979, rs363080, rs2798235, rs1936032, rs2276881, rs363070, rs35892913, rs12502045, rs6446723, rs7685686, rs3733217, rs6844859, rs362331, rs1143646, rs2285086, rs2298969, rs4690072, rs916171, rs3025849, rs7691627, rs4690073, rs3856973, rs363092, rs362310, rs362325, rs363144, rs362303, rs34315806, rs363099, rs363081, rs3775061, rs2024115, rs10488840, rs363125, rs362296, rs2298967, rs363088, rs363064, rs362275, rs3121419, rs3025849, rs363070, rs362273, rs362272, rs362306, rs362271, rs363072, rs16843804, rs7659144, rs363120, and rs12502045. In certain embodiments the compounds are ISIS460065, ISIS 459978, ISIS 460028, ISIS 460209, ISIS 460208, and ISIS 460206.

Therapeutically Effective Dosages

In certain embodiments, administration of a therapeutically effective amount of an antisense compound targeted to the mutant huntingtin allele is accompanied by monitoring of expression of a gene product in an individual, to determine an individual's response to administration of the antisense compound. In certain embodiments, the gene product is huntingtin mRNA or protein. An individual's response to administration of the antisense compound is used by a physician to determine the amount and duration of therapeutic intervention.

In certain embodiments, administration of an antisense compound targeted to a mutant nucleic acid results in reduction of mRNA or protein expression by at least 15, 20, 25, 30, 35, 40, 45, 50, 55, 60, 65, 70, 75, 80, 85, 90, 95 or 99%, or a range defined by any two of these values. In certain embodiments, the mutant nucleic acid is huntingtin nucleic acid, the mRNA is huntingtin mRNA, and the protein is huntingtin protein.

In certain embodiments, pharmaceutical compositions comprising an antisense compound targeted to a mutant allele are used for the preparation of a medicament for treating a patient suffering or susceptible to any of Huntington's Disease, Alzheimer's Disease, Crutzfeldt-Jakob Disease, Fatal Familial Insomnia, Huntington's Disease, Alexander Disease, Parkinson's Disease, Amyotrophic Lateral Sclerosis (ALS), Dentato-Rubral and Pallido-Luysian Atrophy, Spino-Cerebellar Ataxia 1, Pelizaeus-Merzbacher Disease, Torsion Dystonia, Cardiomyopathy, Chronic Obstructive Pulmonary Disease (COPD), liver disease and hepatocellular carcinoma, SLE, Hypercholesterolemia, breast tumors, Asthma, Type 1 Diabetes, Rheumatoid Arthritis, Graves Disease, Spinal and Bulbar Muscular Atrophy, Kennedy's Disease, progressive childhood posterior subcapsular cataracts, Cholesterol Gallstone Disease, Arthrosclerosis, cardiovascular disease, primary hypercalciuria, alpha-thallasemia, OCD, stress-related disorders (including anxiety disorders and comorbid depression), congenital visual defects, hypertension, metabolic syndrome, major depression, breast cancer, prostate cancer, congenital myasthenic syndrome, peripheral arterial syndrome, atrial fibrillation, sporadic pheochromocytoma, congenital malformations, NJD, SCAT, and autosomal dominant retinitis pigmentosa adRP.

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease, disorder, or condition as the one or more pharmaceutical compositions of the present invention. In certain embodiments, such one or more other pharmaceutical agents are designed to treat a different disease, disorder, or condition as the one or more pharmaceutical compositions of the present invention. In certain embodiments, such one or more other pharmaceutical agents are designed to treat an undesired side effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention are co-administered with another pharmaceutical agent to produce a combinational effect. In certain embodiments, one or more pharmaceutical compositions of the present invention are co-administered with another pharmaceutical agent to produce a synergistic effect.

In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the patents, applications, printed publications, and other published documents mentioned or referred to in this specification are herein incorporated by reference in their entirety.

Example 1

Single Nucleotide Polymorphisms (SNPs) in the Huntingtin (HTT) Gene Sequence

The HTT genomic sequence, designated herein as SEQ ID NO: 1 (NT_006081.18 truncated from nucleotides 1566000 to 1768000) was aligned with the HTT mRNA, designated herein as SEQ ID NO: 2 (NM_002111.6), using the EMBL-EBI sequence database (ClustalW2, http://www.ebi.ac.uk/Tools/clustalw2/index.html), and the output is presented in FIG. 1. SNP positions (identified by Hayden et al, WO/2009/135322) associated with the HTT gene were mapped to the two sequences and have been demarcated in FIG. 1 by their reference SNP ID number from the Entrez SNP database at the National Center for Biotechnology Information (NCBI, http://www.ncbi.nlm.nih.gov/sites/entrez?db=snp), incorporated herein by reference. Table 2 furnishes further details on each SNP. The 'Reference SNP ID number' or 'RS number' is the number designated to each SNP from the Entrez SNP database at NCBI, incorporated herein by reference. 'SNP position' refers to the nucleotide position of the SNP on SEQ ID NO: 1. 'Polymorphism' indicates the nucleotide variants at that SNP position. 'Major allele' indicates the nucleotide associated with the major allele, or the nucleotide present in a statistically significant proportion of individuals in the human population. 'Minor allele' indicates the nucleotide associated with the minor allele, or the nucleotide present in a relatively small proportion of individuals in the human population.

TABLE 2

Single Nuclear Polymorphisms (SNPs) and their positions on SEQ ID NO: 1

| RS No. | SNP position | Polymorphism | Major allele | Minor allele |
|---|---|---|---|---|
| rs2857936 | 1963 | C/T | C | T |
| rs12506200 | 3707 | A/G | G | A |
| rs762855 | 14449 | A/G | G | A |
| rs3856973 | 19826 | G/A | G | A |
| rs2285086 | 28912 | G/A | A | G |
| rs7659144 | 37974 | C/G | C | G |
| rs16843804 | 44043 | C/T | C | T |
| rs2024115 | 44221 | G/A | A | G |
| rs10015979 | 49095 | A/G | A | G |
| rs7691627 | 51063 | A/G | G | A |
| rs2798235 | 54485 | G/A | G | A |
| rs4690072 | 62160 | G/T | T | G |
| rs6446723 | 66466 | C/T | T | C |

TABLE 2-continued

Single Nuclear Polymorphisms (SNPs) and their positions on SEQ ID NO: 1

| RS No. | SNP position | Polymorphism | Major allele | Minor allele |
|---|---|---|---|---|
| rs363081 | 73280 | G/A | G | A |
| rs363080 | 73564 | T/C | C | T |
| rs363075 | 77327 | G/A | G | A |
| rs363064 | 81063 | T/C | C | T |
| rs3025849 | 83420 | A/G | A | G |
| rs6855981 | 87929 | A/G | G | A |
| rs363102 | 88669 | G/A | A | G |
| rs11731237 | 91466 | C/T | C | T |
| rs4690073 | 99803 | A/G | G | A |
| rs363144 | 100948 | T/G | T | G |
| rs3025838 | 101099 | C/T | C | T |
| rs34315806 | 101687 | A/G | G | A |
| rs363099 | 101709 | T/C | C | T |
| rs363096 | 119674 | T/C | T | C |
| rs2298967 | 125400 | C/T | T | C |
| rs2298969 | 125897 | A/G | G | A |
| rs6844859 | 130139 | C/T | T | C |
| rs363092 | 135682 | C/A | C | A |
| rs7685686 | 146795 | A/G | A | G |
| rs363088 | 149983 | A/T | A | T |
| rs362331 | 155488 | C/T | T | C |
| rs916171 | 156468 | G/C | C | G |
| rs362322 | 161018 | A/G | A | G |
| rs362275 | 164255 | T/C | C | T |
| rs362273 | 167080 | A/G | A | G |
| rs2276881 | 171314 | G/A | G | A |
| rs3121419 | 171910 | T/C | C | T |
| rs362272 | 174633 | G/A | G | A |
| rs362271 | 175171 | G/A | G | A |
| rs3775061 | 178407 | C/T | C | T |
| rs362310 | 179429 | A/G | G | A |
| rs362307 | 181498 | T/C | C | T |
| rs362306 | 181753 | G/A | G | A |
| rs362303 | 181960 | T/C | C | T |
| rs362296 | 186660 | C/A | C | A |
| rs1006798 | 198026 | A/G | A | G |

Example 2

Design of Antisense Oligonucleotides Targeting Huntingtin Gene SNPs and Inhibition of HTT mRNA in Coriell Fibroblast Cell Lines (GM04281, GM02171, and GM02173B)

Antisense oligonucleotides targeting nucleotides overlapping SNP positions presented in Table 1 were designed and tested for potency in three huntingtin patient-derived Coriell fibroblast cell lines, GM04281, GM02171, and GM02173B (from the Coriell Institute for Medical Research). Cultured GM04281 cells or GM02171 cells or GM02173B cells at a density of 20,000 cells per well were transfected using electroporation with 10,000 nM antisense oligonucleotide. After a treatment period of approximately 24 hours, RNA was isolated from the cells and HTT mRNA levels were measured by quantitative real time PCR using primer probe set RTS2617 (forward sequence CTCCGTCCGGTAGACATGCT, designated herein as SEQ ID NO: 3; reverse sequence GGAAATCAGAACCCTCAAAATGG, designated herein as SEQ ID NO: 4; probe sequence TGAGCACTGTTCAACTGTGGATATCGGGAX, designated herein as SEQ ID NO: 5). HTT mRNA levels were adjusted according to total RNA content, as measured by RIBOGREEN. Results are presented as percent inhibition of HTT mRNA, relative to untreated control cells.

ISIS 387916 (TCTCTATTGCACATTCCAAG, 5-10-5 MOE (SEQ ID NO: 6)) and ISIS 388816 (GCCGTAGCCTGGGACCCGCC, 5-10-5 MOE (SEQ ID NO: 7)) were included in each study as benchmark oligonucleotides against which the potency of the antisense oligonucleotides targeting nucleotides overlapping each SNP position could be compared.

The chimeric antisense oligonucleotides in Tables 3 and 4 were designed as 5-9-5 MOE gapmers. The gapmers are 19 nucleotides in length, wherein the central gap segment is comprised of nine 2'-deoxynucleotides and is flanked on both sides (in the 5' and 3' directions) by wings comprising five nucleotides each. Each nucleotide in the 5' wing segment and each nucleotide in the 3' wing segment has a 2'-MOE modification. The internucleoside linkages throughout each gapmer are phosphorothioate (P=S) linkages. All cytosine nucleobases throughout each gapmer are 5-methylcytosines.

The oligonucleotides are further described in Table 3. The percent inhibition of HTT mRNA by the antisense oligonucleotides in each cell line is shown in Table 4. 'Target allele' indicates whether the gapmer is targeted to the major or the minor allele at the SNP position. The number in parentheses indicates the nucleotide position in the gapmer opposite to the SNP position, starting from the 5'-terminus of the oligonucleotide. 'Start site' indicates the 5'-most nucleotide to which the gapmer is targeted. "Stop site" indicates the 3'-most nucleotide to which the gapmer is targeted. Each gapmer listed in Tables 3 and 4 is targeted to human HTT pre-mRNA, which is SEQ ID NO: 1.

TABLE 3

Chimeric oligonucleotides targeting SNP positions on the HTT gene

| ISIS No | SNP RS No. | Target allele | Sequence | Start Site | Stop Site | SEQ ID NO |
|---|---|---|---|---|---|---|
| 387916 | n/a | n/a | TCTCTATTGCACATTCCAAG | 145466 | 145485 | 6 |
| 388816 | n/a | n/a | GCCGTAGCCTGGGACCCGCC | 16501 | 16520 | 7 |
| 435330 | rs3856973 | Major (8) | TAACACTCGATTAACCCTG | 19815 | 19833 | 8 |
| 435348 | rs3856973 | Minor (8) | TAACACTTGATTAACCCTG | 19815 | 19833 | 9 |
| 435294 | rs3856973 | Major (10) | GTTAACACTCGATTAACCC | 19817 | 19835 | 10 |
| 435312 | rs3856973 | Minor (10) | GTTAACACTTGATTAACCC | 19817 | 19835 | 11 |
| 435864 | rs2285086 | Major (10) | GCTAGTTCATCCCAGTGAG | 28903 | 28921 | 12 |

TABLE 3-continued

Chimeric oligonucleotides targeting SNP positions on the HTT gene

| ISIS No | SNP RS No. | Target allele | Sequence | Start Site | Stop Site | SEQ ID NO |
|---|---|---|---|---|---|---|
| 435889 | rs2285086 | Minor (10) | GCTAGTTCACCCCAGTGAG | 28903 | 28921 | 13 |
| 435878 | rs7659144 | Major (10) | TGGAAATGGGTTTTTCCAC | 37965 | 37983 | 14 |
| 435903 | rs7659144 | Minor (10) | TGGAAATGGCTTTTTCCAC | 37965 | 37983 | 15 |
| 435863 | rs16843804 | Major (10) | TTTAACCGTGGCATGGGCA | 44034 | 44052 | 16 |
| 435888 | rs16843804 | Minor (10) | TTTAACCGTAGCATGGGCA | 44034 | 44052 | 17 |
| 435331 | rs2024115 | Major (8) | TTCAAGCTAGTAACGATGC | 44210 | 44228 | 18 |
| 435349 | rs2024115 | Minor (8) | TTCAAGCCAGTAACGATGC | 44210 | 44228 | 19 |
| 435295 | rs2024115 | Major (10) | ACTTCAAGCTAGTAACGAT | 44212 | 44230 | 20 |
| 435313 | rs2024115 | Minor (10) | ACTTCAAGCCAGTAACGAT | 44212 | 44230 | 21 |
| 435862 | rs10015979 | Major (10) | GCAGCTAGGTTAAAGAGTC | 49086 | 49104 | 22 |
| 435887 | rs10015979 | Minor (10) | GCAGCTAGGCTAAAGAGTC | 49086 | 49104 | 23 |
| 435880 | rs7691627 | Major (10) | AATAAGAAACACAATCAAA | 51054 | 51072 | 24 |
| 435905 | rs7691627 | Minor (10) | AATAAGAAATACAATCAAA | 51054 | 51072 | 25 |
| 435885 | rs2798235 | Major (10) | CAGAGGAGGCATACTGTAT | 54476 | 54494 | 26 |
| 435910 | rs2798235 | Minor (10) | CAGAGGAGGTATACTGTAT | 54476 | 54494 | 27 |
| 435874 | rs4690072 | Major (10) | CACAGTGCTACCCAACCTT | 62151 | 62169 | 28 |
| 435899 | rs4690072 | Minor (10) | CACAGTGCTCCCCAACCTT | 62151 | 62169 | 29 |
| 435875 | rs6446723 | Major (10) | TAATTTTCTAGACTTTATG | 66457 | 66475 | 30 |
| 435900 | rs6446723 | Minor (10) | TAATTTTCTGGACTTTATG | 66457 | 66475 | 31 |
| 435332 | rs363081 | Major (8) | GCTACAACGCAGGTCAAAT | 73269 | 73287 | 32 |
| 435350 | rs363081 | Minor (8) | GCTACAATGCAGGTCAAAT | 73269 | 73287 | 33 |
| 435296 | rs363081 | Major (10) | GAGCTACAACGCAGGTCAA | 73271 | 73289 | 34 |
| 435314 | rs363081 | Minor (10) | GAGCTACAATGCAGGTCAA | 73271 | 73289 | 35 |
| 435886 | rs363080 | Major (10) | AGAGAGAACGAGAAGGCTC | 73555 | 73573 | 36 |
| 435911 | rs363080 | Minor (10) | AGAGAGAACAAGAAGGCTC | 73555 | 73573 | 37 |
| 435914 | rs363075 | Major (6) | AGCCCCTCTGTGTAAGTTT | 77314 | 77332 | 38 |
| 435926 | rs363075 | Minor (6) | AGCCCTTCTGTGTAAGTTT | 77314 | 77332 | 39 |
| 435916 | rs363075 | Major (7) | GAGCCCCTCTGTGTAAGTT | 77315 | 77333 | 40 |
| 435928 | rs363075 | Minor (7) | GAGCCCTTCTGTGTAAGTT | 77315 | 77333 | 41 |
| 435333 | rs363075 | Major (8) | TGAGCCCCTCTGTGTAAGT | 77316 | 77334 | 42 |
| 435351 | rs363075 | Minor (8) | TGAGCCCTTCTGTGTAAGT | 77316 | 77334 | 43 |
| 435918 | rs363075 | Major (9) | ATGAGCCCCTCTGTGTAAG | 77317 | 77335 | 44 |
| 435930 | rs363075 | Minor (9) | ATGAGCCCTTCTGTGTAAG | 77317 | 77335 | 45 |
| 435297 | rs363075 | Major (10) | GATGAGCCCCTCTGTGTAA | 77318 | 77336 | 46 |
| 435315 | rs363075 | Minor (10) | GATGAGCCCTTCTGTGTAA | 77318 | 77336 | 47 |
| 435920 | rs363075 | Major (11) | TGATGAGCCCCTCTGTGTA | 77319 | 77337 | 48 |
| 435932 | rs363075 | Minor (11) | TGATGAGCCCTTCTGTGTA | 77319 | 77337 | 49 |

TABLE 3-continued

Chimeric oligonucleotides targeting SNP positions on the HTT gene

| ISIS No | SNP RS No. | Target allele | Sequence | Start Site | Stop Site | SEQ ID NO |
|---|---|---|---|---|---|---|
| 435366 | rs363075 | Major (12) | ATGATGAGCCCCTCTGTGT | 77320 | 77338 | 50 |
| 435924 | rs363075 | Minor (12) | ATGATGAGCCCTTCTGTGT | 77320 | 77338 | 51 |
| 435922 | rs363075 | Major (14) | TAATGATGAGCCCCTCTGT | 77322 | 77340 | 52 |
| 435934 | rs363075 | Minor (14) | TAATGATGAGCCCTTCTGT | 77322 | 77340 | 53 |
| 435334 | rs363064 | Major (8) | AGAATACGGGTAACATTTT | 81052 | 81070 | 54 |
| 435352 | rs363064 | Minor (8) | AGAATACAGGTAACATTTT | 81052 | 81070 | 55 |
| 435298 | rs363064 | Major (10) | GGAGAATACGGGTAACATT | 81054 | 81072 | 56 |
| 435316 | rs363064 | Minor (10) | GGAGAATACAGGTAACATT | 81054 | 81072 | 57 |
| 435335 | rs3025849 | Major (8) | TTAGTAATCAATTTTAATG | 83409 | 83427 | 58 |
| 435353 | rs3025849 | Minor (8) | TTAGTAACCAATTTTAATG | 83409 | 83427 | 59 |
| 435299 | rs3025849 | Major (10) | AGTTAGTAATCAATTTTAA | 83411 | 83429 | 60 |
| 435317 | rs3025849 | Minor (10) | AGTTAGTAACCAATTTTAA | 83411 | 83429 | 61 |
| 435877 | rs6855981 | Major (10) | GAAGGAATGCTTTTACTAG | 87920 | 87938 | 62 |
| 435902 | rs6855981 | Minor (10) | GAAGGAATGTTTTTACTAG | 87920 | 87938 | 63 |
| 435336 | rs363102 | Major (8) | CTAAAACTAACTTGAGAAT | 88658 | 88676 | 64 |
| 435354 | rs363102 | Minor (8) | CTAAAACCAACTTGAGAAT | 88658 | 88676 | 65 |
| 435300 | rs363102 | Major (10) | ATCTAAAACTAACTTGAGA | 88660 | 88678 | 66 |
| 435318 | rs363102 | Minor (10) | ATCTAAAACCAACTTGAGA | 88660 | 88678 | 67 |
| 435884 | rs11731237 | Major (10) | GGTGGGCAGGAAGGACTGA | 91457 | 91475 | 68 |
| 435909 | rs11731237 | Minor (10) | GGTGGGCAGAAAGGACTGA | 91457 | 91475 | 69 |
| 435337 | rs4690073 | Major (8) | CCTAAATCAATCTACAAGT | 99792 | 99810 | 70 |
| 435355 | rs4690073 | Minor (8) | CCTAAATTAATCTACAAGT | 99792 | 99810 | 71 |
| 435301 | rs4690073 | Major (10) | TCCCTAAATCAATCTACAA | 99794 | 99812 | 72 |
| 435319 | rs4690073 | Minor (10) | TCCCTAAATTAATCTACAA | 99794 | 99812 | 73 |
| 435883 | rs363144 | Major (10) | GAAAATGTGAGTGGATCTA | 100939 | 100957 | 74 |
| 435908 | rs363144 | Minor (10) | GAAAATGTGCGTGGATCTA | 100939 | 100957 | 75 |
| 435338 | rs3025838 | Major (8) | GTAAGGCGAGACTGACTAG | 101088 | 101106 | 76 |
| 435356 | rs3025838 | Minor (8) | GTAAGGCAAGACTGACTAG | 101088 | 101106 | 77 |
| 435302 | rs3025838 | Major (10) | AGGTAAGGCGAGACTGACT | 101090 | 101108 | 78 |
| 435320 | rs3025838 | Minor (10) | AGGTAAGGCAAGACTGACT | 101090 | 101108 | 79 |
| 435339 | rs363099 | Major (8) | CTGAGCGGAGAAACCCTCC | 101698 | 101716 | 80 |
| 435357 | rs363099 | Minor (8) | CTGAGCGAAGAAACCCTCC | 101698 | 101716 | 81 |
| 435303 | rs363099 | Major (10) | GGCTGAGCGGAGAAACCCT | 101700 | 101718 | 82 |
| 435321 | rs363099 | Minor (10) | GGCTGAGCGAAGAAACCCT | 101700 | 101718 | 83 |
| 435367 | rs363099 | Major (12) | AAGGCTGAGCGGAGAAACC | 101702 | 101720 | 84 |
| 435340 | rs363096 | Major (8) | TTCCCTAAAAACAAAAACA | 119663 | 119681 | 85 |
| 435358 | rs363096 | Minor (8) | TTCCCTAGAAACAAAAACA | 119663 | 119681 | 86 |

TABLE 3-continued

Chimeric oligonucleotides targeting SNP positions on the HTT gene

| ISIS No | SNP RS No. | Target allele | Sequence | Start Site | Stop Site | SEQ ID NO |
|---|---|---|---|---|---|---|
| 435304 | rs363096 | Major (10) | GATTCCCTAAAAACAAAAA | 119665 | 119683 | 87 |
| 435322 | rs363096 | Minor (10) | GATTCCCTAGAAACAAAAA | 119665 | 119683 | 88 |
| 435341 | rs2298967 | Major (8) | CTTTTCTATTGTCTGTCCC | 125389 | 125407 | 89 |
| 435359 | rs2298967 | Minor (8) | CTTTTCTGTTGTCTGTCCC | 125389 | 125407 | 90 |
| 435305 | rs2298967 | Major (10) | TGCTTTTCTATTGTCTGTC | 125391 | 125409 | 91 |
| 435323 | rs2298967 | Minor (10) | TGCTTTTCTGTTGTCTGTC | 125391 | 125409 | 92 |
| 435865 | rs2298969 | Major (10) | AAGGGATGCCGACTTGGGC | 125888 | 125906 | 93 |
| 435890 | rs2298969 | Minor (10) | AAGGGATGCTGACTTGGGC | 125888 | 125906 | 94 |
| 435876 | rs6844859 | Major (10) | ACCTTCCTCACTGAGGATG | 130130 | 130148 | 95 |
| 435901 | rs6844859 | Minor (10) | ACCTTCCTCGCTGAGGATG | 130130 | 130148 | 96 |
| 435872 | rs363092 | Major (10) | CAAACCACTGTGGGATGAA | 135673 | 135691 | 97 |
| 435897 | rs363092 | Minor (10) | CAAACCACTTTGGGATGAA | 135673 | 135691 | 98 |
| 435879 | rs7685686 | Major (10) | AATAAATTGTCATCACCAG | 146786 | 146804 | 99 |
| 435904 | rs7685686 | Minor (10) | AATAAATTGCCATCACCAG | 146786 | 146804 | 100 |
| 435871 | rs363088 | Major (10) | TCACAGCTATCTTCTCATC | 149974 | 149992 | 101 |
| 435896 | rs363088 | Minor (10) | TCACAGCTAACTTCTCATC | 149974 | 149992 | 102 |
| 435870 | rs362331 | Major (10) | GCACACAGTAGATGAGGGA | 155479 | 155497 | 103 |
| 435895 | rs362331 | Minor (10) | GCACACAGTGGATGAGGGA | 155479 | 155497 | 104 |
| 435881 | rs916171 | Major (10) | CAGAACAAAGAGAAGAATT | 156459 | 156477 | 105 |
| 435906 | rs916171 | Minor (10) | CAGAACAAACAGAAGAATT | 156459 | 156477 | 106 |
| 435342 | rs362322 | Major (8) | GCTTACATGCCTTCAGTGA | 161007 | 161025 | 107 |
| 435360 | rs362322 | Minor (8) | GCTTACACGCCTTCAGTGA | 161007 | 161025 | 108 |
| 435306 | rs362322 | Major (10) | CAGCTTACATGCCTTCAGT | 161009 | 161027 | 109 |
| 435324 | rs362322 | Minor (10) | CAGCTTACACGCCTTCAGT | 161009 | 161027 | 110 |
| 435868 | rs362275 | Major (10) | AAGAAGCCTGATAAAATCT | 164246 | 164264 | 111 |
| 435893 | rs362275 | Minor (10) | AAGAAGCCTAATAAAATCT | 164246 | 164264 | 112 |
| 435343 | rs2276881 | Major (8) | CATACATCAGCTCAAACTG | 171303 | 171321 | 113 |
| 435361 | rs2276881 | Minor (8) | CATACATTAGCTCAAACTG | 171303 | 171321 | 114 |
| 435307 | rs2276881 | Major (10) | CACATACATCAGCTCAAAC | 171305 | 171323 | 115 |
| 435325 | rs2276881 | Minor (10) | CACATACATTAGCTCAAAC | 171305 | 171323 | 116 |
| 435368 | rs2276881 | Major (12) | GTCACATACATCAGCTCAA | 171307 | 171325 | 117 |
| 435866 | rs3121419 | Major (10) | GAGACTATAGCACCCAGAT | 171901 | 171919 | 118 |
| 435891 | rs3121419 | Minor (10) | GAGACTATAACACCCAGAT | 171901 | 171919 | 119 |
| 435344 | rs362272 | Major (8) | TAGAGGACGCCGTGCAGGG | 174622 | 174640 | 120 |
| 435362 | rs362272 | Minor (8) | TAGAGGATGCCGTGCAGGG | 174622 | 174640 | 121 |
| 435308 | rs362272 | Major (10) | CATAGAGGACGCCGTGCAG | 174624 | 174642 | 122 |
| 435326 | rs362272 | Minor (10) | CATAGAGGATGCCGTGCAG | 174624 | 174642 | 123 |

TABLE 3-continued

Chimeric oligonucleotides targeting SNP positions on the HTT gene

| ISIS No | SNP RS No. | Target allele | Sequence | Start Site | Stop Site | SEQ ID NO |
|---|---|---|---|---|---|---|
| 435369 | rs362272 | Major (12) | CACATAGAGGACGCCGTGC | 174626 | 174644 | 124 |
| 435867 | rs362271 | Major (10) | ACGTGTGTACAGAACCTGC | 175162 | 175180 | 125 |
| 435892 | rs362271 | Minor (10) | ACGTGTGTATAGAACCTGC | 175162 | 175180 | 126 |
| 435873 | rs3775061 | Major (10) | TGTTCAGAATGCCTCATCT | 178398 | 178416 | 127 |
| 435898 | rs3775061 | Minor (10) | TGTTCAGAACGCCTCATCT | 178398 | 178416 | 128 |
| 435345 | rs362310 | Major (8) | AAACGGCGCAGCGGGAAGG | 179418 | 179436 | 129 |
| 435363 | rs362310 | Minor (8) | AAACGGCACAGCGGGAAGG | 179418 | 179436 | 130 |
| 435309 | rs362310 | Major (10) | AGAAACGGCGCAGCGGGAA | 179420 | 179438 | 131 |
| 435327 | rs362310 | Minor (10) | AGAAACGGCACAGCGGGAA | 179420 | 179438 | 132 |
| 435915 | rs362307 | Major (6) | AGGGCGCAGACTTCCAAAG | 181485 | 181503 | 133 |
| 435927 | rs362307 | Minor (6) | AGGGCACAGACTTCCAAAG | 181485 | 181503 | 134 |
| 435917 | rs362307 | Major (7) | AAGGGCGCAGACTTCCAAA | 181486 | 181504 | 135 |
| 435929 | rs362307 | Minor (7) | AAGGGCACAGACTTCCAAA | 181486 | 181504 | 136 |
| 435346 | rs362307 | Major (8) | CAAGGGCGCAGACTTCCAA | 181487 | 181505 | 137 |
| 435364 | rs362307 | Minor (8) | CAAGGGCACAGACTTCCAA | 181487 | 181505 | 138 |
| 435919 | rs362307 | Major (9) | ACAAGGGCGCAGACTTCCA | 181488 | 181506 | 139 |
| 435931 | rs362307 | Minor (9) | ACAAGGGCACAGACTTCCA | 181488 | 181506 | 140 |
| 435310 | rs362307 | Major (10) | CACAAGGGCGCAGACTTCC | 181489 | 181507 | 141 |
| 435328 | rs362307 | Minor (10) | CACAAGGGCACAGACTTCC | 181489 | 181507 | 142 |
| 435921 | rs362307 | Major (11) | GCACAAGGGCGCAGACTTC | 181490 | 181508 | 143 |
| 435933 | rs362307 | Minor (11) | GCACAAGGGCACAGACTTC | 181490 | 181508 | 144 |
| 435370 | rs362307 | Major (12) | GGCACAAGGGCGCAGACTT | 181491 | 181509 | 145 |
| 435925 | rs362307 | Minor (12) | GGCACAAGGGCACAGACTT | 181491 | 181509 | 146 |
| 435923 | rs362307 | Major (14) | AGGGCACAAGGGCGCAGAC | 181493 | 181511 | 147 |
| 435935 | rs362307 | Minor (14) | AGGGCACAAGGGCACAGAC | 181493 | 181511 | 148 |
| 435869 | rs362306 | Major (10) | GAGCAGCTGCAACCTGGCA | 181744 | 181762 | 149 |
| 435894 | rs362306 | Minor (10) | GAGCAGCTGTAACCTGGCA | 181744 | 181762 | 150 |
| 435347 | rs362303 | Major (8) | TGGTGCCGGGTGTCTAGCA | 181949 | 181967 | 151 |
| 435365 | rs362303 | Minor (8) | TGGTGCCAGGTGTCTAGCA | 181949 | 181967 | 152 |
| 435311 | rs362303 | Major (10) | AATGGTGCCGGGTGTCTAG | 181951 | 181969 | 153 |
| 435329 | rs362303 | Minor (10) | AATGGTGCCAGGTGTCTAG | 181951 | 181969 | 154 |
| 435882 | rs362296 | Major (10) | GGGGACAGGGTGTGCTCTC | 186651 | 186669 | 155 |
| 435907 | rs362296 | Minor (10) | GGGGACAGGTTGTGCTCTC | 186651 | 186669 | 156 |

TABLE 4

Comparison of inhibition of HTT mRNA levels by
ISIS 387916 and ISIS 388816 with that by chimeric oligonucleotides
targeting SNP positions on the HTT gene (SEQ ID NO: 1)

| ISIS No | SNP RS No. | Target allele | % inhibition GM04281 | GM02171 | GM02173B | SEQ ID NO |
|---|---|---|---|---|---|---|
| 387916 | n/a | n/a | 96 | 96 | 98 | 6 |
| 388816 | n/a | n/a | 76 | 88 | 85 | 7 |
| 435330 | rs3856973 | Major (8) | 64 | 51 | 36 | 8 |
| 435348 | rs3856973 | Minor (8) | 50 | 88 | 80 | 9 |
| 435294 | rs3856973 | Major (10) | 54 | 46 | 54 | 10 |
| 435312 | rs3856973 | Minor (10) | 20 | 82 | 58 | 11 |
| 435864 | rs2285086 | Major (10) | 54 | 28 | 26 | 12 |
| 435889 | rs2285086 | Minor (10) | 17 | 43 | 41 | 13 |
| 435878 | rs7659144 | Major (10) | 43 | 32 | 39 | 14 |
| 435903 | rs7659144 | Minor (10) | 16 | 37 | 29 | 15 |
| 435863 | rs16843804 | Major (10) | 63 | 78 | 81 | 16 |
| 435888 | rs16843804 | Minor (10) | 58 | 75 | 77 | 17 |
| 435331 | rs2024115 | Major (8) | 56 | 27 | 56 | 18 |
| 435349 | rs2024115 | Minor (8) | 26 | 91 | 66 | 19 |
| 435295 | rs2024115 | Major (10) | 53 | 57 | 62 | 20 |
| 435313 | rs2024115 | Minor (10) | 25 | 87 | 53 | 21 |
| 435862 | rs10015979 | Major (10) | 8 | 51 | 40 | 22 |
| 435887 | rs10015979 | Minor (10) | 40 | 22 | 28 | 23 |
| 435880 | rs7691627 | Major (10) | 43 | 17 | 21 | 24 |
| 435905 | rs7691627 | Minor (10) | 13 | 27 | 15 | 25 |
| 435885 | rs2798235 | Major (10) | 38 | 39 | 30 | 26 |
| 435910 | rs2798235 | Minor (10) | 17 | 30 | 16 | 27 |
| 435874 | rs4690072 | Major (10) | 61 | 34 | 48 | 28 |
| 435899 | rs4690072 | Minor (10) | 50 | 41 | 45 | 29 |
| 435875 | rs6446723 | Major (10) | 28 | 13 | 35 | 30 |
| 435900 | rs6446723 | Minor (10) | 24 | 56 | 37 | 31 |
| 435332 | rs363081 | Major (8) | 76 | 95 | 88 | 32 |
| 435350 | rs363081 | Minor (8) | 27 | 61 | 43 | 33 |
| 435296 | rs363081 | Major (10) | 59 | 77 | 66 | 34 |
| 435314 | rs363081 | Minor (10) | 38 | 66 | 40 | 35 |
| 435886 | rs363080 | Major (10) | 74 | 72 | 79 | 36 |
| 435911 | rs363080 | Minor (10) | 57 | 58 | 54 | 37 |
| 435914 | rs363075 | Major (6) | 95 | 92 | 95 | 38 |
| 435926 | rs363075 | Minor (6) | 88 | 81 | 79 | 39 |
| 435916 | rs363075 | Major (7) | 90 | 92 | 94 | 40 |
| 435928 | rs363075 | Minor (7) | 83 | 79 | 85 | 41 |
| 435333 | rs363075 | Major (8) | 86 | 97 | 91 | 42 |
| 435351 | rs363075 | Minor (8) | 59 | 80 | 58 | 43 |
| 435918 | rs363075 | Major (9) | 83 | 90 | 91 | 44 |
| 435930 | rs363075 | Minor (9) | 29 | 49 | 49 | 45 |
| 435297 | rs363075 | Major (10) | 74 | 84 | 83 | 46 |
| 435315 | rs363075 | Minor (10) | 47 | 63 | 45 | 47 |
| 435920 | rs363075 | Major (11) | 78 | 66 | 83 | 48 |
| 435932 | rs363075 | Minor (11) | 39 | 20 | 19 | 49 |
| 435366 | rs363075 | Major (12) | 80 | 91 | 85 | 50 |
| 435924 | rs363075 | Minor (12) | 37 | 49 | 58 | 51 |
| 435922 | rs363075 | Major (14) | 80 | 90 | 91 | 52 |
| 435934 | rs363075 | Minor (14) | 63 | 70 | 80 | 53 |
| 435334 | rs363064 | Major (8) | 50 | 59 | 44 | 54 |
| 435352 | rs363064 | Minor (8) | 12 | 37 | 48 | 55 |
| 435298 | rs363064 | Major (10) | 81 | 92 | 87 | 56 |
| 435316 | rs363064 | Minor (10) | 69 | 90 | 80 | 57 |
| 435335 | rs3025849 | Major (8) | 0 | 40 | 37 | 58 |
| 435353 | rs3025849 | Minor (8) | 0 | 29 | 18 | 59 |
| 435299 | rs3025849 | Major (10) | 0 | 34 | 67 | 60 |
| 435317 | rs3025849 | Minor (10) | 0 | 38 | 34 | 61 |
| 435877 | rs6855981 | Major (10) | 31 | 59 | 58 | 62 |
| 435902 | rs6855981 | Minor (10) | 0 | 43 | 27 | 63 |
| 435336 | rs363102 | Major (8) | 0 | 21 | 19 | 64 |
| 435354 | rs363102 | Minor (8) | 0 | 36 | 33 | 65 |
| 435300 | rs363102 | Major (10) | 0 | 34 | 24 | 66 |
| 435318 | rs363102 | Minor (10) | 0 | 30 | 20 | 67 |
| 435884 | rs11731237 | Major (10) | 7 | 46 | 51 | 68 |
| 435909 | rs11731237 | Minor (10) | 30 | 47 | 41 | 69 |
| 435337 | rs4690073 | Major (8) | 12 | 0 | 12 | 70 |
| 435355 | rs4690073 | Minor (8) | 0 | 26 | 33 | 71 |
| 435301 | rs4690073 | Major (10) | 23 | 0 | 10 | 72 |
| 435319 | rs4690073 | Minor (10) | 0 | 45 | 53 | 73 |
| 435883 | rs363144 | Major (10) | 24 | 23 | 39 | 74 |
| 435908 | rs363144 | Minor (10) | 27 | 20 | 22 | 75 |
| 435338 | rs3025838 | Major (8) | 31 | 46 | 69 | 76 |
| 435356 | rs3025838 | Minor (8) | 3 | 25 | 17 | 77 |

TABLE 4-continued

Comparison of inhibition of HTT mRNA levels by
ISIS 387916 and ISIS 388816 with that by chimeric oligonucleotides
targeting SNP positions on the HTT gene (SEQ ID NO: 1)

| ISIS No | SNP RS No. | Target allele | % inhibition GM04281 | GM02171 | GM02173B | SEQ ID NO |
|---|---|---|---|---|---|---|
| 435302 | rs3025838 | Major (10) | 39 | 73 | 67 | 78 |
| 435320 | rs3025838 | Minor (10) | 21 | 49 | 32 | 79 |
| 435339 | rs363099 | Major (8) | 84 | 87 | 76 | 80 |
| 435357 | rs363099 | Minor (8) | 71 | 91 | 90 | 81 |
| 435303 | rs363099 | Major (10) | 83 | 92 | 85 | 82 |
| 435321 | rs363099 | Minor (10) | 84 | 95 | 89 | 83 |
| 435367 | rs363099 | Major (12) | 76 | 82 | 72 | 84 |
| 435340 | rs363096 | Major (8) | 0 | 47 | 52 | 85 |
| 435358 | rs363096 | Minor (8) | 0 | 25 | 35 | 86 |
| 435304 | rs363096 | Major (10) | 5 | 33 | 36 | 87 |
| 435322 | rs363096 | Minor (10) | 2 | 30 | 32 | 88 |
| 435341 | rs2298967 | Major (8) | 54 | 72 | 56 | 89 |
| 435359 | rs2298967 | Minor (8) | 25 | 59 | 63 | 90 |
| 435305 | rs2298967 | Major (10) | 66 | 80 | 78 | 91 |
| 435323 | rs2298967 | Minor (10) | 36 | 79 | 66 | 92 |
| 435865 | rs2298969 | Major (10) | 53 | 72 | 79 | 93 |
| 435890 | rs2298969 | Minor (10) | 65 | 46 | 54 | 94 |
| 435876 | rs6844859 | Major (10) | 70 | 67 | 77 | 95 |
| 435901 | rs6844859 | Minor (10) | 39 | 83 | 80 | 96 |
| 435872 | rs363092 | Major (10) | 46 | 41 | 54 | 97 |
| 435897 | rs363092 | Minor (10) | 37 | 69 | 57 | 98 |
| 435879 | rs7685686 | Major (10) | 83 | 31 | 70 | 99 |
| 435904 | rs7685686 | Minor (10) | 30 | 92 | 72 | 100 |
| 435871 | rs363088 | Major (10) | 70 | 55 | 70 | 101 |
| 435896 | rs363088 | Minor (10) | 66 | 74 | 80 | 102 |
| 435870 | rs362331 | Major (10) | 88 | 74 | 88 | 103 |
| 435895 | rs362331 | Minor (10) | 78 | 92 | 86 | 104 |
| 435881 | rs916171 | Major (10) | 0 | 57 | 51 | 105 |
| 435906 | rs916171 | Minor (10) | 14 | 26 | 17 | 106 |
| 435342 | rs362322 | Major (8) | 47 | 74 | 67 | 107 |
| 435360 | rs362322 | Minor (8) | 17 | 58 | 52 | 108 |
| 435306 | rs362322 | Major (10) | 50 | 77 | 65 | 109 |
| 435324 | rs362322 | Minor (10) | 42 | 61 | 64 | 110 |
| 435868 | rs362275 | Major (10) | 54 | 35 | 43 | 111 |
| 435893 | rs362275 | Minor (10) | 3 | 27 | 33 | 112 |
| 435343 | rs2276881 | Major (8) | 59 | 76 | 65 | 113 |
| 435361 | rs2276881 | Minor (8) | 58 | 44 | 20 | 114 |
| 435307 | rs2276881 | Major (10) | 69 | 82 | 81 | 115 |
| 435325 | rs2276881 | Minor (10) | 17 | 47 | 43 | 116 |
| 435368 | rs2276881 | Major (12) | 84 | 96 | 92 | 117 |
| 435866 | rs3121419 | Major (10) | 67 | 61 | 64 | 118 |
| 435891 | rs3121419 | Minor (10) | 53 | 76 | 73 | 119 |
| 435344 | rs362272 | Major (8) | 35 | 46 | 36 | 120 |
| 435362 | rs362272 | Minor (8) | 34 | 68 | 57 | 121 |
| 435308 | rs362272 | Major (10) | 26 | 30 | 35 | 122 |
| 435326 | rs362272 | Minor (10) | 29 | 50 | 39 | 123 |
| 435369 | rs362272 | Major (12) | 66 | 74 | 65 | 124 |
| 435867 | rs362271 | Major (10) | 73 | 74 | 75 | 125 |
| 435892 | rs362271 | Minor (10) | 52 | 74 | 79 | 126 |
| 435873 | rs3775061 | Major (10) | 40 | 32 | 47 | 127 |
| 435898 | rs3775061 | Minor (10) | 13 | 20 | 24 | 128 |
| 435345 | rs362310 | Major (8) | 38 | 55 | 52 | 129 |
| 435363 | rs362310 | Minor (8) | 45 | 67 | 60 | 130 |
| 435309 | rs362310 | Major (10) | 33 | 44 | 56 | 131 |
| 435327 | rs362310 | Minor (10) | 33 | 71 | 61 | 132 |
| 435915 | rs362307 | Major (6) | 61 | 54 | 58 | 133 |
| 435927 | rs362307 | Minor (6) | 31 | 35 | 44 | 134 |
| 435917 | rs362307 | Major (7) | 67 | 76 | 66 | 135 |
| 435929 | rs362307 | Minor (7) | 33 | 34 | 55 | 136 |
| 435346 | rs362307 | Major (8) | 67 | 89 | 66 | 137 |
| 435364 | rs362307 | Minor (8) | 46 | 72 | 66 | 138 |
| 435919 | rs362307 | Major (9) | 84 | 79 | 70 | 139 |
| 435931 | rs362307 | Minor (9) | 74 | 74 | 86 | 140 |
| 435310 | rs362307 | Major (10) | 74 | 81 | 71 | 141 |
| 435328 | rs362307 | Minor (10) | 47 | 69 | 75 | 142 |
| 435921 | rs362307 | Major (11) | 74 | 77 | 69 | 143 |
| 435933 | rs362307 | Minor (11) | 38 | 47 | 74 | 144 |
| 435370 | rs362307 | Major (12) | 64 | 74 | 38 | 145 |
| 435925 | rs362307 | Minor (12) | 60 | 66 | 80 | 146 |
| 435923 | rs362307 | Major (14) | 73 | 66 | 71 | 147 |
| 435935 | rs362307 | Minor (14) | 68 | 75 | 87 | 148 |
| 435869 | rs362306 | Major (10) | 82 | 77 | 81 | 149 |

TABLE 4-continued

Comparison of inhibition of HTT mRNA levels by
ISIS 387916 and ISIS 388816 with that by chimeric oligonucleotides
targeting SNP positions on the HTT gene (SEQ ID NO: 1)

| ISIS No | SNP RS No. | Target allele | % inhibition GM04281 | GM02171 | GM02173B | SEQ ID NO |
|---|---|---|---|---|---|---|
| 435894 | rs362306 | Minor (10) | 28 | 79 | 72 | 150 |
| 435347 | rs362303 | Major (8) | 68 | 74 | 71 | 151 |
| 435365 | rs362303 | Minor (8) | 69 | 83 | 76 | 152 |
| 435311 | rs362303 | Major (10) | 46 | 56 | 72 | 153 |
| 435329 | rs362303 | Minor (10) | 49 | 62 | 39 | 154 |
| 435882 | rs362296 | Major (10) | 29 | 48 | 56 | 155 |
| 435907 | rs362296 | Minor (10) | 42 | 56 | 52 | 156 |

Example 3

Dose-Dependent Antisense Inhibition of Human Huntingtin mRNA Levels in Coriell Fibroblast Cell Lines Gapmers from the study described in Example 2 were selected and tested at various doses in GM04281, GM02171, and GM02173B cell lines. Each cell line was plated at a density of 25,000 cells per well and transfected using electroporation with 750 nM, 1,500 nM, 3,000 nM, 6,000 nM, and 12,000 nM concentrations of antisense oligonucleotide, as specified in Table 5, 6, and 7. After a treatment period of approximately 16 hours, RNA was isolated from the cells and HTT mRNA levels were measured by quantitative real-time PCR. Human HTT primer probe set RTS2617 was used to measure mRNA levels. HTT mRNA levels were adjusted according to total RNA content, as measured by RIBOGREEN. Results are presented as percent inhibition of HTT mRNA, relative to untreated control cells. $IC_{50}$ values are also provided in Tables 5, 6, and 7.

TABLE 5

Dose-dependent antisense inhibition of human HTT in GM04281 cells

| ISIS No. | 750 nM | 1,500 nM | 3,000 nM | 6,000 nM | 12,000 nM | $IC_{50}$ (μM) |
|---|---|---|---|---|---|---|
| 387916 | 51 | 81 | 80 | 91 | 97 | 0.6 |
| 435330 | 24 | 49 | 50 | 73 | 85 | 2.5 |
| 435331 | 23 | 38 | 64 | 72 | 74 | 2.4 |
| 435868 | 3 | 17 | 7 | 29 | 63 | 6.7 |
| 435870 | 53 | 73 | 77 | 86 | 93 | 0.6 |
| 435871 | 28 | 51 | 52 | 78 | 89 | 1.7 |
| 435874 | 14 | 21 | 28 | 64 | 82 | 3.3 |
| 435879 | 42 | 57 | 57 | 81 | 91 | 1.1 |
| 435890 | 48 | 56 | 62 | 76 | 91 | 0.9 |
| 435929 | 10 | 0 | 5 | 12 | 48 | 13.8 |
| 435931 | 20 | 17 | 53 | 62 | 81 | 2.9 |
| 435933 | 0 | 7 | 24 | 43 | 49 | 10.7 |
| 435935 | 0 | 38 | 38 | 62 | 29 | 4.2 |

TABLE 6

Dose-dependent antisense inhibition of human HTT in GM02171 cells

| ISIS No. | 750 nM | 1,500 nM | 3,000 nM | 6,000 nM | 12,000 nM | $IC_{50}$ (μM) |
|---|---|---|---|---|---|---|
| 387916 | 57 | 73 | 81 | 93 | 98 | 0.4 |
| 435330 | 27 | 37 | 0 | 44 | 63 | 4.4 |
| 435331 | 35 | 34 | 19 | 41 | 63 | 3.5 |
| 435868 | 21 | 21 | 39 | 24 | 12 | >12.0 |
| 435870 | 50 | 53 | 57 | 70 | 79 | 0.9 |
| 435871 | 32 | 46 | 45 | 58 | 62 | 3.9 |
| 435874 | 1 | 0 | 4 | 11 | 6 | >12.0 |
| 435879 | 32 | 14 | 17 | 45 | 38 | >12.0 |
| 435890 | 34 | 33 | 40 | 51 | 62 | 5.4 |
| 435929 | 25 | 22 | 31 | 5 | 29 | >12.0 |
| 435931 | 15 | 28 | 27 | 60 | 79 | 3.7 |
| 435933 | 13 | 36 | 21 | 43 | 48 | 12.2 |
| 435935 | 25 | 42 | 27 | 61 | 68 | 3.2 |

TABLE 7

Dose-dependent antisense inhibition of human HTT in GM02173B cells

| ISIS No. | 750 nM | 1,500 nM | 3,000 nM | 6,000 nM | 12,000 nM | $IC_{50}$ (μM) |
|---|---|---|---|---|---|---|
| 387916 | 43 | 67 | 80 | 86 | 97 | 1.1 |
| 435330 | 22 | 21 | 0 | 52 | 62 | 5.3 |
| 435331 | 19 | 17 | 32 | 50 | 55 | 9.4 |
| 435868 | 17 | 25 | 41 | 13 | 26 | >12.0 |
| 435870 | 24 | 57 | 70 | 78 | 75 | 1.8 |
| 435871 | 8 | 30 | 42 | 50 | 48 | 5.0 |
| 435874 | 31 | 35 | 28 | 35 | 42 | >12.0 |
| 435879 | 39 | 44 | 42 | 60 | 64 | 2.5 |
| 435890 | 38 | 36 | 50 | 65 | 73 | 3.1 |
| 435929 | 19 | 17 | 19 | 42 | 35 | 7.7 |
| 435931 | 40 | 19 | 31 | 48 | 71 | 5.8 |
| 435933 | 35 | 24 | 47 | 52 | 59 | 4.4 |
| 435935 | 25 | 23 | 40 | 73 | 77 | 3.7 |

Example 4

Dose-Dependent Antisense Inhibition of Human Huntingtin mRNA Levels in Coriell Fibroblast Cell Lines Gapmers from the study described in Example 2 were selected and tested at various doses in GM04281, GM02171, and GM02173B cell lines. Each cell line was plated at a density of 25,000 cells per well and transfected using electroporation with 750 nM, 1,500 nM, 3,000 nM, 6,000 nM, and 12,000 nM concentrations of antisense oligonucleotide, as specified in Table 8, 9, and 10. After a treatment period of approximately 16 hours, RNA was isolated from the cells and HTT mRNA levels were measured by quantitative real-time PCR. Human HTT primer probe set RTS2617 was used to measure mRNA levels. HTT mRNA levels were adjusted according to total RNA content, as measured by RIBOGREEN. Results are presented as percent inhibition of HTT mRNA relative to untreated control cells. $IC_{50}$ values are also provided in Tables 8, 9, and 10.

TABLE 8

Dose-dependent antisense inhibition of human HTT in GM04281 cells

| ISIS No. | 750 nM | 1,500 nM | 3,000 nM | 6,000 nM | 12,000 nM | $IC_{50}$ (μM) |
|---|---|---|---|---|---|---|
| 387916 | 61 | 78 | 90 | 94 | 97 | <0.8 |
| 435303 | 33 | 39 | 69 | 79 | 91 | 1.5 |
| 435328 | 0 | 12 | 16 | 51 | 75 | 5.3 |
| 435331 | 27 | 48 | 48 | 70 | 82 | 2.1 |
| 435339 | 46 | 37 | 61 | 73 | 89 | 2.3 |
| 435869 | 17 | 35 | 44 | 66 | 80 | 3.3 |
| 435870 | 44 | 60 | 64 | 84 | 84 | 1.1 |
| 435871 | 41 | 50 | 71 | 78 | 87 | 1.2 |
| 435874 | 24 | 36 | 35 | 65 | 73 | 3.1 |
| 435879 | 46 | 52 | 78 | 81 | 92 | 0.9 |
| 435890 | 41 | 53 | 63 | 80 | 86 | 1.3 |
| 435925 | 0 | 14 | 39 | 60 | 87 | 4.2 |
| 435926 | 20 | 28 | 67 | 81 | 89 | 2.0 |
| 435928 | 32 | 49 | 73 | 86 | 86 | 1.8 |
| 435931 | 22 | 24 | 40 | 59 | 90 | 3.8 |

TABLE 9

Dose-dependent antisense inhibition of human HTT in GM02171 cells

| ISIS No. | 750 nM | 1,500 nM | 3,000 nM | 6,000 nM | ☐☐☐☐ nM | $IC_{50}$ (μM) |
|---|---|---|---|---|---|---|
| 387916 | 50 | 64 | 90 | 95 | 96 | 0.7 |
| 435303 | 14 | 32 | 68 | 79 | 85 | 2.8 |
| 435328 | 0 | 12 | 20 | 38 | 55 | 10.3 |
| 435331 | 0 | 13 | 5 | 30 | 36 | >12.0 |
| 435339 | 30 | 40 | 58 | 63 | 49 | 2.5 |
| 435869 | 13 | 25 | 31 | 47 | 87 | 4.0 |
| 435870 | 18 | 31 | 44 | 66 | 74 | 3.5 |
| 435871 | 1 | 20 | 29 | 49 | 64 | 6.5 |
| 435874 | 3 | 6 | 12 | 17 | 31 | >12.0 |
| 435879 | 0 | 2 | 12 | 35 | 44 | >12.0 |
| 435890 | 15 | 16 | 30 | 48 | 72 | 5.8 |
| 435925 | 0 | 0 | 22 | 48 | 29 | 6.3 |
| 435926 | 25 | 28 | 58 | 74 | 85 | 2.3 |
| 435928 | 18 | 53 | 61 | 86 | 83 | 2.5 |
| 435931 | 0 | 4 | 25 | 46 | 68 | 6.7 |

TABLE 10

Dose-dependent antisense inhibition of human HTT in GM02173B cells

| ISIS No. | 750 nM | 1,500 nM | 3,000 nM | 6,000 nM | 12,000 nM | $IC_{50}$ (μM) |
|---|---|---|---|---|---|---|
| 387916 | 27 | 65 | 84 | 81 | 96 | 1.9 |
| 435303 | 23 | 48 | 52 | 76 | 76 | 2.9 |
| 435328 | 8 | 14 | 19 | 34 | 50 | 15.7 |
| 435331 | 10 | 17 | 16 | 27 | 32 | >12.0 |
| 435339 | 28 | 26 | 38 | 67 | 82 | 3.8 |
| 435869 | 12 | 24 | 37 | 45 | 79 | 4.2 |
| 435870 | 20 | 26 | 58 | 53 | 78 | 2.7 |
| 435871 | 15 | 16 | 32 | 45 | 71 | 6.0 |
| 435874 | 13 | 8 | 28 | 36 | 31 | >12.0 |
| 435879 | 22 | 20 | 36 | 53 | 60 | 6.0 |
| 435890 | 21 | 28 | 34 | 54 | 71 | 4.3 |
| 435925 | 2 | 10 | 28 | 43 | 78 | 5.9 |
| 435926 | 7 | 25 | 37 | 73 | 79 | 3.5 |
| 435928 | 15 | 39 | 60 | 73 | 87 | 2.5 |
| 435931 | 13 | 13 | 32 | 61 | 62 | 6.7 |

Example 5

Antisense Inhibition of Human HTT in GM04281 Cells

Additional antisense oligonucleotides were designed based on the gapmers selected from studies described in Example 4. These oligonucleotides were designed by creating gapmers shifted slightly upstream and downstream (i.e. "microwalk") of the original gapmers from Tables 8, 9, and 10. Antisense oligonucleotides were also created with uniform MOE, as well as with various motifs, 2-9-6 MOE, 3-9-3 MOE, 3-9-4 MOE, 3-9-5 MOE, 4-10-5 MOE, 4-11-4 MOE, 4-7-4 MOE, 4-9-4 MOE, 4-9-5 MOE, 5-10-4 MOE, 5-7-5 MOE, 5-8-6 MOE, 5-9-3 MOE, 5-9-5 MOE, 6-7-6 MOE, 6-9-2 MOE, and 6-8-5 MOE.

In addition, antisense oligonucleotides were designed targeting SNP RS Nos. rs2857936, rs12506200, rs762855, and rs1006798 (refer to Table 2). The oligonucleotides were designed targeting either the major allele or the minor allele, and with the SNP position opposite either position 8 or position 10 of the gapmer.

These gapmers were tested in vitro. Cultured GM04281 cells at a density of 25,000 cells per well were transfected using electroporation with 10,000 nM antisense oligonucleotide. After a treatment period of approximately 24 hours, RNA was isolated from the cells and HTT mRNA levels were measured by quantitative real-time PCR. HTT mRNA levels were adjusted according to total RNA content, as measured by RIBOGREEN. Results are presented in Tables 11-19 as percent inhibition of HTT mRNA, relative to untreated control cells.

The gapmers, ISIS 435869, ISIS 435870, ISIS 435874, ISIS 435879, and ISIS 435890, from which some of the newly designed gapmers were derived are marked with an asterisk (*) in the table. ISIS 387916 was included in the study as a benchmark oligonucleotide against which the potency of the antisense oligonucleotides targeting nucleotides overlapping each SNP position could be compared.

The uniform MOE oligonucleotides are 15 nucleotides in length.

The 2-9-6 gapmers are 17 nucleotides in length, wherein the central gap segment is comprised of nine 2'-deoxynucleotides and is flanked on the 5' direction by a wing comprising 2 nucleotides and on the 3' direction by a wing comprising 6 nucleotides.

The 3-9-3 gapmers are 15 nucleotides in length, wherein the central gap segment is comprised of nine 2'-deoxynucleotides and is flanked on both 5' and 3' directions by wings comprising 3 nucleotides each.

The 3-9-4 gapmers are 16 nucleotides in length, wherein the central gap segment is comprised of nine 2'-deoxynucleotides and is flanked on the 5' direction by a wing comprising 3 nucleotides and on the 3' direction by a wing comprising 4 nucleotides.

The 3-9-5 gapmers are 17 nucleotides in length, wherein the central gap segment is comprised of nine 2'-deoxynucleotides and is flanked on the 5' direction by a wing comprising 3 nucleotides and on the 3' direction by a wing comprising 5 nucleotides.

The 4-10-5 gapmers are 19 nucleotides in length, wherein the central gap segment is comprised of ten 2'-deoxynucleotides and is flanked on the 5' direction by a wing comprising 4 nucleotides and on the 3' direction by a wing comprising 5 nucleotides.

The 4-11-4 gapmers are 19 nucleotides in length, wherein the central gap segment is comprised of eleven 2'-deoxynucleotides and is flanked on both 5' and 3' directions by wings comprising 4 nucleotides each.

The 4-7-4 gapmers are 15 nucleotides in length, wherein the central gap segment is comprised of seven 2'-deoxynucleotides and is flanked on both 5' and 3' directions by wings comprising 4 nucleotides each.

The 4-9-4 gapmers are 17 nucleotides in length, wherein the central gap segment is comprised of nine 2'-deoxynucleotides and is flanked on both 5' and 3' directions by wings comprising 4 nucleotides each.

The 4-9-5 gapmers are 18 nucleotides in length, wherein the central gap segment is comprised of nine 2'-deoxynucleotides and is flanked on the 5' direction by a wing comprising 4 nucleotides and on the 3' direction by a wing comprising 5 nucleotides.

The 5-10-4 gapmers are 19 nucleotides in length, wherein the central gap segment is comprised of ten 2'-deoxynucleotides and is flanked on the 5' direction by a wing comprising 5 nucleotides and on the 3' direction by a wing comprising 4 nucleotides.

The 5-7-5 gapmers are 17 nucleotides in length, wherein the central gap segment is comprised of seven 2'-deoxynucleotides and is flanked on both 5' and 3' directions by wings comprising 5 nucleotides each.

The 5-8-6 gapmers are 19 nucleotides in length, wherein the central gap segment is comprised of eight 2'-deoxynucleotides and is flanked on the 5' direction by a wing comprising 5 nucleotides and on the 3' direction by a wing comprising 6 nucleotides.

The 5-9-3 gapmers are 17 nucleotides in length, wherein the central gap segment is comprised of nine 2'-deoxynucleotides and is flanked on the 5' direction by a wing comprising 5 nucleotides and on the 3' direction by a wing comprising 3 nucleotides.

The 5-9-5 gapmers are 19 nucleotides in length, wherein the central gap segment is comprised of nine 2'-deoxynucleotides and is flanked on both 5' and 3' directions by wings comprising 5 nucleotides each.

The 6-7-6 gapmers are 19 nucleotides in length, wherein the central gap segment is comprised of seven 2'-deoxynucleotides and is flanked on both 5' and 3' directions by wings comprising 6 nucleotides each.

The 6-9-2 gapmers are 17 nucleotides in length, wherein the central gap segment is comprised of nine 2'-deoxynucleotides and is flanked on the 5' direction by a wing comprising 6 nucleotides and on the 3' direction by a wing comprising 2 nucleotides.

The 6-8-5 gapmers are 19 nucleotides in length, wherein the central gap segment is comprised of eight 2'-deoxynucleotides and is flanked on the 5' direction by a wing comprising 6 nucleotides and on the 3' direction by a wing comprising 5 nucleotides.

For each of the motifs, each nucleotide in the 5' wing segment and each nucleotide in the 3' wing segment has a 2'-MOE modification. The internucleoside linkages throughout each gapmer are phosphorothioate (P=S) linkages. All cytosine nucleobases throughout each gapmer are 5-methylcytosines.

The oligonucleotides are organized in tables according to the SNP they target. "Start site" indicates the 5'-most nucleotide to which the gapmer is targeted. "Stop site" indicates the 3'-most nucleotide to which the gapmer is targeted. 'Target allele' indicates whether the gapmer is targeted to the major or the minor allele. The number in parentheses indicates the position on the oligonucleotide opposite to the SNP position.

TABLE 11

Comparison of inhibition of human HTT mRNA levels by ISIS 387916 and chimeric antisense oligonucleotides targeted to SNP rs2857936 (nucleobases 1952 to 1972 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 98 | 6 |
| 1952 | 1970 | Minor (8) | 459908 | GCTTTTCATTGAAAAGAAA | 5-9-5 | 26 | 157 |
| 1952 | 1970 | Major (8) | 459916 | GCTTTTCGTTGAAAAGAAA | 5-9-5 | 8 | 158 |
| 1954 | 1972 | Minor (10) | 459904 | CTGCTTTTCATTGAAAAGA | 5-9-5 | 23 | 159 |
| 1954 | 1972 | Major (10) | 459912 | CTGCTTTTCGTTGAAAAGA | 5-9-5 | 8 | 160 |

TABLE 12

Comparison of inhibition of human HTT mRNA levels by ISIS 387916 and chimeric antisense oligonucleotides targeted to SNP rs12506200 (nucleobases 3695 to 3715 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 98 | 6 |
| 3695 | 3713 | Major (8) | 459909 | ACTAGGCCGGGCATGCTGG | 5-9-5 | 48 | 161 |
| 3695 | 3713 | Minor (8) | 459917 | ACTAGGCTGGGCATGCTGG | 5-9-5 | 35 | 162 |

TABLE 12-continued

Comparison of inhibition of human HTT mRNA levels by ISIS 387916
and chimeric antisense oligonucleotides targeted to SNP rs12506200
(nucleobases 3695 to 3715 of SEQ ID NO: 1)

| Start Site | Stop Site | Target allele | ISIS No. | Sequence | Motif | % inhibition | SEQ ID NO |
|---|---|---|---|---|---|---|---|
| 3697 | 3715 | Major (10) | 459905 | AGACTAGGCCGGGCATGCT | 5-9-5 | 33 | 163 |
| 3697 | 3715 | Minor (10) | 459913 | AGACTAGGCTGGGCATGCT | 5-9-5 | 45 | 164 |

TABLE 13

Comparison of inhibition of human HTT mRNA levels by ISIS 387916
and chimeric antisense oligonucleotides targeted to SNP rs762855
(nucleobases 14437 to 14457 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 98 | 6 |
| 14437 | 14455 | Minor (8) | 459910 | AAACAGCTGTTAGTTCCCA | 5-9-5 | 27 | 165 |
| 14437 | 14455 | Major (8) | 459918 | AAACAGCCGTTAGTTCCCA | 5-9-5 | 39 | 166 |
| 14439 | 14457 | Minor (10) | 459906 | AGAAACAGCTGTTAGTTCC | 5-9-5 | 24 | 167 |
| 14439 | 14457 | Major (10) | 459914 | AGAAACAGCCGTTAGTTCC | 5-9-5 | 28 | 168 |

TABLE 14

Comparison of inhibition of human HTT mRNA levels by ISIS 387916
and chimeric antisense oligonucleotides targeted to SNP rs4690072
(nucleobases 62147 to 62173 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 98 | 6 |
| 62147 | 62165 | Major (6) | 460145 | GTGCTACCCAACCTTTCTG | 5-9-5 | 62 | 169 |
| 62148 | 62166 | Major (7) | 460144 | AGTGCTACCCAACCTTTCT | 5-9-5 | 61 | 170 |
| 62149 | 62167 | Major (8) | 460143 | CAGTGCTACCCAACCTTTC | 5-9-5 | 65 | 171 |
| 62150 | 62168 | Major (9) | 460142 | ACAGTGCTACCCAACCTTT | 5-9-5 | 83 | 172 |
| 62151 | 62169 | Major (10) | *435874 | CACAGTGCTACCCAACCTT | 5-9-5 | 76 | 28 |
| 62151 | 62169 | Major (10) | 460022 | CACAGTGCTACCCAACCTT | 4-10-5 | 75 | 28 |
| 62151 | 62169 | Major (10) | 460033 | CACAGTGCTACCCAACCTT | 4-11-4 | 89 | 28 |
| 62151 | 62168 | Major (9) | 460063 | ACAGTGCTACCCAACCTT | 4-9-5 | 77 | 173 |
| 62151 | 62169 | Major (10) | 460073 | CACAGTGCTACCCAACCTT | 5-10-4 | 86 | 28 |
| 62151 | 62169 | Major (10) | 460093 | CACAGTGCTACCCAACCTT | 5-8-6 | 61 | 28 |
| 62151 | 62169 | Major (10) | 460169 | CACAGTGCTACCCAACCTT | 6-7-6 | 16 | 28 |
| 62151 | 62169 | Major (10) | 460188 | CACAGTGCTACCCAACCTT | 6-8-5 | 53 | 28 |
| 62152 | 62168 | Major (9) | 459978 | ACAGTGCTACCCAACCT | 2-9-6 | 87 | 174 |
| 62152 | 62167 | Major (8) | 459999 | CAGTGCTACCCAACCT | 3-9-4 | 48 | 175 |
| 62152 | 62168 | Major (9) | 460012 | ACAGTGCTACCCAACCT | 3-9-5 | 84 | 174 |

TABLE 14-continued

Comparison of inhibition of human HTT mRNA levels by ISIS 387916 and chimeric antisense oligonucleotides targeted to SNP rs4690072 (nucleobases 62147 to 62173 of SEQ ID NO: 1)

| Start Site | Stop Site | Target allele | ISIS No. | Sequence | Motif | % inhibition | SEQ ID NO |
|---|---|---|---|---|---|---|---|
| 62152 | 62168 | Major (9) | 460052 | ACAGTGCTACCCAACCT | 4-9-4 | 51 | 174 |
| 62152 | 62168 | Major (9) | 460083 | ACAGTGCTACCCAACCT | 5-7-5 | 37 | 174 |
| 62152 | 62168 | Major (9) | 460103 | ACAGTGCTACCCAACCT | 5-9-3 | 80 | 174 |
| 62152 | 62170 | Major (11) | 460137 | TCACAGTGCTACCCAACCT | 5-9-5 | 65 | 176 |
| 62152 | 62168 | Major (9) | 460179 | ACAGTGCTACCCAACCT | 6-9-2 | 67 | 174 |
| 62153 | 62167 | Major (8) | 459989 | CAGTGCTACCCAACC | 3-9-3 | 60 | 177 |
| 62153 | 62167 | Major (8) | 460043 | CAGTGCTACCCAACC | 4-7-4 | 24 | 177 |
| 62153 | 62171 | Major (12) | 460138 | ATCACAGTGCTACCCAACC | 5-9-5 | 76 | 178 |
| 62154 | 62172 | Major (13) | 460139 | TATCACAGTGCTACCCAAC | 5-9-5 | 68 | 179 |
| 62155 | 62173 | Major (14) | 460140 | ATATCACAGTGCTACCCAA | 5-9-5 | 79 | 180 |

TABLE 15

Comparison of inhibition of human HTT mRNA levels by ISIS 387916 and chimeric antisense oligonucleotides targeted to SNP rs2298969 (nucleobases 125883 to 125911 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 98 | 6 |
| 125883 | 125901 | Minor (5) | 460166 | ATGCTGACTTGGGCCATTC | 5-9-5 | 83 | 181 |
| 125884 | 125902 | Minor (6) | 460165 | GATGCTGACTTGGGCCATT | 5-9-5 | 88 | 182 |
| 125885 | 125903 | Minor (7) | 460164 | GGATGCTGACTTGGGCCAT | 5-9-5 | 68 | 183 |
| 125886 | 125904 | Minor (8) | 460163 | GGGATGCTGACTTGGGCCA | 5-9-5 | 73 | 184 |
| 125887 | 125905 | Minor (9) | 460162 | AGGGATGCTGACTTGGGCC | 5-9-5 | 88 | 185 |
| 125888 | 125906 | Minor (10) | *435890 | AAGGGATGCTGACTTGGGC | 5-9-5 | 83 | 94 |
| 125888 | 125906 | Minor (10) | 460026 | AAGGGATGCTGACTTGGGC | 4-10-5 | 90 | 94 |
| 125888 | 125906 | Minor (10) | 460037 | AAGGGATGCTGACTTGGGC | 4-11-4 | 86 | 94 |
| 125888 | 125905 | Minor (9) | 460068 | AGGGATGCTGACTTGGGC | 4-9-5 | 90 | 186 |
| 125888 | 125906 | Minor (10) | 460076 | AAGGGATGCTGACTTGGGC | 5-10-4 | 90 | 94 |
| 125888 | 125906 | Minor (10) | 460096 | AAGGGATGCTGACTTGGGC | 5-8-6 | 88 | 94 |
| 125888 | 125906 | Minor (10) | 460171 | AAGGGATGCTGACTTGGGC | 6-7-6 | 87 | 94 |
| 125888 | 125906 | Minor (10) | 460190 | AAGGGATGCTGACTTGGGC | 6-8-5 | 69 | 94 |
| 125889 | 125905 | Minor (9) | 459983 | AGGGATGCTGACTTGGG | 2-9-6 | 80 | 187 |
| 125889 | 125904 | Minor (8) | 460005 | GGGATGCTGACTTGGG | 3-9-4 | 80 | 284 |
| 125889 | 125905 | Minor (9) | 460016 | AGGGATGCTGACTTGGG | 3-9-5 | 90 | 187 |
| 125889 | 125905 | Minor (9) | 460057 | AGGGATGCTGACTTGGG | 4-9-4 | 86 | 187 |
| 125889 | 125905 | Minor (9) | 460087 | AGGGATGCTGACTTGGG | 5-7-5 | 86 | 187 |

TABLE 15-continued

Comparison of inhibition of human HTT mRNA levels by ISIS 387916 and chimeric antisense oligonucleotides targeted to SNP rs2298969 (nucleobases 125883 to 125911 of SEQ ID NO: 1)

| Start Site | Stop Site | Target allele | ISIS No. | Sequence | Motif | % inhibition | SEQ ID NO |
|---|---|---|---|---|---|---|---|
| 125889 | 125905 | Minor (9) | 460107 | AGGGATGCTGACTTGGG | 5-9-3 | 79 | 187 |
| 125889 | 125907 | Major (11) | 460157 | CAAGGGATGCTGACTTGGG | 5-9-5 | 88 | 188 |
| 125889 | 125905 | Minor (9) | 460181 | AGGGATGCTGACTTGGG | 6-9-2 | 62 | 187 |
| 125890 | 125904 | Minor (8) | 459972 | GGGATGCTGACTTGG | Uniform | 18 | 189 |
| 125890 | 125904 | Minor (8) | 459992 | GGGATGCTGACTTGG | 3-9-3 | 90 | 189 |
| 125890 | 125904 | Minor (8) | 460046 | GGGATGCTGACTTGG | 4-7-4 | 59 | 189 |
| 125890 | 125908 | Major (12) | 460158 | CCAAGGGATGCTGACTTGG | 5-9-5 | 79 | 190 |
| 125891 | 125909 | Major (13) | 460159 | GCCAAGGGATGCTGACTTG | 5-9-5 | 82 | 191 |
| 125892 | 125910 | Major (14) | 460160 | TGCCAAGGGATGCTGACTT | 5-9-5 | 87 | 192 |
| 125893 | 125911 | Major (15) | 460161 | CTGCCAAGGGATGCTGACT | 5-9-5 | 78 | 193 |

TABLE 16

Comparison of inhibition of human HTT mRNA levels by ISIS 387916 and chimeric antisense oligonucleotides targeted to SNP rs7685686 (nucleobases 146781 to 146809 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 98 | 6 |
| 146781 | 146799 | Major (5) | 460156 | ATTGTCATCACCAGAAAAA | 5-9-5 | 88 | 194 |
| 146782 | 146800 | Major (6) | 460155 | AATTGTCATCACCAGAAAA | 5-9-5 | 89 | 195 |
| 146783 | 146801 | Major (7) | 460154 | AAATTGTCATCACCAGAAA | 5-9-5 | 89 | 196 |
| 146784 | 146802 | Major (8) | 460153 | TAAATTGTCATCACCAGAA | 5-9-5 | 93 | 197 |
| 146785 | 146803 | Major (9) | 460152 | ATAAATTGTCATCACCAGA | 5-9-5 | 95 | 198 |
| 146786 | 146804 | Major (10) | *435879 | AATAAATTGTCATCACCAG | 5-9-5 | 94 | 99 |
| 146786 | 146804 | Major (10) | 460024 | AATAAATTGTCATCACCAG | 4-10-5 | 88 | 99 |
| 146786 | 146804 | Major (10) | 460035 | AATAAATTGTCATCACCAG | 4-11-4 | 91 | 99 |
| 146786 | 146803 | Major (9) | 460065 | ATAAATTGTCATCACCAG | 4-9-5 | 96 | 199 |
| 146786 | 146804 | Major (10) | 460074 | AATAAATTGTCATCACCAG | 5-10-4 | 94 | 99 |
| 146786 | 146804 | Major (10) | 460095 | AATAAATTGTCATCACCAG | 5-8-6 | 92 | 99 |
| 146786 | 146804 | Major (10) | 460170 | AATAAATTGTCATCACCAG | 6-7-6 | 91 | 99 |
| 146786 | 146804 | Major (10) | 460189 | AATAAATTGTCATCACCAG | 6-8-5 | 94 | 99 |
| 146787 | 146803 | Major (9) | 459981 | ATAAATTGTCATCACCA | 2-9-6 | 85 | 200 |
| 146787 | 146802 | Major (8) | 460002 | TAAATTGTCATCACCA | 3-9-4 | 86 | 201 |
| 146787 | 146803 | Major (9) | 460014 | ATAAATTGTCATCACCA | 3-9-5 | 91 | 200 |
| 146787 | 146803 | Major (9) | 460055 | ATAAATTGTCATCACCA | 4-9-4 | 90 | 200 |
| 146787 | 146803 | Major (9) | 460085 | ATAAATTGTCATCACCA | 5-7-5 | 94 | 200 |
| 146787 | 146803 | Major (9) | 460104 | ATAAATTGTCATCACCA | 5-9-3 | 93 | 200 |

TABLE 16-continued

Comparison of inhibition of human HTT mRNA levels by ISIS 387916
and chimeric antisense oligonucleotides targeted to SNP rs7685686
(nucleobases 146781 to 146809 of SEQ ID NO: 1)

| Start Site | Stop Site | Target allele | ISIS No. | Sequence | Motif | % inhibition | SEQ ID NO |
|---|---|---|---|---|---|---|---|
| 146787 | 146805 | Major (11) | 460147 | TAATAAATTGTCATCACCA | 5-9-5 | 91 | 202 |
| 146787 | 146803 | Major (9) | 460180 | ATAAATTGTCATCACCA | 6-9-2 | 91 | 200 |
| 146788 | 146802 | Major (8) | 459970 | TAAATTGTCATCACC | Uniform | 9 | 203 |
| 146788 | 146802 | Major (8) | 459990 | TAAATTGTCATCACC | 3-9-3 | 67 | 203 |
| 146788 | 146802 | Major (8) | 460045 | TAAATTGTCATCACC | 4-7-4 | 84 | 203 |
| 146788 | 146806 | Major (12) | 460148 | TTAATAAATTGTCATCACC | 5-9-5 | 88 | 204 |
| 146789 | 146807 | Major (13) | 460149 | ATTAATAAATTGTCATCAC | 5-9-5 | 32 | 205 |
| 146790 | 146808 | Major (14) | 460150 | TATTAATAAATTGTCATCA | 5-9-5 | 29 | 206 |
| 146791 | 146809 | Major (15) | 460151 | CTATTAATAAATTGTCATC | 5-9-5 | 33 | 207 |

TABLE 17

Comparison of inhibition of human HTT mRNA levels by ISIS 387916
and chimeric antisense oligonucleotides targeted to SNP rs362331
(nucleobases 155474 to 155502 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 98 | 6 |
| 155474 | 155492 | Major (5) | 460136 | CAGTAGATGAGGGAGCAGG | 5-9-5 | 81 | 208 |
| 155475 | 155493 | Major (6) | 460135 | ACAGTAGATGAGGGAGCAG | 5-9-5 | 84 | 209 |
| 155476 | 155494 | Major (7) | 460134 | CACAGTAGATGAGGGAGCA | 5-9-5 | 87 | 210 |
| 155477 | 155495 | Major (8) | 460133 | ACACAGTAGATGAGGGAGC | 5-9-5 | 85 | 211 |
| 155478 | 155496 | Major (9) | 460132 | CACACAGTAGATGAGGGAG | 5-9-5 | 86 | 212 |
| 155479 | 155497 | Major (10) | *435870 | GCACACAGTAGATGAGGGA | 5-9-5 | 91 | 103 |
| 155479 | 155497 | Major (10) | 460019 | GCACACAGTAGATGAGGGA | 4-10-5 | 92 | 103 |
| 155479 | 155497 | Major (10) | 460031 | GCACACAGTAGATGAGGGA | 4-11-4 | 95 | 103 |
| 155479 | 155496 | Major (9) | 460061 | CACACAGTAGATGAGGGA | 4-9-5 | 87 | 213 |
| 155479 | 155497 | Major (10) | 460071 | GCACACAGTAGATGAGGGA | 5-10-4 | 94 | 103 |
| 155479 | 155497 | Major (10) | 460090 | GCACACAGTAGATGAGGGA | 5-8-6 | 86 | 103 |
| 155479 | 155497 | Major (10) | 460168 | GCACACAGTAGATGAGGGA | 6-7-6 | 84 | 103 |
| 155479 | 155497 | Major (10) | 460187 | GCACACAGTAGATGAGGGA | 6-8-5 | 89 | 103 |
| 155480 | 155496 | Major (9) | 459977 | CACACAGTAGATGAGGG | 2-9-6 | 90 | 214 |
| 155480 | 155495 | Major (8) | 459996 | ACACAGTAGATGAGGG | 3-9-4 | 37 | 215 |
| 155480 | 155496 | Major (9) | 460009 | CACACAGTAGATGAGGG | 3-9-5 | 90 | 214 |
| 155480 | 155496 | Major (9) | 460051 | CACACAGTAGATGAGGG | 4-9-4 | 73 | 214 |
| 155480 | 155496 | Major (9) | 460081 | CACACAGTAGATGAGGG | 5-7-5 | 77 | 214 |
| 155480 | 155496 | Major (9) | 460101 | CACACAGTAGATGAGGG | 5-9-3 | 84 | 214 |

TABLE 17-continued

Comparison of inhibition of human HTT mRNA levels by ISIS 387916 and chimeric antisense oligonucleotides targeted to SNP rs362331 (nucleobases 155474 to 155502 of SEQ ID NO: 1)

| Start Site | Stop Site | Target allele | ISIS No. | Sequence | Motif | % inhibition | SEQ ID NO |
|---|---|---|---|---|---|---|---|
| 155480 | 155498 | Major (11) | 460127 | TGCACACAGTAGATGAGGG | 5-9-5 | 89 | 216 |
| 155480 | 155496 | Major (9) | 460178 | CACACAGTAGATGAGGG | 6-9-2 | 92 | 214 |
| 155481 | 155495 | Major (8) | 459967 | ACACAGTAGATGAGG | Uniform | 81 | 217 |
| 155481 | 155495 | Major (8) | 459987 | ACACAGTAGATGAGG | 3-9-3 | 18 | 217 |
| 155481 | 155495 | Major (8) | 460041 | ACACAGTAGATGAGG | 4-7-4 | 54 | 217 |
| 155481 | 155499 | Major (12) | 460128 | GTGCACACAGTAGATGAGG | 5-9-5 | 73 | 218 |
| 155482 | 155500 | Major (13) | 460129 | AGTGCACACAGTAGATGAG | 5-9-5 | 86 | 219 |
| 155483 | 155501 | Major (14) | 460130 | AAGTGCACACAGTAGATGA | 5-9-5 | 60 | 220 |
| 155484 | 155502 | Major (15) | 460131 | GAAGTGCACACAGTAGATG | 5-9-5 | 73 | 221 |

TABLE 18

Comparison of inhibition of human HTT mRNA levels by ISIS 387916 and chimeric antisense oligonucleotides targeted to SNP rs362306 (nucleobases 181739 to 181767 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 98 | 6 |
| 181739 | 181757 | Major (5) | 460126 | GCTGCAACCTGGCAACAAC | 5-9-5 | 87 | 222 |
| 181740 | 181758 | Major (6) | 460125 | AGCTGCAACCTGGCAACAA | 5-9-5 | 70 | 223 |
| 181741 | 181759 | Major (7) | 460123 | CAGCTGCAACCTGGCAACA | 5-9-5 | 83 | 224 |
| 181742 | 181760 | Major (8) | 460121 | GCAGCTGCAACCTGGCAAC | 5-9-5 | 47 | 225 |
| 181743 | 181761 | Major (9) | 460118 | AGCAGCTGCAACCTGGCAA | 5-9-5 | 75 | 226 |
| 181744 | 181762 | Major (10) | *435869 | GAGCAGCTGCAACCTGGCA | 5-9-5 | 91 | 149 |
| 181744 | 181762 | Major (10) | 460018 | GAGCAGCTGCAACCTGGCA | 4-10-5 | 86 | 149 |
| 181744 | 181762 | Major (10) | 460028 | GAGCAGCTGCAACCTGGCA | 4-11-4 | 89 | 149 |
| 181744 | 181761 | Major (9) | 460058 | AGCAGCTGCAACCTGGCA | 4-9-5 | 85 | 227 |
| 181744 | 181762 | Major (10) | 460069 | GAGCAGCTGCAACCTGGCA | 5-10-4 | 91 | 149 |
| 181744 | 181762 | Major (10) | 460089 | GAGCAGCTGCAACCTGGCA | 5-8-6 | 54 | 149 |
| 181744 | 181762 | Major (10) | 460167 | GAGCAGCTGCAACCTGGCA | 6-7-6 | 85 | 149 |
| 181744 | 181762 | Major (10) | 460186 | GAGCAGCTGCAACCTGGCA | 6-8-5 | 84 | 149 |
| 181745 | 181761 | Major (9) | 459975 | AGCAGCTGCAACCTGGC | 2-9-6 | 86 | 228 |
| 181745 | 181760 | Major (8) | 459995 | GCAGCTGCAACCTGGC | 3-9-4 | 87 | 229 |
| 181745 | 181761 | Major (9) | 460008 | AGCAGCTGCAACCTGGC | 3-9-5 | 83 | 228 |
| 181745 | 181761 | Major (9) | 460049 | AGCAGCTGCAACCTGGC | 4-9-4 | 88 | 228 |
| 181745 | 181761 | Major (9) | 460079 | AGCAGCTGCAACCTGGC | 5-7-5 | 46 | 228 |
| 181745 | 181761 | Major (9) | 460099 | AGCAGCTGCAACCTGGC | 5-9-3 | 44 | 228 |
| 181745 | 181763 | Major (11) | 460108 | AGAGCAGCTGCAACCTGGC | 5-9-5 | 50 | 230 |

TABLE 18-continued

Comparison of inhibition of human HTT mRNA levels by ISIS 387916
and chimeric antisense oligonucleotides targeted to SNP rs362306
(nucleobases 181739 to 181767 of SEQ ID NO: 1)

| Start Site | Stop Site | Target allele | ISIS No. | Sequence | Motif | % inhibition | SEQ ID NO |
|---|---|---|---|---|---|---|---|
| 181745 | 181761 | Major (9)  | 460177 | AGCAGCTGCAACCTGGC | 6-9-2   | 67 | 228 |
| 181746 | 181760 | Major (8)  | 459966 | GCAGCTGCAACCTGG   | Uniform | 26 | 231 |
| 181746 | 181760 | Major (8)  | 459985 | GCAGCTGCAACCTGG   | 3-9-3   | 69 | 231 |
| 181746 | 181760 | Major (8)  | 460039 | GCAGCTGCAACCTGG   | 4-7-4   | 56 | 231 |
| 181746 | 181764 | Major (12) | 460110 | AAGAGCAGCTGCAACCTGG | 5-9-5 | 75 | 232 |
| 181747 | 181765 | Major (13) | 460113 | CAAGAGCAGCTGCAACCTG | 5-9-5 | 36 | 233 |
| 181748 | 181766 | Major (14) | 460115 | GCAAGAGCAGCTGCAACCT | 5-9-5 | 78 | 234 |
| 181749 | 181767 | Major (15) | 460117 | TGCAAGAGCAGCTGCAACC | 5-9-5 | 73 | 235 |

TABLE 19

Comparison of inhibition of human HTT mRNA levels by ISIS 387916
and chimeric antisense oligonucleotides targeted to SNP rs1006798
(nucleobases 198015 to 198035 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a        | 387916 | TCTCTATTGCACATTCCAAG | 5-10-5 | 98 | 6   |
| 198015 | 198033 | Minor (8)  | 459911 | ACCATGATATCTCCAGCAC  | 5-9-5  | 33 | 236 |
| 198015 | 198033 | Minor (8)  | 459919 | ACCATGACATCTCCAGCAC  | 5-9-5  | 26 | 237 |
| 198017 | 198035 | Major (10) | 459907 | CCACCATGATATCTCCAGC  | 5-9-5  | 32 | 238 |
| 198017 | 198035 | Minor (10) | 459915 | CCACCATGACATCTCCAGC  | 5-9-5  | 51 | 239 |

Example 6

Dose-Dependent Antisense Inhibition of Human Huntingtin mRNA Levels in Coriell Fibroblast Cell Lines Gapmers from the studies described in Example 5 were selected and tested at various doses in GM04281, GM02171, and GM02173B cell lines. Each cell line was plated at a density of 25,000 cells per well and transfected using electroporation with 750 nM, 1,500 nM, 3,000 nM, 6,000 nM, and 12,000 nM concentrations of antisense oligonucleotide, as specified in Tables 20, 21, and 22. After a treatment period of approximately 16 hours, RNA was isolated from the cells and HTT mRNA levels were measured by quantitative real-time PCR. Human HTT primer probe set RTS2617 was used to measure mRNA levels. HTT mRNA levels were adjusted according to total RNA content, as measured by RIBOGREEN. Results are presented as percent inhibition of HTT mRNA, relative to untreated control cells. $IC_{50}$ values are also provided in Tables 20, 21, and 22.

TABLE 20

Dose-dependent antisense inhibition of human HTT in GM04281 cells

| ISIS No. | 750 nM | 1,500 nM | 3,000 nM | 6,000 nM | 12,000 nM | $IC_{50}$ (µM) |
|---|---|---|---|---|---|---|
| 387916 | 56 | 81 | 89 | 96 | 98 | 0.6 |
| 435869 | 38 | 49 | 66 | 86 | 91 | 1.4 |
| 435874 | 33 | 27 | 37 | 49 | 62 | 8.4 |
| 435879 | 42 | 55 | 73 | 86 | 96 | 1.1 |
| 435890 | 39 | 51 | 74 | 83 | 89 | 1.3 |
| 459978 | 29 | 33 | 51 | 69 | 86 | 2.5 |
| 459992 | 14 | 27 | 51 | 54 | 84 | 3.2 |
| 460012 | 15 | 24 | 54 | 70 | 81 | 3.1 |
| 460016 | 3  | 36 | 48 | 71 | 77 | 3.3 |
| 460019 | 54 | 59 | 74 | 87 | 94 | 0.7 |
| 460026 | 48 | 47 | 71 | 79 | 88 | 0.8 |
| 460028 | 39 | 38 | 73 | 77 | 87 | 1.4 |
| 460031 | 44 | 62 | 72 | 87 | 92 | 0.9 |
| 460033 | 11 | 38 | 52 | 64 | 87 | 3.0 |
| 460065 | 43 | 54 | 74 | 89 | 96 | 1.1 |
| 460068 | 47 | 28 | 63 | 76 | 90 | 2.6 |
| 460069 | 38 | 50 | 65 | 77 | 91 | 1.4 |
| 460071 | 53 | 61 | 80 | 89 | 93 | 0.6 |
| 460073 | 16 | 39 | 42 | 58 | 75 | 4.0 |
| 460076 | 26 | 47 | 54 | 70 | 86 | 2.1 |
| 460085 | 48 | 60 | 79 | 89 | 94 | 0.8 |

TABLE 20-continued

Dose-dependent antisense inhibition of human HTT in GM04281 cells

| ISIS No. | 750 nM | 1,500 nM | 3,000 nM | 6,000 nM | 12,000 nM | IC$_{50}$ (µM) |
|---|---|---|---|---|---|---|
| 460140 | 6 | 24 | 44 | 44 | 64 | 6.6 |
| 460142 | 2 | 38 | 46 | 46 | 68 | 4.8 |
| 460152 | 35 | 61 | 76 | 92 | 94 | 1.2 |
| 460157 | 51 | 36 | 53 | 74 | 89 | 2.6 |
| 460162 | 64 | 41 | 71 | 76 | 85 | 2.1 |
| 460165 | 41 | 50 | 56 | 76 | 84 | 1.5 |

TABLE 21

Dose-dependent antisense inhibition of human HTT in GM02171 cells

| ISIS No. | 750 nM | 1,500 nM | 3,000 nM | 6,000 nM | 12,000 nM | IC$_{50}$ (µM) |
|---|---|---|---|---|---|---|
| 387916 | 53 | 66 | 88 | 96 | 98 | 0.7 |
| 435869 | 4 | 20 | 36 | 63 | 86 | 3.9 |
| 435870 | 25 | 39 | 48 | 62 | 83 | 2.8 |
| 435874 | 12 | 20 | 18 | 27 | 37 | >12.0 |
| 435879 | 10 | 7 | 11 | 42 | 51 | 10.6 |
| 435890 | 10 | 23 | 29 | 29 | 55 | 9.2 |
| 459978 | 15 | 7 | 6 | 29 | 52 | 12.7 |
| 459992 | 11 | 19 | 26 | 39 | 62 | 8.7 |
| 460012 | 3 | 3 | 10 | 19 | 41 | >12.0 |
| 460016 | 0 | 14 | 12 | 22 | 48 | >12.0 |
| 460019 | 27 | 21 | 41 | 60 | 73 | 4.4 |
| 460026 | 9 | 25 | 30 | 46 | 58 | 7.8 |
| 460028 | 24 | 8 | 32 | 54 | 77 | 5.3 |
| 460031 | 8 | 25 | 42 | 60 | 83 | 3.8 |
| 460033 | 11 | 25 | 30 | 40 | 75 | 4.1 |
| 460065 | 11 | 16 | 11 | 31 | 53 | 10.3 |
| 460068 | 15 | 13 | 39 | 44 | 53 | 8.8 |
| 460069 | 17 | 28 | 37 | 60 | 79 | 3.9 |
| 460071 | 16 | 36 | 58 | 70 | 88 | 2.6 |
| 460073 | 5 | 19 | 24 | 33 | 56 | 8.7 |
| 460076 | 19 | 29 | 44 | 54 | 83 | 3.3 |
| 460085 | 10 | 15 | 17 | 28 | 31 | >12.0 |
| 460140 | 8 | 22 | 22 | 28 | 47 | >12.0 |
| 460142 | 11 | 24 | 28 | 36 | 38 | >12.0 |
| 460152 | 14 | 21 | 8 | 25 | 44 | 22 |
| 460157 | 22 | 21 | 29 | 44 | 66 | 6.7 |
| 460162 | 24 | 55 | 52 | 62 | 82 | 2.8 |
| 460165 | 14 | 34 | 50 | 69 | 81 | 3.1 |

TABLE 22

Dose-dependent antisense inhibition of human HTT in GM02173B cells

| ISIS No. | 750 nM | 1,500 nM | 3,000 nM | 6,000 nM | 12,000 nM | IC$_{50}$ (µM) |
|---|---|---|---|---|---|---|
| 387916 | 37 | 63 | 86 | 88 | 98 | 1.0 |
| 435869 | 10 | 20 | 43 | 70 | 85 | 3.5 |
| 435870 | 24 | 24 | 56 | 72 | 87 | 2.3 |
| 435874 | 0 | 11 | 12 | 30 | 44 | >12.0 |
| 435879 | 4 | 17 | 43 | 64 | 74 | 4.3 |
| 435890 | 31 | 29 | 54 | 57 | 69 | 4.4 |
| 459978 | 7 | 13 | 17 | 35 | 64 | 8.4 |
| 459992 | 18 | 15 | 30 | 51 | 71 | 5.7 |
| 460012 | 0 | 10 | 24 | 37 | 72 | 7.1 |
| 460016 | 15 | 5 | 30 | 38 | 59 | 9.5 |
| 460019 | 10 | 32 | 51 | 65 | 87 | 3.1 |
| 460026 | 0 | 34 | 21 | 55 | 65 | 6.4 |
| 460028 | 0 | 14 | 31 | 51 | 77 | 5.2 |
| 460031 | 0 | 31 | 53 | 71 | 88 | 3.2 |
| 460033 | 11 | 8 | 6 | 52 | 84 | 5.0 |
| 460065 | 19 | 37 | 53 | 58 | 74 | 3.6 |
| 460068 | 17 | 11 | 31 | 59 | 69 | 5.5 |
| 460069 | 11 | 21 | 37 | 55 | 75 | 4.6 |
| 460071 | 6 | 42 | 61 | 83 | 88 | 2.6 |
| 460073 | 7 | 13 | 19 | 49 | 66 | 6.3 |

TABLE 22-continued

Dose-dependent antisense inhibition of human HTT in GM02173B cells

| ISIS No. | 750 nM | 1,500 nM | 3,000 nM | 6,000 nM | 12,000 nM | IC$_{50}$ (µM) |
|---|---|---|---|---|---|---|
| 460076 | 27 | 31 | 49 | 43 | 81 | 2.9 |
| 460085 | 17 | 34 | 51 | 54 | 68 | 4.4 |
| 460140 | 0 | 2 | 28 | 18 | 46 | >12.0 |
| 460142 | 2 | 32 | 37 | 42 | 59 | 7.6 |
| 460152 | 17 | 32 | 35 | 51 | 66 | 5.5 |
| 460157 | 9 | 34 | 38 | 52 | 74 | 4.5 |
| 460162 | 22 | 45 | 57 | 65 | 79 | 2.5 |
| 460165 | 5 | 45 | 52 | 72 | 84 | 3.2 |

Example 7

Antisense Inhibition of Human HTT in GM04281 Cells and GM02171 Cells

Additional antisense oligonucleotides were designed based on the gapmers selected from studies described in Example 2. These oligonucleotides were designed by creating gapmers shifted slightly upstream and downstream (i.e. "microwalk") of the original gapmers from Table 4.

The gapmers were tested in the GM04281 and the GM02171 cell lines. Cultured GM04281 or GM02171 cells at a density of 25,000 cells per well were transfected using electroporation with 10,000 nM antisense oligonucleotide. After a treatment period of approximately 24 hours, RNA was isolated from the cells and HTT mRNA levels were measured by quantitative real-time PCR using primer probe set RTS2617. HTT mRNA levels were adjusted according to total RNA content, as measured by RIBOGREEN. Results are presented as percent inhibition of HTT mRNA, relative to untreated control cells.

The gapmers, from which the newly designed oligonucleotides were derived, were also included in the assay. These parent gapmers, ISIS 435294, ISIS 435295, ISIS 435301, ISIS 435303, ISIS 435304, ISIS 435305, ISIS 435308, ISIS 435330, ISIS 435331, ISIS 435337, ISIS 435339, ISIS 435340, ISIS 435341, ISIS 435344, ISIS 435862, ISIS 435863, ISIS 435864, ISIS 435866, ISIS 435867, ISIS 435868, ISIS 435871, ISIS 435873, ISIS 435875, ISIS 435876, ISIS 435878, ISIS 435880, ISIS 435881, ISIS 435882, ISIS 435884, ISIS 435890, and ISIS 435897 are marked with an asterisk (*) in the table. ISIS 387916 was included in the study as a benchmark oligonucleotide against which the potency of the antisense oligonucleotides targeting nucleotides overlapping each SNP position could be compared.

The chimeric antisense oligonucleotides in Tables 23-48 were designed as 5-9-5 MOE gapmers. The 5-9-5 gapmers are 19 nucleotides in length, wherein the central gap segment is comprised of nine 2'-deoxynucleotides and is flanked on both 5' and 3' directions by wings comprising 5 nucleotides each. Each nucleotide in the 5' wing segment and each nucleotide in the 3' wing segment has a 2'-MOE modification. The internucleoside linkages throughout each gapmer are phosphorothioate (P=S) linkages. All cytosine nucleobases throughout each gapmer are 5-methylcytosines.

The gapmers are organized in Tables 23-48, according to the SNP site they target. "Start site" indicates the 5'-most nucleotide to which the gapmer is targeted. "Stop site" indicates the 3'-most nucleotide to which the gapmer is targeted. 'Target allele' indicates whether the gapmer is targeted to the major or the minor allele. The number in parentheses indicates the position on the oligonucleotide opposite to the SNP position.

TABLE 23

Comparison of inhibition of human HTT mRNA levels by ISIS 387916 and chimeric antisense oligonucleotides targeted to SNP rs3856973 (nucleobases 19815 to 19835 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 19815 | 19833 | *435330 | Major (8) | TAACACTCGATTAACCCTG | 88 | 31 | 8 |
| 19816 | 19834 | 476441 | Major (9) | TTAACACTCGATTAACCCT | 88 | 0 | 240 |
| 19817 | 19835 | *435294 | Major (10) | GTTAACACTCGATTAACCC | 72 | 30 | 10 |

TABLE 24

Comparison of inhibition of human HTT mRNA levels by ISIS 387916 and chimeric antisense oligonucleotides targeted to SNP rs2285086 (nucleobases 28901 to 28921 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 28901 | 28919 | 463570 | Major (8) | TAGTTCATCCCAGTGAGAA | 66 | 12 | 241 |
| 28902 | 28920 | 463573 | Major (9) | CTAGTTCATCCCAGTGAGA | 66 | 36 | 242 |
| 28903 | 28921 | *435864 | Major (10) | GCTAGTTCATCCCAGTGAG | 40 | 18 | 12 |

TABLE 25

Comparison of inhibition of human HTT mRNA levels by ISIS 387916 and chimeric antisense oligonucleotides targeted to SNP rs7659144 (nucleobases 37963 to 37983 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 37963 | 37981 | 476462 | Major (8) | GAAATGGGTTTTTCCACAT | 38 | 0 | 243 |
| 37964 | 37982 | 476439 | Major (9) | GGAAATGGGTTTTTCCACA | 80 | 45 | 244 |
| 37965 | 37983 | *435878 | Major (10) | TGGAAATGGGTTTTTCCAC | 76 | 3 | 14 |

TABLE 26

Comparison of inhibition of human HTT mRNA levels by ISIS 387916 and chimeric antisense oligonucleotides targeted to SNP rs16843804 (nucleobases 44032 to 44052 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 44032 | 44050 | 476471 | Major (8) | TAACCGTGGCATGGGCAGT | 82 | 53 | 245 |

TABLE 26-continued

Comparison of inhibition of human HTT mRNA levels by ISIS 387916
and chimeric antisense oligonucleotides targeted to SNP rs16843804
(nucleobases 44032 to 44052 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 44033 | 44051 | 476452 | Major (9) | TTAACCGTGGCATGGGCAG | 84 | 44 | 246 |
| 44034 | 44052 | *435863 | Major (10) | TTTAACCGTGGCATGGGCA | 89 | 89 | 16 |

TABLE 27

Comparison of inhibition of human HTT mRNA levels by ISIS 387916 and
chimeric antisense oligonucleotides targeted to SNP rs2024115
(nucleobases 44210 to 44230 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 44210 | 44228 | *435331 | Major (8) | TTCAAGCTAGTAACGATGC | 84 | 20 | 18 |
| 44211 | 44229 | 476447 | Major (9) | CTTCAAGCTAGTAACGATG | 87 | 57 | 247 |
| 44212 | 44230 | *435295 | Major (10) | ACTTCAAGCTAGTAACGAT | 85 | 67 | 20 |

TABLE 28

Comparison of inhibition of human HTT mRNA levels by ISIS 387916 and
chimeric antisense oligonucleotides targeted to SNP rs10015979
(nucleobases 49084 to 49104 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 49084 | 49102 | 476470 | Major (8) | AGCTAGGTTAAAGAGTCAC | 55 | 74 | 248 |
| 49085 | 49103 | 476450 | Major (9) | CAGCTAGGTTAAAGAGTCA | 44 | 5 | 249 |
| 49086 | 49104 | *435862 | Major (10) | GCAGCTAGGTTAAAGAGTC | 56 | 49 | 22 |

TABLE 29

Comparison of inhibition of human HTT mRNA levels by ISIS 387916 and
chimeric antisense oligonucleotides targeted to SNP rs7691627
(nucleobases 51052 to 51072 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 51052 | 51070 | 476467 | Major (8) | TAAGAAACACAATCAAAGA | 45 | 21 | 250 |

TABLE 29-continued

Comparison of inhibition of human HTT mRNA levels by ISIS 387916 and chimeric antisense oligonucleotides targeted to SNP rs7691627 (nucleobases 51052 to 51072 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 51053 | 51071 | 476445 | Major (9) | ATAAGAAACACAATCAAAG | 34 | 1 | 251 |
| 51054 | 51072 | *435880 | Major (10) | AATAAGAAACACAATCAAA | 68 | 7 | 24 |

TABLE 30

Comparison of inhibition of human HTT mRNA levels by ISIS 387916 and chimeric antisense oligonucleotides targeted to SNP rs6446723 (nucleobases 66455 to 66475 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 66455 | 66473 | 476463 | Major (8) | ATTTTCTAGACTTTATGAT | 37 | 7 | 252 |
| 66456 | 66474 | 476440 | Major (9) | AATTTTCTAGACTTTATGA | 57 | 0 | 253 |
| 66457 | 66475 | *435875 | Major (10) | TAATTTTCTAGACTTTATG | 42 | 0 | 30 |

TABLE 31

Comparison of inhibition of human HTT mRNA levels by ISIS 387916 and a chimeric antisense oligonucleotide targeted to SNP rs363064 (nucleobases 81053 to 81071 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 81053 | 81071 | 476461 | Major (9) | GAGAATACGGGTAACATTT | 87 | 62 | 254 |

TABLE 32

Comparison of inhibition of human HTT mRNA levels by ISIS 387916 and chimeric antisense oligonucleotides targeted to SNP rs11731237 (nucleobases 91455 to 91475 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 91455 | 91473 | 476468 | Major (8) | TGGGCAGGAAGGACTGAAC | 58 | 56 | 255 |
| 91456 | 91474 | 476448 | Major (9) | GTGGGCAGGAAGGACTGAA | 61 | 69 | 256 |
| 91457 | 91475 | *435884 | Major (10) | GGTGGGCAGGAAGGACTGA | 59 | 49 | 68 |

TABLE 33

Comparison of inhibition of human HTT mRNA levels by ISIS 387916 and chimeric antisense oligonucleotides targeted to SNP rs4690073 (nucleobases 99792 to 99812 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 99792 | 99810 | *435337 | Major (8) | CCTAAATCAATCTACAAGT | 69 | 7 | 70 |
| 99793 | 99811 | 476446 | Major (9) | CCCTAAATCAATCTACAAG | 61 | 0 | 257 |
| 99794 | 99812 | *435301 | Major (10) | TCCCTAAATCAATCTACAA | 63 | 1 | 72 |

TABLE 34

Comparison of inhibition of human HTT mRNA levels by ISIS 387916 and chimeric antisense oligonucleotides targeted to SNP rs34315806 (nucleobases 101676 to 101696 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 101676 | 101694 | 463569 | Major (8) | CTTTTCCGTGCTGTTCTGA | 96 | 95 | 258 |
| 101677 | 101695 | 463572 | Major (9) | ACTTTTCCGTGCTGTTCTG | 93 | 91 | 259 |
| 101678 | 101696 | 463567 | Major (10) | AACTTTTCCGTGCTGTTCT | 98 | 97 | 260 |

TABLE 35

Comparison of inhibition of human HTT mRNA levels by ISIS 387916 and chimeric antisense oligonucleotides targeted to SNP rs363099 (nucleobases 101698 to 101718 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 101698 | 101716 | *435339 | Major (8) | CTGAGCGGAGAAACCCTCC | 94 | 85 | 80 |
| 101699 | 101717 | 476458 | Major (9) | GCTGAGCGGAGAAACCCTC | 92 | 79 | 261 |
| 101700 | 101718 | *435303 | Major (10) | GGCTGAGCGGAGAAACCCT | 96 | 93 | 82 |

TABLE 36

Comparison of inhibition of human HTT mRNA levels by ISIS 387916 and chimeric antisense oligonucleotides targeted to SNP rs363096 (nucleobases 119663 to 119683 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 119663 | 119681 | *435340 | Major (8) | TTCCCTAAAAACAAAAACA | 42 | 21 | 85 |

TABLE 36-continued

Comparison of inhibition of human HTT mRNA levels by ISIS 387916 and chimeric antisense oligonucleotides targeted to SNP rs363096 (nucleobases 119663 to 119683 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 119664 | 119682 | 476451 | Major (9) | ATTCCCTAAAAACAAAAC | 0 | 0 | 262 |
| 119665 | 119683 | *435304 | Major (10) | GATTCCCTAAAAACAAAA | 41 | 27 | 87 |

TABLE 37

Comparison of inhibition of human HTT mRNA levels by ISIS 387916 and chimeric antisense oligonucleotides targeted to SNP rs2298967 (nucleobases 125389 to 125409 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 125389 | 125407 | *435341 | Major (8) | CTTTTCTATTGTCTGTCCC | 83 | 65 | 89 |
| 125390 | 125408 | 476459 | Major (9) | GCTTTTCTATTGTCTGTCC | 89 | 82 | 263 |
| 125391 | 125409 | *435305 | Major (10) | TGCTTTTCTATTGTCTGTC | 92 | 85 | 91 |

TABLE 38

Comparison of inhibition of human HTT mRNA levels by ISIS 387916 and a chimeric antisense oligonucleotide targeted to SNP rs2298969 (nucleobases 125888 to 125906 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 125888 | 125906 | *435890 | Minor (10) | AAGGGATGCTGACTTGGGC | 91 | 64 | 94 |

TABLE 39

Comparison of inhibition of human HTT mRNA levels by ISIS 387916 and chimeric antisense oligonucleotides targeted to SNP rs6844859 (nucleobases 130128 to 130148 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 130128 | 130146 | 476466 | Major (8) | CTTCCTCACTGAGGATGAA | 87 | 64 | 264 |
| 130129 | 130147 | 476444 | Major (9) | CCTTCCTCACTGAGGATGA | 92 | 77 | 265 |
| 130130 | 130148 | *435876 | Major (10) | ACCTTCCTCACTGAGGATG | 94 | 87 | 95 |

TABLE 40

Comparison of inhibition of human HTT mRNA levels by ISIS 387916 and chimeric antisense oligonucleotides targeted to SNP rs363092 (nucleobases 135671 to 135691 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 135671 | 135689 | 476464 | Major (8) | AACCACTTTGGGATGAATA | 51 | 71 | 266 |
| 135672 | 135690 | 476442 | Major (9) | AAACCACTTTGGGATGAAT | 58 | 59 | 267 |
| 135673 | 135691 | *435897 | Minor (10) | CAAACCACTTTGGGATGAA | 48 | 78 | 98 |

TABLE 41

Comparison of inhibition of human HTT mRNA levels by ISIS 387916 and chimeric antisense oligonucleotides targeted to SNP rs363088 (nucleobases 149972 to 149992 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 149972 | 149990 | 476476 | Major (8) | ACAGCTATCTTCTCATCAA | 90 | 65 | 268 |
| 149973 | 149991 | 476460 | Major (9) | CACAGCTATCTTCTCATCA | 86 | 39 | 269 |
| 149974 | 149992 | *435871 | Major (10) | TCACAGCTATCTTCTCATC | 91 | 54 | 101 |

TABLE 42

Comparison of inhibition of human HTT mRNA levels by ISIS 387916 and chimeric antisense oligonucleotides targeted to SNP rs916171 (nucleobases 156457 to 156477 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 156457 | 156475 | 476465 | Major (8) | GAACAAAGAGAAGAATTTC | 38 | 0 | 270 |
| 156458 | 156476 | 476443 | Major (9) | AGAACAAAGAGAAGAATTT | 58 | 0 | 271 |
| 156459 | 156477 | *435881 | Major (10) | CAGAACAAAGAGAAGAATT | 59 | 16 | 105 |

TABLE 43

Comparison of inhibition of human HTT mRNA levels by ISIS 387916 and chimeric antisense oligonucleotides targeted to SNP rs362275 (nucleobases 164244 to 164264 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 164244 | 164262 | 476473 | Major (8) | GAAGCCTGATAAAATCTCT | 83 | 51 | 272 |

TABLE 43-continued

Comparison of inhibition of human HTT mRNA levels by ISIS 387916
and chimeric antisense oligonucleotides targeted to SNP rs362275
(nucleobases 164244 to 164264 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 164245 | 164263 | 476454 | Major (9) | AGAAGCCTGATAAAATCTC | 79 | 61 | 273 |
| 164246 | 164264 | *435868 | Major (10) | AAGAAGCCTGATAAAATCT | 69 | 56 | 111 |

TABLE 44

Comparison of inhibition of human HTT mRNA levels by ISIS 387916
and chimeric antisense oligonucleotides targeted to SNP rs362273
(nucleobases 167061 to 167081 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 167061 | 167079 | 463568 | Major (8) | TGATCTGTAGCAGCAGCTT | 96 | 78 | 274 |
| 167062 | 167080 | 463571 | Major (9) | TTGATCTGTAGCAGCAGCT | 95 | 86 | 275 |
| 167063 | 167081 | 463566 | Major (10) | GTTGATCTGTAGCAGCAGC | 94 | 78 | 276 |

TABLE 45

Comparison of inhibition of human HTT mRNA levels by ISIS 387916
and chimeric antisense oligonucleotides targeted to SNP rs362272
(nucleobases 174622 to 174642 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 174622 | 174640 | *435344 | Major (8) | TAGAGGACGCCGTGCAGGG | 78 | 63 | 120 |
| 174623 | 174641 | 476456 | Major (9) | ATAGAGGACGCCGTGCAGG | 87 | 60 | 277 |
| 174624 | 174642 | *435308 | Major (10) | CATAGAGGACGCCGTGCAG | 76 | 48 | 122 |

TABLE 46

Comparison of inhibition of human HTT mRNA levels by ISIS 387916
and chimeric antisense oligonucleotides targeted to SNP rs362271
(nucleobases 175160 to 175180 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 175160 | 175178 | 476472 | Major (8) | GTGTGTACAGAACCTGCCG | 85 | 52 | 278 |

TABLE 46-continued

Comparison of inhibition of human HTT mRNA levels by ISIS 387916
and chimeric antisense oligonucleotides targeted to SNP rs362271
(nucleobases 175160 to 175180 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 175161 | 175179 | 476453 | Major (9) | CGTGTGTACAGAACCTGCC | 88 | 69 | 279 |
| 175162 | 175180 | *435867 | Major (10) | ACGTGTGTACAGAACCTGC | 91 | 80 | 125 |

TABLE 47

Comparison of inhibition of human HTT mRNA levels by ISIS 387916
and chimeric antisense oligonucleotides targeted to SNP rs3775061
(nucleobases 178396 to 178416 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 178396 | 178414 | 476475 | Major (8) | TTCAGAATGCCTCATCTGG | 61 | 1 | 280 |
| 178397 | 178415 | 476457 | Major (9) | GTTCAGAATGCCTCATCTG | 80 | 50 | 281 |
| 178398 | 178416 | *435873 | Major (10) | TGTTCAGAATGCCTCATCT | 80 | 43 | 127 |

TABLE 48

Comparison of inhibition of human HTT mRNA levels by ISIS 387916
and chimeric antisense oligonucleotides targeted to SNP rs362296
(nucleobases 186649 to 1786669 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 186649 | 186667 | 476469 | Major (8) | GGACAGGGTGTGCTCTCCG | 80 | 58 | 282 |
| 186650 | 186668 | 476449 | Major (9) | GGGACAGGGTGTGCTCTCC | 80 | 64 | 283 |
| 186651 | 186669 | *435882 | Major (10) | GGGGACAGGGTGTGCTCTC | 61 | 61 | 155 |

Example 8

Dose-Dependent Antisense Inhibition of Human Huntingtin mRNA Levels in Coriell Fibroblast Cell Lines Gapmers from the studies described in Example 7 were selected and tested at various doses in GM04281, GM02171, and GM02173B cell lines. Each cell line was plated at a density of 25,000 cells per well and transfected using electroporation with 750 nM, 1,500 nM, 3,000 nM, 6,000 nM, and 12,000 nM concentrations of antisense oligonucleotide, as specified in Tables 49, 50, and 51. After a treatment period of approximately 16 hours, RNA was isolated from the cells and HTT mRNA levels were measured by quantitative real-time PCR. Human HTT primer probe set RTS2617 was used to measure mRNA levels. HTT mRNA levels were adjusted according to total RNA content, as measured by RIBOGREEN. Results are presented as percent inhibition of HTT mRNA, relative to untreated control cells. $IC_{50}$ values are also provided in Tables 49, 50, and 51.

TABLE 49

Dose-dependent antisense inhibition of human HTT in GM04281 cells

| ISIS No. | 750 nM | 1500 nM | 3000 nM | 6000 nM | 12000 nM | $IC_{50}$ (μM) |
|---|---|---|---|---|---|---|
| 387916 | 67 | 88 | 95 | 97 | 99 | <0.8 |
| 463566 | 25 | 65 | 79 | 88 | 95 | 1.5 |
| 463567 | 34 | 73 | 90 | 93 | 98 | 1.1 |
| 463568 | 33 | 56 | 75 | 87 | 92 | 1.3 |
| 463571 | 32 | 21 | 70 | 90 | 93 | 1.4 |
| 476441 | 11 | 27 | 50 | 70 | 87 | 3.1 |
| 476444 | 20 | 31 | 68 | 49 | 93 | 2.3 |
| 476449 | 4 | 28 | 34 | 47 | 77 | 4.9 |
| 476453 | 21 | 21 | 48 | 73 | 85 | 2.7 |
| 476455 | 5 | 19 | 34 | 56 | 80 | 4.6 |
| 476458 | 36 | 72 | 83 | 93 | 96 | 1.1 |

TABLE 49-continued

Dose-dependent antisense inhibition of human HTT in GM04281 cells

| ISIS No. | 750 nM | 1500 nM | 3000 nM | 6000 nM | 12000 nM | IC$_{50}$ (µM) |
|---|---|---|---|---|---|---|
| 476459 | 23 | 59 | 75 | 85 | 91 | 1.5 |
| 476469 | 17 | 27 | 47 | 47 | 67 | 5.5 |
| 476473 | 0 | 6 | 32 | 50 | 68 | 6.2 |
| 476476 | 3 | 7 | 32 | 53 | 86 | 4.9 |

TABLE 50

Dose-dependent antisense inhibition of human HTT in GM02171 cells

| ISIS No. | 750 nM | 1500 nM | 3000 nM | 6000 nM | 12000 nM | IC$_{50}$ (µM) |
|---|---|---|---|---|---|---|
| 387916 | 59 | 79 | 93 | 98 | 98 | <0.8 |
| 463566 | 4 | 33 | 42 | 62 | 79 | 3.8 |
| 463567 | 38 | 41 | 69 | 85 | 94 | 1.5 |
| 463568 | 21 | 26 | 41 | 58 | 64 | 4.8 |
| 463571 | 8 | 23 | 56 | 63 | 75 | 3.7 |
| 476441 | 0 | 13 | 7 | 0 | 12 | >12.0 |
| 476444 | 11 | 0 | 0 | 67 | 59 | 8.8 |
| 476449 | 4 | 27 | 37 | 51 | 63 | 5.8 |
| 476453 | 6 | 40 | 40 | 51 | 73 | 4.9 |
| 476455 | 32 | 15 | 18 | 47 | 61 | 7.8 |
| 476458 | 42 | 54 | 71 | 86 | 84 | 1.2 |
| 476459 | 22 | 38 | 70 | 44 | 73 | 4.3 |
| 476469 | 7 | 24 | 30 | 56 | 58 | 7.8 |
| 476473 | 4 | 10 | 15 | 33 | 43 | >12.0 |
| 476476 | 5 | 16 | 18 | 23 | 41 | >12.0 |

TABLE 51

Dose-dependent antisense inhibition of human HTT in GM02171 cells

| ISIS No. | 750 nM | 1500 nM | 3000 nM | 6000 nM | 12000 nM | IC$_{50}$ (µM) |
|---|---|---|---|---|---|---|
| 387916 | 66 | 89 | 95 | 97 | 99 | <0.8 |
| 463566 | 32 | 55 | 76 | 77 | 93 | 1.3 |
| 463567 | 51 | 61 | 87 | 94 | 97 | 0.7 |
| 463568 | 26 | 23 | 72 | 87 | 94 | 1.6 |
| 463571 | 32 | 34 | 60 | 86 | 94 | 1.9 |
| 476441 | 18 | 18 | 27 | 47 | 44 | >12.0 |
| 476444 | 15 | 0 | 31 | 51 | 58 | 7.1 |
| 476449 | 27 | 33 | 56 | 80 | 81 | 2.6 |
| 476453 | 24 | 28 | 55 | 75 | 83 | 2.7 |
| 476455 | 24 | 26 | 52 | 55 | 73 | 3.7 |
| 476458 | 63 | 77 | 87 | 89 | 94 | 0.2 |
| 476459 | 37 | 55 | 56 | 62 | 86 | 1.5 |
| 476469 | 22 | 41 | 40 | 63 | 76 | 2.9 |
| 476473 | 7 | 28 | 33 | 51 | 73 | 5.0 |
| 476476 | 11 | 29 | 26 | 55 | 69 | 4.6 |

Example 9

Antisense Inhibition of Human HTT in GM04281 Cells by Oligonucleotides Designed by Microwalk Additional gapmers were designed based on the gapmers selected from studies described in Example 4. These gapmers were designed by creating gapmers shifted slightly upstream and downstream (i.e. "microwalk") of the original gapmers from Tables 8, 9, and 10. Gapmers were also created with 3-9-3 or 5-9-5 motifs, and with constrained 6(S)—CH$_3$-bicyclic nucleic acid (BNA) molecules at various nucleoside positions.

These gapmers were tested in vitro. Cultured GM04281 cells at a density of 25,000 cells per well were transfected using electroporation with 5,000 nM antisense oligonucleotide. After a treatment period of approximately 24 hours, RNA was isolated from the cells and HTT mRNA levels were measured by quantitative real-time PCR. HTT mRNA levels were adjusted according to total RNA content, as measured by RIBOGREEN. Results are presented as percent inhibition of HTT mRNA, relative to untreated control cells.

The chimeric antisense oligonucleotides in Tables 52-56 were designed as 3-9-3 or 5-9-5 gapmers. The parent gapmers, ISIS 435869, ISIS 435870, ISIS 435874, ISIS 435879, and ISIS 435890, from which the newly designed gapmers were derived are marked with an asterisk (*) in the table. ISIS 387916 was included in the study as a benchmark oligonucleotide against which the potency of the antisense oligonucleotides targeting nucleotides overlapping each SNP position could be compared.

The 3-9-3 gapmers are 15 nucleotides in length, wherein the central gap segment is comprised of nine 2'-deoxynucleosides and is flanked on both 5' and 3' directions by wings comprising 3 sugar modified nucleosides each.

The 5-9-5 gapmers are 19 nucleotides in length, wherein the central gap segment is comprised of nine 2'-deoxynucleosides and is flanked on both 5' and 3' directions by wings comprising 5 sugar modified nucleosides each.

The internucleoside linkages throughout each gapmer are phosphorothioate (P=S) linkages. All cytosine nucleobases throughout each gapmer are 5-methylcytosines. Bolded and underlined nucleotides in Tables 52-56 indicate the positions of the 6(S)—CH$_3$-BNA molecules (e.g. cEt molecules) in each gapmer. Italicized nucleotides are MOE subunits.

"Start site" indicates the 5'-most nucleotide to which the gapmer is targeted. "Stop site" indicates the 3'-most nucleotide to which the gapmer is targeted. 'Target allele' indicates whether the gapmer is targeted to the major or the minor allele. The number in parentheses indicates the position on the oligonucleotide opposite to the SNP position.

TABLE 52

Comparison of inhibition of human HTT mRNA levels by ISIS 387916 and chimeric antisense oligonucleotides targeted to SNP rs4690072 (nucleobases 62147 to 62173 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | *TCTCTATTGCACATTCCAAG* | 5-10-5 | 97 | 6 |
| 62147 | 62165 | Major (6) | 460266 | *GTGCTA*CCCAACCTTTCTG | 5-9-5 | 63 | 169 |
| 62151 | 62169 | Major (10) | *435874 | *CACAGTGCTACCCAACCTT* | 5-9-5 | 50 | 28 |
| 62151 | 62169 | Major (10) | 460213 | *CACAGTGCTA*CCCAACCTT | 5-9-5 | 22 | 28 |

TABLE 52-continued

Comparison of inhibition of human HTT mRNA levels by ISIS 387916 and chimeric antisense oligonucleotides targeted to SNP rs4690072 (nucleobases 62147 to 62173 of SEQ ID NO: 1)

| Start Site | Stop Site | Target allele | ISIS No. | Sequence | Motif | % inhibition | SEQ ID NO |
|---|---|---|---|---|---|---|---|
| 62151 | 62169 | Major (10) | 460220 | CACAGTGCTACCCAACCTT | 5-9-5 | 24 | 28 |
| 62151 | 62169 | Major (10) | 460221 | CACAGTGCTACCCAACCTT | 5-9-5 | 28 | 28 |
| 62153 | 62167 | Major (8) | 460208 | CAGTGCTACCCAACC | 3-9-3 | 81 | 177 |
| 62155 | 62173 | Major (14) | 460267 | ATATCACAGTGCTACCCAA | 5-9-5 | 37 | 180 |

TABLE 53

Comparison of inhibition of human HTT mRNA levels by ISIS 387916 and chimeric antisense oligonucleotides targeted to SNP rs2298969 (nucleobases 125884 to 125910 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 97 | 6 |
| 125884 | 125902 | Minor (6) | 460233 | GATGCTGACTTGGGCCATT | 5-9-5 | 76 | 182 |
| 125888 | 125906 | Minor (10) | *435890 | AAGGGATGCTGACTTGGGC | 5-9-5 | 75 | 94 |
| 125888 | 125906 | Minor (10) | 460215 | AAGGGATGCTGACTTGGGC | 5-9-5 | 26 | 94 |
| 125888 | 125906 | Minor (10) | 460224 | AAGGGATGCTGACTTGGGC | 5-9-5 | 38 | 94 |
| 125888 | 125906 | Minor (10) | 460225 | AAGGGATGCTGACTTGGGC | 5-9-5 | 49 | 94 |
| 125890 | 125904 | Minor (8) | 460210 | GGGATGCTGACTTGG | 3-9-3 | 97 | 189 |
| 125892 | 125910 | Minor (14) | 460229 | TGCCAAGGGATGCTGACTT | 5-9-5 | 60 | 192 |

TABLE 54

Comparison of inhibition of human HTT mRNA levels by ISIS 387916 and chimeric antisense oligonucleotides targeted to SNP rs7685686 (nucleobases 146782 to 146808 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 97 | 6 |
| 146782 | 146800 | Major (6) | 460232 | AATTGTCATCACCAGAAAA | 5-9-5 | 82 | 195 |
| 146786 | 146804 | Major (10) | *435879 | AATAAATTGTCATCACCAG | 5-9-5 | 84 | 99 |
| 146786 | 146804 | Major (10) | 460214 | AATAAATTGTCATCACCAG | 5-9-5 | 33 | 99 |
| 146786 | 146804 | Major (10) | 460222 | AATAAATTGTCATCACCAG | 5-9-5 | 87 | 99 |
| 146786 | 146804 | Major (10) | 460223 | AATAAATTGTCATCACCAG | 5-9-5 | 75 | 99 |
| 146788 | 146802 | Major (8) | 460209 | TAAATTGTCATCACC | 3-9-3 | 96 | 203 |
| 146790 | 146808 | Major (14) | 460228 | TATTAATAAATTGTCATCA | 5-9-5 | 0 | 206 |

TABLE 55

Comparison of inhibition of human HTT mRNA levels by ISIS 387916 and chimeric antisense oligonucleotides targeted to SNP rs362331 (nucleobases 155475 to 155501 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 97 | 6 |
| 155475 | 155493 | Major (6) | 460231 | ACAGTAGATGAGGGAGCAG | 5-9-5 | 88 | 209 |
| 155479 | 155497 | Major (10) | *435870 | GCACACAGTAGATGAGGGA | 5-9-5 | 86 | 103 |
| 155479 | 155497 | Major (10) | 460212 | GCACACAGTAGATGAGGGA | 5-9-5 | 89 | 103 |
| 155479 | 155497 | Major (10) | 460218 | GCACACAGTAGATGAGGGA | 5-9-5 | 90 | 103 |
| 155479 | 155497 | Major (10) | 460219 | GCACACAGTAGATGAGGGA | 5-9-5 | 88 | 103 |
| 155481 | 155495 | Major (8) | 460207 | ACACAGTAGATGAGG | 3-9-3 | 89 | 217 |
| 155483 | 155501 | Major (14) | 460227 | AAGTGCACACAGTAGATGA | 5-9-5 | 45 | 220 |

TABLE 56

Comparison of inhibition of human HTT mRNA levels by ISIS 387916 and chimeric antisense oligonucleotides targeted to SNP rs362306 (nucleobases 181740 to 181766 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 97 | 6 |
| 181740 | 181758 | Major (6) | 460230 | AGCTGCAACCTGGCAACAA | 5-9-5 | 66 | 223 |
| 181744 | 181762 | Major (10) | *435869 | GAGCAGCTGCAACCTGGCA | 5-9-5 | 69 | 149 |
| 181744 | 181762 | Major (10) | 460211 | GAGCAGCTGCAACCTGGCA | 5-9-5 | 22 | 149 |
| 181744 | 181762 | Major (10) | 460216 | GAGCAGCTGCAACCTGGCA | 5-9-5 | 18 | 149 |
| 181744 | 181762 | Major (10) | 460217 | GAGCAGCTGCAACCTGGCA | 5-9-5 | 56 | 149 |
| 181746 | 181760 | Major (8) | 460206 | GCAGCTGCAACCTGG | 3-9-3 | 83 | 231 |
| 181748 | 181766 | Major (14) | 460226 | GCAAGAGCAGCTGCAACCT | 5-9-5 | 51 | 234 |

Example 10

Dose-dependent antisense inhibition of human huntingtin mRNA levels in Coriell Fibroblast Cell Lines Gapmers from studies described in Example 9 were selected and tested at various doses in GM04281, GM02171 and GM02173B cell lines. Each cell line was plated at a density of 25,000 cells per well and transfected using electroporation with 312.5 nM, 625 nM, 1,250 nM, 2,500 nM, 5,000 nM and 10,000 nM concentrations of antisense oligonucleotide, as specified in Tables 75, 58, and 59. After a treatment period of approximately 16 hours, RNA was isolated from the cells and HTT mRNA levels were measured by quantitative real-time PCR. Human HTT primer probe set RTS2617 was used to measure mRNA levels. HTT mRNA levels were adjusted according to total RNA content, as measured by RIBOGREEN. Results are presented as percent inhibition of HTT mRNA, relative to untreated control cells. $IC_{50}$ values are also provided in Tables 57, 58, and 59.

TABLE 57

Dose-dependent antisense inhibition of human HTT in GM04281 cells

| ISIS No. | 312.5 nM | 625 nM | 1,250 nM | 2,500 nM | 5,000 nM | 10,000 nM | $IC_{50}$ (µM) |
|---|---|---|---|---|---|---|---|
| 387916 | 26 | 49 | 68 | 86 | 94 | 97 | 0.7 |
| 435869 | 0 | 0 | 23 | 48 | 62 | 82 | 3.2 |
| 435870 | 15 | 38 | 50 | 65 | 85 | 88 | 1.3 |
| 435874 | 14 | 22 | 32 | 49 | 65 | 73 | 2.7 |
| 435879 | 0 | 17 | 40 | 61 | 83 | 94 | 1.8 |
| 435890 | 5 | 13 | 37 | 56 | 70 | 82 | 2.3 |
| 460206 | 10 | 18 | 37 | 52 | 66 | 85 | 2.3 |
| 460207 | 20 | 27 | 50 | 65 | 80 | 91 | 1.4 |

TABLE 57-continued

Dose-dependent antisense inhibition of human HTT in GM04281 cells

| ISIS No. | 312.5 nM | 625 nM | 1,250 nM | 2,500 nM | 5,000 nM | 10,000 nM | IC$_{50}$ (μM) |
|---|---|---|---|---|---|---|---|
| 460208 | 21 | 34 | 51 | 63 | 70 | 79 | 1.5 |
| 460209 | 52 | 74 | 89 | 94 | 94 | 95 | 0.2 |
| 460210 | 34 | 61 | 84 | 91 | 97 | 98 | 0.5 |
| 460212 | 13 | 31 | 50 | 62 | 75 | 82 | 1.6 |
| 460218 | 14 | 27 | 50 | 63 | 78 | 86 | 1.8 |
| 460219 | 9 | 32 | 42 | 64 | 77 | 87 | 1.6 |
| 460222 | 19 | 21 | 42 | 57 | 73 | 78 | 1.7 |
| 460231 | 12 | 24 | 41 | 57 | 71 | 84 | 1.9 |
| 460233 | 16 | 28 | 59 | 66 | 72 | 74 | 1.8 |
| 460266 | 4 | 17 | 32 | 48 | 60 | 75 | 2.9 |

TABLE 58

Dose-dependent antisense inhibition of human HTT in GM02171 cells

| ISIS No. | 312.5 nM | 625 nM | 1,250 nM | 2,500 nM | 5,000 nM | 10,000 nM | IC$_{50}$ (μM) |
|---|---|---|---|---|---|---|---|
| 387916 | 32 | 56 | 77 | 89 | 95 | 97 | 0.7 |
| 435869 | 0 | 6 | 22 | 40 | 69 | 84 | 2.9 |
| 435870 | 15 | 19 | 32 | 51 | 68 | 77 | 2.4 |
| 435874 | 0 | 5 | 1 | 17 | 17 | 30 | >10.0 |
| 435879 | 0 | 8 | 0 | 16 | 36 | 47 | 15.3 |
| 435890 | 14 | 16 | 19 | 19 | 39 | 57 | 9.3 |
| 460206 | 5 | 13 | 33 | 41 | 68 | 80 | 2.7 |
| 460207 | 13 | 10 | 22 | 22 | 33 | 39 | 45.6 |
| 460208 | 13 | 15 | 11 | 11 | 15 | 53 | 10.8 |
| 460209 | 8 | 27 | 46 | 70 | 80 | 86 | 1.6 |
| 460210 | 19 | 37 | 55 | 75 | 88 | 96 | 1.1 |
| 460212 | 8 | 23 | 30 | 43 | 57 | 74 | 2.2 |
| 460218 | 15 | 26 | 27 | 36 | 52 | 78 | 3.2 |
| 460219 | 16 | 17 | 32 | 44 | 69 | 76 | 2.5 |
| 460222 | 14 | 3 | 0 | 0 | 13 | 0 | >10.0 |
| 460231 | 6 | 8 | 13 | 16 | 33 | 56 | 10.4 |
| 460233 | 27 | 30 | 39 | 46 | 61 | 73 | 2.4 |
| 460266 | 0 | 15 | 20 | 15 | 18 | 34 | >10.0 |

TABLE 59

Dose-dependent antisense inhibition of human HTT in GM02173B cells

| ISIS No. | 312.5 nM | 625 nM | 1,250 nM | 2,500 nM | 5,000 nM | 10,000 nM | IC$_{50}$ (μM) |
|---|---|---|---|---|---|---|---|
| 387916 | 22 | 47 | 76 | 88 | 96 | 98 | 0.7 |
| 435869 | 10 | 0 | 16 | 38 | 59 | 76 | 3.9 |
| 435870 | 22 | 36 | 44 | 58 | 69 | 81 | 2.0 |
| 435874 | 11 | 6 | 25 | 23 | 32 | 42 | >10.0 |
| 435879 | 0 | 9 | 21 | 30 | 52 | 68 | 4.8 |
| 435890 | 12 | 16 | 30 | 31 | 48 | 66 | 4.5 |
| 460206 | 11 | 13 | 18 | 35 | 59 | 74 | 3.5 |
| 460207 | 15 | 25 | 30 | 37 | 42 | 66 | 4.3 |
| 460208 | 5 | 14 | 27 | 32 | 52 | 51 | 9.0 |
| 460209 | 27 | 49 | 61 | 79 | 81 | 74 | 0.8 |
| 460210 | 19 | 40 | 61 | 77 | 89 | 95 | 1.0 |
| 460212 | 0 | 19 | 32 | 32 | 61 | 78 | 2.9 |
| 460218 | 4 | 17 | 26 | 38 | 64 | 82 | 3.0 |
| 460219 | 5 | 6 | 26 | 47 | 68 | 84 | 2.9 |
| 460222 | 13 | 19 | 23 | 30 | 35 | 50 | 16.1 |
| 460231 | 7 | 33 | 25 | 35 | 54 | 77 | 3.7 |
| 460233 | 11 | 20 | 37 | 52 | 68 | 69 | 2.3 |
| 460266 | 12 | 6 | 10 | 21 | 25 | 47 | >10.0 |

Example 11

Dose-Dependent Antisense Inhibition of Human HTT in GM04281 and GM02171 Cells by Oligonucleotides Designed by Microwalk Additional gapmers were designed based on the gapmers selected from studies described in Example 10. These gapmers were designed by creating gapmers shifted slightly upstream and downstream (i.e. "microwalk") of the original gapmers from Tables 57, 58, and 59. Gapmers were also created with 4-9-4 MOE or 5-9-5 MOE motifs, and with constrained 6(S)—CH$_3$-bicyclic nucleic acid (BNA) molecules at various nucleotide positions.

These gapmers were tested in the GM04281 and GM02171 cell lines. Cultured GM04281 or GM02171 cells at a density of 25,000 cells per well were transfected using electroporation with 2,500 nM or 5,000 nM antisense oligonucleotide. After a treatment period of approximately 24 hours, RNA was isolated from the cells and HTT mRNA levels were measured by quantitative real-time PCR. HTT mRNA levels were adjusted according to total RNA content, as measured by RIBOGREEN. Results are presented as percent inhibition of HTT mRNA, relative to untreated control cells.

The chimeric antisense oligonucleotides in Tables 60, 61, and 62 were designed as 3-9-3, 4-9-4, or 5-9-5 MOE gapmers. The parent gapmers, ISIS 435890, ISIS 460210, ISIS 435879, ISIS 460209, ISIS 435870, and ISIS 460207, from which the newly designed gapmers were derived are marked with an asterisk (*) in the table. ISIS 387916 was included in the study as a benchmark oligonucleotide against which the potency of the antisense oligonucleotides targeting nucleotides overlapping each SNP position could be compared.

The 3-9-3 gapmers are 15 nucleotides in length, wherein the central gap segment is comprised of nine 2'-deoxynucleotides and is flanked on both 5' and 3' directions by wings comprising 3 nucleotides each.

The 4-9-4 gapmers are 17 nucleotides in length, wherein the central gap segment is comprised of nine 2'-deoxynucleotides and is flanked on both 5' and 3' directions by wings comprising 4 nucleotides each.

The 5-9-5 gapmers are 19 nucleotides in length, wherein the central gap segment is comprised of nine 2'-deoxynucleotides and is flanked on both 5' and 3' directions by wings comprising 5 nucleotides each.

The internucleoside linkages throughout each gapmer are phosphorothioate (P=S) linkages. All cytosine nucleobases throughout each gapmer are 5-methylcytosines. Bolded and underlined nucleotides in Tables 60, 61, and 62 indicate the positions of the 6(S)—CH$_3$-BNA (e.g. cEt molecules) molecules in each gapmer. Italicized nucleotides are MOE subunits.

The gapmers are organized in Tables 60, 61, and 62, according to the SNP site they target. "Start site" indicates the 5'-most nucleotide to which the gapmer is targeted. "Stop site" indicates the 3'-most nucleotide to which the gapmer is targeted. 'Target allele' indicates whether the gapmer is targeted to the major or the minor allele. The number in parentheses indicates the position on the oligonucleotide opposite to the SNP position.

TABLE 60

Comparison of inhibition of human HTT mRNA levels by ISIS 387916
and chimeric antisense oligonucleotides targeted to SNP rs2298969
(nucleobases 125888 to 125907 of SEQ ID NO: 1)

| Start position | Stop position | ISIS No. | Sequence | Motif | Concentration (nM) | % inhibition in GM04281 | % inhibition in GM02171 | SEQ ID NO |
|---|---|---|---|---|---|---|---|---|
| 145466 | 145485 | 387916 | TCTCTATTGCACATTCCAAG | 5-10-5 | 5000 | 57 | 24 | 6 |
| 125888 | 125907 | *435890 | AAGGGATGCTGACTTGGGC | 5-9-5 | 2500 | 22 | 0 | 94 |
|  |  |  |  |  | 5000 | 41 | 23 |  |
| 125890 | 125904 | *460210 | GGGATGCTGACTTGG | 3-9-3 | 2500 | 59 | 24 | 189 |
|  |  |  |  |  | 5000 | 81 | 33 |  |
| 125889 | 125905 | 474870 | AGGGATGCTGACTTGGG | 4-9-4 | 2500 | 23 | 3 | 187 |
|  |  |  |  |  | 5000 | 44 | 34 |  |
| 125889 | 125905 | 474890 | AGGGATGCTGACTTGGG | 4-9-4 | 2500 | 38 | 6 | 187 |
|  |  |  |  |  | 5000 | 49 | 25 |  |
| 125889 | 125905 | 474910 | AGGGATGCTGACTTGGG | 4-9-4 | 2500 | 34 | 8 | 187 |
|  |  |  |  |  | 5000 | 49 | 41 |  |
| 125889 | 125905 | 474914 | AGGGATGCTGACTTGGG | 4-9-4 | 2500 | 44 | 14 | 187 |
|  |  |  |  |  | 5000 | 44 | 21 |  |
| 125888 | 125907 | 474918 | AAGGGATGCTGACTTGGGC | 5-9-5 | 2500 | 31 | 0 | 94 |
|  |  |  |  |  | 5000 | 26 | 25 |  |
| 125888 | 125907 | 474922 | AAGGGATGCTGACTTGGGC | 5-9-5 | 2500 | 33 | 14 | 94 |
|  |  |  |  |  | 5000 | 65 | 24 |  |
| 125889 | 125905 | 476332 | AGGGATGCTGACTTGGG | 4-9-4 | 2500 | 23 | 13 | 187 |
|  |  |  |  |  | 5000 | 51 | 42 |  |
| 125888 | 125907 | 476336 | AAGGGATGCTGACTTGGGC | 5-9-5 | 2500 | 5 | 0 | 94 |
|  |  |  |  |  | 5000 | 43 | 9 |  |

TABLE 61

Comparison of inhibition of human HTT mRNA levels by ISIS 387916
and chimeric antisense oligonucleotides targeted to SNP rs7685686
(nucleobases 146786 to 146805 of SEQ ID NO: 1)

| Start position | Stop position | ISIS No. | Sequence | Motif | Concentration (nM) | % inhibition in GM04281 | % inhibition in GM02171 | SEQ ID NO |
|---|---|---|---|---|---|---|---|---|
| 145466 | 145485 | 387916 | TCTCTATTGCACATTCCAAG | 5-10-5 | 5000 | 57 | 24 | 6 |
| 146786 | 146805 | *435879 | AATAAATTGTCATCACCAG | 5-9-5 | 2500 | 39 | 0 | 99 |
|  |  |  |  |  | 5000 | 59 | 19 |  |
| 146788 | 146802 | *460209 | TAAATTGTCATCACC | 3-9-3 | 2500 | 3 | 0 | 203 |
|  |  |  |  |  | 5000 | 13 | 5 |  |
| 146787 | 146803 | 474871 | ATAAATTGTCATCACCA | 4-9-4 | 2500 | 82 | 32 | 200 |
|  |  |  |  |  | 5000 | 83 | 58 |  |
| 146787 | 146803 | 474891 | ATAAATTGTCATCACCA | 4-9-4 | 2500 | 84 | 29 | 200 |
|  |  |  |  |  | 5000 | 89 | 56 |  |
| 146787 | 146803 | 474911 | ATAAATTGTCATCACCA | 4-9-4 | 2500 | 70 | 18 | 200 |
|  |  |  |  |  | 5000 | 83 | 40 |  |
| 146787 | 146803 | 474915 | ATAAATTGTCATCACCA | 4-9-4 | 2500 | 38 | 9 | 200 |
|  |  |  |  |  | 5000 | 74 | 14 |  |
| 146786 | 146805 | 474919 | AATAAATTGTCATCACCAG | 5-9-5 | 2500 | 80 | 7 | 99 |
|  |  |  |  |  | 5000 | 84 | 37 |  |

TABLE 61-continued

Comparison of inhibition of human HTT mRNA levels by ISIS 387916 and chimeric antisense oligonucleotides targeted to SNP rs7685686 (nucleobases 146786 to 146805 of SEQ ID NO: 1)

| Start position | Stop position | ISIS No. | Sequence | Motif | Concentration (nM) | % inhibition in GM04281 | % inhibition in GM02171 | SEQ ID NO |
|---|---|---|---|---|---|---|---|---|
| 146786 | 146805 | 474923 | AATAAATTGTC ATCACCAG | 5-9-5 | 2500<br>5000 | 74<br>83 | 32<br>51 | 99 |
| 146787 | 146803 | 476333 | ATAAATTGTCA TCACCA | 4-9-4 | 2500<br>5000 | 75<br>86 | 28<br>21 | 200 |
| 146786 | 146805 | 476337 | AATAAATTGTC ATCACCAG | 5-9-5 | 2500<br>5000 | 71<br>83 | 6<br>31 | 99 |

TABLE 62

Comparison of inhibition of human HTT mRNA levels by ISIS 387916 and chimeric antisense oligonucleotides targeted to SNP rs362331 (nucleobases 155478 to 155498 of SEQ ID NO: 1)

| Start position | Stop position | ISIS No. | Sequence | Motif | Concentration (nM) | % inhibition in GM04281 | % inhibition in GM02171 | SEQ ID NO |
|---|---|---|---|---|---|---|---|---|
| 145466 | 145485 | 387916 | TCTCTATTGCAC ATTCCAAG | 5-10-5 | 5000 | 57 | 24 | 6 |
| 155479 | 155498 | *435870 | *GCACACAGTAG ATGAGGGA* | 5-9-5 | 2500<br>5000 | 19<br>49 | 1<br>34 | 103 |
| 155481 | 155495 | *460207 | *ACACAGTAGAT GAGG* | 3-9-3 | 2500<br>5000 | 0<br>7 | 0<br>8 | 217 |
| 155480 | 155496 | 474872 | CACACAGTAGA TGAGGG | 4-9-4 | 2500<br>5000 | 35<br>63 | 9<br>37 | 214 |
| 155480 | 155496 | 474892 | CACACAGTAGA TGAGGG | 4-9-4 | 2500<br>5000 | 43<br>69 | 16<br>31 | 214 |
| 155480 | 155496 | 474912 | CACACAGTAGA TGAGGG | 4-9-4 | 2500<br>5000 | 16<br>36 | 9<br>6 | 214 |
| 155480 | 155496 | 474916 | CACACAGTAGA TGAGGG | 4-9-4 | 2500<br>5000 | 22<br>47 | 5<br>7 | 214 |
| 155479 | 155498 | 474920 | GCACACAGTAG ATGAGGGA | 5-9-5 | 2500<br>5000 | 19<br>43 | 0<br>23 | 103 |
| 155479 | 155498 | 474924 | GCACACAGTAG ATGAGGGA | 5-9-5 | 2500<br>5000 | 29<br>48 | 8<br>22 | 103 |
| 155480 | 155496 | 476334 | CACACAGTAGA TGAGGG | 4-9-4 | 2500<br>5000 | 35<br>62 | 7<br>32 | 214 |
| 155479 | 155498 | 476338 | GCACACAGTAG ATGAGGA | 5-9-5 | 2500<br>5000 | 26<br>40 | 9<br>4 | 103 |
| 155479 | 155495 | 474873 | ACACAGTAGAT GAGGGA | 4-9-4 | 2500<br>5000 | 53<br>61 | 9<br>29 | 285 |
| 155479 | 155495 | 474893 | ACACAGTAGAT GAGGGA | 4-9-4 | 2500<br>5000 | 47<br>59 | 5<br>30 | 285 |
| 155479 | 155495 | 474913 | ACACAGTAGAT GAGGGA | 4-9-4 | 2500<br>5000 | 30<br>29 | 16<br>17 | 285 |
| 155479 | 155495 | 474917 | ACACAGTAGAT GAGGGA | 4-9-4 | 2500<br>5000 | 23<br>40 | 12<br>5 | 285 |
| 155478 | 155497 | 474921 | CACACAGTAGA TGAGGGAG | 5-9-5 | 2500<br>5000 | 28<br>43 | 0<br>23 | 212 |

TABLE 62-continued

Comparison of inhibition of human HTT mRNA levels by ISIS 387916
and chimeric antisense oligonucleotides targeted to SNP rs362331
(nucleobases 155478 to 155498 of SEQ ID NO: 1)

| Start position | Stop position | ISIS No. | Sequence | Motif | Concentration (nM) | % inhibition in GM04281 | % inhibition in GM02171 | SEQ ID NO |
|---|---|---|---|---|---|---|---|---|
| 155478 | 155497 | 474925 | CACACAGTAGA TGAGGGAG | 5-9-5 | 2500 5000 | 30 61 | 9 34 | 212 |
| 155479 | 155495 | 476335 | ACACAGTAGAT GAGGGA | 4-9-4 | 2500 5000 | 35 53 | 2 31 | 285 |
| 155478 | 155497 | 476339 | CACACAGTAGA TGAGGGAG | 5-9-5 | 2500 5000 | 15 34 | 0 13 | 212 |

Example 12

Dose-Dependent Antisense Inhibition of Human Huntingtin mRNA Levels in Coriell Fibroblast Cell Lines Gapmers from the studies described in Example 11 were selected and tested at various doses in GM04281, GM02171 and GM02173B cell lines. Each cell line was plated at a density of 25,000 cells per well and transfected using electroporation with 625 nM, 1,250 nM, 2,500 nM, 5,000 nM and 10,000 nM concentrations of antisense oligonucleotide, as specified in Tables 63, 64, and 65. After a treatment period of approximately 16 hours, RNA was isolated from the cells and HTT mRNA levels were measured by quantitative real-time PCR. Human HTT primer probe set RTS2617 was used to measure mRNA levels. HTT mRNA levels were adjusted according to total RNA content, as measured by RIBOGREEN. Results are presented as percent inhibition of HTT mRNA, relative to untreated control cells. $IC_{50}$ values are also provided in Tables 63, 64, and 65.

TABLE 63

Dose-dependent antisense inhibition of human HTT in GM04281 cells

| ISIS No | 625 nM | 1250 nM | 2500 nM | 5000 nM | 10000 nM | $IC_{50}$ (µM) |
|---|---|---|---|---|---|---|
| 387916 | 70 | 83 | 94 | 96 | 98 | <0.6 |
| 460207 | 51 | 63 | 83 | 91 | 93 | 0.5 |
| 460209 | 83 | 93 | 96 | 97 | 97 | <0.6 |
| 460210 | 70 | 89 | 94 | 97 | 98 | 0.6 |
| 474871 | 94 | 97 | 96 | 96 | 95 | <0.6 |
| 474873 | 51 | 73 | 89 | 94 | 95 | 0.5 |
| 474891 | 93 | 95 | 97 | 96 | 95 | <0.6 |
| 474892 | 48 | 72 | 89 | 93 | 95 | 0.6 |
| 474911 | 85 | 92 | 96 | 95 | 94 | <0.6 |
| 474919 | 89 | 94 | 95 | 94 | 96 | <0.6 |
| 474922 | 21 | 47 | 73 | 86 | 96 | 1.5 |
| 474923 | 86 | 94 | 96 | 95 | 94 | <0.6 |
| 476333 | 92 | 94 | 95 | 95 | 96 | <0.6 |
| 476334 | 45 | 70 | 87 | 92 | 95 | 0.6 |
| 476337 | 83 | 92 | 95 | 96 | 96 | <0.6 |

TABLE 64

Dose-dependent antisense inhibition of human HTT in GM02171 cells

| ISIS No | 625 nM | 1250 nM | 2500 nM | 5000 nM | 10000 nM | $IC_{50}$ (µM) |
|---|---|---|---|---|---|---|
| 387916 | 28 | 38 | 63 | 82 | 99 | 1.6 |
| 460207 | 16 | 0 | 20 | 22 | 55 | 10.0 |
| 460209 | 27 | 50 | 61 | 87 | 94 | 9.9 |
| 460210 | 34 | 60 | 80 | 86 | 97 | 0.9 |
| 474871 | 62 | 74 | 84 | 87 | 90 | 0.1 |
| 474873 | 13 | 29 | 61 | 77 | 89 | 2.2 |
| 474891 | 57 | 72 | 80 | 83 | 88 | 0.2 |
| 474892 | 23 | 26 | 51 | 68 | 81 | 2.5 |
| 474911 | 47 | 58 | 68 | 72 | 82 | 0.7 |
| 474919 | 44 | 48 | 65 | 71 | 83 | 1.1 |
| 474922 | 15 | 27 | 49 | 74 | 79 | 2.6 |
| 474923 | 27 | 53 | 74 | 79 | 84 | 1.5 |
| 476333 | 42 | 53 | 75 | 76 | 84 | 1.0 |
| 476334 | 20 | 23 | 58 | 71 | 87 | 2.3 |
| 476337 | 23 | 34 | 60 | 62 | 75 | 2.7 |

TABLE 65

Dose-dependent antisense inhibition of human HTT in GM02173B cells

| ISIS No | 625 nM | 1250 nM | 2500 nM | 5000 nM | 10000 nM | $IC_{50}$ (µM) |
|---|---|---|---|---|---|---|
| 387916 | 38 | 75 | 89 | 95 | 99 | 0.9 |
| 460207 | 13 | 27 | 52 | 46 | 63 | 6.5 |
| 460209 | 79 | 68 | 84 | 90 | 92 | <0.6 |
| 460210 | 37 | 62 | 79 | 92 | 97 | 0.9 |
| 474871 | 74 | 83 | 87 | 92 | 89 | <0.6 |
| 474873 | 22 | 32 | 67 | 72 | 92 | 1.9 |
| 474891 | 69 | 78 | 84 | 89 | 89 | <0.6 |
| 474892 | 26 | 50 | 75 | 83 | 91 | 1.3 |
| 474911 | 50 | 66 | 76 | 86 | 86 | 0.6 |
| 474919 | 57 | 67 | 74 | 87 | 82 | <0.6 |
| 474922 | 15 | 32 | 61 | 71 | 90 | 2.2 |
| 474923 | 49 | 67 | 78 | 83 | 85 | 0.5 |
| 476333 | 58 | 71 | 78 | 87 | 89 | <0.6 |
| 476334 | 20 | 42 | 63 | 76 | 91 | 1.8 |
| 476337 | 48 | 63 | 71 | 79 | 80 | 0.6 |

Example 13

Strategy for Selection of Antisense Oligonucleotides Based on Potency and Selectivity Gapmers from each of the studies described above were selected for further analysis based on potency and selectivity.

Potency was based on the percent inhibition of HTT mRNA achieved by the antisense oligonucleotides targeting a SNP compared to the percent inhibition of HTT mRNA achieved by the benchmark oligonucleotide, ISIS 387916.

Selectivity was based on the ability of the antisense oligonucleotides targeting a SNP to inhibit expression of the major allele and not of the minor allele. The usage of the three cell lines with different genotypes at each SNP position facilitated this process.

ISIS 460065 (5'-ATAAATTGTCATCACCAG-3' (SEQ ID NO: 199)) is a 4-9-5 MOE gapmer targeted to SNP rs7685686 (major allele A, minor allele G) at position 9 of the oligonucleotide. The GM04281 cell line is homozygous AA at SNP position rs7685686. The GM02173B cell line is heterozygous AG at SNP position rs7685686. The GM02171 cell line is homozygous GG at SNP position rs7685686. Therefore, selectivity is shown if ISIS 460065 causes potent inhibition of HTT mRNA in GM04281, less potent inhibition of HTT mRNA in GM02173, and little to no significant inhibition of HTT mRNA in GM02171. $IC_{50}$ values taken from Table 20, 21, and 22, and presented below in Table 66, confirm varying degrees of inhibition in the three cell lines, wherein expression was most reduced in the homozygous AA cell line, moderately reduced in the heterozygous AG cell line, and less reduced in the homozygous GG cell line. $IC_{50}$ is the concentration of antisense oligonucleotide required for 50 percent inhibition HTT mRNA. IC50 values are in μM.

TABLE 66

Genotype of the Coriell cell lines for SNP rs7685686 and comparison of inhibition of HTT mRNA by ISIS 460065 in each cell line

|  | GM04281 | GM02173B | GM02171 |
| --- | --- | --- | --- |
| Genotype | AA | AG | GG |
| $IC_{50}$ with ISIS 460065 | 1.1 | 3.6 | 10.3 |

ISIS 459978 (5'-ACAGTGCTACCCAACCT-3' (SEQ ID NO: 174)) is a 2-9-6 MOE gapmer targeted to SNP rs4690072 (major allele T, minor allele G) at position 9 of the oligonucleotide. The GM04281 cell line is homozygous TT at SNP position rs4690072. The GM02173B cell line is heterozygous TG at SNP position rs4690072. The GM02171 cell line is homozygous GG at SNP position rs4690072. Therefore, selectivity is shown if ISIS 459978 causes potent inhibition of HTT mRNA in GM04281, less potent inhibition of HIT mRNA in GM02173, and little to no significant inhibition of HTT mRNA in GM02171. $IC_{50}$ values taken from Table 20, 21, and 22, and presented below in Table 67, confirm varying degrees of inhibition in the three cell lines, wherein expression was most reduced in the homozygous TT cell line, moderately reduced in the heterozygous TG cell line, and less reduced in the homozygous GG cell line. $IC_{50}$ is the concentration of antisense oligonucleotide required for 50 percent inhibition HTT mRNA. IC50 values are in μM.

TABLE 67

Genotype of the Coriell cell lines for SNP rs4690072 and comparison of inhibition of HTT mRNA by ISIS 459978 in each cell line

|  | GM04281 | GM02173B | GM02171 |
| --- | --- | --- | --- |
| Genotype | TT | TG | GG |
| $IC_{50}$ with ISIS 459978 | 2.5 | 8.4 | 12.7 |

ISIS 460028 (5'-GAGCAGCTGCAACCTGGCA-3' (SEQ ID NO: 149)) is a 4-11-4 MOE gapmer targeted to SNP rs362306 (major allele G, minor allele A) at position 10 of the oligonucleotide. The GM04281 cell line is homozygous GG at SNP position rs362306. The GM02173B and GM02171 cell lines are heterozygous GA at SNP position rs362306. Therefore, selectivity is shown if ISIS 460028 causes potent inhibition of HTT mRNA in GM04281 and less potent inhibition of HTT mRNA in GM02173 and GM02171. $IC_{50}$ values taken from Table 20, 21, and 22, and presented below in Table 68, confirm varying degrees of inhibition between the GM04281 cell line and the GM02173B and GM02171 cell lines, wherein expression was most reduced in the homozygous GG cell line and less reduced in the heterozygous AG cell line. IC50 is the concentration of antisense oligonucleotide required for 50 percent inhibition HTT mRNA. IC50 values are in μM.

TABLE 68

Genotype of the Coriell cell lines for SNP rs362306 and comparison of inhibition of HTT mRNA by ISIS 460028 in each cell line

|  | GM04281 | GM02173B | GM02171 |
| --- | --- | --- | --- |
| Genotype | GG | AG | AG |
| $IC_{50}$ with ISIS 460028 | 1.4 | 5.2 | 5.3 |

Example 14

Strategy for Selection of Antisense Oligonucleotides with cEt Motifs Based on Potency and Selectivity Gapmers from each of the studies described above were selected for further analysis based on potency and selectivity.

Potency was based on the percent inhibition of HTT mRNA achieved by the antisense oligonucleotides targeting a SNP compared to the percent inhibition of HTT mRNA achieved by the benchmark oligonucleotide, ISIS 387916.

Selectivity was based on the ability of the antisense oligonucleotides targeting a SNP to inhibit expression of the major allele and not of the minor allele. The usage of the three cell lines with different genotypes at each SNP position facilitated this process.

ISIS 460209 (5'-TAAATTGTCATCACC-3' (SEQ ID NO: 203)) is a 3-9-3 gapmer with cEt subunits at positions 2, 3, 13, and 14, targeted to SNP rs7685686 (major allele A, minor allele G) at position 8 of the oligonucleotide. The GM04281 cell line is homozygous AA at SNP position rs7685686. The GM02173B cell line is heterozygous AG at SNP position rs7685686. The GM02171 cell line is homozygous GG at SNP position rs7685686. Therefore, selectivity is shown if ISIS 460209 causes potent inhibition of HTT mRNA in GM04281, less potent inhibition of HTT mRNA in GM02173, and little to no significant inhibition of HTT mRNA in GM02171. $IC_{50}$ values taken from Table 57, 58, and 59, and presented below in Table 69, confirm varying degrees of inhibition in the three cell lines, wherein expression was most reduced in the homozygous AA cell line, moderately reduced in the heterozygous AG cell line, and less reduced in the homozygous GG cell line. $IC_{50}$ is the concentration of antisense oligonucleotide required for 50 percent inhibition HTT mRNA. $IC_{50}$ values are in μM.

TABLE 69

Genotype of the Coriell cell lines for SNP rs7685686 and comparison of inhibition of HTT mRNA by ISIS 460209 in each cell line

|  | GM04281 | GM02173B | GM02171 |
|---|---|---|---|
| Genotype | AA | AG | GG |
| $IC_{50}$ with ISIS 460209 | 0.2 | 0.8 | 1.6 |

ISIS 460208 (5'-CAGTGCTACCCAACC-3' (SEQ ID NO: 177)) is a 3-9-3 gapmer with cEt subunits at positions 2, 3, 13, and 14, targeted to SNP rs4690072 (major allele T, minor allele G) at position 8 of the oligonucleotide. The GM04281 cell line is homozygous TT at SNP position rs4690072. The GM02173B cell line is heterozygous TG at SNP position rs4690072. The GM02171 cell line is homozygous GG at SNP position rs4690072. Therefore, selectivity is shown if ISIS 460208 causes potent inhibition of HTT mRNA in GM04281, less potent inhibition of HTT mRNA in GM02173, and little to no significant inhibition of HTT mRNA in GM02171. $IC_{50}$ values taken from Table 57, 58, and 59, and presented below in Table 70, confirm varying degrees of inhibition in the three cell lines, wherein expression was most reduced in the homozygous TT cell line, moderately reduced in the heterozygous TG cell line, and less reduced in the homozygous GG cell line. $IC_{50}$ is the concentration of antisense oligonucleotide required for 50 percent inhibition HTT mRNA. $IC_{50}$ values are in µM.

TABLE 70

Genotype of the Coriell cell lines for SNP rs4690072 and comparison of inhibition of HTT mRNA by ISIS 460208 in each cell line

|  | GM04281 | GM02173B | GM02171 |
|---|---|---|---|
| Genotype | TT | TG | GG |
| $IC_{50}$ with ISIS 460208 | 1.5 | 9.0 | 10.8 |

ISIS 460206 (5'-GCAGCTGCAACCTGG-3' (SEQ ID NO: 231)) is a 3-9-3 gapmer with cEt subunits at positions 2, 3, 13, and 14, targeted to SNP rs362306 (major allele G, minor allele A) at position 8 of the oligonucleotide. The GM04281 cell line is homozygous GG at SNP position rs362306. The GM02173B and GM02171 cell lines are heterozygous GA at SNP position rs362306. Therefore, selectivity is shown if ISIS 460206 causes potent inhibition of HTT mRNA in GM04281 and less potent inhibition of HTT mRNA in GM02173 and GM02171. $IC_{50}$ values taken from Table 57, 58, and 59, and presented below in Table 71, confirm varying degrees of inhibition between the GM04281 cell line and the GM02173B and GM02171 cell lines, wherein expression was most reduced in the homozygous GG cell line and less reduced in the heterozygous AG cell line. $IC_{50}$ is the concentration of antisense oligonucleotide required for 50 percent inhibition HTT mRNA. $IC_{50}$ values are in µM.

TABLE 71

Genotype of the Coriell cell lines for SNP rs362306 and comparison of inhibition of HTT mRNA by ISIS 460206 in each cell line

|  | GM04281 | GM02173B | GM02171 |
|---|---|---|---|
| Genotype | GG | AG | AG |
| $IC_{50}$ with ISIS 460206 | 2.3 | 2.7 | 2.7 |

Example 15

Comparison of SNPs in Various Cell Lines and Mouse Models Associated with Huntington's Disease The genotype at various SNP positions associated with Huntington's disease was compared amongst the three Corriell cell lines, used in the above Examples, as well as with the GM04022 fibroblast, the BACHD mouse model and the YAC18 mouse model.

The donor patient of the GM04022 fibroblast cell line was heterozygous at SNP position rs363125 (NCBI Entrez SNP database), harboring an A allele (adenine) and a C allele (cytosine) at nucleotide 5310 of SEQ ID NO: 2 (van Bilsen, P. H. J. et al., Human Gene Therapy. 19: 710-718, 2008). YAC18 mice were developed with a YAC transgene containing human huntingtin gene (Hodgson, et al. Hum. Mol. Genet. 5: 1875-85, 1996). BACHD mice were developed expressing a full-length mutant huntingtin gene with 97 glutamine repeats under the control of a bacterial artificial chromosome (Gray, M. et al., J. Neurosc. 28: 6182-95, 2008). The comparative genotype at the indicated SNP positions in all four cell lines and mouse models is presented in Table 72.

TABLE 72

Genotypes of the Coriell cell lines and Huntington mouse models

| SNP | GM02171 | GM02173 | GM04281 | GM04022 | BACHD | YAC18 |
|---|---|---|---|---|---|---|
| rs3856973 | AA | AG | GG | AG | GG | AA |
| rs2285086 | GG | AG | AA | AG | AA | GG |
| rs7659144 | CG | CG | CC | CG | CC | GG |
| rs16843804 | TC | TC | CC | CC | CC | TT |
| rs2024115 | GG | AG | AA | AG | AA | GG |
| rs3733217 | CC | CC | CC | CC | CC | CC |
| rs10015979 | AA | AG | GG | AA | AA | AA |
| rs7691627 | AA | AG | GG | AG | GG | AA |
| rs2798235 | GG | GG | GG | AG | GG | GG |
| rs4690072 | GG | TG | TT | TG | TT | GG |

TABLE 72-continued

Genotypes of the Coriell cell lines and Huntington mouse models

| SNP | GM02171 | GM02173 | GM04281 | GM04022 | BACHD | YAC18 |
|---|---|---|---|---|---|---|
| rs6446723 | CC | TC | TT | TC | TT | CC |
| rs363081 | GG | GG | GG | GG | GG | GG |
| rs363080 | CC | CC | CC | TC | CC | CC |
| rs363075 | GG | GG | GG | GG | GG | GG |
| rs363064 | TC | TC | CC | CC | CC | TT |
| rs3025849 | AA | AA | AA | AA | AA | AA |
| rs363102 | AA | AA | AA | AG | AA | AA |
| rs11731237 | CC | TC | TT | CC | CC | CC |
| rs4690073 | AA | AG | GG | AG | GG | AA |
| rs363144 | TT | TT | TT | TT | TT | TT |
| rs3025838 | CC | CC | CC | CC | CC | CC |
| rs34315806 | TC | TC | CC | CC | CC | TT |
| rs363099 | TC | TC | CC | CC | CC | TT |
| rs363096 | CC | TC | TT | CC | TT | CC |
| rs2298967 | TC | TC | TT | TT | TT | CC |
| rs2298969 | GG | AG | AA | AG | AA | GG |
| rs6844859 | CC | TC | TT | TC | TT | CC |
| rs363092 | AA | AC | CC | AC | AA | AA |
| rs7685686 | GG | AG | AA | AG | AA | GG |
| rs363088 | TA | TA | AA | AA | AA | TT |
| rs362331 | CC | TC | TT | TC | TT | CC |
| rs916171 | GG | GC | CC | GC | CC | GG |
| rs362322 | AA | AA | AA | AA | AA | AA |
| rs362275 | TC | TC | CC | CC | CC | TT |
| rs362273 | AG | AG | AA | AA | AA | GG |
| rs2276881 | GG | GG | GG | GG | GG | GG |
| rs3121419 | TC | TC | CC | CC | CC | TT |
| rs362272 | — | AG | GG | GG | GG | AA |
| rs362271 | AG | AG | GG | GG | GG | AA |
| rs3775061 | AG | AG | AA | AA | AA | GG |
| rs362310 | TC | CC | CC | TC | CC | CC |
| rs362307 | CC | TC | CC | CC | CC | CC |
| rs362306 | AG | AG | GG | GG | GG | AA |
| rs362303 | TC | CC | CC | TC | CC | CC |
| rs362296 | AC | AC | AC | CC | CC | AA |

Example 16

Allele-Specific Inhibition Measured in BacHD Cortical Neurons

Antisense oligonucleotides, ISIS 460209 (5'-TAAATTGT-CATCACC-3' (SEQ ID NO: 203)), targeting SNP rs7685686 of human HTT, and ISIS 387916 (TCTCTATTGCACATTC-CAAG (SEQ ID NO: 6)), and with no human or murine SNP target site, were tested for their effect on Htt protein levels in vitro. ISIS 387916 is cross-reactive with murine Htt mRNA (GENBANK Accession No. NM_010414.1, designated herein as SEQ ID NO: 286) at target start site 5763 with one mismatch. ISIS 460209 is cross-reactive with murine Htt mRNA at target start site 6866 with three mismatches.

Primary BacHD cortical neurons, which express human Htt and murine Htt, were isolated in the following way: Embryos were dissected from E15.5-E17.5 pregnant females. Cortices were dissected into ice-cold divalent-free Hank's Balanced Salt Solution (Invitrogen, 14025-134). The cortices were chopped into pieces and digested with 0.05% Trypsin-EDTA (Invitrogen, 25300-120) at 37° C. for 8 minutes. The digestion was halted by addition of complete neurobasal media (Invitrogen, 10888-022). Cells were resuspended in media and treated with DNAse I (Invitrogen, 18047-019). After titration through a 100 ul pipette tip, cells are resuspended in neurobasal media with B27 supplement (Invitrogen, 17504-044), and counted. $1.7 \times 10^5$ cells/well were plated in 24-well plates precoated with poly-D-lysine (BD Biosciences, 354210). Neurons were fed with 200 pa neurobasal media with B27 on the second day in vitro.

ISIS 460209 or ISIS 387916 was added to the supplementary media fed to neurons on division 2 at 0.7 µM, 1.4 µM or 1.5 µM final concentrations. Cells were harvested after 8 days with into 1 mL of media using a cell scraper. Cells were centrifuged at 2,500 rpm for 5 min at 4° C. and the pellets were resuspended in a buffer of 50 mM Tris, pH=8.0, 150 mM NaCl, 1% Igepal, 40 mM β-glycerophosphate, 10 mM NaF, 1× Roche complete protease inhibitor, 1 mM Sodium Orthovanadate and 800 µM PMSF. The lysates were centrifuged after 15 mM incubation and protein concentration was measured with the DC assay (BioRad).

Protein lysates were run on low-bis gels to separate huntingtin alleles (resolving gel—2001:Acrylamide:BIS (10% acrylamide, 0.5% BIS, 375 mMTris pH 8.8; stacking gel—4% Acrylamide-BIS(29:1), 156 mM Tris pH6.8; Running buffer—25 mM Tris, 190 mM Glycine, 0.1% SDS+10 µM beta-mercaptoethanol added fresh). After electrophoresis, proteins in the gel were transferred to a nitrocellulose membrane (Hybond-C Extra; GE Healthcare Bio-Sciences) at 90V for 40' to allow samples to penetrate the stacking gel and then at 190V for 2.5 h to resolve proteins.

Primary antibodies specific for human Htt and murine calnexin protein were used at 1:10,000 dilutions. HRP-conjugated anti-mouse secondary antibody (1:10,000, Jackson ImmunoResearch Laboratories) was used for visualizing proteins using SuperSignal West Pico Chemiluminescent Substrate (Thermo Scientific). Protein bands were quantified using ImageJ software and normalized to calnexin levels. Protein bands were quantified using ImageJ software. Table 73 provides an estimate of the percentage inhibition relative to the negative control sample. The comparative percent inhibitions of the human Htt protein and the murine Htt protein are presented.

TABLE 73

Effect of antisense inhibition on mutant human and wild-type murine Htt protein (percent inhibition normalized to PBS control)

| | Dose (μM) | Human | Murine |
|---|---|---|---|
| ISIS 387916 | 0.7 | 54 | 38 |
| | 1.4 | 75 | 58 |
| | 1.5 | 92 | 88 |
| ISIS 460209 | 0.2 | 71 | 35 |
| | 0.4 | 82 | 41 |
| | 1.5 | 94 | 56 |

Example 17

Dose-Dependent Antisense Inhibition of Human Huntingtin mRNA Levels in Coriell Fibroblast Cell Lines Gapmers from the studies described in Examples, 3, 4, 10, and 12 were selected and tested at various doses in GM04281, GM02171 and GM02173B cell lines. Each cell line was plated at a density of 25,000 cells per well and transfected using electroporation with 0.4747 nM, 1.5011 nM, 4.7463 nM, 15.0079 nM 45.455 nM, 150.0527 nM, 474.4673 nM, 1,500.27 nM, 4,743.833 nM, and 15,000 nM concentrations of antisense oligonucleotide, as specified in Tables 72, 73, and 74. After a treatment period of approximately 16 hours, RNA was isolated from the cells and HTT mRNA levels were measured by quantitative real-time PCR. Human HTT primer probe set RTS2617 was used to measure mRNA levels. HTT mRNA levels were adjusted according to total RNA content, as measured by RIBOGREEN. Results are presented as percent inhibition of HTT mRNA, relative to untreated control cells. $IC_{50}$ values are also provided in Tables 72, 73, and 74.

TABLE 74

Dose-dependent antisense inhibition of human HTT in GM04281 cells

| ISIS No | 0.4747 nM | 1.5011 nM | 4.7463 nM | 15.0079 nM | 47.455 nM | 150.0527 nM | 474.4673 nM | 1500.27 nM | 4743.833 nM | 15000.0 nM | $IC_{50}$ (μM) |
|---|---|---|---|---|---|---|---|---|---|---|---|
| 387916 | 15 | 12 | 4 | 5 | 7 | 26 | 70 | 89 | 98 | 99 | 0.33 |
| 435879 | 0 | 8 | 19 | 13 | 24 | 23 | 45 | 53 | 84 | 93 | 0.25 |
| 435890 | 16 | 1 | 8 | 12 | 25 | 23 | 32 | 52 | 61 | 91 | 0.82 |
| 460209 | 2 | 9 | 21 | 17 | 36 | 46 | 80 | 89 | 94 | 93 | 0.09 |
| 460210 | 4 | 7 | 5 | 19 | 20 | 35 | 69 | 85 | 98 | 98 | 0.21 |
| 476333 | 7 | 10 | 8 | 11 | 42 | 65 | 86 | 93 | 93 | 95 | 0.05 |

TABLE 75

Dose-dependent antisense inhibition of human HTT in GM02171 cells

| ISIS No | 0.4747 nM | 1.5011 nM | 4.7463 nM | 15.0079 nM | 47.455 nM | 150.0527 nM | 474.4673 nM | 1500.27 nM | 4743.833 nM | 15000.0 nM | $IC_{50}$ (μM) |
|---|---|---|---|---|---|---|---|---|---|---|---|
| 387916 | 22 | 8 | 0 | 9 | 0 | 32 | 60 | 90 | 96 | 97 | 0.27 |
| 435879 | 0 | 1 | 6 | 2 | 0 | 0 | 8 | 9 | 46 | 57 | 7.62 |
| 435890 | 0 | 0 | 0 | 6 | 0 | 0 | 0 | 31 | 27 | 71 | 4.37 |
| 460209 | 11 | 5 | 15 | 0 | 0 | 7 | 30 | 69 | 82 | 88 | 0.96 |
| 460210 | 0 | 0 | 0 | 2 | 17 | 18 | 38 | 70 | 93 | 95 | 0.56 |
| 476333 | 0 | 0 | 0 | 0 | 13 | 18 | 44 | 69 | 72 | 91 | 0.75 |

TABLE 76

Dose-dependent antisense inhibition of human HTT in GM02173B cells

| ISIS No | 0.4747 nM | 1.5011 nM | 4.7463 nM | 15.0079 nM | 47.455 nM | 150.0527 nM | 474.4673 nM | 1500.27 nM | 4743.833 nM | 15000.0 nM | $IC_{50}$ (μM) |
|---|---|---|---|---|---|---|---|---|---|---|---|
| 387916 | 3 | 17 | 7 | 25 | 27 | 33 | 65 | 88 | 98 | 99 | 0.19 |
| 435879 | 0 | 6 | 0 | 8 | 3 | 10 | 16 | 24 | 50 | 68 | 3.72 |
| 435890 | 0 | 13 | 0 | 1 | 2 | 12 | 16 | 23 | 49 | 82 | 4.60 |
| 460209 | 0 | 7 | 29 | 2 | 9 | 32 | 52 | 71 | 82 | 86 | 0.27 |
| 460210 | 0 | 13 | 0 | 5 | 16 | 18 | 49 | 74 | 93 | 97 | 0.27 |
| 476333 | 11 | 13 | 20 | 7 | 23 | 36 | 63 | 75 | 83 | 90 | 0.13 |

Example 18

Validation of the Specificity of ISIS Oligonucleotides Targeting SNPs of Human Huntingtin by the Molecular Beacon Assay Some of the gapmers from the study described in Example 17 were tested in GM04022 fibroblasts (from the Coriell Institute for Medical Research).

To verify allele-specific suppression of HTT mRNA in GM04022 fibroblasts by ISIS 435879, ISIS 460209, and ISIS 476333, the Molecular Beacon assay, as described in the van Bilsen at el publication (van Bilsen, P. H. J. et al., Human Gene Therapy. 19: 710-718, 2008), was conducted using 'molecular beacon' synthetic oligonucleotides linked with a fluorophore and quencher. GM04022 fibroblasts were transfected by electroporation with ISIS 435879, ISIS 460209, or ISIS 476333 at 0.06 µM, 0.19 µM, 0.56 µM, 1.67 µM, 5 µM and 15 µM concentrations of antisense oligonucleotide, as specified in Tables 75-77. ISIS 387916 was included in the assay as a benchmark oligonucleotide. The qRT-PCR assay for molecular beacon for the A allele was conducted with the annealing temperature at 56.5° C. The qRT-PCR assay for molecular beacon for the C allele was conducted with the annealing temperature at 62.0° C. Primer probe set RTS2617 was used to measure the total HTT mRNA reduction. The results of the assay are presented in Tables 77-79 as percent inhibition over the PBS control. The results demonstrate that the SNP-specific ISIS oligonucleotides specifically target the C allele of rs7685686 compared to the A allele (Table 80).

TABLE 77

Dose-dependent antisense inhibition of the A allele of rs7685686 in GM04022 fibroblasts

| ISIS No | 0.06 µM | 0.19 µM | 0.56 µM | 1.67 µM | 5.00 µM | 15.00 µM | $IC_{50}$ (µM) |
|---|---|---|---|---|---|---|---|
| 387916 | 33 | 40 | 53 | 90 | 99 | 98 | 0.56 |
| 435879 | 0 | 0 | 50 | 29 | 38 | 47 | 10.8 |
| 460209 | 14 | 4 | 54 | 73 | 81 | 95 | 0.53 |
| 476333 | 2 | 44 | 41 | 77 | 91 | 86 | 0.64 |

TABLE 78

Dose-dependent antisense inhibition of the C allele of rs7685686 in GM04022 fibroblasts

| ISIS No | 0.06 µM | 0.19 µM | 0.56 µM | 1.67 µM | 5.00 µM | 15.00 µM | $IC_{50}$ (µM) |
|---|---|---|---|---|---|---|---|
| 387916 | 41 | 42 | 46 | 86 | 95 | 92 | 0.54 |
| 435879 | 0 | 0 | 75 | 60 | 68 | 81 | 2.9 |
| 460209 | 35 | 48 | 76 | 84 | 88 | 92 | 0.19 |
| 476333 | 22 | 60 | 75 | 84 | 90 | 93 | 0.15 |

TABLE 79

Dose-dependent antisense inhibition of total HTT mRNA in GM04022 fibroblasts

| ISIS No | 0.06 µM | 0.19 µM | 0.56 µM | 1.67 µM | 5.00 µM | 15.00 µM |
|---|---|---|---|---|---|---|
| 387916 | 32 | 59 | 49 | 89 | 98 | 99 |
| 435879 | 0 | 0 | 42 | 25 | 41 | 62 |
| 460209 | 26 | 27 | 54 | 75 | 84 | 96 |
| 476333 | 25 | 51 | 58 | 82 | 92 | 90 |

TABLE 80

$IC_{50}$ ratio (A/C) in GM04022 fibroblasts

| ISIS No | Ratio |
|---|---|
| 387916 | 1.0 |
| 435879 | 4.2 |
| 460209 | 2.8 |
| 476333 | 4.3 |

Example 19

Allele-Specific Inhibition Measured in Cortical Neurons from BACHD and YAC18 Mice In order to identify potential SNPs for screening of human allele-specific ISIS oligonucleotides, the HTT mRNA of YAC18 and BACHD mice were sequenced by the Goldengate 96SNP assay. It was determined that the BAC and YAC mice carried different alleles at several key SNP positions (Table 72) and could therefore be used as a screening tool for allele-specific knockdown. Each of the SNP positions chosen for targeting in the mouse strains were also compared to human HD chromosomes. For each target, approximately 50% of the human HD population is heterozygous for the target expressed in the BACHD mice, but not the YAC 18 mice.

In order to verify the allele-specificity of the ISIS oligonucleotides (described in Examples 2, 9, 17 and 18), the antisense oligonucleotides, ISIS 460207, targeting SNP rs362331; ISIS 460209, targeting SNP rs7685686; ISIS 435879, targeting SNP rs7685686; ISIS 476333, targeting SNP rs7685686; ISIS 460210, targeting SNP rs2298969; ISIS 435874, targeting SNP rs4690072; ISIS 460208, targeting SNP rs4690072; ISIS 435331, targeting SNP rs2024115; and ISIS 435871, targeting SNP rs363088, were tested for their effect on HTT protein levels in BACHD and YAC18 cortical neurons. ISIS 387916, which has no human or murine SNP target site, was used as the benchmark. ISIS 387916 is cross-reactive with murine HTT mRNA (GENBANK Accession No. NM_010414.1, designated herein as SEQ ID NO: 286) at target start site 5763 with one mismatch. It was expected that treatment with the allele-specific antisense oligonucleotides would cause significant inhibition of HTT mRNA in the BACHD neurons and not in the YAC18 neurons. It was also expected that treatment with ISIS 387916 would cause inhibition of HTT mRNA in both sets of neurons.

YAC18 cultures were prepared from E16.5 pregnant female YAC18 (line 60, +/+) mice who had been bred with YAC 18 (line 60, +/+) males. All progeny are thus homozygous YAC 18 (line 60), facilitating pooled cortical cultures. BACHD E16.5 embryos were isolated from pregnant BACHD (+/−) mice who had been bred with pregnant BACHD (+/−) male mice, necessitating single pup cultures and genotyping. Single cortices were isolated, using caution to prevent cross-contamination of samples. Each dissociated cortex was used to seed 5 wells of a 6-well plate. After genotyping, only BACHD (+/−) cultures were used for ASO treatment. The antisense oligonucleotides were added to the supplementary media fed to the neurons on division 2. Cells were harvested after 8 days with into 1 mL of media using a cell scraper. Cells were centrifuged at 2,500 rpm for 5 min at 4° C. and the pellets were resuspended in a buffer of 50 mM Tris, pH=8.0, 150 mM NaCl, 1% Igepal, 40 mM β-glycerophosphate, 10 mM NaF, 1× Roche complete protease inhibitor, 1 mM Sodium Orthovanadate and 800 µM PMSF. The lysates were centrifuged after 15 min incubation and protein concentration was measured with the DC assay (BioRad).

Protein lysates were run on low-bis gels to separate huntingtin alleles (resolving gel—2001:Acrylamide:BIS (10% acrylamide, 0.5% BIS, 375 mMTris pH 8.8; stacking gel—4% Acrylamide-BIS(29:1), 156 mM Tris pH6.8; Running buffer—25 mM Tris, 190 mM Glycine, 0.1% SDS+10 µM beta-mercaptoethanol added fresh). After electrophoresis, proteins in the gel were transferred to a nitrocellulose membrane (Hybond-C Extra; GE Healthcare Bio-Sciences) at 90V for 40' to allow samples to penetrate the stacking gel and then at 190V for 2.5 h to resolve proteins.

Primary antibodies specific for human HTT and murine calnexin protein were used at 1:10,000 dilutions. HRP-conjugated anti-mouse secondary antibody (1:10,000, Jackson ImmunoResearch Laboratories) was used for visualizing proteins using SuperSignal West Pico Chemiluminescent Substrate (Thermo Scientific). Protein bands were quantified using ImageJ software and normalized to calnexin levels. Tables 81-91 provide the percentage inhibition relative to the untreated control sample. The percentage inhibition of human HTT protein levels in BACHD and YAC18 neurons are presented.

TABLE 81

HTT SNPs in BACHD and YAC18 mice and correlation with human HTT SNPs

| SNP | Allele present in YAC18 Mice | Allele present in BACHD Mice | Allele present in human patients with high CAG repeats | % of human patients heterozgous at the SNP position |
|---|---|---|---|---|
| rs2024115 | G | A | A | 48 |
| rs2298969 | G | A | A | 52 |
| rs362331 | C | T | T | 49 |
| rs363088 | G | T | T | 38 |
| rs4690072 | T | A | A | 49 |
| rs7685686 | G | A | A | 49 |

TABLE 82

Effect of antisense inhibition by ISIS 387916 in BACHD and YAC18 neurons

| | 500 nM | 1500 nM |
|---|---|---|
| YAC18 | 69 | 81 |
| BACHD | 84 | 90 |

TABLE 83

Effect of antisense inhibition by ISIS 435331, targeting rs2024115 in BACHD and YAC18 neurons

| | 500 nM | 1500 nM |
|---|---|---|
| YAC18 | 0 | 0 |
| BACHD | 39 | 43 |

TABLE 84

Effect of antisense inhibition by ISIS 460210, targeting rs2298969 in BACHD and YAC18 neurons

| | 500 nM | 1500 nM |
|---|---|---|
| YAC18 | 31 | 51 |
| BACHD | 79 | 89 |

TABLE 85

Effect of antisense inhibition by ISIS 460207, targeting rs362331 in BACHD and YAC18 neurons

| | 500 nM | 1500 nM |
|---|---|---|
| YAC18 | 0 | 0 |
| BACHD | 29 | 44 |

TABLE 86

Effect of antisense inhibition by ISIS 435871, targeting rs363088 in BACHD and YAC18 neurons

| | 500 nM | 1500 nM |
|---|---|---|
| YAC18 | 0 | 0 |
| BACHD | 51 | 68 |

TABLE 87

Effect of antisense inhibition by ISIS 435874, targeting rs4690072 in BACHD and YAC18 neurons

| | 500 nM | 1500 nM |
|---|---|---|
| YAC18 | 9 | 5 |
| BACHD | 30 | 44 |

TABLE 88

Effect of antisense inhibition by ISIS 460208, targeting rs4690072 in BACHD and YAC18 neurons

| | 500 nM | 1500 nM |
|---|---|---|
| YAC18 | 1 | 8 |
| BACHD | 54 | 68 |

TABLE 89

Effect of antisense inhibition by ISIS 460209, targeting rs7685686 in BACHD and YAC18 neurons

| | 500 nM | 1500 nM |
|---|---|---|
| YAC18 | 12 | 32 |
| BACHD | 72 | 83 |

TABLE 90

Effect of antisense inhibition by ISIS 435879, targeting rs7685686 in BACHD and YAC18 neurons

| | 500 nM | 1500 nM |
|---|---|---|
| YAC18 | 0 | 7 |
| BACHD | 36 | 58 |

TABLE 91

Effect of antisense inhibition by ISIS 476333, targeting rs7685686 in BACHD and YAC18 neurons

| | 500 nM | 1500 nM |
|---|---|---|
| YAC18 | 46 | 61 |
| BACHD | 89 | 91 |

What is claimed is:

1. A compound comprising a modified antisense oligonucleotide consisting of 12 to 30 linked nucleosides targeted to a single nucleotide polymorphism site, wherein the modified oligonucleotide comprises a wing-gap-wing motif with a 5' wing region positioned at the 5' end of a deoxynucleoside gap, and a 3' wing region positioned at the 3' end of the deoxynucleoside gap, wherein position 8, 9, or 10 of the modified oligonucleotide, as counted from the 5' terminus of the modified oligonucleotide, aligns with the single nucleotide polymorphism, and wherein the single nucleotide polymorphism is on a mutant allele that is associated with Huntington's Disease.

2. The compound of claim 1, wherein the single nucleotide polymorphism site contains a differentiating polymorphism.

3. The compound of claim 1, wherein the modified antisense oligonucleotide consists of 15 to 20 linked nucleosides.

4. The compound of claim 1, wherein the gap region is 7-11 nucleosides in length, the 5' wing region is 1-6 nucleobases in length and the 3' wing region is 1-6 nucleobases in length.

5. The compound of claim 4, wherein the wing-gap-wing motif is any one of the group consisting of 5-10-5, 2-9-6, 3-9-3, 3-9-4, 3-9-5, 4-7-4, 4-9-3, 4-9-4, 4-9-5, 4-10-5, 4-11-4, 4-11-5, 5-7-5, 5-8-6, 5-9-3, 5-9-5, 5-10-4, 5-10-5, 6-7-6, 6-8-5, and 6-9-2.

6. The compound of claim 5, wherein the wing-gap-wing motif is any one of the group consisting of 2-9-6, 4-9-5, and 4-11-4.

7. The compound of claim 4, wherein at least one nucleoside of at least one of the wing regions comprises a modified sugar or sugar surrogate.

8. The compound of claim 4, wherein each of the nucleosides of each wing region comprises a modified sugar or sugar surrogate.

9. The compound of claim 8, wherein the modified sugar comprises a 2'-O-methoxyethyl modified sugar.

10. The compound of claim 4, wherein at least one of the wing regions comprises a 4' to 2' bicyclic nucleoside and at least one of the remaining wing nucleosides is a non-bicyclic 2'-modified nucleoside.

11. The compound of claim 10, wherein the non-bicyclic 2'-modified nucleoside is a 2'-O-methoxyethyl nucleoside.

12. The compound of claim 10, wherein the 4' to 2' bicyclic nucleoside is 4'-CH($CH_3$)—O-2' bicyclic nucleoside.

13. The compound of claim 4, wherein at least one internucleoside linkage is a modified internucleoside linkage.

14. The compound of claim 4, wherein each internucleoside linkage is a phosphorothioate internucleoside linkage.

15. The compound of claim 4, wherein at least one nucleoside comprises a modified nucleobase.

16. The compound of claim 15, wherein the modified nucleobase is a 5'-methylcytosine.

* * * * *

SEQUENCE LISTING

<160> NUMBER OF SEQ ID NOS: 288

<210> SEQ ID NO 1
<211> LENGTH: 202001
<212> TYPE: DNA
<213> ORGANISM: H. sapiens

<400> SEQUENCE: 1

| | | | | | |
|---|---|---|---|---|---|
| gcccagcagg | tgtcagcctc | attttacccc | gcccctattc | aagatgaagt | tgttctggtt | 60 |
| ccaacgcctc | tgacatatta | gctgcatcat | tttacatttc | tttttttttt | ttccttttaa | 120 |
| atggggtctt | gctctgtcac | ccaggctgga | gtgctgtggt | atgatctcgg | ctcactgcaa | 180 |
| tctccacctc | cgaggttcca | gcgattctct | tgcctcagcc | tcccgagtag | ctgggactac | 240 |
| aggcacccac | catcatactg | gctaattttt | tgtgttttta | gtagagatgg | ggtttcccca | 300 |
| tgttgcccag | gctgatctca | aactcctggg | cttaagcaat | acagccgcgt | tggcctccca | 360 |
| aagtgttggg | attacaagca | tgagctaccc | cacccagctc | attttacatt | tccacttgtt | 420 |
| aaactgaaaa | ctggcccgag | aaagcttctg | tactgccatc | cttgcgtcct | tgcagatgaa | 480 |
| tcgtaaccta | gcatagtagg | taggcagact | gaaaacctaa | cttagcagta | ggcttctgta | 540 |
| acaacagctg | tgtctcagcc | agttcctgca | gccagacttc | aaccactcac | aggccgcaaa | 600 |
| ctgttcaaac | tgtgttcgga | gaaggcgaat | tcatctggct | gttaacgtgc | ctcacttctg | 660 |
| ctttctgtgg | ccactttccc | ttttctgtcc | ataaatttgc | tttgaccaca | cagcatccct | 720 |
| agagtctccc | tgaatctgct | gtgattctgg | gacctgcacc | atttgtgaat | tgttttttt | 780 |
| ttccttgatc | agctaaactc | tgttcaattc | aatttgttgg | aagttttaa | cataccaatg | 840 |
| gtgcaccaag | gttccaattt | ctccacttcc | tcataaataa | gtcattttaa | atggcttttc | 900 |
| agtattccaa | tatttggaag | tattaatgtt | tctaccaatt | ttctattttt | ggacattgag | 960 |
| gttgtttcat | tttttttttc | ttttttgag | acagagtctc | gctccgtcac | ccaggctgga | 1020 |
| gtgcagtggc | ctgatcccgg | cccactgcaa | cctccacctc | cctcctcagc | ctcctgagta | 1080 |
| gctgggatta | caggtgcatg | caccaccaca | cccagctaat | ttttgtattt | ttagtagaga | 1140 |
| tggggtttca | ccatgttggt | caggctggtc | tcaaactcct | gacctcaggt | ggtccacctg | 1200 |
| ccttggcctc | ccaaaatgct | gggattacag | gcctgagcca | ctgcgcctgg | cctcatcttc | 1260 |
| ttgatattaa | tgttgcttta | acatctttgt | ccctgtgttt | tttgttttt | ttttgagac | 1320 |
| ggagtctcat | tcattctgtc | acccaggctg | gagttcagtg | gcgtgatctc | agctcactgc | 1380 |
| aacctctgtc | tcctgggttc | cagtgattct | cctgcgtcgg | tctcctgagt | agctgtgttc | 1440 |
| ctgggtcttt | cgatggttat | ttaatacttc | cctacagtaa | tgccctgtgc | gtacatgcta | 1500 |
| agtgtgatga | aatggttggc | acagttaaat | cttttgaaag | acattgccaa | gtcactcttc | 1560 |
| agaaaagtga | taggaggtca | tagcaatttt | aagaagtcct | catttctaca | tttccttact | 1620 |
| aatctcggtt | ggtgtctctt | caatctttcc | tcacactttt | cttgggtttt | tcctgaatca | 1680 |
| tgagtctact | acatttacac | attttaaagc | atctttagaa | acaggatctc | attttgttgc | 1740 |
| ccaggctaga | gtttggtggc | atgattatag | ctcctcatac | tcctgggctc | aagtgatcct | 1800 |
| tccacctctg | aaaccccaaa | atttgagaaa | ggtctcattt | aatttagaaa | gtttattttg | 1860 |
| ccaaggttga | gggtgcacac | ctgtgatgat | atacgagtta | aaagaaatt | atttaggcag | 1920 |
| atactgaggg | taagaaagtc | ctcggtaagg | ttttctttc | aatgaaaagc | agccccaag | 1980 |
| cattttcttt | tctaacaaag | agcagcctgt | aaaatcgagc | tgcagacata | cacaagcaag | 2040 |
| ctggaagctt | gcacaggtga | atgctggcag | ctgtgccaat | aagaaaaggc | tacctggggc | 2100 |

```
caggcagatc caacatggcg gctccatctt cccttcctt gtcaaccatg tgcacagtaa    2160
ggagcaggca acatagtgtc ccccgagtag agaccaattt gcataataaa aggtgagggt    2220
agggtgggca gcttctttgc atgctatgta aacattatgc ctggtccaac caatctttgg    2280
gccctgtgta aattagacac cacctcctca agcctgtcta taaaaccctg tccattctgc    2340
cgcaggctgg aagacccact ggggcacccc tctctctcta taggagacag ctattcattt    2400
ttctctttct ttcacctatt aaagctccac tcttaacccc actccgtgtg tatctatgtt    2460
cttgatttcc ttggcatgag gcaatgaacc ttgggtatta ccccagaacc ttgggtatta    2520
tgccacttca gtgacacagc ctcaggaaat cctgatgaca tgttcccaag atggtcgggg    2580
cacagcttgg ttttatacat tttagggaga catgagacgt caattcatat atgtaagaag    2640
tacattggtt ccgtccagaa aggcggggac aacttgaggc aggagagag cttctaggtc     2700 acaggtagac aaatggttgc attcttttga atctccgata agcctttcca aaggaggcaa    2760
tcagaatatg cgtctattga ctgggcgcag tggctcatgc ctgtaatgcc agcactttgg    2820
gaggcggagg tgggtggatc acctgaggtc aggagtttga gagcagcccg gccaacatgg    2880
tgaaaccctg tctctactaa aaatacaaaa aattagctgg gcgtggtggc gggcgcctgt    2940
aatcccagct actcgggagg ctgaggcagg agaatagctt gaacccagaa ggaagaggtt    3000
gcagtgagct gagatggtgc cattgcactc cagcctgggc aacaagagtg aaactccatc    3060
tcagaaaaaa aaaaaaagg cctggcaaa gtggctcacg cctgtaatcc cagcactttg     3120
ggaagccgag gcgggcaggt cacaaagtca ggagattgag accatcctgg ctaacatgat    3180 gaaacccat ctctactaaa aatacaaaa aactagctgg gtgtggtggc gagcacctgt      3240
agtcccagct actcggcagg ctgaggcagg agaatggcgt gaaccgggga ggcggagctt    3300
gcagtgagcc gagatcacac cactgcactc cagcccggac gacagggcaa gactctatct    3360
caaattaaaa aaaaaaaaa aaaaaaaaa aagagagag agaatatgca tctatctcag       3420
tgagcagaag gatgactttg aatggaatgg gagcagttcc tagcttgaac ttcccctta    3480 gcttcagtga tttgggggct caaggtatgt tcctttcaca tacctcagcc tcccaagtag    3540
ctgggaccac aagtgcatgc caccacacgt ggctaatgtt ttatttttt tgtaggaata    3600 gggtctcact atgtgtccag gctggtctaa aaccctgag ctcaaatggt cctcccgcct     3660
cagcctcccg aaatgctggg attacaggca tgagccagca tgcccggcct agtctacatt    3720
tttataaatt gctaattcaa agttccctct ccaaaacctc atggttttcc ctgttctcat    3780
cccctgcacc ctcccttccc ctggagtact cacctggcct tggaggtctg gtgtgagccc    3840
ggacttcgat tctaggcaca gcatgtgatg agcgccccca ggtcaaacac ctcccctctg    3900
cggcctgtgc ttcaccgcct tgacagtgag aaaggtctcc cttcggctca ttctcgaagt    3960
ctcaaacttc acttctcctg tgcgctgatt ctgaattcag ccccgtcca aggtcctggc     4020 cccttctct tctgcttggc gtgttgttca tcaccactgt gcactgctga gggtaagtgc     4080
ggttctctgg acctctgctt tatcattaga acagactctt gcggtttccc acgacattcc    4140
tttcacttct cacttggaag atgagccgtg aggaaatcct gtgttgtgtg gtatgtgggc    4200
tgtgcttctg cttgacttga gggccaagca gcattgcaag ccatggtttt aaataagaaa    4260
gaacatttct aaccttcatc ttctagtaag gaaacaagtg ggctttagag ttcttgctca    4320
ggaaagacct atgtcccagt ccaaccggac cttttactaa agagatcttc ctgatcctcc    4380
tccccaggcc aggggagggg tcctccctgg ggttggagcc tttagtaggg ggtcggagac    4440
```

```
acgacgtagc cttcatgaca ttcatagtct agttacacga tccctgtaag ggtcagttga   4500
agtaagtgct acaaaggaag ggaggtgctc agtggagagg gctctctttt atgtattata   4560
tttctttcat ggggagggat atggatcagg gatcagcaga ggtgtttcag tcccgaggga   4620
aagaaagtca gcgtggcttg ggagttggga gcagcaagac agtggctcaa gatatcttaa   4680
gactagtgga gtacaccttg catgttaaaa gccttgctca gggctgcctg gttcttgtag   4740
gacgacagag atggcctagc tctgcatact gcaccccag gggctcagaa cagtgcaaat   4800
gtcagtctat ctgtcagtgg cagagccagc cttggagcag gggtgcaagg aggtctctgc   4860
actggccagg catgcagaac attctgttca gtagcactgg acagaaggcc ccatctagat   4920
gagacagagc tggtggggca ggacaaagac tcctggcagc tcaaacggcc tggcagatgc   4980
ttggagagag ggggcttctt gagacagcac catttctggg aagagagtca cctgggaggg   5040
atgaggccac gctccggctt ggaggtgaag agaggggctg ctgcaagaaa gaattagaga   5100
catgccagcc tttgctgtgt tgcccaggct ggtcatgaac tcttggcctc aagcaatctt   5160
cccacctcag cctccccaag cgctgggatt atagacatga gcccccatgc tggccaataa   5220
aagatgattt tatggagggg atggtggtga aggttgtggg tggtatgaaa tagtaagaaa   5280
tatatattgg tctgcaccca gttcctgcca cagagctcct aaaatcctga aacttcctg   5340
ggtgagcatc ttttgttcta atgaggtgac tcttggtggc tcctggatag gagtgaatca   5400
ccagaaagat caagccagag ttagaagcag aaagtgctgg ctataacaca ggaaagctgt   5460
aacacaaata ataaagtttt tttttttttt tttgagatgg agcctcactc tgttgcccag   5520
gctggagtgc aatggtgcaa tctcagctca ctacaagctc tgcctccag gttcaagtga   5580
ttctcctgcc tcagcctcct gagcagttgg gactacaggt gtgtgccacc acatctggct   5640
aattttgta ttttagcag agacggggtt tcaccatatt aaccaggctg gcctcaaact   5700
ccttaccttg tgatccgcct gcctcagcct cccaaagtgc tgggattaca ggcatgagcc   5760
accgtgcctg gccaaaagac attgttctta aagaatcaa ctaactaacc aaataaataa   5820
aaatctaacc taattaagaa actaaaaata cacaaaaatt aatttcaagg ggagaaaaat   5880
catgtaaaga gagaaagata atgaatactt tgcagaaatt tatgaacata aacataaaac   5940
ttggatgaaa tgcatttcta ggaaaacata atttatcaaa actaaccaca agtaaaatag   6000
aagcctaaat aggatatttt caagagaaga agtaaagttg tcaaagtgct acccttcaaa   6060
aaaacaccag gctcaaacaa tctgacatgg gaatgttagc acaccttaga gagcaaataa   6120
aactttgaat gggcttgaaa tattccagac tctagaaaaa caaaacttcc caattctttt   6180
tataaagcaa gtataaattg ataccaaaat cttataaaga ccttatacaa aacttcatac   6240
caatctcttt tatgaatcaa aaacccttaa taaagtatta ccagacagaa cccaacaata   6300
cataaaaatg tcacatcata acatagtggg gtttatttca ataatgcatg gatggttcaa   6360
tacaaggaaa ttcagtaaca caatataata gatcatgtga atataccccaa agaaaaaata   6420
gattattttc atagatgctg taaaggcatt tgaccaaatt caacacctac tttttaggtg   6480
gtcaataaaa taaattagtt actccttctt tagcatgata aaatatattt atcagcccag   6540
aaggcatcat tttacccgat aagggcacac gctggaggga ataatgttaa aattaggaat   6600
aagaggatag ctagtttctt tcttcttttt tttttttgag acggagtctt gctctgttgc   6660
caggctggag tgcagtggtg caatgttggc tcactgcacg ccccccgcct cccaggttca   6720
agcgattctc ctgcctcagc ctcccgagta gctgggacta caggcgcgca ccaccatgcc   6780
cggctaattt ttttttgtat tttagtagag atggggtttc accatgttgg tcaggctggt   6840
```

```
cttgaactcc caacctcacg tactgggatt accggtgtga gccaccacgc cagcccaact   6900
actttcaaca ttatccttaa tactgatgct tattgactta ctatggggtt acctctagat   6960
aaatccataa taagttgaaa atataagtaa aaaatgccct taatacacct aacctaccaa   7020
acatcatagc tgagcccagc ctgccttagc tatgctcaga cactgacgtc agcctacaat   7080
tggcaaaatc acacagcagc acagtctact gcagagcatc tgctgtttgc ccttgtgact   7140
gcgtggctgc ctgggagctt cccagcttca caagacagta ttacgtagca catcactagc   7200
ctggggaaag atcaaagttg aaaatttgaa gtgtggtttc cattgaatgt gtactgcttt   7260
tgcaccatca tcaagtcaaa aaattttagt tgaaccagcc taagtttggg accatcttta   7320
ttttcaggag gaacttccat gtacattgat gacggacgat agaatccgtt tctatcatcc   7380
taatgaacat aatgaataaa tccagacaaa cataaacatt aacagagtaa gcagctttcg   7440
gggctggaag ccagaagagg gtgggagcgc agagagagag gccaaacacc agggctgctt   7500
ctgctttgcg ggtatttgct gatctggaca aggtatctgg aaggctgagc taagcctcct   7560
ttttttttga ggtggcgtct cactctgttg ccaggctgga gtgcaatggt gcgatctcag   7620
ctcactgcaa cctccacctc cctggttcaa gcgattctcc tgcctcagcc tcccgagtag   7680
ctgggattac aggctcccgc cactacaccc agctgatttt tgtaattta gtagagacgg   7740 ggtttcacca tgttggccag gatggtctcg atctcttgac gtcatgatct gtccacctcg   7800
gcctcccaaa gtgctgggat tataggcgtg acccaccgtg ccccgtctga gctaagcctc   7860
ttgagcatag gggactaaaa atgaaatcta gcgcatgcca agtttagggt cccaggcaat   7920
tcctttccac tttggggtcc actttggggt ccaccccacc caagaagaag gatgacttgg   7980
aagtaaacca gctctgaaat atggatggtc ctctgggacc ataccaatcc cttcatatca   8040
accacatcca gttcctcaaa actggaactt ggattaagat ggcctaggac ttctagtgtc   8100
ccaggagcct ggcattgcaa acaaaaatcc tctccggaag aagataatac cttaagcttc   8160
aaatgactct ctaataaatt tcaaatacaa tgtccagcac acaaacacaa attaccagga   8220
acgtgatatg aggcctgatg gatgggaatt agcagaaact tcaggcatga gaaacatacc   8280
ctcagaggcc tagaatctat ctagtgtcta gataatggag atatgaaata cagacactta   8340
aacaactatg tttcccatgt tcaaagagga aatttgcaaa acttgaaagt gttggcagga   8400
aatcagaaac tataaaatgt gacaacagca tactttagag tcagtataaa ttacggtccc   8460
gaaaactgca gaattccaga acttaatggt aaagcaaggg tttaacagca gaatagaaat   8520
agccagagag aactaggaag taagtcagat gacactaccc agaataaggc actgagaggc   8580
caaggaatgg aaaatgcaga agaaaggata tggtgagagg atctaatata catttatttg   8640
gagtaccagg gagagagaga aggagaagaa cagaagccgt gtttcaagga cggtgactga   8700
gaggcttcga aactgatgaa agccatcagt tcacaaattc aaagcccagt gaattccaag   8760
gagaaaaaaa gaaatcccata ctgtgaaagc aagtccagac aatgacaaac accatcaaca   8820
atacacagga caggcataag atgcatttaa tggggacact cagaggcaga gggttatcag   8880
aaggaggcac ttctctccca agttctcatc atcccaggc cagggacagc tggtcacacc   8940
ttagggagtt cactaggaga gggatctggc ttccttgtcat tctgggtatt tgtagggaaa   9000
ttggaaggga accgagagca cctagccaat cgcatagcaa tgggagattt caggctgtgg   9060
ggaatgtctt tgctggtgaa aagaacatcc tgaccttaga aatctttcac cgaggggat    9120 ctgcgttcca gaacttctgg agctggtata ggtaaggctt tgagctttcc tactgagcca   9180
```

```
gcctgttgct aggttaccaa aggggacctc gagggccatc tggccaacaa gcagacttgt   9240
ctctccttac accccagac gtatcactgc aaaactacag aaaaccaaag acagagaaaa    9300
tcttaaaagc agccagattt aaaaaatggc atattagttt caaagcagca gccatgaaat   9360
tgacagctga tgtctcaaca gcaagaatga aaagtggaag acaggccagg tgtggtggct   9420
caggcctgta atcccagcac tttgggaggc cgaggcgggt ggatcacgag gtcaggagac   9480
caagaccatc ctggctaaca tggtgaaacc ccgtctctac taaaaataca aaaaattag    9540 tcgggcatgg tggtgggtgc ctgtagtccc agctactcgg gaggctgagg caggagaatg   9600
gcgtgaaccc gggaggcgga gcttgcagtg agccgagatt gtgccactgc actccagcct   9660
gggtgacaga gcaagactct gtctcaaaaa aaaaaaaaaa aaaaaaaaaa aaagggtgac   9720
gaagcttcaa tctcctgaaa ggaagcaact gccgcctttg attcgatacc caccaaaatc   9780
cgtgaagaag gaaggcaaaa taaaaacact tcctgattga actggaaaga tttccgcaat   9840
agaagaccca ctgtccaagg aattctaaag gatgctttcc aggcagaaga aaatgacccc   9900
agaggaagat cagagattca ggaaagaaat ggagagtgat aaaaatgaaa aattcggggg   9960
ccaatttaaa caaagctga ctgctctaca actgttgtgt ctctatcttt tgtaacatat    10020
atgtgtgtgt agctttttt ttttttttg tcaagatgga ttctcactct gtcgcccagg    10080
ctacagtgaa atggcacggt ctcggctcac tgcaacctct gccccttggg ctcaaatgat   10140
tctcttgcct cagcctcctg agtagctgag attacaggtg cctggcacaa tgcctggcta   10200
atttttgtat ttttactaga gatgggattt ctccatgttg gccaggctgg tcttgaacac   10260
ctgacctcag gtgatccacc tgcctgggcc tcccaaagtg ctaggattac aggcgcgagc   10320
cactgcatct ggcctatgtg tgtgtttata tggaattaaa acacatggca ataatccct    10380 ccaaattggg agaaaccaaa aatagcattt aaatgttgta agctccctgc ataatcaaga   10440
agagaataga tttacgttag atttttgatac ctggaggatg aatgttgtaa tttctagggt   10500
gaccatgaaa agaggagaca acggtgtatg tttttttttt tttgagatgg agtctcactt    10560
tgtcacccag gctggagtgt gtggtgtga tcttggctca ctgcaacctc ctcctcttgg    10620
gttcaggcca tcctcccacc taggcctcca gagtaggtgg gatcacaggc acctgccacc   10680
acacctggct aatttttttt ttttttaaa tatttagtag agatggggtt tcaccatgtt    10740
ggccaggctg gtcttgaact cctgacctca ggcgatctgc ctacctctgc ctctcaaagt   10800
gctgggatta caggtgtgag ccatcgcgcc cggccaacag tgatcacttt caaactaaca   10860
gaggttcaaa aataaaatca gacttaacca aaaaccaggt aacagagctg gtaggatata   10920
cagaaagact gacctcacgt atatcaacga ttacagttaa tattaatgaa ggaaatgctc   10980
tagtttaaaa acgaggggttg tcaaagaccc cacataagaa gctccttacc agcggtgcac   11040
ctagaaccta aggaaacagg acagatgaag gaggacgcgc cccgccgct gtcctgcgcc     11100 tcagccatcc tatgagacgg gaaaggtttc tgtctgcagc tgggcccgtg ctctttacca    11160
gctcctggct ttcttctctg gaaggttcct gcctgttttg ccctcacacc tgctcctctc    11220
tcagccctct caggggtggg gctggaggcc accaaagagc ctcctctgct ctccagttgc    11280
tcgactgctc ctcatttccc cctggggtct gcgtcagggt ttccttcttt tccagcccca    11340
ccccgcgtgc atcccacctg gtctcgggtc ggggctgctc ccgcttactg cccctgccc    11400 aggctggtgt gcacccctc tggctgcttt caaggcctct tctctcttct cggcaggaca    11460
ggcacaggca ggtggccagg tgtcatgctt agctccccgc ccagtgagat tctttcattt    11520
aacaatcttc ccctgaatag ttcatgttca ttgctgaaaa tttgaaaaat atggaaaagc    11580
```

```
acaaagatta agatataaac cgccctcaat tcccctgccc agagagagtc actgctatga   11640
cttggtgact aggaaccttta tttctctctc gctcttttt tttttttga dacagagtct   11700 tgctctgtca cccaggctgg agtgcagtgg ctcgatctca gctcactgca acctccgcct   11760
cctgggttca agcgattctc ctgcctcagc ctcttgagta gctgggatta caggcacctg   11820
ccaccatgcc cggctaattt ttgtatttt agttgagaga gggtttcatc ttgttggtca   11880
ggcggacttg aactcctgac ctcaggtgat cagcccacct cggcctccca aagtgctggg   11940
attacaggtg tgagccactg cgccttcatc tctcttctgt gtatgtgtac gctgttttt   12000 ctttagaatg ggggacgtta tcaggctcta catggtgtgt agtcggctag catgttgtaa   12060
gcctttccct gtgtcacaag tgctcatctg aacaggatt ctaatgactg cctgtggcta   12120
tgttgggatt cctttaactc agctccttct gcccagcatc tatcttttt ccatcttttg   12180 tcctaagtgt tgctataata aatcattgat cacacatgcc tgactgtttg cataggataa   12240
attacgggaa atgtttttgc tgttcaggga ctgtgcccat ttttaggcct cagagacacc   12300
atgccagact gcccagtatt gatctttact cttttagat gatgccaaac ttttctgtga   12360
actttaaaaa cctgtgtctt gacagtccat ttctgtaagt ctttcacatt agatttcctg   12420
tcaggatgat agtcaattct aggcagatga tgttttctca gccatggctg aagcagttgt   12480
gatttgttgt ggccatgtaa agtcccgatg atccattgcc tccctggatg ggttggaata   12540
atttggtttg ggagcatata acagaatgac ctggagtcac agcagctcag acggaagtgt   12600
atttctccct tacagatgaa agaattccag gccaggctgg aatgacaact gcacacagtc   12660
atctgggccc cctccttcca gctcccatca ccccaggatg tggcttttat gcagatgatc   12720
caaaatggct gctcaagtcc cagccaacac atcccattcc agggagcagg aaaaaggtgt   12780
gtctttccct tcattttatg tgattccttt ctagaagtac tactcattac ttctgcttgc   12840
atctccctgg ctagcactta cttagttata tggccatagc tagctgaagg aaggacaggg   12900
actgtcatac actagctaag aggcaaactg cttagataaa aaggtctcta aagaaggtca   12960
gagcggctgc tagggtgcaa ctctattact tattgttatg ggacgaactg tgtccctcat   13020
tcaggttgat gtcctaagcc ccagaacctc agaatgggat tgtatttgga gacaggttct   13080
ttaaggaggt aaggaggcta aaatgagatc attagggtgg gccataatcc gactgatgtc   13140
ttacaagaag agattaggac acggacatgc tcagagggac ggccacgtga ggacaccaag   13200
aaaggcagct gtctgcaagt caaggacagg gctcagggga aaccaaccctt gccaacacct   13260 tcatctcgga cttctagcct ctaggaccat gagaagatac atttctgttg tttaagctgc   13320
ccggtctgtg gtactttgtt atggcagccc aagtaaacaa atacagtcat ctgctgctgg   13380
aacaaatcac cccagcactg tggcttggca gcacacatgt ctagtcatag agttatatgt   13440
agttacgtgt agagccatat gtatcgtcac acgttctgtg ggtcaggaat ttggacccag   13500
cttaaccagc tccacttctc gccagggttc agtcaaatac cagctgcctc ccacctgaga   13560
gctcagccgg ggaagggtcc cttttccaatc tcacgtggtg ttgcaggat ccagttcctc   13620 atggcctgct ggactgagaa cctcagttct cactgcctgt tggccagagg ccgcctttat   13680
gtcctcgcca tgtgggcctc tccaacatgg cagctgactt catcagagca tccatgccaa   13740
gaaggcaaca gagagggcca gggagactga agtcataccc ttttgcgacc tagtcatggg   13800
gtgacattcc atcacctttg cccattggtt agaagcaggc caccaggtac agcccaagct   13860
cacggggagg ggtcatacaa gggtgtcaat accaggaggt gagggtgct ggggccatct   13920
```

```
tatgagtctg cccactgagg taactaacaa ccttgaggcc tgacacagtg gacaaaggcc    13980
cttattaaca gcagagaact gggaacttta tttatttatt tatttttgag acagagtctc    14040
actcttgtca cccaggctgg agtgcaatgg catgatcttg gctcactgca acctccacct    14100
cccaggttca gcaattctg cctcagcctc cggaatagct gggactacag gcatgcacca     14160
ctacacccgg ctaattttg tattttagt agagacaggg tttcgccatg ttggccaggc      14220
tggtctcgaa ctcctgacct ctggtgatct gcctgcctg gcctcccaaa gtgctgggat     14280
tacaggcgtg agccaccgca cctcgctgga acttaatttt tttagagaca gtgtcgctct    14340
atcacccaag ctggagtgca gtggtgcaat cctagctcac ttgcagcctc aaattcctgg    14400
gttcaggtga tcctcccaca tcagcctccc aagaactggg aactaacagc tgtttctctg    14460
ctgtccttct caagaaaagg gaggctactg ctaccccact ggggacaatg ctgggtttcc    14520 cttaggaca ggctctgaga caaggcggag gtgctgtttg tggccacaga gcaggggact     14580
ctgggttgca ggtgtggcct ggctaaagta ggctttactg gctcctctc tgcctgcatc     14640 accccccggc tgggcggttg tctctgaggc caaccttact ccctgctggg caggctggac    14700
agctgccctc tccgtttgcc cctctaccac ccaaaaggca ggaggctctg gagaccagga    14760
ccctgcccgc cacggcctgt gtcccaggcg tgagggggtg cccacagac ctctgctgag     14820 ctgctgctga atgacgcccc ttggggggtcc tgccggaagg tcagagcagg ggtgcactcc   14880
cataaagaaa cgcccccagg tcgggactca ttcctgtggg cggcatcttg tggccatagc    14940
tgcttctcgc tgcactaatc acagtgcctc tgtgggcagc aggcgctgac cacccaggcc    15000
tgccccagac cctctcctcc cttccggggc gctgcgctgg gaccgatggg gggcgccagg    15060
cctgtggaca ccgccctgca ggggcctctc cagctcactg ggggtggggt gggggtcaca    15120 cttgggtcc tcaggtcgtg ccgaccacgc gcattctctg cgctctgcgc aggagctcgc     15180
ccaccctctc cccgtgcaga gagccccgca gctggctccc cgcagggctg tccgggtgag    15240
tatggctctg gccacgggcc agtgtggcgg gagggcaaac cccaaggcca cctcggctca    15300
gagtccacgg ccggctgtcg cccgctcca ggcgtcggcg ggggatcctt tccgcatggg     15360
cctgcgcccg cgctcggcgc ccctccacg gcccgccccc gtccatggcc ccgtccttca     15420
tgggcgagcc cctccatggc cctgccctc gcgcccac ccctccctcg ccccacctct      15480
caccttcctg ccccgccccc agcctcccca ccctcaccg gccagtcccc tccctatcc     15540 cgctccgccc ctcagccgcc ccgcccctca gccggcctgc ctaatgtccc cgtccccagc    15600
atcgccccgc cccgccccg tctcgccccg cccctcaggc ggcctccctg ctgtgccccg     15660
ccccggcctc gccacgcccc tacctcacca cgccccccgc atcgccacgc ccccgcatc     15720 gccacgcctc ccttaccatg cagtcccgcc ccgtccttc ctcgtcccgc ctcgccgcga     15780
cacttcacac acagcttcgc ctcaccccat tacagtctca ccacgccccg tccctctcc    15840 gttgagcccc cgcgccttcgc ccgggtgggg cgctgcgctg tcagcggcct tgctgtgtga    15900
ggcagaacct gcggggggcag gggcgggctg gttccctggc cagccattgg cagagtccgc   15960
aggctagggc tgtcaatcat gctggccggc gtggccccgc ctccgccggc gcggccccgc    16020
ctccgccggc gcagcgtctg ggacgcaagg cgccgtgggg gctgccggga cgggtccaag    16080
atggacggcc gctcaggttc tgcttttacc tgcggcccag agcccattc attgcccgg      16140 tgctgagcgg cgccgcgagt cggcccgagg cctccgggga ctgccgtgcc gggcgggaga    16200
ccgccatggc gaccctggaa aagctgatga aggccttcga gtccctcaag tccttccagc    16260
agcagcagca gcagcagcag cagcagcagc agcagcagca gcagcagcag cagcaacagc    16320
```

```
cgccaccgcc gccgccgccg ccgccgcctc ctcagcttcc tcagccgccg ccgcaggcac    16380
agccgctgct gcctcagccg cagccgcccc cgccgccgcc cccgccgcca cccggcccgg    16440
ctgtggctga ggagccgctg caccgaccgt gagtttgggc ccgctgcagc tccctgtccc    16500
ggcgggtccc aggctacggc ggggatggcg gtaaccctgc agcctgcggg ccggcgacac    16560
gaaccccccgg ccccgcagag acagagtgac ccagcaaccc agagcccatg agggacaccc    16620
gccccctcct ggggcgaggc cttcccccac ttcagccccg ctccctcact tgggtcttcc    16680
cttgtcctct cgcgagggga ggcagagcct tgttgggggcc tgtcctgaat tcaccgaggg    16740
gagtcacggc ctcagccctc tcgcccttcg caggatgcga agagttgggg cgagaacttg    16800
tttctttta tttgcgagaa accagggcgg gggttctttt aactgcgttg tgaagagaac    16860
ttggaggagc cgagatttgc tcagtgccac ttccctcttc tagtctgaga gggaagaggg    16920
ctgggggcgc gggacacttc gagaggaggc ggggtttgga gctggagaga tgtgggggca    16980
gtggatgaca taatgctttt aggacgcctc ggcgggagtg gcgggggcagg gggggggcgg    17040
ggagtgaggg cgcgtccaat gggagatttc ttttcctagt ggcacttaaa acagcctgag    17100
atttgaggct cttcctacat tgtcaggaca tttcatttag ttcatgatca cggtggtagt    17160
aacacgattt taagcaccac ctaagagatc tgctcatcta agcctaagtt ggtctgcagg    17220
cgtttgaatg agttgtggtt gccaagtaaa gtggtgaact tacgtggtga ttaatgaaat    17280
tatcttaaat attaggaaga gttgattgaa gttttttgcc tatgtgtgtt gggaataaaa    17340
ccaacacgtt gctgatgggg aggttaattg ccgagggatg aatgaggtgt acatttacc    17400
agtattccag tcaggcttgc cagaatacgg ggggtccgca gactccgtgg gcatctcaga    17460
tgtgccagtg aaagggtttc tgtttgcttc attgctgaca gcttgttact ttttggaagc    17520
tagggggtttc tgttgcttgt tcttggggag aattttttgaa acaggaaaag agagaccatt    17580
aaaacatcta gcggaaccccc aggactttcc ctggaagtct gtgtgtcgag tgtacagtag    17640
gagttaggaa gtactctggt gcagttcagg cctttctctt acctctcagt attctatttc    17700
cgatctggat gtgtcccaga tggcatttgg taagaatatc tctgttaaga ctgattaatt    17760
tttagtaata tttcttgttc tttgtttctg ttatgatcct tgtctcgtct tcaaagttta    17820
attagaaaat gattcggaga gcagtgttag cttatttgtt ggaataaaat ttaggaataa    17880
attattctaa aggatggaaa aacttttggg atatttggag aaattttaaa acaatttggc    17940
ttatctcttc agtaagtaat ttctcatcca gaaatttact gtagtgctttt tctaggaggt    18000
aggtgtcata aaagttcaca cattgcatgt atcttgtgta aacactaaac agggctcctg    18060
atgggaagga agacctttct gctgggctgc ttcagacact tgatcattct aaaaatatgc    18120
cttctctttc ttatgctgat ttgacagaac ctgcatttgc ttatcttcaa aatatgggta    18180
tcaagaaatt tcctttgctg ccttgacaaa ggagatagat tttgtttcat tactttaagg    18240
taatatatga ttaccttatt taaaaaattt aatcaggact ggcaaggtgg cttacacctt    18300
taatccgagc actttgggag gcctaggtgg acgaatcacc tgaggtcagg agtttgagac    18360
cagcctggct aacatggtga aaccctgtct ctactaaaaa tacaaaaatt agctggtcat    18420
ggtggcacgt gcctgtaatc caagctacct gggaggctga ggcaggaaaa tcgcttgaac    18480
ccgggaggca gagtctgcag tgagttgaga tcacgccact gcactccagc ctgggtgaca    18540
gagcgagact ctatctcaaa aaaaatttttt tttaatgtat tattttttgca taagtaatac    18600
attgacatga tacaaattct gtaattacaa aagggcaata attaaaatat cttccttcca    18660
```

```
cccctttcct ctgagtacct aactttgtcc ccaagaacaa gcactatttc agttcctcat    18720
gtatcctgcc agatataacc tgttcatatt gtaagataga tttaaaatgc tctaaaaaca    18780
aaagtagttt agaataatat atatctatat attttttgag atgtagtctc acattgtcac    18840
ccaggctgga gtgcagtgat acaatctcgg ctcactgcag tctctgcctc ccaggttcaa    18900
atgcttctcc tgcctcagcc ttctgagtag ctgggattac aggcgcccac caccatgtcc    18960
agctaatttt tgtattttta gtagagatgg ggtttcacca tgttggccag gctggtcttg    19020
aactcctgac cttgtgatct gtccacctcg gcctcccaaa gtgctgggat tacaggtgtg    19080
agccaccatg cctggctaga ataataactt ttaaaggttc ttagcatgct ctgaaatcaa    19140
ctgcattagg tttatttata gttttatagt tattttaaat aaaatgcata tttgtcatat    19200
ttctctgtat tttgctgttg agaaaggagg tattcactaa ttttgagtaa caaacactgc    19260
tcacaaagtt tggattttgg cagttctgtt cacgtgcttc agccaaaaaa tcctcttctc    19320
aaagtaagat tgatgaaagc aatttagaaa gtatctgttc tgttttttatg gctcttgctc    19380 tttggtgtgg aactgtggtg tcacgccatg catgggcctc agtttatgag tgtttgtgct    19440
ctgctcagca tacaggatgc aggagttcct tatgggctg gctgcaggct cagcaaatct    19500
agcatgcttg ggagggtcct cacagtaatt aggaggcaat taatacttgc ttctggcagt    19560
ttcttattct ccttcagatt cctatctggt gtttccctga ctttattcat tcatcagtaa    19620
atatttacta aacatgtact atgtgcctgg cactgttata ggtgcaggc tcagcagtga    19680 gcagacaaag ctctgccctc gtgaagcttt cattctaatg aaggacatag acagtaagca    19740
agatagataa gtaaaatata cagtacgtta atacgtggag gaacttcaaa gcagggaagg    19800
ggatagggaa atgtcagggt taatcgagtg ttaacttatt tttatttta aaaaaattgt    19860 taagggccttt ccagcaaaac ccagaaagcc tgctagacaa attccaaaag agctgtagca    19920
ctaagtgttg acatttttat tttatttttgt tttgttttgt ttttttgag acagttcttg    19980 ctctatcagc caggctggag tgcactagtg tgatcttggc tcactgcaac ctctgcctct    20040
tgggttcaag tgattctcat gcctcagcct cctgtttagc tgggattata gacatgcact    20100
gccatgcctg ggtaattttt ttttttttccc ccgagacgga gtcttgctct gtcgcccagg    20160
ctggagtgca gtggcgcgat ctcagctcac tgcaagctcc gcttcccgag ttcacgccat    20220
tctcctgcct cagtctccca gtagctggga ctacaggcg cctgccacca cgtccagcta    20280 attttttgt atttttaata gagacggggt ttcaccgtgt tagccaggat gatcttgatc    20340
tcctgacctc gtcatccgcc gaccttgtga tccgcccacc tcggcctccc aaagtgctgg    20400
gattacaggc atgagccact gtgcccggcc acgcctgggt aattttttgta tttttagtag    20460 agatggggtt ttgccatgat gagcaggctg gtctcgaact cccggcctca tgtgatctgc    20520
ctgccttggc ctcccaaagt gctaggatta caggcatgag ccaccatacc tggccagtgt    20580 tgatattta aatacggtgt tcagggaagg tccactgaga agacagcttt ttttttttt    20640 tttttgggg ttgggggca aggtcttgct ctttaaccca ggctggaatg cagtatcact    20700
atcgtagctc acttcagcct tgaactcctg ggctcaagtg atcctcccac ctcaacctca    20760
caatgtgttg ggactatagg tgtgagccat cacacctggc cagatgatgg cttttgagta    20820
aagacctcaa gcgagttaag agtctagtgt aagggtgtat gaagtagtgg tattccagat    20880 gggggaaca ggtccaaaat cttcctgttt caggaatagc aaggatgtca ttttagttgg    20940
gtgaattgag tgagggggac atttgtagta agaagtaagg tccaagaggt caagggagtg    21000
ccatatcaga ccaatactac ttgccttgta gatggaataa agatattggc atttatgtga    21060
```

```
gtgagatggg atgtcactgg aggattagag cagaggagta gcatgatctg aatttcaatc   21120
ttaagtgaac tctggctgac aacagagtga aggggaacac cggcaaaagc agaaaccagt   21180
taggaagcca ctgcagtgct cagataagca tggtgggttc tgtcagggta ccggctgtcg   21240
gctgtgggca gtgtgaggaa tgactgactg gattttgaat gcggaaccaa ctgcacttgt   21300
tgaactctgc taagtataac aatttagcag tagcttgcgt tatcaggttt gtattcagct   21360
gcaagtaaca gaaaatcctg ctgcaatagc ttaaactggt aacaagcaag agcttatcag   21420
aagacaaaaa taagtctggg gaaattcaac aataagttaa ggaacccagg ctctttcttt   21480
tttttttttt tgaaacggag tttcgctctt gtcacccggg ctggagtgca atgatgtgat   21540
ctcagctcac taaaacctct acctcctggg ttcaagtgat tcttctgcct cagcctccca   21600
agtaactggg attacaggcg tataccacca tgcccagcta attttgtgt ttttagtaga   21660 gatggggttt caccatgttg gccaggctgg tctcgaactt ctgacctcag gtgatccact   21720
cgcctcagcc tgccaaagtg ctgggattac aggtttgggc cactgcaccc ggtcagaacc   21780
caggctcttt cttatactta ccttgcaaac ccttgttctc attttttccc tttgtatttt   21840
tattgttgaa ttgtaatagt tctttatata ttctggatac tggattctta tcagatagat   21900
gatttgtaaa aactctccct tcctttggat tgtcttttta cttcttgat agtgtctttt   21960 gaagtgtaaa agttttaat tttgatgaag tcgagtttat ctattttgtc tttggttgct   22020
gtgcttcaag tgtcatatct aagaaatcat tgtctaatcc aaagtcaaaa aggtttactc   22080
ctatgttttc ttctaagaat tttagagttt tacatttaag tctgatccat tttgagttaa   22140 ttttatata tggttcaggt agaagtccaa ctttattctt ttccatgtgg ttattcagtt   22200
gtcccagcac tgtttgttga agagactatt cttccccat ggaattatct tagtacccttt   22260 gttgaaaatt aatcgtcctt aattgtataa atttatttct agactgtcag ttctacctgt   22320
tggtctttat gtcgatcctg tgccagtacc atacagtctt gattactgaa gtttgtgtca   22380
cagtttaaat tcatgaaatg tgagttctcc aactttgttc cttttcaaga ttgatttggc   22440
catgctgggt cccttgcatt tccgtacgaa ttgtaggatc agcttgtcag tttcaacaaa   22500
gaagccaagt aggattctga gagggattgt gttgaatctg tagatcaact tggggagtat   22560
tcgcatctta acaatattgt cttccaccta tgaacatggg caaactttgt gtaaatggtc   22620
agattgtaag tatttcgggc tgtgtgggca cagtgtctct gtcacagcta cgcggctctg   22680
ccattgtagc atgaaagtag ccataagcaa tatgtatgag tgtctgtgtt ccaatagaat   22740
tttattaatg acaaggaagt ttgaatttca tataattttc acctgtcatg agatagtatt   22800
tgattatttt ggtcaaccat ttaaaaatgt aaaaacattt cttagcttgt gaactagcca   22860
aaaatatgca ggttatagtt ttcccactcc taggttaaaa tatgatagga ccacatttgg   22920
aaagcatttc tttttttttt tttttttttt tttttgagac ggagtttcac tcttgttgcc   22980
caggctggag tgcagtggcg cgatctcggc tcactgcaac ctctgcctcc caggttcaag   23040
acattctcct gcacggcctc cctagtagct gggattacag gcatgcgcca ccacacccag   23100
ctaattttgt attttagta gagacggggt ttctccatgt tggtcaggct ggtcttgaac   23160
tcctgacctc aggtgatcca cccgcctcag cctcccaaag tgctgggatt acagggtgtg   23220
agccaccaca ccctgctgga aagcatttct ttttggctg tttttgtttt tttttaaac   23280 tagttttgaa aattataaaa gttacacata tacattataa aaatatcttc aagcagcaca   23340
gatgaaaaac aaagcccttc ttgcaagtct gtcatctttg tctaacttcc taagaacaaa   23400
```

-continued

```
agtgtttctt gtgtcttctt cccagatttt aatatgcata tacaagcatt taaatgtgtc    23460 atttttttgtt tgcttgactg agatcacatt acatatgtat ttttttactt aacaatgtgt    23520
catagatatt gttccatagc agtacctgta attcttatta attgctatgt aatattttag    23580
aatttctttt taaaagagga cttttggaga tgtaaaggca aaggtctcac atttttgtgg    23640
ctgtagaatg tgctggtgac atattctctc taccttgaga agtccccatc cccatcacct    23700
ccatttcctg taaataagtc aaccacttga taaactacct ttgaatggat ccacactcaa    23760
aacatttagt cttattcaga caacaaggag gaaaaataaa ataccttata aagcactgtt    23820
taatattgta ttaaattgga tcaatttggg ggctagaatg tatgttagag acatgatatg    23880
tccataggtc cttgctatca cagtgaggtc tcagggacag tcgtttggta tcatttggga    23940
tctcataagc agactctctc tgcttgacct gacaaatcag agtctgtgtt ttaacaggtt    24000
cagtgagtga cttacatgca cattggagtt tgggaagctc cactgtaggt gcttagacct    24060
tacctttgtt gttgctaata acaatgcaag catttgggag gaagacctgt gttgctcata    24120
tgtgtccagg tgtagctgag gtggccttgc ttatctgctg tagggccgtt gagcatttct    24180
gtagctgtga tgagtgagct gaggtgagcc tgcggagagc tcccagccat tggtagtggg    24240
actcgcttag atgaactgga aggacccttt catctgagca gccactatgg agaaaaacaa    24300
ccgaatgagg ggagagacaa tgtgcaattt tatttagggc acaaaggaga gctgtggtta    24360
gaaggtgaca tttgagtgga aagggggcaa gccatgtgta tagcgggaga agagaggtcc    24420
aggcagagtt aacagaaggc agaaatgctt tccatgtttg agaaccagta aggaggccag    24480
tggctgaagt aaggtgaagg gcagaaataa ggatgaggct gcgagagatg agaggttaga    24540
gacgagcgtc ttgtgcacca agataagctt gtgtggtcaa aacaagtagt ttaatttatg    24600
tttttaaaag atcattttgg ctgggcacaa tggttcatgc ctgtaatacc agtagtttga    24660
gacggtgtgg tgggaggatt gcctgaggcc agacgaccag catagccaac atagcagcac    24720
ctataaggtc tctacaaaaa actttaaaaa attagctggg catagtggtg tgtgcctgta    24780
gtcccagcta ctcaggaggc tgaggaggct ggaggattgc ttgagtccag gagtttgagg    24840
ctgcagtgag ctatgattat gccactacac tacaacctgg gcaagagagt gagaccctgt    24900
ctctaaatat acacacacac acacacacac acacacacac acacacacac acacacacac    24960
acacacatat atatgtatat atatgcattt agatgaaaag atcactttga caataccaca    25020
tgctggtgag gatttagaaa aactaggtca cttattgctg gtgggaatat aatatagtac    25080
ggccactctg gaaaacagtt tggcagtttg tcataaaact gaacataccg ttagtataca    25140
gcccagcagc aactacaatc ctgggcatta atcctagaga aatgaaacct taatgttcac    25200
ataaaaacct atactcaagt atgcatagca gctttacccca taatatctaa gaactggaat    25260
cagctcagat gtccttcaac aggtgaatgg ttaaactact cagtaataaa aaggaatgag    25320
ctactgatag catgcaacag tttaggtgaa gttatgctaa tgaaaaaagc caatcccaaa    25380
aggttataca tactgtatga ttctatgttt ttttgcaatg gcacagtttt agggatggag    25440
aatagattag tggttgcctg gggttagaga tggggtagta gagtaggtta tggtggcag    25500 aggagagaaa agagagggag gtgaatgtgg ttataaaagg acaacacagg ggaatacttg    25560
taatggaaat gctttgtctt tttttttttt tttttttttt tggcgacaga gtcttgctct    25620
gttgcccagg ctggagtgca gtggcatgat cttttctcac tgcaacctct gcctcctggg    25680
ttcaagtgat acttgtgtct cagtctccca tgttcagagt gaaacaaacc agaggtaatg    25740
ttcatccaaa taatccaaca cacatgacat taaaacatca agatcaggtc ggacgtggtg    25800
```

```
gctcatgcct gtaatcccag cacttttggg aggccaaggt gggcagatca cttgaggtca   25860
ggagttcgag accagccggg ccaacatgat gaaaccccat cttgactaaa aatacaaaaa   25920
ttagccgggc atggtggtgt gcacctgtag tcccagctac ttgggaggct gaggcaagag   25980
aactgcttga acccgagggg cagaggttgc agtgagctga gagtgcgcca ttgcacttca   26040
gcctgtgtga cagagtaaga ctccatctcc aaaaaaaaaa aaccaagatc aattaaaata   26100
cagcattact gggccgggtg tggtggctca cacctgtaat cccagcactt tgggaggccg   26160
agatgggcag atcacgaggt caggagatcc agaccatccc ggctaacacg gtgaaacccc   26220
gtctctacta aaaatacaaa aaattagcc gggtatagtg gtgggtgcct gtagtcccag   26280
ctacttggga ggctgaagca ggagaatggt gtgaacccgg gaggcagagc tggcagtgag   26340
ctgagatcgc gccactgcac tccagcctgg gcgacagagc aagactccgt ctcgggggaa   26400
aaaaaaaaat aaataaatag aatgctgtag tgtccttgag tttacatgcc cctccttacg   26460
cttgtgtgcc cgtgcagatt gcttgattac acaattagag gaggctggcg gaggattgtt   26520
ttaatttttt ttttttttgag acagtctggc tctgttcccc aggctagagt gcaatggcgc   26580
aatcttggtg cactgcaacc tctgcctcct gggttcaagc agttcttctg ccgcagcctc   26640
ccgagtagct gggattatag gcgcccgcca ccacgcccaa ctatttttg tattttagt    26700 agagcagcgt ttcaccatgc tggccaggct ggtctcgaac tcctgacctc agatgatctg   26760
ctgccccagc ctcccaaagt gctgggatta caggcgtgag ccacacctgg ccgtttgttt   26820
taattttgaa ggtgaagtga aagtgactac atttaccaaa agtgattgaa aagccaggac   26880
tgttcttacc ctgttttttcc agttcttgct cagagcaagg tggtttcttt ttcacttaat   26940
caccatactt acttttcatg tagaacaagt cagtttgagt tatcagttca tcatcttaac   27000
taaattccat gggggaagga attagtttta gtttcttaaa cttccaggtt tgcttattgg   27060
acaaaatgag atagcaaggc agtgttttta agttagattt tttatttctt tggtaataca   27120 atttctcag aaacttagta gtcttttagt ttagttgttt ttagttggtc ctatgttttg   27180
gatcacccct ctctacttta ttttgatagt gccaactgtg aagacatctg aagccatagg   27240
tttggatggg aaggaggcat ctttagcctg atcatcttcg ccaggctgtt tatctccttt   27300
tgcttggctg agaagtctta ataggaggct tattcccagc tatttgggga catagaagca   27360
gttagccatt gcttatattt tactgaggtc tgtgtggtat gttgattgta gtcagttaac   27420
gattttgaga actgaaggca gcctggtata tatagagtag gtattagact gtgtttcttc   27480
taattgaatt tcccatctct tgtaatctat gccatcatct tctgtactgc tgagaaagaa   27540
agaaagtttc taatcaaact ataccactgg ttgtaagatg cagtttggct ttagtgatgt   27600
taacacatga ttcaaacgtg aaattgattg agtattggtg aaatacagag gagatttaaa   27660
gccagaagac ctgggtttaa atgctggctg tatgacttca tatctgtgtg atcttgggca   27720
tgtcatggtt ggcacttcaa tttcttctct ctataatggg ggaagtgagg ccagtcatgg   27780
tggctcatac ctataatccc agtgctttgg gaggccaaga tgggaagatc gcttgaggcc   27840
aggagtttga gcaattgggc aacatcgtga ggccccgtct ctacaaaata tttgaaaaa   27900 attagccagg cccagtggtg cgtgcctgtg tccgcgcca ctcaggaggc tgagacggga   27960 ggatccttc agcctaggag tttaaggcta aagtgagcca tgattgtgct atcgtactcc   28020
agcctgggca gcagagcaag atcctgactc taaaaaaaag taaataaag taaatgggg    28080 gaaatgaact gctttagtaa catcatctgt tttttctgtg agcagcgtag cttgacagcc   28140
```

```
attggtgaac tcgtgccctg tgcttccctg tccagatccc cattctgccc gcaacatgga    28200
gtataacggt ttattcatag tagtcgagaa acactcactg aatgaatgaa tgaggtgtag    28260
aactaagtgg agtgggtaat tcaacacata ttaatttcct tcttttttt attttagaa     28320 agaaagaact ttcagctacc aagaaagacc gtgtgaatca ttgtctgaca atatgtgaaa    28380
acatagtggc acagtctgtc aggtaattgc actttgaact gtctagagaa aataagaact    28440
ttgtatattt tcagtcttaa tgggctagaa tattctttgt gtcccagcta ttttaaatgg    28500
attcagaaat ccatttaaga tgaagaagga ccctttttcc atatttctgg ctatatacaa    28560
ggatatccag acactgaaat gaataatgtt ccctttttgt aatcttttat gcaaaaatta    28620
aaaccattat ggtaattgaa caacatgttt atgtttagtt aacacccttta gcaactatag   28680 ttattttaaa accatctatg gtttgatatt tttgcatttg ttgcaatagt aggaacagca    28740
caagacagtt cagtttgtct ctcttatttg cttttttctg gcagtttgct gtcctattgt    28800
acctctgctc ctagcagtgg ctggagccca ctcctctgtg cttcgggatt agtggggatc    28860
gtggggcatt gactgtaggt cagctttcct tgcttgatct ttctcactgg gatgaactag    28920
cagcaccttc ttttgtagct gctttgcttt tgactatctt tctgaccgtt gttcctagta    28980
gctgtagatg gtaaatatat ttaggcctgt ttccaatggc tcagtaggag acatattcac    29040
ctatgatatc tgaattctgt tacccacatg ggcatgcgtg aaatagttgc cttgccttac    29100
tttcccttgg aataaataat tcatgttatt ctcctggtag aagctagaaa aagctttat    29160 agtcagtcag aaaaaaattt ttagacaaat aatcttgatt ttagtactga caaaaacgtg    29220
tggtgattct ttttttaatt ttttttttgag acggagtttc actcttgttg cccaggctgg    29280
agtgcaatgg cgtgatctcg gctcactgca acctctgcct cctgggttca agtgattctc    29340
ctgcctcagc ctcccaagta gctggagtta caggcatgtg ctactgtgcc cagctaattt    29400 tgtatttta gtagagatgt tggtcaggct gatctcgaac tcccaacctt aggtgatctg    29460
cccgcctcag cctcccaaag tgctgggatt acaggcgtga gccagggcgc ccggtgattc    29520
atttgttttt tcaaaaaatt tcctcttggc cattgctttt cacttttgtt tttttttttt    29580
ttttgagacg gagtcacgat ctgtcaccca ggctggagtg cagtggcatg atcttggctt    29640
actgcaagct ctgcctccca ggttcacgcc attctcctgc ttcagcctgg cgagtagctg    29700
ggactacagg tgctcgccac cacacccggc taatttttg tattttagt agagatgggg     29760 tttcaccgtg gtcttgatct cctgacctca tgacccgctc aactcagcct cccaaagtgc    29820
tgggattaca ggcgtgagcc accgcgcccg ccctctctt gtcttttat tgtggtaaaa     29880 tgcacataaa attgactgtc ttaaccattt ttaggggtac agttcagtat atatattcgt    29940
aatgttgtac agccatcact gccatctact tcataagttt ttcttctgtc aaaactgaac    30000
atctgtcttc attaaactcc ctatcatcca ttctttcctg tagtcccttt ctactttctg    30060
tctgtatgag tgtaactgct ctggagacct catgtaagtg gattcctaca ggatttgtgt    30120
tttttttttg gtgatctgct tattttaat gcctctgtgc atttgtatta tatctttca     30180 aagtgatttc acaaaaccgt ttcattttag gttaactcat ttctgttgtt tgtgaaatac    30240
tgtgtatgat tctgttctgt ttctgtctaa tttgtggaaa tgttgtggga agaaaatgaa    30300
ataacaaatg agcatatgtc ctgaaaataa aaatataaaa attctaagtt agcatgctat    30360
tgtagaatac aacgctatga taaaagtagg aaaaaaaaag gtttgaattc tatctctgct    30420
acctgtgtaa gctgggtgac tttagataag ctgtaacgtg tttgagcctt actggctcat    30480
ttttgaaatg taatccctag ttacacagtt cttgtgggat cagatggtac atgtgaaaca    30540
```

```
ctgtgaaaaa gcaactgcat agatatgttc attagccacc tgagcgggaa gcgtatccca   30600
ttgcgatgcc catcatccaa agctatatgt tatctttact ttttttttt tgagacagag    30660 tcttgctctg ttgcccaggc tagagtgcag tggtgcaatc tcagctcact gcaagctcca   30720
cctcccgggt tcacgctatt ctcctgcccc agcctcccaa gtagctggga ctacaggcac   30780
ccgccaccat gcctggctaa attttttgtat ttttagtaga gatggggttt caccgtgtta  30840
gccaggatgg tcttgatctc ctgacctcgt gatccgcccg cctcggcctc ccaaagtgct   30900
gggattacag gcgtgagcca ctgcccctgg ccatctttac tttttttgtg aaatgacttt   30960
aaatacttgg caaacatttg gtcattgttc atctgatctc caccatccag gtctcagaga   31020 acataattc tctctgaaag cttattgacc caggaaataa gatctctttc aatctgagtg    31080
cgtcaggctt tattcttgtc attttgtctt tgataatttt tcaaatggaa ttcatggaat   31140
gttggcttat attcatatat tagtaaagta tgttgagaca tcttaagatt gatttgtggt  31200
tctatatgcc atattaaatc aaaataatag ctgttaatgg ttttcacatt agtctgtctc   31260
ttgtttttat ggagtaatgc tgagagttca ttatgcttgt tctacagaag agcatgttaa  31320
aaggagtttt tggagtcaga gaggttattc ttggtttcat aggatacact ctatactttt   31380
tagggatttc agagtatata gctgaaggtg atattttatg taaatatgtt ttatggaaac   31440
ttattgctca tcgctgtttc ctgttaactc tcctaaaata taattaaact tttgaacttt   31500
ttttatagct tttgtgctag actaattttt gtctctaatg aggttatata aatggcagct   31560
tctgacgttt tcaatgtagg aagtcattta aaacttcatg tatattgtga aaatgtagtc   31620
tgctttaagc tctctaaagt ggtctaagtt actggttcct aagtatggat gagcatcaaa   31680
atcatctgga aaatttgtta aaaatacagt aatgaaggca cctcactgtc cttttttccca  31740 aacatacttc tgcattctgt ttgagtaggt agggactaca catttttcac aagtatcctc   31800
ttgggaatac ccaggaatgc ttacttgagc aacctcttac taatatgtac cttgataagg   31860
tggctaggta aacataaata tacaaaaatc catagatctc ccatatatta gcataaatca   31920
gctagaaaat ataacgttta aagatctagt tcacagtagc accaatatat cgaactctaa   31980
ggaatcgata aatatgcaaa aactttataa aaacttctgt taatgtttct gaaagatata   32040
ggtgaccact ttctagatag gaagatttta tattactaag ttgaatttc tctaaattaa    32100 cacagaaatt taaaataatc ttgatcaaaa ttctagtaga ggtattttg aacttgttca    32160 ctgcaagaat aaatacataa ttgcaaagaa tatctcaaaa tcatcaccag gctggtgtg    32220 gtggcccatg cctgtaatcc cagcacttg ggaggctgag gcaggcagat cacctgaggt    32280
caagagtttg agaccagctg gaccagtgcg gtgaaacact gcctctacta aaaatacaaa   32340
aattagctgg gtgtggtggt gcatgcctgt agtcccagct acttgggagg ctgaggcagg   32400
agaattgctt gaacccagga ggtacaggtt gcggtgagcc tagatcgcac cactgcattc   32460
cagcctgggc gacaagagca aaattctgtc tcaagaaaaa agagaaaaaa gaaaagaaa   32520 tcaacactaa tatggtgaga cttaatgtat gtgacattaa aatagtgatt ggatgttaaa   32580
acaggtatag aacagaaaga agagtgtatg tgtgtatctg tatgaattta tgatgggtgt   32640
aacatatatg tattagggaa atgagggaaa tgatacattt ctctgacttt gggagaacat   32700
tatatctcta cctcatattg caaacaaaca taaagttcag attaattacc taaatgtgaa   32760
aaaatgaaat aatttctta aaaaatgtaa tcttagtttg aggaaggtta acattataaa    32820
ggaaaaaact gttttgagtg gaatatagtt caatatgtca aaatccacct tcaacaaaat   32880
```

```
tgaaagtaaa ttgaacttgg ggaaagtatt gacagcatat agatcaaagg ttactagcct    32940
gtgtaaagag cagttataaa tatcgttaag aaaaacactg tcgacctgtc ggcaccttgt    33000
tctccgactc ccagcctcca gaactgtgac gagtaagtgc ttattgttta aaccacccag    33060
tctgtatgtg gtattttgtt atagaaactc aagctgatta ggacactagt aatcagtaga    33120
ctgaaactga aacaaaaata agaacctttt ttacctgtca aattggcaaa cattaagaat    33180
attcagattt ttgtcagagg tgatacaacc ttctaagaag gcaatttggg aaaatataaa    33240
gctttagatt attatatgtc tgacctagca gttttacctc tagggtgctt accectagga    33300 aagtgtgtaa tgatattggt gcagtgccct tcatcccatt agaaaattaa aaataacctt    33360
aatggcctac cactaaaagg ggattgaaaa tttaagatat atttatttat gtgtttattg    33420
agatggagtc ttgcactgtc cgcctgggcc agagtgcaat ggtgcgatct cggctcactg    33480
caacctctgc ttcccggggtt catgtgattc tcctgcctca gcctcctgag tagctgggat    33540
tacaggctca caccaccgca cccggctaat ttttgtatt tttagtagag atggggtttc    33600
actgtgttgg ccagactggt ctcgaactcc tgacctcatg atccgcgccc ctcggcctcc    33660
cagtgttggg attacaggtg tgagccactg cgcctggcca gatacattta tacaagagaa    33720
tgttagttaa cattcataga tatttatatt ttgtttactt tttattaaaa aaattttttt    33780
tagagacagg atcttactct gtcacccagg caggatgcag ttgcacaatc atagcccact    33840
gcagcctgaa ctcctgggct taagtgatcc ttctgcctca gccttttgag tacctggggg    33900
actttaggca gtgctactat acctggctaa ttttaaatg tttttatagat gagatcttgc    33960 tgtattgccc aggctggtct agaattcctg ggcccaagtg atcctcccac cttggcctcc    34020
caaagcgctg agattacagg catgagccac cacttctgac caatagatat ttatatttgt    34080
gactggaaaa tatattaaca atgtgttaaa aaattcagtt aaaaaataat gaaagatttt    34140
tgcttctggc taagatagaa taacaaggac agcatttatc ttcttgcctt gaaatagttg    34200
aaaacggaag aaatatatgt aacagtggtt ttcaagttat tgggcatcag gcaaagaaga    34260
atagttatcc caggaaaatg aatgtggaga gccctacaat ttccttacat tactgcctgg    34320
tcatggcaag aggaaaaact gagaggagac tgaggctgag ccagtggttt gctgggttga    34380
ggaggcagag ctgggagtgc agagatgcaa ggtggtgaga gcccatatgg aagaatacca    34440
gggaagagag ctgcagaggg agctccggag acctgcaccc tgccctctca gtaccctgtc    34500
atgtgtgtag ctgagtactg acgagcactt gcttgtgcgg aaatgaccca gggctggagg    34560
tagagccacc tgaaaggatt agaaggaaca gttgctgaaa gtcacacagg gccaggaaga    34620
atttctaatc acaccagttg gagtggaaaa cctcagctct catagagcag gtagggtact    34680
cagaagggtt tgcccaccta gccccagact aagtttcgtt actctgaccc tacctaatat    34740 taaaagaga ttaattaaat tgttcgcaac aaaaataata tatttcagtg tttgtaacac    34800
gtagaagtga attgtatgac aatagcataa aggctggaag agcagaaatt gacatgtatt    34860
tgcgctgggc agaataatgc tcccctcttt ccccaaaaga tatcaagtcc taatccctgg    34920
agcctgtaaa tattacttta tatggaaaat tgttttatga tgtgattaaa ttcaggatct    34980
tgagatgagg gggctatctt ggatgatctg ggtaggcact aaatgcaatc acatatatat    35040
aaaaaggagg cagagggaga ttttacacac agagagaagg ccctgtgaag atggaacaga    35100
aagatttgaa ggtgctggcc ttgaaaattg gagtgatgaa gctataagcc aaggaatgca    35160
gcagccacca aagctggaag aggcacggag cagttctcat ttagagccta ctccagaggg    35220
aatgtggtgc tgccaattcc tttttttttt ttttttttaa gatatcattt accccttaa    35280
```

```
gttggttttt ttttttttttt tttttttttta gtatttattg atcattcttg ggtgtttctt   35340
ggagaggggg atttggcagg gtcataggac aatagtggag ggaaggtcag cagataaaca   35400
tgtaaacaaa ggtctctggt tttcctaggc agagggccct gccacgttct gcagtgtttg   35460
tgtccctggg tacttgagat tagggagtgg tgatgactct taacgagtat gctgccttca   35520
agcatctgtt taacaaagca catcttgcac cgcccttaat ccatttaacc cttagtggac   35580
acagcacatg tttcagagag cacggggttg ggggtaaggt tatagattaa cagcatccca   35640
aggcagaaga attttcttta gtacagaaca aaatggagtg tcctatgtct acttctttct   35700
acgcagacac agtaacaatc tgatctctct ttcttttccc acatttcctc cttttctatt   35760
cgacaaaact gccaccgtca tcatggactg ttctcaatga gctattgggt acacctccca   35820
gatggggtgg cggccgggca gagggctcc tcacttccca gatggggcgg ccgggcagag   35880
gcgcccccca acctcccaga cggggcggcg gctgggcggg ggctgccccc cacctcccgg   35940
acggggcggg tggccgggcg ggggctgccc accacctccc ggacggggcg gctggccggg   36000
cgggggctgc cccccacctc ccggacgggg cgggtggccg ggcgggggct gcccccacc   36060 tcccggacgg ggcggctggc cgggcggggg ctgccccca cctcccgac ggagcggctg   36120 ccgggcggag gggctcctca cttcccggac ggggcggctg ctgggcggag gggctcctca   36180
cttctcagac ggggcggctg gtcagagacg ctcctcacct cccagacggg gtggcagtgg   36240
ggcagagaca ttcttaagtt cccagacgga gtcacggccg ggcagaggtg ctcttcacat   36300
ctcagacggg gcggcgggc agaggtgctc cccacttccc agacgatggg cggccgggca   36360
gagatgctcc tcacttccta gatgggatga cagccgggaa gaggcgctcc tcacttccca   36420
gactgggcag ccaggcagag gggctcctca catcccagac gatgggcggc caggcagaaa   36480
cgctcctcac ttcctagacg gggtggcggc tgggcagagg ccgcaatctt ggcactttgg   36540
gaggccaagg caggcggctg ggaggtgaag gttgtagtga cccgagatca cgccactgca   36600
ctccagcctg ggcaacactg agcactgagt gagcgagact ccgtctgcaa tcccggcacc   36660
tcgggaggcc gaggctggca gatcacttgc agtcaggagc tggagaccag cccggccaac   36720
acggcgaaac cccgtctcca ccaaaaaaca cgaaaaccag tcagacatgg cggtgcgtgc   36780
ctgcaatccc aggcacttgg caggctgagg caggagaatc aggtagggag gttgcagtga   36840
gtagagatgg tggcagtaca gtccagcctt ggctcggcat cagagggaga ctgtgcgagg   36900
gcgagggcga gggcgaggga attccttaat ttcagtttag tgatactaat tttggactct   36960
ggcctctaaa actgtgaaag aaaaaatttt ttgtttgttt gtttcttta agccacatag   37020 tttgtggtaa tttgttacag cagctgcagg aaactaattt atgctgcatg tgaaatggtg   37080
taataaggta gattgtgatg aagatacata gtataaacaa ttaagcaaca actaaaagca   37140
caacaaggaa ttatagctaa tgaaccaaaa aaggagatta gaataataaa aatggtgaat   37200
cccaaagaag ccagaaatag gggaagaggc aaataaagga agaaagagc ttgatggtag   37260 atttcaacct aactatgtca aaaaggacat tacatgtaaa aggcagcgat ttttcagatt   37320
gaatggaaaa gtaagactcg gtatatgctg ctgcctgcaa gaaacacatt ctaaatataa   37380
aggcaaaaat aacctacagg taacagaacg gaaagaagtt cactgtgctt acaagaatta   37440
gatgcaagct agactggttc tgttaatatc agacaaagtg gatttcaaag caaaggctct   37500
tgcccaggat gagatggtca tttcataatg atgaagggga ttcgttcatc agcctggcat   37560
agcaagctga aatgtttatg caccggacta cagagctaaa atacatgaag caaagcctga   37620
```

```
cagaactaca agtagaaaca gacaaatcca cagtgataga gatttcagta gccgctctca    37680
atgatttgta gaacacgtag ccataatatc tggatctaga acacttgacc aacactgtcc    37740
cctgtgcaac ctcattggca tttacaggac actccaccca gcaccagcag aagagacact    37800
ctctcaagtg ctcacagaat gtttgccaag atagagcaga tgctgggcca taaaacaagt    37860
ctctaaatta aaagcattca aattattcag agtatgtttt ctgacctcag tatcattaag    37920
ttggaatata ttataggaag ataacctgga aaagcctcag atatgtggaa aaacccatttt   37980 ccacatggcc catgggtcag aagtgaagtc aaaagggaaa tttgaaagtc ttttggattg    38040
actgatataa aaacaataga tttctaaact tgtggggtgc tgttacagca tagtaaatgg    38100
aaatttctag cattaaatgc ctgttttagg aaagaaagat ttcaaatcaa tgacctcagc    38160
ttctaccttt ggaaacttga aaatgacaag caaatggaat ccagagttac cagaagggcc    38220
aggtacggtg gcttatgcct gcagttctgc cactttggga ggccgaggca ggtggattgt    38280
ttgagactgg cagttgaaga ccagcctggg cagcctaggg agaccccata tctacaaaaa    38340
acaaaaaaat tagccaggtg tggtggcatg tgcctgtagt cccagctaac caggagtcta    38400
aggtgggagg attgcttgag tctgggaggt tgaggctgca gtgaactgtg attgtgccac    38460
tgtgttccat cctgggcaac agaatgagac cctgtctcaa aaacaaaaac agttactaga    38520
agaatggaca tcataaagat aggagcagaa gtcagtaaaa tagaaaacaa aaatacatag    38580
gaaatcaata aaaccaaaag ctggttcatc aagaacatca ataaattggt aaagctgata    38640
ggaaaaacag tgaagtcaca aattagcaat atcaggaatg agggagatga cagtagtata    38700
gattatatag atattaaaag gactgtatga ggcaggtgtg gtggttcacg cctgtaatcc    38760
cagcaccttg ggaggccgag gtggacagat cacctgaggt caggagtttg ggaccagcct    38820
ggccaacatg gtgaaactct gtctctacta aaaatacaaa aattagttgg tcgtggtgct    38880
gtgtgcctgt aatcccagct acttgggagg ctgaggcagg agaattgctt gaacctggga    38940
ggcggaggtt gcagtgagct gagattgtgc cgttgcactc cagcctgggt gacagagcaa    39000
gactccatct caaaacaaat aaataaataa aaaggactat atggtaatat tatgaacaac    39060
tttatgccaa taaatttgac aacttataga tgaaatggat gagttccttg aaagacacag    39120
aaactattaa agctctctca agaagatata gataagctga ttagccctat atctatttta    39180 ttgaattta a atgtaaaaat caatatttag ttactgaaaa acttttaagt gtggttggaa    39240
atggtatacg aacttttca actgaatttt atgaagtcta atcacaggta aaggttttct    39300
gatgaaaatt tagtgtctga attgagatat actgtaaaaa atgttatata tcttaattat    39360
ttcttcacat taattacatg ttgaaataat actttgggtg tattgggtta aattaaatat    39420
tatgaaaatc ttgcctgttt tcttttact tttgatgcgt cagctaggaa atataaaagt    39480
gtagctcaca ttctgtttct gttgacagta ctgctttgga gcacagtgtt tgaatgatct    39540
atcatttcaa agacctttcc tcagttcgtt attcatggct gtctgtattc cacatagata    39600
aggtctgaaa tactgctaag tggcatgttt tgttttatgc ttttataagt tgttgatca    39660 ttactgatgt ggacttttgg tgcctcttag gctcattgct atcttccaac cattgtttgc    39720
aatttttacc tagagataaa gagaaagaga catttggttt cagagtagtt agattgggat    39780
catgaaagag caacctcatt ttgatgcttc aaaaatagca catccccgt attactggga    39840 tttgctattc ttgggattac ttcaagaaca tccttgtgtt actggtttgg atgcttctga    39900
atgctgtgaa gtcagtttca tgtacatggc tcatcagttt agctctctct tggctttgtt    39960
tagacagttg gagcatgatg gcctaaacag cttctttcaa ttaaacatt t taaaatagtt    40020
```

```
tacaaatagt aaacaaactc cagttttttgt gactctttgt ctcgcacaac aaaaacacaa    40080
tctgaccatg atcatctggc atcttagggt gaaatatggt tatactttgg cccataccga    40140
aagcaagatt aaaaagggc aggagagata gactgctgaa ctgattttca aggttccaag     40200
aatattgtag gttaagagta aaagtaaact tttggtagaa agcagtgggt tgtctaggat    40260
tgaagtatct gaagttttta acgaaaatt taaaagaaa aatgagaatt gccttacaag      40320
tacaatctct tctttttaa aaaataaact ttattttgaa atagtttag atttatagaa      40380 aaaaattaga tagggtagga agttttcata taccctacat ccagttaccc cagttattat    40440
catcctaatt tagtgtgaga cattttcatg tttaatgaat caatattgat atgctattaa    40500
cttaagtcca gactttattc agattttctt aatttctatg taatgtcctt tttctgttcc    40560
agaattccat gcaggacacc ggatacctca ttacatttca ttgtcatgtc accttaggct    40620
cctcttgaca gtttctcttc ttttttgct tagaaattct ccagaatttc agaaacttct     40680
gggcatcgct atggaacttt ttctgctgtg cagtgatgac gcagagtcag atgtcaggat    40740
ggtggctgac gaatgcctca acaaagttat caaagtaaga accgtgtgga tgatgttctc    40800
ctcagagcta tcattgttgt aggctgagag aagaagcgat cattgagtgt tcttctgttt    40860
tgagtccctg aggatgtctg cacttttttc ctttctgatg tatggtttgg aggtgctctg    40920
ttgtatggtt tggaggtgct ctgttgtatg gtttggaggt gctctattgt atggtttgga    40980
ggtgctctgt tgtatggttt ggaggtgctc ttgtatggtt tggaggtgct cttgtatggt    41040
ttggaggtgc tctgttgtat ggtttggagg tggtcttgta tggtttgcag gtgctctatt    41100
gcatggtttg caggtgctct attgtatggt ttggaagtgc tcttgtatgg tttggaggtg    41160
ctcttgtatg gtttggagat gctctattgt atggtttgca ggtgctctat tgtatggttt    41220
ggaagtgctc ttgtatggtt tggaggtgct cttgtatggt tggaggtgc tctgttgtat    41280 ggtttggagg tgctctgttg tatggtttgg aggtgctctt gtatggtttg gaggtgctct    41340
attgtatggt ttggagatgc tctggtatct gcctgcattg cttgccacac ctgcccggtc    41400
agaaggcgct atgttgacaa ttgtgcctgc acggtgccta ggtcaatgaa gggaaccgat    41460
ggtagccact ggatgctcct gggaaaatgt cactacaggc accagagaag ccagagctat    41520
gcccaaattt ctatgagtct cagttttctt aaccataaaa tgggatcaat gttttgtgg    41580 catgtgtatg agtgtgtgtc tgtgtatgtg tgaggattaa attgtgtatg tgtgaggact    41640
aattgccact actggatcct caaagtggta agaagtgttc ttattaataa tgacatcctt    41700
acactcttac ccagcaagat tgatgggtgt ggcactgctt ctcttttcc atcacatggt     41760 ttccatggta tccttttgcc cagggaatct ttgctttgtg gctagcactt tgttgtttgg    41820
ctaatcacgc tttctgtggt caggacgctg gcttctctgg agccatggga ttctagctcc    41880
ctgtcttgtc cctagagtgg tcactgtctt ctctctccgc ttgcaattcc tgctttgctc    41940
gcatctcact tatgcagtga cgtatatcag tttcaccttg ttctccgtgc tgctgatca     42000 ttggcaccac ttgcatggtg ccatttaggg cctgcttcca gttaagcttg cttctccaca    42060
ggcctaaata tccttgcttg cttcttttat tctcactggc aggaccaggg cggtctgtct    42120
ttgcatgaga cagggtctcg ctcagtcacc caggctggag tgcagtggct gatcacggct    42180
cattgcagcc ttgagctacc gggctcaagc tatcctcctg gcttggcccc ttgagtagct    42240
gggactacag gcgtgcacca ccatgcccag ctaattttta aaattatttg tagagatggg    42300
atctcgccag gttgcccagg ctggtcttga acgcctgggc tcaagtgatc ctccctcctt    42360
```

```
ggtttcccaa agtgctggga tcacaggtgt gagccactgt gcctggccct tgatgtttca   42420
gttcttgata tttgatcctc agagtcagaa atctaaaaa gagggctatc ccaggttgcc    42480
ttggttcatg gcaaatggga cgttaagagg gcagagagaa tatgaacaga aactgttcta   42540
atattggtca tttaatgtgt aagtattgtt cttttttaaa cctccttcat ttttttttcca  42600 ggaattgctg gacacagtgg cttggtgtgt gtctgaggac tgtaggccat ggccctaggt   42660
tgtggtttta ggtctcaggt gctcttcctg gctgtctcct tgcttctttc ccatgtcctc   42720
ttctttgttt ccagccattt ctcccttatg cttaagtttg gtgcagcagg gtttggctgc   42780
tctcagattc ctgcttcctc agatgctgta gttgtcaggc ccagcgggct ggcagcggga   42840
tcaggatctg gctaggtttg ctctcactgt ggcagagtag ggggaggcgt gggagagcac   42900 gtgtgaccc  aggccagctg tagggagcat aggcatggtc acgtagcctt caggtcctag   42960
actttgtctt ctcatgagta tggctgtgtg tgtatggtga aaactaggtt ctacttagcc   43020
caagaaaatg ggcacatttt gcatgtggtt tctgtagaga aatgcactgg gtatctgaca   43080
tagcctggca gcatgcctcc ctcaggtagg ttagtctcag gcggtgaagc acgtgtgtcc   43140
agcaagaact tcatatgtgg cataaagtct ccgttctgtg aggtgctggc aaatcaccac   43200
caccgtcaag aggctgaagt gatttttgtc tagggaggca ggaaaggctt cctggagtca   43260
gcagccagta ggtgaaagag tagattgagg accttcttaa tcatcaccgc ctcttgtctc   43320 aagggggtgcc aggaagctgt ggaggctgaa cccatcttat gctgccagag agtgggacac  43380
catgagggtc aggtcaaggg gttgtacctt gtttggtaga gaattagggg ctcttgaaga   43440
ctttggatgt ggtcagggga gtgtatcatt taggaagagt gacccggtga ggacgtgggg   43500
tagaggagga caggtgggag ggagtccagg tgggagtgag tagacccagc aggagtgcag   43560
ggcctcgagc caggatggtg gcagggctgt gaggagaggc agccaccttgt gtgtctgcgg  43620 aagcaggggc aagagggaag aggccagcag cgtgctgcca tcacccagcg actggcgtag   43680
attgtgagag accattccct gctcttagga ggggctgagt tttagttttc tcttgttata   43740
caataagctt ggtatttgtt tacaaaacat ttgtaaagct aaatcaaggt ttgataaggc   43800
ttctagtttt atttaagaag taatgttgaa ataaatgttt gtccaattcg ctttgctcat   43860
ttaaggactt tcagtacaaa ctgcaacaac aggattagga tttaaacgtt tctgagatgt   43920
ttttactcct cagaatttcc cagaatgtga tctggttttg atttttcaagc ttgctgaccc  43980 aataggttaa cccacaagtt ttacgaagac catctcagtc cacttacatc aactgcccat   44040
gccacggtta aagagatcat cgactgatgt ttggcacagc ttcctccctc ttgggtgggc   44100
aagcatttgg aagagaaggc tcctatgggt gagagtgggg caccaaagtc ttccctgtcc   44160
catcccctag cttgagaagc ccttctctaa tgtggacttt gtgccgttag catcgttact   44220
agcttgaagt tgaccatctg gacgtacttt ctggtttagc ctcacaagtg agcaaggagg   44280
gttgagagat gtgctgtgag gaatgtgggg ccccagctgg cagcaggctc tgggtcaggg   44340
gggcagggac cacgggcata cctgacagtg aggaggggcc acacctgcag aaaaggatgc   44400
aggactccgc cttgggaagt gttctaggcc agagcgaggg tctgtggttt ataagtacac   44460
ccacagtgct cggacctg cagatgtcca gggtgccgtc tgagcccgta tcatccaaca    44520
gaatgttctg ctagtgaaga ttaaagattt actccagggg ctttaggatt tattatatat   44580
atataaatcc tatatatata attttttttt ttttttttt tgagatggag tttcgctctt    44640
gttgcccagg ctggagtgca atggcgtgat cttggctcac tgcaacctcc gcctcccggg   44700
ttcaaactat tctcctgcct cagcctctcg agtagctggg attacaggcg cccaccacca   44760
```

```
cacccggcta attttttgtat tttttagtag agacggagtt tctccatgtt ggtcaggctg    44820
gtcttgaact cctgacctca ggtgatctgc ccgccttggc ctcccaaagt gctgggatta    44880
caggcatgag ccaccccacc tggccaggat ttattgtatt tgaaccatct accattttaa    44940
ttttgatgtt atgtagtatt tgatgataat gaaagttaaa ttgttttcct ttccattttt    45000
ctgtttaagt gaatgacctg tatctagttt attcagtaac ttcctgcata tatttgtttc    45060
tttcattctt aatgaatata ttcttaattt agttgctatt atgttttgct ttgccccaaa    45120
attgaaatct tagtttcctt ttagctcgtt ttagaactag tgatgggatg tgtcttccat    45180
aaatctcttg tgatttgttg taggctttga tggattctaa tcttccaagg ttacagctcg    45240
agctctataa ggaaattaaa aaggtgggcc ttgcttttct tttttaaaaa tgttttaaat    45300
tttaaatttt tataggtaca cgtatttttgt aggtacatgt aaatgtatat atttatgggg    45360
tacatgagat attttgatac aggtatacaa tacataataa tcacaccatg gaaagttgga    45420
tatccatgcc ctcaagcatt tatcctttgt gttacaaaca atccagttac atgctttact    45480
tatttttattt tattttttgag acagagtctt gctttcaccc atgctagagt acagtggcat    45540
gaccttggct cactgcaacc tccgcctccc gggttcaacc gaactttggg ctggtctcaa    45600
actcctgacc tcaggtgatc cgcccgcctc ggcctcccaa agtgttggga ttacaggcgt    45660
gagccactgt gccgggcctg attgtacatt ttaaaataac taaaacagtc agggcacagt    45720
ggctcatgcc tgtaatccca gcatttgggg aggctgaggc aggtgatcac ctgagatcag    45780
gagttcgaga ccagcctggc caacatggag aaaccctgtc tctactaaaa atacaaaaat    45840
tagccaagtg tggtggcggg cgcctgtaat cctggctact cgggaggctg aggtagggga    45900
atcgcttgaa cctgggggtg gaggttgcag tgagccgaga tcacgccact gcattccagc    45960
ctgagcgaca gagtgagact ttgtctcaaa aaataaaaat gaaataaaat tgggccgggt    46020
gtggtggctc acaccttagt cccagcactt tgggaacctg aggcaggtgg atgcttgaga    46080
ccaggagttt gagaccagca tgggcaacat ggcaaaacgc tgtctgtaca gaaattagct    46140
gggtgtggtg gtgcacaact atagtctcag ctacttggga gattgaggtg ggaggattaa    46200
ttgagcctgg aaggttgaat ctataggtag ctgagattgt gccactgccc ttcagcctgg    46260
gcgaccaagt gagaccctgt ctcaaaagaa aacaaaaaaa acaaaaaaca aaccactatt    46320
atcgactata tattattgtc tatgatccct ctgctgtgct gtcgaatacc aggtcttggg    46380
cccttatttc catcactgag caaacttcac tctgttaagc agcaggtgtg ggatttcatc    46440
gttattcagt aattcacaat gttagaagga atgctgtttt ggtagacgat tgctttactt    46500
ttcttcaaaa ggttactctt tattagatga gatgagaatt aaaaatggta acttactttta    46560
tatctttata attgaagccc actagacctt aaagtagtta ccagatgttt tatgcattta    46620
aatggccttt tctctaaaat tagaaagtaa caaggaaaga aaatgcttcg tttctatgca    46680
accctcttgg tgactagtat gtgactctta atgcaaccct cattgcaccc cctcagaatg    46740
gtgcccctcg gagtttgcgt gctgccctgt ggaggtttgc tgagctggct cacctggttc    46800
ggcctcagaa atgcaggtaa gttgtacact ctggatgttg gttttttgtcg ggggccagct    46860
gctactgatc ctttatgtct cagctcagat gtcatttcaa aagtctgctc tgccctctcc    46920
aaattgcagt cgaccttgcc ctgtttatgt ttccctcata gcactaatcc atgtcagaaa    46980
ttgtcacgta cagtctatct gtgtgcttgt ttattttcta tcccaccctt ccgcaagaga    47040
cttatgggat gtgtgcccca ggacagcagg ggtcttactg tcttatgctc tgttgcagcc    47100
```

```
cagcagcgat aacagtgtct gcacatagta cttgcttaaa agatacttgc caaattgttg   47160
aaggttgagg taccaattc attattgctg actataggag ttatagcaaa atatccattt    47220
gtctgttaca tgagttaaaa atatggttgt tgcactgtga atagtttggt ttagtcaaaa   47280
cagttgtatc ttaacggatt gagaaacaaa agcaggacca cttttcatca gctccctcct   47340
tctccttaac cagcaataca tgctgatgct gatatcccat agaccctcag ctccatcctg   47400
agtcactggg aatgtggtct aaaccctcac tattaatatg aactgagttt caataagaat   47460
cttatatggg tcgggcatag tggctcatac ctttgatccc agcacttcag gaggccaagg   47520
caggtggatt gcttgaccca gactaggcaa catggtgaaa cgccgcctct acaaaaaata   47580
caaaacttag ccaggcatgg tggtgcgtgc ctgtggtcac agccactcga gaggctgagg   47640
tgggaggatc acttgagcct gggaggtgga ggtcgtgttg agccaagatc gcaccactgc   47700
actccagcct gggcaacaga gtgagacctg tctcaaaaaa accaaaatcc agaaaagaac   47760
ttatatggct gcagaggtat aatcactaag gaaatttcct tttgtataat cttttttctt   47820
ttactatcat ttaaaaaaat gtgttatatt tctgaagcaa cacatccagg ttctgcacat   47880
agcagccaaa gtgaccttaa agaatataac tgggtcttgt cattcccta tttaaactct    47940 tgtacccatt tcccagtgcc gtttagatag agattccaga ctcgtcaatg gctctgtcac   48000
ctcagacacc ctgcattgac tcattagtct gattagagtc aggttttct tcctcctgat     48060 ggttttttt tcccccttag ttctcagcgg aacagtcact tccttaggga ggtttcccca    48120
gccaccctct gaggccgtgc ttgttgccag actctgccac tagagggcag ggctgcacca   48180
ctcctggcac ctcgcacccg gcctgccctg tcactctgtg tgttgggtga attcctgtga   48240
tctgtgactc actgctctgt gtcctacaca ttcggctttt cttctctccc cacaacccca   48300
ttttataatt ctccttttc aggaaagctt tattcccatt taaaaatttt tgttttaaa    48360 atggtatttt cttacactta ttttctaatt aaaaatgagt gttttaagaa gtattatgat   48420
ttactgcaaa taatttttaa acccagcctt ttagatcctc tgtgatcata agagaaatga   48480
aggatgtctc ccaacacttg agcttcatcc acatttcatc ctcctgttct ttcagctgag   48540
tttttcccat cccattaggg actgttggaa tataaaactg gcttttccct aacagggaat   48600
gaattgcttc tgtttctcct gaaggagagc tggaagaatg acttgcgttc ttttgcatac   48660
acaggcctta cctggtgaac cttctgccgt gcctgactcg aacaagcaag agacccgaag   48720
aatcagtcca ggagaccttg gctgcagctg ttcccaaaat tatggcttct tttggcaatt   48780
ttgcaaatga caatgaaatt aaggtatgat tgttgcctca ggtcacaaac atgcgagtga   48840
tgctgtgagt gagtctgtgg agggtgaggg cttctgaaca gggagtcctg tgggagtgct   48900 tcttgggta tgttgtatgt cgtaatttag actaccatca tttgtgttat ttttgaggca    48960
cctaaggact tctttccact tctcatttct tactgtgggg tgaagagttg aattgggaga   49020
tggtttctag atgcaaattg aaaaggcatt tttccagagc agatttgttt tcggcgtact   49080
agagtgactc tttaacctag ctgcgggaag atgactgtgc caagactgca ggtaggagaa   49140
agctcactga cgaggccttg tgggtctgaa cgtcctgcag ctatcagagc ctgttggctt   49200
cctgttgtgc attccaacaa atcatcttca aacccacttt agtgttttgt ttataatgtc   49260
cagaaatagt gaccctgtca catgctctac agattacagg attcttagcc tcttcctttt   49320
tggtaggtca gtcctgggtt tgagcccaag tgaccctcct gggaggtgat gatacacact   49380
gggtagagtg gaatcagatg gacttggatt agaattctgt cctctttact agttattttc   49440
ctctaggcaa actgcccaac agctctaagc tatttccttc gtattctgaa aaataagcct   49500
```

```
taatgggacc catatagggc aactctgaga gtaaaataaa ggaatatgtg ttagagtgta   49560
gcatagtcac ccacgggaag ggcttagatg ttagctgcta ctgctcttat tagctgaatg   49620
atttggaata aactgttagc ctctctcatg tttttctct tgagcttcga agttttcttg    49680
ttaatactaa ggagatattc aaactagtca tggggttttg gaatgacgaa gggagatgat   49740
gaatctaaag aatttagtgt aatatttctt catgctcagt aaatggtagt ttctgctgct   49800 gttatttta ttaccatctc tttggaatgg gagtaggtgc tcctttgtgg tcagaggctg    49860
tgagagctcc acagcgccag tttgcccatc tgtacactgg ggtctgttga aggcagtccc   49920
ctctgtgata tctctggctg tcagagctca gatgatagat ggtattttg tactcttagt    49980 tctcatcatt ttcatgattt cgatcaccat ttgagtatga tgatgctaac actttgttga   50040
acgtagaatc cgttaattac ttccttcctg aacctttggc attaaaaaaa atctattctg   50100
ctacctctct gctcatttat ggttattcaa atttattatc aagagcctgg tacagtggct   50160
tgtgcctata attgtagcta cttgggaggc tgaggtagga ggattgcttg aggccaggag   50220
tttgagacca gcctgggcaa gatagtgaga ccctatctct aaaaaaactg aaaaaaaatt   50280
agctggacat gatggcatgt gcctgtggtc ctagctactc aggaggctga cacaggaggc   50340
tcggttgagc ccaggagttg gagttcgagg ctacactgag ctgtgattgt gccaccacac   50400
tccagcatgg gtggtaaaac aagatgccat ttcttaaaaa aaaaaatat atatatat      50460 attatcaatg aaattcagta gtaccaacag gattataaac aaagatagta gttcccttcc   50520
tactttttct cttaatcctt gtgtctcaca ggcaaacata actcttagta tttcttccaa   50580
tatttacttt catgtttctt tctttctttc ttttttttc tttgagatgg agttttgctc    50640
ttgttgccaa ggctggagtg caatgacgca atcttggctc accacaacct ctgtctcccg   50700
ggttcaagcg attctcctgc ctcagcctcc tagtagctgg gattacaggc atgcatcacc   50760
acgctcggct aattttgtac ttttagtaga gatggggttt ctccgggttg gtcaggctgg   50820
tctcgaactc ctgacctcag gtgatcctcc cacctcagcc tcccaaagtg ctgggattac   50880
aggcgtgagc cactgcgccc agcaacttcc acatttctaa ataacatgct tctactgcta   50940 ttttttttt caatttaga catttttta cttttcactat agttctatca gaattcagtg     51000
tgtacgttat tatgcctaag taaatagtca tggttgctta cgtattatat ttctttgatt   51060
gtgtttctta tttgatgaga aagctgtgtt ttttgctctg ggttgaaact ggagagagga   51120
cctggggagg aggaggagga cagatgaagt tggtgactgt accttcatgg ccatagctgg   51180
gttctcagca cccggggatc tgctgatcac ctactcatag gccaggcccc tatcgaagtt   51240
ctaggtgacc cagtgctggg gacggggggg ccacctgcaa ggtctaatca tggaggtggg   51300
ggctacagtg ttggcttgtg ctgggccag catccttagg aaggcatctt ggaggtggag    51360
gagacagccg cccacttctt gattgggggcc ttcagcagca ccagcttctt gggcaggctg   51420
gtgctggctt tcatcaccat gtcgtgttca atcttcttcc agatcctgac ttctaggttc   51480
agctttcctc agaccctggt tcctttcaga ggccattgct gctgccttgc tctttgctgg   51540
cttgtgcctt gattatatgt ctttgtacaa cttttgtttt tcctggagtt aatcttcaca   51600
tctgttttct tggagttaat cgttacctct atatcgcttg cttattattc tttggccttt   51660
ttgtcttctc acaccttcca acttctttgt aatatgtgtt tagtacaatt tttcatgaca   51720
ggtagtttac tgaatcagtt tttcccccagt gtggtcatcc aacttgagtt atccagctct   51780
ctgccccagt ctgggcaggt tgatcttcag gtctgtagta cacttgtatc ctaggacttc   51840
```

```
tctttgccat tagcctggaa tttcctttgc agttctcccg ttggatgccc agttcctaga    51900
tgccatatgt ttttctatcg tctagtagct tcctgagaga agatgaatgg gagggaaatt    51960
gtatgaggtt ttgcattcat aaaaatgcca tttttttttcc tgtacacttg gctgggtatg   52020
gtgttctggg gtagaaatca ttttccctca gaaatgcaaa gtctttgccc tgttgtctta    52080
aaatctccaa cgtgacccga ttccttaacc tatgaatgta cttttctttg gaagctttcc    52140 attttttgggg aggtgaagtg ctaggtactt agtaggcctt ttaatttgga aacttacatc   52200
ccttcagttc tgggaaaatt ttcttaacat ttctctgaga agttcttgcc ttttatttttc   52260 tgtgttctct cctgaaattg gttagttgga tgttggtcct cctagattga ctcacatctt    52320
acctttttct tttctttttc tggtacttt tagatatcca tctcaaactc ttctattcat     52380
tgttatgttt ttaacttctt tcttttcttt gtctcttgat ggggtcttgc cctgttgccc    52440
aggttgtggt gcagtggtgc gatcatagct cactgcagcc tcaaattcct gggctcaagc    52500
agctgttctg cctcaccctc ccaagtagtt gggactacag gtatgcacca ccacgtccag    52560 ctatttctt tactttttttt ttttttttttt tgagatggag tcctactctg tcgcccaggc   52620
tagagtgcgg tggtgggatt ttggctcact taagcctctg cctcccaggt tcaagcagtt    52680
ctcctgcctc agcctctcaa gtagctggga ttacaggtgt gcaccaccat gcccggctaa    52740 ttttttgtatt tttagtagag ccagagtttc accatgttgg ccaggctggt ctcgaacgcc   52800
tgacctcagg tgatccgcct gccttggcct ccgaaagtgc cgggattaca ggcgtgagcc    52860
catcattaga tctttaaata ccagtatcta taagtctttt cctcttgagt cagctagtat    52920
ccctggaagg aaaattactca ttttcctgct tggaggctat aagcttggct atgtttatcc   52980
tgcaaccggg gactggaagg gaggggactg acagtgttgc tggtcagggt gccctcttac    53040 ttttttgtttt ctgtgtgcat ctcacgtctg tcctcagcct atgtaaacac ctcttgagat   53100
tatccctctc aatctttgcc ggaggtgggg gaggggctgc ttcctgggct gccttggatt    53160
ggagggaaga cctcaggtga gtgggtggga atttgcccaa ggagccatga gaccagccac    53220
tatttcaccc tctccatccc tccactttca gatgtatgtg gcgcctccaa agcccgagct    53280
cttcttggcg tctgtggctt caataagctt gcttttttgct ggtatccctc ctaccctccc   53340
ctgtccccag caaagcttgc atttgaactt cttcctacgg gctaacaaat cagtcagtta    53400
tgtagctctt gttactttttt agcttccgaa gttttgttga cacccgtagt ctgctaatgt   53460
ccctgttctg ttcttttctgt tcgtgtaaat atatgcttta tacaacttct ttacatgatt   53520
tttgtggggt ttctgggtag cagagcttca caagttcaat ccagcgtgtt ggattagaaa    53580
tctcccaccc tctggtttat tcttattctc aaaattacct gccaaacact gatactccct    53640 tgttttttcct tttcctgaca ggaaatgtac ataccataca ggacagaaat cattagtgta   53700
tcccttggtg aataaccaca aagtgaactt aaccccttgta accgccaccc aggtcaagac   53760
agaatattac caagcactca gaagcctctc ccctattccc ccgtcactgc tcctgccttc    53820
ctccccaagg tcatgactgc tggcttctaa ttccagagtc tgttttaaa ttctgtgtac     53880 atagaccatg gattaagtgt tcttttttgtc tggtttattt tggtcgacat taagttcatg   53940
agagtcttct atattatcgt gtgtattagt attcctgtag ttttaggagc ttcatagcat    54000
tccattgtag ggatatacca cagtttattc attgtattat cactgggttg tttctagttc    54060
ttggctattg cgagcagtgc tactgtgacc actcttaggt gtgtcttttg gagtacatgt    54120
gcaggtttcc atcttgcaca gctagaggtg gagttgttgg gtgatagggt gtgtgcatct    54180
cagctgcagt agaaactgcc aaatagcttt ccttgagtgc ttgtaccagc tcaccctttt    54240
```

```
gccactgtgt atggggattc caggagctct ggtcctcgct agcacttgga attgctgatg   54300
cttttactct tagccttcct gatgggtgtt ttctggaatc acattatgat tttaatttcc   54360
attccttaaa gtaccettgg ctctgaagtt taatgattca tgcatctctt cccttttgaa   54420
gtactcttac aggtatgttg tgcatgtgtt gaaaagtggc actatctatt ctaaaataca   54480
gtatgcctcc tctgtgtttg aacagttgta gcgtggcctt ggggcctcct gttagctggc   54540
ttggagaagg gattcttggg attgtagaga ttagacctga ggaggcccct tggagctctc   54600
tgactaaatt ttattcttta ttattccaaa ctatttaagc tcaccgtgtg ctgactcatc   54660
ataataatga gtagctctca ttgtgcttgt ctatttggac tcatacaatg atttttttt    54720 tttctttgag acagagtctt gctctgttgc ctaggctgga gtgcagtggc acaatctcgg   54780
ctcactgcag cctccacctc ccaggttcaa gtgattcttg tgcctcagct tctcaagtag   54840
ctgagactgc aggtgcgtac caccatgcct ggctaatgtt tgtattttta gtagagacgg   54900
ggtttcacca tgttggccag gttggtctca aactcctgac ctcaagtgat ctgccttctt   54960
cagcctccca agtgctggg attacaggtg tgagccactg agcttggcca aagtagtttt    55020
ttaagatgtt agtatctttt cttgcagcta aaaaagtttg tcagagatga ttctactttg   55080
ttctccaggt gttttctcag ggagaaattg gaggcagtaa gccactgggg gagtcctgtg   55140 gctgggggg gggtagtcc tgtggctcct tgtcagggag tcctgtggct ggcaaggaga     55200
gaagtcctgt ggctgggttg ggagggagtc ctgtggctgg gtctcatcc tgtgcctaac    55260 agtgtccaga ggtgccgaga ccagctcagt cggggagacc ctaacccagc agcgctagag   55320
gaattaaaga cacacacaca gaaatataga ggtgtgaagt gggaaatcag gggtctcaca   55380
gcctttagag ctgagagccc tgaacagaga tttacccaca tatttattaa tagcaaacca   55440
gtcattagca ttgtttctat agatgttaaa ttaactaaaa gtatcccta tgggaaacga    55500 ggggatgggc cgaattaaaa gaagaggttg ggctagttaa ccgcagcagg agcatgtcct   55560
taaggcacag atcgctcatg ctattgtttg tggcttaaga atgcctttaa gcggttttcc   55620
accctgggtg ggccaggtgt tccttgccct cattcctgtc aacccacaac cttccagtgt   55680
gggcattagg gccattatga acatgttaca gtgcttcaga gattttgttt atggccagtt   55740
ttggggccag tttatggcca gattttgggg ggcctgctcc caatacagag gtctcgtgta   55800
aattccctgg gaggcgataa gcctctgaga aacagactat gctaaccacg ccatgaaaga   55860
gaaacttatt tataaatcag atgccagtta ctagtttact gcttatttgc ccaggcgtag   55920
ctctgacaga gtccccgact catagtgctt gctcagtgca tgctgaacaa tgattggaat   55980
caagtcatgg ctcagagcat agttttgaat aatgggaaat ggatgttctt aagtaacata   56040
gtcaccaaga taatgcgact agctgggtca cccctttca attttaggat attttttatca   56100 agatttaaat ggccatcatt agagttatag cactttctcc tttggattgt cctagaggcc   56160
catgagaaag tattccctaa tttcttagga aacagtttg tgggtagtat gcggtcatgt    56220
ccagttaaat tgcagatatt tccgatcgaa gatgttccag tcctgagaac ttcgtgacat   56280
tagcaggact tctacaagcc atctcttagg gtggggcatt tactgcagtt ggctagtact   56340
cttttctcct taactttgtc atttgttgat tttttttaa ctgtccccaa atactgtggg    56400
cagagtgtat ctagaattga ggcctccacc attgcggaga ggacatggat gctgagcagt   56460
cccctgagtg aaggttataa agaagcaaat agactacaca tgtctgtaaa ctgctcttga   56520
gtgtcccaaa tttggggtac ttcagttcag ctgtaggaaa agcctcaaac tgtttatact   56580
```

```
ttgcaagaat tggaaacttc taattcacgt taagttttat gtaatacatg ataagcttca   56640
taggagcttc atcttttatc tacttggact tttgcttccg taggttttgt taaaggcctt   56700
catagcgaac ctgaagtcaa gctcccccac cattcggcgg acagcggctg gatcagcagt   56760
gagcatctgc cagcactcaa gaaggacaca atatttctat agttggctac taaatgtgct   56820
cttaggtaag gtggaggcat atgagtggaa gagtctccag catgtactca agatagacct   56880
ttgaaataaa taaaaccaga tgatccctca gcttctagac caggctattt ggcactggtt   56940
gattgaatgt gaactgcact ggggctgctg tgagcccgca tgggtctctg tgaccctgca   57000
gatgcagccg tgcccaggga ctgggcagtg ggtgtgggct ggtgtgagcc ctgtctgcca   57060
cccagggcct ggccctctgt ctgtgtcggc catgactatg gtgagtcttg taggcttgag   57120
actgtgcctc gggttcctgc gggttctctg taggtcagtt gacagtttct cctgttgttt   57180
gggtaactgt ggaaacgaac actggcaagt gctgaagcga gcatgtggac gtgcgatatg   57240
aaataacgac ctggctttca aaggcagtga ggctctctgg aaaggacctt gctgagctag   57300
ggatgtgggt gtgtagccat tcccagtggg cctcatggcg tactcgttca tgatcatgtt   57360
tgtgccatct tgatctctca ggatctcttc tttttttaaca gattaagccg ggaatctcca   57420
aacagtgagt cagatgttaa gatgtcttgc ttccacccce acaggcttac tcgttcctgt   57480
cgaggatgaa cactccactc tgctgattct tggcgtgctg ctcaccctga ggtatttggt   57540
gcccttgctg cagcagcagg tcaaggacac aagcctgaaa ggcagcttcg gagtgacaag   57600
gaaagaaatg gaagtctctc cttctgcaga gcagcttgtc caggtaggag cacagggttt   57660
actctaggcc ctgcatgtga atgactgaca ttcaaagaac cgattaattt ggaagagaag   57720
cggcagaacc gagagttaga ggtgtggact ctggagctgc gctgctcgtt tccaacccta   57780
ggtgctgacc tctagctgtc ttccctctgt atgtccctgt caccgtgagt caaatgcggg   57840
tgatgcctcc tcaggtgccg tgttacctaa gcctctcaga gaccactgct accctgtttc   57900
taaaaccaga ggtcacgata tgtgttcatc cacccagtaa atactgattg agcacccact   57960
gtgtgctagg ctctgggata ggggctgggt atacaatggt gagtatttca gctgcagctt   58020
ctgccccgtg gaggctgtgg cctagcacac tggtctaggc acggtggtat atgctcactc   58080
aaggagatag ggacgtggtc gtttggggtg tcggaacaaa atgtcggaac ttctctttcc   58140
aatgcagaga aaccttgcag taattctaat gtactgtgat tggcagttga cttcagttct   58200
ttgtagcacg cttactcagg ttatttcact aactatgtaa ccatgcagcc tcattttaag   58260
caattggatt ttttgaactt tacttaaaat gttatgtcag gttttttatt gtgcttaatg   58320
tgtgccattt agctaagttt tgtaggatac gaaattgtaa gtggcttaaa atgattctta   58380
atagaatcat gaattgaaga taatgctaat aatttaagca ctgagttagg tagtgtttgt   58440
aaaatgctta gaatgcttcc tggcacatgt taaggccatg taagtgctgc gtgttgataa   58500
acagctgagc aaaagtggac tcttaagaaa gtattgggc tgagagttct gttccaacca   58560
gctgcccttt ggttatttt cagaataaaa gcagagtctc atgggatatg acatttatat   58620
ttccttcaca aaaacactg ctgagtgttt tgttgagtaa aaagggtgta gccatggtaa   58680
taatacattt aaaatatagt ttatttcatc tttaccttgc cttgttttt ttttaagcta   58740 gcttttatt gagaattcca cacatacaaa agtatcaact catgaccagt tatatttcat   58800
ttataatcct acttctccct tttttatta tttgaaagca aaccccaatt atcctcttat   58860
ttcatctata agtatttcag tatctctata gatgaggact cttctttatt tttaaaactt   58920
tattttaaaa atgatggtca gatgcagtgt tcatgcctgt aatcccagaa ctttgggagg   58980
```

| | | | | |
|---|---|---|---|---|
| ccaagctggg | cggatcactt | gaacctggga | gtttgagacc | agcccgggaa | acatggcgaa | 59040 |
| accccatgtc | ttaaagaaaa | aaatcagcca | agtgtggtga | tgcatgcctg | tagtcccagc | 59100 |
| tacttgggag | gctgagatgg | gagggtcaca | tgagcctgga | agatcaaggc | tgcagtgatc | 59160 |
| catgattgta | ccactgcact | ccatcctggg | tgatggagca | agattctgtc | tcaaaaaaac | 59220 |
| aaaactgcaa | acaacgtca | caaaacagtg | ccattgttag | acctgaaaat | attaaacatt | 59280 |
| tcctacatca | aatacccacc | aactcattat | caattttct | ctctactctt | ttggaatcag | 59340 |
| catctaaata | aaattggtcg | ataaggattg | taaatctctt | tgatgaactg | gttccctcc | 59400 |
| atcccagttt | ttttcccta | gagttcattt | attgagaaac | cagattgttt | gtcttctaag | 59460 |
| ttttcctgtg | gtctgatata | ctgcttccat | ctccactgtg | taaattaaca | ccttttctc | 59520 |
| ttctctgtat | ttcctgtaaa | tcaataattg | gaggaaaagc | cttgtcagat | ttagtgtata | 59580 |
| ttttatatct | gagtccagta | tttcttatat | aatatttaa | gataagtgta | ctcttttaaa | 59640 |
| aagtattgaa | actatatgct | cattttttt | taactgatgc | ttttaagaag | gctgcttgat | 59700 |
| cataaaagtt | tagagatcat | tggtctgatg | ggaaaagcaa | ataattacta | aaccgtttag | 59760 |
| caaggttgag | gtgcacatgg | tgggggcctgg | agaagttcag | tcatgagccg | tcacttatgg | 59820 |
| gcacgtggaa | tctgacccgg | cacagagttg | ggagaagaca | ggagctttat | agacagaaaa | 59880 |
| tgtggtcttt | gctaagtccc | aggagtgaaa | gggtgagaca | gtgctcacag | cacacgagtg | 59940 |
| tgggtgcgta | gacagagcaa | gggtgggtcc | tgaaaaggcc | tgcaggcttt | ctcatagatt | 60000 |
| agcaagagtg | ctggttacgg | aggtttctaa | catttgtgaa | cagatcgaaa | ctgtgttaaa | 60060 |
| ttgggattgc | agtaatcctg | gaaggacagg | gatagagggt | gaagggaaa | aaagggtatg | 60120 |
| gatgtgagac | ttaattgctg | atttttctta | gacctttctc | caaagtaaat | aaatgatgtg | 60180 |
| gcacattttt | gaactggcaa | attctaaact | ctagatatga | ttatctctat | aacatatctt | 60240 |
| actccatctt | cttttgacta | aaaactgttc | ttaattaaat | taccatgaga | cgttcaattc | 60300 |
| agcaaatgta | gtttggctaa | ccatatttaa | ttagaattta | atataatcct | aggcctggcc | 60360 |
| aaactattaa | gcaagtgtgg | gcaaaatatt | gataattta | gatatgcagg | aacttagttt | 60420 |
| gctttccatg | tgtgcttttc | gaaaaaggaa | taaattgaaa | aatagaggaa | gccctgaaat | 60480 |
| ccaagaagca | aactctctca | cctaggcatg | cagtaaaagc | aattctagga | tgattgctgt | 60540 |
| ttggcgcgta | gttcgtatta | gaaaccattc | ttcttgaata | aatagtatgt | ttaagaagct | 60600 |
| gggcagaggg | aaggcatatg | catatattat | caacaaggag | ggagaaaaag | gcaattagta | 60660 |
| accatccata | ggagggtcag | caagatttat | aaaggaaatt | tgtgatccaa | gtatgaagca | 60720 |
| aaataaggtg | cagaataaat | tttaagcaag | taatagatta | gagtaagaga | acccatttga | 60780 |
| ccattaacct | tgggacattc | tctttcaaat | gacatggagt | agtactgaaa | tctttctttc | 60840 |
| tttctgagtc | taggttattg | tgactggact | cagaaagaaa | tatttcatta | ttgcagtgaa | 60900 |
| taacatttgt | gaacattatt | gttcataaat | tatgcagtga | ataacattta | tgaacacgtg | 60960 |
| atgtgtaaga | tacatactgt | ttattttag | ttaagttttt | tggctcaact | tctaggcaga | 61020 |
| gaacattaaa | tgtaaatagt | gttacctagg | agcatgtaaa | tggaaatctc | catagtatga | 61080 |
| aagcagtgct | gttgctaaca | gaattagga | gggggcagat | gaggtgaagg | aaatgtgggt | 61140 |
| gctgatttcc | ttattacatt | gagaggagcc | aggagattct | tgttcaaaa | tggatggctt | 61200 |
| aagaagtcaa | agtataagct | gattacgtag | agcaggtacc | caaaaatgtt | ttgtgtaagg | 61260 |
| ggccagatag | taaatatttt | cagtcttgca | ggccatccca | agtctgtggc | agctactcaa | 61320 |

```
cactacctttt gtagcatgaa agcagccaca ggcagcccat aaatgtggct ctgttccggt    61380
gaaactttag gtacaaaagc aggtgcaggc cagacctgac ctgtgcactg tggtttgctg    61440
acctgggatt cagggtata gaagttacca tcagaagagc taaaagtgag acttttact    61500 ttatactctt ctacactgtc tgattttgaa aaaagaaac atgtatttta taatattaaa    61560 gataggtg gcaaatagca aataaaaata cagaatacca gtgaaatttg aacttcagat    61620
acattatgag taattttatg gtgtaagtat attccaaatc atgtgggaca tacttacact    61680
acaaaattat ttgttgttg tttacagttt aaatttgagt gccttgtatt ttatctggca    61740
actgtaatta aaggaaaaa gaataaaattc attatgttca taatgtga tatagcaggg    61800 gtccccaacc cccaggctgc agagtggtac tggtccatgg gtccccaacc cccaggctgc    61860
agagcggtat tggtccatgg cctgttagga accaggctgc ccagcaggaa gtgagcagca    61920
ggtgagctgg cattcccacc tgagcaccgc ctcctgtcag atcagtggca gcattagatt    61980
cccataggag tgcaaaccct attgtgaact gcacatgtga ggggtctagg ttgtgcgctc    62040
cttatgagaa tctaatgcct gatgatctga ggtggaacag tctcgtcttg aaaccatccc    62100
ctggccctgt ggaaaaattg tctcccatga aaccagtctc tggtgccaga aaggttgggt    62160
agcactgtga tatagtatta aaagtgctaa taaatatggc atactgcctt taaaatgtct    62220
ggtagctctt tctcagtggc actcataata gtgttttttg attttaaat gtgtgtcaag    62280 ctgactctcc cctccgtgta tgctgggctt tattttccct ttcctagtca ccagttttgg    62340
gaaatagaga tcttcattct catgctgctc ctctagtgca agtgctccat ttattttaa    62400 ggaattaata taacaaaaaa tcatgggaat ttagaaaaca acatggaagc taatgatcac    62460
attggtggaa gtgataggga aatatttagg gggagaagtt aaggtataaa ctttgtcaat    62520
gaagtcctat taaaaacaac aaaaaagtga agcttaggat gcattttata aactctgacc    62580
agaacacctg tgtttctctg tttctaggtt tatgaactga cgttacatca tacacagcac    62640
caagaccaca atgttgtgac cggagccctg gagctgttgc agcagctctt cagaacgcct    62700
ccacccgagc ttctgcaaac cctgaccgca gtcggggca ttgggcagct caccgctgct    62760
aaggaggagt ctggtggccg aagccgtagt gggagtattg tggaacttat aggcaagtta    62820
ttagcaaggt ctactcttac aattaacttt gcagtaatac tagttacact ctattgatta    62880
tgggcctgcc ctgtgctaag cagtctgcat tccatcttcc ttgccaaaac ttataataca    62940
aatttcatct ttatttata aataggggag ttgggctggg tgtggtggct cacgcctgta    63000
atttcagcac tttggaagga tcgcttcagc ccaggagttt gagacaacct ggccaagtga    63060
gaccctgtct ctacaaaaaa aaaaaaaaa aaaaattag ctgggcatgg tggcacatgc    63120
ctgtagtccc agctgctttg gaggctgagg tggtaggatt gcttaagccc aagaggttga    63180
ggctgcagtg aatcttgatg gcagctgcac tgagcctggt gacagagcaa gatgctgtct    63240
caaaataaat ttaaaataa aataagagaa ttaaagttta gcaggttggg tggcaaaatg    63300
aggccacaca tttaaagccc ctcctcctga ttctttttctc tgccttggct gcctcctgtg    63360
gcattttagg tgctgagaaa tgaaaacagt agggaaaata gttccaggat cctcatgtta    63420
atttgccaga aatggcatct tcaagtcgtc agagggatct gagagttcct tcctggcctg    63480
acttgagaaa atccgtctgt ccccagctct gcgtctgcct ccactgccca gtcacctcct    63540
ctccatgctc ttggggctgg gccctacccc accatgcagt gctgcctgg agcagtgagc    63600 ttggtgggtc ctgtctggca tgagagctgc ctttgggagc tggatcccag cctctaccac    63660
tgggtctggt gcctagcagg ctatggataa acttctgctg actccggcct ctcctaagcc    63720
```

```
actgcaacgt ggtcggtgta gtgcacagtg tgtgtgcagc gtggccttac tcacagcctc   63780
cacattagag agaatctgac tgaagtctta ctgctgcctc gtgtgaacat aaatgtttgc   63840
cagaaccatg agcaggaaat gttaatctgc cttgtttcct gtcctttaca cggaagaatt   63900
tttttctgta tggaatgcgt gccttacaaa taatgagtgg aaatacccat cgctaatgaa   63960
aagttatact tgactgttag tcagctaaat aatctgagat ttctaatact tttaatttgg   64020
cttttacaat gcaatttatc ttagcttttt tgatttctta ggtcatatct ttagaactat   64080
atatttgaat gttaatgtaa ttttcatatt gaattaaaa tgttgaactg cgatgttaag   64140
tgtttcctgt ggaaaaacgt tcacattttc tctagtttta agttgaatc aagctgtttg   64200 aagattttca catttcttct agattttatc agcttgttac tttatctgtc actttctgtg   64260
atttgcagct ggagggggtt cctcatgcag ccctgtcctt tcaagaaaac aaaaaggtga   64320
ttatttcaga aatcagagtc ttgtgttgaa tcttactgat tttcttgtat ttctgtaatg   64380
taatgtatct tgtatttctt gtaatactgt attggactct gtgtatatct cttctcagat   64440
gagtgattat atgtgtgaat gttgctggaa tctgataacc aggcctgaat agttttgtag   64500
ggtggctttt aaaaattact ttcatatcag aattgctttg tcataaattt tgaacgcatc   64560
ataaatttct aatgttcggg gtcagcagac ttttttttgta aagggacaga gtgtaaacat   64620 cttagctta tgggccatat ggtctctttt gcaacattca gctctgccct gtgacaggaa   64680
tgcagttgta aagacatgag ctactggcca gctatgttcc agtagaactt tacttacaga   64740
aacagacagg ctgtagtttg ccaataccctg ccttagggaa tgtgttgtta tattttgtga   64800
gttaccttct cagtaaattt tatttagtat tagtcaggaa tattattaag tagcttcttt   64860
tccagcctgg tcaacatagt gagacccggt ctctaccaaa acaaaacaaa acaaaaaaac   64920
agccacgcat gtggcatgtg cctgtagcct cagctgctgc tcaggggct gaggcaagag   64980 gattgtttga gcccaggagt ttgaggtcac agtgagctgt agtcatgcca ctgcactcca   65040
gcctaggcaa cagaatgaga ccttgtgtct taaaaaaaa aagtttcctt tgttgggtta   65100
ttttaatttg gacctggtta tcatttttca gccatattta actttgtaca tatcagaatg   65160
ttctgataaa acttaacttt tattaaagtg tttgtgtatat aatctgctag ttttggtaca   65220
cattatcttt tgcaatgcca gttattttct tttccagtgt gggtttgcat aggaaaagaa   65280
ttgctgtcac tttctattt gaaatcttaa aagactgatc ctttttgtg tcatgatttg   65340 agtatttaat tgagagccta atgcctaata ttatttgcag tattaaatgg gatcttaaca   65400
ggaatagcat tctagccttc attgaattaa gtaaacattt cttaagagaa cttggaatct   65460
ataatatttg cgtcatcata gtatgagata cttaatcaag tttgagattt tagtgaaaca   65520
ttgtttagaa gccaaaagga ttctaggaaa aattaatgtc tatattcttg aattaggaga   65580
gattttggga cgtgtgacta agttacgctg acacttgttt gtttcttagt cgcttttcc   65640 agtggcggtg agaacgaaga tgactgattc acattgctca gatgagttta tcctcttctg   65700
gctgggacat gggatatatc ctgtctcttt taagcctttt tggtattttt cccccattga   65760
gagctgtgtc ttcaaactct tctgttatag ctggaaaatc cttttaagt gaaatctgcc   65820 caaattataa gacagatgaa ggtagagttg tgttggatat aggattaggg tgaaagtagt   65880
gggggtgtcc tggagcctct cttctggtgg cagcctagct cttgtgcctt tgaggaaatt   65940
accctgggga cggctctgtg gaacatattt gcaaaccact gatttggaag atagagatgg   66000
cttttgttaa gatctgaatt caccttttg gcattttatt tgatttctca aggtaaagaa   66060
```

```
cttattttgt aataaagttt cctattattt agtagatagg ccaagttgct gtgttaattc   66120
catgtagatt ttgggtttcc tttgctcatt ttttcactct taatctcaca tcattgtaag   66180
tttatggaag ttatcatact tctgactttt tctttgaaga gcagaaatta gaaattccca   66240
ataattattt tgatagtgtc atttaatgac actcacatgt gatgtagcca caaagattta   66300
atgagttcag ttttaaatca tattaagact gttggtttca tttgttctca ttaatgtaat   66360
tctgaagatg aacaataaaa tgtatttta gaactttcaa atgaaatatt atttcatcct   66420
tccagatcat ataatgctta agttctgatt gttaatcata aagtctagaa aattaaaaga   66480
taataaaatg aaagtgactt ttaggtatta gagtttatt ataaattctg gtgtgtcatt   66540
ggagctatga catgaatatt tcaaaggcca atagcattgg atctttacag ttataactta   66600 ccattttta gtttaagtag taatatagat tatttaataa tcaaaatcaa taaatattaa   66660
ttattaaaat gttttgtggt atagtttgag aatcattgct tttaactttt tccatatagg   66720
tttattgact ttaatagcat tctaaacata acatctctac attctttgtg tttaatactg   66780
tggaggtata aaaatactta tatatgatga taaactatat tagagtaaat taaatattct   66840
tatgagtttc attttagagt gcatttactt aattttgaag tccttatttt tagcaaacta   66900
aaaggaatgt tggtacatta tttactaggc aaagtgctct taggagaaga agaagccttg   66960
gaggatgact ctgaatcgag atcggatgtc agcagctctg ccttaacagg tagttctcac   67020
tagttagccg ctggtgtgga ccttcactgt ctgccttcca cccctgccc ttcctgctcg   67080 tcccctgca cctggtggac agcacgactg ggggcagcag tggagccagg ttgcttaaat   67140
ggggcatatt cgggcttctt ttataatact tactctgaag cttgtgtgtc tgtggtgttt   67200
gcatcatata tttgttgttt tccatggttt aggctgtttt aaaattaggt ttatggcttg   67260
agcatagggc tttgtgagta ggggatggca ggtcgaaaca tctcatgagt tggatgggtt   67320
atgctggggg ttgggaaatg ggatgaaaaa ttatgggatg aaaaattgcc tatggatagt   67380
ttaacttgaa agaatctgcc tttgtttaca gatagttatc tttttctttt ttgagatag    67440 agtctcacac tgtcacccag tgcagatacc cagtgtcact ggagtgcagt ggtgtgctct   67500
tggtgcactg cagcctccgc cttctgggtt ccagcgattc tcctgcctca gcctcccaag   67560
tagctgggac tacaggtgcc cgccaccacg cttggctaat ttttgtattt ttttgtggag   67620
acgggttttt gccatgttgg tcaggctggt cttgaactcc tgacctcaag tgatctgcct   67680
gcctcagcct cccacagtgc cgggattaca ggagtgagcc actgtgcccg ccagttaca    67740 gatacttatc taatgaaatt ctctgtgtac tttataaaag atgaggatta actgaaggta   67800
ctaataactg gattatatga gggtggtttt ggttgtataa tcctatctaa aagaatattt   67860
tagctataac tgaaagtaag acttaaatat ttagagagga aaatctgaat aattctagta   67920
gtaattattt atttacaaaa taaaaataga tttttttttg attacacaaa ttaaacaaca   67980
ataaaacatc acagcaatcc ggatactata aagctcacat gcttaccgac ccaactgccc   68040
caggagtgac cactgccaac agcttcatgt cgaccttttt gccataattt ttatatagcc   68100
ttttttgttt ttaaatggta atttagaaag tcaactagga aaatgtgtta caggtttatc   68160
ttccaggaga ataggactgg agtcgagatc ttgaatgtgg cttggaagaa ggcaagccca   68220
ccccagagag atgagttgac agttgtttct gaccactgct tgcttagagg gcctgcgtgt   68280
ctgtgaccgc ctagctttgc gcccctgact aggctgcccc ttaattacaa atgtctttat   68340
atattgctcc agctaaggct tggagtagtc ggttaagaac ttgaacttcg ttttttgcag   68400
tgaaacagca tttgagaata tcaccttctg ataagcctta ttttataagg tgggtactgt   68460
```

```
agtgggaggc agtgtgagag atgcttgaag gatgcactgc tgtcctgcat ttcagcatct    68520
tcaggatgct gtgcagctga acatttgat aacggtggaa ctgttcgtta ttttgcaagc    68580
ctgtgattcc ctattgaatg ttttctctcg ccatttgaca aatgagtgtt tctctgtctt    68640
cagcctcagt gaaggatgag atcagtggag agctggctgc ttcttcaggg gtttccactc    68700
cagggtcagc aggtcatgac atcatcacag aacagccacg gtcacagcac acactgcagg    68760
cggactcagt ggatctggcc agctgtgact tgacaagctc tgccactgat ggggatgagg    68820
aggatatctt gagccacagc tccagccagg tcagcgccgt cccatctgac cctgccatgg    68880
acctgaatga tgggacccag gcctcgtcgc ccatcagcga cagctcccag accaccaccg    68940
aagggcctga ttcagctgtt accccttcag acagttctga aattgtaagt gggcagaggg    69000
gcctgacatc tttttttta tttttattt gagacagagt ctcactccat agtgcagtgg    69060
aggccgggca caggggctca tgcctgtaat cccagcactt gggagactg aggcaggcgg    69120 atcacttgag gtcaggagtt cgagaccagc ctggccaaca tggtgaaacc ctgtctctac    69180
taaaaataca aaaattagtt gggcgtggtg gcacatgtct gtagtcccag ctgttaggga    69240
ggctgaggca ggagaattgc ttgagcctgg gaggcagagg ttgcaatgag ccagatcgt    69300 gacactgcac tccagcccgg gcaacagagc aagactccat tcaaaaaaa ataaaaaat    69360 aaagtgcagt ggctcgttct cagcccactg caacttctgc ctcccaggct cgagcgattc    69420
tcccgcctca gcctcctgag taggtgggat tacaggtggg caccaccaca ctcagctaat    69480
gtttgtattt tcagtagaga cagggtttca ccatgttggc caggctggtc tcaaactcct    69540
gaccttagat gatccaccca ccttggcctc ctaaagtatt gggattatag ttgtgagcca    69600
ccatgcccgg ccctgccacc tgccatcttt tgagttcttc cctggagacc tagacctgaa    69660
ccctcctgct tgttctcttg ttatctaata cccctattga cagcgcagct tagatcatta    69720
atggagagct tgacctcatc tgataccttc actgaaggaa acaacttagt gtcttttgtg    69780
ttgaacactg aggtaaaaaa ttggaatagt tgattatatg aactctgcta aaattgagtg    69840 catttacat ttttaaggc cttgttgggc cctggttaaa taattatttt taaaaatcct    69900
taaggagcct attataaaca gatctgtggt cttaatgaaa tgtgattaat actgtgcatt    69960
attttaagaa cttttgactt ttcaaaaaac ttttacaaca tttcccattt gatagcggca    70020
taggtttaag cacttctcat ctctaagtta gtggacaaaa aaccctcatg gatagtctaa    70080
taatgtttgc tacaagtcca tgttgagttt tatactccat tttattttca gttttaaaaa    70140
ctgtggttaa atatgtgtaa cataaaattt atgttcttaa ccatttttg cgtatacagt    70200 tcgctggtat taaatacatt taaataatgt catggaatca ttgctaccac ccatctctgt    70260
aaccttttga tcatgtaaca ctgaagctct gttcccattg aactctattc ctcctttccc    70320
gccaagtccc tggcaaccac gattcttctt tctgtcttct gaatttgact actttgggtt    70380
ctcatatact ttaggagtca cacagtattt gttttactta gcataatgtc cccaaagctc    70440
atgcatgttg tagcctatgt tagaacttcc taatgtttca ggccaaatac tattccattg    70500
tatggatagg ccacattttg cttttccatt cctctgtcca tggacacttg tattgcttca    70560
tgttttagcc attgtgaatc atgctgttat gaacgtgggt gtacagatag ctcctggaga    70620
ctctgctttc cattttttg gctaaatacc cagaaatgga gttgcttta cattccaatt    70680 ttaatttaaa acattcatat cattgagtgt tttacttaat agtatagtag ttaacaaact    70740
taataaaata gtattttggt aataaatttgc tggtagtcca ttgttcagtt ttttaggta    70800
```

```
aattacacag gacatttcaa gtggacatga aacatcttgt gatgtggaat catgccccaa   70860
gctgatggct aaacatatga aataccatac cctaaattta gtagatttag tctttgcaat   70920
ttaggagata acctgttata ttgttaggtt tttgtcgaaa agctttgtcc tcatatttcc   70980
aacttgctgt aaaatttgtt tgtgaagaca aatattttg tatgggtttt ttcttttca   71040 tattaaaaag aaatgtccac attggaattt ttttggagtt tttagagcta atagagcttt   71100
tcataatgta gtgggaatga gtgatcagta agctcttagc agtttccatg cgtgcatttc   71160
tgtgccttga aataaatgac agatgagtac atttgtgttc tgtgtgtaaa atgtgctctt   71220
tcctcattgc acttccatgt tggagggctt gtctcttggt gatcacactt caaaattctc   71280
acagcccccc ttgaaccgtt taggtgttag acggtaccga caaccagtat ttgggcctgc   71340
agattggaca gccccaggat gaagatgagg aagccacagg tattcttcct gatgaagcct   71400
cggaggcctt caggaactct tccatgggta tgtggactac aggtgatgcg ctacaaagtg   71460
gtttgtattc agacctggac atcttaatta tatctttgct tccaagaaga agtcctttga   71520
tactgttttc tgagttctga atagctgatg aaaatgacca attgaggaat aatcatactt   71580
tttcttgatc taaatcttat acttttgagt tatcttagca taaatgtata attgtatttt   71640
aagtggaaat ttgtcactta atcttgattt ctctgttttt aaagcccttc aacaggcaca   71700
tttattgaaa aacatgagtc actgcaggca gccttctgac agcagtgttg ataaatttgt   71760
gttgagagat gaagctactg aaccgggtga tcaagaaaac aaggtgaggg ataggcttt   71820 gagacgactt ggtgtttctg agcttgtgtg aggatttaaa atcgccctgg ctactgtcta   71880
ctttattgct ttcccatccc tgggccttta aatttcccct ttaaatacca gctcttccca   71940
ggcctgttgt tttctgcctt tccaggtact acccacagcc ttgagaattg cctgagttct   72000
gcctcctttg agagtgtgcc ccagacaaat ctattctgta ctgaatgttt ccttgtctga   72060
tttcttggat cattcatttg atggttgcgt atggcctgca acgtttcttg ttttggttct   72120
actgaactgt tctaaaagtc tctcttcata ttatcttttt acatgtaaat gtaactgtct   72180
tcacttttaa ttcctcaagg acaaggaata gcgtttcaca gttcgtccca tcaatcagaa   72240
ttatagcctt tggcatctcc ctatctacca ggcccacttc ctcttagatt tgggcttccc   72300
caggctgttg cctttcccca gtagcttct gcttgtcctg tagaagacct ttcatgcttt   72360
gcttctgcag cagccgttcc tgaatgccta gtgtcaactg ccttcttacc acgcccaccc   72420
tccctgcatg ctgcatttat cccctgccac agccctgtga ccctgtgtcc tgctgcctct   72480
gacttgtctg tttctgcttg gccatggtct ctgtgaggtc aggtgtgcat atgggcacaa   72540
accagggcat ctctttatcc ccagcacctg gcttaagtgc tgctctggaa ctatctgttg   72600
aatgaactaa tgcatgaatg tattgttgag tatgagacaa acaagtgtca ttgtctcctt   72660
tctagccttg ccgcatcaaa ggtgacattg gacagtccac tgatgatgac tctgcacctc   72720
ttgtccattg tgtccgcctt ttatctgctt cgttttgct aacaggggga aaaaatggtg   72780
agtacaaaag gggatgtgca cagttgaagg aaataactag gtttcagagg tcagcttggt   72840
ggcctgtttt tgccttgcgt gcagcagagg aagtagaatc tgaggatgag tttggttttc   72900
actagccgag gggagggagg aaatgatggg agcaggtagg ttattgggtc tggttttgtt   72960
catttgaaaa caatctgttg tttgaggctg aaggtggctt gggtgatttc ttggcagtgc   73020
tggttccgga cagggatgtg agggtcagcg tgaaggccct ggccctcagc tgtgtgggag   73080
cagctgtggc cctccacccg gaatctttct tcagcaaact ctataaagtt cctcttgaca   73140
ccacggaata ccctggtatg ttaaaagttc acatcttatt ttctcagatt taatcattat   73200
```

```
tgtaaaaact atttcagtat tgactatttt agttttagag cagtaagtgt tttgagttca    73260
tttgggatat ttgacctgcg ttgtagctct tcagaaaaca catgaatagt gaagttcttt    73320
gtttcatggg ttccctttag atgaaaccca tagaggagaa aagtagaaac ctcagcacgt    73380
aagagccaac atatatacac atcggattta aacctaaagc acaaattgtg cctggtcgca    73440
gtggcgctga gtcgcactca gccaggccag gcattcacac tcagggtgag tgggaaccag    73500
gactggctga ggcagcagtg gacccaagtc tccatcgcgc ccatgcttac tatgagcct    73560 tctcgttctc tcttttctt tgggtgagag ggtacacttg tgtttttgaa tttatatgag    73620
gtaagtgtgt aatagggttt tttctaatct tttttaagtg gaatctggaa ttttaatcag    73680
atttattatc tgacaaccta gaattataat ccagaaagtc tgtggtattg aggacatatt    73740
ggcaatatga tgaatctcta attcttaaat cctgaaactt ttttttttt aatcacttag    73800 ggttattata gtgaagtcat ttctgaattt ggatcttctc ttcacacctc tttttctctt    73860
tcctgagaat taagcttttg tttcgagtta gaaagttgat agtagggaat tgttccatgg    73920
ctgagcaatt tatctccaca gaggaacagt atgtctcaga catcttgaac tacatcgatc    73980
atggagaccc acaggttcga ggagccactg ccattctctg tgggaccctc atctgctcca    74040
tcctcagcag gtcccgcttc cacgtgggag attggatggg caccattaga accctcacag    74100
gtaacggcca gtttttcagc tgtgttttt ctagttatgc ttactaaggt ttaagtttag    74160
atgatgatgt ttgttgcttg ttcttctggt taggaaatac attttctttg gcggattgca    74220
ttcctttgct gcggaaaaca ctgaaggatg agtcttctgt tacttgcaag ttagcttgta    74280
cagctgtgag ggtgagcata atcttctgtg gaaccatttc ttcacttagt ggacatttta    74340
tcattgctac aattaaaatt ggagcttaat aggaaatatt tccatgcact ctaaagctgt    74400
aaccagtaat acccaccatg tatccatctc tcagctttag aaagaaaacg ttgccagtaa    74460
agttaatgct tcataaactt cagtttaagt tctaattctc agaatatttg tttgaaatag    74520
acctcttcct aaaggatata tttagaaata acctatcatt aagtgtaaag tctgttgaat    74580
atgctgggca cggtgactca cacctgtaat ctgaccactt tgggaggcca aggtggaagg    74640
attgcttgag cccaggagtt caagactatg gcaacatag ttgaccctgt ccctacagaa    74700
aattaaaaaa aaaaaaaaa aaagtagctg ggtatggtgg tgcatacctg tagtctcagc    74760
tactcgggaa gctgaggtgg aggggggatt gcttgagccc cagagatcaa ggctgcagta    74820
aggcgtggtt acaccactgc cctctagcct gggcaacaga gtgagactgt ctcaaaaata    74880
atagtaataa taatcagttg aattaaaaaa aaaaaaaaa aaaccactgt gctaggccca    74940
tagtatggta agagttaaag tgagccttag ggattattta ctcaacctct gtttctgtat    75000
aaagtggaat aggctcaatt ctttaagtga tagcatgttg aaccttcca taccaactgg    75060 ctcataagtc acaactggcc agtcaacaag agtaaaaatt aactggtaaa aatcaaagca    75120
aaaaacctac aattgtcaaa tttgtgggat aactccccct tttaaaatgt catgcctgac    75180
agtaatttct ctctagtttc caggttttca gtcagttgtg tcttttttga gcagaaggaa    75240
gcatgctaag agctcaatct tgtggctagc tgggggtctt tgtgtcagcc atgcatgtga    75300
tggtgcccct gggtgcttgg ggctgcaggg gaggggtaca gcagtagggg cctgttctgt    75360
tctctcgtgc tgtggagtac atagtgacat agtggggtgg tccttggtgt aggtcccttg    75420
ttcctacccc tgggtctgag atttatttag aagtggtgtt ggggctgtgc ggcaggcccc    75480
tctgtaactg atcaatgttt gtgaagttgc tgtttgagag ttgaaaccat gacataagca    75540
```

```
gaaatggaag gaagaaagaa ccagttatgt gaaagggaca catttacttt taagcttgta    75600
tttactgaga taaagtattc ttaatcaatg ttcttgagag gtgtgggaaa aatgcaacat    75660
cctggttgca gttaaaccca gaacattgtg tgttgaagag tgacggttct caaaccgtca    75720
agacgcgggt actgagtggg actaacctgc tgtcctcttg ccttggacct tgtgttccag    75780
aactgtgtca tgagtctctg cagcagcagc tacagtgagt taggactgca gctgatcatc    75840
gatgtgctga ctctgaggaa cagttcctat tggctggtga ggacagagct tctgaaaacc    75900
cttgcagaga ttgacttcag gtaagtgagt cacatccatt agatttcatg aactaagctc    75960
aattgaaagt tctgggatca cttgatgcaa ggaatgatgt tatcaagtac cctgtccatc    76020
agaaatccga gtggtttagg tagatgacag tgattttctc ctcccagtgg cttttgctg     76080 aactttgccc tatgcttgga attttatttt attttattat ttatttagag acaagatctt    76140
gctctgtcgc ccaggcttga atgcagtagc acaatcatag ctcactgaag ctttgaactc    76200
taggactcaa gtggtcctcc tgcctcagcc tcccgattag ctaggagaat aggtgtgtgc    76260
cgtcacactg gctaatattt tttgtagaaa tggggtcttg ctatgttgcc caggctggtc    76320
tcaaactcct gggcttgatt gatcctccat cttggcctcc caaagtgctg ggattacagg    76380
catgagccac tgtgcctggc ctagaatttt aaaatataag tagaagagta gatttttttt    76440
tttggtagtc ctcgtcattt aagtattctg gatagtggga ataaaagagc ttagaatttt    76500
tcatctttgt cttaaacttt taaaaaaatg tagcttatat taattctgct tgtttaaaaa    76560
gaatatactc ttcattatac tgaacctagg taagacagct ggtttatatt ttgttgcaat    76620
taaaaaacgt gagctgtggt tgcagtgagc caagattgtg gccattgcac ttcagcctgg    76680
caacagagtg agacttggcc tcaaaaaaaa aaaataaca tgagctgtgt tggcactttc     76740
attttctaag agtagttttg gctggagaag ttttctttca gtactttctt ttagaaggga    76800
aattttcctt tataatttag ggtttgtttt ttttttttcc aagccacctt ttatagagcc    76860
cttgtgggtt atttcattta atccttagaa tgttataaaa tctgggcttg ttctcggctc    76920
cacccacaga tagggacgct gagcgtgcat gagtgggcag caagatagca ggttatggag    76980
ggcccagctc accccttctg tggcttgagc caatttttata gggcacttac agagtctttt    77040
gaaatagtat ttattttgaa gaaaaagaaa aacagtttac tgagtactgt cttattgagt    77100
ctggaattgt gagaggaatg ccacctctat ttatttaaag ccattggcct ttttgttgt     77160 tttgagtaag tgctgcccaa ggtccttcca gggcacctgg atgagcctgc tctggagcaa    77220
gctggcggta agtgtttact gagtaactaa atgatttcat tgttaaatgt gctcttttgt    77280
taggctggtg agcttttttgg aggcaaaagc agaaaactta cacagagggg ctcatcatta    77340 tacagggta agcggtttat ttttgtgaga tgctgtttta ccttcaagaa ggtgaaagtg     77400
aggctttcct tgtggaattt ctctaaatgc attcgtcatg ttttagatgt ttatttcaca    77460
gtttatatca tgaaagttat aatcttgtca tatggattta agtctagtaa tgttgagttc    77520
tttctcacta gctttccaaa atatcttacc taaaatttag tcaaatacaa gattatgttt    77580
atttttatta tccttctctc taaagctttt aaaactgcaa gaacgagtgc tcaataatgt    77640
tgtcatccat ttgcttggag atgaagaccc cagggtgcga catgttgccg cagcatcact    77700
aattaggtat ttaccaatat tttatctctt ttccttttt  ggttgaagta ctaaaagata    77760
cgagaatgga aagagaggga agaattcaaa ggatgtagag cagtattcct gaatctgagc    77820
tcatttcagc cattctattc ttaaactata atgaaaaaaa aatccaaaaa agtctaaaat    77880
tataattaaa aaaacaacaa aatactaact gtccattgta aaaagtaatg cactttcatt    77940
```

```
gtaaaaattt tggactatag agaatagtac taagaagaaa aaaaaaatca ccttcaattc    78000
tgctgccacc tggaggtaat cactgttaat attttgctat atactctatg agtttcttgt    78060
tcaaaatcag gtcaaaatta catgcaattt tgtaatctga caatttccac ttaatatttt    78120
attagcattt tcctgttatg aaacagtaat tttagttatg ggtcgttgtt ttgctatgcg    78180
gttgggataa aattttatat acttttttg gcaattactt attatacata aatgtttgtg    78240
tatagttttc ttttctgag aattcctgga agttgagtta ccaggcccgg ctttgaattt    78300
ttttttttat ttttttttg agacagagtc ctgctctatt gtccaggtgc tatctcggct    78360
cactgcaacc tctgtctccc tggttcaagc gattctcctg cctcagcctc ccgagtagct    78420
gggattacag gggcacacca ccacgcccaa ttaattttg tatttttagt agagacaggg    78480
tttcacgata ttggccaggc tggtctcgaa cttctgaccc cgtgatccac ctgcattggc    78540
ctcccaaagt gctgggatta caggcgtgag ccatggcgcc tggccaggct ttaaatttaa    78600
aacaaatctt ctaatagctt tatggaggtt ataatttaca tttcttgaaa tgtactcact    78660
ttgagtgtat agtaaactcc aattttatca catttctgtc accccaaatg tatccttgtg    78720
cccatttgct gtaacctccg gttcctgccc caactcctag gcagccactc atctattttc    78780
tgtcccttaa gatttgtgtt ttcgccaggc gctcatgcct gtaatcccag cactttggga    78840
ggccgaggtt ggtggatcac ttgaggtcag gagttcgaga ccagcctggc caacatggtg    78900
aaaccttgtc tctactaaaa atacaaaaat tagtcggatg tggtggcaca cgcctgtaat    78960
cccagctact cgggaggctg aggcaggaga atcacttgaa cctgggaggc ggaggttgca    79020
gtgagcagag atcgcgccac tgccttccaa cctgggcaac agagagagac tgtctcaaaa    79080
caaacaaaga tttgtatttt ctggacattt tatagtactg gggtcatagt atagatggac    79140
ttttgcattt ggcttctttt acttaattgt gagattggtt cttgttgtag catgtatcag    79200
tagtttgttc attttattg gcgaaagtat tctattatat gaataatacc atattttatc    79260
tatccatcag atggatatta tagagttcat gttttggcta atttatgaat tatggtactg    79320
tgaacatttg cctgcaagat tttgtgtaga catgtcttca tttctcttga gtagatcacc    79380
tagaagtgga tttttaaata attttggtac ttactgtgaa actgctcttc aaaaacatac    79440
cattgttcct tccttccttc cttccttcct tccttccttc tttccttcct ccctcctcc    79500 ctcccttccc tacttccctc tccctttccc tttcccttcc cctttccct tccccttccc    79560 gcctgcctgc ctgcctgcct tccttccttc cttccttcgt ttctttctac atatacacat    79620 tttttaaat ttcaatggtt tttggggtac aagtggtttt tggttacatg gctgaatttt    79680
ggttacatgg tgaagtctga gattttagta cacctgtcac ccgagtagtg taccttgtac    79740
ccaatatgta gttttttgtc cctcaccttc cagccttccg ccttgtgagt ctccaatgtc    79800
cattatacca cactgtatgc ccttgcgtac ccacagctca gctcccactt ctgagaacat    79860
atagcagaaa catgccaaag tatactccca ctaccagaat gtgattgtgc ctgattcttc    79920
tcaccagtac aaatatttca aaaaaagtta aatatgtatc agttttttgg gcagaagttg    79980
atacttctct ttatttattt atttttttg agatagggtc tcattctatg atgcccaggc    80040
tggagtgtgg tggtgcgatc tcggctcact gcagtctctg cctcccaggt tcaagtgatt    80100
cccacgtcag cctcccagga agctggaatt acaggcgagg gccaccactg ccagctaatt    80160
tttgtatttt ttggtagaga tggggttca ccatgttggc cagactggtc tcaagctcct    80220
gacctcaagt gatccacctg ccttggcctt ccaaagtgct gggattacag gcgtgagcta    80280
```

```
ccacacccgg ctgatatttc tttttaaaat aacttacctt cttttgaaag taatacatgt    80340
ttaatgaaca gaatttaagg aaaatataaa aaaacgaaat aatctttgta atcaaactac    80400
tgaaaagaaa accaaagtta cattttggtg catattcttt ttcattttca tcattgtaat    80460
ttgcatttct ttgattactt gtgagacact cctttcattt acttaatagg tttatatgac    80520
ttgcctattc agagattttg cagctttacc attttctgca aatgatagca acttcttttt    80580
gtttgtttgt ttgtggagac agagtctcgc tctgtcactc aggcaggaat gcagtggtgg    80640
aatcttggct cattgcaact attgcctcct gggttcaagc gattttcctg cctcagcctc    80700
ccaagtagct gggattacag gagtgtgcca ccatgcccgg ctaatttttg tatctttagt    80760
agagatgggg ttttgccatg ttggccgggc tgatcttgaa ctcctggcct caagcggtcc    80820
ccctgtctcg gcctcccaaa gtgctgggat tacaggcgtg agccaccgta cccagccagt    80880
agttacttct tatattctag aaaaaattct actcatgatc aagtctccat gaggaaagag    80940
actttaattg aagatcatgg ggcttgcaga ccaatatgat aaaatagttc attgtttcta    81000
aaagtattac tgagtgttga tggcagatat gaacccttt gttttgtag gaaaatgtta    81060 cccgtattct ccatttgaat tcagtttaga tttgttagga atcgcagctt aagctttgcc    81120
atctgggagt gtttgggaca gttttgcaga caaaattgca aaagtgccta aggaatgcag    81180
ctggcattca gacctgctct gtgctcagta ctctgtggac agacactgtt cagcacttgt    81240
tgatcagaag gtttagaaag agaactttca agttggttt ttaattaaag catttaatag    81300
tgtaaataga aagggattaa attttatgac agacaaaaga aagtacagca cccagctggg    81360
cgtgggggct cacgcctgta atccagcact atggggggct gaggtgggtg gatcacgagg    81420
tcaggagttc aagagttcaa gaacagcctg gccaaggtga tgaaaccctg tctctactaa    81480
aactacaaaa attagccggg cgcggtggca ggcgcctgta atcccagcta ctcaggaggc    81540
tgaggcagga gaatcacttg aacctggacg gcagaggttg cagtgagcca agattgcacc    81600
attgtactcc ggcctgggcc acagagtgac attctgtctc aaaaaaaaaa aaaaaagaaa    81660 aaagaaagt acagcaccca gttatgtccg agtgggtgca tgagagtgac cctgagattg    81720
gagacaacgc tgtcacgtgc ttgaagaacg ccacctgaga aagggggcga gaagtggtgt    81780
ccgctggtaa ccagaggtgt tggcttagcc atctgcaggg aggagggtgg tctatcacag    81840
gtgagtttca tctactttct taagcaaatt aaccttactt ttgtgttagg cttgtcccaa    81900
agctgtttta taaatgtgac caaggacaag ctgatccagt agtggccgtg gcaagagatc    81960
aaagcagtgt ttacctgaaa cttctcatgc atgagacgca gcctccatct catttctccg    82020
tcagcacaat aaccaggtat gctgacccag tggcatcttc acattgtcgg gaaaatgccc    82080
tttcctgatg ccttttcttta ggctttaatt gaaaacattt tatttctag aaaaaagctt    82140 cagctcagga tgtttgagtg taggtcagtc ctttgatagg atattatcat tttgaggatt    82200
gaccacacca cctctgtatt taagctctgc cacaatcact cagctgtgac actgtaaatc    82260
tcttaatagt ttattacatt ccatgtgctg acagttgtat ttttgtttgt gacacttacg    82320
tattatctgt taaaacattt tcactttagt tgtgttacct ttaaagagga ttgtattcta    82380
tcatgcctgt tgattttttg gtgagcgggc tattaaagtc agtgttattt agggttatcc    82440
actagttcag tgatttgcga gattatcatt cacatttatt gtggagcttt tgaatatcgt    82500
gtcaaatggc cacatatatc ccattcttat ctgcttctta ggtgagtggg acacagtgct    82560
ttaatgaagc tataatcttc agaattctag cttgcagaga agattgcaga agtgataaga    82620
cttgtgcttt ttaattttgt cttttaaatg ttattttaaa aattggcttt atatgatact    82680
```

```
cttttttttct gctgagtaac agtgttttac aaaacttgga ctaaatgact tctaagctta   82740
aatgatcact tgatgctttt tttctgaatt aggaactcag cttatcaaat atcaaagtca   82800
taattcctga ataaataacg tcttttttca tgtaaagact gctttaaaaa acacatggaa   82860
ggctgggtgc ggtggctcac gcctgtaatc ctaacacttt gggaggccca ggtgggcagg   82920
tcgcttgagc tcaggggttc aagaccaccc agggcaacat ggcaaaaccc acctctactc   82980
aaatacaaaa aattagccag gcgtggtggc gggcccctgt aatcccagct actcgggagg   83040
ctgagggatg agaatcactt gagccccgga ggcagaggtt gcagtgagcc aagattgtgc   83100
cattgcactc ccagcttggg ctacagagtg agactctgtc tcaaaaaaag acacacacac   83160
aaacaaaaaa aacatggaga cattttttg gccaccttaa tatttcccct cagataattt   83220
cctttgttta aactcagaac tggcattttc tctcttggag aagattcagg acaaatactc   83280
ctttaagata agtagaagca gtgaaagagg atttgattat caggaatttg ataagcttag   83340
aataaattgt tgcttcttaa tgtcatttca gaagatgaat atttattaat agatgccaac   83400
tgagatatca ttaaaattga ttactaacta ctacttggaa aagtctccca gttccaaact   83460
tcagcaggcc tcttgacaat tcagctgtgg tcaattgggt cttgcgtgat agatacaatg   83520
accaattgtg cagcagagtg tgctgcttag ctgcctattc tgttagcatt catgtgttaa   83580
cttaaaatca taatctcctt agttttgttg agtgtctccg tggacaagac actgtgaggg   83640
atacaaaatc agattggctt tattcaaacc actggggtat tataattcat ttataattta   83700
ttttattttt tgcctttttt ccatgtgttc taaaggaatt agagtttgta tataactata   83760
atgggggata gaaattgaca tgtgccatga agggaatgca aaaagtgcc gtgggagatg    83820 agaagtggag aaaggaattt ctttttttctt ggaagcagga ataacttcat gaagcatgta   83880
tttcaactta aacagatagt aggcaacgct gtaagggag tatggctgca gcaaaagtgt    83940
tcggggcaga ctgggaggaa gggagggaat aaattcagcc attgttatgg aataatgatc   84000
aaaatttatt ttcagcccgt ttcacttaaa agttgagact gcttaacttt ttttaatctt   84060
taatcttaaa cttttaaatg ccatttgatc tttaaaaata tatgttttaa tagtgtattt   84120
taagtctcta tattttgtt attagaatat atagaggcta taacctacta ccaagcataa    84180
cagacgtcac tatggaaaat aacctttcaa gagttattgc agcagtttct catgaactaa   84240
tcacatcaac caccagagca ctcacagtaa gtctctttct tgatcggtct tactgacatt   84300
gtaatagttt ttggtagctt gtatggccag ttagttgtat ggtcatctta cggtgaggtg   84360
cttgtcttac agctcttact tatccatgag gcttgctaag aaattgtgct tctgtgaaaa   84420
gaatctcagc ttactccagg aatgtaaatg actatgtttt ttctgattat taaagtaata   84480
cacgcccaaa ataaaaaaat tcagccaatt taggaagaca caacaattaa aataagccag   84540
gcatggtggc tcatgcctgt aatcccagca ctttgggagg ccaaggttgg gggctcactt   84600
gaggtcagga gtcggatacc agcctggcca acgtggtgaa accccatctc tactaaaaat   84660
acaaaaatta gctgggcgtg gtggcgggcg cctgtaatcc cagctactca ggaggctgag   84720
gcaggagaat cgcttgaacc tgggaggtag aggttgcagt gagctgaggt caagccactg   84780
cactccagcc tgtgcaatag agcgagactc tgtctcaaaa aaaaaaaaaa aaaagaaaa    84840 gaaaaaagta aactactgtc acctgcattg gtaatgtatc agaagtttaa aatgtctaga   84900
ttataattaa ctcagtgacc tggtaatata tactaaggga aaaatattta aatttttcat   84960
ttttacattt ttatttttttt aattttatta tttttttttt gagacagagt tttgctcttg   85020
```

```
ttgcccaggc tggagtgcaa tggcatgatc tcagctcacc acaacctcca cctcccgggt   85080
tcaagcaatt ctcctgcctc agcctcctga gtagctggga ttacaggcat gcaccaccat   85140
gcccggctaa ttttgtattt ttagtagaga cagggtttct ccatgttggt caggctggtc   85200
tcaaactccc aacctcaggt gatccgccct cctcgacccc ccaaagtgct gggattacag   85260
gtgtgagcca ccatgcctgg ccttacattt ttataataag aatttatgtt gctgacatta   85320
gaaaagaacc ataatatcca agaatccaag aataattaaa ttatgtacat atgctagtat   85380
atagtgtgat gctttggaga atttttaaca atatggagat gtataatctg gattgtaata   85440
ttgagtgaaa aaaggcagaa tacaaacctg gtgggggtat agtcggattt cagttaagaa   85500
aaataatatt tacatatata catttctcac actggcagat aatcaccaag ataaattttg   85560
ggattgtgga tgatttttt cttctttata tttttcagat attctcaaat tttctaaaat   85620
gagcaagtat aacttttgtt atcagaaaaa aataatatac aaaagtaatg ttaatttgct   85680
ggtgaccagg ttaaaccttt ttatttttat tttttgagat ggaatctcac tctgttgccc   85740
aggctagagc acagtggcat gatcttggct cactgcagcc tccgcttcct gggttcaaat   85800
gattctctgg ccccagcctc ctgagtggct ggaattacag gcgtgtggca ccacacctgg   85860
ctaatttttg tattttagt agaggtaggg tttcaccagg ttggtcaggc tggtctcgaa   85920
ctcctgacct cgtgatccac ccacctcggc ctcccaaagt gctgggatta caggcgtgag   85980
ctactgcgcc cagccagacc ttttatttt atttgacaaa agaaatactt ccatgttata   86040
gaagactaaa tattgtttgg gctgtctgca gtatggtctt cccttgattt gttcaaaata   86100
tcgtaaactt tgcttattta tttttattgt ggccgactgt gtcgggcact gttgtaggct   86160
tgggatggaa aaacaggatt cctgcccta gggtttctgc aggctggtca gggagacgat   86220
gtggtaagct ggagctcagc tcctaaggat gtgcagggc agttgagagg cggaagggtg   86280
ggagatcatt ccagggtgtg ggcagcacag gaacctctct tcattgggat ataattgcca   86340
ttctgataac acgtgtttga ggtgtctaaa gtaggaagtt gtaccatggt gggacagata   86400
tcctgtggtt atcatacaca gatctcagtt tcttctcat tgtttgtact ttttataaag   86460
ggtaacagga gatataattc aataaaacctt tgtggtgttt gggtgtgatt ttattgtttc   86520
tttcttctca gtttggatgc tgtgaagctt tgtgtcttct ttccactgcc ttcccagttt   86580
gcatttggag tttaggttgg cactgtgggt atgtattttc ctcagtatat attaatagtt   86640
gtctacaaca gtatgacata aacatagtta ttaggatgcc cttttctttt cttttaagt   86700 ctttatcaa tttggctttt tggaaaaata tctgatggaa tacttgtttc tgctatatta   86760
gctgtgtgag actagtgaca ggagctgtgg gaaatgaatg ccaaatgttc ttaggcattg   86820
atgggaattt cagggtgtgg tcttcaagtt catttaaggg aattttcata tgctggcaaa   86880
aggcttttct cattagcttg actctttcca aaattatttg ctgtgaatta aagtttagg   86940 aacctttttt cacttaattg tgacctagca tacgaaatgg tgatgattta ggaactactg   87000
ttcttgtatt aacagctttt atttaaaaat gattttcctc cagtagatgg ccctactagc   87060
atctgggaaa taatttcaag tcttctccag cattcaggaa taggctttca ttttgtgtat   87120
caattactga gaatgatttt ggtgactcac atcacatttg agaagtaaac ctgcagattt   87180
cttgtgtgtg tcagcaaatg accaactgat atttgcttga agtggattac attatctgct   87240
ctagaatgat tgcttttccca ccttcctcac atacagactg agcagctacg gtttctaatc   87300
ataggtctgg cactagactt cacttctggg caacttggc attggagtaa aatgtattaa   87360
tttaaagaaa gttaaaaatc cgttcaagta aacatacagt tctaatactt tttacaattt   87420
```

-continued

| | | | | | |
|---|---|---|---|---|---|
| aaaatataga | tttaaatgat | aaaataaaaa | agaaaatatg | ggtagacacc | ataatcctcg | 87480 |
| tttctgcatc | tgttcacaag | gggttgatat | ttatgagttc | tattctccat | atccattcta | 87540 |
| tgttctctta | atgctcagtc | agcacctcag | gtggttggag | ttcaatgctt | ggtagtttga | 87600 |
| cttacactgt | cttttctagg | ggattgagcc | ctgggtagtc | ctgcttattt | gaggttgcaa | 87660 |
| tttgtctttc | aataacttt | actacaagat | atggcgtgtt | aaaggatacc | attggggaac | 87720 |
| caacataata | atatcaggaa | aactaaccac | gtcagacctg | ccccattgtg | tatcaagtac | 87780 |
| actattttc | catagtaata | aagagttcac | cccagccaat | tctcttttat | tttgtgcctg | 87840 |
| tttactcaat | ggcattaaca | tgcccaaatg | tctgggtagc | tgtctcatct | ccagttcagc | 87900 |
| agaaccattg | tcatatgccc | tagtaaaagc | attccttcat | tggacactta | ggccccaata | 87960 |
| cttcattca | gatctactac | ctgatttcat | ttctcaaatg | attttatgg | agctctgatt | 88020 |
| tataggaaag | atgttagttg | attaaaaata | aaacaatttc | tgagctggta | taaaatgtat | 88080 |
| tgtgacatgc | cttcctcttg | gaattgcaag | agaaaggaag | actgttgttt | gcttaaaaat | 88140 |
| tgtctataat | ttgactttgc | aaatgtctgc | ttccagagtg | cctccactga | gtgcctcaga | 88200 |
| tgagtctagg | aagagctgta | ccgttgggat | ggccacaatg | attctgaccc | tgctctcgtc | 88260 |
| agcttggttc | ccattggatc | tctcagccca | tcaagatgct | ttgattttgg | ccggaaactt | 88320 |
| gcttgcaggt | actggtactg | agttgaaaca | gggactccag | gacttggatt | ttgatttcct | 88380 |
| taggggaat | ggggtggtg | agcatatgag | gggaaaatac | tataaggtca | ttgccagtga | 88440 |
| tggcttgtcc | ctttagtcaa | atttcagatg | ttacctatat | gcataaacac | atgcagttgg | 88500 |
| cagctgttct | gtgctgagta | ttttaaagta | gcctcttccc | aatatagccc | ctcagttaac | 88560 |
| tacaagtaaa | ctcattttga | atttcatttt | aatgggcacc | atatgccagt | actccctcgg | 88620 |
| gcactgggat | gttaagaaag | tataatgtat | ggacttcatt | ctcaagttag | ttttagatta | 88680 |
| gaggggata | cacgtaaaca | aaagtgcagt | ggtcacacag | agtggcccta | atcactctcc | 88740 |
| ttgggcagat | ttatgggctg | gtaggaaaga | gcacaacacg | gagagggtgt | agcaccttgg | 88800 |
| cgatgataat | ggaggatgtg | gccagcaagg | aagacggagt | ccattgaaat | tgattttggg | 88860 |
| agaagttgcc | aatctccatg | aaagaattgg | ggcctgtgct | atttgcttca | ggggctata | 88920 |
| ggagagtttc | gtgaaaggga | ctaaaagatg | agtatttaa | taagatcatt | catccaactt | 88980 |
| gaacatgggc | tggaggagaa | ggtagggaga | ctcaggagat | taatgttgat | gctaaggcaa | 89040 |
| gataatggct | ttgggactgt | agggaagaca | ctgattgtaa | gagaatgaag | gaggcagaat | 89100 |
| tgccaggcct | ggttcaccaa | ctgaacttcg | gttgtgaaga | caaagaaacc | tgggatgact | 89160 |
| tcacatcctg | ggcaggtgtg | tggtggtgac | agtcatggaa | attgggaaca | cagatttgtg | 89220 |
| cgggaaacat | cagtttcagt | ttgagttttgg | cttatcagtt | gaatatcagg | cacagatgtc | 89280 |
| tggccaactc | tcaacatagg | gtcttaaatg | acttcagttc | cccaagcaat | ttgtccttcc | 89340 |
| catgctattg | gggtggagag | gtaatgtctg | tgcccatatc | acagccagtg | ctcccaaatc | 89400 |
| tctgagaagt | tcatgggcct | ctgaagaaga | agccaaccca | gcagccacca | agcaagagga | 89460 |
| ggtctggcca | gccctggggg | accgggccct | ggtgccatg | gtggagcagc | tcttctctca | 89520 |
| cctgctgaag | gtgattaaca | tttgtgccca | cgtcctggat | gacgtggctc | ctggaccgc | 89580 |
| aataaaggta | atgtcccact | tgggtgctgg | attcatacag | ccttaatgac | tatgggtttc | 89640 |
| cagactacct | ttgtttagta | atctgtccct | tctttattct | cttttttgctt | taaatgaaca | 89700 |
| aaattgctca | gattgtgaca | ctaaatttaa | catcaaaatg | tgaccatgtg | gatgggtgca | 89760 |

| | |
|---|---|
| gtggctcgtg cctgttattc cagcactttg ggagactgag gcaagtggat cacttgaggc | 89820 |
| caagagttcg agaccagcct gggcaacatc acgaaacccc ctctctacta aaaatacaaa | 89880 |
| aaattagatg ggttgggccg ggcgtggtgg ctcaagcctg taatcccagc actttgggag | 89940 |
| gccgaggtgg gcggatcacg aggtcaagag atcaagacca tcctggctaa cacagtgaaa | 90000 |
| ccccgtctct actaaaaata caaaaaatt atctgagcat ggtggcgggc gcctgtagtc | 90060 |
| ccagctgctc gggaggctga ggcaggagaa tggcgtgaat ccgggaggcg agcttgcag | 90120 |
| tgagccgaga tcgtgccact gcactccagc ctgggtgaca gagcgagact ccgtctcaaa | 90180 |
| aaaaaaatta gatgggcatg gtggtgcgtg cctgtaatcc cagctacttg ggaggctgag | 90240 |
| gcaagagagt tgcttgaacc tgggaggcgg agtttgcagt aagccttgat tgtgccgctg | 90300 |
| cactccagcc tgggtgacag agtcagactc tttccaaaag aagaaaaaaa tgtgaccatg | 90360 |
| tgttttatag ctctttagt atcatcagtc actgttatcc ctaagaggga aatacctagc | 90420 |
| tttagtttta ggtttccagc attagccaag aaagctcaga attgatgttc ctggccaagt | 90480 |
| acctcattgc tgtctcctta aatcttggtt aatggctact gtcctggcta gcatagttat | 90540 |
| ggagcatttc catggttgta gaatgttctg ccaatctcag ggacagtttt gcttttctgt | 90600 |
| gaagcaataa aatcaacttc aaaacaaatg ttaactattt gtacaatgga tttaagatag | 90660 |
| accagttcac atacttttt ttttttttt ttttgagatg gagtttcatt cttgttgcct | 90720 |
| gggctggagt gcaatggtgt gatctcagct cactgcaact tctgcctcct gggttcaaac | 90780 |
| gattcttctg cctcagcctc tcgaggcaga ttacagctgg gattacaggc atgcaccacc | 90840 |
| acacccagct aattttttg tagttttagt agagacgggg tttcaccatg ttggtcaggt | 90900 |
| tggtctcaaa ctcctgacct gaagtgatct atccgcttcg gcctcccaaa gtgttgggat | 90960 |
| tacgggcatg agccaccacg cccagcctaa gatagaccag ttcacttact gtttatatct | 91020 |
| gattactctc tctttgcctt gtcttctacc tttaaaaatc tccctactaa cttcccattc | 91080 |
| tcctttagct gccatcagtc ttctcccttc tctgcaaaca tctctggaga gtcccagcct | 91140 |
| cagcccacag agcttcccac tgctctgagg tggaccttgt ttgcaaggct tctttggctc | 91200 |
| tcttggcctg gaccctgtct actacttcag ccatccttcc ttaacccctg ctggtggttt | 91260 |
| ctgttgccac actccatagc agcgtttccc gcccagatca tgtctttaca tctctgggca | 91320 |
| ctgctctggt cctgcctgcc tttccctctt tgtatcctgc aggctgctac ccccatcttg | 91380 |
| agtgtcctct tcagttggct ttcagagggc ctcctgggtg ttcccttacc cacttgccac | 91440 |
| tccccagtca ctgggttcag tccttcctgc ccaccagcac atgctttcta ggctctgtcc | 91500 |
| taggccgtct tctctctttg tagtctctgg gccagtgctg ttctagagag tggcagaatt | 91560 |
| ttctataacc atggcagtgc tccatagcta tgccaggcaa gacagtagcc actaaacaca | 91620 |
| tatagctgtt gagcccttga aatgcagcta gtgtgactga agaactgaac cccgattcgg | 91680 |
| tttaattttc attaaattta aatttaaata accttatgtg ggtagtggct ccagtattgg | 91740 |
| gcagggcagc ctgagagtcg gggctgttct cctgtcttca gtgtctagat gagggacctc | 91800 |
| agaggacctg tctctggagc tgcagttcaa tgtagccagc tgccccgtga cacttacata | 91860 |
| tagctgattt gtggatatgt cagacacggt gtgatgagct cagctttctg tcctcctccc | 91920 |
| cacatctgcc cctgccccat ttaccccact tgtgtcttta tcaagctaga aacaggtcac | 91980 |
| cacaagtctt catttccact caccaagtct tttgtttccc ctactaaata ttttgcgaga | 92040 |
| agaaagtgtg taccttgta ttcacataca tgtacatgca catatacatg cacatatgca | 92100 |
| ggggtcccca acctctgtta aaaaccggac tgcaggccgt gcgtggtggc tcacgcctgt | 92160 |

```
aattccagaa ctttgggagg ccgagaccag tgcatcacaa ggtcaggaga tcgagaccat   92220
tccggctcac acggtgaaac cccgtctcta ctaaaaatac aaaaaaaaat tagccgggtg   92280
tggtggcggg cgcccatagt cccagctacc tgggaggctg atgcaggaga acggcgtgaa   92340
cctgggaggc ggagcttgca gtgagccgag attgtgccat tgcactccag cctgggcgac   92400
agagcgagac tctgtctcaa aaacaaaaca aaacaaaaaa aaaaaaaacc aggctgcaca   92460
ggaagaagtg agcaagcatt accatctgag ctctatctcc tctcaggcca gtggtggcat   92520
tagattctca taggagcgtg tatgagttcg ttctcacact tctgtaaaga catacctgag   92580
acatataaag aaaagaggtt taattggctc acagttctgc aggctgtaca ggcttctgtt   92640
tctgggaagg cctcaggaaa cttgcagtca tggcagaagg tgaaggggaa gtaggcacat   92700
cttcacatgg cccacaggaa aaagagagaa ggagagagag agagagacag agagagagag   92760
agaaaaagaa agattgagag ggagagagga gggagaaagg agagtgcctg taggggagt    92820 tgctacacaa aggagcacca gggggatggt gctcaaccat tagaaactac ccccatgatc   92880
caatcacctc ccaccaggcc ccacctccga cactggagat tacaattcag catgagattt   92940
gggtggggac acagagccaa accatatcag agcatgaacc ctattgtgaa ctgcacattt   93000
gagggatcta ggttgcatgc tccttatgag aatctaatgc ctgatgatga tttgaggtgg   93060
aacagtttca tcccgaaacc atcccccgcc aaccctggtt tgtggaaaaa ttgtcttcca   93120
cagaaccggt ccctggtgcc aaaaagtttg gggacctctg cacatatgca tgcacctgta   93180
catggacaca taatacatgt acatatgcat actttatatt ctctgccact tctggtccag   93240
actgatatac tatctcattt ggattactgc actagccttt tgttttggaa acagcatttt   93300
ttaaaaaatt taatttaatt tttttgagat agggtgtcat tctgttgccc agcttggagt   93360
gcagtgtcat gatcatagct cactgcggcc tcgatctccc aggctcaagt gatccttctg   93420
cctcagcctt ctcagtagtt gggactacag gcatacccac catgcccagc taatttttg    93480 attttttttt ttttttgaga cagagtctca gcctgtcgcc caggctggag tgggttggcg   93540
cgatctcagc tcactgcaac ttctgcctcc caggttcaag tgattctcct gcctcagcct   93600
cccgagtagt tgggattaca ggcgcctgcc accacaccca gctaactttt tgtatttta    93660 gtagagacgg ggtttcacca tgttggccag gctggtctcg aacttgtgac ctcgtgatta   93720
gcccgcctcg gcctcccaaa gtgctgggat tacaggcgtg agctaccgct cccagccagg   93780
aaacagcatt cttgagataa ttcatataat tcacccattt aaagtatata attcattctc   93840
tttagtatgc ccacagagtt gtacagccat caccagaatc agttttagaa cccataaagg   93900
aactctgtac tctttaccca aaacctccat gcctccagct gcaggcagcc actaacctgc   93960
cttctgtctc tgtgactcta cgtcttctgg acattactgt ggatgggctc atacagtcag   94020
tgagcttgtg actggtgcct tctaccaagc agggttttca gtgtagcagc ctctctgttt   94080 ttctttttt tttaaattgt gacggaactt ctgcctcccg ggttcaagcg attctcctgc    94140
ctcagcctcc cgagtggctg ggactacagg cccatgtcac catgcctggc taatttttt    94200 tttttttt tttagtagag atgggttttca acatgttagc cagggtggtc tcgatctcct    94260
gacttcatga tccgcctgcc tcggcctccc aaagtgctgg gattacaggc gtgagccacc   94320
atgcccggct aacctttcat ttactgtctg catttcttcc ctgatgcctt ccagtccatg   94380
cacccgattg tagccattca tcctattatg gtttaaggtg actgtcttag tcagcatggg   94440
ttgccataac aaaataccat agcctgggtg gcttcaacaa cagaatttac ttctcacact   94500
```

```
tctggaggtt gggaagtcca agatccagga ctttcgcctt gccctcatgt ggtgaggggg      94560
tgaggaagct ctgtggggcc tcttatatat ggatgctaat ctcattcatg agggtctgc      94620 cctcatgacc cagtcacctc ccaaaggccc cacctcctaa taccatcacc ctggtaatta      94680
agtttcagtg tataaatttg ggggactata gacattgaaa ccataacaag cacttttcta      94740
agatcaggga gtgagtaagt agcagagcta ggacctcaat tccacatgtc agtcatcttg      94800
ccttcactct gctccatgat ggctgcctcc tagagcattg ggagtctcga tgttctatat      94860
gctctcatgt gttgtgtatt ggagatagtt gaggctttat gaatacatct ggatttgttg      94920
acttctagct ttgctggtaa ccagctgtga ccttgaataa gttacttcat ctctgagcct      94980
gtttcctctt ttagaaacag gagtttaaaa tgctgctttg ggttgggcac ggtggctcat      95040
gcctgtaatt ccagcacttt gggaggctga gatgggagga tcactggagc ttggagttcg      95100
agaccagcct gggcatcata gtgtgagatc ctgtctcctc aagaaattaa aaaattagct      95160
gggtgatgtg gcgtgtgcct gtggtcccat ctactctgga ggctgaggtg ggaggattgc      95220
ttgagcccag gaggttgagg ctacaatgaa atatgattgc accccatcct gggtgacgag      95280
tgagaccctg tctcaaaaaa gaaaaaaaaa atgctgcttt gtaccccttt catgtcatgg      95340
cgtcatggcc aacatagaat gccctggttg tttgctgttg gagggcatgg gcctgggggc      95400
tccctgaggg ctccttccat cttcaactca ttctctgtgc acctgttagg aagttgtggg      95460
ccagtcccta ccatgtatca ttgtgtgggt aaaagtaaat aaaatgtgta cagtgtctga      95520
actgtacata tcagggtcca agaacaaaat gagtgacatg ggttagctct ttttaataaa      95580
tggtaaaacc aaatattcta attttcagtt ttgttatact tccatcacat gtttttgttt      95640
ttttgttttt tgttttttgtt tttctatttt aggcagcctt gccttctcta acaaaccccc      95700
cttctctaag tcccatccga cgaaagggga aggagaaaga accaggagaa caagcatctg      95760
taccgttgag tcccaagaaa ggcagtgagg ccagtgcagg taggaaacag cgtggggaag      95820
ggagggacat gagtgcagca tctgtcatgt agaaacatag gatttaagta acttggtgtt      95880
ttagagaaat aaatataata cacatcagta aagtgagaga agtttctcc aggtgcggtt      95940 caagatatta gaaactaatg actgatgtac acagaccacc ttttggtctg aagcatttct      96000
aagtgccact ggctgacatg cagcccctac agcctccagg cttccagccc tagcatggag      96060
catcactctc ctatgcttcc ctggttgcag gtgatggctg gagaggcctc ctgattttca      96120
gtaagggaag tggtgtagat gcttaggaat agatgtagtg agtgaaaaaa ctgattctga      96180
tatgtcaaaa attctgattg gaaatggaat atttacattt ggaagagcta aaggcgagag      96240
aaagtgggga taaagtcatc tgagttggag gagcttaaac cattcacaag tttggaggac      96300 cttttttttac ccatgaaaag gtcagaacag aaggggctag gatttaggtg tgactgcagt      96360
ttattgaatt cccatccata ctgctctcgg tgggcagtgg caggggcagg agaggagcct      96420
ggcaaagcat gaagtgactg ctgctgcctc tgctatctgg gacgcctggc cacctgtctg      96480
tacagtctcc ctccagaccc attctcacgc tgtctcttgg cacccagggg ccagtgatgg      96540
ttctcccatt tgttttgtgt atatagcatt tatatcaagg ctatttattt atttatttat      96600
tttatttatt tatttttttg agacagagtc tcactctgtc acccaggctg gagtgcagtg      96660
gtgcaatctc ggctcagtgc aagctctgcc tcctgggttc aagcaattct cctgcctcag      96720
cctcctgagt agctgggact acaggtgtgc accaccacac ctggctaatt ttttgtattt      96780
tttattagtg gagacggggt ttcaccttgt tggccaggat ggtcttgatc tcctgacctc      96840
gtgatccgtc cacctcagcc tctcaaagtg ctgggattac aggcatgagt cactgtaccc      96900
```

```
ggcctattta tttatttta attgacaaaa ttgtatatat ctgtaatata caacatgatg   96960
tttgaaatat gtgtacattg gccaggcgtg gtggctcaca cctgtaatcc cagcactttg   97020
ggaggctgag gtgggcggat cacgaggtcg ggagttcaag accaaactgg ccagcatggt   97080
gaaatcctgt ctctactaaa aataccacaa aaaaaaaaaa aaaaaaaaaa agccgggcat   97140
ggtggctcgc gccagtcgtc ccagctactt gggaggctga ggcaggagaa ttgcttgaat   97200
ctggcaggtg gaggttgcag tgagctgagt tcatgccact gcactctagc ctgggcgata   97260
gagcgagact ccgtctcaaa aaaaaaaaaa aaagaagaaa tacatatgca ttgtggaatg   97320
gctaattaac ctgtgcatca cctcacgtat cattgttttg tggtgagaac acttaaaatc   97380
tactctttca gtgattttct tgcatatggt acattgctat taactgcagt caccatgcta   97440
tacagtagat ctcttgaact cattcctcct gtctataaat gaaattttgt atccttgacc   97500
aacacattca aggttttttt tgagatggag tcttcttcac ccaggctgga gtaccatggc   97560
acgatctcat ctcactgcaa cctccgcctc ccaggttcaa gcaattctcc tgcctcagcc   97620
tcctgagtag ctgggattac aggcacatgc tactgcacct ggctaatttt tgtattttta   97680
gtagaagtgg agtttcacca tgttggccag gctggtctcg aactcctgac ctcaagtgat   97740
ccgcctgcct tggcctgcca agtgctggga ttacaggtg tgagccactg cacccggcct   97800
caagcgtttt aaaagatgct cttttctaag gattgactgt agtacaggag gaagattgac   97860
ctgttgaaaa gcctcagcct ttacaagtgt aaaattatca gtatattact atcatctttc   97920
tgatgaatta aataaactaa ggactccaag tcaaagtct tcaaactgaa gtagaatagt   97980
tgtatatagt gcttggcact ttaatattta gtatcggttt aatgataatg tttgtgcctt   98040
tgccgtcttt aaaacatttt tacatcatcc ctgtttgatt acttggtgtg ctcatgaagt   98100
tgttggccac taaggaatct taggctcaga gaggttctgg aattggccag tggtccttga   98160
atcagctgct cctatgattc tctaactgat ttctcacaaa gcaaacaagc aatcataaca   98220
aaacaactgt gcacactgct cttcttattt tgttatttaa aaagtactta ggctctactt   98280
atgtttgtta gtcaatttct cattacttct agttaatcaa aaggtcagag gaaatacttg   98340
aatattttca tactagaata cttaaaaaa tcatgatttc cagtaatctc tttaaaactt   98400
ggcaagttat tttgatctaa aagtttatct tttgtgtgca tattttaaa gcttctagac   98460 aatctgatac ctcaggtcct gttacaacaa gtaaatcctc atcactgggg agtttctatc   98520
atcttccttc atacctcaaa ctgcatgatg tcctgaaagc tacacacgct aactacaagg   98580
tatgggcctc tgcatctttt aaaaatatat atgcacacat acttacgtct aatggatagt   98640
tgatgttttt cttatgattt gtaggatgta aagcccttt gagatatgag ttacatttag   98700
ttttttcaag tttgtttgtc tttcagcttt gtttatgata gcttctatca tacaggtgtt   98760
ttggattttc atattgtttg tactcacagc taagattgat tacagtgaca gagctaggat   98820
gtgcagccag gttataggg gaagtggccc tggtggagtc tggagggatc cgtgtacagg   98880
cttccttccc tcccgtgagg ctcacacaaa aatacagcaa catgctggtc ctgcaggtac   98940
cctctgccta acatgagcca caattccaga ctcacagaag aaaagcaggt gttcggcata   99000
aaccatgtgt ttcaaatagt ctgggcatgg tgagccactt gttatcagct agggaaagtt   99060
tatgtcagcg taagaaactg ttcaccagat accccaaga gccagccttt ctgtctaggg   99120
atgttttagt ttttagttc atttttttt ttaactttaa aattttctgt tcatctgcaa   99180
tttgttagat atgaagtatg tgtctaattt aattttgtt tttggttgtc cccaataatg   99240
```

```
tttacagaag aatttttctg cactaattgg cttgagttac ttacattctc atagttctct   99300
agtttcagta gtttcatttta ttatttgtt atatcaatct atctgtctgc tcatctatta   99360
gaagcatcct tgttttttt ttttctttt tagacagagt cttgctctgt ccccaggttg    99420
gagtgcagtg gtgcaaccat gcctccctgc agtctcaggg ctcaagtgat cctcccacct   99480
cagctcctga gtacctggga ctaccggcat gtgccaccac acccagctaa tttttacatt   99540
ttttgtagag acagggtctc cctaagttgc ctgggctggt ctcaagctcc tggcttaagt   99600
aatcctccct ccttggcctc ccaaagtgct gggattacag gtgtgagcaa ctgcacccgg   99660
ctacaagtat acttcttaat tattgtagct taatggtatt tatgagggga tcagttcccc   99720
tgttgttctt tagaattttc tggatattct tctttattga ttttgggatg tgaacaatag   99780
aatcaacttc tacttgtaga ttgatttagg gagaacttat acctcagatg ttaagtcacc   99840
ctgtccagaa tgtgggatgc tttcctattt gttcagaact ttttaaatta cctcagaagc   99900
acatgaaatt taaaggattt taaaaaaaac ttaaagatta tttcacatag ctcttgcaca   99960
tttcttgata aatgaatcct caggtattcc tctgtttttg ttactaatag ttacttctta  100020
tgggttttt ttcccctgaa aatcatttat caaacgtatg tggcttattt tctgaaggat   100080
gtttgataat tttggaagat atgaaagtct tcatatttta caaggtttga ggtctcttta  100140
agctgcatgg ttctcatgtc agctcccaaa gcagaagacg gcatgttgaa aaatgccgta  100200
gagaagatac ttcttttcca cctgttttca actcatatca tcttgaattt cagggcacct  100260
ttccatgctc ctagtgcttg ctatctgttt attatttcc ttcctgaata ccctgaactc  100320
cagcatgttc tgctgtaatt ctggcctccc tggcatcttg gactcctgtt tcctttgctc  100380
tgtcatcccc gcggtcagct cctgctgcgc agcttctcag ctgaagtgcg tttggagtgc  100440
ctggcgtgtc ttgctggatc tttgagtatt gcctctggtt tccttggttc cttctgctga  100500
gttgctcagc gtctccactc cccatttctt gtgtggccct tcctgcactc ctctgattcc  100560
ttttgtcttc cctggtttct tgctttggtt tcgagtctcc acagaacttt tgcagctctt  100620
ctgaagacct ggaagctttt tcatcttaat tctcatctca tgacctcttt tcccttcttt  100680
gagagctaga acttcccatg gtgaacttct ctttccagaa ttccatgcct tcttttccct  100740
cccacttacc tgttgtccag gagaggtcag attgctgtgc atattggagg agaacccttt  100800
cttccctggg ctcttcatct cacatgacat caccacatca cctcgttcct tggaccctca  100860
gtggtgtcac tgctggattt ttcttccctt tggctggcct tagggcacac ccaggttgac  100920
tagcgtagtc atggtattta gatccactca cattttcagt ttctgtgtct gtctcttgcc  100980
tgcttctgac ttcgcccaga gaaagcttct cttttcacaag ggttcttaga tttatgttca 101040
ctgagcacct tcttttctga ggcagtgttt taccaatatt tattttccta gtcagtctcg  101100
ccttaccttt cttgttatgc atgtctttgg tcctgaccca ttctctgagt ctgtaaaata  101160
gaattgctgt ataatttaat tacatgaaat cctttagaat cttaacacat cttacacctg  101220
atttaatatt ttattgtatc caaattgaac caaccctatg tgaatttgac agtgattct   101280
cccagggatc ctagtgtata aggaatagga cttagtattt tctattttt gatataccac   101340
ataccagata ctgattatga tggacattta accctttttt ctcattatga aagaaagtta  101400
ggaattattt cttccagtag cgccagtgta acctgaaagc ctttgaaaga gtagttttg   101460
tatagctatc tgaaaggaat ttcttttccaa aatattttc cagtgctgac aacaaacacg  101520
cagacacacc ctgcaaggtg agtgtacggc gccgcacagt ggaggcatct gctgcagccg  101580
tcgatgtttg tgtctttggt tgtacattat gagatcgtga cagggccagt aaccgtgtgt  101640
```

```
tctctccttc accttcccaa ggtcacgctg gatcttcaga acagcacgga aaagtttgga  101700
gggtttctcc gctcagcctt ggatgttctt tctcagatac tagagctggc cacactgcag  101760
gacattggga aggtttgtgt cttgttttt ctccttgggt tgtggctggc acacttgatg  101820
tgcgtcttct gggctgagtt catctaggat ggagcctggt tctccagggt gcctccggga  101880
gactcctccc tgccccacgt gcttgcgtca caggacccaa gtctgactct gccttagcca  101940
tgaagtttag ggggaagttt ctatttgtat tctattttg tctgttatca tgtattagct  102000
tagacccagt ttagtttgga aaatcagtgg gtttcaaaat gtgtttgtag agtcctttat  102060
ttcttaactt gaccttttca agtggaaagg ggcaaaacag acgggtaagg gggcggggcg  102120
ggaggtgtga cttgctcttt tgtgcctgag gaagtaacag agctggggtt gacagtcata  102180
ttctctgaca cagatagtct ctgacttatc tcacagaaag tcagcggcag agcctgagtt  102240
aaaagtctcg tagattttct ttttcttttt tttggtggct aatttcagtt ttatttatat  102300
ttgtttattt atttattata ctttaagttc tgggttacat gtgcagaatg tgcagttttg  102360
ttacataggt atacacgtgc catgatggtt tgctgcaccc atcaacccat cacctacatt  102420
aggtatttct cctaatgtta tccctccccc agtcccctca ctcccatgg gccccggtgt  102480 gtgatgttct cctccctgtg cccatgtgtt ctcattgttc aatttccact tgtgagtgag  102540
aacatgcggt gtttggtttt ctgatcttgt gatagtttgc tgagaatgat ggtttccagc  102600
atcatccatg tgcctgcaaa ggacatgaac tcatcctttt ttatggctgt atagtattcc  102660
atggtgtata tgtgccacat tttcttaatc cagtctatca ttgatggaca ttcgggttgg  102720
ttccaagtct ttgctattgt gactagtgcc acaataaaca tacatgtgca tgtgtcttta  102780
tcgtagaatg atttataatc ctttgggtat atgcccagta atgggattgc tgggtcaaat  102840
ggtatttcta gttctagacc tttgaggaat cgccagactg tcttccacaa tagttgaact  102900
aatttacact cccaccaaca gtgtaaaagt gttcctattt ttccacaacc tctccagcat  102960
ctgttgtttc gtgactttt aacgatcgcc atcctaactg gcgtgagatg gtatctcatt  103020
gtgattttga tctgcatttc tctaatgacc agtggtgatg agcattttt cgtatgtctg  103080 ttggctgcat aaatgtcttc ttttgcgaag tgtctgttca tatcctttgt ccattttttg  103140
atggggttgt ttgctttttt ttcgtaaatt tgtttaagtt ctttgtagat tctggatgtt  103200
aatcttttgt cagatgggta gattgcaaaa attttatccc attctgtagg ttgcctgttc  103260
actctgatga tagtttcttt tgctatgcag aagctcttta gtttaattag atcccgtttg  103320
tcaatttggg cttttgttgc cattgctttt ggtgttttag acatgaagtc tttgcctatg  103380
cctatgtcct gaatgttatg gcccaggttt tcttctagga ttttatggt cctaggtctt  103440 atgtttaagt ctttgatcca tcttgagttg atttttgtgt aaggtataag gaaggggtcc  103500
agtttcagtt ttctgcatgt ggctagccag ttttcccaac accatttatt aaatagggaa  103560
tcttttcccc attgcttatg tgtgtcaggt tgtcaaaga tcagatgatt gtagatgtgt  103620
ggtggtattt ctgaggcctc tgttctgttc cattggtcta tatatctgtt ttggtaccag  103680
taccatgcag ttttggttac tgtagtgttg tagtatagtt tgaagtcagg tagtgtgatg  103740
cctccagctt tgttcttcta gcccaggatt gtctggctga tgcaggctct ttttggttc  103800 catatgaagt ttaaaatagt ttttccaat tctgtgaaga aagtcagtga tagcttgatg  103860
gggggatagc attgaatcta taaattactt gggcagcaa ggccatttt acgatattga  103920 ttcgtcctat ccatgaacat ggaatgtttt tctatttgtt tgtgtcctct cttatttcct  103980
```

```
tgagcagtgg tttgtagttc tccttgaaga ggtccttcac atcccttgta agttgtcttc 104040
ctaggtgttt cattcccttta gtagcatttg tgaatgggag ttcactcatg atttggctct 104100
ctgtttgtct gttattggtg tataggaatg cttgtgattt ttgcacattg attttgtatc 104160
ctgagacttt gctgaagttg ctaatcagct taaggagatt ttgagctgaa ccaatagggt 104220
tttctaaata tacaatcatg tcatctgcaa acagggacag ttttacttcc tctcttccta 104280
tttgaatacc ctttattgct ttctcttgcc tgattgcgct ggccagaact tccaatacta 104340
tgttgaatag gagtggtgag agagggcatc cttgtcttgt gccggttttc gaagggaatg 104400
cttccagttt ttgcccattc agtatgatat tagctgtggg tttgtcataa atagctctta 104460
ctatgttgag atacgttcca tcgataccta gtttattgag agttttttagc atgaaaggct 104520 gttgaatttt gtcaaaggcc ttttctgcat ctgttgagat aatcatatgg tttttgttgt 104580
tggttctgtt tatgtgatgg attacgttta ttgatttgcg tatgttgaac cagccttgca 104640
ttccagggat gaagctgact tgattgtggt ggataagctt tttgatgtgc tgctggattc 104700
agtttgccag tattttattg aggattttca catcgatgtt catcagggat attggcctaa 104760
aattctcttt ttttgttgtg tctctgccag gctttggtat caggatgatg ctggcctcat 104820
aaaatgagtt agggaggatt ctctcttttt ctattgattg aatagtttc agaaggaatg 104880 gtaccatctc ctctttgtac ctctggtaga attcggctgt gaatccatcc tggactttttt 104940 ttggttagta ggctattaac tattgcctca agtttagaac ctgttatcag tctattcaga 105000
gattcagctt ttttctggtt tagtcttggg agggtgtatg tgtccaggaa tttatccatt 105060
tcttctagat tttctagttt atttgggtag agatgtttat agtattctct gatggtagtt 105120
tgtatttctg tgggatcggt ggtgatatcc cctttatcgt ttttattgag tctatttgat 105180
tcttctctct tttcttcttt attagtcttg ctagcggtct acctatttta ttgatctttt 105240
caaaaaacca gcacctggat tcattgattt tttttggagg gtttttttttc gtgtctctat 105300 ctccttcagt tctgctctga tcttagttat ttttttgtctt ctgctagctt ttgaatttgt 105360
ttgctcttgc ttttctagtt cttttaattg tgatgttagg gtgttaattt tagatctttt 105420
ctgctttctc ttgtgggcat ttagtgctat aaatttccct ctacacactg ctttaaatgt 105480
gtcccagaga ttctggtatg ttgtgtcttc gttctcattg gtttccaaga aaatttttat 105540
ttctgccttc atttcgttat ttacccagta gtcattcaag agcaggttgt tcagtttcca 105600
tgtagttgtg tggttttgag tgagattctc aatcctgagt tctaatttga ttgcactgtg 105660
gtctgacaga cagtttgttg tgatttctgt tctttttacat ttgctgagga gtgttttact 105720
tccaactatg tggtcagttt tagaataagt gcaatgtggt gctgagaaga atgtatgttc 105780
tgttgatttg gggtgcagag ttctgtagat gtctattagg tccgcttggt ccagtgctga 105840
gttcaagtcc tggatatcct tgttaatttt ctggctcatt gatctgccta atattgacag 105900
tggggtgtta aagtctccca ctattaccgg gtgggagtct ctttgtaggt ctctaagaac 105960
ttgcttcatg aatctgggtg ctcctgtatt ggggcgtgt atatttagga tagttagctc 106020
ttcttgttga attgatccct ttaccattat gtaatggcct tctttgtctc ctttgaactt 106080
tgttgattta aagtctgttt tatcagagac taggattgca atccctgctt ttttttttgct 106140 ttccatttgc ttgttagatc ttcctccatc cctttatttt gagccaatga gtgtctttgc 106200
atgtgagatg ggtctcctga atacagcaca ccaatgggtc ttgactcttt atccaatttg 106260
ccagtctgtg tcttttaatt ggggcattta gcccatttac atttaaggtt aatattgcta 106320
tgtgtgaatt tgatcctgtc attatgatcc tagttggtta ttttgcccgt taactgatgc 106380
```

```
agtttcttca tagcgtcagt agtctttaca atttggcatg ttttgcagt ggctggtact 106440
ggttgttcct ttccatgttt agtgcttcct tcaggagctc ttgtaaggca ggcctggtgg 106500
tgacaaaatc tctgcatttg cttgtctgta aaggatttta tttctcgttc acttatgaag 106560
cttagtttgg ctggatatga aattctgggt tgaaaatact tttttaaag aatgttgaat 106620
attggctccc actctttct ggcttgtagg atttctgcag agagatctgc tgttagtctg 106680
atgggcttcc ctttgtgggt aacccgacct ttctctctgg ctgcccttc cttcatttca 106740
atcttggtgg atctgatgat tatgtgtctt ggggttgctc ttctcgagga gtatctttgt 106800
ggtgttctct gtatttcctg aatttgaatg ttggtctgcc ttgctaggtt ggggaagttc 106860
tcctggataa tatcctgaag agtgttttct aacttggttc tattctcccc atcactttca 106920
ggtacaccaa tcaaacgtag atttggtctt ttcacatagt cccatatttc ttggaggctt 106980
ggttcatttc ttttcactct ttttctcta atcttgtctt ctcgctttat ttcattaatt 107040
tgatcttcaa tcactgatat ccttcttct gcttgattga atcggctgtc gaagcttgtg 107100
tatacttcac aaaattctcg ttctgtggtt tttagctcca tcaggtcatt taagctcttc 107160
tctcacactgg ttattctagc cattagtcta acatttttt caaggttttt agcttccttg 107220
tgatgggtta aacatgctc ctttagctcg gagaagtttg ttattaccga ccttctgaag 107280
cctacttctg tcaattcatc aaactcattc tccatccagt tttgttccct tgctggtgag 107340
gagttgtgat cctttggagg agaagaggtg ttctggtttt tggaatttc agcctttctg 107400
ctatggtttc tccccatcat tgtggttta tctacctttg gtctttgatg ttggtgacct 107460
acggatgggg ttttggtgtg ggtgtccttt ttgttgatgt tgatgctatt cctttctgtt 107520
tgttagtttt cctctaaca gacaggcccc tcagctgcag gtctgttgga gtttgctgga 107580
ggtccactcc aggccctgtt tgcctgggca tcaccagcag aggctgcaga acagcaaata 107640
ttgctgcctg atccttcctc tggaaacatc gtcccagagc acgaaggtgt ctgcctgtat 107700
gaggtgtttg ttggcccta ctgggaggtg tctcccagtc aggctacatg ggggtcaggg 107760
acccacttga ggcagtctgt tcattatcgg agcttgaatg ccgtaccggg agaaccactg 107820
ctctcttcag agctgtcagg cacgtatgtt taaatctgga gaagctgtct gctgcctttt 107880
gttcagatgt gcccttcccc cagaggtgga atctagagag gcagtaggcc ttgctgagct 107940
gcagtgggct ctgcccagtt cgagcttccc tgctgctttg tttacactgt gagcatagaa 108000
ccacctactc tagcctcagc agtggtggac accctcccc cagccaagct cctgcatccc 108060
aggtcgattt cagagtgctg cgctagcagt gagcaaggcc ccatgggcgt gggacccgct 108120
gagccaggca caggagagaa tctcctggtc tgctggttgt gaagactgtg ggaaaagtgc 108180
agtatttggg caggagtgta ctgctccttc aggtacagtc actcatggct tccttggct 108240
tggaaaggga agtcccccga cccttgtgc ttcccaggtg aggcaacacc ccgccctgct 108300
tcggcttgcc ctccgtgggc tgcacccact gtccagcaag tcccagtgag atgaactagg 108360
tacctcagtt ggaaatgcag aaatcacctg tcttctgtgt cgatctcact gggagctgta 108420
gactggagct gttcctattc ggccattttg gaagcatccc ttgttttttg aggtggagtc 108480
ttgctctgtc gcccaggctg acgtgcatcg gcacaatctc ggcccactgc aacctttgcc 108540
tcctggttc aagcgattct cctacctcag cctccggagt agctgggatt acaggcacct 108600
gccaccatgc ctggctaatt ttttgtattt ttagtggaga tgggggttca ccacattggc 108660
caggctagtc tcgaactcct gaccttgtga tccacccacc tcagcctcct agagtgctgg 108720
```

```
gatcacaggt gtcagccacc acgcccagcc atattttcag atctccctct ctttgcccta  108780
aaccactgtg cttaataagt agttttttagt ggccagcagt ctccatgtat aacacatttt  108840
agcaaaatgg aaaatactat atgttttaaa tttgaacgtg agattatact gaaataaaaa  108900
tcatctaact gggattcttt aaatagtaag attttctttt ttgtatgtgg gttttttttt  108960
aaccttatta ttatgactgt catatataga aatggctgtt tttcagttac agtcagtgaa  109020
tgtatcaaat gctgccttat ccaaataata aaagtaaatt attaataagt cacaatttaa  109080
tgaagattga tgttagttga tctttatatt cttgaaatca gccatatggt tgtgtgtgta  109140
tgtatatatt tttaaaggta cataaagata ataagctcat ctctgaaaat ttttacattt  109200
ggcataagaa taactggata attaagcatc ttattctctg gcctgtgtct ttacagttaa  109260
aggtagattt actcacctct cctttttttgt ttttctaagt tcatcttttt tgctgtttca  109320
agacagaggc ccatttttagc tttctcgcat atccttttgt ttgtactttg aagcctcac   109380 ctgcttaatt gttgagtttt tatccgtggt cttttagagg gggatatgta gggtagaagc  109440
tttcacaggt tcttgtttgc acttggcccc tgactgtttt gaggaatctc cctcactgac  109500
tcacagcatg gcaaggtttc agatctcttt ctgccacaca gcagttctga ggcagctgga  109560
aagatatcca gatgcttaga ttgtcaggcc aggcttgaga tatacaaact attgagcctt  109620
atctgtgacc ttgcttaggt gaaggcatca gagcccctgc accaacatgc ataggcctct  109680
gcatgtgtgc ggggctgggt gttgaggtct gagcacaagt gtagctggag aggtgagctt  109740
gatgtggcga cgggtatgag caggttttct tcagacttct gtgagtttac ctagttccag  109800
gatttaaagg cacagagact ttagaattaa aatagaatca ttttctttttt ctaaatagca  109860 acactaggaa taaaaaataa taattccaca ttcttgacag gtaatgtttt ttcttgtctt  109920
ctaatcctta tttattccat actcattttt atacataatt gaaatgtatt atgcattgga  109980
tttttctttt gcattatatt atagacgatt tttcatgtaa ctccttactg ttccattttta  110040 tatgttttgt ctggtttaag actttatctg caaaccggga aactgtctct acaaaaagaa  110100
aaacaaaaat agttggccgc agtggcatgc gtctgtggtc ccagctactc ggggctgagg  110160
tgggaggatt gcttgagcct tgggaggttg aggctgcaaa gagccatgat catgccattg  110220
cactccagca tgggtgacag actttatact gtctgttttg ggtgatttga taatgatatg  110280
ccctgatgta gttttttttat atctgtgtt tcttgtgcct gggtttattg aggttgggtc  110340
tgtggcttca tagtattttt aaagtttgga aaatttttagg ccattctttc tttctttctt  110400
tctttttttt tttttttgaga cagtgtctcg ctctgtcgcc tgcgttggag tgcagtgaca  110460
ctatcttggc tcactgcaag ctctgcctcc tgggttcacg ccattctcct gcctcagcct  110520
cctgagtagc tgggactaca ggcgcctgcc accacgcctg gctaattttt tgtatttttta  110580 gtagagacga ggtttcactg tgttagccag gatggtctca atctcctgac ctcgtgatct  110640
gcccgcctgg gcctcccaaa gtgctgggat tacaggcgtg agccactgca cccagctagg  110700
ccattatttc ttcaaagatt tttttctgc cctgcctccc tcctttttttc cctctcttaa  110760 agggggctgtg atttcctgaa tgattgctta gtgttgtccc atagcttact gatgctcttt  110820
tcagtgtttg attgttttat gtgttttctg ttttgtatag tttctattat tgtgtttca   110880 agttctctga tcttttcttc tacagtgtct actctgttgt taatctgtta atctgttgtt  110940
aatcctgtcc agcgtatttt tttttttgtt tttgaaacag tctcactctg ttgcccaggc  111000
tggagtttag tggtgcgata tcagctcact gcaacctcca cctcccaggc tcaagcaatt  111060
cttctgcctc agcctcccga gtagctggga ctataggcac gtgccaccac acctggctaa  111120
```

```
tttgtgtatt tttattagag atggggtttc accatgttgg ccaaactggc cttgaactcc   111180
tgacctcagg tgattcatcc gcctcggtct cccaaagtgt tgggattata ggcatgagcc   111240
accgtgtctg gcccctgttc agtgtatatc actaattttg ttttatctc tagaagtttg   111300
atttaggtct tttaaaaatg tctccctgtg tttctgttta gctttgtgaa cacaattgta   111360
ataactgttt taatatcctt ctctgctagt tctaagatct tctaataact tcccagttct   111420
tggtgtttct cattggttga ttgatactcc tcgttttggg ttgtattttc ctgcctcttt   111480
gtatggctgc caattttta ttggatgccc aaccttgtga attttacttt gttggatgct   111540
atatattttt gtgttccat agatcttctt gagctttgtt ctgaggttag ttgagttaca   111600
tatagatggt ttactctttt gggtcttgct ttataatttg tcagatgggt tggagcagtg   111660
cttagtttag gactaatttt ttttttggac taattattcc tctttaggaa taattaggta   111720
ccatgcttag gaggcaagac catcctgagt actctaccta atgaaccaga aagtttgggt   111780
tttccagtcc gcctgctgag aacagtgact ttctagccct gtgtgagcgc tgagctctgc   111840
tccttctaat cctttccaat gcttcttttcc ctggcctcag ggagttttct cacacacata   111900
tctctgctga gtactcgaga gggaccttcc ccagatctcc agagctctct ctgtcttgtt   111960
ttctcttctc tggtgctctg tcttatgaac tgtggctgtc ttggtctcct tagattctca   112020
gcacctcttc aattcagagg gttgcctgtc cctcctcctt gtgccacagc ctaggaactc   112080
tctcaaagca gcgagttggg gcagccatag ggctgactta gtctctcgtc tcccagggat   112140
cactgtcctt cattgctcat gtccagtgtc ttgaggactc tgggttttgt ctgttttgtt   112200
ttttggtttg ctttggttgt ctcaggcagg agggtaaacc cagtccctca ccctcattgt   112260
gctcagtagt ggaagtctca ctctattaca ttagatatta gtatttgtag cagagccctg   112320
gttccctggt acttggggag ctcttgaaag gccagaaaca gcatgctttc tcacctttc   112380
cagggcttca gtttctggtg cacatcaagc attccataca catttgttaa agtcctttgt   112440
tagacaagta gtgattcaca ggttctattt gtaattttt cagttaacat gtattgggta   112500
tctgctggga gctagtaaaa acaaaaagtg gtgtgtgaca aattcaattc tgacaagaac   112560
aaccttaaac acttagaata tactttgagc atatcagaat tttaaaaatg tgtggccctt   112620
gagtatttga aaccaacaag aatctattgc ttattagtag aggatatttt gttaaacaag   112680
tggagagaga ggcattttca gtctaattgg tgttggcttt tagcagctga tggaaaccag   112740
ttcgtgatta gccaggcagt ggtgaaacag gctgtgcatt ctgaatgcct aggtatctag   112800
gcattcagaa tggtggcgct ctttgagtta gcatcttctt cttcttgat tcttttttt   112860
ttttttttga gatggacttt cgctcttgtt gcccaggtaa caactccagt gcaatggcgc   112920
catctcggct cactgtaacc tctgcctccc tggttcaagc gattctcctg cctcagcctc   112980
tcaagtagct gggattacag gtgtgcgcca ccacgcctgg ctaattttgt attttggta   113040
gagatggggt ttcactatat tggtcaggct ggtcttgaac tcctgacctc aagtgatgca   113100
cctgcctcga tctcccaaaa tgctgggatt acaggcgtga gccaccactc ccagcccctt   113160
cttgattctt gaaaggaca ttgggtgctg tacatctcgt tatagatgtt gataaaaatg   113220
cttgtgagaa gagtaacatt aaggtagtta tttggtcatt tttgcagatt attttaagac   113280
aattctagga ctgatttgtg gtaaatcaca cattgctgta tcatagttgt gttcactgaa   113340
catattcagg ggctctacag atgcagggct cttagctgct ttgcacactt ctgaattcct   113400
gccctgcgaa caggactgga tacctaatag acaacaggta cttgataaca gtttattgaa   113460
```

```
ttaatgagtg aatgaacaga tacataaatg catgaaagaa tggttgtaat gtatataact    113520
tggatttcaa gacttttttac tgactgttca aaataagaaa ttgaaaactt tcctctgatt   113580
ttcctctact atttacacaa tttaaatgga agttatcttg taccttcaat ttctgtctag   113640
gattcgtaca ataacgggtc atctctgagt cgcttaatgt ctcacttgtc tttctacagt   113700
gtgttgaaga gatcctagga tacctgaaat cctgctttag tcgagaacca atgatggcaa   113760
ctgtttgtgt tcaacaagta agagcttcat tcttttcctc ttctgttaag acgttcgggt   113820
atgacagcaa aacgctgcta ctccttaaga ggcaggcgct gttggcataa tcagctggga   113880
ggattgtggg gtccagcgca gcacttttg gctcagtcca tgattgagcc aagaggccat    113940
ccttcccttc actccccagg aggacgaggt ctgtcactgt ggagggcaga ggacaccaga   114000
agctcctctg caacctcgct agttaacttc cagtccctcg gagtttctgt ttagaatgct   114060
caatctcatt tagaattgca aggaaaccca aaacgcctat ttaaggtaca aacagcactt   114120
catacaatat ctcatgaggt attaatagtg attcacagga agaatttcac gctgtgagtc   114180
tttgctaaca tatccagtta tttacagatg gatttgatat ttgtgtggga gattcttaaa   114240
agtgttgttc acgccacatt gttgatgcct catttttttc actgtagttg ttgaagactc   114300
tctttggcac aaacttggcc tcccagtttg atggcttatc ttccaacccc agcaagtcac   114360
aaggccgagc acagcgcctt ggctcctcca gtgtgaggcc aggcttgtac cactactgct   114420
tcatggcccc gtacacccac ttcacccagg ccctcgctga cgccagcctg aggaacatgg   114480
tgcaggcgga gcaggagaac gacacctcgg ggtaacagtt gtggcaagaa tgctgtcgtt   114540
ggtgaagca cgaaagagca agcaggaaat actttgtaaa agaataaaaa cgaaaaatgt    114600
tagcgaacat cttctaatag tctgctgtat tcagagaact ctaggagata tatatggttg   114660
atgcaaagat gatttaaggc atagcccggc cttccaagaa gtgtgtggcc agtgagtgag   114720
atgggcttgg gacttacaca tctcagaggt gggggtagag gaggaggaac actgagtggg   114780
ctgagaagca gccagctctc attgccaaag tgtgtcagca aaccagaatg cagttcataa   114840
tgtccccacc cattcaaagc acaggacctg tagagtggtg tggcatgtgt tggtggcact   114900
tttcaggcct gtaacaagga tgaaagaaca gcttcatagc agcacagtag tgctggtgtt   114960
cagaggtgtg tgaaggccat agaagcatct tggatatatt accttgtgtt ttgtcagctt   115020
tatgactaga agtctctttt cacttaaatt tgttttttt ttttttgaga cggagtcttg    115080
ctctgtcgcc caggctggag tgcagtggtg caatctcagc tcactgcaag ctctgcatcc   115140
tgggttcatg ccattctcct gcctcagcct cccgagtagc tgggactaca ggcgcctgcc   115200
atcacgcctg gctaactttt ttttgtattt ttagtagaga cggggtttca ccatgttagc   115260
caggatggtc tcgatctcct gacctcgtga tctgcccgtc ccggcctccc aaagtgctgg   115320
gattacaggc gtgagccacc gcgcccggcc tcttttcact taaatttatg tttgtgtttt   115380
taatgcctag tatacaggac ttcttaaatt gccttaagta tgaacaggta tttgagttgc   115440
taatctgtat agtagcaata atagaatccc ttgttttttcc ttttataaat ttagcgatta   115500
aatagctaca attaaaacac tagagtcagg agtcaaggaa aatacccatg ttccaggctg   115560
tatgttagtg atgtacttac tatatattgg agtttcagga gtaagtctgt ttcaatgctt   115620
tctgtaacca tttggggtat taataagcat gtgagtgtgt gcatgtttgg gttaatttca   115680
tatatgtttc ttagaaggga tatcattgat gtaaatattt taaaggcttg tcctccaaaa   115740
aaatcatgta atttcttcta aattactgat cttttaaatg accttcacct ttctctcaaa   115800
tctcacttaa gactgggctg agtagtcagt ttcctgtagc agaaaaaagc tcagacttga   115860
```

```
gtagccttct gcgagtgagg agacttgatg gctgtcaggc agctgtaaac tctaaataga  115920
gtgtcattat ctgaagaggg cgatgctgcc acactgagtg gcctttcaag ttgtttctca  115980
atctgacacg ttctgatcgt gtgaatgtga aattggtttg agcaggagta tatctgagtg  116040
cagaggagat tatttaaaga tattctcatt ctctgcttcc cttttattcc catttggcag  116100
atggtttgat gtcctccaga aagtgtctac ccagttgaag acaaacctca cgagtgtcac  116160
aaagaaccgt gcagataagg taaatggtgc cgtttgtggc atgtgaactc aggcgtgtca  116220
gtgctagaga ggaaactgga gctgagactt ccaggtatt tgcttgaag cttttagttg  116280 aaggcttact tatggattct ttcttctt ttttcttttt tatagaatgc tattcataat  116340
cacattcgtt tgtttgaacc tcttgttata aaagctttaa aacagtacac gactacaaca  116400
tgtgtgcagt tacagaagca ggttttagat ttgctggcgc agctggttca gttacgggtt  116460
aattactgtc ttctggattc agatcaggtt tgtcacttt atctttcatc catcatacct  116520
gttcctaatt tagtacaaat taccctaaaa gacactgaaa tctactttaa agaaatgtgg  116580
tctgcatgtt tccctcatca gttgctgctg cttatctttt tcatgcacct agctggtgca  116640
gaaggcctgg ggcatagcca gcctcagcaa gtcagcatcc ttgccccagc tccctggact  116700
caaggctaac ctggggttgg ctgttaggga tttccaaagg tttgtcccat ccacttgcct  116760
cccctccaaa ataagtttga atttaaattg tgagatacaa ttaagattta ttgtttgggg  116820 aacattttg caaaatctag agttagttta aacagattat caattattac cataattgat  116880
catctgcagt ttcaagctat ctaacaggtt cacttacctc tttaaaaagg aatggaattt  116940
agcaggacag taactgagac ccgtgctcct ggagtccatg tgggagctgt gtggctctgc  117000
acaagcattt gcacgcttcc cctcttgact gcattacctt cctcctatag ttgctgtggg  117060
caccagattc tggctagtcc tgtcccttca tgatgcacat tttcctcaag attcgtccca  117120
gttaaatcac tgcagatgaa actgcctttt catcgtcaaa atttaactgt catttttgag  117180
ccgtgatctt gggctacttt cttatgtggg gtaggaatat ttgtgagtta gaaatattac  117240
acttctctat ttccttctag acgtaaatct gttaatcctg tcagcactgt tactcacctg  117300
aaagggtctg tttccctagg agaactgagg gcactcggtc aacactgatt ttccacagtg  117360
ggtattgggg tggtatctgc ttgttttttt tgttgttgtt gtttgttttt ttttgttttt  117420 ttttgagat ggagtctcgc tctgtcaccc aggctggagt gcaggggtgc gatctcggct  117480
cactgccagc tccgcctcag aggttcacgc cattctcctg cctcagcctc ccgagtagct  117540
gggactacag gcacccacca ctacgccagg ctaatttttt gtattttag tagagacgag  117600 gtttcactgt gttagccagg atggtctcca tctcctgacc tcgtgatctg cccgcctcgg  117660
cctcccaaag tgctgggatg acaggcgtga gccaccgcgc ccggcctggg gtctgctttt  117720
aatgaaggag gcatcaaggg gtgggctttg cgttggcctg atgctttcat ctttctttca  117780
caaaccctgt ccgaagaaaa tccgtctaaa tgggccattg ctctcctcag gaaatagtca  117840
ttgggaactt cttttcctt cctttgacac taggaggctg actggggaga gccctggtc   117900 tatggctgtg ggcagcaggg gctgagagga gcaggctctc agggggcac gggtaccca   117960 agggaagcca gagccctgat ttgttccatt ctagtaagaa caaagactgc tctggtttca  118020
tgtttgttct gattgccttt catcaaccgg tccccttct cccagttctt aagattcagt   118080
acagtgacag ttttatgaac aagaatagaa cactagaaca gacaaaccat tgaactctat  118140
gctgataaag atttattgag ctcctgctgt atgtttgcat tctgcccaga ggctctgaga  118200
```

```
aaaccaggcc atatgctcca tgctttatcc atggaagctc cccgtcaggt tgggaaagct 118260
gacagctgca gggaatacag tgtgacacaa aactggctcc catgcagccc ttacgtgtcg 118320
cctctcagat ggttggggga cgaaggtcga ctcctttggg tatcttatta ctaaaccagt 118380
ttcagggaat ctgtgccacc ctatctgcca ttaacgtgaa cagatgagtc cccaaggtgt 118440
aattttgggt attgtctgat gtctcttgga atttattatt tgttttccca atgagatttc 118500
acctcagggt atagtaaagt tgttgagggg attcctggat gtgttctgca attatctagg 118560
ctgatttcag aatagagtta tgcttatagt caaatttatc agctgtcaag aattttattt 118620
aaaatttatg cagataagca ggaggaaaag aagcctggtt tttacatttt aatcctatta 118680
ttgatgtgaa attttatttt ccttcctgta ggtgtttatt ggctttgtat tgaaacagtt 118740
tgaatacatt gaagtgggcc agttcaggta atagcatttt attatttag attttttttct 118800 tcttcttgtg tacttacatg taatttaggt tattaagtga atgtttaaac tactgttagg 118860 cattttgct gttttctta aatggaaatc tgactaacat actgtgcatt tttgcttctc 118920
ttaaaaatta atgtatatct caagacttgt ttggaagtag ttatgtatct gaaaattcca 118980
tatgttgtca gtattcattg cacatttcaa agcatttaat tgtgttgaca gatggtggaa 119040
tgaaatcttg tggtggagca ctagttttta aatcttctta gagaaagcag ttttatataa 119100
tgttgtcttt agtaattatt atgcatttgt attctctgca gctttttctt gctagatgtt 119160
gaggttttaa tacttcttgc tagtccatta caggtttata attattaaaa gttaaaattc 119220
ttttagtacc taaatgcctt aataaacatt gtaattagga aaatttagtg cagaaggaaa 119280
gtgttcccag attccctggg gtctggaaac atagtgttta ttctaattac atgcacactc 119340
cactgtgttt tggggcaagt tactgtttct cttttgagtt tcaatttctt caagagcaaa 119400
gaggcagagg agagctagga agatcgtagc tgctgtgccc ctgtgccgtc gggtgccttc 119460
tacctgctgc ctccgaacct ttacacatgt ccctgctctg cgcgagggca cagatgggat 119520
gcactgtggc aggggtgggg ttagagtaga tcacggacac ctgttagctt gatgtgtgct 119580
tgctgtcaag gttgaatcat gaattatttt atgttgctta tattgatatg tatcttaatt 119640
ttaaaagaaa ggtctaaatg gatgttttg tttttaggga atcagaggca atcattccaa 119700
acatcttttt cttcttggta ttactatctt atgaacgcta tcattcaaaa cagatcattg 119760
gaattcctaa aatcattcag ctctgtgatg catcatggc cagtggaagg aaggctgtga 119820
cacatggtaa cgggacacac ctttcactgt cgtcttcggt gtcgtgatgt gcttggcagt 119880
gttcgttttc atatacccac tttgaacgtt gtcagtggca gccatgtgct tctcaggctc 119940
tgcatgtgtg tctgtgtatg tgaaggtact ggttagagac gtttcaaaag agaagagagc 120000 atattctttta ctctcagcaa tttgtaatct tctcagggaa aaaaattcaa gaaacagtaa 120060
gataacctaa ggtacagata gattctgaat ataaagttcc tgttcattca catgaaacgc 120120
taaaagttct tcacttgatc ttagccaaaa ggccaagaag cgatgcaaca ctaaaaattc 120180
ttaaatcgaa cttgccgtga attaaatttt gatctctcat ccagtggtat tggagatata 120240
gtttgacttg ggttcagggc tttctgtttt gcctgatgat tttgctggag cttaaataag 120300
gaacccagga gatggccagc tgtgcaagcc cccagcctgt ggaaggagct agtgtggttt 120360
tatgaatgag ttgcaaatct ttctttgagc tttttgaact gatcttccag cattgcccta 120420
ttgacccctc cctgactcct ttgctggaat ctgtaggctt ttgaactttg acagggacac 120480
atcctaagac ccttgcaaac tcccagatgt gagaatggca ctactactta gagtcttttc 120540
gactcagcgt gtgtgcagaa gagcatcaac cgggctgtgt tgcgaggcag ggccttggct 120600
```

```
gacctctcag tgtttacata gctaagccag ttagtgtttg ccacggcctc acaagggctt    120660
cagattcaca cagccaaagt atagattatt aaaggcatag gtgtttggtt tcctggactt    120720
ggagggtctt tggacagaaa atcagtaggc aaccacaccc agtactttgt gctgggaagc    120780
ttggtcatct gtgagagggt cagagagtat acccatgcgt gcatgccacc gaagggtcag    120840
tgagtattcc tgtgtgtgca tgtctcaggg ccggagagag tatgtgtcac tgagaggtca    120900
gagtgtttgt gtgtgtgtca aagagggttg cattgtgccc ttcactgagg ggtcagaggg    120960
tgcctcgcgt gtgtgtgtgt gtacgtgtgt gtgtgtcact gaggggtcag agtgtgcctg    121020
tgtgtgtgct tgtgtgtgcg tacatgtcac tgaggggtca gagtgtgcct ctgtgtgtgt    121080
gctcatgtgt gtgcatacgt gtcactgagg ggtcagagtg tgcctctgtg tgtgctcatt    121140
tgtgagcgta tgtgtcactg agggggtcag agtgtgcctc tgtgtgtgtg ctcatgtgtg    121200
agcgtatgtg tcactgaggg ggtcagagtg tgcctctgtg tgtgtgctca tgtgtgagcg    121260
tatgtgtcac tgaggggtca gtgttcctat gtgctcatga cattgagggt cagagtgtgc    121320
ctgtgtgcca atgaaaggca tttcttatat tttttatat gtggtcatag tagaccagtt    121380
aatttatttt gactcctgtg ttagaccaaa ataagacttg ggggaaagtc ccttatctat    121440
ctaatgacag agtgagttta cttaaaaaag cataataatc cagtggcttt gactaaatgt    121500
attatgtgga agtctttatt gtcttttcag atgaatcaag tagattattc ttgagaccag    121560
gaatgttgct gttttggtta tttggaaagt tttatcattt tcaaattgac ttttgaattt    121620
gagtcacctt ttttcagaag tggtgttaaa ttataggagc cctaggtttt ttttcttttt    121680
ttagaagtca tcacaaaatg atcagtgttc agaggaagag ctttgacctt ccacatggta    121740
taatgattga taaccttaat tcatctctta ccataaacca agtatgtgta agggttttct    121800
ttatttcttg aaagcatttt gtagatgttg agagcagttt tccaaatgta atttccatga    121860
aatgcctgat aagggtaccc ttttgtcccc acagccatac cggctctgca gcccatagtc    121920
cacgacctct ttgtattaag aggaacaaat aaagctgatg caggaaaaga gcttgaaacc    121980
caaaaagagg tggtggtgtc aatgttactg agactcatcc agtaccatca ggtaaggaga    122040
atgtatgttg gaactgtcgt ggatacttta ttgacccgtg cagatggaag gaagtgccat    122100
gtggtaacgc tcactgttaa ctgtgttact ttgaaccagg tttgggcttt ctggggcctg    122160
ggtagatgcc ggtgcagggg gatggggagg gaggcggggg gtgggggggt gtggtggagt    122220
tggggaggtg cagtggcagg aggtgttgtt ggtgtgtatc cttttttttt ttttgagatg    122280
gagtctctct ccgtcgccca ggctggagtg tggtggcacg atcttggctc attgcaagct    122340
ccacctcccg ggtttaagca attctcctgc ctccacctcc cgagtagctg ggattacagg    122400
catgcaccac catgcccagc aaatttttt tttgtattt ttagtagaga tggggtttca    122460
ccatgatggc caagctgttt cgaactcctg acctcaagtg atcctcctgc cttggcctcc    122520
caaagtgcta ggattacagg cgtgagccac catgcccagc ctggtgttta tctttaaagt    122580
gggcacagcc acaggagttc acctgactcc tggtctgaga gtcacgagat cgttcaagat    122640
agtgaggccc tcttttccaa aacgaggacc aaaaatcaat tgacagtgtt ggtcaagatg    122700
gtagaaacct taaaatgata gaaatctcaa ctctgaaata aaaactttat ttgtatattt    122760
atttaccact attttgacat agggctaagg tcttttttctt tgagctgatt tctggttttg    122820
ttttcttaaa gtggcataag aattcaaaga cattttgagg aaggctgagt gcagaaatct    122880
ctctttttaa atgacttctc ctttcttta acttgcactg ttgtctagcc ctcacttatt    122940
```

```
ttgtcaattc ttttagctg tttgtctttg aatcttcata aagccatagc ttttctcata    123000
agaagcagca ctttctttgt tcattcatat tttaatgaac ccctgtagta tttaattaaa    123060
tacttaatgc ctaattaaat cacataattg caatgcaaaa gtacatgtat cataaagagg    123120
tctgaaaatg agcaactggc aagcaggtgg tggcaggcag agctgcttgg gtgggtgggt    123180
gtcatggaga ggagttcatc agccacatgt tcagtgagct ctggatatgt ctgtttagaa    123240
atgatcacta ataaacttgt gctcaaccat gtatacctct gggaagcagg tgctcttcag    123300
tagattgcct ctgcagagaa cacagaattg aagtgaatgt ccacaaaggc aatgagccac    123360
ctgcagaata gtttagtcaa ggctgtgttt gaagtttgcc aaagattaat atacatttga    123420
ttttcatgtt gtgccttttc tctgattgtg aaatattaca aattctatac aaataacaat    123480
gatggcaaat cctcctgagc aaagtgtgca ccttgtatgt gccctagagg aacttgtgtt    123540
tcgttctgat tccctacat ttctcatgtc atagagtggg ggttgcatta gtgtcccct    123600
gtcctcgctg ggatcacatc tgtttggatc ctagagtctt ccagctgaac tgggacaagt    123660
ataacagacg gacacgtagg ggtggaaagg cgtctcttgg cagcagactt tctaattgtg    123720
cacgctctta taggtgttgg agatgttcat tcttgtcctg cagcagtgcc acaaggagaa    123780
tgaagacaag tggaagcgac tgtctcgaca gatagctgac atcatcctcc caatgttagc    123840
caaacagcag gtttgtcccc gcagccttgg cttgttgttg catagtgatg gtagcttaag    123900
gtccttgtga aaggtgggtg gctggaatca gctcttcctt cagtcctaat ctgtgccttg    123960
atagcagttc tccgtgctag tcatgggaca gctgacttca tttcttctca caatgccatc    124020
tcaggttggt attgcccacc tactttacag ggggatccc acagctccga gaggttatgg    124080
aggtgatcag gcagcacaca gctttagagt gctggggtga gggcgggcca aggctaactc    124140
taaagcccga acccttacct cctacactgc ctcctgcatt ctggtcaacc cagtgtttta    124200
tttggtggtt agattttgt ttttgttacc ttactgcttg taatttagca gttttccttt    124260
cctttccctt cctttccttt ccgacagggt ctcactctgt cacccaggct agagtgcagt    124320
cgtgtaatct cactgcaaca acctctgcct cccaggttca accaattctc ccacctcagc    124380
ctcctgagta gcaaggacca caggtgtgca ccactacgcc tggctagttt tttgtatttt    124440
tagtagagat gaggtctcgc tgtgttgccc aggctggttt taaactcctg ggcgcaagtg    124500
atccaccaac cttggcctgc caaagtgctg gcattacagg tgtgagccac ctcgcctggc    124560
ctattcatca ctaatcagaa tttctatgat caaatgacat gaatcattgt ttccacaact    124620
gcagtggaag gaaatggcct ggcagtgcca gtttcagaag cagcctgccc ccagtcaggc    124680
acaggccact gtgcccccag tgtagcagca cctctgtagc tcacagagaa gggtggtggg    124740
gacctccttg aggcagctct gccagaaaat ctcatgagct gcctggcaca gcttgaggtt    124800
gcctttaag tggactcagc aaatacatgt ttgttcatct tgattataca caataaacaa     124860
ctactctgta tagtacgagt agtccgtggt ttttggcatt tgatttaaac ttagaggcat    124920
gtgatattga tgttactgcc ttcatgactg caccccatt ctgatttcat aatgaatgt     124980
tatcttgaga ccagttagac aacaggacag ggatcttggc ttctggtgag attgacagca    125040
gttttagtgt ggtcagggtc tccctgccta cagatggttt tagaatgtg ccctggaagc     125100
tttatcccat tcttttctgt gcgtaatctg agtgagtgg agatcgaagg cctgaataca     125160
tagtaaatac ctgacttaat atctgccgca atggaaattg tgtgatacaa catttatgaa    125220
acgcttagtg cagcacctgc caggtagctc accacaggtg catgttgcat tcagaagtag    125280
tgctagatac tatcctgtta ctggcagtgc atacatcagt gatcaaagca gattaaagaa    125340
```

```
agacccctg ccttcttgga gtgaagattt tgttgggatg cgggtaaggg gacagacaat   125400
agaaaagcaa gtgagtgaag tctataccat ggcggctgat caggaacacc gtacagaaga   125460
atccaggagg gaagagagtt aggtggtgtc tgcggtggga gtggcattgt tcagctggtg   125520
atgagaagaa gctttggtga tctggtgaca tttgagtgaa tttgcagaaa ggaaagatac   125580
aagcctagga gatacctggg gaaggaacat tccaggcaga gcaaatagca gtgcaaaggc   125640
cctggcgggg ggcggacatg ctgttagggt acaagcaatg agggtggagg agtggggcag   125700
ccatggggag ggaagggagt gaggcctggt ggggtgaggc cagtgtggag gagccttgag   125760
agggtttgcg ctgatgtggt gtaggtttta gcaggatcat tcttattcct gagttgagaa   125820
tagccttgag ggggaggtga gggcagagca gggccaccca tgtgagaccc ggcactggag   125880
tggaatggcc caagtcagca tcccttggca gcatgaaagc aaaaccagca aggtttgctg   125940
gtggcttaga tgtggcatgt gagagagagc agggctttgg gggtgatttc agggtgagga   126000
cagggtggct gtgacaagg tagggcagac attgggggca gcaggaggtc agagcctgtc   126060
tggatgtagc agttgagacc ccataggtgc ctaatgaggt gaggccagca tcaggtgtat   126120
gagcctggag ttgtcgagag actgtgggc aggggtcag catctgagat gtccactcac   126180
agtggaccca gactggctgg agaggaggag gagcttgaat accgagcctg ctgagtccca   126240
gctccaaggt caggtaggtg aggggagcca gtgctgggc aggggagta ggcaggtgtg   126300 gggttcctaa agccaagatt tttttaagg cattttgtgc aggagggcga catctgctgt   126360
cagcaccttg gaacttggc ccaggtttgg cagcaccgag ggcactgatg agtgctttg   126420 gaggagcaaa gggagccaaa ccctaatggg aatgtgttcc tgaaaggaca ggagagagac   126480
ttgggaaaag gttttacttg aagagggaac ggagaaatag ggcagtagcc agaggaggag   126540
aggagtcggc aatgggttaa gttggcagaa atgaaggcct gtttacgcac tgagggcaga   126600
agcaacaggg aggatcagtt catgacacag gagacacaaa tcgccgttgt ggtgttcaca   126660
gacatgggtt aggattggct gcatggatga cagagcactg tgggttctcc cagagttgct   126720
ggggaggagg cagagttggt gagcacaggc gagggtccag gatgcaggaa tcctggagct   126780
caagtcagtt gttcccttgt tgtaagatgt ggccagtgtt gtgagcttca catctgtgcc   126840
ttgaaaaaca cacatctgt ttgcagagtt gtttactatg tatacacact cagtagaaac   126900
aaaaattgga aacagtcagt gcccaccatc aataagtaat ggttgaacac actgtggtat   126960
aagcttagac tattttagct tgggctattt tgcatgatta aaaatgttct ggccaggtgt   127020
ggtggctcat gcctgtaatc ccagcacttt gggaggccaa gcaggcaga ttgcttgagc   127080 tcaggagttt gagaccagcc tgggcaacat ggtgaaaccc tgtctctact agaaatacaa   127140
aaagtagctg ggtgtggtgg tgtgcgcctg tagtcctggc taactcagga ggctgaggtg   127200
ggaggatcac ttgagcccat tcgtgcgcca ctgcactcct ggggcacaga gtgagactct   127260
gttagaaaga gagagagaga aagaagagag agggagggag gaaggaagga aggaaataaa   127320
tggaagaaat ggaagggagg aaggggaggg aggaaggaag aaaggaagtt cagccagttg   127380
ccttgggagt tctccattgc actgggttaa gtgagaagag cagagacgtt tatgattttt   127440
caaaacaact aaaacaaaac ctctgtgggt gaggggcaa ggatatggct ataggaacat   127500
ggggcagatt aagaaaggga tatacacaca ccacttagca tttgttacaa ctgttgtggg   127560
agggatggag tgcagaaaaa gaaaaaaaa agtgcacacc atcccatgta tgtgtataca   127620
aagggacgct tggaagactg gtccccaaaa tgttggtaat gattgtgtca gggtgctgca   127680
```

```
gtgctagttg attttttttc acactttttgt atatttgagt cttttacaga aagcatttat   127740
tatttatgta ataaaaatct aaatgacaag atttctgtta tgggaaaaat gtagctatac   127800
agtgttgttg taaaaatgtt tgcttggttc accactgaac ttaaaatgct tttaaatgag   127860
ggaaggtgac gatgagatga ttatgatgat ttgcccttga gttacatagc tggtgtacag   127920
gaagctgtcg tttcttttgg cttacgtaga aatgtttgtg gtgtctaatt ccacagatgc   127980
acattgactc tcatgaagcc cttggagtgt taaatacatt atttgagatt ttggcccctt   128040
cctccctccg tccggtagac atgcttttac ggagtatgtt cgtcactcca aacacaatgg   128100
tgagtctctc gcctggctca gcagatgaat ctggacggct tgttcaggct ctgattactg   128160
ggaccacccc cagaatgtct gagtcagtca gtttgggtag ggcttcttga gagtttgctt   128220
tttttttttt tttttttttt ggtgtggggg tggtgcggaa cagagtctca ctctgtcgcc   128280
caggctggag tacagtgtca tgatctcggc tcactgcaag ctctgccttc cagcttcaca   128340
ccattctcct gcctcagcct cccgagttgc tgggactaca gcgcccacc accacgcccg   128400
gctaattttt ttgtattttt agtagagatg gggtttcacc gtgttagcca ggatggtctt   128460
gatctcctga cctcgtgacc cgccatctc agcctcccaa agtgctggga ttacaggcgt   128520
gagccaccgc acccggcctt tttatttttt ttggagatgg agccttgctc tgtcacccag   128580
gctggagtac agtggcgcta cctcgactca ctgcaacctc cgcctccgg gttcaagcaa   128640
ttttcctgcc tcagcctccc gagtagctgg gactacaggt gcgtgccact gtgcccggct   128700
aattttttgt attttttagta gagacggggt ttcactgtgt tagccaggat ggtcgcgatc   128760
tcctgacctt gtgatccgcc cgcctcggcc tcccaaagtg ttgggattac aggtggctct   128820
cgcaccaagc caagagtttg catttttagc aaattcccag gtgaaactaa tgcctgcttt   128880
tctgggagca cactttggga ctcagtgata gagaggttta ttggtaggat agtaaaaatag   128940
gagttatttt ctttcacaaa attggcaatt gggggaaatt taatcttcct tttttcttca   129000
gctgtgactt atgtattatg tttattttag gcgtccgtga gcactgttca actgtggata   129060
tcgggaattc tggccatttt gagggttctg atttcccagt caactgaaga tattgttctt   129120
tctcgtattc aggagctctc cttctctccg tatttaatct cctgtacagt aattaatagg   129180
ttaagagatg gggacagtac ttcaacgcta gaagaacaca gtgaagggaa acaaataaag   129240
aatttgccag aagaaacatt ttcaaggtat gctttctatc tgagcctata actaacccat   129300
gccttttggg aagtcacgtg atgtttcaca gtcagtaagt ctggaataat acctggtctt   129360
gcttcacttc tgagttgggt aaagaagtct gtatcagtgt aattttctaa tccgtcctgc   129420
attatctatg gctcttggtt catacctgtc ttgaagttct gtcatgttct gtctcttgtc   129480
ctcagtagag atgctacagc agtggctcgc ctcaggcagg gcagggcagt ggggtggctg   129540
tcctgggggc aggcagtagg ggcacgctga cgtcagggaa gttgaaaccc aagagaagcc   129600
agtaaaagtg agtctcagat tgtcaccatg tgctggcagt tttacacgct gtcagtaata   129660
aaagtcttct ccctgcaggg cagcctgcct ccaataaata cgtgtagtat caaatcctgt   129720
cttccctcat aaattgtttg gaagctcccc aaggacagtg atgaggcact cgtaagtgct   129780
tgctgcctag atgggtccct ctccaccttt gctagattct gagcattcac tgagttagag   129840
ctgcttctgc aaatgtgctg cttctgctaa gtggctgtga cttcatgcag ccttcacttg   129900
gtttgtcatc agtggagatg ccctgtgttg tcgaaggaga taagcccagt aagcctgctg   129960
ggcacctttt ggtttgcagg ttcagcaggc agccatgggc tttccctgtg tcgcattgaa   130020
gcagctggct aaaattgatg atacattaaa ttcctgtgac agatgatcag cttgtatttg   130080
```

```
tgtaatggtg tacagttcac aaagcttaaa aaaatgctac ctgccatttc atcctcagtg   130140
aggaaggtga tacacagaga gaccaagtga ctgtgtccac ggcgacggcg ctctgcattt   130200
cactttagcg gttaatgtac tctacctata tttttacttt atatttacca tatatctttt   130260
catgtatact tggcgtaagt gctttatagt agtcacctaa ttcactgtca tcttttttgt   130320
ttcttggaag gtttctatta caactggttg gtattctttt agaagacatt gttacaaaac   130380
agctgaaggt ggaaatgagt gagcagcaac atactttcta ttgccaggaa ctaggcacac   130440
tgctaatgtg tctgatccac atcttcaagt ctggtaggtg aatcacatta gtcttcctgg   130500
agtgtctcgt tccccattct gcactataca ctctcagagt gtaggagctg tgctgcccgg   130560
tagaaactct gccttgccca gtgtgccagt tgaaaatatt tgttgctgta agagtacacc   130620
tgataccatg tgacccagca gttccactct tgggtatata cccaaaagaa tggaaagcag   130680
ggtggtgaaa agatatttgc atgccagcat tcatagcagc attattcacg atagctaaaa   130740
tgtggaacca actgaagtgt ccctcgatgg atgaatggat aagcaaaatc tggtgtatat   130800
ttacagtgga atattattca gccttaaaaa aaggacattc tgacacatgc tacaacatgg   130860
gtgaccctta aggacattat gctaaatgaa ataagccagt cacaaaagga caaatactat   130920
gtgattccac ttacatgagg gacctggagt agttaattca tagatataga aagtagaatg   130980
gtggttgcca ggggctgcag gggaggggag ttattttac aagatgaaga gagttattct   131040
agaaatgaat ggtggtgatg gttgtataac attatgaatg tacttaatgc tactgaactg   131100
tacagttaaa aatagttaag aggaccaggt gtcatggctc atgcctgaaa tccaagcact   131160
ttgagaggcc aaggcaggag gattgcttga gccaaggagt ttgagaccag cctcagcaac   131220
atggtaggac cccatctgta caaacaaact agccggggat agtggtgtgc atgtggtccc   131280
agctactcag gagactgagg ctggaggatc gcttgagccc aggaggttaa gtctctagtg   131340
agatgtgttc atgccactgc actccagcct cggctataga gtaagaccct gcctcaaaaa   131400
aacaaaacaa aacaagacaa gagccaaaaa tggttaagat gggccaatca cagtggctta   131460
tgcctgtaat cccaacactt tgggaggtca aggtaaaagg atcacttgaa gccaggagct   131520
tgggaccagc ctgagcaaca tatcgagacc cctatctcta caaagaaaat caaaaactag   131580
ctagatatgg tgggcacatg cctgtagtcc cagctacttg ggaggctgag gtgggaggat   131640
ctcttgagct caggagttcg aggctgcagg gagctattat tgcactccag cctgggctac   131700
agaatgatac cctgcctctt attaaaaaaa aatccaaaaa aaaaaaaag taaacctgag   131760 agcttcctcc tcctgtgtta aatttggagg ccaagatgtt tttgttactt ttacaaatga   131820
tcaaggacgg tgaaggttgg gcatggtagc tcacacctga aatcccagca ctttgggagg   131880
ctgaggcggg gtgatcgctt gagcttgaga ccagcctgga caacatagca agagacccca   131940
tctccacaaa aataaaaaaa taaaaaaaaa tagccaggag tagtggcatg agcctgagcc   132000
caggaggtca agctgtagtg agccatgatc atgccactgc actccagcct gggcgagatc   132060
gagaccatgt ctctagagaa agaaaatgac aaggacagtg aacccaagaa agtcataaga   132120
tgccagctgt gcagcaagca tggaaagcag ccagtccaaa ttaggacagt gtgttttcca   132180
agaagaacga tcgtttgtaa tgagaatgct ttgctttaaa taaatgacta aatagctaga   132240
agcctagttc taggggatag gcacgtcttt cttctctcaa gaaaatagaa aggcaattct   132300
aatttctagt aacagcaaac agcattaagt catggtccaa atatgaggca aaccaaaatg   132360
tggcttgatt gttcagcagt tgatctgttg gaagcccttg atattaaaaa ggttctcctt   132420
```

```
taagcggctt aggagtcacg atcaaagacc tatagaaaga gatgccatcc ttctaggatc    132480
cttggctctc ttgggaacta gattcagata gtcataatgt aaatactgct tgagctttct    132540
ttctttcttt ctttctttct tttttttttt gagacagagt ttcactcttg ttgcccatcc    132600
tggagtgcaa tggtgccatc tcggctcacc gcaacctctg cctcccaggt tcaagcaatt    132660
ctcctgcctc agcctcccga gtagctggga ttacgggcat gcaccaccac gcctggctaa    132720 tttttttgtat ttttagtaga gacagggttt ctccatgttg aggctggtct cgaactcctg    132780
acctcaggtg atccacccgc ctcggcctcc caaagtgctg ggattacagg tgtgagccac    132840
cgcacccggc ccgagctttc atttttgaaa tcaatgtatg actgaaacac tgaagactta    132900
ctgacttaat tatggtttca gaacagaatg aaaatgtctt cggttctgat gaatataaaa    132960
ggaaaactaa ccaagttaat ttggcaagta gatggtagag atagaggtgg ggagtggaag    133020
gggaactaaa atcttcacct agcattgttg ggattatatg gttacatcat ctgaagttga    133080
cagaccaaaa tatagaggct tcagaggtct ccaaatagaa ctaaacatgt aattcagatt    133140
gttaggaggt agtataaatg agctaaatct catctttatt acggtagagt taatgggtga    133200
tgtctaaagt tgtctgaagt ctataaatca tgacaaatta tgatgtggtg attgtattca    133260
acagtctttc agttgcaggg ataaaacccc agtttaaact agagtaagag aaagaatgtg    133320
ttggtttaag ctcctggaaa gtgcaggcaa gggtagttgg taggactgca tctagtgttg    133380
taattctgtg gtctgcattg tatatttatg catctcagct ctgctttctt cttttcattt    133440
atataatttt taaattttat tttaaagata gggtctcact ttgtcgccta ggctgaagtg    133500
cagtggcatg aagtgcagtg cgaggctcac tctagcctcg aactcctggg ctctagagtt    133560
cttcctgcct cagccttcta agtagctgag acaataggca tgtaccaaca tgcctggata    133620
ggttttaaaa ttttttgta gaaatggaag tcttgctgtg ttgcccaggc gggtctttaa    133680
ctcttagctt caggcgatcc tcctgcctct gcctcccaaa atgctgaggt tataggtgtc    133740
acccaccacg cccagtctca tctctgcttc ctgtgttagt tttgttctct ggtgggctgt    133800
tttcacatga ccgaagatga cctctagcag gctgtgttct cagcccctca gtaggccta    133860 tgtgattggc cttgcatgag taatatgggt gaccataaac ccctgaatgc tctggtccac    133920
atgggccaaa tgggagactg acagcattc cattgatgag gaggtggggc tggtctccgg    133980
gagtaaggga gaggagcaca tgcagtaact gatggtctgc tgcaagggat agcagcacag    134040
cagttagaat tttggaggta actaccagaa ctgaaaacag aaatgataac aagtagttgc    134100
cttaaaaagg gatgggagca gggtgctttt gtgatcaaag ctccttcctc ttactggatt    134160
tttgtacaca ttttgcatac atatcttaga gtaaaagata gcattttcag ccttggtcca    134220
tttgaggata ctcttggcgt ggcccgcctc catgctagca ggctctggtt gtgccaagtt    134280
cagttgagca tcctggctct tgcctgcacg gaacttccag tcagtgcgtc agtatcacaa    134340
gtcttgatat ttcctatgaa gaagaacagt agtgcagtga cagacgaaat gggtgggcag    134400
gcagaggcag gatttctgag ggagagaagt agctagcttt ttgcagagaa gagttccggc    134460
acccaagaga gcagctgaga gtacaggcag gcaggcagga tgccggtagg gcccggccgc    134520
acggcgccac agaatcctgg agaaaggggc tcttcatgg cctctgcatt cagctgctgt    134580
caccctccgc acaggccatg gccaaaattt aatttcata gtggactcta gttttgagc    134640 cttacttgct attattgaaa taattttctt gtttctttt aaagatcttc ggattatgct    134700
tcactgacca ctgtaataag tttaaagttg agaaaatatg gcttgttaat gaatgatagg    134760
tcaattttag tatgttggtc attttaatat tttgccacca gttggtttgg atttgatgcc    134820
```

```
aggaggagac agcctcattt ctaaggacta gtcttgcctt tgtgggataa gggtggtgtg   134880
ttctgtgtcc ttctacatgt ccgagcgatc tctgtgcagc tcaaatgtgg tcactgtctt   134940
attgcgctga tttcctctcc ttccatctca caattgaggc aaaatattgt tactgttgaa   135000
gtgttgtcca ataggacttc cagcagagac aggatgtctg cactgtctaa tttagttgcc   135060
tttagccaca tgtggtgttc tgtacctgaa atgtggctgg tctgattgga tagcttaatt   135120
tataatttta tttaattta attaacttaa atttaaacag ctctgtgtgg atagtggctc   135180
ctgtatgaga cagtgcaggt ctgttgagaa gcagctttac tggtgggagt ggagggcttg   135240
gagagggcac gtgggtttcc tgctggtatc ttttgacctt atttaatctg cccaacattt   135300
gcaagtaagt tgtgtgtgtg tgtatatata aatgtgtgtt tctgtcttct tgtttccttt   135360
gactgcattt atttgaaaga cactaggtgg cagaattact gtatttgatt ggtttcaaga   135420
taagagttga aataattcat ctcgtgtttt tatataagta aggtgtgttt agcatgtaaa   135480
attggtaata tgtattcacg tactgcttaa acaaaggcta tgaattccac ccataaaccg   135540
aaaatgaaga cctttaaatt tgtccatttc aggcgtgggt acttcttaaa taatacctgg   135600
ttcaggaact agtcagaatg gcacccttga ctttttgttt cctgcttttc ctcttgttgg   135660
gagaggaggg tattcatccc aaagtggttt gcctatttca cattccatct aggataagca   135720
gaatagccaa gaaagatagc tgtcctcctg tttacaacat tggggtaac cagcatccct   135780 ctcttttggt ccaagataga ctggtttaga aacagatgat ggcaccagag gcccaggagg   135840
tggaaacatc agctttgttt gttgtccatg tggctgaatt agagctgtct ggccttgtag   135900
cctcaacacg gccttccagc tttgctcacc gtgattttca aggacacatc ttgtgctctt   135960
ccctgcctgc catccagact atacccagtc agggtggcag gagctgctgc cccttcctcc   136020
ctgagtcctg gtcgtgggtg gtggagatgt gccatgacgc tcacggaggc atgctcaccc   136080
cttcctctgt ggcagagggg atggctgcac gacagctctt ccctgtcctt tccaaagcgt   136140
ctgtggttcc acttttggg gcaaagcagg aatactggaa gagagagaaa gtggtccttt   136200
ctatagtaat aaagttgaca ttgattcaag ttcatgcttg gggaaaggac agggctacta   136260
acaattataa tgctgggagc aatggaattt tctcatgggt atgtggtagg tttaatttta   136320
attatcccag ttaattctta gaactgctct gtgaagtatt tcccgctttg tgcttaagtt   136380
ctaaaagatc ctgtgccaaa accaagaatg aaaacccaag cattctttct tgcccatcga   136440
tctttctctc atcaggccac ttcttgggtt gatagtggtg agtgtagccg ctgccacttt   136500
cagaataccc accatgggcc ccagtcactg tgtggcgtgg agaagagatg gttctctctg   136560
tgtcatagct gaacaagccc agcccagaga ggtttctgcc ctaggagctc tcgatggtgg   136620
aattgggatg cgatcccaca tcctgcctgt tttgaaaaca gcattcttta tttccaattc   136680
ctgcttccat tgttcctttt aatatttctt tgtttagctc acaaaaacac ggcttgcgga   136740
gctgctgcgt gcagctgtag ctgtttctct gggtgcagcc tgcatccgcc ttcctgcccg   136800
cctcctttcc tgcactgcca tcgtggtctc cgggcacttg gtcccttcct cttcccctga   136860
gtccctttgg ctcccctgtg ccacccttgt gatccacagg ctctgccttc tttctgtctc   136920
agactgctgc tcatcactac tcgggaccct aggaagggag gttccaccga gaagcatctt   136980
ctcatctcag ccacgttctc agtgccactg ttgtctttgt taggtaatgg tagctactgt   137040
aacaaataaa ccaacatttc catggcttca caccagagaa ggttgttttct tggtttatg   137100 acaatgtatt gagggtgttc ttggttcacg gatggttttc ctccatgtgg gaattcgggg   137160
```

```
acccaggctc ctttccttct tttggttctg ttctccaggc cttcacatcc tctgtgtctg   137220
gttggggaca aggagaggga aggtaaagaa ggctttgtgg ccttggataa gtgacaggca   137280
tgcctttgct ggtgttctct cgtggtgaca ggtcacagcc ccaccctgta aaggggact   137340 gagagacgtc gtcctgctgc ttcccagcag cagcactgtg gtctctgatg tgttttctgt   137400
gaggataaaa acaggtgatt ccaggatgag gaaagtcagg gaaacccttg gaaggagggg   137460
accaggcggg tgtcaccatg ggattagtgg tggcttcaga atgagctgca gcgagtgcca   137520
tgccttctaa agcttttgct attctgatat gcccacacca tgcccagcag gtgtctgcct   137580
tgctctccgc agagagagtg atgaatcctt ctcatgagcc tctgtccagt tgttcctccc   137640
tccacctgga agggaccctg ggttcctcat aacatcccag cggaacaggg gaccttctat   137700
cctgtcccca agttcatcct catcctcctg ccggcttcct ggcccctctt atgtctgctt   137760
cctgacgcca catccttctg gattctctgg aattgaattt tgcctttgat gcttatttaa   137820
aaatatccat tgcaggccag gtgtggtggc tcacacctgt aatcctgtgc actttgggaa   137880
gccaaggtgg gcagattgct tgagcccagg agtttgagat tagcctgagc aacatgttga   137940
aatcctgttt ctatagaaaa tacaaaaatt agctgggcat ggtggcgcac acctatactc   138000
ccagctactc aggaacctga gacaggagga tcaattgagc cccggaggcc aaagctacag   138060
tgggctgtga tcgtgccact gtactccagt ctggtcaaac agagtgagac cctgtctgaa   138120
aaaaaaaaaa aaatccattg catacttcac cgtagcgaaa catgtatgtc ttacctttcc   138180
tttcctgcct gtagctgctc ttttacactt aacagccaca ctaagccagc cttaaatgaa   138240
aaacaaacca gcacttcctg tgccctcctg cttccttcat gaggggtccc tccctctgtg   138300
tacactccat tctcattgcc catggtggtt tgtttccctc ttgtttctca agccatggca   138360
gcctgcctct tgccctcttt actaaaaagg cctttgcaga ggctgcctgt gttctttctt   138420
tctaggtctc tctcatccta ggccctccag cttgattctg tggagctgcc ctcttgtcac   138480
tcagtagctt gtggggtctt ctctgtctag ccacttaatt gattgtgttc ctcgagttgc   138540
tgtccatggt ctctcgttac tgtttttctct gtgtttctgc ctctctcctt ggccttggta   138600
ggtccatccc ctttgtgacc ttggctgttg ctctcatgga caactttctc ttgctggtcc   138660
ttgtagtcct ggcatccagc ttctcgacac gggacttgtc ctgccagtac ctcagacttg   138720
cacttaaaat tgaactagca ccactgtcac tctccagggc ctcttcttgt taattagatc   138780
attagggatg ttcagaatcc cagcatcata gtatgttcct cctcccgcta ccccaggaac   138840
cctaacctta cctcctcctc tctatctact aggaggtggc cctcagagtc cgtctcatct   138900
tccacctgaa cttccctaat aggctccagc agctgccacc ccgggggctg agtacttcct   138960
ccatgccttg tgcagtgctg agccctttac ctgggttctc ctgtttgctc cttattacag   139020
ccctgcgaac agatactgct cttaattcca tcttacacct aaggaagctg aggccccagg   139080
taaggtgcat ccaaggtcac ccaggtagta gacagtagag ccacgatctg aaccaggcag   139140
tctgattcag agcctgtgtt gacactcagc cacctagaac acagcttgga ttgtgggttt   139200
ctattacctg ttcaaaaccc ctacatcccg ggtctgtccc tgcacgtgct ctgtggcctg   139260
gctgcatctt ccttgaaggc agtgcatgcc tcttcactca gggggcccat gcaggaacag   139320 agggcccac agaaggatga ggccagtgca gaatgggctg gaggggacaa tgctgaccag   139380
gaagcaagtg tagagaaatc ccaggaaacc tggaggagcc agagacaagg cattagaact   139440
cctcgtcgtg acctggtctg cattctctga gtgtgctgct tctgttagct cgcttccttg   139500
gtctcaggtt atagtttaag gcattgtgga gccctaaaaa gcctgtactc tgttttacc    139560
```

```
tgtttagga  ccctttcact  ttggggatgt  gttgatttt   tttttttttt  tttttttttt  139620
tttgagatag  agtctcgctc  cattgcccag  gctagagtgc  agtggcacga  tcttggccac  139680
tgctgcccct  gcctcctggg  ttcaagcaat  tcttgtgctc  ccgcctccca  aatacctggg  139740
attacaggca  cccgccacca  cactcggcca  atttttgtat  ttttagtgga  gacagggttt  139800
taccatgttg  gtcaggctgg  tctcgaactc  ctgacctcaa  gtgatctgcc  caccttggcc  139860
tcccaaagtg  ctgtgattat  aggcgtgagc  caccacaccc  ggcctgaaat  ttaaatcaga  139920
aataaaattt  tgatcccaac  agtgatgcca  ggcagcccag  atctggggga  gagggtggcc  139980
ttggccagct  gggcctttct  ctgtttccca  agtcttgctg  cctctccctg  ctgggctttg  140040
cagcctgtgc  atgtctctgt  gcctttgacc  ttgtttatcc  aaaggagagg  atagaatgaa  140100
gtcatgattc  ctggagccct  gagaaggatg  ctgtggagaa  atttgccggt  agaatctagc  140160
tgagtgtgtt  gctgaggtgc  cagcattgtg  tgtggggagg  ctgaccgctt  ggcctgccta  140220
ggcccaggat  gctccatggc  cgggcacaga  ggccacttgg  ctgtcaggtg  tcaggagcct  140280
gcagagggca  cacagagcct  ggaccgcagg  ggggtcctgc  tttctcacct  ggcctccttc  140340
agcatttctg  tccctcagtc  cttagcaagc  ccaggagctg  ttgagtttgg  caggtgccga  140400
gtgctgttcc  tgcctgtgta  gctgtggctc  agtcctgtgg  gggcccgct   gtggcccgag  140460
tgcagtgatt  cgaggcgctg  agtgttccct  gactccttct  ccaggagctg  tgttcagact  140520
ttcgcagctc  ttggcttgga  gctcctggag  gcttggcat   tgccgaccaa  tgtggaggtc  140580
gacagtgaga  gaggaggaat  gctagctttc  ttgaccagtc  cattaaataa  gtgggatatt  140640
ggccaggcac  ggcggctcac  gccttaatcc  cagcactttg  ggaggctgag  gcgggtggat  140700
cacgagctca  ggagttcaag  accagcctgg  ccaacatggt  gaaaccccct  ctatactaaa  140760
aatacaaata  ttagctgggc  gtggtggcag  gcgcctgtaa  tcctagctac  ttgggaggct  140820
gaggcaggag  aacagcttga  aaccggaagg  tggagtttgc  agtgagccaa  gattgcgcca  140880
ctgcactcca  acctgggcaa  caagagcaaa  actctatctc  aaaaaaaaaa  aaaaaagtag  140940
gatatctgtt  tctgcttaga  aaaatcagaa  ttttctaaat  gccaggtgtt  ctgaatacgt  141000
aagtatggga  gacgactcag  cctgtttcat  ttttatgtaa  aatcttcgcg  tagccatgtg  141060
gcactggacc  gagatgaaag  caaagacatt  tctccttaac  tttgtttcta  ggaatgttcc  141120
ggagaatcac  agcagctgcc  actaggctgt  tccgcagtga  tggctgtggc  ggcagttct   141180
acaccctgga  cagcttgaac  ttgcgggctc  gttccatgat  caccacccac  ccggccctgg  141240
tgctgctctg  tgtcagata   ctgctgcttg  tcaaccacac  cgactaccgc  tggtgggcag  141300
aagtgcagca  gaccccgaag  taggttcata  atgccccaca  gcccagggcg  ccagcccagc  141360
accctgtcct  gagactccca  gtaacctgag  ctttggccac  cgttaaagca  ttttcatttt  141420
ccatttttg   tgagggcttg  tgaaatttct  gctgcatatt  aatattcctt  tcatggacag  141480
catattattg  ggacaaacat  gcggtccagc  taaaggcatt  caaaatagca  gttgcttct   141540
aaatgcgatt  ttctttggca  ggttctttga  caccattgca  tcttgtggga  tatgcttgtc  141600
atgctctgtg  gctcctacta  agttctagtc  cttaaattgg  ttccatagcc  agacatgttg  141660
caatgtctta  acctcattat  aaagtaaatg  tggttctggt  tatccttaga  taatgaagta  141720
acagtgtagc  aaatttcaaa  acctcttgga  aatgttattt  taccattcaa  aaaggcttac  141780
taaggttctc  gttatgggtg  gccctctttt  tgcaaaaggt  tttcaggctt  aagctccatt  141840
tctaggtgct  ccaacactcc  attatttgta  tatgtatgga  aataaaagct  gtgaccaccc  141900
```

```
ccaaccctgg cccccgccca gctgaatcct cagcacagta tttctggaag gctcaagatc    141960
ccacgctggg gaaaagaagt tctggagaca aaagagggca ggtgctgccg tgcctctctg    142020
ctcagtatgg atactggacc ttgtgctgcc agggctccca gtagggccag ttcatggcac    142080
tcagctggaa agtccactgt tgggaggcat tcttaaccat ccactctgtg ccgtatgtag    142140
tggggtctgg tcattctgtt ggaggagaca gaccagtgac gacatttgaa atgcttggtg    142200
gatgtcttag gcctgttacg atgactgagc actgtggggg caggagacag aaagtcagtg    142260
tctcctagtt ctgtgctgct ttaacgtgca tagaaatcag ctgcggattc agcagatcac    142320
tccttttctg acagatgggc ctgcttactc tgatgttata tcagaaagct ctgaatctgg    142380
gaattgtgtc ccctgaattg gagtaacaga aatgcttaga tgatgagtgt ttaaaagaaa    142440
taaaccaaag gtaaatttag tttggaattc agcaagcgtc ttcattcagc cctctgaggg    142500
caaactacag ctttttgtaa atgtaggtaa attctgtgac tgtttcgtga cccctctga    142560 tccagttttc ctttataacc ttctgtattg ttccttctat tatcctgaaa taacattaat    142620
agattaggct gggcgtggtg gctcatgcct ataatcccag caccttggga agccaaggcg    142680
ggcagatcac ctgaggccag gacttcgaga ccagcctggc caacatgatg aaatgctgtc    142740
tctactgaaa ataacaaaaa ttagccgagc atggtgacag gtgcctgtag tccctgctac    142800
tcagaaggct gaggcgggag aatcgcttga acctaggagg aaaaggttgc agtgagctga    142860
gatcgcgcca ctgcactcta gcctgggtga cagagtgaga ctccatctca aaaaaaaaa    142920 aaaaaaaaaa aaattaatgg atcaatggat ttttaaccta ataattaaat ttcaaaaaat    142980
atcgttcttt aatggtaatg taaaggtaaa attaagataa tatgtaacaa gcatgtgagt    143040
gtctaaggtg tccccgtggt ggaaggaaaa aataaatccc cataagtgtc caagatgccc    143100
atagagagca gagctgttct ggtttaaacc cctgctctta gcactgtgtt tttccagctg    143160
tgggtggtgg gggatgagta tcttttatt tccatgagat gagaaaatg aattactaga    143220 agtgtgaaat acaaaacaca gctgctcttt ttttagccat agactcagca gccataaaat    143280
tgctgtatcc agttgcagaa attcctgctg cttactcttg accctctctc ggtttgtgtg    143340
catctcctct caggctggct cccagatggg agctggctcc aggcgacact gggtgctctg    143400
ctccaggagg tccttatgtg ggtcctgccc tagcctagcc cctctcttat ggactctgtc    143460
actgtgggtt tatgattcac tctcaatctg tcttacctct tggtgaactg ttagagtcct    143520
gcctatactt tggcgcttgt gggtgtgttg tggtacacat gatgtgttgg tcacttccca    143580
gctcatcttg ttctgagtca ccctagattt gggacattca ttcgccacca gtaccgggcg    143640
gtgtatggcc tgagatttgg gggggcttgt gctgctacaa attgggctg aatttgagtt    143700 gacagtggac cttctttatg tctactgctc atatttgaat tgcaaatact gcctcttctc    143760
tttcagaggc tcattaccct atagctgtat tattgcaaag tgcacaatta cagcttgagt    143820
gtaagtcaca ctgcgctggc aggacggccc actgagaaag gcacgtttc ctgttcgtta    143880 gttttcacat tgacacataa tttacaatac agtaaaatgt acttttctat caactgtagt    143940
cagtaacagc ccccctcccc caaccacatc aagatataga ggagtgctgt cacttcaaac    144000
agttccctct tcctctgcca catcctgccc ctccccaggt ctaaccacca atccgtgctc    144060
tgtccctctg ttcagcccat tgcagaaggc catagaaata gaatctatag gctaggtgtg    144120
gtggctcatg cctgtaatcc cagtattttg agaggctgaa gtgggaggat gacttgaggc    144180
tgggagttca agactagcct gggctgccta gcaagacccc atctccagaa aaaaaaaatt    144240
taaaaattac aatcacgtcc ctgtagttca gctgcttggg aggctgaggc aggaggatca    144300
```

```
cttgagctca ggagttagag gttacagtga gctatgatcg tgccactgtg ctccagccta   144360
ggtgacacag caagacgttg tctctgggga aaaagaaag aaacggaacc acgcggtgtg    144420
cagccttctg agtctggccc ctttcggtga gcagtgtcta aagttctgtc gcgtgttgcc   144480
cacgcgtcgg tggctcgctc cttgcaactg ctgagcattg tatggctagg ctgtagtttg   144540
ttttcacttc accagttggg aaacagagaa aaggcacttt ttaaaaagtt taaatctgta   144600
gaattttggt ttttaccagt tctcttctaa atcctgaggg attacaggaa aagttgttgt   144660
atttcagaat attcttagct tgatgtgacc tctgtccccg ttaaggccct ttgccgcaat   144720
gggaaggacg tcgctcggtc agaccctgaa ggtcagaggg gcagtttggg agtgtgtcaa   144780
cattttaact gtatggacta gagccaagag tctcaaggtt tataattccc acgtattcaa   144840
aaagaaaaaa acaataaagt gagaagtcag tgtagagtga aataacctgt gttagtgggg   144900
aagaagtgtt tttaaacagg atttccataa cgtataacat caacatgttt agagtggtga   144960
tgtttcattg ggaaacgaac agtaaaacat gaaagcaggg aggttttcat tctggcagtt   145020
ggcaactttc acggcagatg gagaatttca aaagcaattg ctcaattatc aaacatagcc   145080
agtgtgagtt ctgaaataaa ggtgctgatt gaatgtgcag ctttatggtg gattttgcta   145140
ttcaggcaag cattttaatt ttctgcctgt taaattctgt tttctttagt ttttcatatg   145200
tggtttattg tagcttagga atagataact gagagtatat attacacata caacattctg   145260
atatggcaat atttaaaaca acttgtctgt tttagaacta gaattaaaca taatcatctt   145320
cagtattttg caaataagct cactgccatc cagaaacatt gtcaatgcat ctgttgctcc   145380
ttctagaaga cacagtctgt ccagcacaaa gttacttagt ccccagatgt ctggagaaga   145440
ggaggattct gacttggcag ccaaacttgg aatgtgcaat agagaaatag tacgaagagg   145500
ggctctcatt ctcttctgtg attatgtcgt aagtttgaaa tgcctgtaaa cggggttgag   145560
ggaggtgggg accaggagaa catcctgtgt agatgacact tgcatggacc ctctggaacc   145620
cagaccgccc ggtgtcctgc caagctccat cgaaactaaa tctagaatga atgtttactt   145680
ctgctgtgac atataattgg agaccaggcc tggccttcca gtcactggat tctaagttgg   145740
actgtgagag tttttgcagc tgactcattt atcaaatgcc cggctattgg ctcacgccta   145800
catgatgctg ggtatgtttg ttaatttgag ggaagcaatg gaataataat aactaatgat   145860
ttaaaaaaca aagtaagtgc attgactgta gtggggttct gatttttaaat ttttttaaaa   145920 attaataccca ggagcagtgg cttatgccta aattccagca actcgagagg ctgaggtagg   145980
aagatcactt gagcccagga gtttgagaca agcctgggct atggtgtgag acacccatct   146040
ctaaaaaaat aaaaaataaa aaattatcca agtgtggtgg ctcgtgcctg taatcacagc   146100
tctttgagaa gctgagggcg gaggatggct tgagcctggg agttcgagac cagcctggca   146160
acacagagaa accctgcctc taccaaaaaa agaaagagag gaagaaagaa aaattagcct   146220
ggcgtggtgg tgcatgcctg tggtcccagc cacctgagag actgagaagg gaggattgct   146280
tgagcccaga gtttgaggc tgcagtgagc tgtgactgtg tcactgcact ccggcctggg    146340
tgacaaggcg agacccctgc tctaaaataa ttttttaag ttaatttgta gaaaaggtgt    146400
tagatgttct ttgtcacatt ttatgatgga ttcctgtttta aatgccgttc tctttaaaga  146460
aaaaaaaata acttgtggga gttttaacc ataaaactag catcacatat ttaccatgga   146520
gaatttacaa aaaaacaaat aaacggagga aaataaaacc tcctgtaatc atactactca   146580
gagataactt gctgttagat tttggtctag atttaatact ttttctatat ttatattaaa   146640
```

```
aatatttaaa acatatgcat ttctttgtca caaacatggt atcttataga tactactgtc   146700
acatagcaaa acagtgttaa atattctgaa tcagaaaagg aagccgactc tccaactgaa   146760
agaggtgtta tcctagagac ttttttctggt gatgacaatt tattaatagt cactttttgc  146820
tttactttct ctattgaagt agttttccta ttttgttcta cttttaagga taatataatt   146880
tataatgctg tttttcacag aaatataaga aaaagatac taatttata agttaataaa     146940
gtttgatcat cccaaatcca aaatctgaa atccaaaatg ctccaaattc tgaagctttt    147000
tgagtgctga cattatgttc aaaggaaatg ttcattggaa ggtttcagat tttcggattt   147060
agggagctca acaaataagt ataatgcaca tatttcaaaa cctgaaaaaa atcctaaatt   147120
cagaatactt ctgatcccaa acatttcaga taagggttat tcaacctgta ctgtcagatg   147180
atcccaaatg aaaaatatta atcgttaacc aaatatcaag gaattgatca cattttacag   147240
tttctgccta ggattatgaa tcaagatgaa aaggctctgc atgtttaaaa atatatattt   147300
ttattttctt ataaatctta aatatctaca cttaagattt atttgatatg tgggatccat   147360
tcatattttg gattcaacag ttctgtcaaa actgtggcag tgatagggga ttcttttttt   147420
cccactgaac tatcacaaaa ttggaaaaag agtaattgga gaaccccact ggcttagccg   147480
gcccgaagcc cgggagaggg caggcagtgc tgtggatggg gtcatcccag cgcaacgctg   147540
cccctgctac ctgcggatct cgctgaggcc tgcctttgtc ctttgaccct tggccatttg   147600
ttagtgtctc tgagagctgg actgctgtac cctacttccc caggggggcct aacttcacac  147660
agcctctgcc gcagtgcgtg gttggaggtg acggccttgg taaatcgagt ttcctacctc   147720
ctcaattatt tgtgctcata cactgtatat ttttagtgag gttatatttt gggatgtgtt   147780
ttctccttct tacccttttct ggcctttcta tggcattaat acctggtctc ttcttgtgta   147840
cttgaaaatg aatctctcat catattttttc cttagtgtca gaacctccat gactccgagc  147900
acttaacgtg gctcattgta aatcacattc aagatctgat cagccttttcc cacgagcctc  147960
cagtacagga cttcatcagt gccgttcatc ggaactctgc tgccagcggc ctgttcatcc   148020
aggcaattca gtctcgttgt gaaaaccttt caactgtacg tcttcatcct gccgactatt   148080
gccagttgca gttttccctg ccttaaaaat ggagtattga aatttttaac tttaatttct   148140
gatttgcaaa atagtcatct tttgttctttt tccttcttgc tgttagccaa ccatgctgaa   148200
gaaaactctt cagtgcttgg agggatcca tctcagccag tcgggagctg tgctcacgct   148260
gtatgtggac aggcttctgt gcaccccttt ccgtgtgctg gctcgcatgg tcgacatcct   148320
tgcttgtcgc cgggtagaaa tgcttctggc tgcaaattta caggtattgg gaagagaaac   148380
cctgatattg atttatattg aaaatttagc aggccaagca aaacaggtgg ctggcttttt   148440
cctccgtaag tatggtcttg acatggtcac cgatagaaac atggaaacat ctgcaaactt   148500
gccgttactc gtgtgtccga tctgactgtt tcttgtattt ttttctagtc tgcccttact   148560
aggatgaact gtacacatca gttcatcctt tttaaatgag catgaggtta ttttgggttg   148620
ttaggtgtta caaacacact aatgtgtttt tgtctattag agcagcatgg cccagttgcc   148680
aatggaagaa ctcaacagaa tccaggaata ccttcagagc agcgggctcg ctcagaggta   148740
atgctgaaaa cacaggtcgt ccttgtgtta ggacaaccca ggatataaag gatatagatt   148800
tgtacgggaa taaattcaca ggacaagaaa tcgatgtgcc ttataggtgg gtttactgca   148860
gaagtgccat aatagaacct tcctactttt aaaacaacca gatctcactt tctaaagagt   148920
aaaggatgac cggcaggatc acgtctgtga cgtgagtgga ggcagtttgc actcctggtg   148980
gctgtttgag aggtagcatt tagaatgcct gtattcactg tcctgtgatg agtgggaaaa   149040
```

```
taggttatca ggtttatctt agcaaaatca aagcatgtca tctaattgct aaacaagagt 149100
tggcaaatct gagagacatt actcaatcct tggcatgcag gacttacatc tgcatcctgt 149160
tgccatttta tgtcttcaaa gcatttaatc atttagttgt gtttgcaaag tctttgagaa 149220
gcctttgtca gaaatcccta catctcctat gtgagtgtat ttccatgact gcagaataag 149280
ttaaactttt accttttttcc ttcccttgcg gggcggggtg gggggcaggg attgtgtgtg 149340
tgagagggag agagagacag cagagaagga gaatataatt atcatgctgt gtactttgag 149400
ctgaaactgc aaaaaaggaa aaacacacaa aaattattat gcttttcagt ctttagagta 149460
ccttgtctat tatgcttttc agtctttaga gtaccttgtt gatggtgttt ttaaatggga 149520
ttgggcacaa ttaggtggac agtttgggat gattttcag tctgtagggc caagctcttt 149580
tgtaatttgc attatgaagt tgtcactctc atagcagatg gcgggagata aactattatt 149640
acttttttgac cctagactta gtcttcagtc cagatgaggg agattaaaag attataaata 149700
tcttgtgcca gatgaggtga tttattttg aaatgaccat gaattcctat cagttgtctt 149760
actgggatat ttgatagtgg aatttgtgca tttgagtctt agatgatctg ttttacattt 149820
attaagaaag cctttattag ctttttatact gtgtattgcc tgttgcagtg tttgagtata 149880
aatgaaattt ctggaaaata ttaatggagt acaaactgtg atacttaaaa gtaaactagg 149940
gcctgcattt gtatcatgac ctgtttgagt attgatgaga agatagctgt gaagaaaaag 150000
gtttaaacaa gtgtatttc ctttaagaag ccactaatag tgcatctcct tagagtgtat 150060
atttctagaa tcctagtgtg cagagtttag actaagacta aaaaaaaaaa aaaacaaatt 150120
atactgtaat ttcatttta tttgtatttt agacaccaaa ggctctattc cctgctggac 150180
aggtttcgtc tctccaccat gcaagactca cttagtccct ctcctccagt ctcttcccac 150240
ccgctggacg gggatgggca cgtgtcactg gaaacagtga gtccggacaa agtaagtgtc 150300
cagcgtgtct gcatgggagg cacagggcgc tgagtgcctc tgtcacctgt ggcagataca 150360
gagagtgcag aggaggtgcc gtggacccaa ggagttctgg cgctcggctc ggctcagtga 150420
agctgtggtt agagacgtgg ggggccatca aggtctgagg gagccaagca gtgctgatgt 150480
gggaccottt tggtaggagt gtggggtgag tagttagtgg gtgaatcaag gaatagtcgg 150540
ccgtggcctg caggcccctg actgcacagg ccttcaagca catgtcaatg ccgttagcct 150600
ccctccatct cctcatacct tctggccacc tgtgagttgc actgccactg ccagccattc 150660
tggtatgttg tcagcacctc cactgctcat acctcatggt tagggaccac ctggagcctt 150720
ggtagagcct tggtagagcc ttggtactct actttcctgg acaaagttca gcttatgaat 150780
atgaatttag atttcaaaaa ccagcagccc aagtataaga agcgaaggt tcagtcctgc 150840
cttcttaggc tctattcgct aagcacctgc cctgccctgg ttgctgggga gatgagta 150900
aagcagacaa cccaggagag gatggcaaag gggccgctaa cccttagtgg tttagctata 150960
tttggaaggc ctattggaag ttcaccaggt gaaggggag gctgtgaggg tgcccaggca 151020
ggtaacagaa gtccaaaggg gaaaacctgt ggtgtggtga gccgtatagc cacagcctgc 151080
cggccggcag ccctctcagc ctagtgcggt gttcccaagc actggcctag gcctgtagct 151140
ccagggatgt gaagtcccct tgaacgccgc ccatcatgtt ccccttatcc attttttct 151200
tcccaggact ggtacgttca tcttgtcaaa tcccagtgtt ggaccaggtc agattctgca 151260
ctgctggaag gtgcagagct ggtgaatcgg attcctgctg aagatatgaa tgccttcatg 151320
atgaactcgg tacgggggga gcagtggagg caaggaatcc tcagcttttc ttgtgacttc 151380
```

```
caagtgggat tgtctcatc atcatgtgac ccacttgttg acaacacatg ttggggactc   151440
cagtctgggc agggacggga tgtcggagag actccactct gaatgggcc gggaagtggg    151500 gaggactcca tttcagatgg ggtcgggaca tgggggttat gctgatcgag acagaaaagc   151560
acattgtttc agccacatta gaatccacgg aggtgttgtt ttgaaatcca gctggcccca   151620
aggctgggtg tatggtttgg gatgagaact atctggcctc cactggagga acaaacacag   151680
gatgttatca tctaagctcc atggccaaga cagaatggaa gtcaaggttg cgtatttgcc   151740
gtagacttca acacagtgtc gtaatgcgtg acgtcaataa cttgtttcta gtgtcttgga   151800
agttgatctt tagtcgtaaa agagacccct tggatgcagcg agatttcctc tactcacacc   151860
tctgttagat gtagtgaggt tcttcacccc ccaaccccag atgtcagagg gcaccctgcg   151920
cagagctagg aggccatgca aagccttggt gtccctgtcc ctcacccgtg ggcaggtcct   151980
gtgagcagtg gggggccac ctcttgggta tggtgcagcc atggcccaag cagggcttct    152040
tctcagacct actaggacgg gagaaacctc ctggtgcttt agccctgcgt tgatatgcag   152100
caaatgggag ggaagtgggc acctgggagg acaaatgcct gtagaggccg ggagtgacgg   152160
caggtgttca tgaaaagaga ccttgtgggg agggcaacac aacagtgtgt tctgatgtac   152220
tgaagagctc aactgaaaac aacaggagaa ttagcccaaa atccatttac taaaattgtt   152280
tatctttttt ttttttttg agacaaagtc tcgctgttgt cccccaggct ggagtgcaat   152340
ggcgctatct tggctcactg caacctccgc ctcctgggtt catacgattc tcctgcctca   152400
gcctcccaaa tagctggtat taacaggcat gcaccaccac gcccggctaa ttttgtatt    152460 tttagtagag acgggatttc accatgttgg ccaggctggt ctcaaactcc tgacctcagg   152520
tgatccgccc acctcggcct cccaaagtgc tgggattata ggcctgagcc accacgcccg   152580
gcctaaaatt gtttatctta agattcatgc agtgaaagct aacttactga gtgataaatt   152640
tgcttagtga tctgtttatt aggttttcca aatttgctaa ttgggctttg aacagctgta   152700
aaagttctga ctgtaaaaga aagcttcaac ttttggcatt catgatgctt ttctgagtat   152760
taaactaaga tagatgtttt acctgaagga tcggccacca atctttaaat ggctaaacaa   152820
aagggttgct aaaacataat ccaaattgac ataagaaata ccattttcc aaccaaaatt    152880 ttggcattca tatggctact tttacgtatt tcagctgcat ttgaacatct ttttcaaact   152940
ttagggtggt tggtgtatca ctgaggtctt ggatgacact ttagctttga ttttgttttt   153000
atgaattaaa attgtcatac caaaatttt atttcaagca aatccaagag cataaaaaat    153060
taaaatatta cttaaaatac taagagagaa cagatatata ttttactaag catatgttga   153120
atgaaattgt tcaaatattt ataacaggca tagagtagaa ttttcttaaa atatttttg    153180 atggtatacc aatttgtatt ttctcagaaa catttgcctt attctttttt ctgttgtgtt   153240
tttcttacct gattgaaagc tcataatctg ttgttattgt ttgttaacct ttaatgctct   153300
gatttcagga gttcaaccta agcctgctag ctccatgctt aagcctaggg atgagtgaaa   153360
tttctggtgg ccagaagagt gcccttttg aagcagcccg tgaggtgact ctggcccgtg    153420
tgagcggcac cgtgcagcag ctccctgctg tccatcatgt cttccagccc gagctgcctg   153480
cagagccggc ggcctactgg agcaagttga atgatctgtt tggtaattaa aattaaaatt   153540
tatcttattt ttaaaaagca ttccagggcc agtatagtac tttgcaccaa gtaaatgtac   153600
aataaaggca gtggatctaa tacattgaaa gcgtttacag aggtagctaa agagcagcac   153660
gggtgtcctc ggctcagaat tcttcctgt gtgtttgcca ctttgccatt cattgacatg    153720
gtcatggaca tagggctcta agcccttgag gaaggctggg ccagacctca ggggagatgc   153780
```

```
agccccaaac cacgtgcagt cctgtggacg gatgtgtaga gtgccactg aggaacaatg    153840 tcttgagctt tcatcagatt ctcagagaat tgcttgactg cctttcgaag ttgatgcatc    153900
tgtgctcacg tttgcaccca cccacgaggt ccttctgttt caggggatgc tgcactgtat    153960
cagtccctgc ccactctggc ccgggccctg gcacagtacc tggtggtggt ctccaaactg    154020
cccagtcatt tgcaccttcc tcctgagaaa gagaaggaca ttgtgaaatt cgtggtggca    154080
acccttgagg taagaggcag ctcgggagct cagtgttgct gtggggaggg ggcatggggc    154140
tgacactgaa gagggtaaag cagttttatt tgaaaagcaa gatctctgac cagtccagtc    154200
acttttccat ctcagcctgg cagtaagtct tgtcaccgtc aagttattgt agccatcctt    154260
caccctcacc tcgccactcc tcatggtggc ctgtgaggtc agccaggtcc ccttctcatc    154320
tgcacctacc atgttaggtg atcctaatt ttagagacat gaaaataat catctggaag    154380 tactttatgt cttaagttgg cctggacatg tcagccaagg aatacttact tggtttgtgt    154440
tagtgcttgt aattcgcccc cagaatgtgt acacgttctg gatgcattaa agtctggcct    154500
gtatccttaa agggccatcg ctgtgctgcc tgccctcagc aaggacacac tttgcagacc    154560
cacagaggct ccgcctccac ctcacaccaa agaaagggag gagtccaaag gcatcagtg    154620 ccattactca caaaatgata aatacaccct tattctgaac cacgtggagt catatggttt    154680
gtgatccctg tccttcaggt ttcagcttag tggggaagtg ggaaagtcag cgtgtgatca    154740
cagcacaggg tgattgctgc tgattatatt atgtgcctgc tgtatgcagg atgaaatact    154800
ttatatgcgt catcttattt gactctcaca accccctgtg agataggctc tgttactccc    154860
atttgacagg tgaggaaagc aaggcttaga gaatttcagt gacttgccca ggtcctctga    154920
gctaggaagt agccattctg gcatttgaac ccaaggcctg ctatccctag aacccacgct    154980
ctcaaattca acctatgaca gaggcaagcc ctggtgctgt gggagcccca aggaagagcc    155040
tctggcctgg tggccacgta gcccaggaga gatttctaca ggagcccaca gcgctgaagg    155100
agagagaggc agcagagtaa gggggctttg tggcagagag gggactggca cttggggaa    155160 taggtgggtc aggactgaat gtaatggagc catgtcagag ctgtccttct ggaagggcaa    155220
gggcacctgg acgcgctgcc cctcagtgct ttggacggtt ccacaactgt gattcacacg    155280
gcttccccaa acgaaggtac acgagtgggc attctgtgac tcggtacttc cctttaggcc    155340
ctgtcctggc atttgatcca tgagcagatc ccgctgagtc tggatctcca ggcagggctg    155400
gactgctgct gcctggccct gcagctgcct ggcctctgga gcgtggtctc ctccacagag    155460
tttgtgaccc acgcctgctc cctcatctac tgtgtgcact tcatcctgga ggccggtgag    155520
tccccgtcca tgaacggtgg gttcctatca tagttcctgt ctgcttcacc atgttttat    155580 tttgtgctgc ctgtttgcca ggtactaagc taggaattgg ggatggagag gtagataaaa    155640
tatgcatcag gaagggctgg gccccatctc ttactctcca atatattgga gtctacactg    155700
gaatttaact ggaatttgct tttttagtca ttttatttag attttgaagt ttcagctttc    155760
atcaaaaata cctctaaact ttatgtctct gtgatctttg gtcttagctg ttttatgtat    155820
ttagtcttat atgatcataa gattaataac attacattca gaagattatt tgttttctgt    155880
cagagttaaa atgtttgttt ttatactgca ttgtaatatt aacgtactgt aaaataaaag    155940
tggcttgttc ttttcaagga acagtatcct caacaagggt cattagccac aattttaaa    156000 aaattggacg tcatagttta catgttagag ggcgttttga agctttgtat ttttaaatta    156060
aatgttatag agtgatgttt tcatgtttca taattgtttt catctgtgca tttgtagcca    156120
```

```
acttgaaaac aaagatccag ggattactac ttaaaagcca gacttcttgg aggttatagt   156180
gatgattttg atagtatctt gagccgtctc ataataacct cagggtgaga gatggccaac   156240
aggagacagt cgagggactt agaaatctga atgaaatctg aagttcaaat cttcagacat   156300
ataccactaa ccaagagatt ggtacctcag tctagtattg tctgtttgtc taaaattggt   156360
tctaaggaat ctaggctagt ctgtctatcc ctttcaactt ttgtgaggct gcacaaatgt   156420
aaaatgttga ataaaaagca ctgatggaag tgtgtagaaa ttcttctctt tgttctgttg   156480
taattttagt tgcagtgcag cctggagagc agcttcttag tccagaaaga aggacaaata   156540
ccccaaaagc catcagcgag gaggaggagg aagtagatcc aaacacacag agtaagtctc   156600
aggacccatt tttttcttac atgttgttcc tccaggactt aaaaatcatt cacagagacg   156660
tgcaccgcgg tgagtgtgga ctcctggaag cgcaccgtag ctccgctgtg tcctgctgct   156720
cctccctagc tgtcagggag gctgtagtcc attgctttgc cagctctttt gtttccgagt   156780 gaacaccta tccgtacaca tgcggctgtc tctgaccota cagaccagct gggatgccac   156840
tgggggagcg ctcccttccc cccgcacttc ccacactctg cagttattct gagatccttg   156900
agggcaggga acaggtttgt cttctttgtg ttctcagaaa ttaatgctcg gcctctggtc   156960
agcaagcaac aaccttttgt tgagtgataa tgaataaata aatgtttccc acatgagtat   157020
tcagtaacct cagtgtcagg ttcagccatc tgttttggtg atatttaaa agaaaattcc   157080 gcttttccta cagaaaaaaa aaaaaatcca atcccagtg atttaagcca gttatagact   157140
tagacatata ctacggcttt tcatgcactt tcctcccaat tctagagtag gtattttact   157200
aggaaaatgg tggcagtgcc tgttgggagg aagattcttt ggccaagtgt cttttgttct   157260
tgccagggcc cctaggctgc tggggtgctt cagcttcttt agcccagtgt ctggtgggga   157320
atggcccctg ttgcctgtcc cacagaggtg ggggtgcctc acctggagcc tgtccacaca   157380
ttttacacag cacgcttacc tggagcatca ggcatctttt ccatgctctg tggctcagga   157440
aacacgcctt tcaatcatg agtgcaccag tgcttttggg cttttctcc ccgcttttgt   157500 gcaatcctgg ttgtggatgg agttttcctg tctttagtct tctgcatagt acttttctct   157560
tctggttccc ggttcaaggt tttgtaatta gagaatgacc cagaagcaat ggcatttaa   157620 tgcacagcca aggacttctc tgaatttgta tctcaaacct ctgtgggtcc ttcaggcttc   157680
agtttgtgat ttcatgattt cttgttgcta cctaaggaat atgaaaacac ccacctcct   157740 actctgcatc ttccagccga gtggcacctc aggctgtgga tcctgtgctt ctgtggtgag   157800
gataagaata gtgccaaccg tgtggattga aatcaatcag ttaatccctc catgtaaagc   157860
acctggaacg gatgacagtc ttgttatgaa tactcaacaa atgctatcat gattttagt   157920 tagatttcca ttgctttaaa acagttgaga catcttggcg gtttgagtta gagcaacggg   157980
ccctgaagtg ggttctgttt gggtgaagat gattatgctt attccccatg gccctcttta   158040
ggcaagagtg ggaagctttc tttgtttttt taatcacctc gataggacgt tacttcttaa   158100
aggtcatcca ataaatatta ataggccggg cgcggtggct cacgcctgta atcccagcac   158160
tttgggaggc cgaggcgggc ggatcacgag gtcaggagat cgagaccatc ccagctaaaa   158220
cggtgaaacc ccgtctctac taaaaataca aaaaattagc cgggcgtagt ggcgggcgcc   158280
tgtagtccca gctacttggg aggctgaggc aggagaatgg cgtgaacccg ggaggcggag   158340
cttgcagtga gccgagatcc cgccactgca ctccagcctg ggcgacagag caagactccg   158400
tctcaaaaaa aaaaaaaaat attaataaag ccaactcgtt agcgtggggc ttaattgctt   158460
aagtccaatg agaagtcctt ctctatccta ggaagttgcc caaactgtag aatctcgtgg   158520
```

```
cctgtgggta atagccacgt aatacacact cactgcctca acaaatcata ttttagtagg 158580
tatgatattc tagactcaag acaccattct gtggatcttc ccaagggtgt gaagtgtcca 158640
cagcgtctgc cttgggagtt tccatgccca ccagaaccat gccccaagcc cctcaagcac 158700
tctgacctag gaaagccagt gaagcaagga tgacaacatg gcccttttgat actagctgag 158760
ggacagacac aggtcctggg agaccagaga aagacgaggg gcagaggagg tgtcctaaag 158820
gaagtctgag gctgaggagc cacaggatgg cttccagctg tcacaggctg ctgctggcct 158880
tatcacagag agtgggccag agggctggga accaaggcca gagctcaggt tcaggaccat 158940
tccagcaatc ccagcagaaa atggggagaa ttgtatggta taggcggata tgaaggtaga 159000
atctgcaggc cttcagtggc caactcagag tctaagtgga ttccacagtt acagcttgag 159060
cagctggttg taggtcatgc tttctacact gggcatatag gatgtgtttt ttaaaaagtc 159120
ctctcttaac cgttgcttgt ttagatccta agtatatcac tgcagcctgt gagatggtgg 159180
cagaaatggt ggagtctctg cagtcggtgt tggccttggg tcataaaagg aatagcggcg 159240
tgccggcgtt tctcacgcca ttgctaagga acatcatcat cagcctggcc cgcctgcccc 159300
ttgtcaacag ctacacacgt gtgccccac tggtgagtct gctcgttcct tgcagaagac 159360
caagtacggt gaaaggcacc ggtaggccct gggctgggca cacgtgagag ggcgggacag 159420
aatccccgca gcccagaggc tgcctgctgt ggttctggtg cccactgtgg ttctggtgcc 159480
aggctgcttt cctcaggcac cacgtgtgga ggtcgctagt agaaatactg ggttttctaa 159540
aatgaactga ggccctacat ccctaagaga ttagtgttag acctgattct agagcaacta 159600
gaccactttg cttaatagca gaccagaaac cacaccccct cgagtgagtg agattttcct 159660
ttggagataa ttcatgtttt tctacacagt tttgcagttg tcttcagaat tggtttaaag 159720
taggtgttat tgccaggcgc agtagctcat gcctgtaatc ccagcacttt gggaagccaa 159780
ggtgggcgga tcacttgagg tcaggatttc gagaccagcc tggccaacat ggtgaaaccc 159840
catctctact aaaaatataa aaattagcca ggtgtggtgg tgtacgcctg taatcccagc 159900
tactcaggag actgagacag gagaatcgct tgaacccagg aggcgaaggt tgcagtaagc 159960
cgagatcgcg ccactgcact ctagcctggg caacagagca agactccgtc tcaaaaaaaa 160020
aaaaggtagg tgttattgat cagaacccct gtttcagata acatgaggag cttagcttga 160080
ggagagtgag ggttgatgga gggggactga cttctgccca gtgaaatggc atcatctccc 160140
accagcccgc tgaaataaga tgatgggcc tgttccttag ggcctgcagc atcctcaggc 160200
aggaaagaaa ggccgacctg gcagggtgtg agccagcagg tgtaggtcag ggagaatgga 160260
gccaggtccc agggaagagg cttgtggctg cctgagaagg gtgcgtgcct gcctgtgtgt 160320
gtgtgtgcac gtgtgtgtat gtatgctgga gagtctaggg aggcttgctc caaggacgca 160380
gtattgtttg atcctgagag ataaggattc tgccgcaggg aatgaaggta ttccagatgg 160440
cgggcttatt ccgaagaaga ggccagtgcc tggcggtgct ggaagcagtt gcagaacagg 160500
gagttgtagg cttctcctggg aagagagcag cagggggtgct ggagaagcag gccacacttg 160560
ctgcatgggg ttgctctcgg ccccactctt ggtgcacagc gagtcactgt gggttcatta 160620
gcatctggtt atgagacagt aactgctcct ttggagggc tcgtggagac catgcaggag 160680
ggcacggtct tgaggtcatg ccgtccagag cacacctgag gataggccag gacgggctgc 160740
acgctgtagg taaaattcct ccagcaagct cttcactggc attgaggagt tccctgagtg 160800
cggtcatctg gaaggcagct gtaacaggca ctgcagtctc tccctgggtg ggtaccagag 160860
```

```
aggagcatag gggagcataa ccgatttaaa gagagggctt tcctgtggtg aggtaagaga    160920
ttagctggtc attatcatag agccccctct gcctttgtgc agatgggctg tgggaatcct    160980
ggggttccgt tgggtccttt gtcacctcac tgaaggcatg taagctgagc tggccagacc    161040
gtgagctgat cctgccactt gaacagcatc aagcctgcct ctggattctt ctgtgcatgg    161100
cacttgtctg agcacctcac gcacagagaa ctggacttca gagtttacag aaataagctg    161160
tatggttcat tttcatgcct gcttgccaat aaacatatct gagctgaacc tcattgaacg    161220
cctgccttta ttctagcaca gcacctgctg tttgtgggcg aggggtgctg tctctaactc    161280
ctgcctgctt ctcccagcac tccctgagtg gggtgtgcca gcagcctcag gatgaggaca    161340
ggaagtggga gggcagagca gatttgggag ggccacttga tggggaagga agtcccagga    161400
agcagttgga gctgttttct gggggagaag gtgccagctc tgggacagtg ttggggtagt    161460
gaggagggag cccagtggag agaagtcggg cttcctgctt cctcacagta tgtctgtcct    161520
gactcaactc ggatgatgtc acttcctttt catcttctca ggtgtggaag cttggatggt    161580
cacccaaacc ggggagggat tttggcacag cattccctga gatccccgtg gagttcctcc    161640
aggaaaagga agtctttaag gagttcatct accgcatcaa cacactaggt actcttgggg    161700
cctctccttc aggtcaccat tgtcggacat ctaccgggag gaaatccaga gcccccagta    161760
ctgggatctt ctcatttgac tccagaaaag atttaagcat gataataata caaacctatg    161820
tgaatacatt ttgcagtgtt ggcaaaactc cttttatact gagaaaatag atcccagttc    161880
ctgtgttttg tggcttgaat cccagctttg tgtattccgg gcttgtttga agtcaggaaa    161940
ggttcatgtg tagtggacaa cgtgagacca aattctgcct tagattttgc atttaggcta    162000
aacagtggca gcacttgtct cagaatgttt tcttgtgttc accagtctga tcctgttgtg    162060
tctcagtggt ccatttttctc atatgggaac aagcagacgg gagcagatgg agtcaggttt    162120
cttggcactc gccttcccca gagcctagag gcagcatggg gagaaagcag gcttggggct    162180
cagacagtcc tggtctgctt ccagccctcc tacctgagca gcgcagggca agtccgtcta    162240
acctctagag accctcagtt ttgtcatatg taaaatgggg gtcgtgtcta tttcatagaa    162300
ttgttgcaga tttagaaatt acatttctaa acaaatgtta cccttatttt ctaaataagt    162360
gtctaaatga ataagtcacc acttttgccc ctatttgatg gcaagaggtg tgatcttgtg    162420
gtgggactgt aatcagtcag ttctcagtga ctgtgccctg ctgtggtgtt tcctggaatg    162480
ttcctgtctt gtcctagaaa gtctggcagg ggcaccctga ctccactgtc cagtcctctc    162540
cccagtccct cgggcttctg cagatttgag gcttgtttgg atcccagaag gttgtggcag    162600
gagacacctt gcctctactt tccccttat aattcaatgt ccaaagagag ccctgagcag    162660
gtacctcacg ccagctgcct cacggagctc ctcctcttcc tggctgtgag gatcggtatc    162720
agtggcctcc tgctctctcc cccttgccta acacgagcac ctttgcttac ttgggtgccc    162780
ttgctcttga actgcccatc ggacgtgcgt gacccaagac tgtgccgcag tccttgcctt    162840
gtctgtgctc attttctttg ttcattttt tccctgtaac gtaaattgtt atatttgtct    162900
gtatctgtgt ctgaatcagt cctgcacgct ctccttctct ctgtctcttg ttctttcttt    162960
accccgttta tcacgtgggac cccgatgtcc attgctctag ttctcctgtc ctaagcaccc    163020
catcccgtct ctctggcctt accacaagtg gcgtggctgc ctcagacatc atgatgggga    163080
catgaagcac agctgtcaga aacaactgtt cgttagatac actcgaatgc agctcatcaa    163140
tagggatgga gggtctgtcg gatgtatttt cactgaatcc ccgttcctac cttgatacac    163200 tcttttttaat ctattcttct agacaggtca gaggaaccat tactttgact tttaaatttt    163260
```

```
tagcagcttt attgaggtag aattcacata ctacagattt cacccactct aagcggacag    163320
cttggtggcc attagtttta tccacagagt tgtgcagcca gctgcacagt ctcagggctg    163380
gactccaggg aagattttag cccatttagt gagtggggca gaagtggccc tggccctgca    163440
cgaggttgcc tgcatgggcg tccctgccct gtccctgtgt ctgctccact gggggttgac    163500
caggctgcca gggccgactt gggcctgtgc cacctgcctc tcatgtgtct cggacagtgc    163560
agccgatgtc tatacttcgg tttcctcaat gatgaaatgg aggggatagt gttccccgca    163620
tcatagaact gtgtgaggtt taagggactc actgcccttg gcgtggagcc ttctccaggg    163680
gccgtgctgt gtcggcgtag ctgtcagctc tccgttacag gcttgagaag ggttgacact    163740
ctctcatgta acatttatat ttctaggctg gaccagtcgt actcagtttg aagaaacttg    163800
ggccaccctc cttggtgtcc tggtgacgca gcccctcgtg atggagcagg aggagagccc    163860
accagaagta aggccacacc ctgtgctggt tggcacatgg gcagttatgg ccgcttgcag    163920
gcctttggtg gggaataaaa taaggcagca agctggtgtt ctttttttct cttaccttat    163980
ttttgaaaga gtagctgaat ggtgtcttga ctgatattcc agagcaggga caaagcctgc    164040
tgaggtctgg gggctgcgat taccaatggc tggaatgcat tttattacgg tgcattccat    164100
gttaaggatc aatacgattg tgccctttct ggaaaatatc ttttagttta tcaatattca    164160
gaggagtgta ggttgaatta aaatgaaaag gcactttata aaggccatga gtagtacctg    164220
gtttcatttt tctaatgtct tgcagagatt ttatcaggct tcttgaagtg ttcacgtaca    164280
ttacgctaac acgatattaa taataactgt gctctggtac agcggagcca gcagaatggg    164340
aagttgtgga atgcaggccc ttgattctga tagaaggtgt ggtttgaact cacagaaatg    164400
acagtttgga gggtagacat atgtcacaag tcatcaagat tgtctttaaa ttcatgcata    164460
gaagctaaca gggtgtcata agcaaggcct gtaaaatgta tgagggaatt caaagataat    164520
ttattaaaaa gtaattcatg tttggagttt tgtgcccaaa ggagtccttg atttgaaaaa    164580
tgggcttttg cccatcagat tgtttcaggg cccgtgtgtg cggaggccct gccttgtgcc    164640
ccgtgagctc agcctgacag aaatcctttg gtagcactta aggctcctct tcctcccatt    164700
gaggcaggga agactctggg ttctgcaggc agaggtggtt gtgggtgtct tgctgctctt    164760
gttgacatgt gggctctcct tccaggaaga cacagagagg acccagatca acgtcctggc    164820
cgtgcaggcc atcacctcac tggtgctcag tgcaatgact gtgcctgtgg ccggcaaccc    164880
agctgtaagc tgcttggagc agcagccccg gaacaagcct ctgaaagctc tcgacaccag    164940
gtttgcttga gttcccacgt gtctctggga catagcaggt gctggggaca gtgggttccc    165000
cgctgaagcg tccagcagct tcaaccaggc cgttttcctt cattgctaga attgaaaaca    165060
ccgtccgtgt ggcctgtgca ggagatgcag acccaaaggt ggcctcctgg tcagtgagaa    165120
gctggaaacg tgacaggaac tgacgtgggg ttattgagca tttagggaa gacgttagca    165180
gagcaggaat gagcaggcaa ctagtagaac acccacttaa gggctcacgg acaggtgctc    165240
acttaggaag tgagtttcat ttggtattac accaggttcc tttaggcaaa gcggagggaa    165300
agttctggtg ttttcactt gtaagatttt gaaggaaaca aaacactctt tacctttttt    165360
ctaaaatgta ggtttgggag gaagctgagc attatcagag ggattgtgga gcaagagatt    165420
caagcaatgg tttcaaagag agagaatatt gccacccatc atttatatca ggcatgggat    165480
cctgtccctt ctctgtctcc ggctactaca ggtacctgag ggaaagggtg cggggggagcg    165540
gttgtacttg ggctagaatg agagaagact ggcatgctca ccacaccagt gatgcgggaa    165600
```

-continued

```
gacctgagtg tggtctgagt tggaggctgt ggtgctaaat acgctgcccc tttcataagc 165660
aggagtctta gtcaggccca gggaggaagt aaaatctgga aatgaatgag aagcattctc 165720
tcctgccagt caagaaatga gaagcgaaag aattctcacg ggctgtaaga ccagcaggat 165780
ttaaaagttg aattagttgc ttatgttaag aactcaacca agttcatcta cacaagctga 165840
atctccagct tttcctaaga aaccatgtgt ggcagtggct gcagggcagg gcacagctgg 165900
gcctgagcac cccgctccct gcacctctcc cctccctggg ccctgcctgt cactgcccac 165960
tctcccacca agccttccgg ttgtgtgcct gccctatcac aggcatcgga gcttgtcacc 166020
tggtttaaaa gaagagagtt gtgtgggdat ttgggatgca cgttttcac tcaaaagtat 166080
tttagcgtag agctctgtga ttccgtagct atttaggagt ttaagcacct tgaaggcttt 166140
aattgcagaa agttctatgt ggacgtgcaa tgtgttatac gcagtgtcta tgagactcaa 166200
atgtttatta gggcgttgaa gtaaactgag cacttggagg gccatggatc cagccttcaa 166260
ggagctcata agtcaggagg acccaggagc aatgacctgt catagaaggc agaaaagagg 166320
ggcacagagg tgggtgggag gcatacacag gcagctcctg gagctccaag gggagcaagt 166380
gcttccaggg aagggggcgt ggaggcccct ttggaggagg caagttgatc tggggtctgg 166440
cagagggtta gctggggaca tttagcggga ggctggtgcc cgggaattgg ggggatgccc 166500
agcagaaaga catgaggagg ctggcctggg gcgtgggggg gtgtgaaagg ttaagtgggg 166560
gcattatcct gctcccgctc ctgccggctg tatctggtca gcctgggcac cgaggtgggg 166620
ttctggaagg cactgttcac caaaatgctt atctgggtcc cccagagagc ttgcctgcct 166680
ggactgtcgg ctcgcctgca actgctgact cctaagcttt tgcagctcag cccacaacca 166740
gttcctattc acagaggtgg gagctgaggg gtgacaagtg actgctgcag tcttatttgt 166800
catagagaaa aagtgacaga gtccagcttg cccactggcc ctgccagctt aactggttat 166860
aaagtgacaa atccccaaga cccacagggc tctgcacaac ctgggccctc ctgccagtgg 166920
cggcgagggc aggtggctca cggctgggtg cctgtctggg caggagctgg gctggtatgg 166980
ggtgggcctg cggccctgcc ccctgtgca gatcaagact cagggtgctg gtgttcacag 167040
gtgccctcat cagccacgag aagctgctgc tacagatcaa ccccgagcgg gagctgggga 167100
gcatgagcta caaactcggc caggtcagtc tcgcgccccc gccgcctggc ctctgtccgt 167160
ttctgtcctc agactttggc gcttgacaca cccaggagaa aagctcagtg cacttttaa 167220
atgaaaggaa gttttccttt tttttaaaaa aaaatttaat gttcattgtt tttatctgtt 167280
ttattcctag gtcccgcaag cagaggaagc attagttttg tttttattta tgttctgtat 167340
tccagaaagt agttaagaga cctcacatgt agcgatagag atgtgtgtaa gagacagtga 167400
gagggcgtga cttggactta agcaaggacc gtgagacaca aaaagggggg tgaggacaga 167460
gtggagtcag ctgaaatgct caggaggaag tagacgccat gaagggccat ggtatggggg 167520
gccgcaggcg tggccgtgag tgtccctggg gccagctctt gggggctcc ctgagtgtcc 167580
ctgtccctgt ggccagttct gggtgggagc ccgtgtgca ggcagacagc tcggccactt 167640
cctagcaggt cacattggtc tgtgcttctg tttcctcctc agataagtga agggattcaa 167700
gggtctgggt gtggtggcta acacctgtaa tctataacat tttaggaggc tgaggcagga 167760
ggcttacctg agctcaggag gttgaggctg cagtgagcca tgattgcacc actgcactcc 167820
agcctgggca acagaccagt actctgtccc ttaaaaaaaa atgtaaacag aaacgtaggg 167880
ccatttgcat atgatggcac atggcgtgga gccctacagg tgtatgctgg gcggggcccg 167940
gctgtgctgg ccgacttgca ccttcccctc caccccggtg ctgtgtcttt cgctcaccgg 168000
```

```
gttcctgatt tagtgaaagc agttgtgcag gacagttctc tttgtagctt ttgtttctgt  168060
ggaaatgggt cagaatatgg tgtttagaaa cacttatgag ctctgagagt ttcctcttct  168120
gagttcctgg cctgcagcct tcacagcaga aaccctgtga tgtcacaagc ctgtttctgt  168180
tccctgctct ctgcctgtac tgtcctgttt tgtgcctgcc ggtttcagtg acaggaagca  168240
gggagctact ggaccagcct gtattttttct agacatagtt ggaaaaagaa gtcccactct  168300
tctgtccttt cacctttgac agatgtttcc accccaagat aagtgaaaat gaccaatagg  168360
atgcactgta tttttcatga aagtgtttct gaagggcagg ctgagagtga gaggcctggg  168420
gctcactggg tgcctctggc cttgtcctgg gcccagggac actggtctgt gcccgaggta  168480
ttccctatcc ccccaacccc gctgcatttg ccacatcct tcaatgtttg cgttgtgtcc  168540
agcgtccgca aaccaactgt catgggatca tactggggct gaagtacggt cccacccctg  168600
ccctgtctgg ggctgaagta cagtgccacc cctgccctgt ctggggctga aggacagtgc  168660 caccccctgcc ctgtctgggg ctgaagtaca gtgccacccc tgccctgtct ggggctgaag  168720
gacagtgcca ccccttccct gtctggggct gaaggacagt gccacccctg ccctgtctgg  168780
ggctgaagga cagtgccacc cctgccctgt ctggggctga aggacagtgc cacccctgcc  168840
ctgtctgggg ctgaaggaca gtgccacccc tgccctgtct ggggctgaag gacagtgcca  168900 ccctgccct gtctggggct gaaggacagt gccacccctg ccctgtctgg ggctgaagga  168960
cagtgccacc cctgccctgt ctggggctga aggacagtgc caccctgcc ctgtctgggg  169020 ctgaaggaca gtgccacccc tgccctgtct ggggctgaag gacagtgcca ccctgccct  169080 gtctggggct gaaggacagt gccacccctg ccctgtctgg ggctgaagga cagtgccacc  169140
cctgccctgt ctggggctga aggacagtgc caccctgcc ctgtctgggg ctgaaggaca  169200
gtgccacccc tgccctgtct gggatgttta gcccctagat gccactggac tgagccgcta  169260
cttgcttttg ggaagagggg gtggggggtta gggtctggg cgaggggagt gcaggggctc  169320
ctccttggcc tgagagctgt tcatacagac tcctcgccca ctccctgcag ggtgctgggt  169380
cccagggggg aaatggccct tggtgccaag aacgtgagtt ggggctagtg ccagtgatga  169440
tggagaacag cttttatgg gcacacagcc cacagcactg tgccaagtgc tcgaggcttc  169500
ccgagaacca ggcagaaagg aggacagtcg aggtgtgctg actgcgtggt ggctgcgtga  169560
tctagagcgc gggtcacaaa ggcgcgaggg agctctggcc ttgggtttac cgcaatgact  169620
gccagtgcgg gagactggaa aaggaatctc acgtattggt tccgtgtttt ggggactcca  169680
ttcagatgtc acttaggagt gaaagcatcc cttcgtagag cctctttctg tgtcaccctc  169740
ctcagctgct cctggggttg actggcccct gattcatgcc tttagcatgt gctggagctt  169800
cccagcagct gtccagcccc tgccccaccc tctctgtggg ctcccttgcc cgtaacctgg  169860
ggtgtctgaa cgacccttgc taaggggcag actgttagac ggtaggcatg tgctgagtcc  169920
cagtggccac acccacccac caggagcctg gcactgtggc cgcagcactg agcagtgccc  169980
cgtttctgtg gcaggtgtcc atacactccg tgtggctggg aacagcatc acacccctga  170040 gggaggagga atgggacgag gaagaggagg aggaggccga cgcccctgca ccttcgtcac  170100
cacccacgtc tccagtcaac tccaggtttt ccaatggcct ttttctttt aacagaaatt  170160 tgaaatttct tatcagtcat ttgatttgtt tgaggtgctt cttgaaatga gcctctcatc  170220
tcatgtactt ggaaaatacc catctcgcat attccacagg aaacaccggg ctggagttga  170280
catccactcc tgttcgcagt ttttgcttga gttgtacagc cgctggatcc tgccgtccag  170340
```

```
ctcagccagg aggaccccgg ccatcctgat cagtgaggtg gtcagatccg taagtgagcc   170400
ttcccattcc cctcacacct gcacgtgcca cacgcaccac acacgccaca caccccacac   170460
acacacaccg cccacacaca tgccacttgc acacacaccc ctcatgcatg caacacacac   170520
acaggccaca cgcaccatag acaccacaca cacatgccac atgcacacac atacacggca   170580
tgcaccatac acacaacaca cacagcacac atgccacaca cacgccac accacatgca   170640 ccacacacat gccacatgca cacacactcc acatgcatgc accacacaca cacacacaca   170700
ccacacacac cacatgcacc accacacaca ggttacatgc acaaacaca cacatgccac   170760 gtgcacacac cccacacacc acatgtatgt gccacacaca gcacaaacc acacacatgc   170820 accacacaca tgccacatgt gcatgcacca gacacatggc acacactaca cacacgccac   170880
gtgcacacac cccacacaca tgtacgcacc acacacatgc cacacacaca tgcaccacac   170940
acatgccaca tgtacacaca tgtatataca caccccacac cacacacaca ccacttgcac   171000
accacgcaca cacaccacat gcgcacacac acaccacata cgccacatgt acacaccata   171060
cacacaccat acatgcacca cgtgtaccac gcacccacac agacacagca cacgcataca   171120
ccacacacac acgcacacat gcgtcccgca cagtaatgtc tcttgggtgt aagaacacga   171180
cttgccagta gtagcgttct ggatgcgttg cctggattct aacagcgcga ttctcccctt   171240
gccctcctgg ttttccacat ctccagcttc tagtggtctc agacttgttc accgagcgca   171300
accagtttga gctgatgtat gtgacgctga cagaactgcg aagggtgcac ccttcagaag   171360
acgagatcct cgctcagtac ctggtgcctg ccacctgcaa ggcagctgcc gtccttggga   171420
tggtaagtga caggtggcac agaggtttct gtgctgaagc cacgggggcc catctgcctt   171480
gggacctggt gttggccaga ggtgccgggt gcggctgcct ccttccaaga gttgacccga   171540 accgactcc acgcccacg tgagctgcag tgcttctcag atggaggggg ttcagcgacg   171600
gtcagtgcca ttcacaggtc actgtgatgt gggttgtggc ggccaagcca tggtttgggg   171660
tcccgtatcc ctgggcttat gacatcattg tagtagccca tccccacaga accacggtgt   171720
gtggtggcgc tgaggcatcg tagatggtgg aaatgctact ggcttcccca tgctctgccc   171780
tgaggcctga ctgcctcact ccccttctca gttatgttcc aggcccccg agcttcctgg   171840 ctggacagct tctctcctgg gggccgtttt gtcacagtga ccctgtgttt ctagtcccaa   171900
atctgggtgc tatagtctct ttttagcgtg gtggttgtct tagtctttt tggctgctac   171960 cacaagttac cttagactgg gtaatttata aacagtggaa atttacttct caccgttctg   172020
ggggctggaa gttttcatgg tcaaggtgcc agcagatttg gtgtgtgatg agggctgctc   172080
tctgcttcat agatggcatc ttctggctgg gtcctcacgg tggaaggagt gaacaagctc   172140
cctcaggcct tttagaaggg ccccaatcca caagggctct cccatcatga cctcatcacc   172200
tcccaaggcc ccaccttctt gtactgtggc actgcaaatt aggtgtcagt gtaggagttt   172260
caggagggat agaaacattc agaccatccc agcggtcaag tgttcatcct cttgagttcc   172320
tccttattct gcttctggtt tatcaggatt cagccagtgc agcatggtac ctgtattctg   172380
tggcacatca ccacatggta tttgccaagt atccatcacc tgcacacgtg aaatcattgc   172440
ccgtgggtcc cgacatctgg cgaagcatat tcaaggatgg cagaactgtc agagctggca   172500
cctctggttc cttgtcatgt ggcattacct agtaatccat tttatgatag caatggaaac   172560
tcatttcttc aacaaacacc tgagtggctg ccgtgtgcca gccgtctggg gcccttggtg   172620
agaatggcat ggtggtgccc atcagggcct gcctagcccg tgctctggac gggctcctgt   172680
gtgtcaggaa cgacaatgct gtcatgacgg tgaatgattt ttttttttgc catcactcca   172740
```

```
gccgctaaca tttgcggagc tcttcctccc gcaccccac  ctgacaaggc caagggtgac 172800
cttggcccca ccctaggcgg ccaaggtcag aggttagctg gcttgtctgg gtcacacaaa 172860
atgcagcaga ggttgaggtg agcacatgtc cgtgacctgg agcctgactc cctctctgcg 172920
agtcttgact gctcttgcct agactctgtc ctccccgagc ccaaacgcca gtcatcttcc 172980
cttgtgggtg tccttcagcc tggtgccatg ctggtgactc agcagccgtc cagggagtgg 173040
aaacaattga gtgtgtgggt tccctgtgtg ggcatctctc ttcacggcga acaccctctg 173100
ggtgttgccc acacgatgtc aaagcggctc ttggaagggg tccttctcct tgtgggaag 173160
tttcagctgc tgggctaact tgaattgtaa ctgtggtttt gtgctcaggc ccagatcccc 173220
ctaggcaagt gttgtgccat cagtaatcaa atgagaaata atcattttga aaagcagatc 173280
ctaaggcagg atggtcatgg acactcactc ccagctcttt gtgcactcat gctttctgga 173340
agatggccat cctctgtgaa ggttttcagc gcgtcatgct tggtacccac gtatccagag 173400
catgtcgttt tgaggtattt gcccaccgtt gtgaaatccg tgccacccga gagcaggtcc 173460
tgatgtgggg ctttcagaag tgggacctgg ggccgtacgc agtccttagg gagggccgt 173520
gtggcgttgt gcgtgtgagg ggatagcaca gggtgaggtg ggggcccaag aaggaagtga 173580
cccacaaaga acagcctcct cttttggtcc ttgttcctgg gatggctggg agtggcttct 173640
gtgtcgtccg gccatttccc ctgcggagag gctcctacca ctgccgagaa cctcatcatt 173700
ccacaaaaac aagaggccgc ctggccatcc agcgctccat gggaattctg tgtccccata 173760
gtcttgggct gaaggagggt gacattcctt gctgacttct gcaggggtct cctcactgtt 173820
aaagagcaga ttgaaagtga agaacgtggg ctaagtgttt aggtcgatat ttaaccctgc 173880
taggttttgg atactaagtg aaattgaggc cattttggtt gaagttgaca gaaaccacta 173940
tcagggatcc ccaagactac cccaggcttt tctagaaaga ctctcagcta agatgtgtta 174000
tggtaaaagc acacaaaaca aaatcagcaa agaaaattag caagggcaga ggcccatggg 174060
gcgatgtccc gaggacacca ggcttgagct tccagaatcc tctcccagcg gggtcgtgca 174120
ggacgcactt aactccccgc acagtgagcc gtgacagcgc gtgtgcagtg tcgtcgccag 174180
gaaagcacac tagagactcg gtgccagggt ttttactggg ggctgggcac atgggcaccc 174240
tctgcctgcc tcgtgcccag actctggact cccggaggga aggcaagttc tcagcaccaa 174300
ccctggtgcc cacacaagca gctgagcaca gggagcccct cctcagtgag gatggtgggc 174360
accgtcccaa caccagccag gggccagcct tgcacacagg cctctcagga tggtctccgg 174420
cctgctgtgt agtctcttct gcacacaagc gtgagggcag cgcccccgcc tcggctgtgg 174480
ggaggagcca ctgggacgtg agctctggtg gcatgcagca gcttttgtct gtgtgtgcct 174540
aggacaaggc cgtggcggag cctgtcagcc gcctgctgga gagcacgctc aggagcagcc 174600
acctgcccag cagggttgga gccctgcacg gcgtcctcta tgtgctggag tgcgacctgc 174660
tggacgacac tgccaagcag ctcatcccgg tcatcagcga ctatcctcc tccaacctga 174720
aagggatcgc ccagtgagtg ggagcctggc tggggctggg gcggggtct cagaatgagc 174780
tgtgaaggaa gcagcatcac cctctccaag tgcccaggct cctggccaga tggcaggcca 174840
ggtatcagtg ggaacccagg tgggtgccat ggctgaggtc agtgagacgc aagagcacag 174900
gtgcgtccta gaggcttcct cgggcacctc cagcgagctg gagctctcgc ctctgctgct 174960
gtctcatgtg gcgcttagca cactctccca cgtgccatt cctgactctg ctctcgaggc 175020
catcggctct cattctctgc tcccagaacc ctgttattac ccaggctagc ctcctctctg 175080
```

```
caccttcccc gccctggccc agtacctccc tcttgtttcc actgtgattc cgacctcacc    175140
ttatcttaaa gctgctggac ggcaggttct gtacacacgt gtccttgaca aagcacggct    175200
ggtgccgcaa cccctcagcg agcaagtcaa gctcttcaca gcgatgtctt acaagcgcag    175260
agggctctgt gacaccctgg tctcaccgcc actcttccaa agtcgcagag gctttagcag    175320
agatgggccc agcctctctg agtcataggc ttctgcacac gggagctgtc tttagaggga    175380
gggtggaatt tcatcagcca cccacatggg ggagttgagg gcaagaatta ggagcaaaga    175440
tgggaagggg tctgggagga atggccagtg atcccctttg acaagtgggc aggaaacggg    175500
ggctaggtca aagttgagtg gaagacctgg agggagacgg gaaggtctct gtaggcacag    175560
ttcagacagg agggaggtgt gagccagggc acatgccggt ggccgtctgg caggatttgg    175620
gacatgctgg agcagggaca gcggctcatc aggggccatt gccctcatcc aggccagagt    175680
gtcacaagcc cgtggggagg cccttctcgc ctgtcatcct tgctgggcag tgggtgctgt    175740
gctagcagga caggcggacg gctggcaact gtctctgcat ccctggagcc tggcataggg    175800
ccaagtcaca cggggcacag gcctgcaaat caggcacata tgttggtgca gtgacgtgat    175860 tttgggggc agccccagaa caggcccag acacaggcca aagccctgcc tgtgctggtg    175920 tgtgggctg ttctatggct cttgctgtgg gcatggagga ctcagggaag gagagttgag    175980
gtggtccagg agttgcgttt gggatgcaga gagcttgtgg catccaggta gaaatggtgc    176040
gtggggctga cctcagcacc atgggcagag gggccgtgtc acgtgcctcc gaggtggagg    176100
tgggaccacg tggtgacaga tatacgcatc actgggcacg tttttgtggg tgttgggggg    176160
catcgtattg gctcctctgt tcacagtggc cactcattca gtccctggct accaggtcct    176220
cactgtgcca tggggaaggc cggcgctgtc ggggatcac agaaggcagc acgtcatgat    176280
ggcatgtgcc atgaaggaaa agcacagggc actcaggaag tagaggggac tggcctgggg    176340
tgtgggaatc tagggcctcg ttagggaca gagagaggaa gtgtgtggtg gccagcatgg    176400
aggtggccac aggggaggct gagttaggcc gagagggcag ggcgttgggg aggtagacgg    176460
gctcagccac tcaggagtg gtcaagcaga ggctgaaggg tcaggccagg ttgcaggggc    176520
ctgggggagc cactcaggat aggcgctccc gggagcccgc ctggcccata gctctacact    176580
cccgcgtggg gccggacatg ctgtgaagcc ctctccacgt tggatggggg tggctgagcc    176640
tggatgctgt ctcccgtttt cagctgcgtg aacattcaca gccagcagca cgtactggtc    176700
atgtgtgcca ctgcgttta cctcattgag aactatcctc tggacgtagg gccggaattt    176760
tcagcatcaa taatacaggt gagtgggccc tggctgtctt cctctgcaca cggggagtgg    176820
gcttcccttc tcttttcctt gcaggatcat accagtgggc cagttttgac ttggtcggga    176880
ggaggcatga acacctgaga ctgtcagcg attctttgac acagaggcct ttctccctgt    176940
gcagatgtgt ggggtgatgc tgtctggaag tgaggagtcc acccctcca tcatttacca    177000 ctgtgccctc agaggcctgg agcgcctcct gctctctgag cagctctccc gcctggatgc    177060
agaatcgctg gtcaagctga gtgtggacag agtgaacgtg cacagcccgc accgggccat    177120
ggcggctctg ggcctgatgc tcacctgcat gtacacaggt gagcatgtac acggtgccca    177180
taaggccagc ccaagtcctg ttcaaggag gcaggagcat gctcactcaa ggggacctcga   177240 ctaggtgccc tctgatttca cacttctggt gttgccccaa gccggcccca tcaccttgca    177300
agaaaggctc tggagcccc agggctggag tacctggtca gggttgaccg tccctgtggt    177360
cactcatccc atgtgctga gctgggctgg gtcctgggca agcaaggggc tgatatcacc    177420
tgctttcaga tctccaggga ctcactggac ccctgtgtac aaagcactgt ctacagagcc    177480
```

```
tattgggttg tatagaggta accttcgtac tgaacacttt tgttacagga aaggagaaag   177540
tcagtccggg tagaacttca gaccctaatc ctgcagcccc cgacagcgag tcagtgattg   177600
ttgctatgga gcgggtatct gttctttttg ataggtaaga agcgaagccc catccctcag   177660
ccgttagctt ccctagaact ttggcctgaa gctgtgcttt tgtgtgtgtc tgctgatccc   177720
ctggcgctgt tgctggagtc ctgccagtga ttccccacca cagcctgacc atgggctgcc   177780
ttggctcagg gttccactgg cgagctggtg gtccttggac cccagcactc aggtgtagcg   177840
ttgaccagtt ccaaggttgt cccagtgcct gcccatctct cctgagggct caggacagt    177900
acctggcagt tggggtgtg gcaggggca ggaatgacca gcctctggga gggtgggca     177960
gaagcctgta cagtgaggag gagctggctc agcctggctg cctatcgtga gagggagcc    178020
cacgggctg tgggaggggg gccgtggtgc ctgtgagcag ggtgaggagc agcggcagga    178080
ggatgaaggt ggaacccaca catgcatctt tgagacccgt gtggtcagtg gcttctgccc   178140
cccaccaccc cccactgctg tgcgtgcata gaattggctt ccctcacctg ctctggaagt   178200
gggttaggag cttggtaggg cttttctca aggacaaggg cccctgattt gctctcaggc     178260
ctcagtcctg gcgacatggt ggatctggag ccttgttgca ctgccttgcc tgtgctctcc   178320
aatcagggtg gccagtgggg agccatttgg cttttctcaa gagcatactc aggtggacct   178380
tgctccactg tttgaccaga tgaggcattc tgaacagcca agcctgtgct ggtctgtttt   178440
catgttgatt ttttttttc ttttcttttt gagatggagt ttttcccttg tcacccaggc   178500
tggagtgcaa tggtgtgatc tcggctcact gcaacctccg cctcccgggt tcaagtgatt   178560
ctcctgcctc agcctcccta gtagctggga ttacaggcac acaccaccat gcccagctaa   178620
ttttgtgtt tttagtagag acggggtttc accgtgttgg ctgggctggt ctcgaactcc     178680
tgaactcaag tgatccaccc tccttggcct cccaaagtgc tgggattgca ggcgtgagcc   178740
actgcgcccg gcccccatgt cgatttttaa atgcacctct gcatcgttct tcagtcccca   178800
tatgctcact gagcaccact gcgactggca gacgggcaca gggaggcgcc acgaccagtc   178860
ctggccttca aggggcttgt ggtctagtgg gcccaatgct aggtggcgag tgctccaaag   178920
agtgtggtgc acgccttccg cttgaccgct ctccagacgc cacagggagg cacctcgcag   178980
ctgaccacag atttctctct gtggagcagt gtcttcagag cggctgccat gccactgctg   179040
ggcgagggtc tgcgggcggg tagagccagg agcacctgtg aggaagtgca ctgccatttt   179100
cgtagctgct tcccgtgtgt ctcagttaca cacggctggc atgtgtgcac tgatgagacg   179160
ggaacgtgat ggttgctttt cagcactgaa agggatactg ctcaggggc gtgtttcagg     179220
atctggttag ggaagaagca gcgagagcac agatggggcc ctgtgtggta acaagaaaaa   179280
agtcctggtt gacaacagtg ccacgaagcg ttagaacaca tagggatgtt tgtgagcat    179340
ttgcatgtgg aaagcagcaa aaacataatg ggaacgggtt cttttgttat gattttaaa     179400
aatctctttt gtaacatcct tcccgctgcg ccgtttctgc atattccttt atgtagcttt   179460
caaactcctc ttaggagttc tggtccctac agggcgtggg agcccaggct ttacgtagct   179520
ttcaaactcc tcttaggagt tctggtccct acagggtgtg ggagcccagg cctgtgccg     179580
agcagcctgc ctccacgagc tagacagagg aagggctggg gttttgcctt tttagtctca   179640
aaattcgtac tccagttgct taggctctga cttttccccac ttggaaagtc cctcacggcc   179700
gagggtccct cccagccctg atttcacatc ggcatttttcc ccagtattag agccaaggcc   179760
ctccgcgggc aggtggggca gctgtgggag ctggtgccag tctctgacct gcgtccctcc   179820
```

```
tcccaggatc aggaaaggct ttccttgtga agccagagtg gtggccagga tcctgcccca   179880
gtttctagac gacttcttcc cacccccagga catcatgaac aaagtcatcg gagagtttct   179940
gtccaaccag cagccatacc cccagttcat ggccaccgtg gtgtataagg tgaggttgca   180000
tgtgggatgg ggatggagtg ggaaagcctg gaggtggagt tgcctccgac ttcccagcag   180060
attcgccagc agagcccagc tcctccgctt taaagcagca atgcctctgg cccccacccc   180120 accccgcca cccaggcgca gcaggtgctt cccgtcccc cagccctgac actcaggcac   180180
ctgcttgctc cttgcaggtg tttcagactc tgcacagcac cgggcagtcg tccatggtcc   180240
gggactgggt catgctgtcc ctctccaact tcacgcagag gccccggtc gccatggcca   180300 cgtggagcct ctcctgcttc tttgtcagcg cgtccaccag cccgtgggtc gcggcgatgt   180360
atcctctctg gtccctggt gctggccccg tttcccttgt caacaccgag gctcatgttt   180420
catgataagg ttttgaaacc taacctttgc aaaaacccca cagatgccag ggtgacaggc   180480
cctcagcccc agggaagtaa aatgctgaca ggggtacaga aggagcacg tccagacatt   180540 tgctgaccag ggcctctcag aggggccggt gtatggcagg agggtcgcag ctgagggggcc   180600 tttctgtgga gggcctgggt gagggagcg agggtgggcg gtggtctctg cagacgtccc   180660
gcccactcgc gggctctgtg tggctgggct tctcctgaca ctgcttctca ttagctttgg   180720
tcattgtgcc tcgatcgccc tctcggggaa aggcttaagt aaagatccag ttcccacccc   180780
cagatgctgg ctgccaggag tttcccttc cacagcccctt ccccaagaca gaccacaaga   180840
gcctccaagc agcacagttg tcctggtgct gacagcacag ccttgccgg cgtgcctggc   180900 acggctctgc cctcactgca ttggagcagg gctagtggag gccagcggaa gcaccggcca   180960
ccagcgctgc acaggagcca ggccaggtga gtgctgccga gtgggtgccc tgcctgcagg   181020
gcatccagcc agccaagggt tgcaggaatg gaggtggagg cgctgatgca gctggaggca   181080
tccaggtggc ccttccgggg ctctgctcgc tctccaggct ccctggaccc ctttgtagac   181140
tgtttcagga gaggaactcc caggtgagga caggaggca gcattcccct catttgccgg   181200 ccttttttcct taactcctgc accagcctcc cacatgtcat cagcaggatg ggcaagctgg   181260
agcaggtgga cgtgaacctt ttctgcctgg tcgccacaga cttctacaga caccagatag   181320
aggaggagct cgaccgcagg gccttccagt ctgtgcttga ggtggttgca gccccaggaa   181380
gcccatatca ccggctgctg acttgtttac gaaatgtcca caaggtcacc acctgctgag   181440
cgccatggtg ggagagactg tgaggcggca gctggggccg gagcctttgg aagtctgcgc   181500
ccttgtgccc tgcctccacc gagccagctt ggtccctatg ggcttccgca catgccgcgg   181560
gcggccaggc aacgtgcgtg tctctgccat gtggcagaag tgctctttgt ggcagtggcc   181620 aggcaggag tgtctgcagt cctggtgggg ctgagcctga ggccttccag aaagcaggag   181680
cagctgtgct gcacccatg tgggtgacca ggtcctttct cctgatagtc acctgctggt   181740
tgttgccagg ttgcagctgc tcttgcatct gggccagaag tcctccctcc tgcaggctgg   181800
ctgttggccc ctctgctgtc ctgcagtaga aggtgccgtg agcaggcttt gggaacactg   181860
gcctgggtct ccctggtggg gtgtgcatgc cacgccccgt gtctggatgc acagatgcca   181920
tggcctgtgc tgggccagtg gctgggggtg ctagacaccc ggcaccattc tcccttctct   181980
cttttcttct caggatttaa aatttaatta tatcagtaaa gagattaatt ttaacgtaac   182040 tcttctatg cccgtgtaaa gtatgtgaat cgcaaggcct gtgctgcatg cgacagcgtc   182100
cggggtggtg gacagggccc ccggccacgc tccctctcct gtagccactg gcatagccct   182160
cctgagcacc cgctgacatt tccgttgtac atgttcctgt ttatgcattc acaaggtgac   182220
```

```
tgggatgtag agaggcgtta gtgggcaggt ggccacagca ggactgagga caggccccca   182280
ttatcctagg ggtgcgctca cctgcagccc ctcctcctcg ggcacagacg actgtcgttc   182340
tccacccacc agtcagggac agcagcctcc ctgtcactca gctgagaagg ccagccctcc   182400
ctggctgtga gcagcctcca ctgtgtccag agacatgggc ctcccactcc tgttccttgc   182460
tagccctggg gtggcgtctg cctaggagct ggctggcagg tgttgggacc tgctgctcca   182520
tggatgcatg ccctaagagt gtcactgagc tgtgttttgt ctgagcctct ctcggtcaac   182580
agcaaagctt ggtgtcttgg cactgttagt gacagagccc agcatcccct ctgccccgt    182640 tccagctgac atcttgcacg gtgacccctt ttagtcagga gagtgcagat ctgtgctcat   182700
cggagactgc cccacggccc tgtcagagcc gccactccta tccccaggcc aggtccctgg   182760
accagcctcc tgtttgcagg cccagaggag ccaagtcatt aaaatggaag tggattctgg   182820
atggccgggc tgctgctgat gtaggagctg gatttgggag ctctgcttgc cgactggctg   182880
tgagacgagg caggggctct gcttcctcag ccctagaggc gagccaggca aggttggcga   182940
ctgtcatgtg gcttggtttg gtcatgcccg tcgatgtttt gggtattgaa tgtggtaagt   183000
ggaggaaatg ttggaactct gtgcaggtgc tgccttgaga ccccaagct tccacctgtc    183060 cctctcctat gtggcagctg gggagcagct gagatgtgga cttgtatgct gcccacatac   183120 gtgagggga gctgaaaggg agccctcct ctgagcagcc tctgccaggc ctgtatgagg     183180
cttttcccac cagctcccaa cagaggcctc ccccagccag gaccacctcg tcctcgtggc   183240
ggggcagcag gagcggtaga aagggtccg atgtttgagg aggcccttaa gggaagctac    183300
tgaattataa cacgtaagaa aatcaccatt ccgtattggt tgggggctcc tgtttctcat   183360
cctagctttt tcctggaaag cccgctagaa ggtttgggaa cgaggggaaa gttctcagaa   183420
ctgttggctg ctccccaccc gcctcccgcc tcccccgcag gttatgtcag cagctctgag   183480
acagcagtat cacaggccag atgttgttcc tggctagatg tttacatttg taagaaataa   183540
cactgtgaat gtaaaacaga gccattccct tggaatgcat atcgctgggc tcaacataga   183600
gtttgtcttc ctcttgttta cgacgtgatc taaaccagtc cttagcaagg ggctcagaac   183660
accccgctct ggcagtaggt gtcccccacc cccaaagacc tgcctgtgtg ctccggagat   183720
gaatatgagc tcattagtaa aaatgacttc acccacgcat atacataaag tatccatgca   183780
tgtgcatata gacacatcta taattttaca cacacacctc tcaagacgga gatgcatggc   183840
ctctaagagt gcccgtgtcg gttcttcctg gaagttgact ttccttagac ccgccaggtc   183900
aagttagccg cgtgacggac atccaggcgt gggacgtggt cagggcaggg ctcattcatt   183960
gcccactagg atcccactgg cgaagatggt ctccatatca gctctctgca gaagggagga   184020
agactttatc atgttcctaa aaatctgtgg caagcaccca tcgtattatc caaatttgt    184080 tgcaaatgtg attaatttgg ttgtcaagtt ttgggggtgg gctgtgggga gattgctttt   184140
gttttcctgc tggtaatatc gggaaagatt ttaatgaaac cagggtagaa ttgtttggca   184200
atgcactgaa gcgtgtttct ttcccaaaat gtgcctccct tccgctgcgg gcccagctga   184260
gtctatgtag gtgatgtttc cagctgccaa gtgctctttg ttactgtcca ccctcatttc   184320
tgccagcgca tgtgtccttt caaggggaaa atgtgaagct gaaccccctc cagacaccca   184380
gaatgtagca tctgagaagg ccctgtgccc taaaggacac cctcgcccc catcttcatg    184440 gagggggtca tttcagagcc ctcggagcca atgaacagct cctcctcttg gagctgagat   184500
gagccccacg tggagctcgg gacggatagt agacagcaat aactcggtgt gtggccgcct   184560
```

-continued

```
ggcaggtgga acttcctccc gttgcggggt ggagtgaggt tagttctgtg tgtctggtgg    184620
gtggagtcag gcttctcttg ctacctgtga gcatccttcc cagcagacat cctcatcggg    184680
ctttgtccct cccccgcttc ctccctctgc ggggaggacc cgggaccaca gctgctggcc    184740
agggtagact tggagctgtc ctccagaggg gtcacgtgta ggagtgagaa gaaggaagat    184800
cttgagagct gctgagggac cttggagagc tcaggatggc tcagacgagg acactcgctt    184860
gccgggcctg ggcctcctgg gaaggaggga gctgctcaga atgccgcatg acaactgaag    184920
gcaacctgga aggttcaggg gccgctcttc ccccatgtgc ctgtcacgct ctggtgcagt    184980
caaaggaacg ccttcccctc agttgtttct aagagcagag tctcccgctg caatctgggt    185040
ggtaactgcc agccttggag gatcgtggcc aacgtggacc tgcctacgga gggtgggctc    185100
tgacccaagt ggggcctcct tgtccaggtc tcactgcttt gcaccgtggt cagagggact    185160
gtcagctgag cttgagctcc cctggagcca gcagggctgt gatgggcgag tcccggagcc    185220
ccacccagac ctgaatgctt ctgagagcaa agggaaggac tgacgagaga tgtatattta    185280
attttttaac tgctgcaaac attgtacatc caaattaaag gaaaaaaatg gaaaccatca    185340
gttgttgctg tgtgaggctt gctttgcttc atgagaacct agaccttgct gagctggagt    185400
cttaggaagc agtctcctaa gtgcttctcc agcaggggca gaaactgtcc caccagctaa    185460
catctggcat tatggagggt cccccaggca gctgccagca gggacaggcc ccgtgttttc    185520
tgtagccagg gatgaggaag tggccccagg gcatgggcct ggctgggtgc ttctgcaagg    185580
gccttcccaa accacagtac aggtggtctt cctgccctgc agatgggagc tgtgggagct    185640
gctggagctg ctggagcctt catggtcaag tgacatcata agcttatatg acatacacaa    185700
gcctcaggac ttggcccatg gcactgaagc aggtcatcag gcccagcaca gagactagag    185760
ctgtgttctc acagggccca ccaccttcc acctccttgg ccattgacac ctgcgtccct     185820
ggcccagctg ctcccaggta accccaaag cagctggcac atcccacctc tggtgtggcc     185880
ggggctgctg tgtgtccgca gggcctgccc cgtctattct agcttgtttg tcctgtctga    185940
accagcgcct actccaagaa gcctctgctc agcccagcgg ggatgcttct aagctccgga    186000
cgagcctctc ggaagccttg tgattggtg tgtagtcat cttgggatgc agatgtctta     186060
ccaacctgca agaacaaaaa ccctgtggct tcctctggtg cagggtattt agtcaatgtt    186120
tgctgaggtc ccgtctggtt ctggctaatt ggcaggggtc gtccacccat tctttccctg    186180
ctctgctgtc tgtgccagga gagacggggg ccagtcggcc aaggggccag ctcctgctgc    186240
ctgctcctct tgggcacgtg cggggcccc ctttctctga gcaggatag ggatcagtct      186300 gccggaggga tgtggtggac aggcctaaag catttggggc ggggcatgcc acttgagctc    186360
cctaaatctg tctcctcata ggtgacaccg ctccagggcc cccagtggc ctctcctttc     186420 agagctacct aaattctggt cacttcagag aaatggagca ccccttctc cctggtccag     186480 gtgtggacag cctggcacac tgagcacacc tggcatggct ggtaatttca gaaagaagag    186540
gggccggggt ccagtgggaa gcagcggtga acccctcgtg agtgggcttt gcagtccctc    186600
cccatgccac ggcagagctg ccctcaacac agccttcctc ttcctcatcg gagagcacac    186660 cctgtccct tgccgagctg tgccctgtgc cttcggtggt atttgatttt ggctgctact     186720
ggctttgttg ggatctggaa gtcgcttccc ctgcgtggtg cgtggagcac tgtaagtcag    186780
atgagggaag tagccagggt gaggtgagta ccgggtggag ccgccactga agggactggg    186840 tagggggggcc ttgcctctac atgatgtgac acagccaacc gaggacagag gaagcccgt    186900 tcctgggggt gtggggtgca cccctcaggg aagcctgcag tggggcctga ggaaaggcat    186960
```

```
cctccgcgag cccacgagtc tggtccatga gcaccgtgac agtgtctgtg ggtagaggtg    187020
gacccggcct tgtgtcatca ccaggacctc ttttgggaaa ccatgtggac atcgcttgcg    187080
ggtcccccag gctctgcagc cccagcagcc tggctgcctt ttgggcaagt ggcttgagcc    187140
acagaggacc cagtcctgtt gcagccacat cctctggggg ggcccgccag tgtggccggc    187200
tttctccacc ctacaccagg cctccaggtg tcctggtcgg gggtgtctgg gccctgggtg    187260
ggccctgtgg acctgtgagg tcagggtcag ggcatcactg gaggcagagg gctgaagttg    187320
tgggtctggg ttcccctttgt gtgcacaggc ccctgccctc catgcttggt caggcagcta    187380
cccccaaaac tgctaggaca ggctggtcct gaggtggatc ctggcccctg taccctctgg    187440
acagcccacc cgcccaacct tctaccctgc cccagcggcg gcagtgttgg ccacatcctt    187500
cccctcctgg ccccaattgc tctggggaag tccaggctcc ggagcctgcc caggggcccc    187560
ccgtgatttg ggcccaggac tccacgtggt tctctgcctt cacccaagcc ctgaactcct    187620
cagctgccaa atccccaccc atctgcacag gctgtgctca ccactgctgc tcctggaagg    187680
tgcccctcag tgggacgccc acctcctctc tgggcttctg tgtttgggag ccctgctgcc    187740
cccacccttg gtcagtcccc atgtcctgct ggcctgtcag gcagggcaga aaatccaccc    187800
agaaatgctg agcaggatga gagtctagtt gggcccagcc tcattattta aaggggatgg    187860
aggcctaggg agcatgcttc tagcctgagc ccagcagggc cccgcccatg tcccaggtct    187920
gcaccaggga cagctcctgc cgaggcctga cctgcccctt ctccctcagg tgctgctggt    187980
tgaccagcct ctggccctag gagacccgt agcgactgag ggtcccagca ggccatgcag    188040 cttttgccaag gtacgagccc ctccccagca ggggacagat gtggggaccc tcccaggcag    188100
gagcagctgg gtgcctggtg ctgccatctg ctgcctgcct ggttcttgtc ctcacattgg    188160
aggtcagtgt gagggctctg cctcgggaaa ggccatggag cttgccctgt ccagggcctc    188220
ccatgtgcac tgagcctggg aagagagggt tggagttgag ccttttaccc tgggaatgct    188280
gcctggagga tggtgcgggt gtggggtggc accctgccag gcagggccct gcctccctgc    188340
gcccactgga actcgggcag gcaggggtgt aggtgcctcc tctagagccg tccggtgggg    188400
gcccccggca gtggtggtgg tgtccactgg ccagcagctg ccccttcagc caggacagta    188460
ggcctgacgc tgtccccagc agctccaagg tggatttgtg gaaggggta gagggcacgt    188520 agaggcccca tgacctcccc agggttctgg gagggctgtg ccccttagc cagcaccatg    188580 ctgggtgata tagtcagatc ctgttacccc tgttgtggag gtgaggaaac aggttagtgg    188640
ggaggacatg actaaggtcc atgctgagtc gctagagctg cacccagaac cactgctggg    188700
accccatgcc tttctgctta cccccttgtgc cgggagatgc caagagatgc tgggagccag    188760
ccccacctct gcccttggag tcatggctac ggaaagggca ttcggaccgg tccctgacct    188820
caccggggag ggccgaaccc tgttcctgag gagccagggc ttcctagagg aggtaggcct    188880
tctagtcact ccttcatctg caggcactcc acagagctct ctgtgccagc cccagcacg    188940 gagggctgac cttagtcgag tggagatgcc ccagtgccag gcagtaggga tgatgtctcc    189000
tgaggcccag atggaaggga ctggactagt ctcatgggc tgatggtggg gccaggcctt    189060 gaccaggac ccagtgtagg gggtgcagag acccctctga gttcctcaca catccctggg    189120
gccctcccca tacacttcct atcctgactg cgggcaagag ggagcccag ttcgccttcc    189180 ctatgctggg cacccacagt ggggctgggc accccgccca tgcccctgcc ctgtccttcc    189240
cctgagagcc tcggtcccac ctccaaggtg cctcagagga cagcagggc agcgggcaga    189300
```

```
ggccgagatg cctcctcatt ccaggctcag ctgcccttct tggggcagcc cacacctgag 189360
agtctcctgc agttggtcag gcctgaggag ggcagggggg tgcctgctgt ccctctgctg 189420
accacagtgg catttagcct gggcaccgcg cccagcacag tccatgctgc acaggtgccg 189480
tgggctccac agagccctgc ctgacatgca tgtgttacgt ttcgggtgcc gatgcccttg 189540
ggcggcactt ctccgggcag aaccccaggc caccgctccg gttccggttc cgctgcatc 189600
tggggctctc ggcaggctgt ggtcctccgg ccagcctggg gcatctcagt cccctcagcc 189660
ccacaggggc ctgccccgca gcctgggcct cgagcccgtc tccgcacgc tgtgccgaat 189720
ctggctgccc atcagctccc tgcgtaccca gactgtgccc tgccatgccc gtggctcttc 189780
ccaggagtgc cctgtggcct cccctggct tgctgggctg attccctcct gtgtctcaaa 189840
cagagctcac ctttgccatc actgctgtcc tcaccggccg gtgccagagg cccgtgtctg 189900
tgtaccctgt gtctgcacct ctgggcaggg cctggctctg accaacccgg gcttccagtg 189960
tccacagacc taaggcccag ggcgcctggg ggctggagca agagaagcaa aaggagccaa 190020
gggtggggt ttggggttct tgtgagggcc cagccccagg accccaggac caggacccc 190080
aggagcccca gggcccagcc ccagttcaga aggcagggc cttctgaggg agcttaaggg 190140
tcccacagcc caggaccccc accagggcca gtggccagcg ttgggggact cagcctcctc 190200
gtcgctcgtc ctctctgttt ctcccacctt ttgcccccct tctccttgcc tgttcccacc 190260
cgaggccccc tcttggcctg cgtgagccgg ggcggcactg aactggggc cgatccgcct 190320
gggcggcggt gagaggcagg gccgggagcc gggccgctgg gtttgggcct ggccgctcg 190380
ccgcaatatt gatgggccgt cagtgcagcc ctgattcctg tgctttcagt taaaaggttt 190440
ctgttgttgt agcttatgca gttgctctgt tgctatggaa acgtgacatc aaaatgacgt 190500
ttcccgttta aaagctttta actaaattcc tgcctgtcag atgtaggccc cattttgagc 190560
gtggagctgc cttcgagcga gcgtgagcgg cgcctcccgc ccatggtgcg tggggccggg 190620
ccggggccct cgctgagcgc gctctctcac cccacaggcg cctccggcat ggcggcggcc 190680
gaggggcccg gctacctcgt gtctccccag gcggagaagc accggcgggc ccgcaactgg 190740
acggacgccg agatgcgcgg cctcatgctg gtctgggagg agttcttcga cgagctcaag 190800
cagaccaagc gcaacgccaa ggtgtacgag aagatggcca gcaagctctt cgagatgacc 190860
ggcgagcgca ggctgggcga ggagatcaag atcaagatca ccaacatgac cttccagtac 190920
aggtgggcga gcgggcagtg tgggccccac caggacgggc gggcccgggc gtggcgggcc 190980
gctcctgact tcttggagc tctgagtcgg acgatgtgt gggtcgtggc ctgcctgtcg 191040
gtctcctctg gccgggtatg ggcagaaccc cacggggtga cgggcccc acggaaaccg 191100
tgtgtgcagc cttccattgg ggaagtgggg aaactgaggc ccagcaaggg caggaaacca 191160
gtctaagagc tgaggggtag caggggtggg gctggtgctg ggcagaggcc aggatggctc 191220
ccaggacgta tgggcggtct gggcactgtc cctcggaggc agcaacactc atggtggtgc 191280
ccactgacct cacaccctgc tcccccatag ggaggcggcg gctgccagtg ccctccccac 191340
caccaagctc ccaagctcag caggggtttc aggggcctac tgcgtcattg gggaaattga 191400
gactgcaagt gagaaggagg ctcagtgctc tgcgacttgg agcatccact gagcctctgc 191460
catgagccgg tgagccccac tggggctggc cctagggtca cggtggggta tttccagaaa 191520
tcaccaggtg aggtgcagga ccagccagcg catgggtggg gcttacggtg cgaagaagaa 191580
agaggtggag gcctgccctg gcccaggact cccagcgtgg gggctcccgg cctgccccca 191640
cctctgctcc tgctacatgg caggtgggcc cttcctgccc tggcaacctg cagggaaggc 191700
```

```
cggaggggac cacccagcca gggagatgtt ggcgtctagg aggggacagg tgtggtccca   191760
cacacccagc atcttaaagt gcgtgggtcc ccagcccatt aggacagggt cccgggtggg   191820
caggggtcat ggtggggtga aggtctcagg cacaggcaag gtcacaggtg cggtgagggt   191880
cttgcagggt gtgaaggtca taggtgtgcg gtgaaggtca caggtgtggg gtgatggttt   191940
tgggtgtggg gagggtcttg cacggagcga gggtggcagc aagagctgga agctgcaggg   192000
ggagaatggc agcagagagc acccggccct gtgggcggcc tggacagggc tgggcctggg   192060
gctgccggag agcctgtcag cttccaggat gggagtggcc tcactcagct gctccacctc   192120
cgggtcaggc aggtgagcct ggggcagaga ggctgagagc acctgagcca cttgtgggag   192180
aggccacccc cactgccccc ctcaggcgag gagccggcct ccagcacagc agaagggaac   192240
ccccagtccc cagccctagt gggagtgggg aagaggccca gcaaggcccc ggacagaccg   192300
ccagcctgtg aggtctccgc tttcagttgc gttgatttga ttttttctga gccttgaagg   192360
aggggtccgg ggcctggccc tgcccaaagg cccctaggca ggcccaaagg ccgggaccta   192420
gggtgctgag catgacggat gttgggtttg agcggctggc ttgcgacgtg agggctgagg   192480
tgtgagcctg ggtatcttca gaggttcggt ggacacaggc agctgcccgc ggccccactg   192540
ttcccgtggc ctcctagtcc tgctcaggca cctggtgagg aagggacgca gagggcagtg   192600
ggaggtggcc acgactgttc cagcaggctc ccctctgact caggaattca cgggcaccac   192660
ctccctggct ggctctggtt ggtgtctggc caggttattc attatttatg ctgaaagcct   192720
cttcagagtc ccaggggagg gtttctgtct ccattcctgg aggctgagag atgagggtgc   192780
agcagagtgg gggcctccac tccagaccct gcagtctggg ctggccaagg gctgcaccgg   192840
tgcactgcac gtcatggctg atgaagcact tccacaccgc agcccctcag agctgccaca   192900
gtcagcctta gttcaccgag ggggaagctg aggcccagag catgagaggg acttgcccag   192960
ggccacatag tccttagcag aggaagctgt ggctgggtga ctcgatcttt gtccttttc   193020 tttatacccg cagtctcccc atagcagagg cttttctttt ttttttcttt ttctttttttt   193080 tttttttaca agaactcttt atatattaag gctgttgggc tgaagaagcc tgagagggtg   193140
gctggttctg tggagcatgg tttgttgaag tacagtttgg gggcctccta cactgagaat   193200
aggccttttc tcgtttctcc aaagagtggg ctggctcaag tagggcagag agagaagcct   193260
ggggcagagg ttagggatgg gcacccagcg cctgccctca cacgctctgt gctggtgtct   193320
tcacagccac gtgccaccct gggcagcatc ccctgctcac catctggctg tgcctgtttg   193380
ctgggggcac ctcattcaga atccagctta ttgtttccaa cggccaatgg ccacaccctg   193440
gcaggtagca agagtaggag agaggagaca cccactccga gcacaggttg ggtttggagc   193500
ccggccttgg ggcactctgt cactcaaagg cagagtgggg agtgggcact gggccttagg   193560
aggtactggg tccagtgagg cagagatgcc cctgccccac ccccaccttg tggcttcttc   193620
cctggcctgg ccagagctgt ctggccgcca tgggccctg tgtctcctgc cttgacctcc   193680
cagagggcag ccgaggccca gggaggcct ggggacttag cctctcaggg caggacctgt   193740
ctgcaggagt aggtgggtgc tgggggtccc agtggtaatg aggcatcagg cagtgtggga   193800
aggggcccat ccggcccacc ccagggcctc tgggcaggtt gcaggttgta gcgctggatc   193860
taggctcctg cccagactgt aggttcaacc aagaatggca tgggagccca gcctgctgtt   193920
tgctttatta aatctgccct gtagctgggg gagggcttta ctttgatcat cactatgtca   193980
ttgatataaa aatagaggct cagagaggtg aatgaacctg cccaaagtca cacagcaaag   194040
```

```
tgtggagatg agatactgac tcagggctgt ggacactgaa gcctgtgctc taacgccagt    194100
ggctgtcgct ccctgaggca ttctctcccg aacaacacag ttattatatt acaaaatatt    194160
atcactatat ttatatatct tataatacct tattattaca ataaaacctt attactctac    194220
ctttcaaaat gaattattta aaagcagta tttgctcatt gcagagagtc tagaaactat     194280
agaaaagcaa gggaaaagca ataggaccag ccccaaggtc ccagcatgca cagataacct    194340
tagtaatact gggacgtgtg cttccttttt aacatctgag cccgtgtagg tcctgaagcc    194400
cagcttcttt ctaagtccat tgtcatcttg accctggagc ctggccgatt tgctgggga    194460 ggcccttgcc agccgagagc ggctcctgcc tgtgccggcg tggcgcgccc ctctgctgag    194520
gctgggcagg acaggggctg ggccagctct gttt ctcacc cttggctctt gtgtctctcg    194580

ттт caggaaa ttaaaatgca tgacagatag cgagtccgcc ccgcccgact ggccctatta    194640
cctagccatt gatgggattc tggccaaggt ccccgagtcc tgtgatggca aactgccgga    194700
cagccagccg ccggggccct ccacgtccca gaccgaggcg tcctgtcgc cgcccgctaa    194760 gtccacccct ctgtacttcc cgtataacca gtgctcctac gaaggccgct tcgaggatga    194820

tcgctccgac agctcctcca gcttactgtc ccttaagttc aggtagtgtg tctgcttgtc    194880 cttccctgc cctggggtat tcagccccc accaттттaga gaaagggact gggagtggca    194940
aggccggcgg cggcggccac agtggttgca gaggccgtgg ctgcgggcag cgcctccagg    195000
gacaggcggc ctcagaccag ggagggcttt agtgtccaca ggcagaccga gtttgtctcc    195060
cagctccatc acttttgagc tgcacggaaa gttccttgac ttctctggcc tcagtctccc    195120

tcctataaaa tgggggtaaa tcagtacctt tctcagaggg tggctgggag catcacagga    195180
gagaagacgc agcatgggc ccggcacacg gagggagacc aagccccaga ccccagaatg    195240 cgcccctgg ccтccстттag cccacacaga ccccaccctc acaggctagc tgccctctca    195300
gcactgggga gggtgtcggg ctgcacctca tcacgtgttg ccgtgggcat gacccgtccc    195360
ctctgccatc catcccacac ctcagacccg tcctgtctg ccacgtgac tgtgcctgca    195420 agatgctcac agggcagccg ggagccaggc agcatgcagg acagacacct gcggggtggg    195480 ccтgggggagc ccagagaagg тgcттттттgag gaggggacat ttggggtggg ctttcaaggt    195540
aaaatagaag ttggccattt ggaggcaaga acaggaagat tgtggatttg agtcacagct    195600

tctcccctgc cctggtcttc aagтcттттcт gacaggaggt gtcagaaaag tatctttagt    195660
agagaaggcg tctccgagga gggtccctct catgccgggg gccgctgctt gactcaggat    195720

ttctcattga agacctgaga caaaaacgct tttgctggca gctagaagga accagcagga    195780
ggcctgagat ttgtggctgt tgttcccgtg gactgagccc agttctcaga ctcagctgcc    195840

tggggccttg cacaggactg gggcgtgggg gctgccctcc ctgatcaggc ccaaagcgcg    195900
gatctcacgc ccctgaggtt ggctgtaccc tctcagctca gagcagagtg tgggccaggg    195960
atgagcaggc actggagcag ggccctgggt tctgtgggtt ttggcagctc ctgccccttc    196020
agggaggtct gctgagacca cggggтggccc ctaccccagc agcagagctc tcaggaggcg    196080
cccacagggc tggactgcct ttactcacca cctctaccag agctctgagg tcctggggag    196140
agagcccagg cctcttgtgg gccccacacc ctctaggtgc ctgtccttct gcctctctac    196200
caaggtgtgc cggccccatt tctaggccgc cgggagataa ggggctcac atctcaggcc    196260 ctcctcctg ggactcagt ttccccatct gcctaaggcc gggtggggct ggtggtcttg    196320
gcttccctac aggggtcctg agtactctgc actacccagc accccccacc cctgccttca    196380

tctctccctg ggggtggtct ctccacccct ggcccccaac tggggctgag cccccacctg    196440
```

```
cccagtttgg tgggtgaagg gtgctccctg gcaggatatg cccctctgca gcccagaaca  196500
tcccaccctt tccagaccga aggggtgtgg attgtcctgg gaccctggtc attggggtca  196560
tccgctagtc gcaaaggacg gcaatgcctg tggcctctct ttctttcttt ttcttttttt  196620
ttttttttga gacggagtct cgctcttgtg cagagagcag tggcgcgatc ttggctcact  196680
gcaacctccg cctcgtgggt tcaagcgatt ctcctgcctc agcctcccga gtagctggga  196740
ttacaggcac cgccacaac gcctggctaa tttttgtatt tttagtagag atggggtttc  196800
accatgttgg ccaggctggt cttgaactcc tgacctcagg tgatccacct gcctctgcct  196860
cccaaagtgc tgggattaca ggcataagcc tccacacccg gccacccctg ttactttctg  196920
tcaaaggcgg tgggttctgg cccctccttt gcacatggaa tatgagaccc tgagtaagtg  196980
acctgactcc ctggggcctc agtttcccca tttgcccagt aggattgtcg ggagggtccg  197040
gtgaggcccc tggtgtgccc aggctctgtg gccagcacgt ccacagccgg cactgtcctt  197100
ccaggtcgga ggagcggccg gtgaagaagc gcaaggtgca gagctgccac ctgcagaaga  197160
agcagctgcg gctgctggag gccatggtgg aggagcagcg ccggctgagc cgcgccgtgg  197220
aggagacctg ccgcgaggtg cgccgcgtgc tggaccagca gcacatcctg caggtgcaga  197280
gcctgcagct gcaggagcgc atgatgagtc tgctggagag gatcatcacc aagtccagcg  197340
tctaggccag caggcggcgg cggcggcggg gccgggcggc tggtggtact gctcaggcca  197400
cccagggcag gccactcagg ccaggcgggc aaggggccg ccccgcgagc ggagaccgcc  197460
ttccacctgg cctctggcag gatgtccctt ctgaggggta ttttgaggaa ccccaggcc  197520 ctggggaccg tgaggctcca gtctccagca tgaatgccct tcctcggaca caggccaggg  197580
cctctggggt tcactccgag taagaacgtc ctagagccac tctccagtgt cgttactatc  197640
aatgatactt gacgtggctt tgatattaaa cgtatacttt ttcattcttg cctggaacgc  197700
acagtttgct gttgctggct tggtgaggat gccctgattg atggatcccg aaaatgaaag  197760
cagatggaaa cgggttgggg caggctggag ctggggagc tctctcctga agggaaccct  197820
gtgtcctccc tcaccaggac ctctgcgtct ctccttaaat ggcctctgac gcctgatgaa  197880
aaccccagcg accttccagg aggcttttat tcagctctgt ttggagcatc aggtgtttcc  197940
actgcctcct tagcaatgac actaataaaa gtcgtaacac ctgttcacat gcacagccct  198000
gttgagtgtt ctgggtgctg gagatatcat ggtggatgac acaaaggccc tggcctcttg  198060
gagcttatgc tcccatgcgg ggaagacaca tgggtcagta gagaaatggt tgcaggttgt  198120
gataagtgct ggaagggagg ggttggcctg aggacacgga ggcagacata cgtggagctg  198180
ggaacagtgg ccacacaggg aacggccagt gcgaaggccc agaggcagag gacactggag  198240
caagcccagc agcagctagg aggctggtgg ccagcagcca ggcacggaa gcccgtgcag  198300 cccgtgggga ggagtgttca tgcttttcaa gcttagtggg agtcttttgg ccagtgcagc  198360
tctgggtctg acatcggtgg gggacagagg ggtggtggag cggccacagc tgcaagctca  198420
cctcactgcc ggcccttcca ccagtttcaa actctttcta gaagctccag ctttcccaaa  198480
gctgaattct ctatgagcct ccttggccgg gactcgggcg tctggttgcc ctggctgcaa  198540
aggaggctgg ggccaggtgt gtttgagtca cctcctggaa ttaggcaagt tgctgcccaa  198600
atagaaggtt gttggcaggt gggtcagcag gtgaacagca tggtttgact cagggttcag  198660
aaaaatctcc ctctgctgc caagcgagca ggccgtggag acaggtgcag aggcaggtgt  198720
ggcagcaggc atcctgccag gcagtgctgc agtcatcctg cgacaagcag cagcagctca  198780
```

```
tcctaccctc tagggggtct tgaggtcagc caggcaagag agcagcttgg actccactgg    198840
gtgtgggacc agcctgtgga ccatggtggt gtggagggtg ccctcggcct gcctgtgtga    198900
aggagaggcc ggcgtgttct gtggagccca aaggggagct gggcaagcag gattcacttc    198960
actctgaggg tcctggagct cccaccctcc tcagccatct ccccagagcc tgtgtgccga    199020
ggactcggcc catgttgctg tgggatgaga ggcagagtgt cgtgagggtg taaggagcgg    199080
cggcagtggt gggaggaggg agcagcagcc agcgctacgg tgccagtttc cagctgccag    199140
atgacgccgc tgaccctgtg gttgagaaga gatgcacaga gccagctctt gcaagccagt    199200
gtggctgcca tagcacctgc cgagaagcag aaggaagggt ggcccagga ggacagagga     199260
tgcgggcaca tctgatgcgg gcctgagttt tgggagcttt tgctctagcc agtttccagc    199320
tccgggaccc acccgcctcg taggcaagac accacccaag aaatcatttg cttaacaaac    199380
acactgggct ccaactggac acctgtgcca ccctagatgc tgggaaccca gccatgacac    199440
aggcacctgc ccccagctgc tgaccactga ggctggctag cagctcccat ggggccagtg    199500
tggggttccc cagcctccta acaggagcc agtcacaagc cctcgagagg aagggtgcc     199560
cgcggccctg gcaggaaggt taggctggac gctcccacaa gacataacag atggaggttc    199620
taaatgatgt agcaacttct tcaccctgaa actgctgtag agtcagccat gacgcaccgg    199680
tacttcagta actgccaggc atccgggaca gcacaccgcg agtcgctgct gtgcttgggt    199740
tagaagtggt ttggtctgtt ttcttctcgc cctctctaat cagagtcagt gattcatgcc    199800
cttccatcac cttagagaag gggcaggcgc tgcccgacct tctccaggct ggagcagcat    199860
cgcctcatgt cagcagaact cagctgtaga atatcgtggg gttggtgcct ttcatcagca    199920
gcatgtcctt aacaactttc tgatttcttc cttagttgtt ggtccattaa ggagaaaaaa    199980
aatgatctca gccattgcta aaatatttga taagattcag caaagcagca tgttaacatt    200040
gaaaactaga atcaggagcc aggcagatgt gcttgctttt cacctgtagt atttcatgtt    200100
gttttgacgt ttttagctaa tgcattaaga taaataaaca aaagccgggc acggtggttc    200160
acgcctgtaa tcccagcact ttgggaggct gaggcgggag gatcctctga ggtcaggagt    200220
tcaagaccag cctgaccaac atggagaaac ctcgtcatta ctaaaaatac aaaattagct    200280
gggcgtggtg gtgcatgcct gtaatcccag ctacttggga ggctgaggca ggagaatcgc    200340
ttgaacccgg gaggcggagg ttgcagtgag ctgagattgc accactgcac tccagcctgg    200400
gtgacagtga aactcggtct caaaaaaaaa aaaaaattaa aaaagataa ataaaataag     200460
caggataaga aatgaagaaa gtagagttac ctttgttttc agatttcatt tttgtatacc    200520
cagaaagcca aatgtacaaa agactgggag ctctttaaac cagcttaaac ttgttgaaaa    200580
tgaggatgaa gaaatatccc attcagagtt ggaatgaatt taacccagaa ggaacaggac    200640
ctctactgaa gagaactatg cagtcttact gaaaaatcta ataatacct gagcgctgga     200700
gaaacttcgc acactcctga aagctccaaa gtcaatgtca tcattttatt aatgtcattc    200760
caaacatagt ctcaataata tcacttcttg gttttgacat ggacgcgatg atgtttaaat    200820
tcatatgaaa aaagaacggg gccaaaagtc caaggccagt cagcgtgaga agaccgctcg    200880
gcctccctcg gagtcgggga gttggaaccg cagactgaga tcatgtggct gctgaggcc     200940
aggacgaacg tcgggaaatg gagactcctg cgttgctggt gggatgtggt gcagccgctt    201000
ccaggagcaa tttggtgtcc cgtcctaaag ctgaagaaac gcatttcctc tggtcagtgc    201060
cactcctaga caggccaccc tgcggcagcc gtcctcaaac tggtctgagg accctcaac     201120
gctcttaaaa atcattaaaa gtgggccagg tgcggtggct cacacctgta atcccagcac    201180
```

-continued

```
tttgggaggc caagacaggc ggatcacgag gtcaggacat tgagatcatc ctggctaaca  201240
cggtgaaacc ccgtctctac taaaaataca aaaaattagc cgggcgtggt ggcgggcgcc  201300
tgtagtccca gctacttggg aggctgagcc aggagaatgg cgtgaaccca ggaggtggag  201360
cttgcagtga gctgagatca ctccactgca ctccagcctg gcagcagag cgagactctg  201420
tctcaaaaaa aaataataaa taaataaata aaataaaat aaaataaat tcattaaaag  201480
tgccaaagaa cttttgctta tgtgagttct aatgaccaat attaatacac attagaatat  201540
cttattagaa attaaacctg agacctttag aaaacatgta ttcatttcaa aatagcaata  201600
aacccatgac atattaacat aaataacaat tgtatgaaaa atatattttc caaaacaaaa  201660
agttttcggg agaagtgtgg catagtttta catggtcgta aatctctggc ttaagagaag  201720
cccactgggc tctcagcagg ctctgggtcc gtccactttg ggggtgtttt ggttgtgaag  201780
tataggagtg aatggagaag ctcattctta cccagatgtg tatttgaaaa gaaaaggaac  201840
atttttaataa cctttgcaaa taatcggtat attcttccgt gatcctattc caacactgga  201900
caggtggtgg tttgttttt ttttttggag acggagtccc gctctgtcac tcaggctgga  201960
gtgcagtggc gcgatttcag ctcactgcaa gctccgcctc c                      202001

<210> SEQ ID NO 2
<211> LENGTH: 13481
<212> TYPE: DNA
<213> ORGANISM: H. sapiens

<400> SEQUENCE: 2
gctgccggga cgggtccaag atggacggcc gctcaggttc tgcttttacc tgcggcccag    60
agccccattc attgccccgg tgctgagcgg cgccgcgagt cggcccgagg cctccgggga   120
ctgccgtgcc gggcgggaga ccgccatggc gaccctggaa aagctgatga aggccttcga   180
gtccctcaag tccttccagc agcagcagca gcagcagcag cagcagcagc agcagcagca   240
gcagcagcag cagcagcagc aacagccgcc accgccgccg ccgccgccgc cgcctcctca   300
gcttcctcag ccgccgccgc aggcacagcc gctgctgcct cagccgcagc cgccccgcc   360
gccgcccccg ccgccacccg gcccggctgt ggctgaggag ccgctgcacc gaccaaagaa   420
agaactttca gctaccaaga agaccgtgt gaatcattgt ctgacaatat gtgaaaacat   480
agtggcacag tctgtcagaa attctccaga atttcagaaa cttctgggca tcgctatgga   540
acttttttctg ctgtgcagtg atgacgcaga gtcagatgtc aggatggtgg ctgacgaatg   600
cctcaacaaa gttatcaaag ctttgatgga ttctaatctt ccaaggttac agctcgagct   660
ctataaggaa attaaaaaga atggtgcccc tcggagtttg cgtgctgccc tgtggaggtt   720
tgctgagctg gctcacctgg ttcggcctca gaaatgcagg ccttacctgg tgaaccttct   780
gccgtgcctg actcgaacaa gcaagagacc cgaagaatca gtccaggaga ccttggctgc   840
agctgttccc aaaattatgg cttcttttgg caattttgca aatgacaatg aaattaaggt   900
tttgttaaag gccttcatag cgaacctgaa gtcaagctcc ccaccattc ggcggacagc   960
ggctggatca gcagtgagca tctgccagca ctcaagaagg acacaatatt tctatagttg  1020
gctactaaat gtgctcttag gcttactcgt tcctgtcgag gatgaacact ccactctgct  1080
gattcttggc gtgctgctca ccctgaggta tttggtgccc ttgctgcagc agcaggtcaa  1140
ggacacaagc ctgaaaggca gcttcggagt gacaaggaaa gaaatggaag tctctccttc  1200
tgcagagcag cttgtccagg tttatgaact gacgttacat catacacagc accaagacca  1260
```

```
caatgttgtg accggagccc tgagctgtt gcagcagctc ttcagaacgc ctccacccga    1320
gcttctgcaa accctgaccg cagtcggggg cattgggcag ctcaccgctg ctaaggagga    1380
gtctggtggc cgaagccgta gtgggagtat tgtggaactt atagctggag ggggttcctc    1440
atgcagccct gtcctttcaa gaaaacaaaa aggcaaagtg ctcttaggag aagaagaagc    1500
cttggaggat gactctgaat cgagatcgga tgtcagcagc tctgccttaa cagcctcagt    1560
gaaggatgag atcagtggag agctggctgc ttcttcaggg gtttccactc cagggtcagc    1620
aggtcatgac atcatcacag aacagccacg gtcacagcac acactgcagg cggactcagt    1680
ggatctggcc agctgtgact tgacaagctc tgccactgat ggggatgagg aggatatctt    1740
gagccacagc tccagccagg tcagcgccgt cccatctgac cctgccatgg acctgaatga    1800
tgggacccag gcctcgtcgc ccatcagcga cagctcccag accaccaccg aagggcctga    1860
ttcagctgtt acccttcag acagttctga aattgtgtta gacggtaccg acaaccagta    1920
tttgggcctg cagattggac agccccagga tgaagatgag gaagcacag gtattcttcc    1980
tgatgaagcc tcggaggcct tcaggaactc ttccatggcc cttcaacagg cacatttatt    2040
gaaaaacatg agtcactgca ggcagccttc tgacagcagt gttgataaat ttgtgttgag    2100
agatgaagct actgaaccgg gtgatcaaga aaacaagcct tgccgcatca aggtgacat    2160
tggacagtcc actgatgatg actctgcacc tcttgtccat tgtgtccgcc ttttatctgc    2220
ttcgtttttg ctaacagggg gaaaaatgt gctggttccg gacagggatg tgagggtcag    2280
cgtgaaggcc ctggccctca gctgtgtggg agcagctgtg gccctccacc cggaatcttt    2340
cttcagcaaa ctctataaag ttcctcttga caccacggaa tacctgagg aacagtatgt    2400
ctcagacatc ttgaactaca tcgatcatgg agacccacag gttcgaggag ccactgccat    2460
tctctgtggg accctcatct gctccatcct cagcaggtcc cgcttccacg tgggagattg    2520
gatgggcacc attagaaccc tcacaggaaa tacattttct ttggcggatt gcattccttt    2580
gctgcggaaa acactgaagg atgagtcttc tgttacttgc aagttagctt gtacagctgt    2640
gaggaactgt gtcatgagtc tctgcagcag cagctacagt gagttaggac tgcagctgat    2700
catcgatgtg ctgactctga ggaacagttc ctattggctg gtgaggacag agcttctgga    2760
aacccttgca gagattgact tcaggctggt gagcttttgg aggcaaaag cagaaaactt    2820
acacagaggg gctcatcatt atacagggct tttaaaactg caagaacgag tgctcaataa    2880
tgttgtcatc catttgcttg gagatgaaga ccccagggtg cgacatgttg ccgcagcatc    2940
actaattagg cttgtcccaa agctgttta taaatgtgac caaggacaag ctgatccagt    3000
agtggccgtg gcaagagatc aaagcagtgt ttacctgaaa cttctcatgc atgagacgca    3060
gcctccatct catttctccg tcagcacaat aaccagaata tatagaggct ataacctact    3120
accaagcata acagacgtca ctatggaaaa taaccttttca agagttattg cagcagtttc    3180
tcatgaacta atcacatcaa ccaccagagc actcacattt ggatgctgtg aagctttgtg    3240
tcttctttcc actgccttcc cagtttgcat ttggagttta ggttggcact gtggagtgcc    3300
tccactgagt gcctcagatg agtctaggaa gagctgtacc gttgggatgg ccacaatgat    3360
tctgaccctg ctccgtcag cttggttccc attggatctc tcagcccatc aagatgcttt    3420
gattttggcc ggaaacttgc ttgcagccag tgctcccaaa tctctgagaa gttcatgggc    3480
ctctgaagaa gaagccaacc cagcagccac caagcaagag gaggtctggc agccctggg    3540
ggaccggggc ctggtgccca tggtggagca gctcttctct cacctgctga aggtgattaa    3600
catttgtgcc cacgtcctgg atgacgtggc tcctggaccc gcaataaagg cagccttgcc    3660
```

-continued

```
ttctctaaca aacccccctt ctctaagtcc catccgacga aaggggaagg agaaagaacc    3720
aggagaacaa gcatctgtac cgttgagtcc caagaaaggc agtgaggcca gtgcagcttc    3780
tagacaatct gatacctcag gtcctgttac aacaagtaaa tcctcatcac tggggagttt    3840
ctatcatctt ccttcatacc tcaaactgca tgatgtcctg aaagctacac acgctaacta    3900
caaggtcacg ctggatcttc agaacagcac ggaaaagttt ggagggtttc tccgctcagc    3960 cttgatgtt  ctttctcaga tactagagct ggccacactg caggacattg ggaagtgtgt    4020
tgaagagatc ctaggatacc tgaaatcctg ctttagtcga gaaccaatga tggcaactgt    4080
ttgtgttcaa caattgttga agactctctt tggcacaaac ttggcctccc agtttgatgg    4140
cttatcttcc aaccccagca agtcacaagg ccgagcacag cgccttggct cctccagtgt    4200
gaggccaggc ttgtaccact actgcttcat ggccccgtac acccacttca cccaggccct    4260
cgctgacgcc agcctgagga acatggtgca ggcggagcag gagaacgaca cctcgggatg    4320
gtttgatgtc ctccagaaag tgtctaccca gttgaagaca aacctcacga gtgtcacaaa    4380
gaaccgtgca gataagaatg ctattcataa tcacattcgt ttgtttgaac ctcttgttat    4440
aaaagcttta aaacagtaca cgactacaac atgtgtgcag ttacagaagc aggttttaga    4500
tttgctggcg cagctggttc agttacgggt taattactgt cttctggatt cagatcaggt    4560
gtttattggc tttgtattga acagtttga  atacattgaa gtgggccagt tcagggaatc    4620
agaggcaatc attccaaaca tcttttttctt cttggtatta ctatcttatg aacgctatca    4680
ttcaaaacag atcattggaa ttcctaaaat cattcagctc tgtgatggca tcatggccag    4740
tggaaggaag gctgtgacac atgccatacc ggctctgcag cccatagtcc acgacctctt    4800
tgtattaaga ggaacaaata aagctgatgc aggaaaagag cttgaaaccc aaaaagaggt    4860
ggtggtgtca atgttactga gactcatcca gtaccatcag gtgttggaga tgttcattct    4920
tgtcctgcag cagtgccaca aggagaatga agacaagtgg aagcgactgt ctcgacagat    4980
agctgacatc atcctcccaa tgttagccaa acagcagatg cacattgact ctcatgaagc    5040
ccttggagtg ttaaatacat tatttgagat tttggcccct tcctccctcc gtccggtaga    5100
catgctttta cggagtatgt tcgtcactcc aaacacaatg gcgtccgtga gcactgttca    5160
actgtggata tcgggaattc tggccatttt gagggttctg atttcccagt caactgaaga    5220
tattgttctt tctcgtattc aggagctctc cttctctccg tatttaatct cctgtacagt    5280
aattaatagg ttaagagatg gggacagtac ttcaacgcta gaagaacaca gtgaagggaa    5340
acaaataaag aatttgccag aagaaacatt ttcaaggttt ctattacaac tggttggtat    5400
tcttttagaa gacattgtta caaaacagct gaaggtggaa atgagtgagc agcaacatac    5460
tttctattgc caggaactag gcacactgct aatgtgtctg atccacatct tcaagtctgg    5520
aatgttccgg agaatcacag cagctgccac taggctgttc cgcagtgatg gctgtggcgg    5580
cagtttctac accctggaca gcttgaactt gcgggctcgt tccatgatca ccacccaccc    5640
ggccctggtg ctgctctggt gtcagatact gctgcttgtc aaccacaccg actaccgctg    5700
gtgggcagaa gtgcagcaga ccccgaaaag acacagtctg tccagcacaa agttacttag    5760
tccccagatg tctggagaag aggaggattc tgacttggca gccaaacttg gaatgtgcaa    5820
tagagaaata gtacgaagag gggctctcat tctcttctgt gattatgtct gtcagaacct    5880
ccatgactcc gagcacttaa cgtggctcat tgtaaatcac attcaagatc tgatcagcct    5940
ttcccacgag cctccagtac aggacttcat cagtgccgtt catcggaact ctgctgccag    6000
```

```
cggcctgttc atccaggcaa ttcagtctcg ttgtgaaaac ctttcaactc caaccatgct   6060
gaagaaaact cttcagtgct tggaggggat ccatctcagc cagtcgggag ctgtgctcac   6120
gctgtatgtg gacaggcttc tgtgcacccc tttccgtgtg ctggctcgca tggtcgacat   6180
ccttgcttgt cgccgggtag aaatgcttct ggctgcaaat ttacagagca gcatggccca   6240
gttgccaatg gaagaactca acagaatcca ggaataccgtt cagagcagcg ggctcgctca   6300
gagacaccaa aggctctatt ccctgctgga caggtttcgt ctctccacca tgcaagactc   6360
acttagtccc tctcctccag tctcttccca cccgctggac ggggatgggc acgtgtcact   6420
ggaaacagtg agtccggaca aagactggta cgttcatctt gtcaaatccc agtgttggac   6480
caggtcagat tctgcactgc tggaaggtgc agagctggtg aatcggattc ctgctgaaga   6540
tatgaatgcc ttcatgatga actcggagtt caacctaagc ctgctagctc catgcttaag   6600
cctagggatg agtgaaattt ctggtggcca gaagagtgcc cttttgaag cagcccgtga    6660 ggtgactctg gcccgtgtga gcggcaccgt gcagcagctc cctgctgtcc atcatgtctt   6720
ccagcccgag ctgcctgcag agccggcggc ctactgagc aagttgaatg atctgtttgg    6780
ggatgctgca ctgtatcagt ccctgcccac tctggcccgg gccctggcac agtacctggt   6840
ggtggtctcc aaactgccca gtcatttgca ccttcctcct gagaaagaga aggacattgt   6900
gaaattcgtg gtggcaaccc ttgaggccct gtcctggcat ttgatccatg agcagatccc   6960
gctgagtctg gatctccagg cagggctgga ctgctgctgc ctggccctgc agctgcctgg   7020
cctctggagc gtggtctcct ccacagagtt tgtgacccac gcctgctccc tcatctactg   7080
tgtgcacttc atcctggagg ccgttgcagt gcagcctgga gagcagcttc ttagtccaga   7140
aagaaggaca ataccccaa aagccatcag cgaggaggag gaggaagtag atccaaacac    7200
acagaatcct aagtatatca ctgcagcctg tgagatggtg gcagaaatgg tggagtctct   7260
gcagtcggtg ttggccttgg gtcataaaag gaatagcggc gtgccggcgt ttctcacgcc   7320
attgctaagg aacatcatca tcagcctggc ccgcctgccc cttgtcaaca gctacacacg   7380
tgtgccccca ctggtgtgga agcttggatg gtcacccaaa ccgggagggg attttggcac   7440
agcattccct gagatccccg tggagttcct ccaggaaaag gaagtctta aggagttcat    7500 ctaccgcatc aacacactag gctggaccag tcgtactcag tttgaagaaa cttgggccac   7560
cctccttggt gtcctggtga cgcagcccct cgtgatggag caggaggaga gcccaccaga   7620
agaagacaca gagaggaccc agatcaacgt cctggccgtg caggccatca cctcactggt   7680
gctcagtgca atgactgtgc ctgtggccgg caacccagct gtaagctgct tggagcagca   7740
gccccggaac aagcctctga aagctctcga caccaggttt gggaggaagc tgagcattat   7800
cagagggatt gtggagcaag agattcaagc aatggtttca aagagagaga atattgccac   7860
ccatcattta tatcaggcat gggatcctgt cccttctctg tctccggcta ctacaggtgc   7920
cctcatcagc cacgagaagc tgctgctaca gatcaacccc gagcgggagc tggggagcat   7980
gagctacaaa ctcggccagg tgtccataca ctccgtgtgg ctggggaaca gcatcacacc   8040
cctgagggag gaggaatggg acgaggaaga ggaggaggag gccgacgccc ctgcaccttc   8100
gtcaccaccc acgtctccag tcaactccag gaaacaccgg gctggagttg acatccactc   8160
ctgttcgcag ttttttgcttg agttgtacag ccgctggatc ctgccgtcca gctcagccag   8220
gaggaccccg gccatcctga tcagtgaggt ggtcagatcc cttctagtgg tctcagactt   8280
gttcaccgag cgcaaccagt ttgagctgat gtatgtgacg ctgacagaac tgcgaagggt   8340 gcaccccttca gaagacgaga tcctcgctca gtacctggtg cctgccacct gcaaggcagc   8400
```

```
tgccgtcctt gggatggaca aggccgtggc ggagcctgtc agccgcctgc tggagagcac    8460
gctcaggagc agccacctgc ccagcagggt tggagccctg cacggcgtcc tctatgtgct    8520
ggagtgcgac ctgctggacg acactgccaa gcagctcatc ccggtcatca gcgactatct    8580
cctctccaac ctgaaaggga tcgcccactg cgtgaacatt cacagccagc agcacgtact    8640
ggtcatgtgt gccactgcgt tttacctcat tgagaactat cctctggacg tagggccgga    8700
attttcagca tcaataatac agatgtgtgg ggtgatgctg tctggaagtg aggagtccac    8760
cccctccatc atttaccact gtgccctcag aggcctggag cgcctcctgc tctctgagca    8820
gctctcccgc ctggatgcag aatcgctggt caagctgagt gtggacagag tgaacgtgca    8880
cagcccgcac cgggccatgg cggctctggg cctgatgctc acctgcatgt acacaggaaa    8940
ggagaaagtc agtccgggta gaacttcaga ccctaatcct gcagccccg acagcgagtc     9000 agtgattgtt gctatggagc gggtatctgt tcttttgat aggatcagga aaggctttcc     9060
ttgtgaagcc agagtggtgg ccaggatcct gccccagttt ctagacgact tcttcccacc    9120
ccaggacatc atgaacaaag tcatcggaga gtttctgtcc aaccagcagc catacccca    9180 gttcatggcc accgtggtgt ataaggtgtt tcagactctg cacagcaccg gcagtcgtc    9240 catggtccgg gactgggtca tgctgtccct ctccaacttc acgcagaggg ccccggtcgc    9300
catggccacg tggagcctct cctgcttctt tgtcagcgcg tccaccagcc cgtgggtcgc    9360
ggcgatcctc ccacatgtca tcagcaggat gggcaagctg gagcaggtgg acgtgaacct    9420
tttctgcctg gtcgccacag acttctacag acaccagata gaggaggagc tcgaccgcag    9480
ggccttccag tctgtgcttg aggtggttgc agccccagga agcccatatc accggctgct    9540
gacttgttta cgaaatgtcc acaaggtcac cacctgctga gcgccatggt gggagagact    9600
gtgaggcggc agctggggcc ggagcctttg gaagtctgcg cccttgtgcc ctgcctccac    9660
cgagccagct tggtccctat gggcttccgc acatgccgcg ggcggccagg caacgtgcgt    9720
gtctctgcca tgtggcagaa gtgctctttg tggcagtggc caggcaggga gtgtctgcag    9780
tcctggtggg gctgagcctg aggccttcca gaaagcagga gcagctgtgc tgcaccccat    9840
gtgggtgacc aggtccttc tcctgatagt cacctgctgg ttgttgccag gttgcagctg     9900
ctcttgcatc tgggccagaa gtcctccctc ctgcaggctg gctgttggcc cctctgctgt    9960
cctgcagtag aaggtgccgt gagcaggctt tgggaacact ggcctgggtc tccctggtgg    10020
ggtgtgcatg ccacgccccg tgtctggatg cacagatgcc atggcctgtg ctgggccagt    10080
ggctgggggt gctagacacc cggcaccatt ctcccttctc tcttttcttc tcaggattta    10140
aaatttaatt atatcagtaa agagattaat tttaacgtaa ctctttctat gcccgtgtaa    10200
agtatgtgaa tcgcaaggcc tgtgctgcat gcgacagcgt ccggggtggt ggacagggcc    10260
cccggccacg ctccctctcc tgtagccact ggcatagccc tcctgagcac ccgctgacat    10320
ttccgttgta catgttcctg tttatgcatt cacaaggtga ctgggatgta gagaggcgtt    10380
agtgggcagg tggccacagc aggactgagg acaggccccc attatcctag gggtgcgctc    10440
acctgcagcc cctcctcctc gggcacagac gactgtcgtt ctccacccac cagtcaggga    10500
cagcagcctc cctgtcactc agctgagaag gccagccctc cctggctgtg agcagcctcc    10560
actgtgtcca gagacatggg cctcccactc ctgttccttg ctagccctgg ggtggcgtct    10620
gcctaggagc tggctggcag gtgttgggac ctgctgctcc atggatgcat gcctaagag    10680 tgtcactgag ctgtgttttg tctgagcctc tctcggtcaa cagcaaagct tggtgtcttg    10740
```

```
gcactgttag tgacagagcc cagcatccct tctgccccccg ttccagctga catcttgcac    10800
ggtgacccct tttagtcagg agagtgcaga tctgtgctca tcggagactg ccccacggcc    10860
ctgtcagagc cgccactcct atccccaggc caggtccctg gaccagcctc ctgtttgcag    10920
gcccagagga gccaagtcat taaaatggaa gtggattctg gatggccggg ctgctgctga    10980
tgtaggagct ggatttggga gctctgcttg ccgactggct gtgagacgag cagggggctc    11040
tgcttcctca gccctagagg cgagccaggc aaggttggcg actgtcatgt ggcttggttt    11100
ggtcatgccc gtcgatgttt tgggtattga atgtggtaag tggaggaaat gttggaactc    11160
tgtgcaggtg ctgccttgag accccccaagc ttccacctgt ccctctccta tgtggcagct    11220
ggggagcagc tgagatgtgg acttgtatgc tgcccacata cgtgagggggg agctgaaagg    11280 gagcccctcc tctgagcagc ctctgccagg cctgtatgag cttttcccca ccagctccca    11340
acagaggcct cccccagcca ggaccactc gtcctcgtgg cggggcagca ggagcggtag    11400
aaaggggtcc gatgtttgag gaggccctta agggaagcta ctgaattata acacgtaaga    11460
aaatcaccat tccgtattgg ttgggggctc ctgtttctca tcctagcttt ttcctggaaa    11520
gcccgctaga aggtttggga acgagggaa agttctcaga actgttggct gctccccacc    11580
cgcctcccgc ctccccgca ggttatgtca gcagctctga gacagcagta tcacaggcca    11640
gatgttgttc ctggctagat gtttacattt gtaagaaata acactgtgaa tgtaaaacag    11700
agccattccc ttggaatgca tatcgctggg ctcaacatag agtttgtctt cctcttgttt    11760
acgacgtgat ctaaaccagt ccttagcaag gggctcagaa cacccccgctc tggcagtagg    11820 tgtcccccac ccccaaagac ctgcctgtgt gctccggaga tgaatatgag ctcattagta    11880
aaaatgactt cacccacgca tatacataaa gtatccatgc atgtgcatat agacacatct    11940 ataatttac acacacacct ctcaagacg agatgcatgg cctctaagag tgcccgtgtc    12000
ggttcttcct ggaagttgac tttccttaga cccgccaggt caagttagcc gcgtgacgga    12060
catccaggcg tgggacgtgg tcagggcagg gctcattcat tgcccactag atcccactg    12120 gcgaagatgg tctccatatc agctctctgc agaagggagg aagactttat catgttccta    12180
aaaatctgtg gcaagcaccc atcgtattat ccaaattttg ttgcaaatgt gattaatttg    12240
gttgtcaagt tttgggggtg ggctgtgggg agattgcttt tgttttcctg ctggtaatat    12300
cgggaaagat tttaatgaaa ccagggtaga attgtttggc aatgcactga agcgtgtttc    12360
tttcccaaaa tgtgcctccc ttccgctgcg ggcccagctg agtctatgta ggtgatgttt    12420
ccagctgcca agtgctcttt gttactgtcc accctcattt ctgccagcgc atgtgtcctt    12480
tcaaggggaa aatgtgaagc tgaacccccct ccagacaccc agaatgtagc atctgagaag    12540
gccctgtgcc ctaaaggaca ccccctcgccc ccatcttcat ggagggggtc atttcagagc    12600
cctcggagcc aatgaacagc tcctcctctt ggagctgaga tgagcccccac gtggagctcg    12660 ggacggatag tagacagcaa taactcgtgt tgtggccgcc tggcaggtgg aacttcctcc    12720
cgttgcgggg tggagtgagg ttagttctgt gtgtctggtg ggtggagtca ggcttctctt    12780
gctacctgtg agcatccttc ccagcagaca tcctcatcgg gctttgtccc tccccgctt    12840 cctccctctg cggggaggac ccgggaccac agctgctggc cagggtagac ttggagctgt    12900
cctccagagg ggtcacgtgt aggagtgaga agaaggaaga tcttgagagc tgctgaggga    12960
ccttggagag ctcaggatgg ctcagacgag gacactcgct tgccgggcct gggcctcctg    13020
ggaaggaggg agctgctcag aatgccgcat gacaactgaa ggcaacctgg aaggttcagg    13080
ggccgctctt cccccatgtg cctgtcacgc tctggtgcag tcaaaggaac gccttccct    13140
```

```
cagttgtttc taagagcaga gtctcccgct gcaatctggg tggtaactgc cagccttgga    13200
ggatcgtggc caacgtggac ctgcctacgg agggtgggct ctgacccaag tggggcctcc    13260
ttgtccaggt ctcactgctt tgcaccgtgg tcagagggac tgtcagctga gcttgagctc    13320
ccctggagcc agcagggctg tgatgggcga gtcccggagc ccacccagac ctgaatgct     13380 tctgagagca aagggaagga ctgacgagag atgtatattt aattttttaa ctgctgcaaa    13440
cattgtacat ccaaattaaa ggaaaaaaat ggaaaccatc a                        13481
```

```
<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ctccgtccgg tagacatgct                                                20

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
ggaaatcaga accctcaaaa tgg                                            23

<210> SEQ ID NO 5
<211> LENGTH: 29
<212> TYPE: DNA
<213> ORGANISM: Artificial Sequence
<220> FEATURE:
<223> OTHER INFORMATION: Probe

<400> SEQUENCE: 5
tgagcactgt tcaactgtgg atatcggga                                      29

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
tctctattgc acattccaag                                                20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
gccgtagcct gggacccgcc                                                20

<210> SEQ ID NO 8
<211> LENGTH: 19
<212> TYPE: DNA
<213> ORGANISM: Artificial Sequence
<220> FEATURE:
```

<223> OTHER INFORMATION: Synthetic Oligonucleotide

<400> SEQUENCE: 8
taacactcga ttaaccctg                                                19

<210> SEQ ID NO 9
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 9
taacacttga ttaaccctg                                                19

<210> SEQ ID NO 10
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 10
gttaacactc gattaaccc                                                19

<210> SEQ ID NO 11
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 11
gttaacactt gattaaccc                                                19

<210> SEQ ID NO 12
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 12
gctagttcat cccagtgag                                                19

<210> SEQ ID NO 13
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 13
gctagttcac cccagtgag                                                19

<210> SEQ ID NO 14
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 14
tggaaatggg tttttccac                                                19

```
<210> SEQ ID NO 15
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 15
tggaaatggc tttttccac                                               19

<210> SEQ ID NO 16
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 16
tttaaccgtg gcatgggca                                               19

<210> SEQ ID NO 17
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 17
tttaaccgta gcatgggca                                               19

<210> SEQ ID NO 18
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 18
ttcaagctag taacgatgc                                               19

<210> SEQ ID NO 19
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 19
ttcaagccag taacgatgc                                               19

<210> SEQ ID NO 20
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 20
acttcaagct agtaacgat                                               19

<210> SEQ ID NO 21
<211> LENGTH: 19
<212> TYPE: DNA
<213> ORGANISM: Artificial Sequence
<220> FEATURE:
<223> OTHER INFORMATION: Synthetic Oligonucleotide
```

```
<400> SEQUENCE: 21
acttcaagcc agtaacgat                                              19

<210> SEQ ID NO 22
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 22
gcagctaggt taaagagtc                                              19

<210> SEQ ID NO 23
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 23
gcagctaggc taaagagtc                                              19

<210> SEQ ID NO 24
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 24
aataagaaac acaatcaaa                                              19

<210> SEQ ID NO 25
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 25
aataagaaat acaatcaaa                                              19

<210> SEQ ID NO 26
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 26
cagaggaggc atactgtat                                              19

<210> SEQ ID NO 27
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 27
cagaggaggt atactgtat                                              19

<210> SEQ ID NO 28
<211> LENGTH: 19
```

```
<212> TYPE: DNA
<213> ORGANISM: Artificial Sequence
<220> FEATURE:
<223> OTHER INFORMATION: Synthetic Oligonucleotide

<400> SEQUENCE: 28
cacagtgcta cccaacctt                                              19

<210> SEQ ID NO 29
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 29
cacagtgctc cccaacctt                                              19

<210> SEQ ID NO 30
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 30
taattttcta gactttatg                                              19

<210> SEQ ID NO 31
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 31
taattttctg gactttatg                                              19

<210> SEQ ID NO 32
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 32
gctacaacgc aggtcaaat                                              19

<210> SEQ ID NO 33
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 33
gctacaatgc aggtcaaat                                              19

<210> SEQ ID NO 34
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 34
```
gagctacaac gcaggtcaa                                        19

<210> SEQ ID NO 35
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 35
gagctacaat gcaggtcaa                                        19

<210> SEQ ID NO 36
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 36
agagagaacg agaaggctc                                        19

<210> SEQ ID NO 37
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 37
agagagaaca agaaggctc                                        19

<210> SEQ ID NO 38
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 38
agcccctctg tgtaagttt                                        19

<210> SEQ ID NO 39
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 39
agcccttctg tgtaagttt                                        19

<210> SEQ ID NO 40
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 40
gagcccctct gtgtaagtt                                        19

<210> SEQ ID NO 41
<211> LENGTH: 19
<212> TYPE: DNA
<213> ORGANISM: Artificial Sequence

```
<220> FEATURE:
<223> OTHER INFORMATION: Synthetic Oligonucleotide

<400> SEQUENCE: 41
gagcccttct gtgtaagtt                                                      19

<210> SEQ ID NO 42
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 42
tgagcccctc tgtgtaagt                                                      19

<210> SEQ ID NO 43
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 43
tgagcccttc tgtgtaagt                                                      19

<210> SEQ ID NO 44
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 44
atgagcccct ctgtgtaag                                                      19

<210> SEQ ID NO 45
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 45
atgagccctt ctgtgtaag                                                      19

<210> SEQ ID NO 46
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 46
gatgagcccc tctgtgtaa                                                      19

<210> SEQ ID NO 47
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 47
gatgagccct tctgtgtaa                                                      19
```

```
<210> SEQ ID NO 48
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 48
tgatgagccc ctctgtgta                                                 19

<210> SEQ ID NO 49
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 49
tgatgagccc ttctgtgta                                                 19

<210> SEQ ID NO 50
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 50
atgatgagcc cctctgtgt                                                 19

<210> SEQ ID NO 51
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 51
atgatgagcc cttctgtgt                                                 19

<210> SEQ ID NO 52
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 52
taatgatgag cccctctgt                                                 19

<210> SEQ ID NO 53
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 53
taatgatgag cccttctgt                                                 19

<210> SEQ ID NO 54
<211> LENGTH: 19
<212> TYPE: DNA
<213> ORGANISM: Artificial Sequence
<220> FEATURE:
<223> OTHER INFORMATION: Synthetic Oligonucleotide
```

-continued

<400> SEQUENCE: 54
agaatacggg taacatttt					19

<210> SEQ ID NO 55
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 55
agaatacagg taacatttt					19

<210> SEQ ID NO 56
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 56
ggagaatacg ggtaacatt					19

<210> SEQ ID NO 57
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 57
ggagaataca ggtaacatt					19

<210> SEQ ID NO 58
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 58
ttagtaatca attttaatg					19

<210> SEQ ID NO 59
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 59
ttagtaacca attttaatg					19

<210> SEQ ID NO 60
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 60
agttagtaat caattttaa					19

<210> SEQ ID NO 61

-continued

```
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 61
agttagtaac caattttaa                                                  19

<210> SEQ ID NO 62
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 62
gaaggaatgc ttttactag                                                  19

<210> SEQ ID NO 63
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 63
gaaggaatgt ttttactag                                                  19

<210> SEQ ID NO 64
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 64
ctaaaactaa cttgagaat                                                  19

<210> SEQ ID NO 65
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 65
ctaaaaccaa cttgagaat                                                  19

<210> SEQ ID NO 66
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 66
atctaaaact aacttgaga                                                  19

<210> SEQ ID NO 67
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 67
```
atctaaaacc aacttgaga                                                19

<210> SEQ ID NO 68
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 68
ggtgggcagg aaggactga                                                19

<210> SEQ ID NO 69
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 69
ggtgggcaga aaggactga                                                19

<210> SEQ ID NO 70
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 70
cctaaatcaa tctacaagt                                                19

<210> SEQ ID NO 71
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 71
cctaaattaa tctacaagt                                                19

<210> SEQ ID NO 72
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 72
tccctaaatc aatctacaa                                                19

<210> SEQ ID NO 73
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 73
tccctaaatt aatctacaa                                                19

<210> SEQ ID NO 74
<211> LENGTH: 19
<212> TYPE: DNA

```
<213> ORGANISM: Artificial Sequence
<220> FEATURE:
<223> OTHER INFORMATION: Synthetic Oligonucleotide

<400> SEQUENCE: 74
gaaaatgtga gtggatcta                                               19

<210> SEQ ID NO 75
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 75
gaaaatgtgc gtggatcta                                               19

<210> SEQ ID NO 76
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 76
gtaaggcgag actgactag                                               19

<210> SEQ ID NO 77
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 77
gtaaggcaag actgactag                                               19

<210> SEQ ID NO 78
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 78
aggtaaggcg agactgact                                               19

<210> SEQ ID NO 79
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 79
aggtaaggca agactgact                                               19

<210> SEQ ID NO 80
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 80
ctgagcggag aaaccctcc                                               19
```

<210> SEQ ID NO 81
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 81
ctgagcgaag aaaccctcc                                                19

<210> SEQ ID NO 82
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 82
ggctgagcgg agaaaccct                                                19

<210> SEQ ID NO 83
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 83
ggctgagcga agaaaccct                                                19

<210> SEQ ID NO 84
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 84
aaggctgagc ggagaaacc                                                19

<210> SEQ ID NO 85
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 85
ttccctaaaa acaaaaaca                                                19

<210> SEQ ID NO 86
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 86
ttccctagaa acaaaaaca                                                19

<210> SEQ ID NO 87
<211> LENGTH: 19
<212> TYPE: DNA
<213> ORGANISM: Artificial Sequence
<220> FEATURE:

```
<223> OTHER INFORMATION: Synthetic Oligonucleotide

<400> SEQUENCE: 87
gattccctaa aacaaaaa                                                      19

<210> SEQ ID NO 88
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 88
gattccctag aacaaaaa                                                      19

<210> SEQ ID NO 89
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 89
cttttctatt gtctgtccc                                                     19

<210> SEQ ID NO 90
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 90
cttttctgtt gtctgtccc                                                     19

<210> SEQ ID NO 91
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 91
tgcttttcta ttgtctgtc                                                     19

<210> SEQ ID NO 92
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 92
tgcttttctg ttgtctgtc                                                     19

<210> SEQ ID NO 93
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 93
aagggatgcc gacttgggc                                                     19
```

```
<210> SEQ ID NO 94
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 94
aagggatgct gacttgggc                                                19

<210> SEQ ID NO 95
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 95
accttcctca ctgaggatg                                                19

<210> SEQ ID NO 96
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 96
accttcctcg ctgaggatg                                                19

<210> SEQ ID NO 97
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 97
caaaccactg tgggatgaa                                                19

<210> SEQ ID NO 98
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 98
caaaccactt tgggatgaa                                                19

<210> SEQ ID NO 99
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 99
aataaattgt catcaccag                                                19

<210> SEQ ID NO 100
<211> LENGTH: 19
<212> TYPE: DNA
<213> ORGANISM: Artificial Sequence
<220> FEATURE:
<223> OTHER INFORMATION: Synthetic Oligonucleotide
```

```
<400> SEQUENCE: 100
aataaattgc catcaccag                                              19

<210> SEQ ID NO 101
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 101
tcacagctat cttctcatc                                              19

<210> SEQ ID NO 102
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 102
tcacagctaa cttctcatc                                              19

<210> SEQ ID NO 103
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 103
gcacacagta gatgaggga                                              19

<210> SEQ ID NO 104
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 104
gcacacagtg gatgaggga                                              19

<210> SEQ ID NO 105
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 105
cagaacaaag agaagaatt                                              19

<210> SEQ ID NO 106
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 106
cagaacaaac agaagaatt                                              19

<210> SEQ ID NO 107
<211> LENGTH: 19
```

```
<212> TYPE: DNA
<213> ORGANISM: Artificial Sequence
<220> FEATURE:
<223> OTHER INFORMATION: Synthetic Oligonucleotide

<400> SEQUENCE: 107
gcttacatgc cttcagtga                                                 19

<210> SEQ ID NO 108
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 108
gcttacacgc cttcagtga                                                 19

<210> SEQ ID NO 109
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 109
cagcttacat gccttcagt                                                 19

<210> SEQ ID NO 110
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 110
cagcttacac gccttcagt                                                 19

<210> SEQ ID NO 111
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 111
aagaagcctg ataaaatct                                                 19

<210> SEQ ID NO 112
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 112
aagaagccta ataaaatct                                                 19

<210> SEQ ID NO 113
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 113
```
catacatcag ctcaaactg                                              19

<210> SEQ ID NO 114
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 114
catacattag ctcaaactg                                              19

<210> SEQ ID NO 115
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 115
cacatacatc agctcaaac                                              19

<210> SEQ ID NO 116
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 116
cacatacatt agctcaaac                                              19

<210> SEQ ID NO 117
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 117
gtcacataca tcagctcaa                                              19

<210> SEQ ID NO 118
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 118
gagactatag cacccagat                                              19

<210> SEQ ID NO 119
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 119
gagactataa cacccagat                                              19

<210> SEQ ID NO 120
<211> LENGTH: 19
<212> TYPE: DNA
<213> ORGANISM: Artificial Sequence

```
<220> FEATURE:
<223> OTHER INFORMATION: Synthetic Oligonucleotide

<400> SEQUENCE: 120
tagaggacgc cgtgcaggg                                                  19

<210> SEQ ID NO 121
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 121
tagaggatgc cgtgcaggg                                                  19

<210> SEQ ID NO 122
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 122
catagaggac gccgtgcag                                                  19

<210> SEQ ID NO 123
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 123
catagaggat gccgtgcag                                                  19

<210> SEQ ID NO 124
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 124
cacatagagg acgccgtgc                                                  19

<210> SEQ ID NO 125
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 125
acgtgtgtac agaacctgc                                                  19

<210> SEQ ID NO 126
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 126
acgtgtgtat agaacctgc                                                  19
```

```
<210> SEQ ID NO 127
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 127
tgttcagaat gcctcatct                                            19

<210> SEQ ID NO 128
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 128
tgttcagaac gcctcatct                                            19

<210> SEQ ID NO 129
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 129
aaacggcgca gcgggaagg                                            19

<210> SEQ ID NO 130
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 130
aaacggcaca gcgggaagg                                            19

<210> SEQ ID NO 131
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 131
agaaacggcg cagcgggaa                                            19

<210> SEQ ID NO 132
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 132
agaaacggca cagcgggaa                                            19

<210> SEQ ID NO 133
<211> LENGTH: 19
<212> TYPE: DNA
<213> ORGANISM: Artificial Sequence
<220> FEATURE:
<223> OTHER INFORMATION: Synthetic Oligonucleotide
```

```
<400> SEQUENCE: 133
agggcgcaga cttccaaag                                                19

<210> SEQ ID NO 134
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 134
agggcacaga cttccaaag                                                19

<210> SEQ ID NO 135
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 135
aagggcgcag acttccaaa                                                19

<210> SEQ ID NO 136
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 136
aagggcacag acttccaaa                                                19

<210> SEQ ID NO 137
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 137
caagggcgca gacttccaa                                                19

<210> SEQ ID NO 138
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 138
caagggcaca gacttccaa                                                19

<210> SEQ ID NO 139
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 139
acaagggcgc agacttcca                                                19

<210> SEQ ID NO 140
```

```
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 140
acaagggcac agacttcca                                            19

<210> SEQ ID NO 141
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 141
cacaagggcg cagacttcc                                            19

<210> SEQ ID NO 142
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 142
cacaagggca cagacttcc                                            19

<210> SEQ ID NO 143
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 143
gcacaagggc gcagacttc                                            19

<210> SEQ ID NO 144
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 144
gcacaagggc acagacttc                                            19

<210> SEQ ID NO 145
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 145
ggcacaaggg cgcagactt                                            19

<210> SEQ ID NO 146
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 146
```
ggcacaaggg cacagactt                                           19

<210> SEQ ID NO 147
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 147
agggcacaag ggcgcagac                                           19

<210> SEQ ID NO 148
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 148
agggcacaag ggcacagac                                           19

<210> SEQ ID NO 149
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 149
gagcagctgc aacctggca                                           19

<210> SEQ ID NO 150
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 150
gagcagctgt aacctggca                                           19

<210> SEQ ID NO 151
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 151
tggtgccggg tgtctagca                                           19

<210> SEQ ID NO 152
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 152
tggtgccagg tgtctagca                                           19

<210> SEQ ID NO 153
<211> LENGTH: 19
<212> TYPE: DNA

<213> ORGANISM: Artificial Sequence
<220> FEATURE:
<223> OTHER INFORMATION: Synthetic Oligonucleotide

<400> SEQUENCE: 153
aatggtgccg ggtgtctag                          19

<210> SEQ ID NO 154
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 154
aatggtgcca ggtgtctag                          19

<210> SEQ ID NO 155
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 155
ggggacaggg tgtgctctc                          19

<210> SEQ ID NO 156
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 156
ggggacaggt tgtgctctc                          19

<210> SEQ ID NO 157
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 157
gcttttcatt gaaaagaaa                          19

<210> SEQ ID NO 158
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 158
gcttttcgtt gaaaagaaa                          19

<210> SEQ ID NO 159
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 159
ctgcttttca ttgaaaaga                          19

<210> SEQ ID NO 160
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 160
ctgcttttcg ttgaaaaga                                                    19

<210> SEQ ID NO 161
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 161
actaggccgg gcatgctgg                                                    19

<210> SEQ ID NO 162
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 162
actaggctgg gcatgctgg                                                    19

<210> SEQ ID NO 163
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 163
agactaggcc gggcatgct                                                    19

<210> SEQ ID NO 164
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 164
agactaggct gggcatgct                                                    19

<210> SEQ ID NO 165
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 165
aaacagctgt tagttccca                                                    19

<210> SEQ ID NO 166
<211> LENGTH: 19
<212> TYPE: DNA
<213> ORGANISM: Artificial Sequence
<220> FEATURE:

<223> OTHER INFORMATION: Synthetic Oligonucleotide

<400> SEQUENCE: 166
aaacagccgt tagttccca                                          19

<210> SEQ ID NO 167
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 167
agaaacagct gttagttcc                                          19

<210> SEQ ID NO 168
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 168
agaaacagcc gttagttcc                                          19

<210> SEQ ID NO 169
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 169
gtgctaccca acctttctg                                          19

<210> SEQ ID NO 170
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 170
agtgctaccc aacctttct                                          19

<210> SEQ ID NO 171
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 171
cagtgctacc caacctttc                                          19

<210> SEQ ID NO 172
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 172
acagtgctac ccaaccttt                                          19

```
<210> SEQ ID NO 173
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 173
acagtgctac ccaacctt                                                       18

<210> SEQ ID NO 174
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 174
acagtgctac ccaacct                                                        17

<210> SEQ ID NO 175
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 175
cagtgctacc caacct                                                         16

<210> SEQ ID NO 176
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 176
tcacagtgct acccaacct                                                      19

<210> SEQ ID NO 177
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 177
cagtgctacc caacc                                                          15

<210> SEQ ID NO 178
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 178
atcacagtgc tacccaacc                                                      19

<210> SEQ ID NO 179
<211> LENGTH: 19
<212> TYPE: DNA
<213> ORGANISM: Artificial Sequence
<220> FEATURE:
<223> OTHER INFORMATION: Synthetic Oligonucleotide
```

```
<400> SEQUENCE: 179
tatcacagtg ctacccaac                                              19

<210> SEQ ID NO 180
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 180
atatcacagt gctacccaa                                              19

<210> SEQ ID NO 181
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 181
atgctgactt gggccattc                                              19

<210> SEQ ID NO 182
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 182
gatgctgact tgggccatt                                              19

<210> SEQ ID NO 183
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 183
ggatgctgac ttgggccat                                              19

<210> SEQ ID NO 184
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 184
gggatgctga cttgggcca                                              19

<210> SEQ ID NO 185
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 185
agggatgctg acttgggcc                                              19

<210> SEQ ID NO 186
<211> LENGTH: 18
```

```
<212> TYPE: DNA
<213> ORGANISM: Artificial Sequence
<220> FEATURE:
<223> OTHER INFORMATION: Synthetic Oligonucleotide

<400> SEQUENCE: 186
agggatgctg acttgggc                                                 18

<210> SEQ ID NO 187
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 187
agggatgctg acttggg                                                  17

<210> SEQ ID NO 188
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 188
caagggatgc tgacttggg                                                19

<210> SEQ ID NO 189
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 189
gggatgctga cttgg                                                    15

<210> SEQ ID NO 190
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 190
ccaagggatg ctgacttgg                                                19

<210> SEQ ID NO 191
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 191
gccaagggat gctgacttg                                                19

<210> SEQ ID NO 192
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 192
```

```
tgccaaggga tgctgactt                                          19
```

<210> SEQ ID NO 193
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 193

```
ctgccaaggg atgctgact                                          19
```

<210> SEQ ID NO 194
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 194

```
attgtcatca ccagaaaaa                                          19
```

<210> SEQ ID NO 195
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 195

```
aattgtcatc accagaaaa                                          19
```

<210> SEQ ID NO 196
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 196

```
aaattgtcat caccagaaa                                          19
```

<210> SEQ ID NO 197
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 197

```
taaattgtca tcaccagaa                                          19
```

<210> SEQ ID NO 198
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 198

```
ataaattgtc atcaccaga                                          19
```

<210> SEQ ID NO 199
<211> LENGTH: 18
<212> TYPE: DNA
<213> ORGANISM: Artificial Sequence

```
<220> FEATURE:
<223> OTHER INFORMATION: Synthetic Oligonucleotide

<400> SEQUENCE: 199
ataaattgtc atcaccag                                                  18

<210> SEQ ID NO 200
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 200
ataaattgtc atcacca                                                   17

<210> SEQ ID NO 201
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 201
taaattgtca tcacca                                                    16

<210> SEQ ID NO 202
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 202
taataaattg tcatcacca                                                 19

<210> SEQ ID NO 203
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 203
taaattgtca tcacc                                                     15

<210> SEQ ID NO 204
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 204
ttaataaatt gtcatcacc                                                 19

<210> SEQ ID NO 205
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 205
attaataaat tgtcatcac                                                 19
```

```
<210> SEQ ID NO 206
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 206
tattaataaa ttgtcatca                                                19

<210> SEQ ID NO 207
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 207
ctattaataa attgtcatc                                                19

<210> SEQ ID NO 208
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 208
cagtagatga gggagcagg                                                19

<210> SEQ ID NO 209
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 209
acagtagatg agggagcag                                                19

<210> SEQ ID NO 210
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 210
cacagtagat gagggagca                                                19

<210> SEQ ID NO 211
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 211
acacagtaga tgagggagc                                                19

<210> SEQ ID NO 212
<211> LENGTH: 19
<212> TYPE: DNA
<213> ORGANISM: Artificial Sequence
<220> FEATURE:
<223> OTHER INFORMATION: Synthetic Oligonucleotide
```

<400> SEQUENCE: 212
cacacagtag atgagggag                                                    19

<210> SEQ ID NO 213
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 213
cacacagtag atgaggga                                                     18

<210> SEQ ID NO 214
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 214
cacacagtag atgaggg                                                      17

<210> SEQ ID NO 215
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 215
acacagtaga tgaggg                                                       16

<210> SEQ ID NO 216
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 216
tgcacacagt agatgaggg                                                    19

<210> SEQ ID NO 217
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 217
acacagtaga tgagg                                                        15

<210> SEQ ID NO 218
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 218
gtgcacacag tagatgagg                                                    19

<210> SEQ ID NO 219

```
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 219
agtgcacaca gtagatgag                                               19

<210> SEQ ID NO 220
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 220
aagtgcacac agtagatga                                               19

<210> SEQ ID NO 221
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 221
gaagtgcaca cagtagatg                                               19

<210> SEQ ID NO 222
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 222
gctgcaacct ggcaacaac                                               19

<210> SEQ ID NO 223
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 223
agctgcaacc tggcaacaa                                               19

<210> SEQ ID NO 224
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 224
cagctgcaac ctggcaaca                                               19

<210> SEQ ID NO 225
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 225
```
gcagctgcaa cctggcaac                                          19

<210> SEQ ID NO 226
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 226
agcagctgca acctggcaa                                          19

<210> SEQ ID NO 227
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 227
agcagctgca acctggca                                           18

<210> SEQ ID NO 228
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 228
agcagctgca acctggc                                            17

<210> SEQ ID NO 229
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 229
gcagctgcaa cctggc                                             16

<210> SEQ ID NO 230
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 230
agagcagctg caacctggc                                          19

<210> SEQ ID NO 231
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 231
gcagctgcaa cctgg                                              15

<210> SEQ ID NO 232
<211> LENGTH: 19
<212> TYPE: DNA

```
<213> ORGANISM: Artificial Sequence
<220> FEATURE:
<223> OTHER INFORMATION: Synthetic Oligonucleotide

<400> SEQUENCE: 232
aagagcagct gcaacctgg                                                  19

<210> SEQ ID NO 233
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 233
caagagcagc tgcaacctg                                                  19

<210> SEQ ID NO 234
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 234
gcaagagcag ctgcaacct                                                  19

<210> SEQ ID NO 235
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 235
tgcaagagca gctgcaacc                                                  19

<210> SEQ ID NO 236
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 236
accatgatat ctccagcac                                                  19

<210> SEQ ID NO 237
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 237
accatgacat ctccagcac                                                  19

<210> SEQ ID NO 238
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 238
ccaccatgat atctccagc                                                  19
```

<210> SEQ ID NO 239
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 239
ccaccatgac atctccagc                                                    19

<210> SEQ ID NO 240
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 240
ttaacactcg attaaccct                                                    19

<210> SEQ ID NO 241
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 241
tagttcatcc cagtgagaa                                                    19

<210> SEQ ID NO 242
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 242
ctagttcatc ccagtgaga                                                    19

<210> SEQ ID NO 243
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 243
gaaatgggtt tttccacat                                                    19

<210> SEQ ID NO 244
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 244
ggaaatgggt ttttccaca                                                    19

<210> SEQ ID NO 245
<211> LENGTH: 19
<212> TYPE: DNA
<213> ORGANISM: Artificial Sequence
<220> FEATURE:

```
<223> OTHER INFORMATION: Synthetic Oligonucleotide

<400> SEQUENCE: 245
taaccgtggc atgggcagt                                            19

<210> SEQ ID NO 246
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 246
ttaaccgtgg catgggcag                                            19

<210> SEQ ID NO 247
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 247
cttcaagcta gtaacgatg                                            19

<210> SEQ ID NO 248
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 248
agctaggtta aagagtcac                                            19

<210> SEQ ID NO 249
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 249
cagctaggtt aaagagtca                                            19

<210> SEQ ID NO 250
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 250
taagaaacac aatcaaaga                                            19

<210> SEQ ID NO 251
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 251
ataagaaaca caatcaaag                                            19
```

```
<210> SEQ ID NO 252
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 252
attttctaga ctttatgat                                              19

<210> SEQ ID NO 253
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 253
aattttctag actttatga                                              19

<210> SEQ ID NO 254
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 254
gagaatacgg gtaacattt                                              19

<210> SEQ ID NO 255
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 255
tgggcaggaa ggactgaac                                              19

<210> SEQ ID NO 256
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 256
gtgggcagga aggactgaa                                              19

<210> SEQ ID NO 257
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 257
ccctaaatca atctacaag                                              19

<210> SEQ ID NO 258
<211> LENGTH: 19
<212> TYPE: DNA
<213> ORGANISM: Artificial Sequence
<220> FEATURE:
<223> OTHER INFORMATION: Synthetic Oligonucleotide
```

<400> SEQUENCE: 258
cttttccgtg ctgttctga                                              19

<210> SEQ ID NO 259
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 259
acttttccgt gctgttctg                                              19

<210> SEQ ID NO 260
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 260
aacttttccg tgctgttct                                              19

<210> SEQ ID NO 261
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 261
gctgagcgga gaaaccctc                                              19

<210> SEQ ID NO 262
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 262
attccctaaa aacaaaaac                                              19

<210> SEQ ID NO 263
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 263
gcttttctat tgtctgtcc                                              19

<210> SEQ ID NO 264
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 264
cttcctcact gaggatgaa                                              19

<210> SEQ ID NO 265
<211> LENGTH: 19

```
<212> TYPE: DNA
<213> ORGANISM: Artificial Sequence
<220> FEATURE:
<223> OTHER INFORMATION: Synthetic Oligonucleotide

<400> SEQUENCE: 265
ccttcctcac tgaggatga                                                        19

<210> SEQ ID NO 266
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 266
aaccactttg ggatgaata                                                        19

<210> SEQ ID NO 267
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 267
aaaccacttt gggatgaat                                                        19

<210> SEQ ID NO 268
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 268
acagctatct tctcatcaa                                                        19

<210> SEQ ID NO 269
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 269
cacagctatc ttctcatca                                                        19

<210> SEQ ID NO 270
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 270
gaacaaagag aagaatttc                                                        19

<210> SEQ ID NO 271
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 271
```
agaacaaaga gaagaattt                                          19

<210> SEQ ID NO 272
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 272
gaagcctgat aaaatctct                                          19

<210> SEQ ID NO 273
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 273
agaagcctga taaaatctc                                          19

<210> SEQ ID NO 274
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 274
tgatctgtag cagcagctt                                          19

<210> SEQ ID NO 275
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 275
ttgatctgta gcagcagct                                          19

<210> SEQ ID NO 276
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 276
gttgatctgt agcagcagc                                          19

<210> SEQ ID NO 277
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 277
atagaggacg ccgtgcagg                                          19

<210> SEQ ID NO 278
<211> LENGTH: 19
<212> TYPE: DNA
<213> ORGANISM: Artificial Sequence

```
<220> FEATURE:
<223> OTHER INFORMATION: Synthetic Oligonucleotide

<400> SEQUENCE: 278
gtgtgtacag aacctgccg                                                19

<210> SEQ ID NO 279
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 279
cgtgtgtaca gaacctgcc                                                19

<210> SEQ ID NO 280
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 280
ttcagaatgc ctcatctgg                                                19

<210> SEQ ID NO 281
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 281
gttcagaatg cctcatctg                                                19

<210> SEQ ID NO 282
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 282
ggacagggtg tgctctccg                                                19

<210> SEQ ID NO 283
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 283
gggacagggt gtgctctcc                                                19

<210> SEQ ID NO 284
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 284
gggatgctga cttggg                                                   16
```

<210> SEQ ID NO 285
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 285
acacagtaga tgaggga                                                    17

<210> SEQ ID NO 286
<211> LENGTH: 10081
<212> TYPE: DNA
<213> ORGANISM: Mus musculus

<400> SEQUENCE: 286

| | | | | | |
|---|---|---|---|---|---|
| gcactcgccg | cgagggttgc | cgggacgggc | ccaagatggc | tgagcgcctt | ggttccgctt | 60 |
| ctgcctgccg | cgcagagccc | cattcattgc | cttgctgcta | agtggcgccg | cgtagtgcca | 120 |
| gtaggctcca | agtcttcagg | gtctgtccca | tcgggcagga | agccgtcatg | gcaaccctgg | 180 |
| aaaagctgat | gaaggctttc | gagtcgctca | agtcgtttca | gcagcaacag | cagcagcagc | 240 |
| caccgccgca | ggcgccgccg | ccaccgccgc | cgccgcctcc | gcctcaaccc | cctcagccgc | 300 |
| cgcctcaggg | gcagccgccg | ccgccaccac | cgccgctgcc | aggtccggca | gaggaaccgc | 360 |
| tgcaccgacc | aaagaaggaa | ctctcagcca | ccaagaaaga | ccgtgtgaat | cattgtctaa | 420 |
| caatatgtga | aaacattgtg | gcacagtctc | tcagaaattc | tccagaattt | cagaaactct | 480 |
| tgggcatcgc | tatggaactg | tttctgctgt | gcagtgacga | tgcggagtca | gatgtcagaa | 540 |
| tggtggctga | tgagtgcctc | aacaaagtca | tcaaagcttt | gatggattct | aatcttccaa | 600 |
| ggctacagtt | agaactctat | aaggaaatta | aaagaatgg | tgctcctcga | agtttgcgtg | 660 |
| ctgccctgtg | gaggtttgct | gagctggctc | acctggttcg | acctcagaag | tgcaggcctt | 720 |
| acctggtgaa | tcttcttcca | tgcctgaccc | gaacaagcaa | agaccggag | gaatcagttc | 780 |
| aggagacctt | ggctgcagct | gttcctaaaa | ttatggcttc | ttttggcaat | tcgcaaatg | 840 |
| acaatgaaat | taaggttctg | ttgaaagctt | tcatagcaaa | tctgaagtca | agctctccca | 900 |
| ccgtgcggcg | gacagcagcc | ggctcagccg | tgagcatctg | ccaacattct | aggaggacac | 960 |
| agtacttcta | caactggctc | cttaatgtcc | tcctaggtct | gctggttccc | atggaagaag | 1020 |
| agcactccac | tctcctgatc | ctcggtgtgt | tgctcacatt | gaggtgtcta | gtgcccttgc | 1080 |
| tccagcagca | ggtcaaggac | acaagtctaa | aaggcagctt | tggggtgaca | cggaaagaaa | 1140 |
| tggaagtctc | tccttctaca | gagcagcttg | tccaggttta | tgaactgact | ttgcatcata | 1200 |
| ctcagcacca | agaccacaat | gtggtgacag | gggcactgga | gctcctgcag | cagctcttcc | 1260 |
| gtaccctcc | acctgaactc | ctgcaagcac | tgaccacacc | aggagggctt | gggcagctca | 1320 |
| ctctggttca | agaagaggcc | cggggccgag | gccgcagcgg | gagcatcgtg | gagcttttag | 1380 |
| ctggagggg | ttcctcgtgc | agccctgtcc | tctcaagaaa | gcagaaaggc | aaagtgctct | 1440 |
| taggagagga | agaagccttg | gaagatgact | cggagtccag | gtcagatgtc | agcagctcag | 1500 |
| cctttgcagc | ctctgtgaag | agtgagattg | gtggagagct | cgctgcttct | tcaggtgttt | 1560 |
| ccactcctgg | ttctgttggt | cacgacatca | tcactgagca | gcctagatcc | cagcacacac | 1620 |
| ttcaagcaga | ctctgtggat | ttgtccggct | gtgacctgac | cagtgctgct | actgatgggg | 1680 |
| atgaggagga | catcttgagc | cacagctcca | gccagttcag | tgctgtccca | tccgaccctg | 1740 |
| ccatggacct | gaatgatggg | acccaggcct | cctcacccat | cagtgacagt | tctcagacca | 1800 |

```
ccactgaagg acctgattca gctgtgactc cttcggacag ttctgaaatt gtgttagatg   1860
gtgccgatag ccagtattta ggcatgcaga taggacagcc acaggaggac gatgaggagg   1920
gagctgcagg tgttctttct ggtgaagtct cagatgtttt cagaaactct tctctggccc   1980
ttcaacaggc acacttgttg gaaagaatgg gccatagcag gcagccttcc gacagcagta   2040
tagataagta tgtaacaaga gatgaggttg ctgaagccag tgatccagaa agcaagcctt   2100
gccgaatcaa aggtgacata ggacagccta atgatgatga ttctgctcct ctggtacatt   2160
gtgtccgtct tttatctgct tcctttttgt taactggtga aagaaagca ctggttccag    2220
acagagacgt gagagtcagt gtgaaggccc tggccctcag ctgcattggt gcggctgtgg   2280
cccttcatcc agagtcgttc ttcagcagac tgtacaaagt acctcttaat accacggaaa   2340
gtactgagga acagtatgtt tctgacatct tgaactacat cgatcatgga gacccacagg   2400
tccgaggagc tactgccatt ctctgtggga cccttgtcta ctccatcctc agtaggtccc   2460
gtctccgtgt tggtgactgg ctgggcaaca tcagaaccct gacaggaaat acattttctc   2520
tggtggactg cattccttta ctgcagaaaa cgttgaagga tgaatcttct gttacttgca   2580
agttggcttg tacagctgtg aggcactgtg tcctgagtct ttgcagcagc agctacagtg   2640
acttgggatt acaactgctt attgatatgc tgcctctgaa gaacagctcc tactggctgg   2700
tgaggaccga actgctggac actctggcag agattgactt caggctcgtg agttttttgg   2760
aggcaaaagc agaaagttta caccgagggg ctcatcatta tacagggttt ctaaaactac   2820
aagaacgagt actcaataat gtggtcattt atttgcttgg agatgaagac cccagggttc   2880
gacatgttgc tgcaacatca ttaacaaggc ttgtcccaaa gctgttttac aagtgtgacc   2940
aaggacaagc tgatccagtt gtggctgtag cgagggatca gagcagtgtc tacctgaagc   3000
tcctcatgca tgagacccag ccaccatcac acttttctgt cagcaccatc accagaatct   3060
atagaggcta tagcttactg ccaagtataa cagatgtcac catggaaaac aatctctcaa   3120
gagttgttgc cgcagtttct catgaactca ttacgtcaac aacacgggca ctcacatttg   3180
gatgctgtga agccttgtgt cttctctcag cagcctttcc agtttgcact tggagtttag   3240
gatggcactg tggagtgccc ccactgagtg cctctgatga gtccaggaag agctgcactg   3300
ttgggatggc ctccatgatt ctcaccttgc tttcatcagc ttggttccca ctggatctct   3360
cagcccatca ggatgccttg attttggctg gaaacttgct agcagcgagt gcccccaagt   3420
ctctgagaag ttcatggacc tctgaagaag aagccaactc agcagccacc agacaggagg   3480
aaatctggcc tgctctgggg gatcggactc tagtgccctt ggtggagcag cttttctccc   3540
acctgctgaa ggtgatcaat atctgtgctc atgtcttgga cgatgtgact cctggaccag   3600
caatcaaggc agccttgcct tctctaacaa acccccttc tctaagtcct attcgacgga   3660
aagggaagga gaaagaacct ggagaacaag cttctactcc aatgagtccc aagaaagttg   3720
gtgaggccag tgcagcctct cgacaatcag acacctcagg acctgtcaca gcaagtaaat   3780
catcctcact ggggagtttc taccatctcc cctcctacct caaactgcat gatgtcctga   3840
aagccactca cgccaactat aaggtcacct tagatcttca gaacagcact gaaaagtttg   3900
gggggttcct gcgctctgcc ttggacgtcc tttctcagat tctagagctg gcgacactgc   3960
aggacattgg aaagtgtgtt gaagaggtcc ttggatacct gaaatcctgc tttagtcgag   4020
aaccaatgat ggcaactgtc tgtgtgcagc agctattgaa gactctcttt gggacaaact   4080
tagcctcaca gtttgatggc ttatcttcca acccagcaa gtctcagtgc cgagctcagc    4140
```

```
gccttggctc ttcaagtgtg aggcccggct tatatcacta ctgcttcatg gcaccataca    4200
cgcacttcac acaggccttg gctgacgcaa gcctgaggaa catggtgcag gcggagcagg    4260
agcgtgatgc ctcggggtgg tttgatgtac tccagaaagt gtctgcccaa ttgaagacga    4320
acctaacaag cgtcacaaag aaccgtgcag ataagaatgc tattcataat cacattaggt    4380
tatttgagcc tcttgttata aaagcattga agcagtacac cacgacaaca tctgtacaat    4440
tgcagaagca ggttttggat tgctggcaca agctggttca gctacgggtc aattactgtc    4500
tactggattc agaccaggtg ttcatcgggt ttgtgctgaa gcagtttgag tacattgaag    4560
tgggccagtt cagggaatca gaggcaatta ttccaaatat attttcttc ctggtattac    4620
tgtcttatga gcgctaccat tcaaaacaga tcattggaat tcctaaaatc atccagctgt    4680
gtgatggcat catggccagt ggaaggaagg ccgttacaca tgctatacct gctctgcagc    4740
ccattgtcca tgacctcttt gtgttacgag gaacaaataa agctgatgca gggaagagc    4800
ttgagacaca gaaggaggtg gtggtctcca tgctgttacg actcatccag taccatcagg    4860
tgctggagat gttcatcctt gtcctgcagc agtgccacaa ggagaatgag gacaagtgga    4920
aacggctctc tcggcaggtc gcagacatca tcctgcccat gttggccaag cagcagatgc    4980
atattgactc tcatgaagcc cttggagtgt taaataccctt gtttgagatt ttggctcctt    5040
cctccctacg tcctgtggac atgcttttgc ggagtatgtt catcactcca agcacaatgg    5100
catctgtaag cactgtgcag ctgtggatat ctggaatcct cgccattctg agggttctca    5160
tttcccagtc aaccgaggac attgttcttt gtcgtattca ggagctctcc ttctctccac    5220
acttgctctc ctgtccagtg attaacaggt taaggggtgg aggcggtaat gtaacactag    5280
gagaatgcag cgaagggaaa caaaagagtt gccagaagaa tacattctca aggtttcttt    5340
tacagctggt tggtattctt ctagaagaca tcgttacaaa acagctcaaa gtggacatga    5400
gtgaacagca gcatacgttc tactgccaag agctaggcac actgctcatg tgtctgatcc    5460
acatattcaa atctgaatg ttccggagaa tcacagcagc tgccactaga ctcttcacca    5520
gtgatggctg tgaaggcagc ttctatactc tagagagcct gaatgcacgg gtccgatcca    5580
tggtgcccac gcacccagcc ctggtactgc tctggtgtca gatcctactt ctcatcaacc    5640
acactgacca ccggtggtgg gcagaggtgc agcagacacc caagagacac agtctgtcct    5700
gcacgaagtc acttaacccc cagaagtctg gcgaagagga ggattctggc tcggcagctc    5760
agctgggaat gtgcaataga gaaatagtgc gaagaggggc ccttattctc ttctgtgatt    5820
atgtctgtca gaatctccat gactcagaac acttaacatg gctcattgtg aatcacattc    5880
aagatctgat cagcttgtct catgagcctc cagtacaaga ctttattagt gccattcatc    5940
gtaattctgc agctagtggt ctttttatcc aggcaattca gtctcgctgt gaaaatcttt    6000
caacgccaac cactctgaag aaaacacttc agtgcttgga aggcatccat ctcagccagt    6060
ctggtgctgt gctcacacta tatgtggaca ggctcctggg cacccccttc cgtgcgctgg    6120
ctcgcatggt cgacaccctg gcctgtcgcc gggtagaaat gcttttggct gcaaatttac    6180
agagcagcat ggcccagttg ccagaggagg aactaaacag aatccaagaa cacctccaga    6240
acagtgggct tgcacaaaga caccaaaggc tctattcact gctggacaga ttccgactct    6300
ctactgtgca ggactcactt agcccctttgc ccccagtcac ttcccaccca ctggatgggg    6360
atgggcacac atctctggaa acagtgagtc cagacaaaga ctggtacctc cagcttgtca    6420
gatcccagtg ttggaccaga tcagattctg cactgctgga aggtgcagag ctggtcaacc    6480
gtatccctgc tgaagatatg aatgacttca tgatgagctc ggagttcaac ctaagccttt    6540
```

```
tggctccctg tttaagcctt ggcatgagcg agattgctaa tggccaaaag agtcccctct    6600
ttgaagcagc ccgtggggtg attctgaacc gggtgaccag tgttgttcag cagcttcctg    6660
ctgtccatca agtcttccag cccttcctgc ctatagagcc cacggcctac tggaacaagt    6720
tgaatgatct gcttggtgat accacatcat accagtctct gaccatactt gcccgtgccc    6780
tggcacagta cctggtggtg ctctccaaag tgcctgctca tttgcacctt cctcctgaga    6840
aggaggggga cacggtgaag tttgtggtaa tgacagttga ggccctgtca tggcatttga    6900
tccatgagca gatcccactg agtctggacc tccaagccgg gctagactgc tgctgcctgg    6960
cactacaggt gcctggcctc tggggggtgc tgtcctcccc agagtacgtg actcatgcct    7020
gctccctcat ccattgtgtg cgattcatcc tggaagccat tgcagtacaa cctggagacc    7080
agcttctcgg tcctgaaagc aggtcacata ctccaagagc tgtcagaaag gaggaagtag    7140
actcagatat acaaaacctc agtcatgtca cttcggcctg cgagatggtg gcagacatgg    7200
tggaatccct gcagtcagtg ctggccttgg gccacaagag gaacagcacc ctgccttcat    7260
ttctcacagc tgtgctgaag aacattgtta tcagtctggc ccgactcccc ctagttaaca    7320
gctatactcg tgtgcctcct ctggtatgga aactcgggtg gtcacccaag cctggagggg    7380
attttggcac agtgtttcct gagatccctg tagagttcct ccaggagaag gagatcctca    7440
aggagttcat ctaccgcatc aacacccatg ggtggaccaa tcgtacccag ttcgaagaaa    7500
cttgggccac cctccttggt gtcctggtga ctcagcccct ggtgatggaa caggaagaga    7560
gcccaccaga ggaagacaca gaaagaaccc agatccatgt cctggctgtg caggccatca    7620
cctctctagt gctcagtgca atgaccgtgc ctgtggctgg caatccagct gtaagctgct    7680
tggagcaaca gccccggaac aagccactga aggctctcga taccagattt ggaagaaagc    7740
tgagcatgat cagagggatt gtagaacaag aaatccaaga gatggtttcc cagagagaga    7800
atactgccac tcaccattct caccaggcgt gggatcctgt cccttctctg ttaccagcta    7860
ctacaggtgc tcttatcagc catgacaagc tgctgctgca gatcaaccca gagcgggagc    7920
caggcaacat gagctacaag ctgggccagg tgtccataca ctccgtgtgg ctgggaaata    7980
acatcacacc cctgagagag gaggaatggg atgaggaaga agaggaagaa agtgatgtcc    8040
ctgcaccaac gtcaccacct gtgtctccag tcaattccag aaaacaccgt gccggggttg    8100
atattcactc ctgttcgcag tttctgcttg aattgtacag ccgatggatc ctgccatcca    8160
gtgcagccag aaggaccccc gtcatcctga tcagtgaagt ggttcgatct cttcttgtag    8220
tgtcagactt attcaccgaa cgtacccagt ttgaaatgat gtatctgacg ctgacagaac    8280
tacggagagt gcacccttca gaagatgaga tcctcattca gtacctggtg cctgccacct    8340
gtaaggcagc tgctgtcctt ggaatggaca aaactgtggc agagccagtc agccgcctac    8400
tggagagcac actgaggagc agccacctgc ccagccagat cggagccctg cacggcatcc    8460
tctatgtgtt ggagtgtgac ctcttggatg acactgcaaa gcagctcatt ccagttgtta    8520
gtgactatct gctgtccaac ctcaaaggaa tagcccactg cgtgaacatt cacagccagc    8580
agcatgtgct ggtaatgtgt gccactgctt tctacctgat ggaaaactac cctctggatg    8640
tgggaccaga attttcagca tctgtgatac agatgtgtgg agtaatgctg tctggaagtg    8700
aggagtccac cccctccatc atttaccact gtgccctccg gggtctggag cggctcctgc    8760
tgtctgagca gctatctcgg ctagacacag agtccttggt caagctaagt gtggacagag    8820
tgaatgtaca aagcccacac agggccatgg cagccctagg cctgatgctc acctgcatgt    8880
```

```
acacaggaaa ggaaaaagcc agtccaggca gagcttctga ccccagccct gctacacctg    8940
acagcgagtc tgtgattgta gctatggagc gagtgtctgt tctctttgat aggatccgca    9000
agggatttcc ctgtgaagcc agggttgtgg caaggatcct gcctcagttc ctagatgact    9060
tctttccacc tcaagatgtc atgaacaaag tcattggaga gttcctgtcc aatcagcagc    9120
catacccaca gttcatggcc actgtagttt acaaggtttt tcagactctg cacagtgctg    9180
ggcagtcatc catggtccgg gactgggtca tgctgtccct gtccaacttc acacaaagaa    9240
ctccagttgc catggccatg tggagcctct cctgcttcct tgttagcgca tctaccagcc    9300
catgggtttc tgcgatcctt ccacatgtca tcagcaggat gggcaaactg gaacaggtgg    9360
atgtgaacct tttctgcctg gttgccacag acttctacag acaccagata gaggaggaat    9420
tcgaccgcag ggcttttccag tctgtgtttg aggtggtggc tgcaccagga agtccatacc    9480
acaggctgct tgcttgtttg caaaatgttc acaaggtcac cacctgctga gtagtgcctg    9540
tgggacaaaa ggctgaaaga aggcagctgc tggggcctga gcctccagga gcctgctcca    9600
agcttctgct ggggctgcct tggccgtgca ggcttccact tgtgtcaagt ggacagccag    9660
gcaatggcag gagtgctttg caatgagggc tatgcaggga acatgcacta tgttggggtt    9720
gagcctgagt cctgggtcct ggcctcgctg cagctggtga cagtgctagg ttgaccaggt    9780
gtttgtcttt ttcctagtgt tcccctggcc atagtcgcca ggttgcagct gccctggtat    9840
gtggatcaga agtcctagct cttgccagat ggttctgagc ccgcctgctc cactgggctg    9900
gagagctccc tcccacattt acccagtagg catacctgcc acaccagtgt ctggacacaa    9960
aatgaatggt gtgtggggct gggaactggg gctgccaggt gtccagcacc attttccttt   10020
ctgtgttttc ttctcaggag ttaaaattta attatatcag taaagagatt aatttttaatg  10080 t                                                                   10081

<210> SEQ ID NO 287
<211> LENGTH: 20
<212> TYPE: DNA
<213> ORGANISM: Artificial Sequence
<220> FEATURE:
<223> OTHER INFORMATION: Primer

<400> SEQUENCE: 287
attacagtct caccacgccc                                                  20

<210> SEQ ID NO 288
<211> LENGTH: 20
<212> TYPE: DNA
<213> ORGANISM: Artificial Sequence
<220> FEATURE:
<223> OTHER INFORMATION: Primer

<400> SEQUENCE: 288
gacaagggaa gacccaagtg                                                  20
```